United States Patent
Li et al.

(10) Patent No.: US 9,941,479 B2
(45) Date of Patent: Apr. 10, 2018

(54) TETRADENTATE CYCLOMETALATED PLATINUM COMPLEXES CONTAINING 9,10-DIHYDROACRIDINE AND ITS ANALOGUES

(71) Applicant: Arizona Board of Regents on behalf of Arizona State University, Scottsdale, AZ (US)

(72) Inventors: Jian Li, Tempe, AZ (US); Guijie Li, Tempe, AZ (US); Zhi-Qiang Zhu, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 178 days.

(21) Appl. No.: 14/728,848

(22) Filed: Jun. 2, 2015

(65) Prior Publication Data
US 2015/0349279 A1    Dec. 3, 2015

Related U.S. Application Data

(60) Provisional application No. 62/006,509, filed on Jun. 2, 2014.

(51) Int. Cl.
*C07F 15/00*    (2006.01)
*H01L 51/00*    (2006.01)
(Continued)

(52) U.S. Cl.
CPC ...... *H01L 51/0087* (2013.01); *C07F 15/0086* (2013.01); *C09K 11/06* (2013.01);
(Continued)

(58) Field of Classification Search
CPC .......................... C07F 15/0086; C07F 15/0093
See application file for complete search history.

(56) References Cited

U.S. PATENT DOCUMENTS 4,769,292 A   9/1988 Tang et al.
5,707,745 A   1/1998 Forrest et al.
(Continued)

FOREIGN PATENT DOCUMENTS

CN   1777663   5/2006
CN   1894269   1/2007
(Continued)

OTHER PUBLICATIONS

Murakami; JP 2007258550, English machine translation from EPO, Oct. 4, 2007. 80 pages.
(Continued)

*Primary Examiner* — Matthew E. Hoban
(74) *Attorney, Agent, or Firm* — Fish & Richardson P.C.

(57) ABSTRACT

Platinum complexes suitable for use as phosphorescent emitters or as delayed fluorescent and phosphorescent emitters having the following structure:

Formula I (Continued)

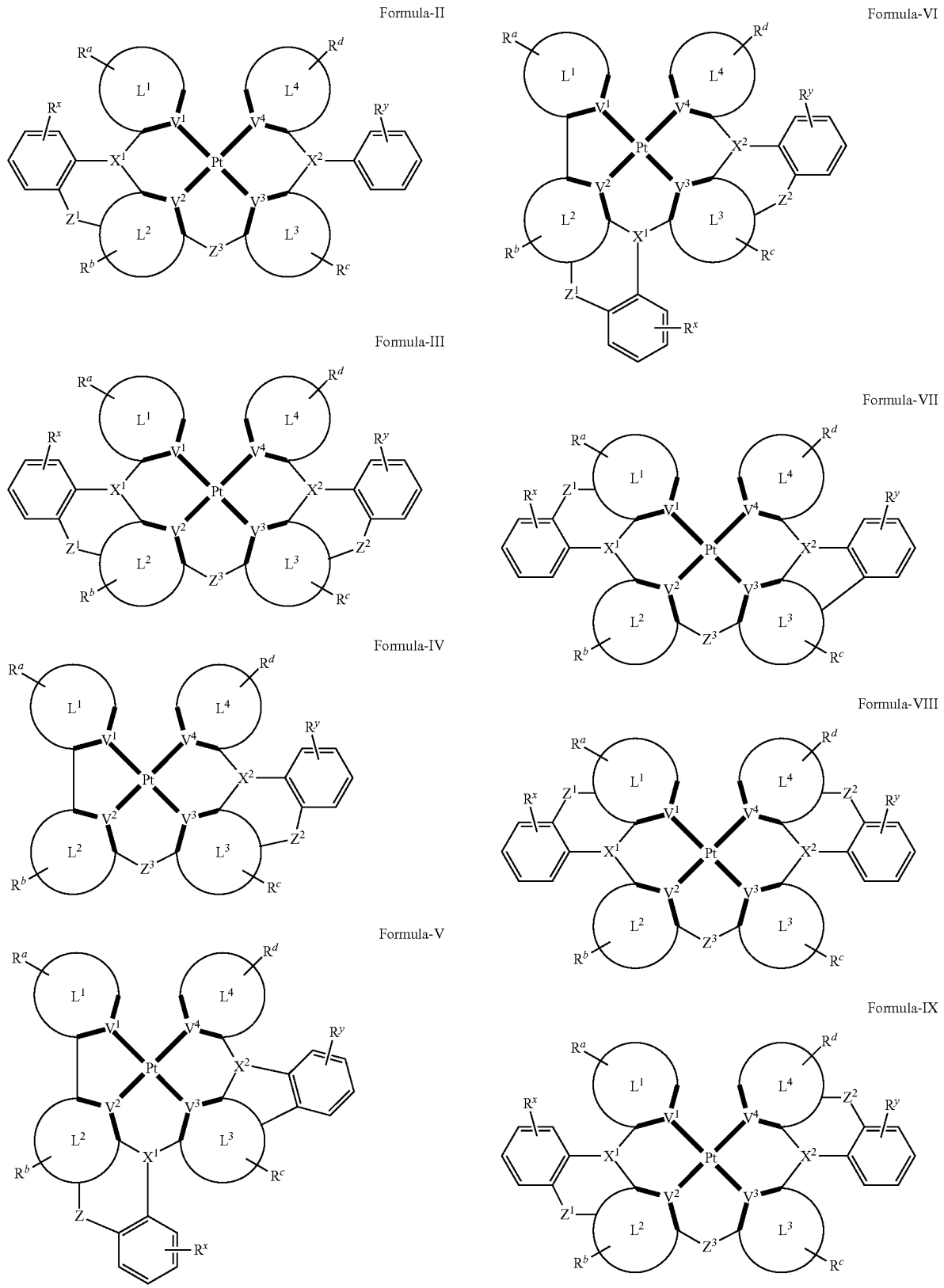

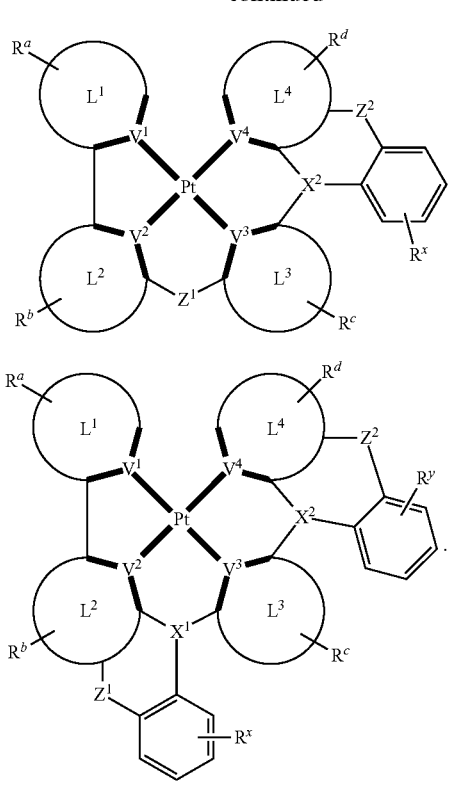

Formula-X

Formula-XI

15 Claims, 4 Drawing Sheets

(51) Int. Cl.
    *C09K 11/06*     (2006.01)
    *H05B 33/14*     (2006.01)
    *H01L 51/50*     (2006.01)

(52) U.S. Cl.
    CPC ...... *H05B 33/14* (2013.01); *C09K 2211/1007* (2013.01); *C09K 2211/1014* (2013.01); *C09K 2211/1022* (2013.01); *C09K 2211/1029* (2013.01); *C09K 2211/1044* (2013.01); *C09K 2211/185* (2013.01); *H01L 51/5016* (2013.01)

(56) References Cited

U.S. PATENT DOCUMENTS

| | | |
|---|---|---|
| 5,844,363 A | 12/1998 | Gu et al. |
| 6,200,695 B1 | 3/2001 | Arai et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,505 B2 | 4/2016 | Brooks |
| 9,324,957 B2 | 4/2016 | Li et al. |
| 9,382,273 B2 | 7/2016 | Li et al. |
| 9,385,329 B2 | 7/2016 | Li et al. |
| 9,425,415 B2 | 8/2016 | Li et al. |
| 9,461,254 B2 | 10/2016 | Tsai |
| 9,550,801 B2 | 1/2017 | Li |
| 9,617,291 B2 | 4/2017 | Li |
| 9,673,409 B2 | 6/2017 | Li et al. |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 2002/0068190 A1 | 6/2002 | Tsuboyama et al. |
| 2003/0062519 A1 | 4/2003 | Yamazaki et al. |
| 2003/0186077 A1 | 10/2003 | Chen |
| 2005/0170207 A1 | 8/2005 | Ma et al. |
| 2005/0260446 A1 | 11/2005 | MacKenzie et al. |
| 2006/0073359 A1 | 4/2006 | Ise et al. |
| 2006/0094875 A1 | 5/2006 | Itoh et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0302753 A1 | 11/2012 | Li |
| 2013/0048963 A1 | 2/2013 | Beers et al. |
| 2013/0168656 A1* | 7/2013 | Tsai ............... C07F 15/0086 257/40 |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0203248 A1 | 7/2014 | Zhou et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |

(56) References Cited

U.S. PATENT DOCUMENTS

| | | |
|---|---|---|
| 2016/0133862 A1 | 5/2016 | Li et al. |
| 2016/0197291 A1 | 7/2016 | Li et al. |
| 2016/0285015 A1 | 9/2016 | Li et al. |
| 2016/0359120 A1 | 12/2016 | Li |
| 2016/0359125 A1 | 12/2016 | Li |
| 2017/0005278 A1 | 1/2017 | Li |
| 2017/0012224 A1 | 1/2017 | Li |
| 2017/0047533 A1 | 2/2017 | Li |
| 2017/0066792 A1 | 3/2017 | Li |
| 2017/0069855 A1 | 3/2017 | Li |
| 2017/0267923 A1 | 9/2017 | Li |

FOREIGN PATENT DOCUMENTS

| | | |
|---|---|---|
| CN | 101142223 A | 3/2008 |
| CN | 101667626 A | 3/2010 |
| CN | 102449108 A | 5/2012 |
| CN | 102892860 A | 1/2013 |
| CN | 102971396 A | 3/2013 |
| CN | 104232076 A | 12/2014 |
| CN | 104693243 A | 6/2015 |
| CN | 105367605 A1 | 3/2016 |
| CN | 105418591 A1 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 A | 9/2005 |
| JP | 2005310733 A | 11/2005 |
| JP | 2006047240 A | 2/2006 |
| JP | 2006232784 A | 9/2006 |
| JP | 2006242080 A | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007042875 A | 2/2007 |
| JP | 2007053132 | 3/2007 |
| JP | 2007066581 A | 3/2007 |
| JP | 2007073620 A | 3/2007 |
| JP | 2007073845 A | 3/2007 |
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 | 4/2007 |
| JP | 2007096259 A | 4/2007 |
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009266943 A | 11/2009 |
| JP | 2009267171 | 11/2009 |
| JP | 2009267244 | 11/2009 |
| JP | 2009272339 A | 11/2009 |
| JP | 2009283891 | 12/2009 |
| JP | 2010135689 | 6/2010 |
| JP | 2012222255 A | 11/2012 |
| JP | 2013525436 | 6/2013 |
| JP | 5604505 | 10/2014 |
| JP | 2014221807 | 11/2014 |
| JP | 2015081257 | 4/2015 |
| KR | 102006011537 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| TW | 201710277 | 3/2017 |
| WO | WO2000070655 | 11/2000 |
| WO | WO2004003108 A1 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 A1 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 A2 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 A1 | 1/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 A1 | 9/2015 |
| WO | WO2016025921 A1 | 2/2016 |
| WO | WO2016029186 A1 | 2/2016 |

OTHER PUBLICATIONS

Murakami; JP 2007324309, English machine translation from EPO, Dec. 13, 2007, 89 pages.

Dorwald; "Side Reactions in Organic Synthesis: A Guide to Successful Synthesis Design," Chapter 1, 2005 Wiley-VCH Verlag GmbH & Co. KGaA, Wienheim, 32 pages.

Wong; Challenges in organometallic research—Great opportunity for solar cells and OLEDs, Journal of Organometallic Chemistry, 2009, 694, 2644-2647.

JP2009267244, English Translation from EPO, Nov. 2009, 80 pages.

JP2010135689, English translation from EPO, Jun. 2010, 95 pages.

Chi et al.; Transition-metal phosphors with cyclometalating ligands: fundamentals and applications, Chemical Society Reviews, vol. 39, No. 2, Feb. 2010, pp. 638-655.

Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

(56) References Cited

OTHER PUBLICATIONS

Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6, Aug. 25, 2013.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)$_3$ and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, vol. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O NCN Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate ONCN ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-043598.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), vol. 26, No. 41, 2014, pp. 7116-7121.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.

\* cited by examiner

TETRADENTATE CYCLOMETALATED PLATINUM COMPLEXES CONTAINING 9,10-DIHYDROACRIDINE AND ITS ANALOGUES

CROSS-REFERENCE TO RELATED APPLICATION

This application claims priority to U.S. Ser. No. 62/006,509 entitled "TETRADENTATE CYCLOMETALATED PLATINUM COMPLEXES CONTAINING 9,10-DIHYDROACRIDINE AND ITS ANALOGUES," filed on Jun. 2, 2014, which is incorporated by reference herein in its entirety.

TECHNICAL FIELD

The present disclosure relates to multidentate platinum complexes suitable for use as phosphorescent or delayed fluorescent and phosphorescent emitters in display and lighting applications.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting, and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

The present disclosure relates to platinum complexes suitable for use as emitters in organic light emitting diodes (OLEDs), display and lighting applications.

Disclosed herein are complexes of Formula I:

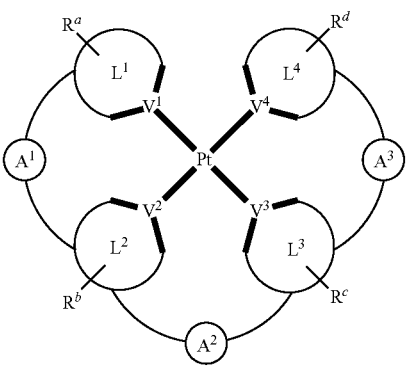

Formula I wherein each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene, wherein each of $V^1$, $V^2$, $V^3$, and $V^4$ is coordinated with Pt and is independently N, C, P, B, or Si, wherein each of $A^1$, $A^2$, and $A^3$ is independently present or absent, and if present each of $A^1$, $A^2$, and $A^3$ is independently $CH_2$, $CR^1R^2$, $C=O$, $CH_2$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$, wherein each of $R^a$, $R^b$, $R^c$, and $R^d$ is independently present or absent, and if present each of $R^a$, $R^b$, $R^c$, and $R^d$ independently represents mono-, di-, or tri-substitutions, and each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula II, Formula III, Formula IV, Formula V, Formula VI, Formula VII, Formula VIII, Formula IX, Formula X, or Formula XI:

Formula-II
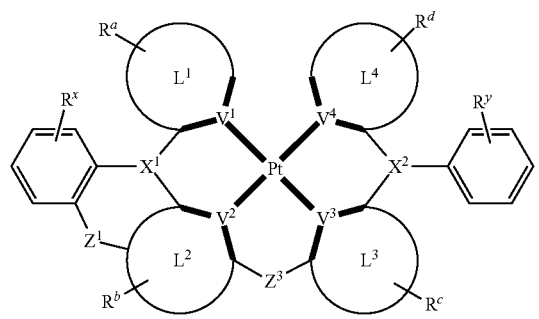
Formula-III
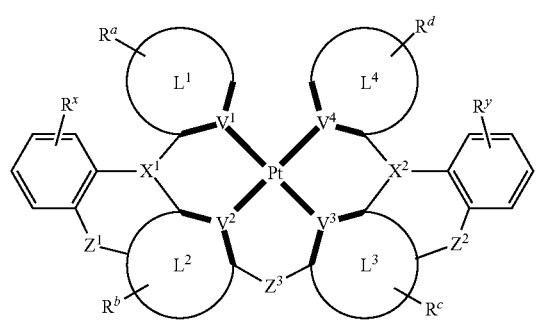
Formula-IV
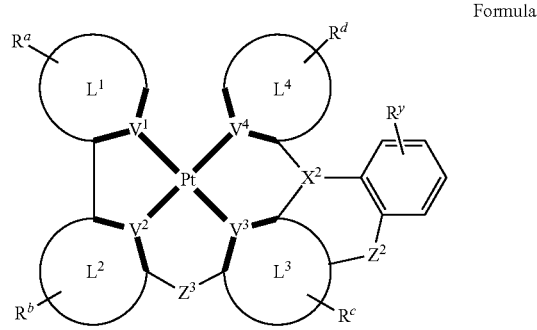
Formula-V
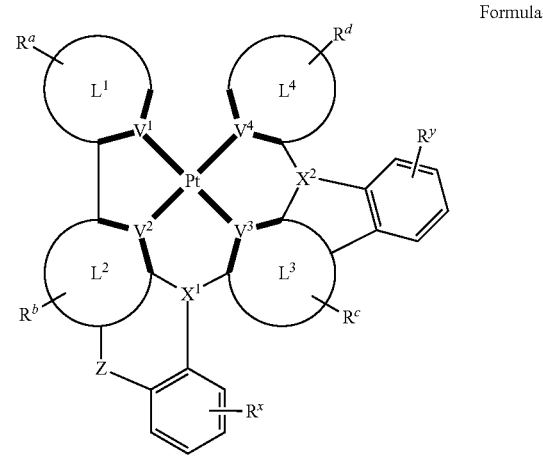
Formula-VI
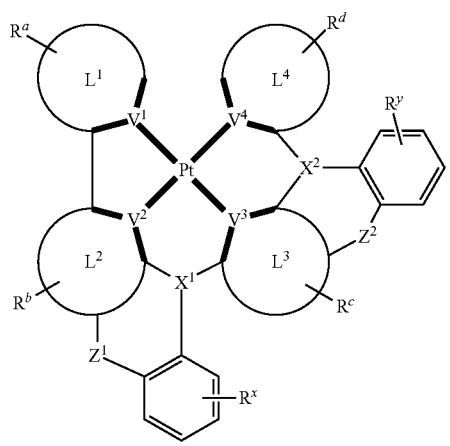
Formula-VII
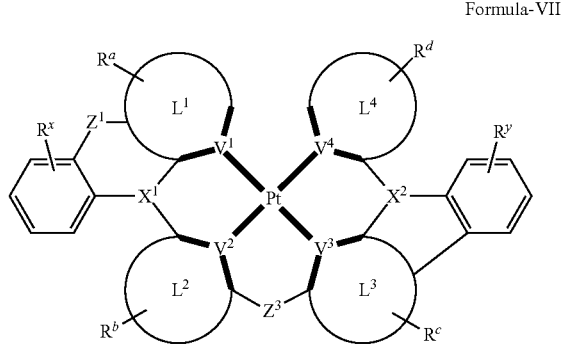
Formula-VIII
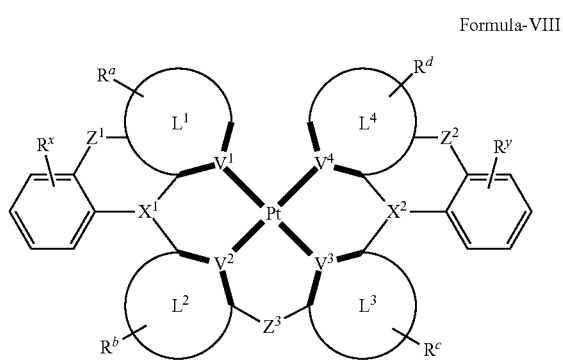
Formula-IX
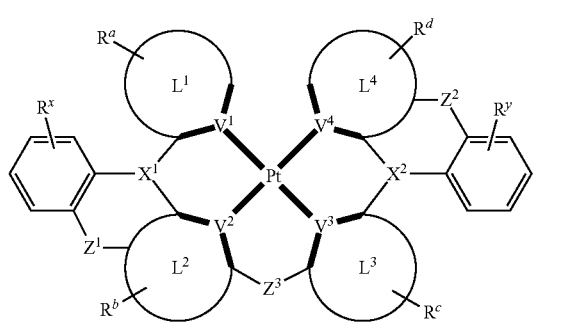

-continued

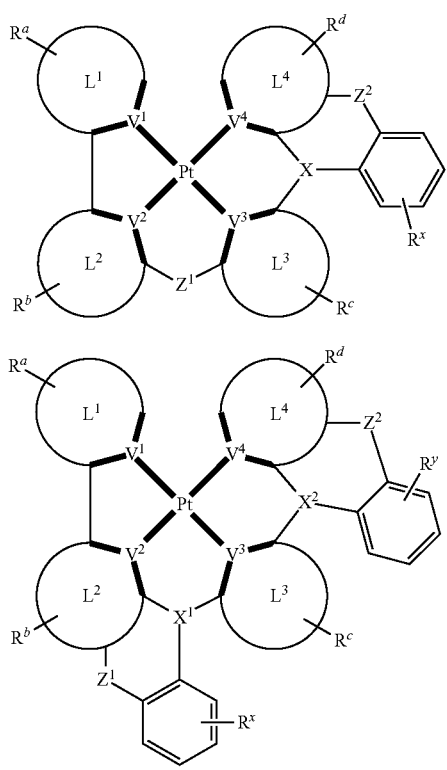

Formula-X

Formula-XI wherein each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene, wherein each of $V^1$, $V^2$, $V^3$, and $V^4$ is coordinated with Pt and is independently N, C, P, B, or Si, wherein each of X, $X^1$, and $X^2$ is independently CH, $CR^1$, SiH, $SiR^1$, GeH, $GeR^1$, N, P, P=O, As, As=O, B, Bi, or Bi=O, wherein each of Z, $Z^1$, $Z^2$, and $Z^3$ is independently $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, wherein each of Ra, Rb, Rc, Rd, Rx, and Ry is independently present or absent, and if present each of Ra, Rb, Rc, Rd, Rx and Ry independently represents mono-, di-, or tri-substitutions, and each of Ra, Rb, Rc, Rd, Rx and Ry is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Also disclosed herein are compositions including one or more compounds disclosed herein.

Also disclosed herein are devices, such as OLEDs, including one or more compounds or compositions disclosed herein.

Figure 1:
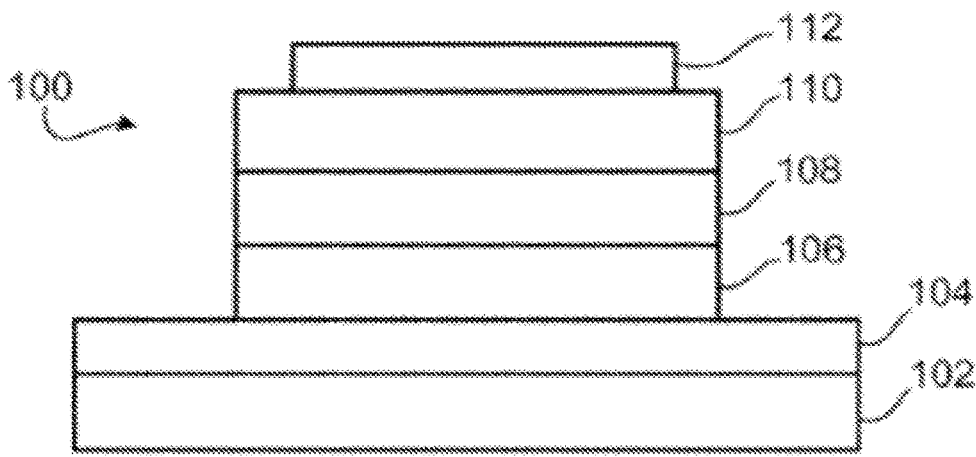
FIG. 1 depicts a device including a complex as disclosed herein.

Additional aspects will be set forth in the description which follows. Advantages will be realized and attained by means of the elements and combinations particularly pointed out in the claims. It is to be understood that both the foregoing general description and the following detailed description are exemplary and explanatory only and are not restrictive.

DETAILED DESCRIPTION

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom can connect two groups such as, for example, an N and C group. A linking group is in one aspect disclosed as A, $A^1$, and/or $A^3$ herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulas herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)$OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COO CH$_2$CH$_3$)]$_n$—CH$_3$, and —[CH$_2$CH(COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl" as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

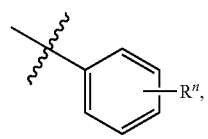

which is understood to be equivalent to a formula:

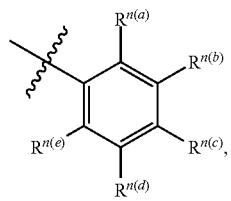

wherein n is typically an integer. That is, R$^n$ is understood to represent five independent substituents, R$^{n(a)}$, R$^{n(b)}$, R$^{n(c)}$, R$^{n(d)}$, R$^{n(e)}$. By "independent substituents," it is meant that each R substituent can be independently defined. For example, if in one instance R$^{n(a)}$ is halogen, then R$^{n(b)}$ is not necessarily halogen in that instance.

Several references to R, R$^1$, R$^2$, R$^3$, R$^4$, R$^5$, R$^6$, etc. are made in chemical structures and moieties disclosed and described herein. Any description of R, R$^1$, R$^2$, R$^3$, R$^4$, R$^5$, R$^6$, etc. in the specification is applicable to any structure or moiety reciting R, R$^1$, R$^2$, R$^3$, R$^4$, R$^5$, R$^6$, etc. respectively.

1. Compounds

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. Excitons decay from triplet excited states to ground state to generate luminescence, which is phosphorescence. Because the strong spin-orbit coupling of the heavy metal atom enhances intersystem crossing (ISC) very efficiently between singlet and triplet excited state, phosphorescent metal complexes, such as platinum complexes, have demonstrated their potential to harvest both the singlet and triplet excitons to achieve 100% internal quantum efficiency. Thus phosphorescent metal complexes are good candidates as dopants in the emissive layer of organic light emitting devices (OLEDs) and a great deal of attention has been received both in the academic and industrial fields. In addition, much achievement has been made in the past decade to lead to the lucrative commercialization of the technology, for example, OLEDs have been used in advanced displays in smart phones, televisions and digital cameras.

However, to date, blue electroluminescent devices remain the most challenging area of this technology, due at least in part to instability of the blue devices. It is generally understood that the choice of host materials is a factor in the stability of the blue devices. But the lowest triplet excited state ($T_1$) energy of the blue phosphors is high, which generally means that the lowest triplet excited state ($T_1$) energy of host materials for the blue devices should be even higher. This leads to difficulty in the development of the host materials for the blue devices.

The platinum complexes described herein can be tailored or tuned to a specific application that requires a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can generally exhibit different optical properties, including emission and absorption spectra. The color of the metal complexes can be tuned by modifying the conjugated groups on the fluorescent luminophores and ligands.

The emission of such complexes can be tuned, for example, from the ultraviolet to near-infrared, by, for example, modifying the ligand or fluorescent luminophore structure. A fluorescent luminophore is a group of atoms in an organic molecule, which can absorb energy to generate singlet excited state(s), the singlet exciton(s) produce(s) decay rapidly to yield prompt luminescence. In another aspect, the complexes can provide emission over a majority of the visible spectrum. In a specific example, the inventive complexes can emit light over a range of from about 400 nm to about 700 nm. In another aspect, the complexes have improved stability and efficiency over traditional emission complexes. In yet another aspect, the complexes can be useful as luminescent labels in, for example, bio-applications, anti-cancer agents, emitters in organic light emitting diodes (OLED), or a combination thereof. In another aspect, the inventive complexes can be useful in light emitting devices, such as, for example, compact fluorescent lamps (CFL), light emitting diodes (LED), incandescent lamps, and combinations thereof.

Disclosed herein are compounds or compound complexes comprising platinum. The terms compound or compound complex are used interchangeably herein. In one aspect, the compounds disclosed herein have a neutral charge.

The compounds disclosed herein can exhibit desirable properties and have emission and/or absorption spectra that can be tuned via the selection of appropriate ligands. In another aspect, any one or more of the compounds, structures, or portions thereof, specifically recited herein may be excluded.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLEDs), luminescent devices and displays, and other light emitting devices.

In another aspect, the compounds can provide improved efficiency and/or operational lifetimes in lighting devices, such as, for example, organic light emitting devices, as compared to conventional materials.

Compounds described herein can be made using a variety of methods, including, but not limited to those recited in the examples.

The compounds disclosed herein can be a delayed fluorescent and/or phosphorescent emitter. In one aspect, the compounds disclosed herein can be a delayed fluorescent emitter. In another aspect, the compounds disclosed herein can be a phosphorescent emitter. In yet another aspect, the compounds disclosed herein can be a delayed fluorescent emitter and a phosphorescent emitter.

Disclosed herein are complexes of Formula I:

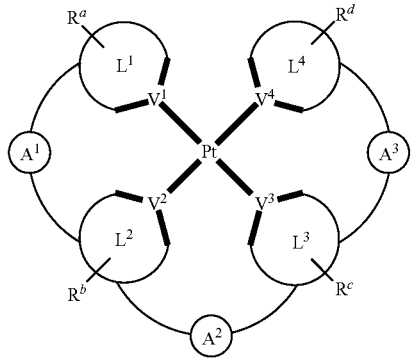

Formula I wherein each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene, wherein each of $V^1$, $V^2$, $V^3$, and $V^4$ is coordinated with Pt and is independently N, C, P, B, or Si, wherein each of $A^1$, $A^2$, and $A^3$ is independently present or absent, and if present each of $A^1$, $A^2$, and $A^3$ is independently $CH_2$, $CR^1R^2$, $C=O$, $CH_2$, $SiR^1R^2$, $GeH_2$, $GeR^1R^2$, $NH$, $NR^3$, $PH$, $PR^3$, $R^3P=O$, $AsR^3$, $R^3As=O$, $O$, $S$, $S=O$, $SO_2$, $Se$, $Se=O$, $SeO_2$, $BH$, $BR^3$, $R^3Bi=O$, $BiH$, or $BiR^3$, wherein each of $R^a$, $R^b$, $R^c$, and $R^d$ is independently present or absent, and if present each of $R^a$, $R^b$, $R^c$, and $R^d$ independently represents mono-, di-, or tri-substitutions, and wherein each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula II, Formula III, Formula IV, Formula V, Formula VI, Formula VII, Formula VIII, Formula IX, Formula X, or Formula XI:

Formula-II

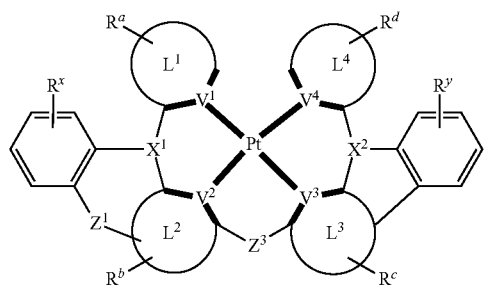

Formula-III

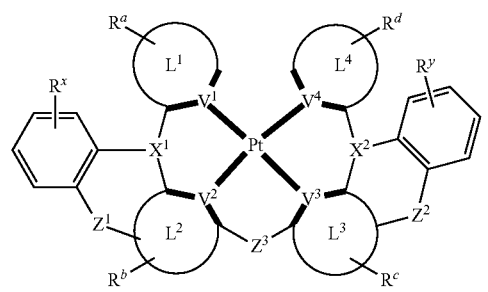

Formula-IV

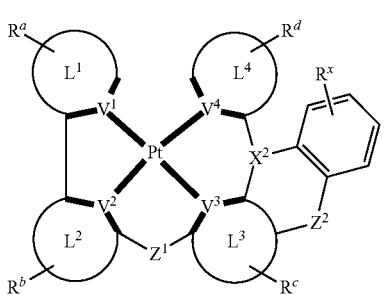

Formula-V

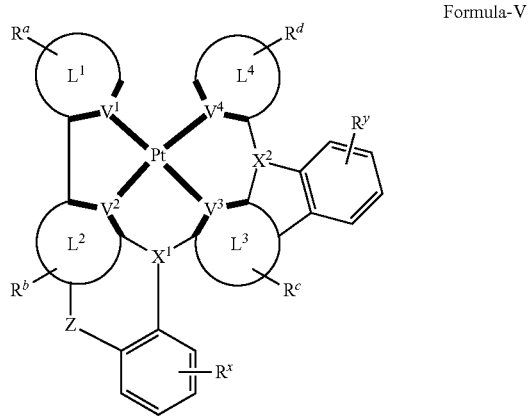

Formul-VI

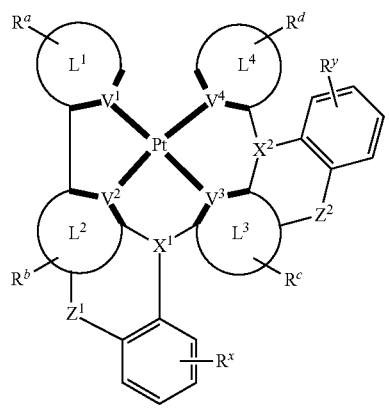

Formula-VII

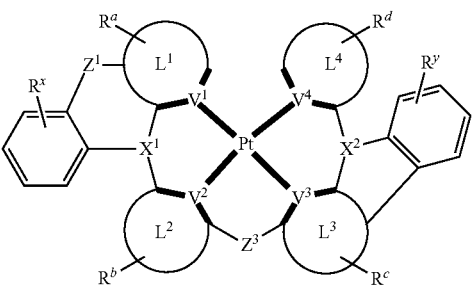

-continued

Formula-VIII

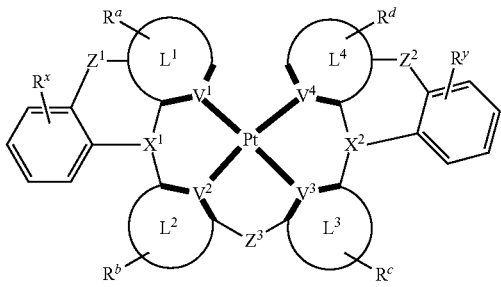

Formula-IX

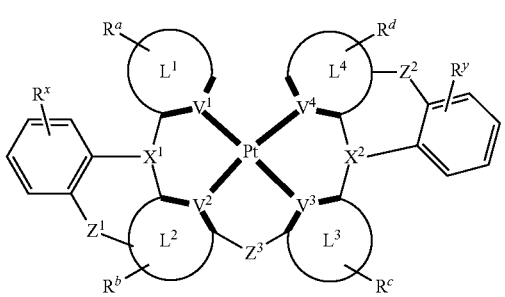

Formula-X

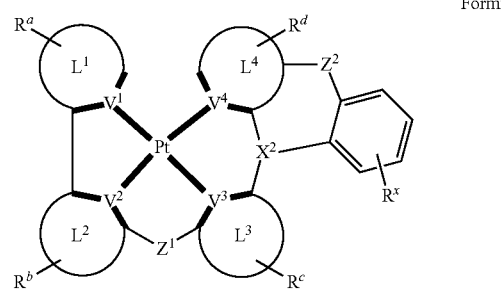

Formula-XI

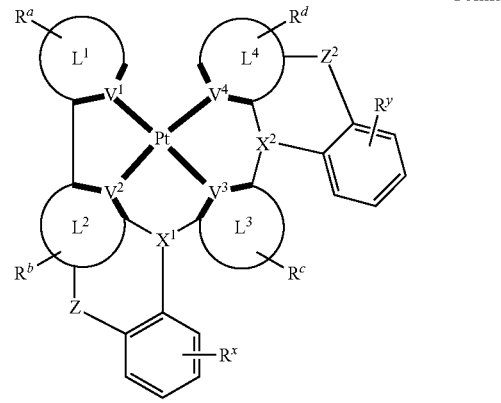

wherein each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene, wherein each of $V^1$, $V^2$, $V^3$, and $V^4$ is coordinated with Pt and is independently N, C, P, B, or Si, wherein each of X, $X^1$, and $X^2$ is independently CH, $CR^1$, SiH, $SiR^1$, GeH, $GeR^1$, N, P, P=O, As, As=O, B, Bi, or Bi=O, wherein each of Z, $Z^1$, $Z^2$, and $Z^3$ is independently $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, wherein each of $R^a$, $R^b$, $R^c$, $R^d$, $R^x$, and $R^y$ is independently present or absent, and if present each of $R^a$, $R^b$, $R^c$, $R^d$, $R^x$ and $R^y$ independently represents mono-, di-, or tri-substitutions, and each of $R^a$, $R^b$, $R^c$, $R^d$, $R^x$ and $R^y$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

A. V Groups

In one aspect, each of $V^1$, $V^2$, $V^3$, and $V^4$ is coordinated with Pt and is independently N, C, P, B, or Si.

In another aspect, each of $V^1$, $V^2$, $V^3$, and $V^4$ is independently N or C.

In yet another aspect, each of $V^1$, $V^2$, $V^3$, and $V^4$ is independently P or B.

In yet another aspect, each of $V^1$, $V^2$, $V^3$, and $V^4$ is Si.

B. A Groups

In one aspect, each of $A^1$, $A^2$, and $A^3$ is present or absent, and if present each of $A^1$, $A^2$, and $A^3$ is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$.

In another aspect, each of $A^1$, $A^2$, and $A^3$ is independently O, S, or $CH_2$.

C. X Groups

In one aspect, each of X, $X^1$ and $X^2$ is independently CH, $CR^1$, SiH, $SiR^1$, GeH, $GeR^1$, N, P, P=O, As, As=O, B, Bi, or Bi=O.

In another aspect, each of X, $X^1$ and $X^2$ is independently N, $CR^1$, or P=O.

D. Z Groups

In one aspect, each of Z, $Z^1$, $Z^2$, and $Z^3$ is independently $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$.

In another aspect, each of Z, $Z^1$, $Z^2$ and $Z^3$ is independently O, S, or C $CR^1R^2$.

E. L Groups

In one aspect, $L^1$ is aryl, cycloalkyl, cycloalkenyl, heteroaryl, heterocyclyl, carbene, or N-heterocyclic carbene. In one example, $L^1$ is aryl, cycloalkyl, cycloalkenyl, heteroaryl, or N-heterocyclyl. In another example, $L^1$ is aryl or heteroaryl. In yet another example, $L^2$ is aryl.

In one aspect, $L^2$ is aryl, cycloalkyl, cycloalkenyl, heteroaryl, heterocyclyl, carbene, or N-heterocyclic carbene. In one example, $L^2$ is aryl, cycloalkyl, cycloalkenyl, heteroaryl, or N-heterocyclyl. In another example, $L^2$ is aryl or heteroaryl. In yet another example, $L^2$ is aryl.

In one aspect, $L^3$ is aryl, cycloalkyl, cycloalkenyl, heteroaryl, heterocyclyl, carbene, or N-heterocyclic carbene. In one example, $L^3$ is aryl, cycloalkyl, cycloalkenyl, heteroaryl, or heterocyclyl. In another example, $L^3$ is aryl or heteroaryl. In yet another example, $L^3$ is aryl.

In one aspect, $L^4$ is aryl, cycloalkyl, cycloalkenyl, heteroaryl, heterocyclyl, carbene, or N-heterocyclic carbene. In one example, $L^4$ is aryl, cycloalkyl, cycloalkenyl, heteroaryl, or heterocyclyl. In another example, $L^4$ is aryl or heteroaryl. In yet another example, $L^4$ is heteroaryl. In yet another example, $L^4$ is heterocyclyl. It is understood that $V^4$ can be a part of $L^4$ and is intended to be included the description of $L^4$ above.

In one aspect, for any of the formulas disclosed herein, each of

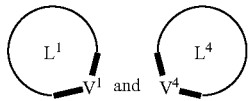

is independently one following structures:

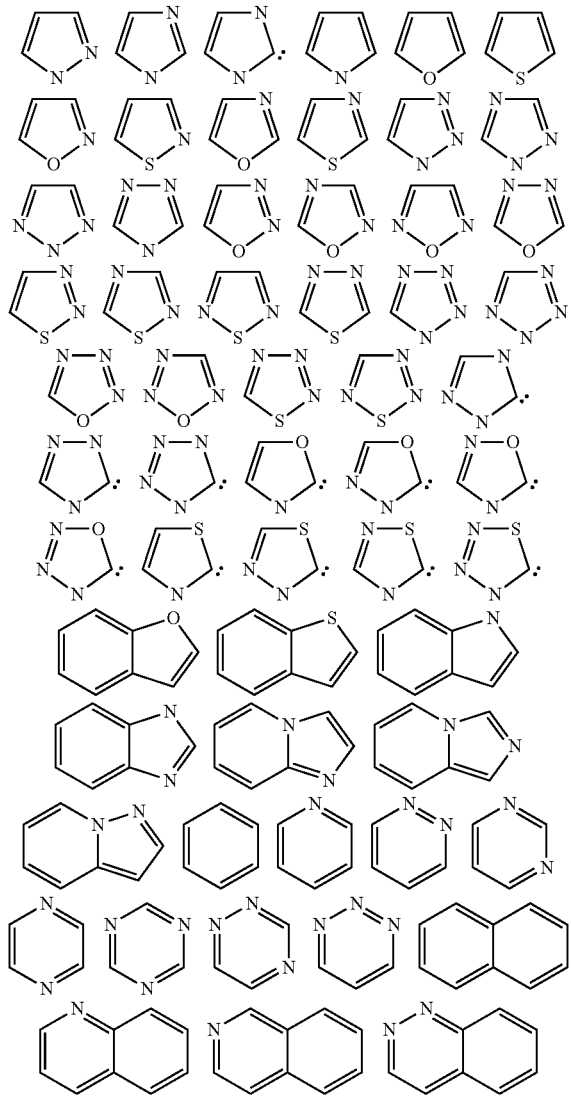

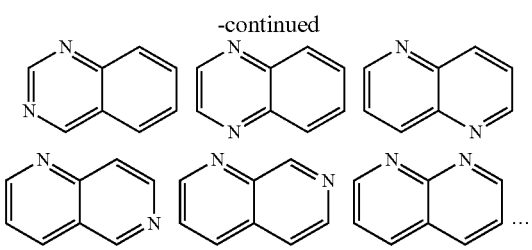

It is understood that one or more of $R^a$, $R^b$, $R^c$ and $R^d$ as described herein can be bonded to

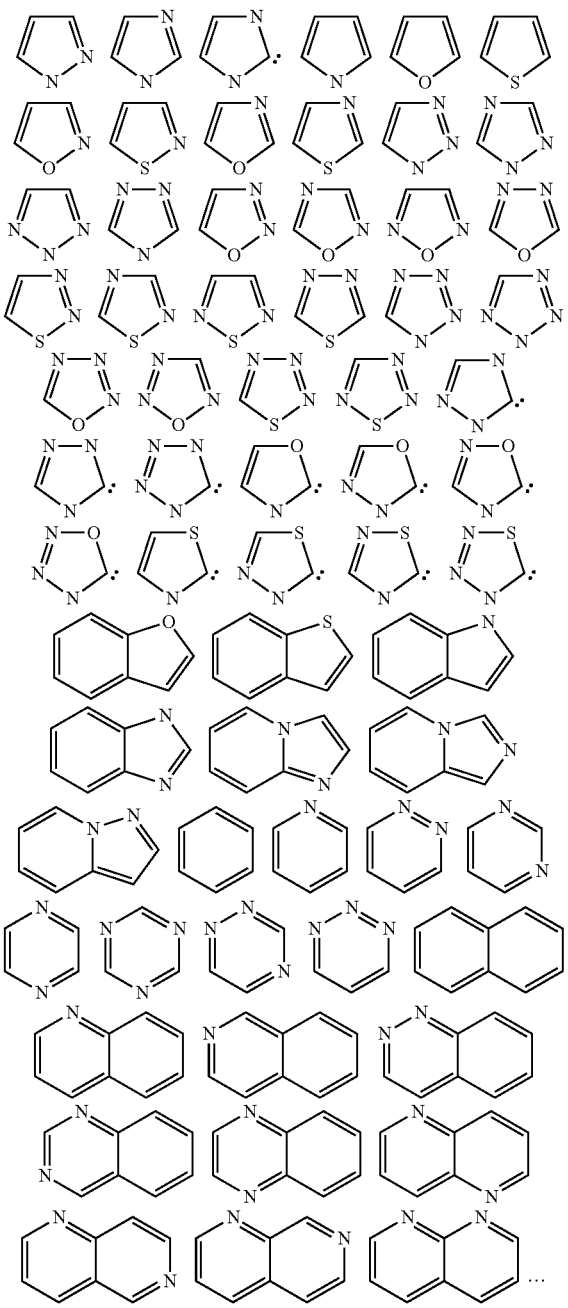

as permitted by valency.

In one aspect,
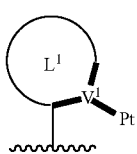
has the structure
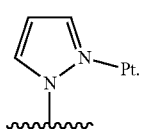
In one aspect, for any of the formulas illustrated in this disclosure, each of
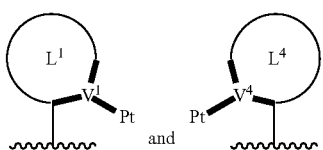
is independently one of following structures:
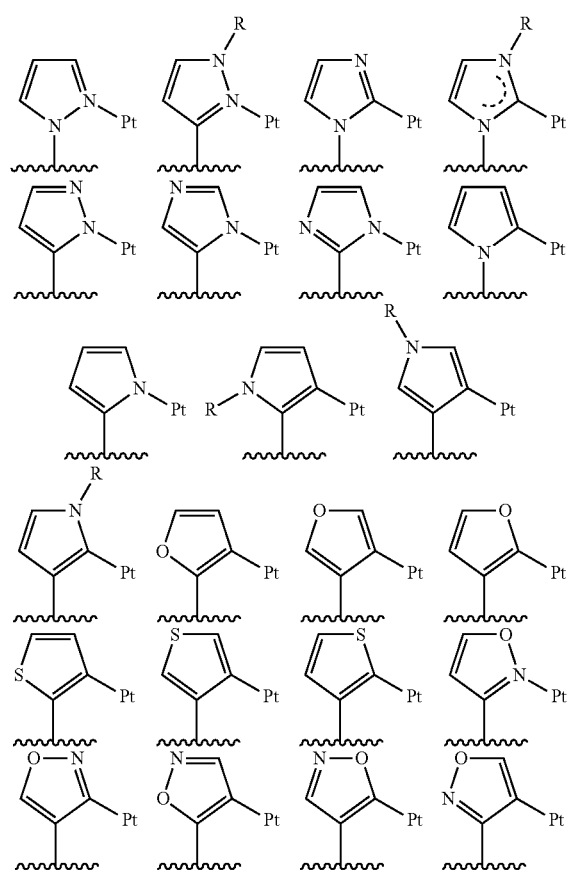
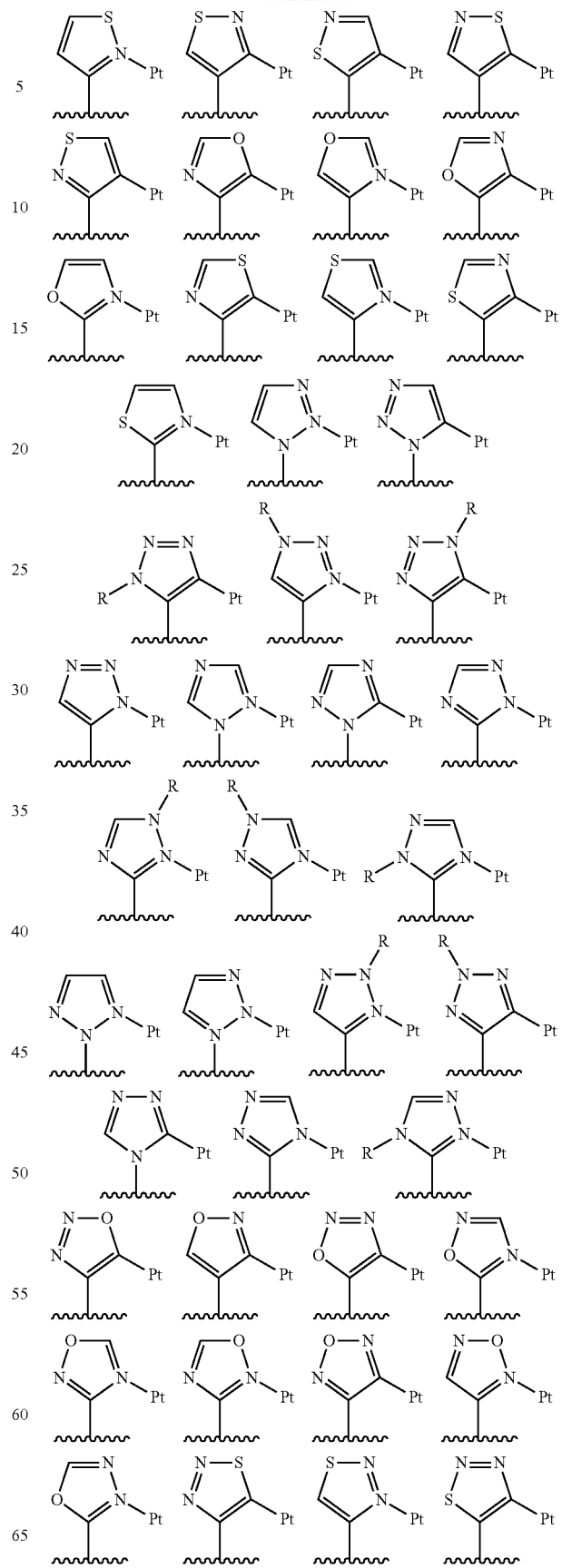

-continued

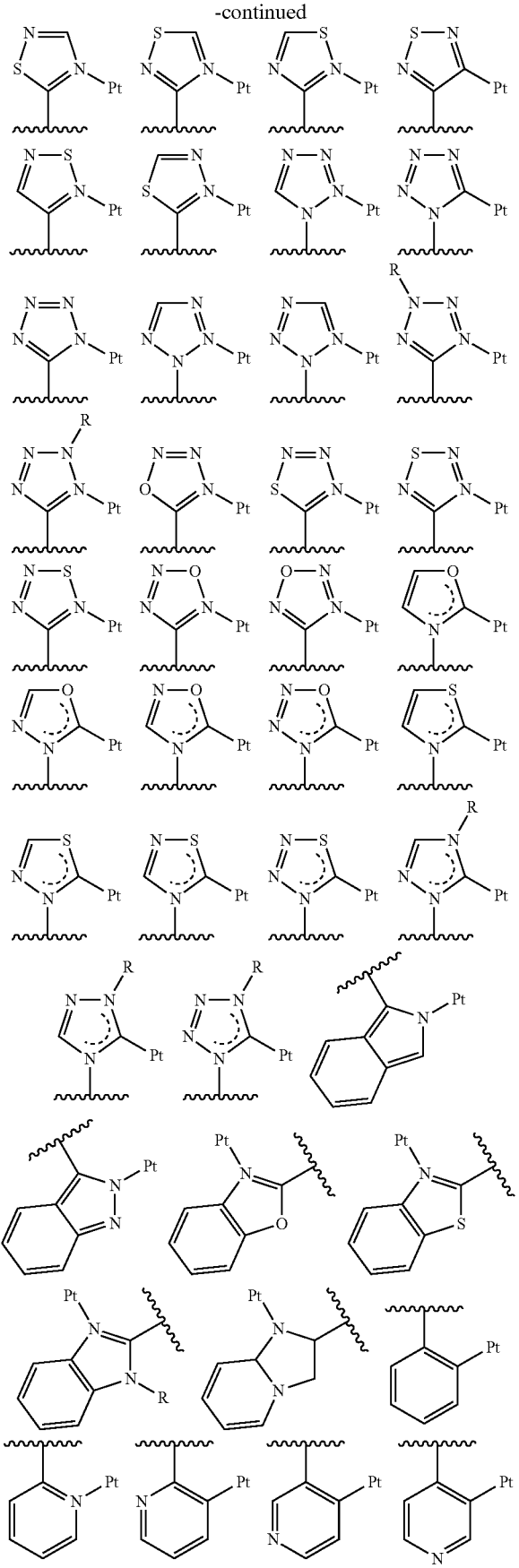

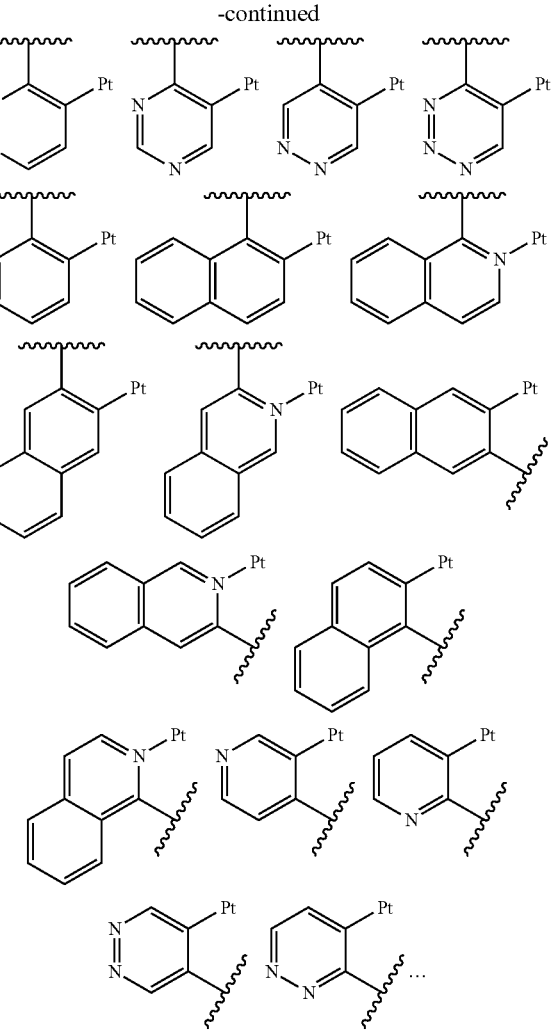

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect,

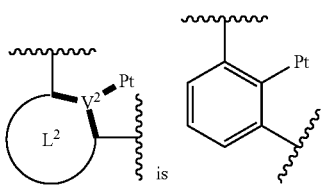

In one aspect,
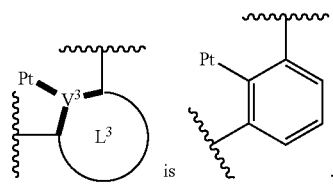
is
In one aspect, for any of the formulas disclosed herein, each of
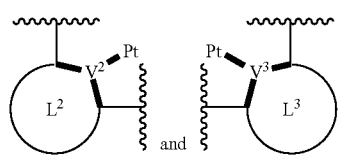
is independently one of the following structures:
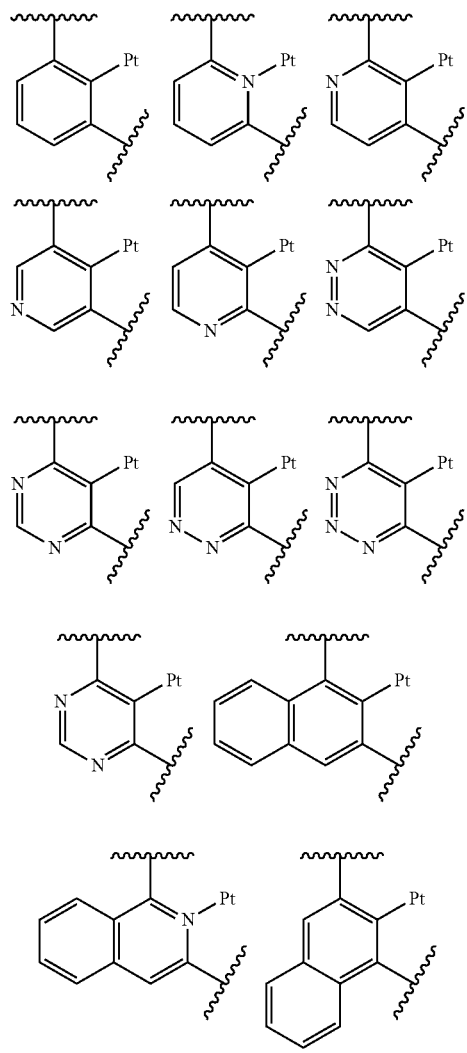
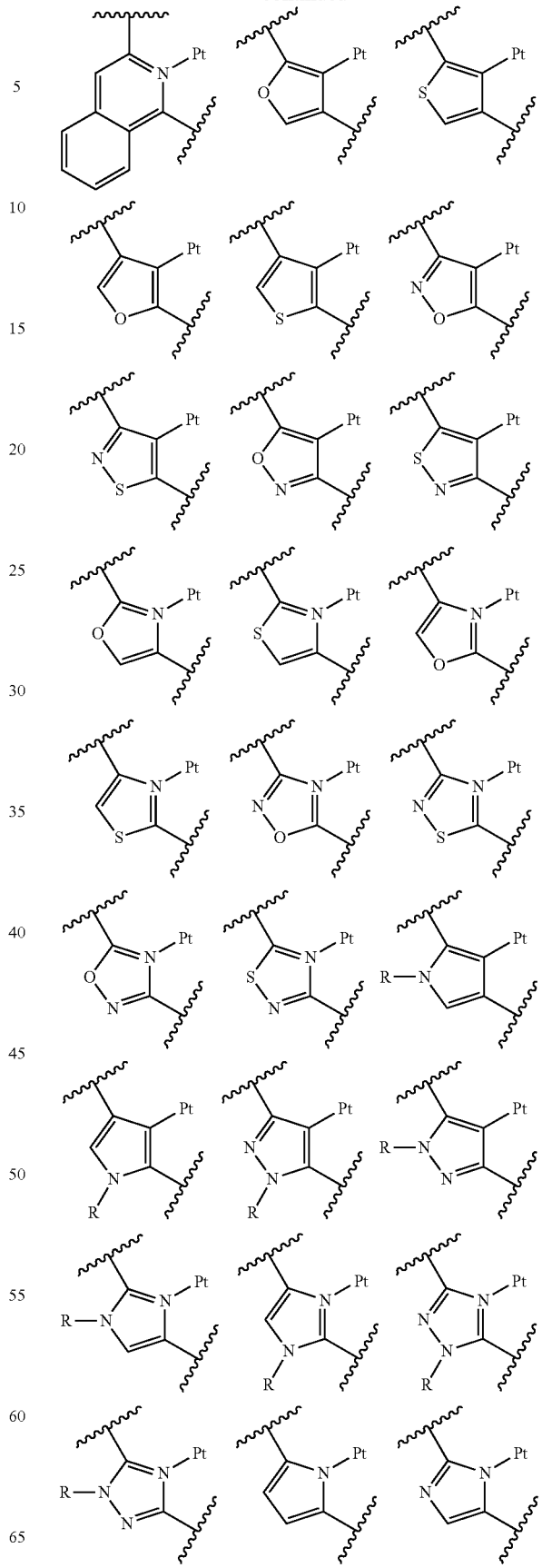

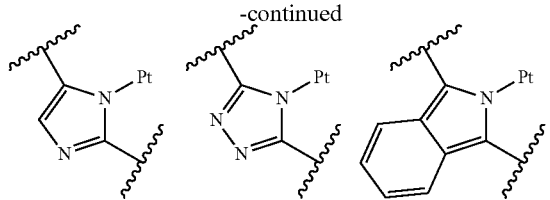

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas disclosed herein, each of

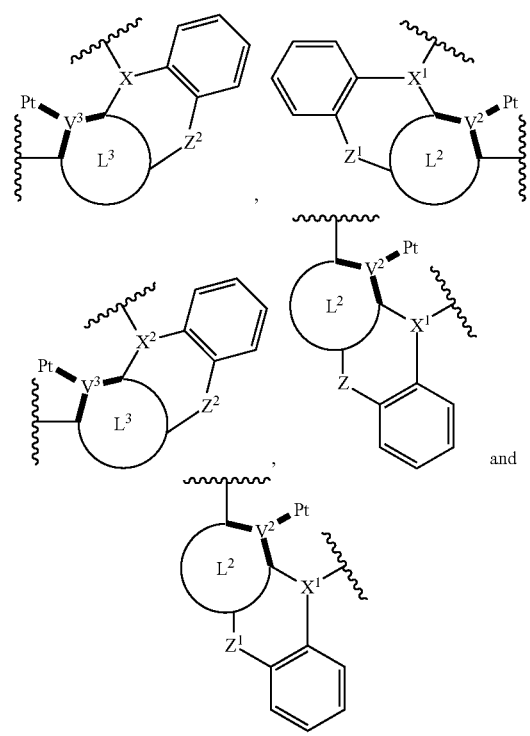

is independently one of the following structures:

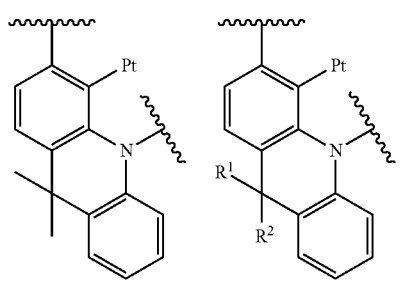

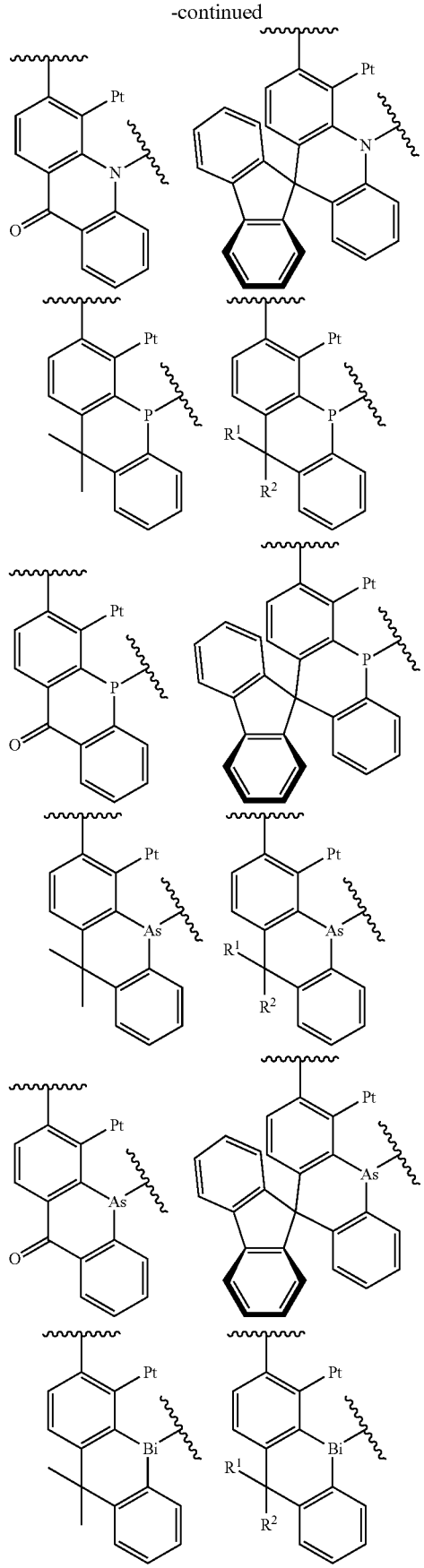

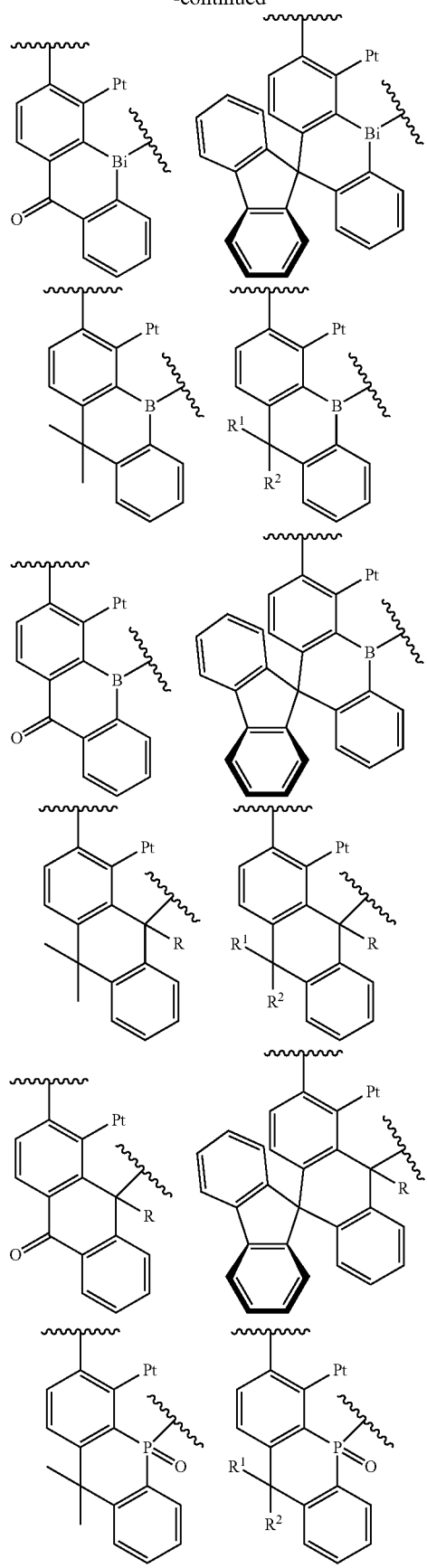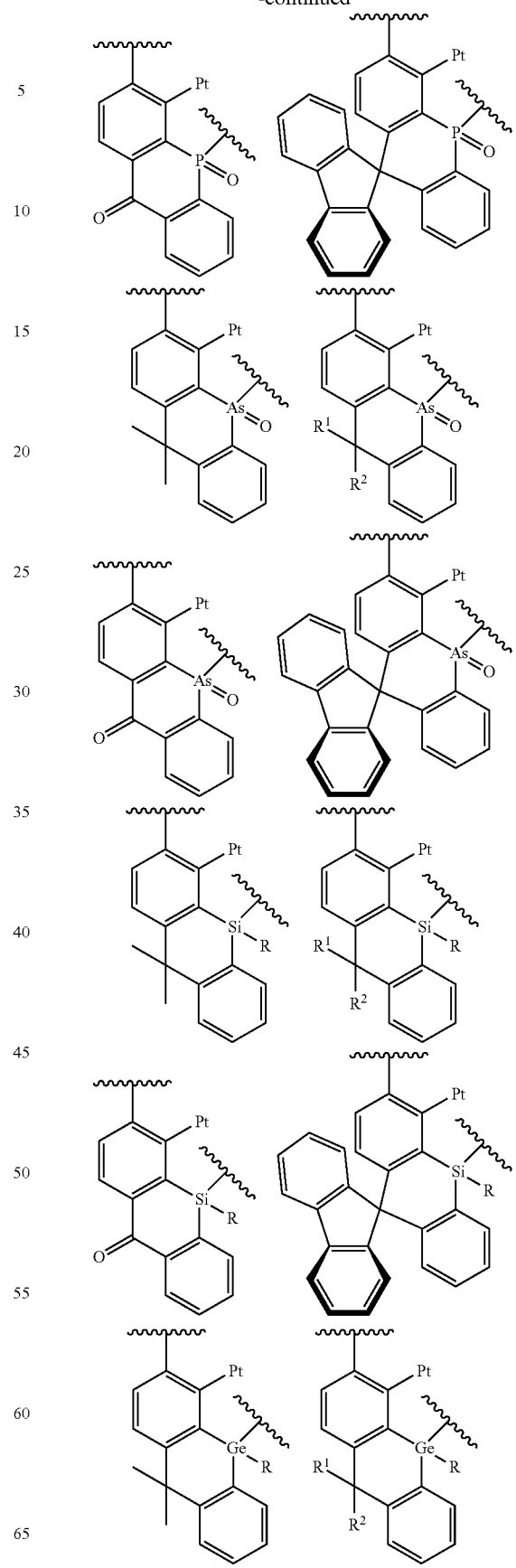

-continued
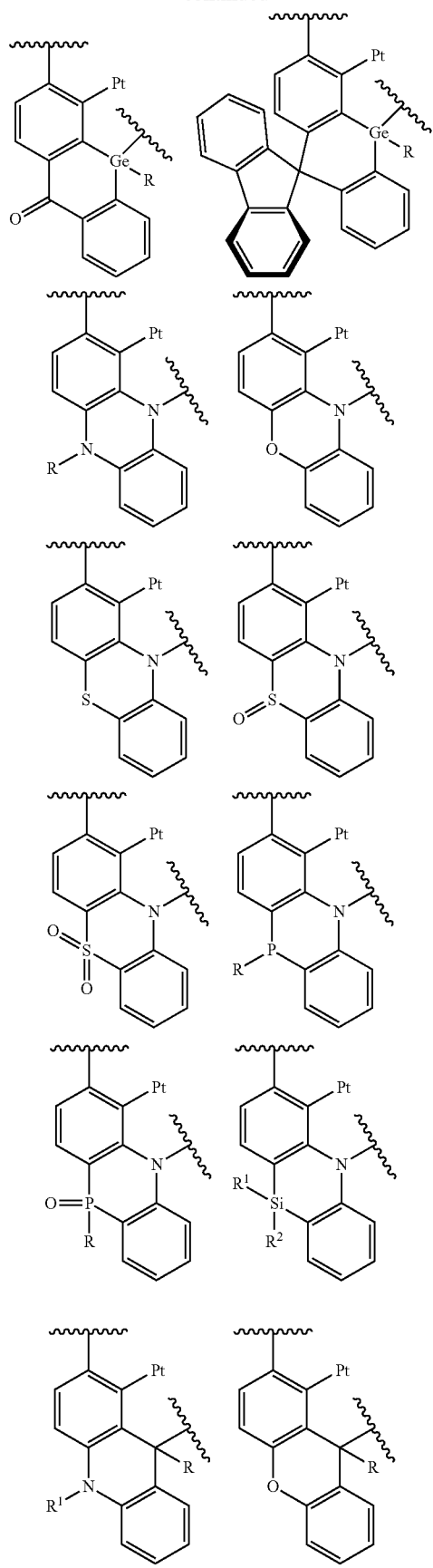
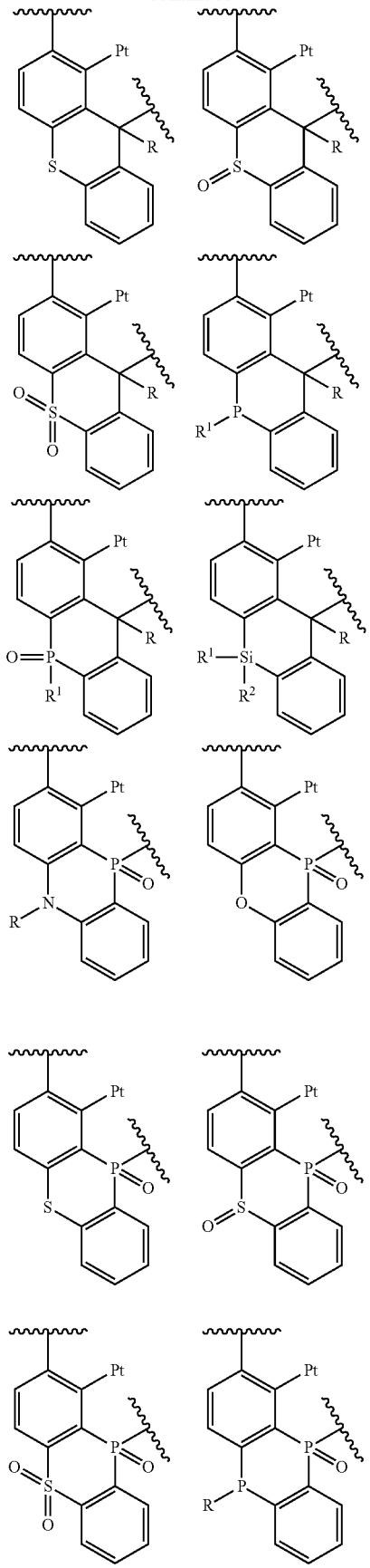

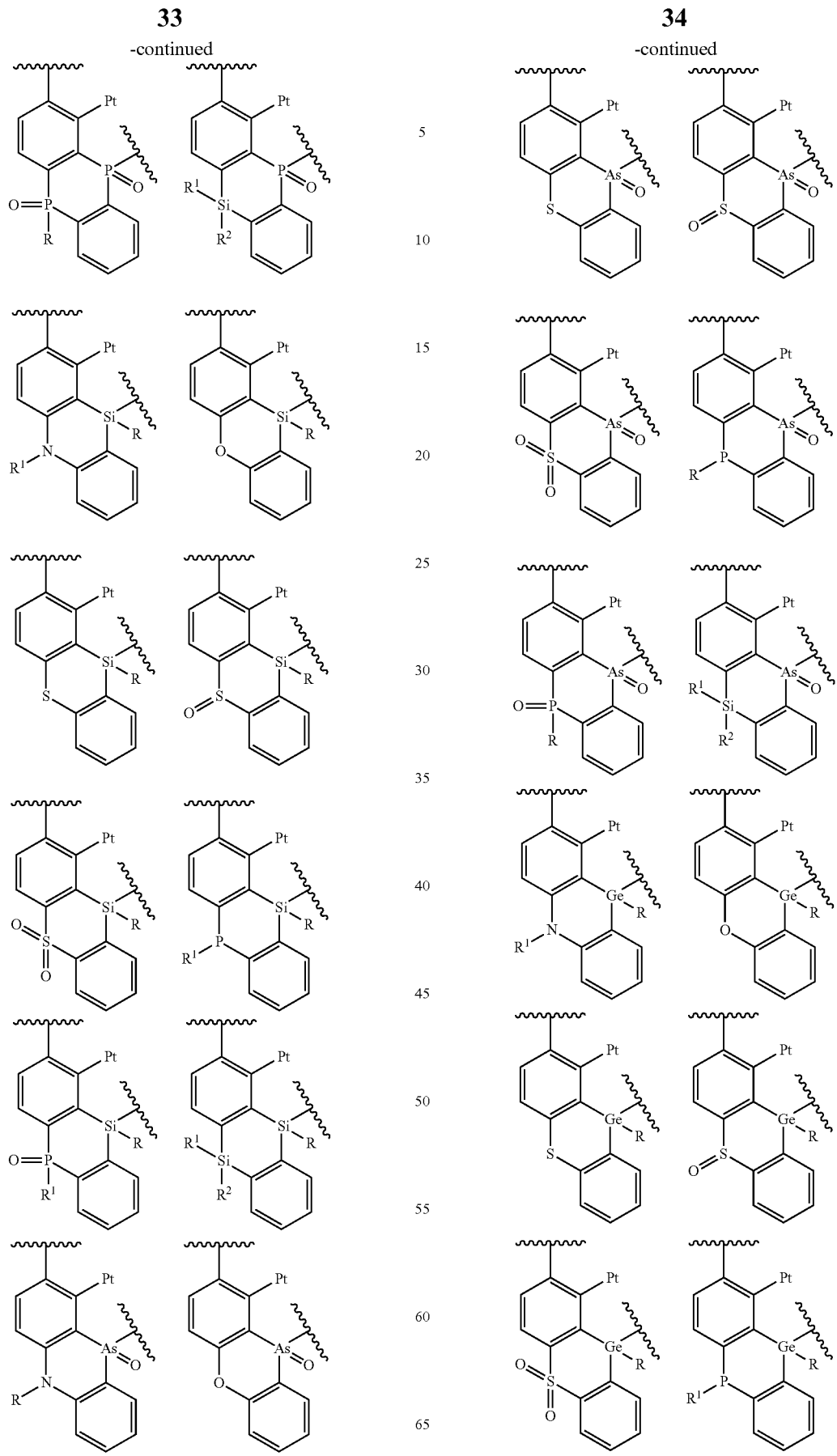

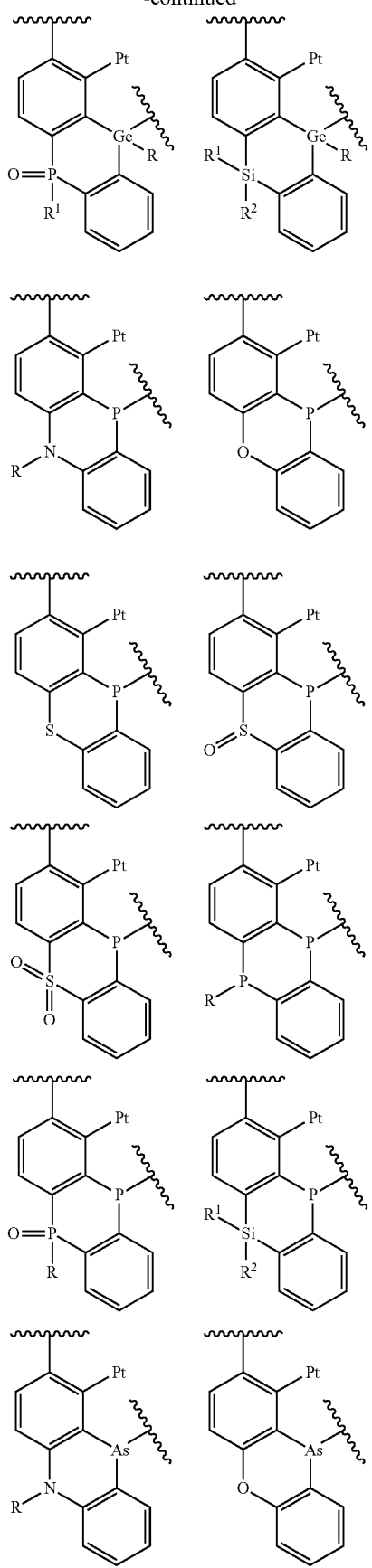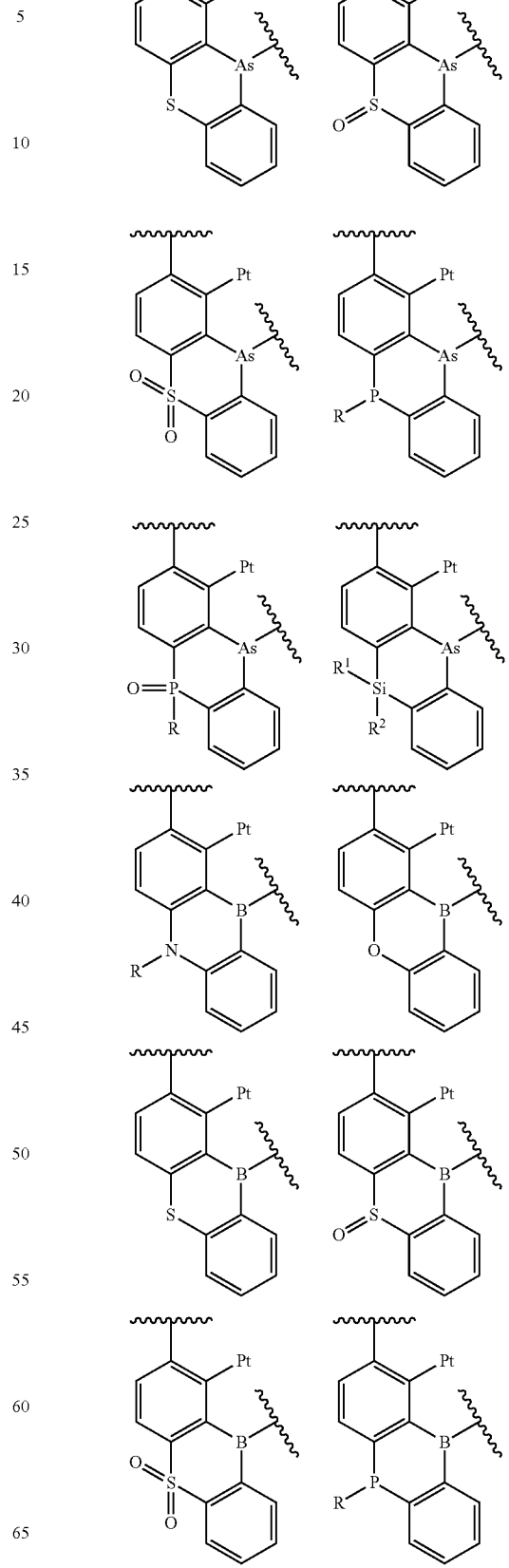

-continued
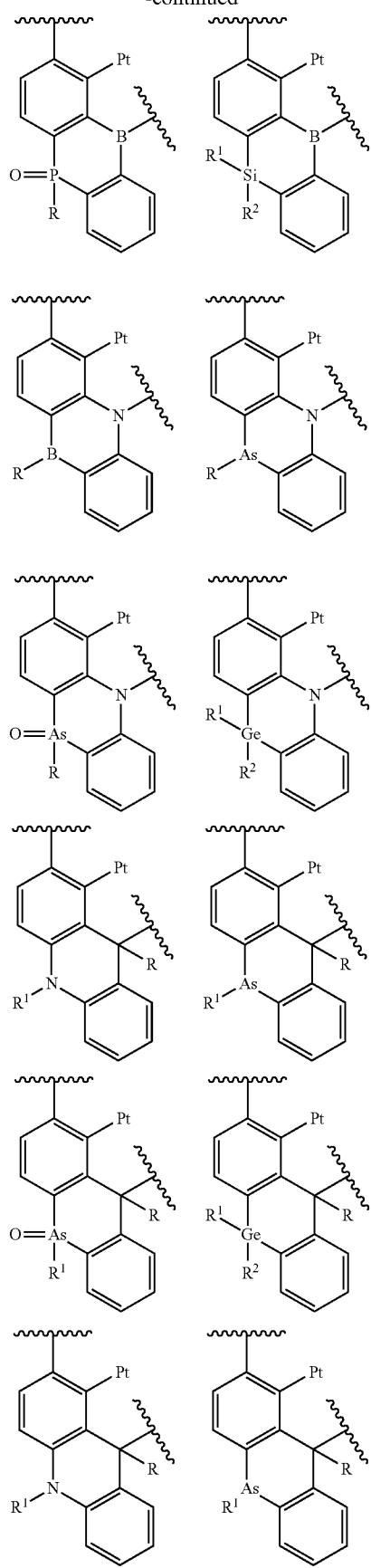
-continued
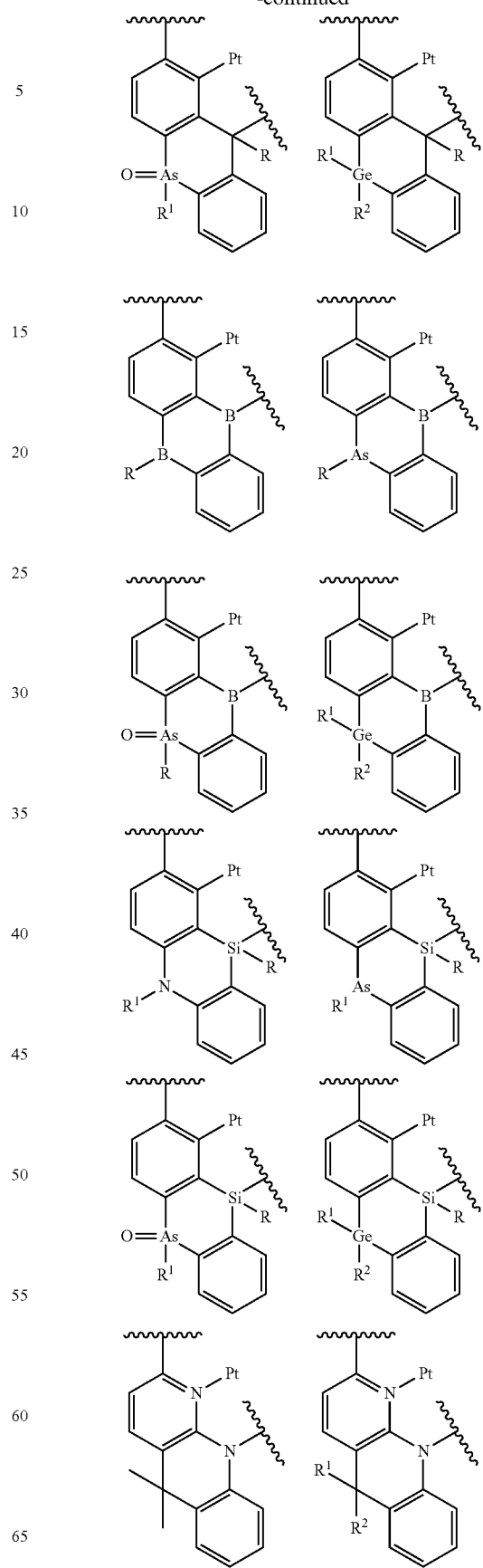

39
-continued
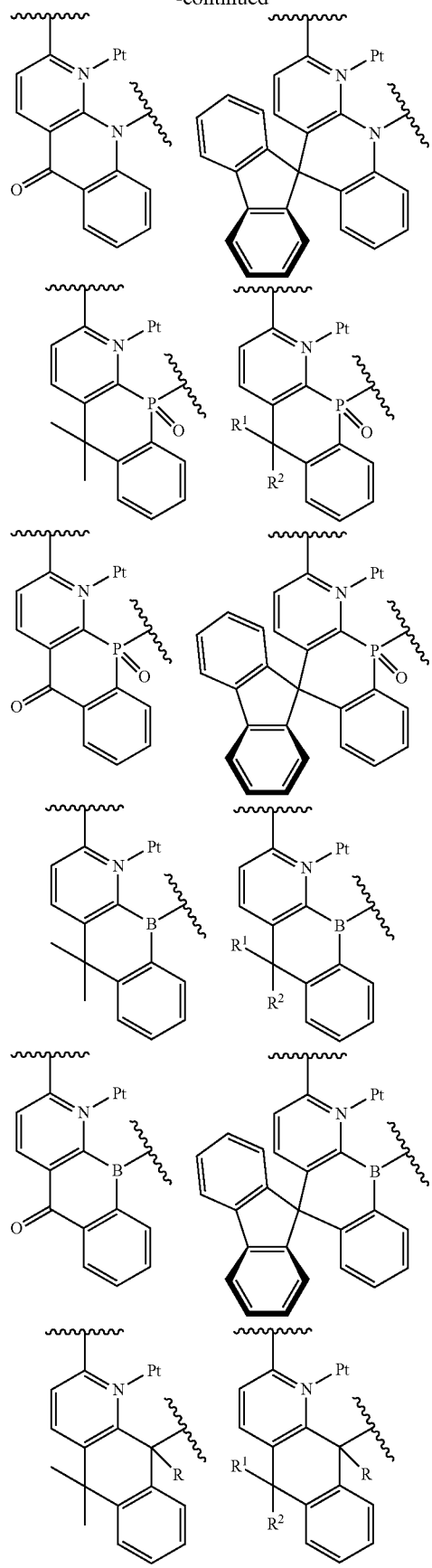
40
-continued
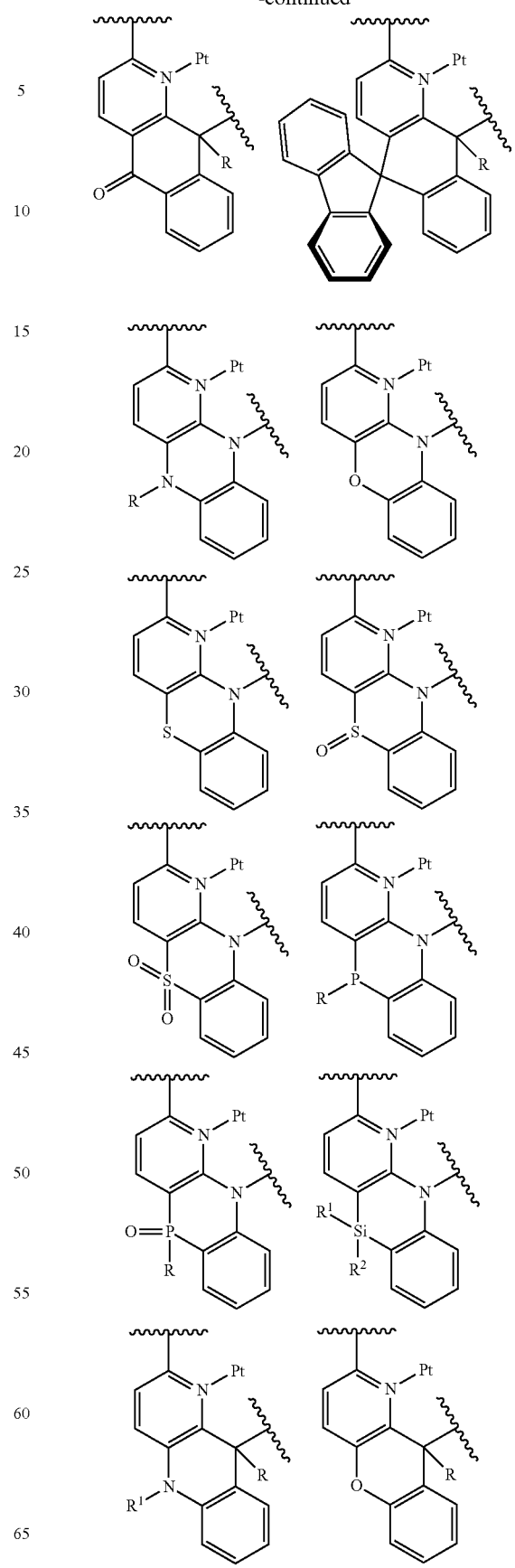

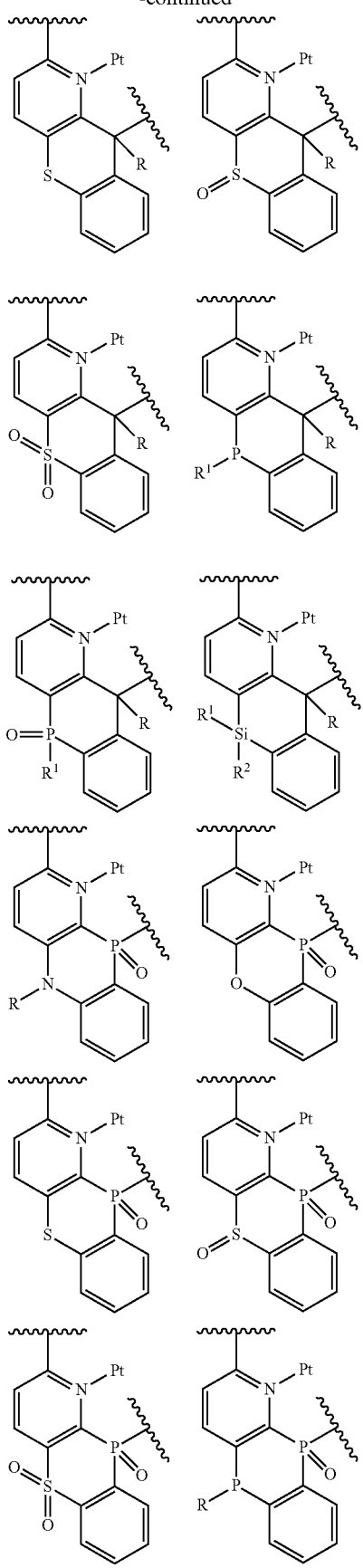
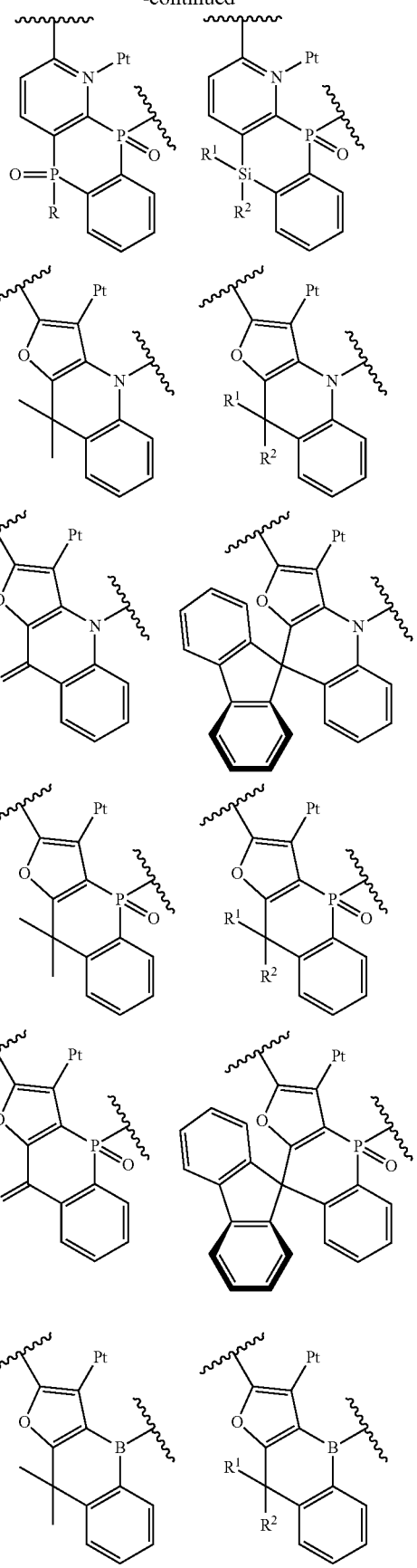

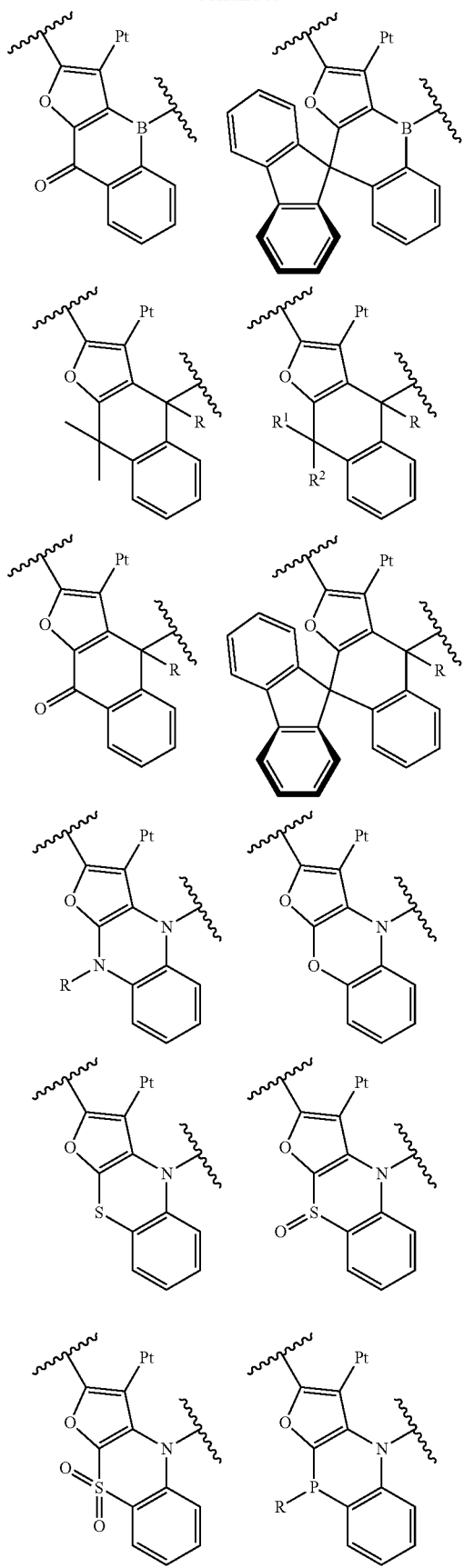
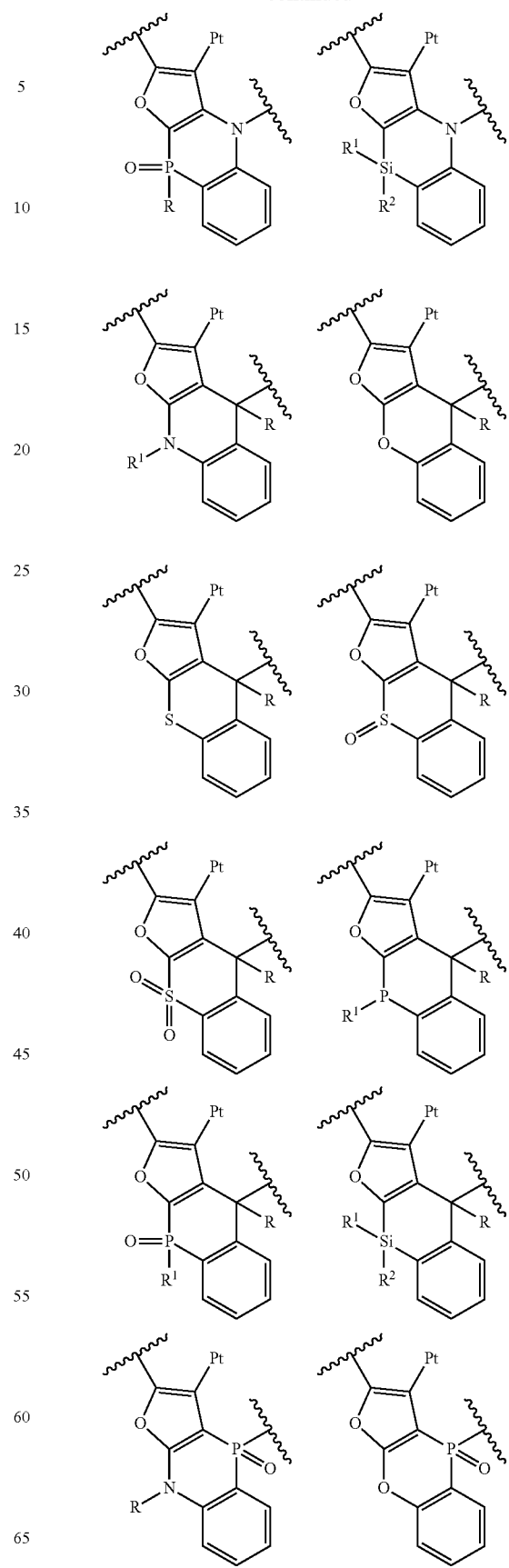

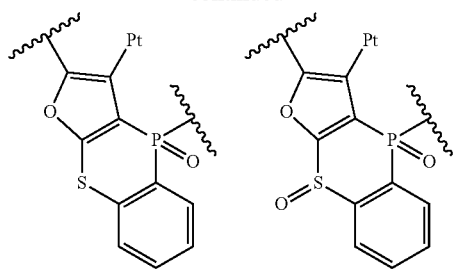
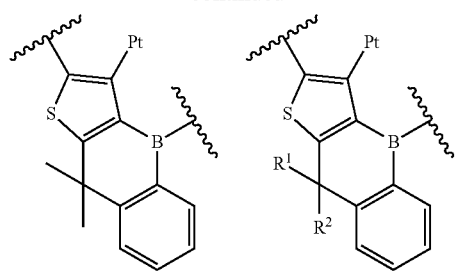
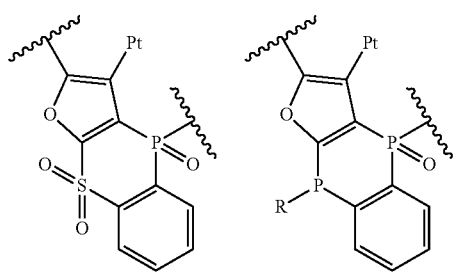
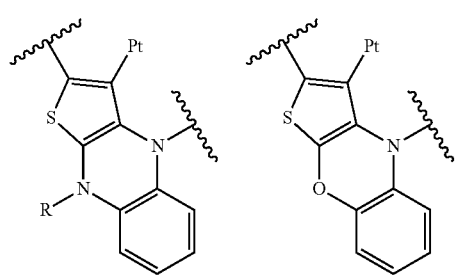
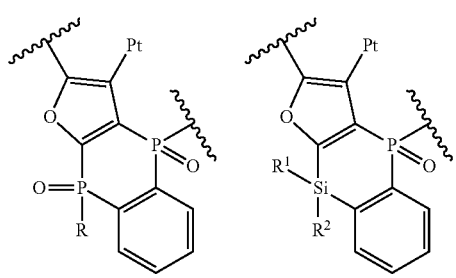
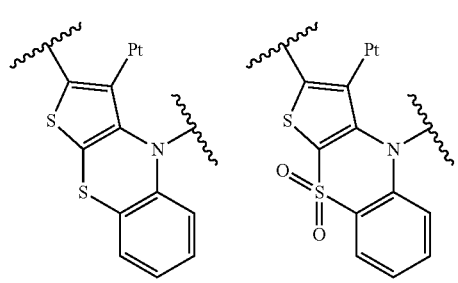
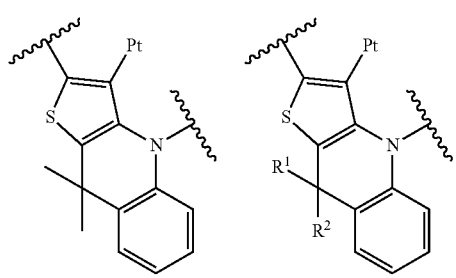
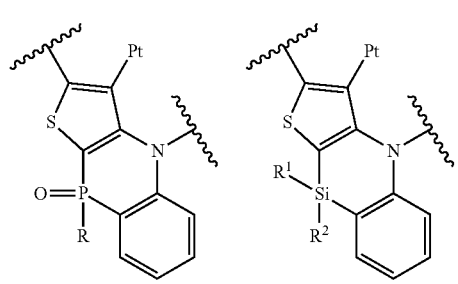
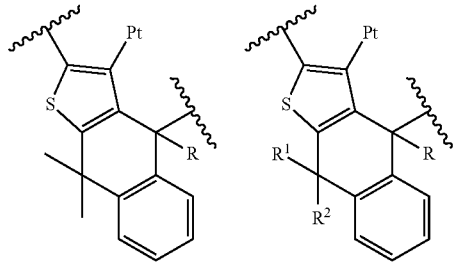
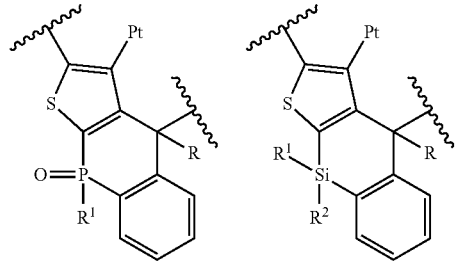
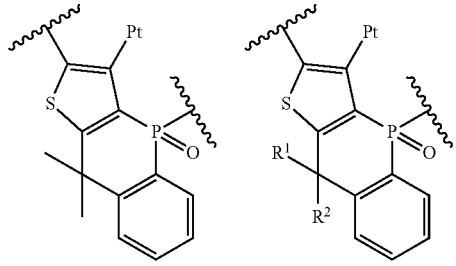
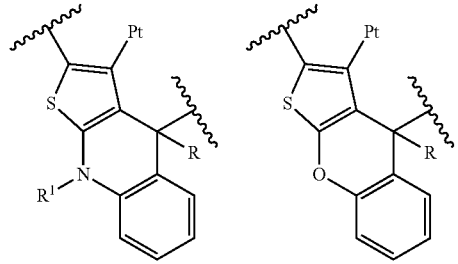

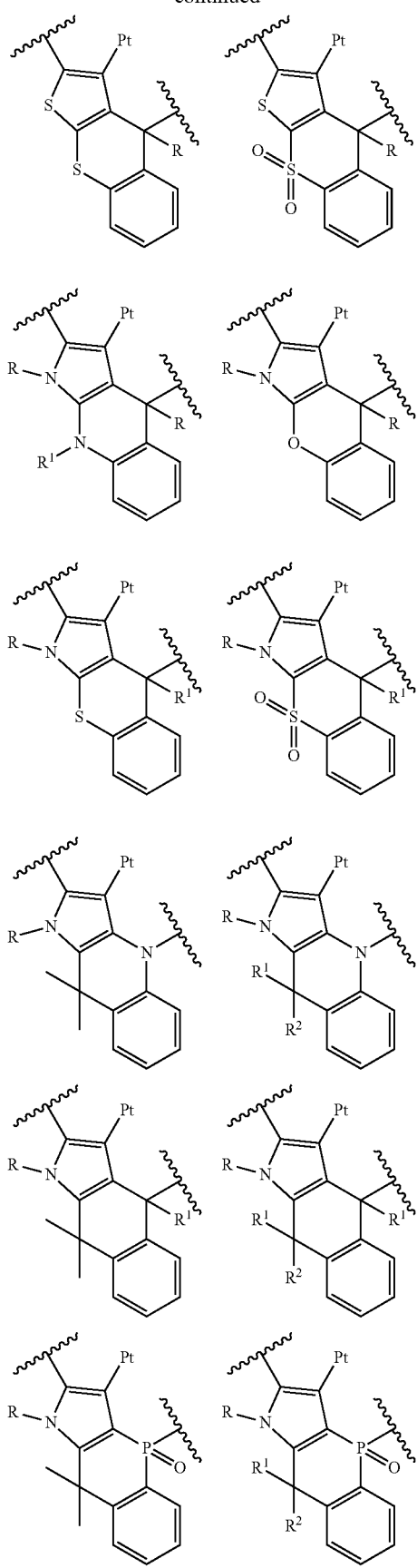
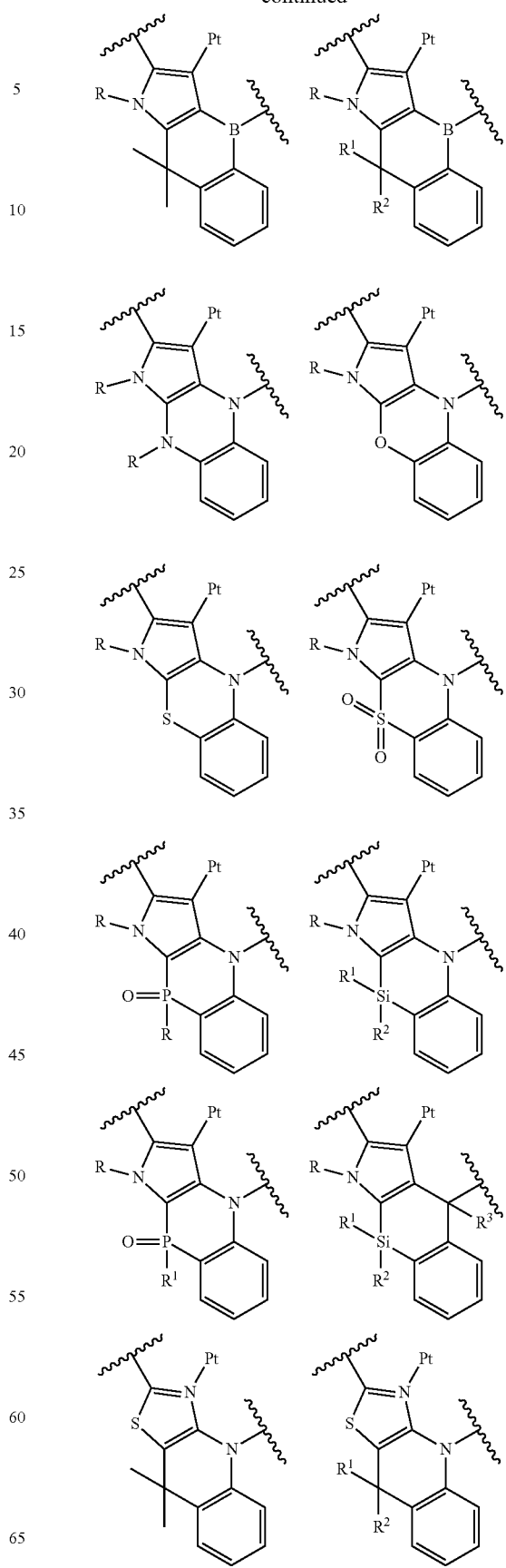

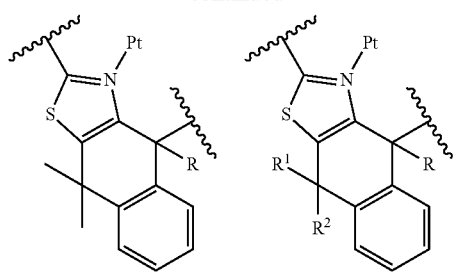
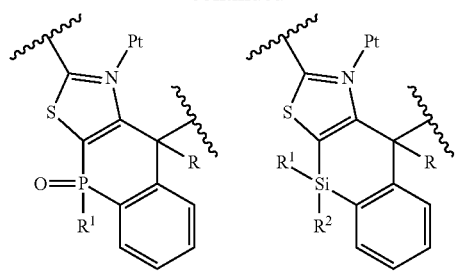
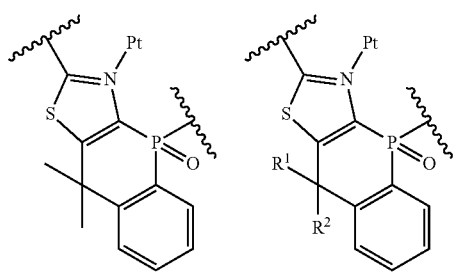
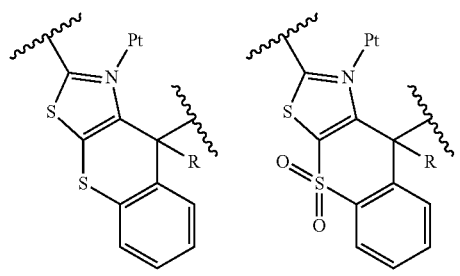
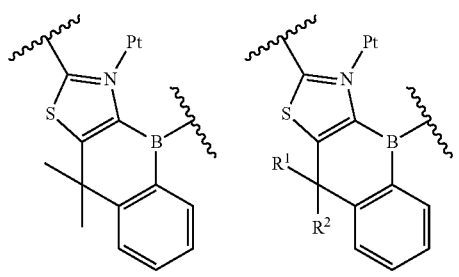
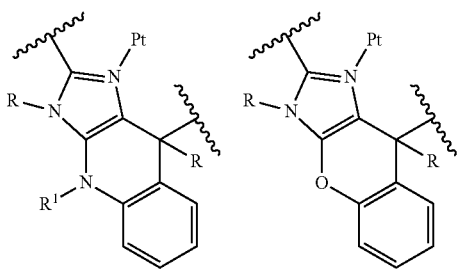
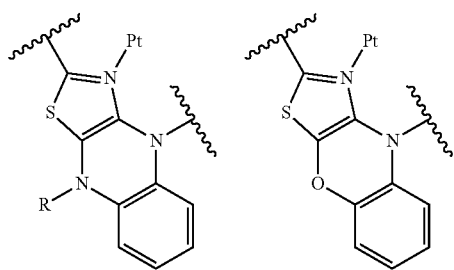
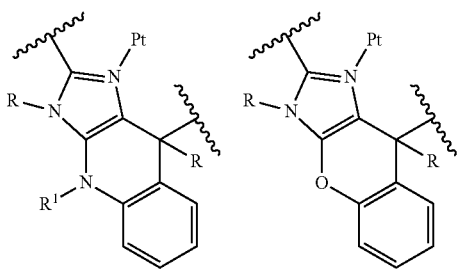
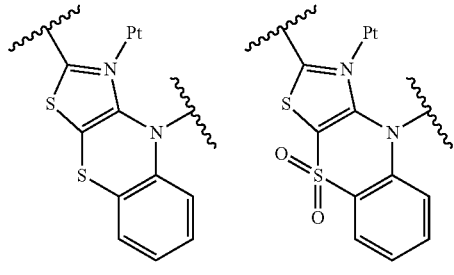
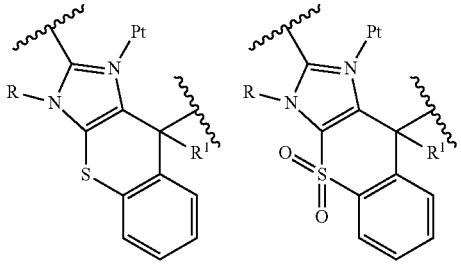
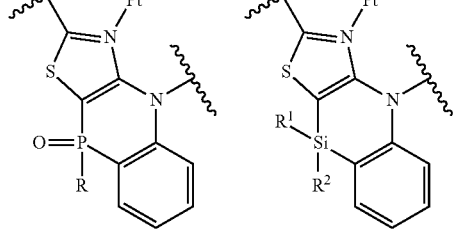
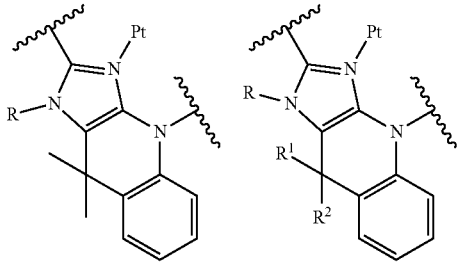

51
-continued
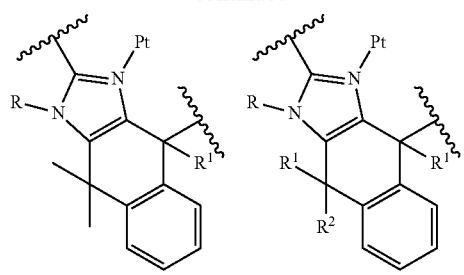
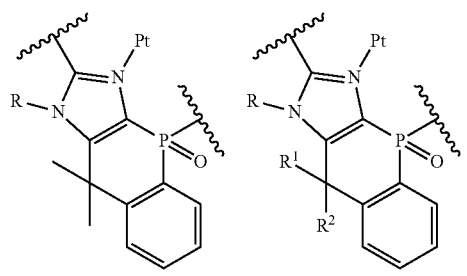
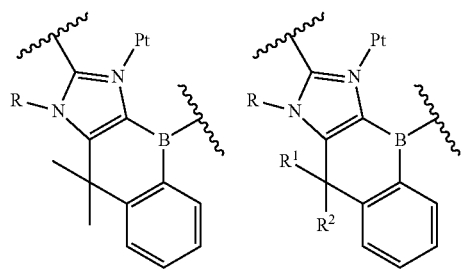
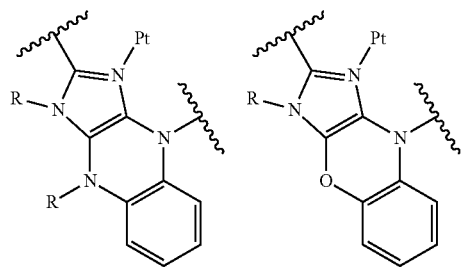
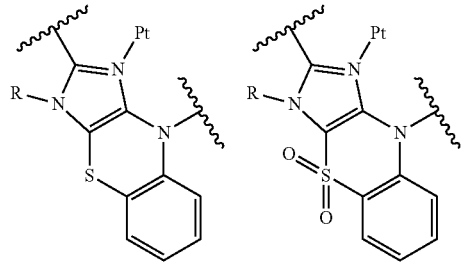
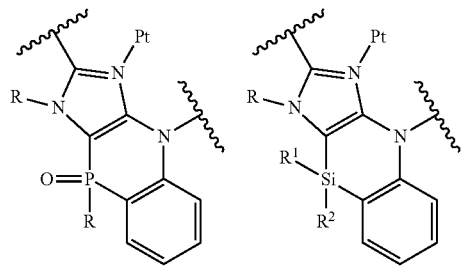
52
-continued
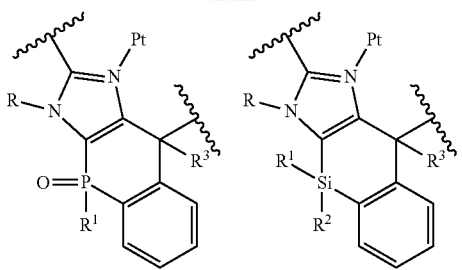
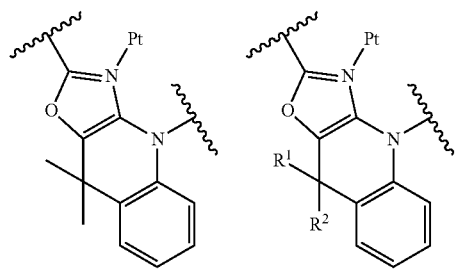
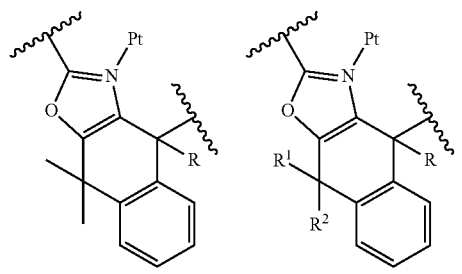
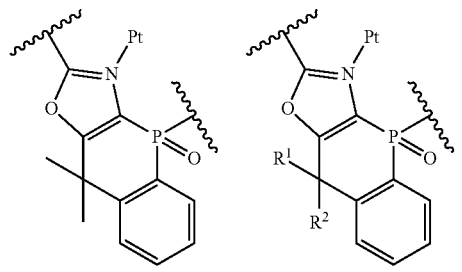
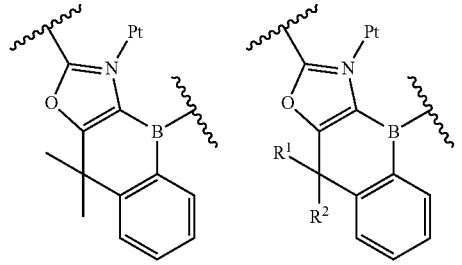
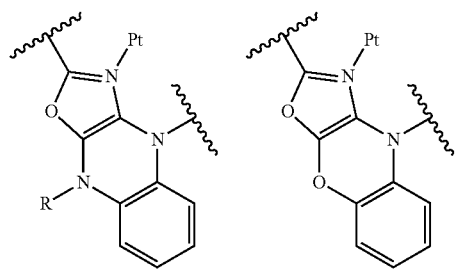

-continued
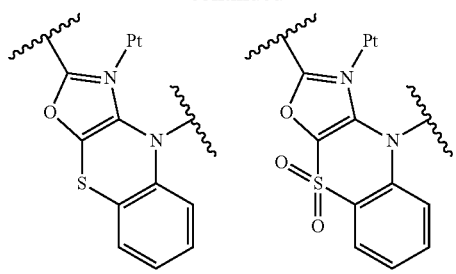
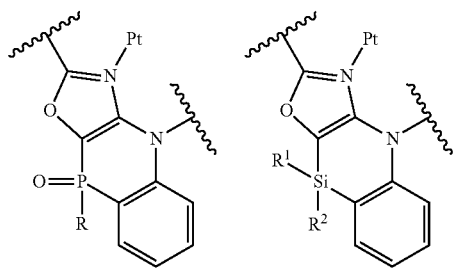
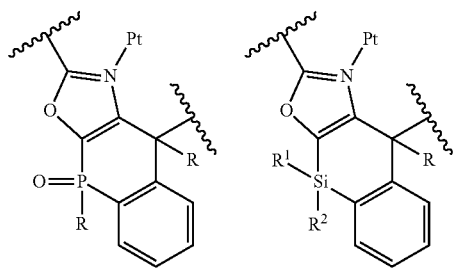
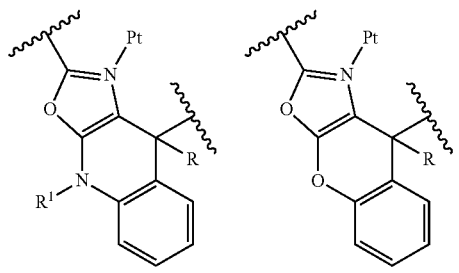
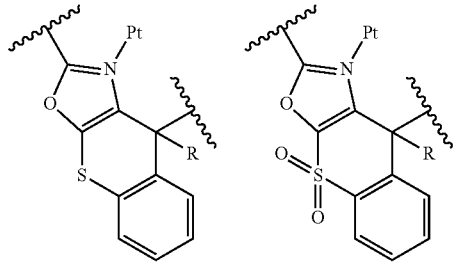
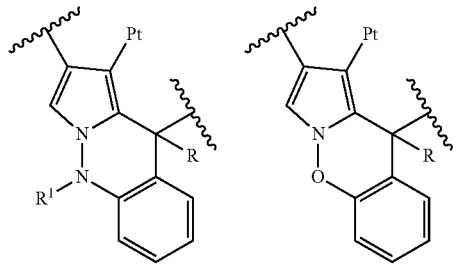
-continued
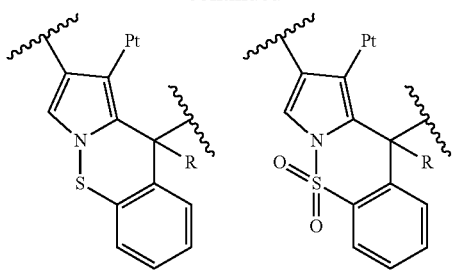
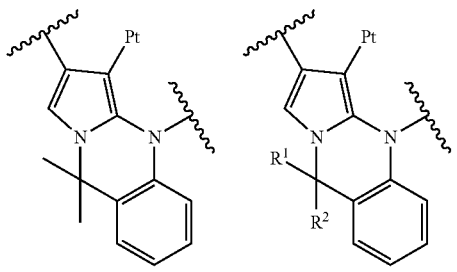
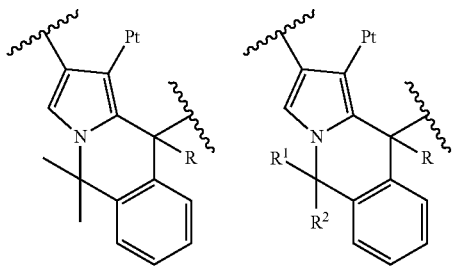
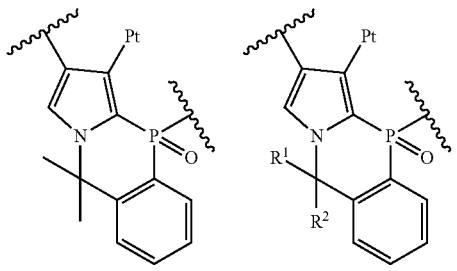
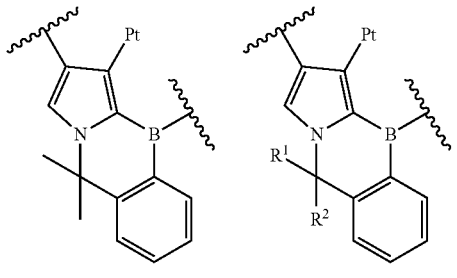
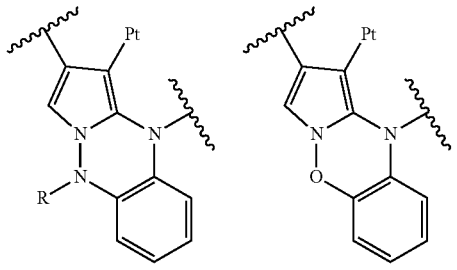

-continued
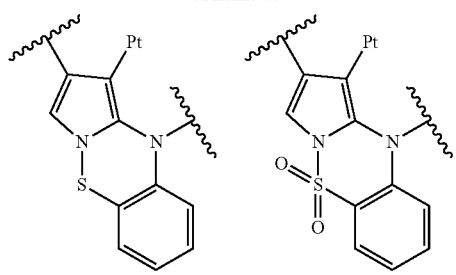
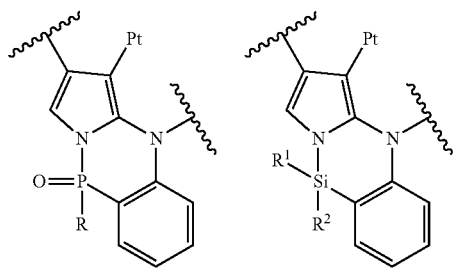
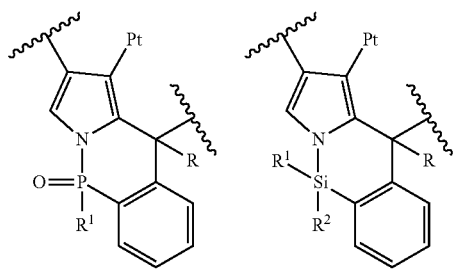
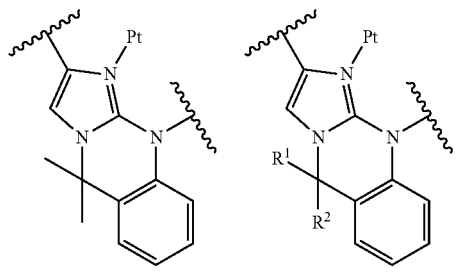
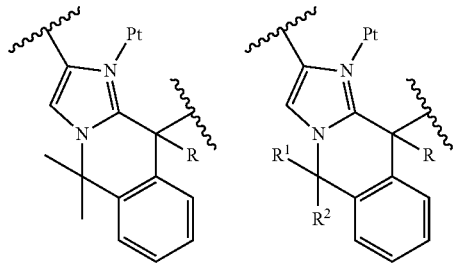
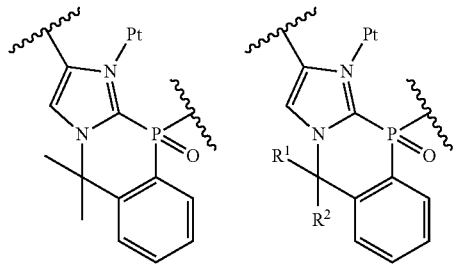
-continued
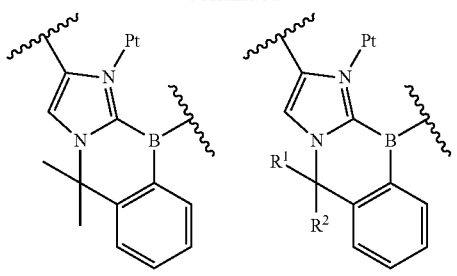
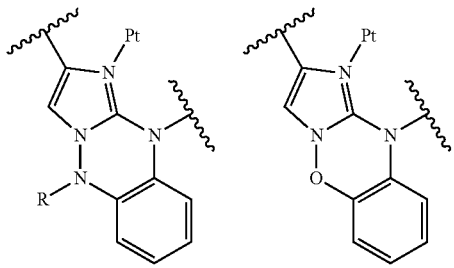
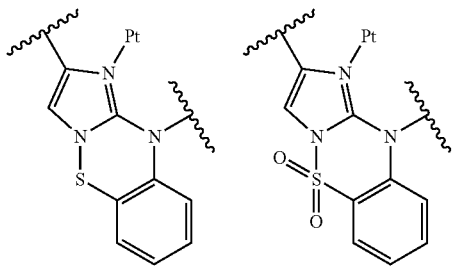
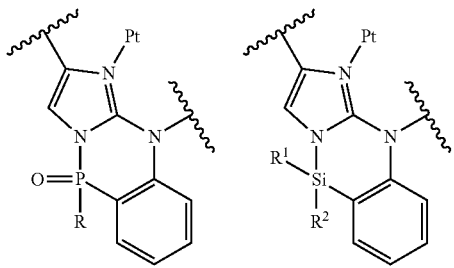
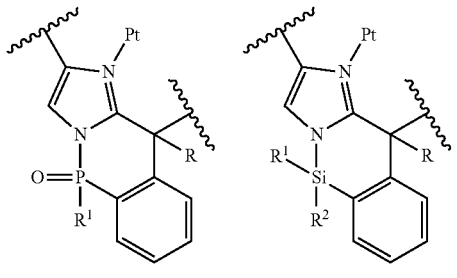
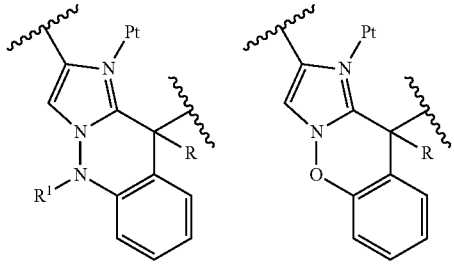

-continued

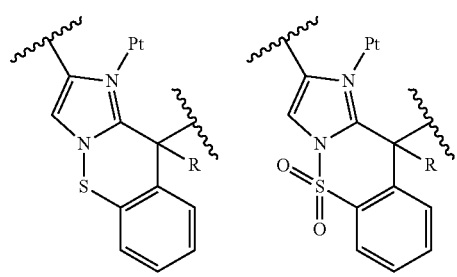

wherein each of R, $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In another aspect, for any of the formulas disclosed herein, each of

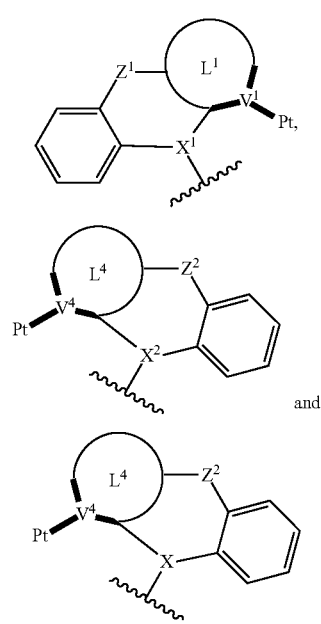

and is independently one of the following structures:

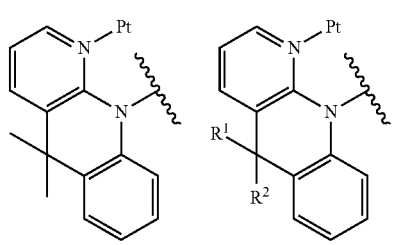

-continued

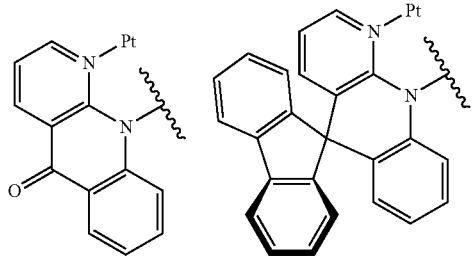

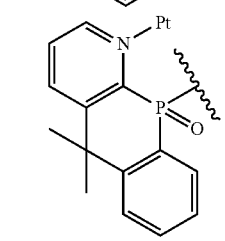

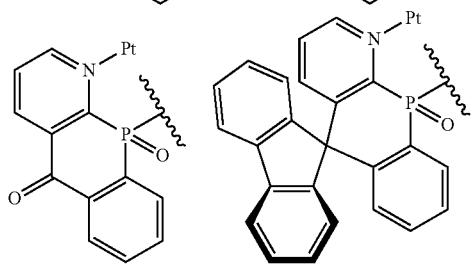

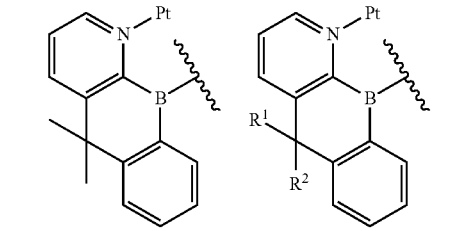

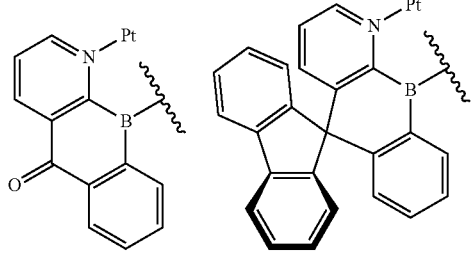

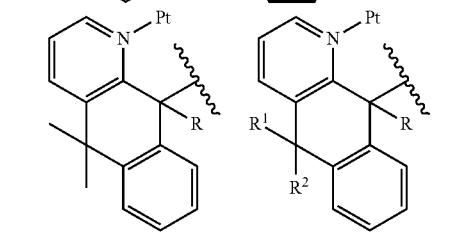

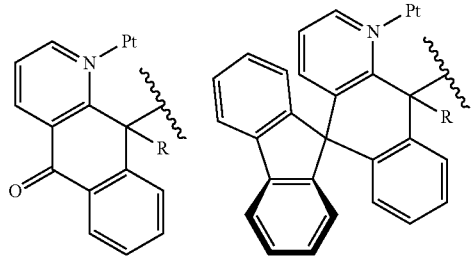

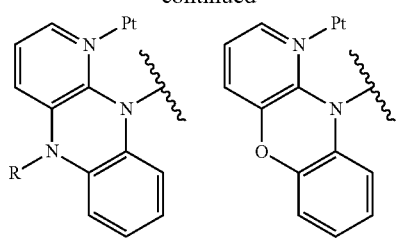
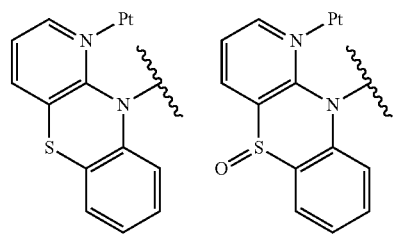
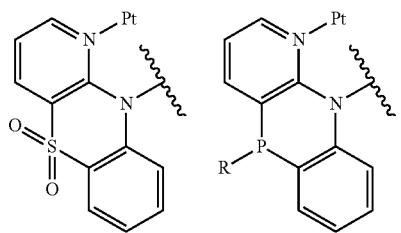
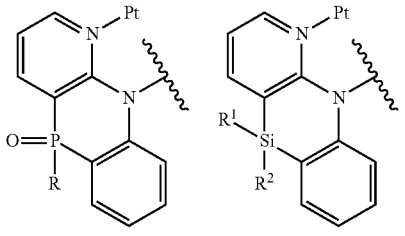
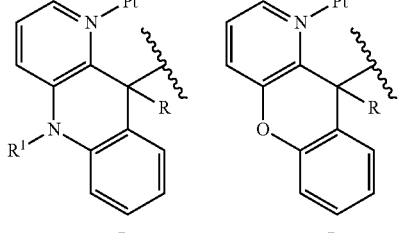
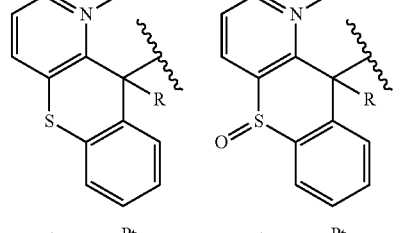
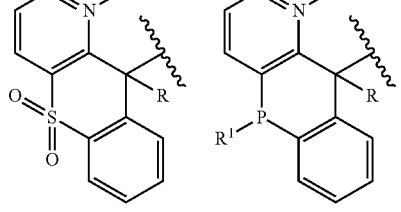
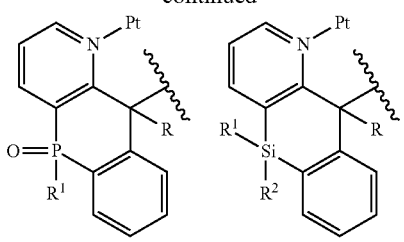
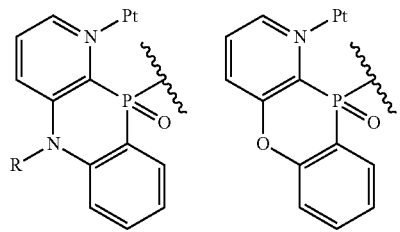
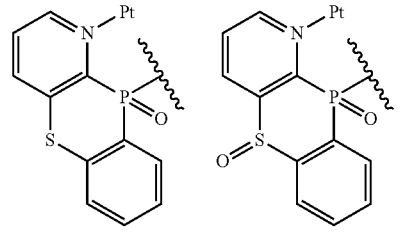
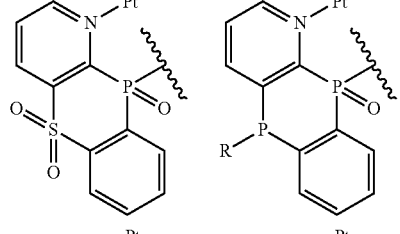
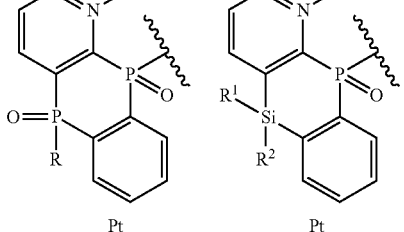
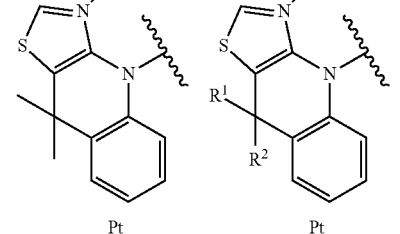
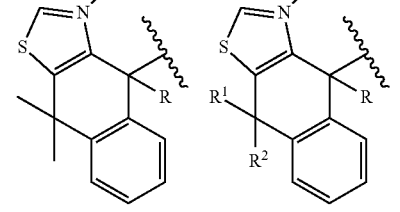

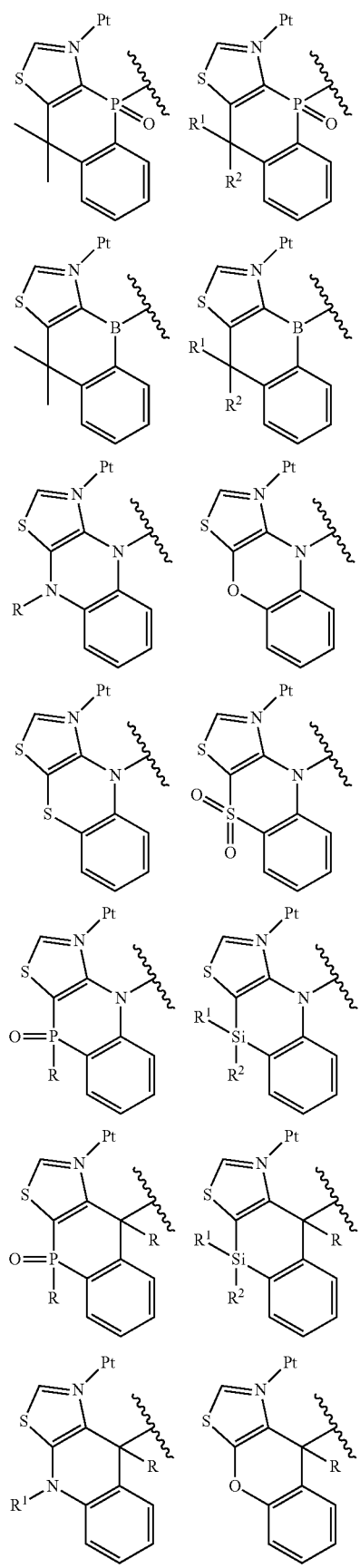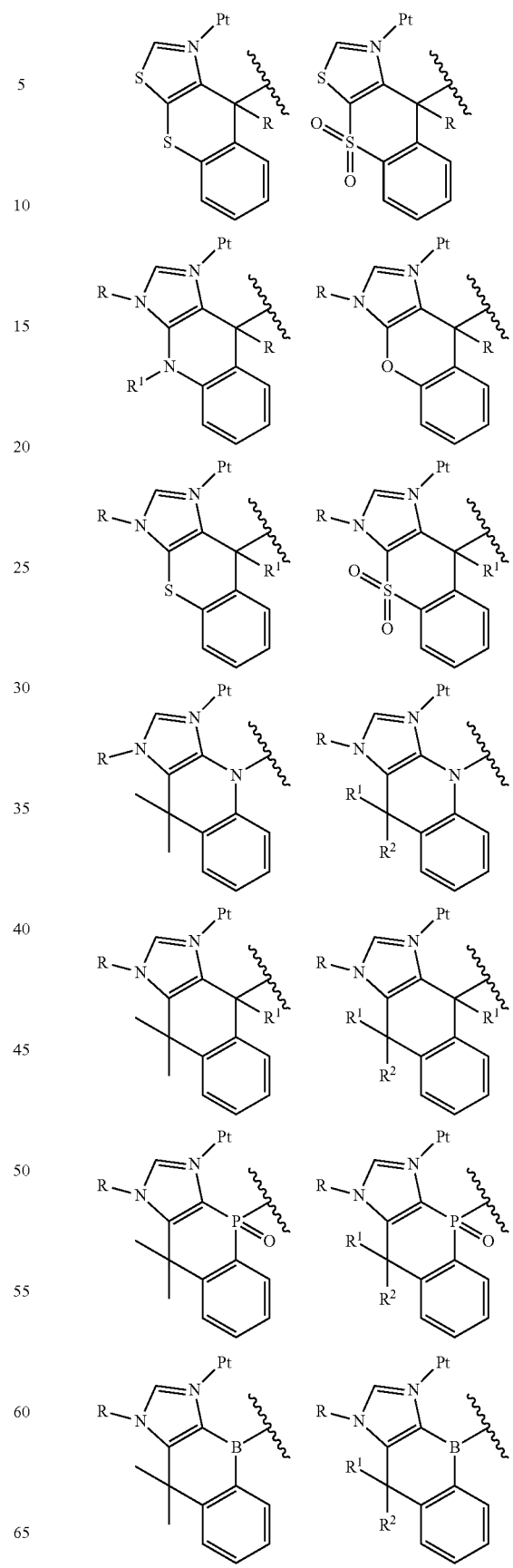

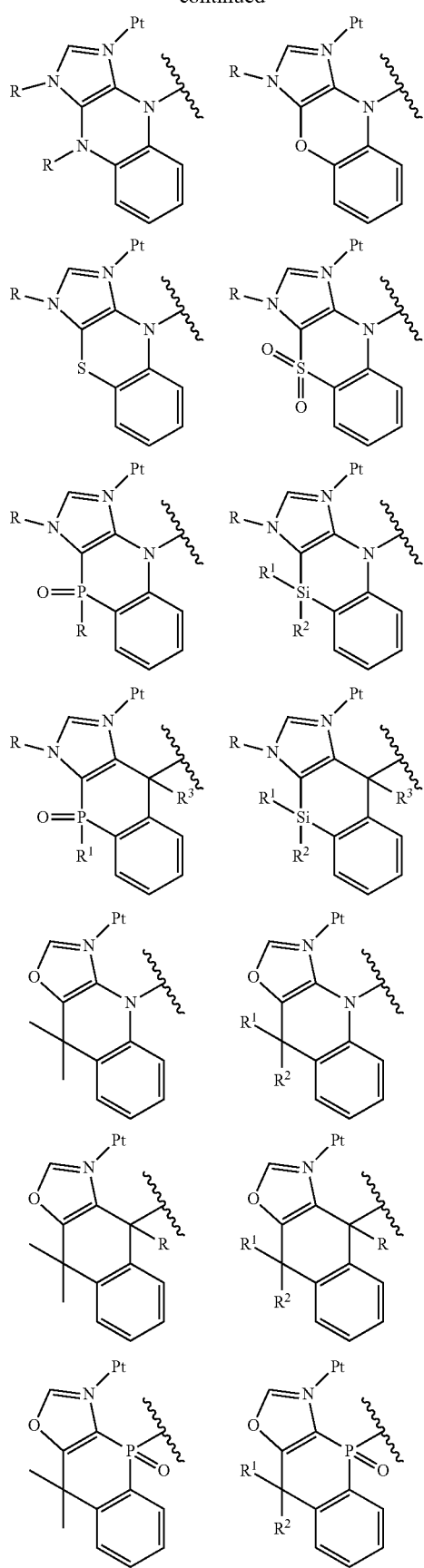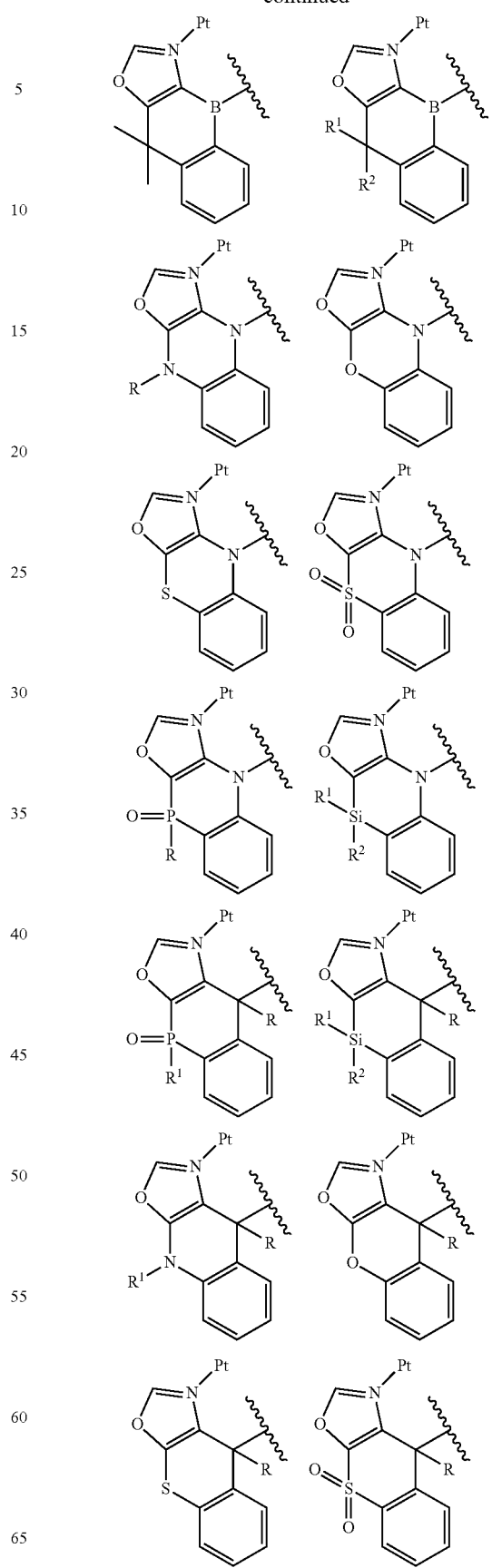

-continued

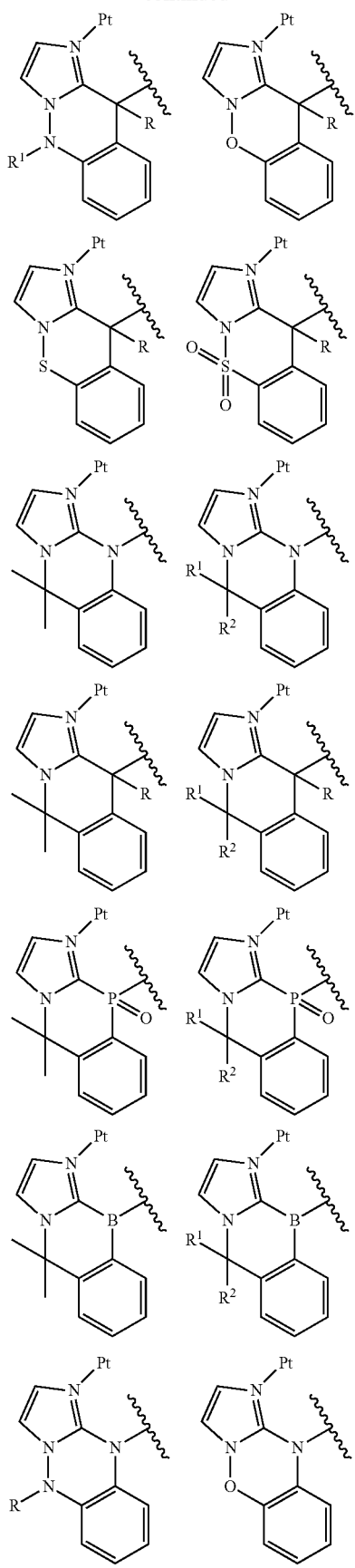

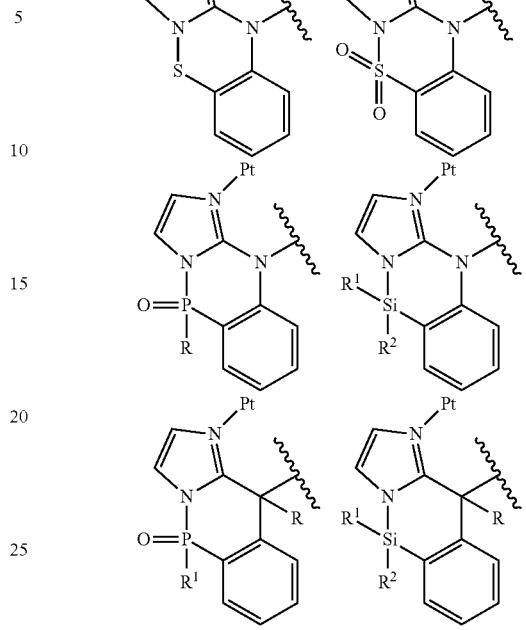

wherein each of R, R¹, R², and R³ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

F. R Groups

In one aspect, at least one $R^a$ is present. In another aspect, $R^a$ is absent.

In one aspect, $R^a$ is a mono-substitution. In another aspect, $R^a$ is a di-substitution. In yet another aspect, $R^a$ is a tri-substitution.

In one aspect, $R^a$ is connected to at least $Y^1$. In another aspect, $R^a$ is connected to at least $Y^2$. In yet another aspect, $R^a$ is connected to at least $Y^3$. In one aspect, $R^a$ is connected to at least $Y^1$ and $Y^2$. In one aspect, $R^a$ is connected to at least $Y^1$ and $Y^3$. In one aspect, $R^a$ is connected to at least $Y^2$ and $Y^3$. In one aspect, $R^a$ is connected to $Y^1$, $Y^2$, and $Y^3$.

In one aspect, $R^a$ is a di-substitution and the $R^a$'s are linked together. When the $R^a$'s are linked together the resulting structure can be a cyclic structure that includes a portion of the five-membered cyclic structure as described herein. For example, a cyclic structure can be formed when the di-substitution is of $Y^1$ and $Y^2$ and the $R^a$'s are linked together. A cyclic structure can also be formed when the di-substitution is of $Y^2$ and $Y^3$ and the $R^a$'s are linked together. A cyclic structure can also be formed when the di-substitution is of $Y^3$ and $Y^4$ and the $R^a$'s are linked together.

In one aspect, each $R^a$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In one aspect, at least one $R^a$ is halogen, hydroxyl, substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, or any conjugate or combination thereof.

In one aspect, at least one $R^b$ is present. In another aspect, $R^b$ is absent.

In one aspect, $R^b$ is a mono-substitution. In another aspect, $R^b$ is a di-substitution. In yet another aspect, $R^b$ is a tri-substitution.

In one aspect, each $R^b$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In one aspect, at least one $R^b$ is halogen, hydroxyl, substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, or any conjugate or combination thereof.

In one aspect, at least one $R^c$ is present. In another aspect, $R^c$ is absent.

In one aspect, $R^c$ is a mono-substitution. In another aspect, $R^c$ is a di-substitution. In yet another aspect, $R^c$ is a tri-substitution.

In one aspect, each $R^c$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In one aspect, at least one $R^c$ is halogen, hydroxyl, substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, or any conjugate or combination thereof.

In one aspect, at least one $R^d$ is present. In another aspect, $R^d$ is absent.

In one aspect, $R^d$ is a mono-substitution. In another aspect, $R^d$ is a di-substitution. In yet another aspect, $R^d$ is a tri-substitution.

In one aspect, each $R^d$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, at least one $R^x$ is present. In another aspect, $R^x$ is absent.

In one aspect, $R^x$ is a mono-substitution. In another aspect, $R^x$ is a di-substitution. In yet another aspect, $R^x$ is a tri-substitution.

In one aspect, each $R^x$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In one aspect, at least one $R^x$ is halogen, hydroxyl, substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, or any conjugate or combination thereof.

In one aspect, at least one $R^y$ is present. In another aspect, $R^y$ is absent.

In one aspect, $R^y$ is a mono-substitution. In another aspect, $R^y$ is a di-substitution. In yet another aspect, $R^y$ is a tri-substitution.

In one aspect, each $R^y$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In one aspect, at least one $R^y$ is halogen, hydroxyl, substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, or any conjugate or combination thereof.

In one aspect, each of R, $R^1$, $R^2$, $R^3$, and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, mono alkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In another aspect, each of R, $R^1$, $R^2$, $R^3$ and $R^4$ is independently hydrogen, halogen, hydroxyl, thiol, nitro, cyano; substituted or unsubstituted: aryl, cycloalkyl, cycloalkenyl, heterocyclyl, heteroaryl, alkyl, alkenyl, alkynyl, or amino.

G. Exemplary Compounds

In one aspect, metal complexes illustrated in this disclosure can comprise one or more of the following structures. In another aspect, they can also comprise other structures or portions thereof not specifically recited herein, and the present disclosure is not intended to be limited to those structures or portions thereof specifically recited.

Structures 1
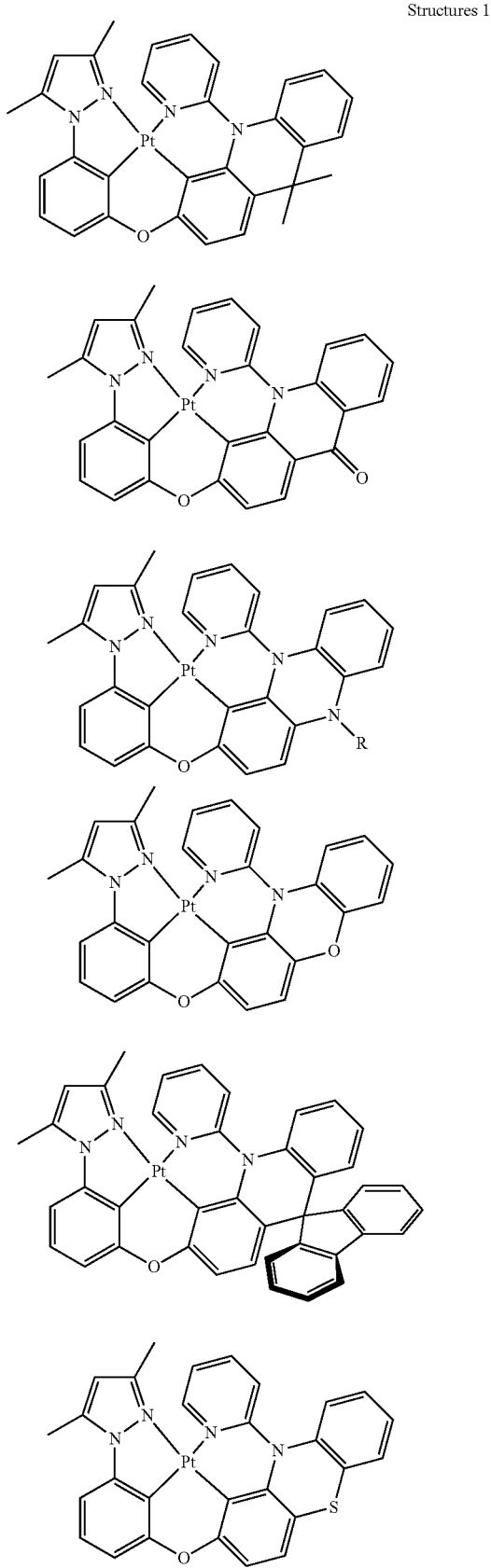
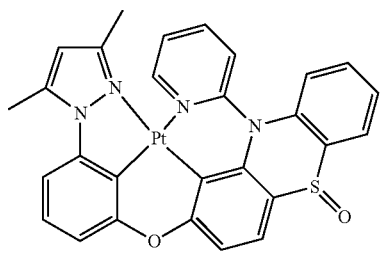
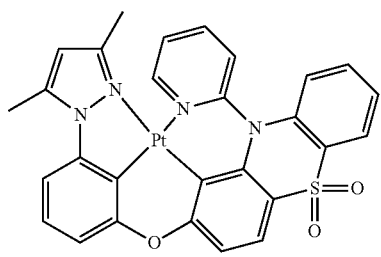
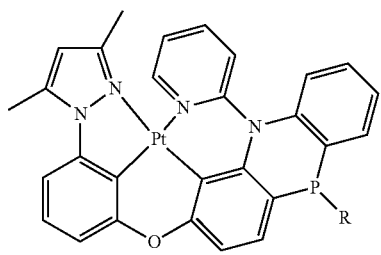
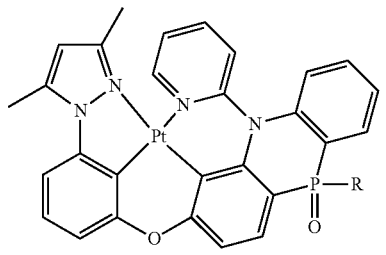
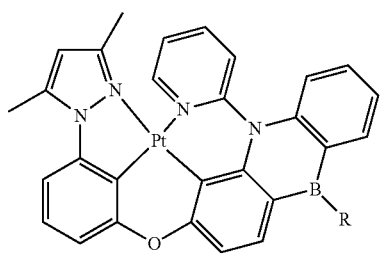
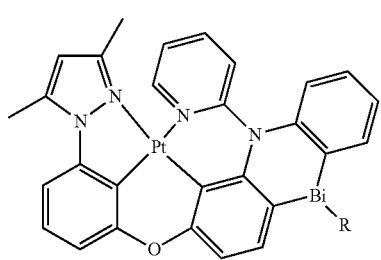

-continued
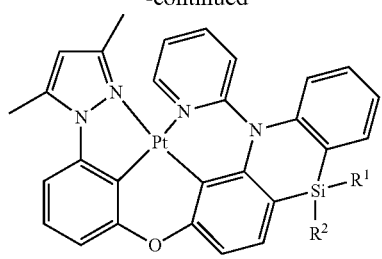
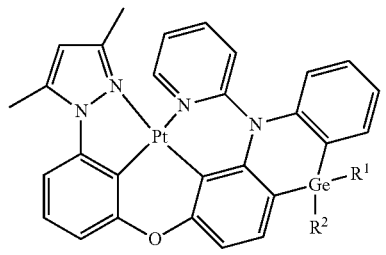
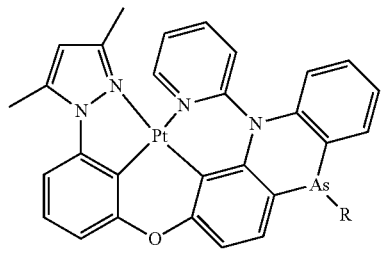
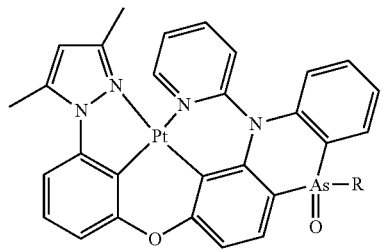
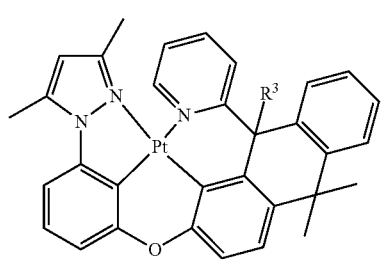
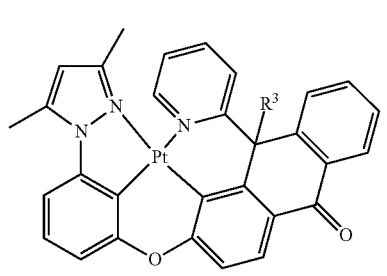
-continued
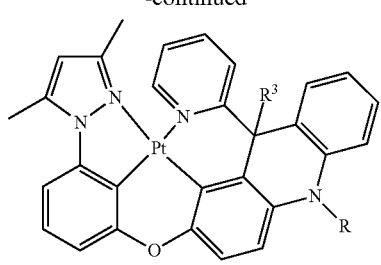
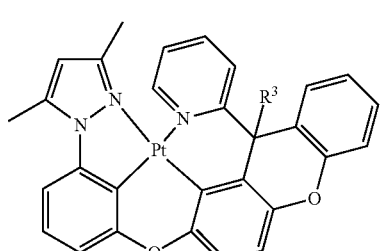
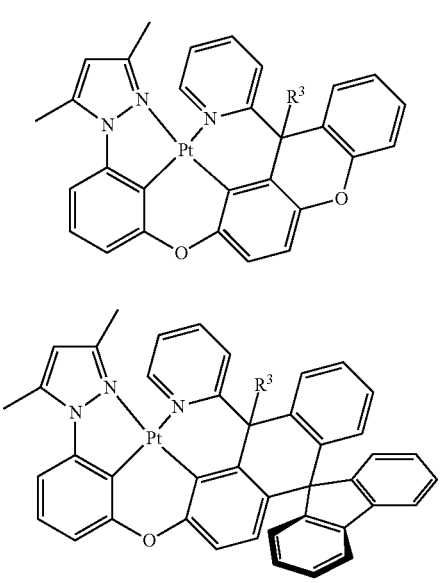
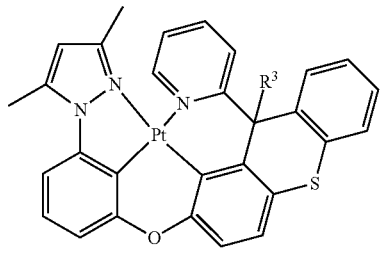
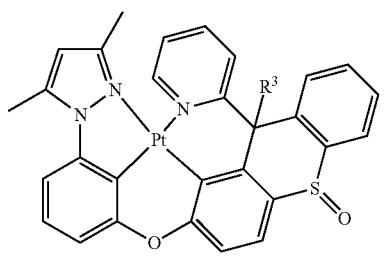
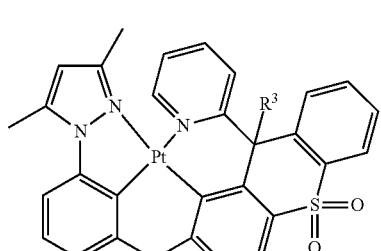

73
-continued
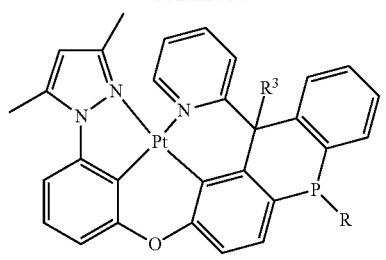
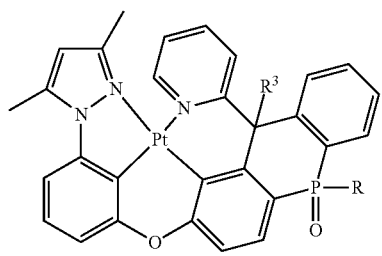
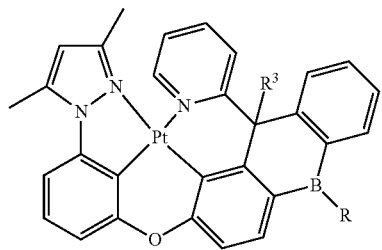
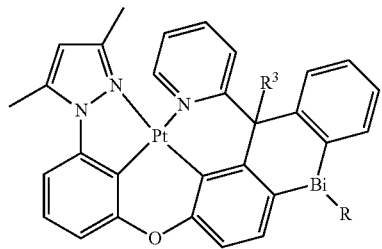
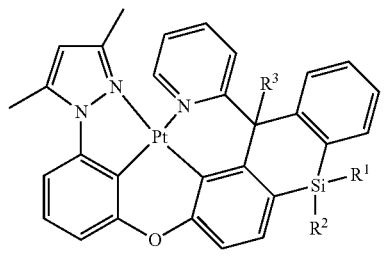
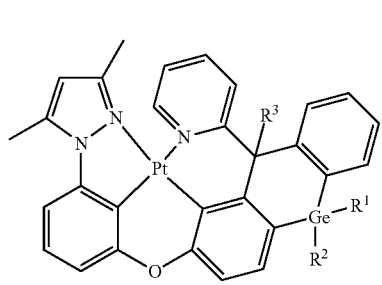
74
-continued
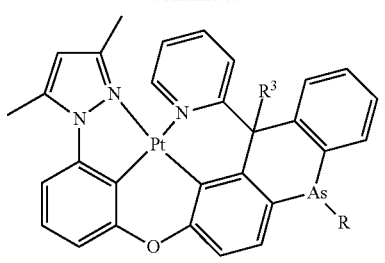
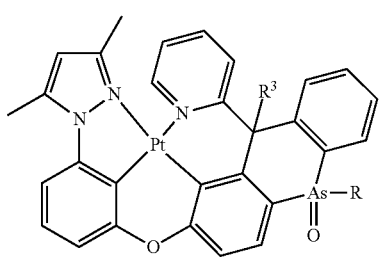
Structures 2
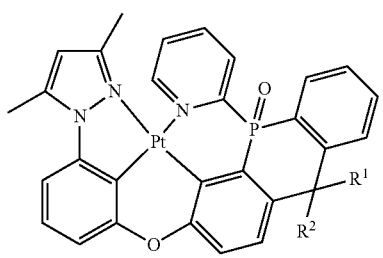
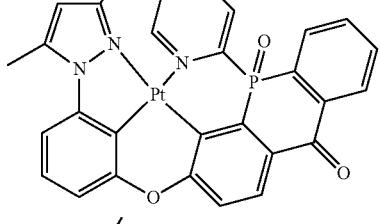
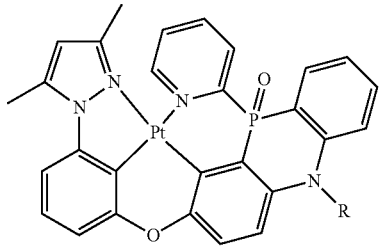
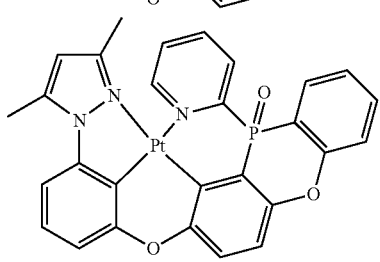

75
-continued
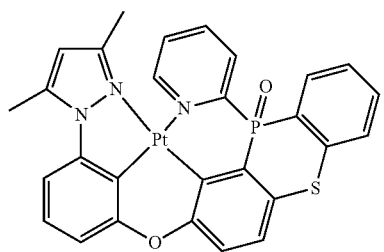
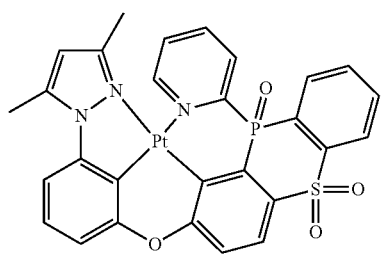
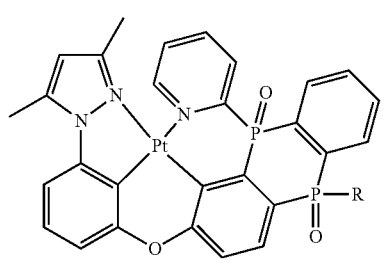
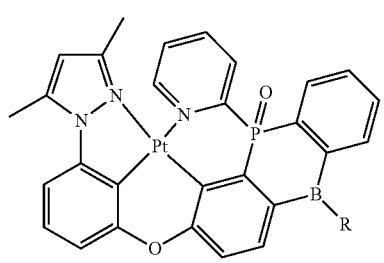
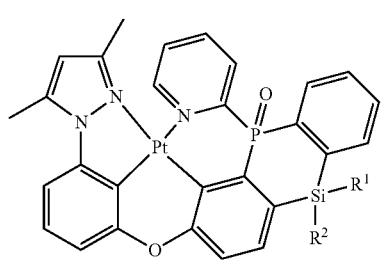
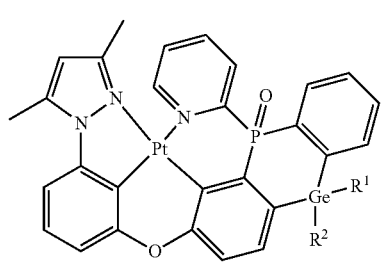
76
-continued
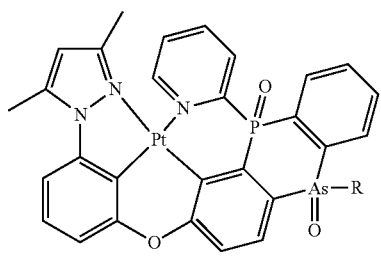
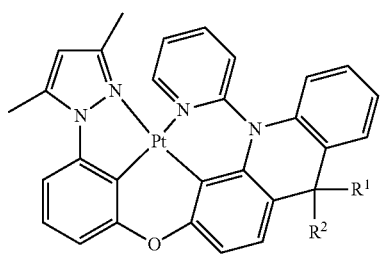
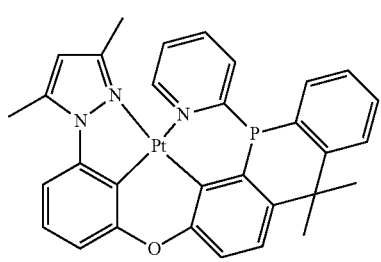
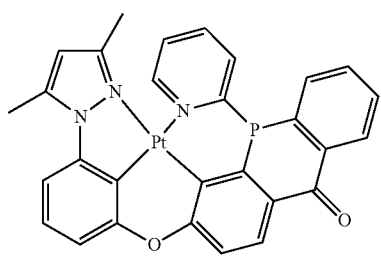
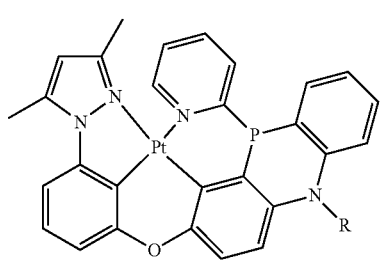
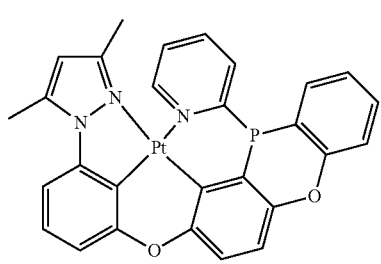

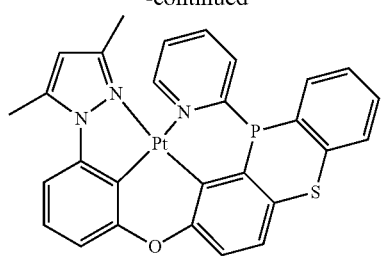
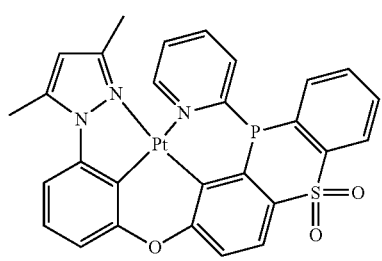
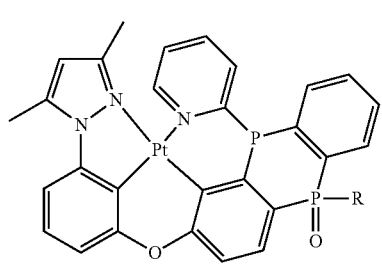
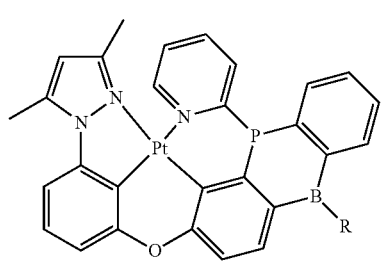
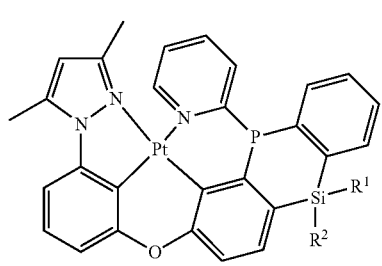
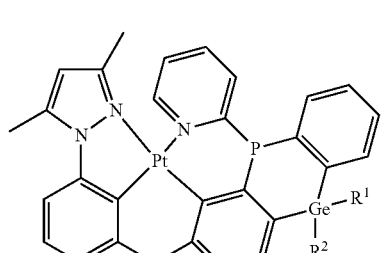
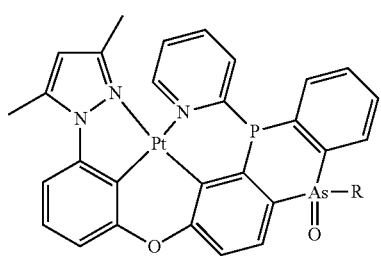
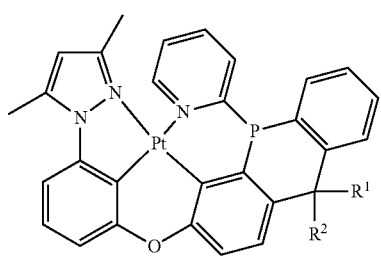
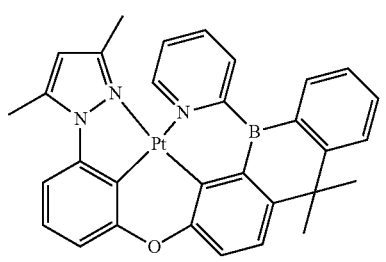
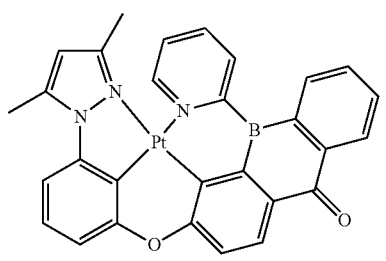
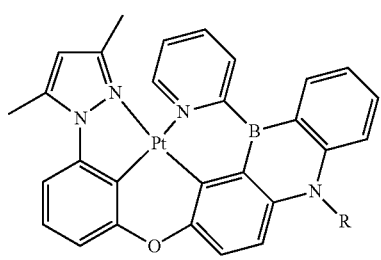
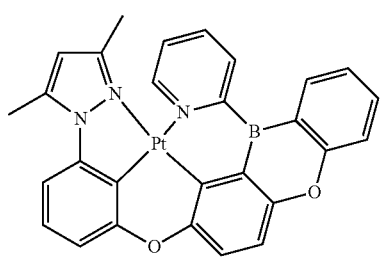

-continued
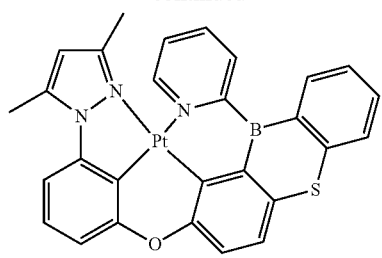
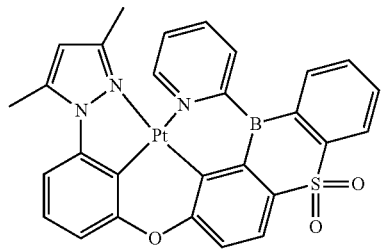
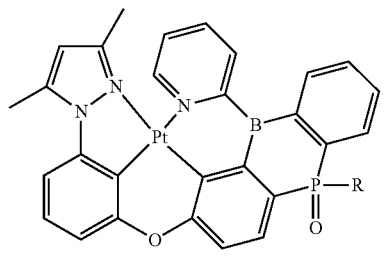
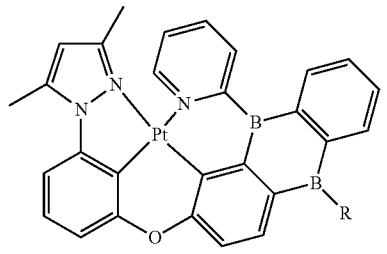
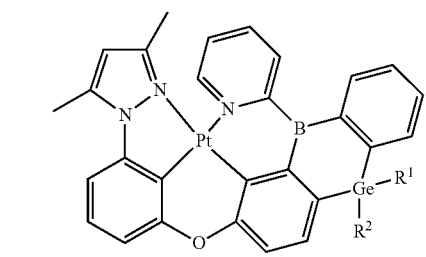
-continued
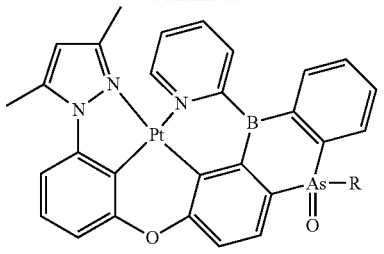
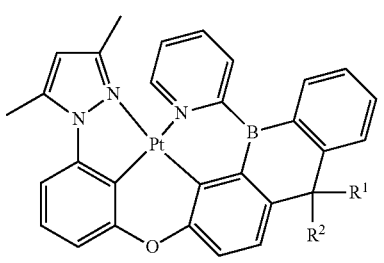
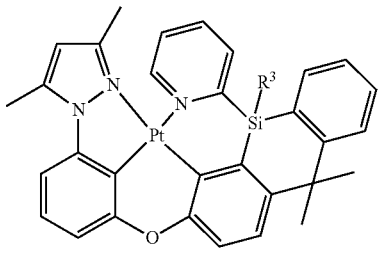
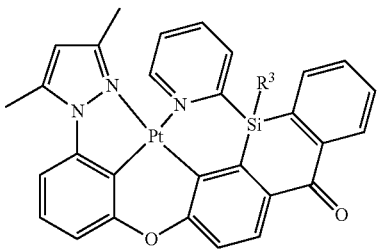
Structures 3
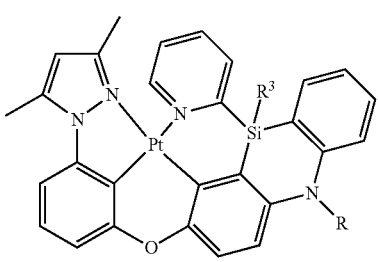
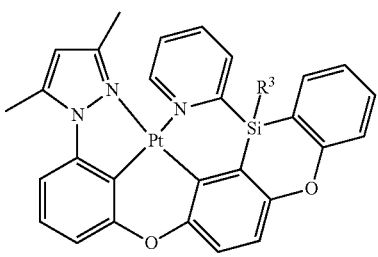

81
-continued
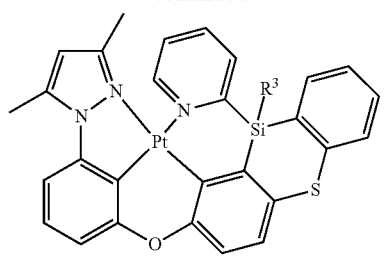
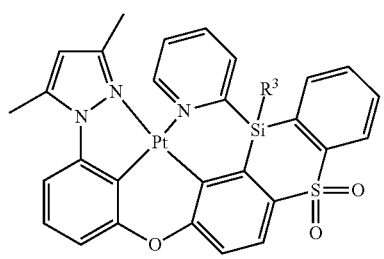
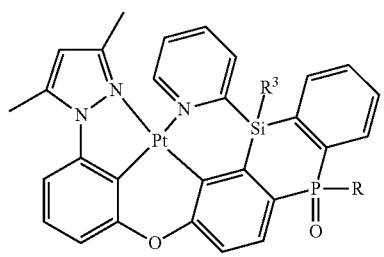
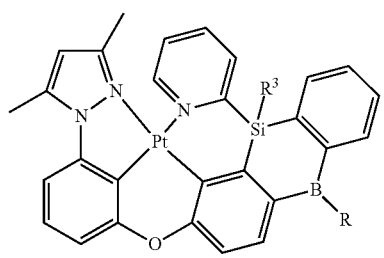
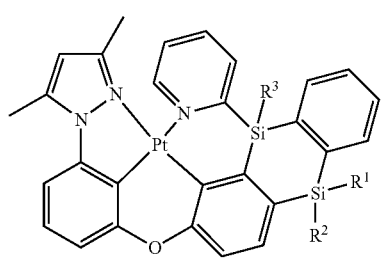
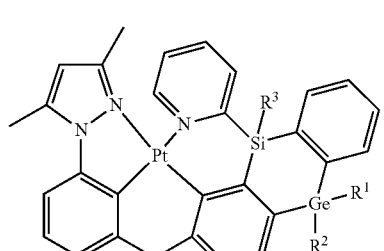
82
-continued
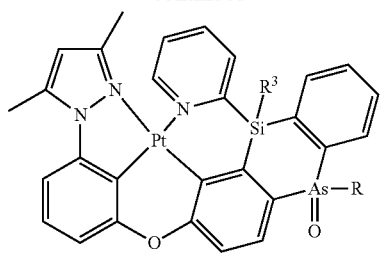
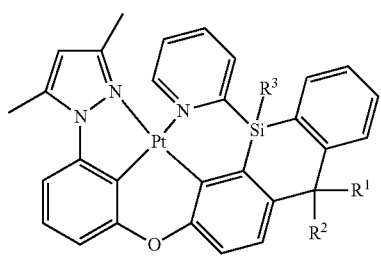
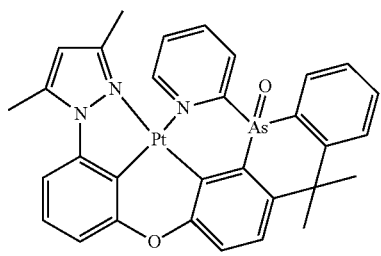
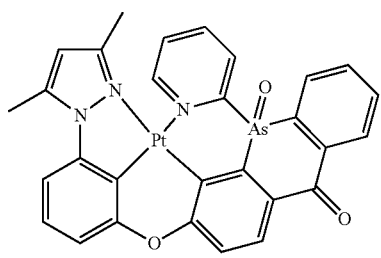
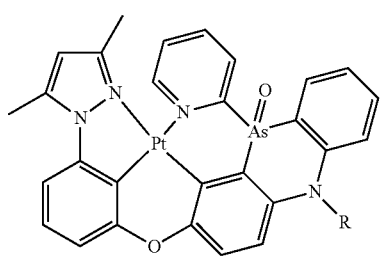
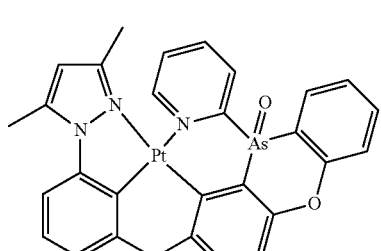

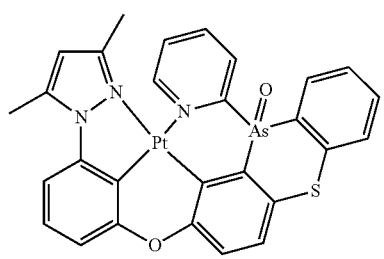
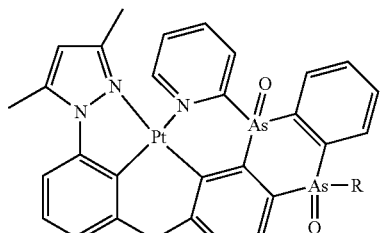
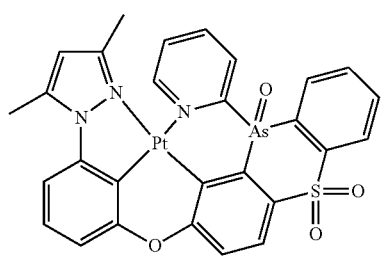
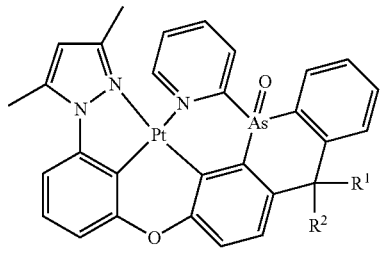
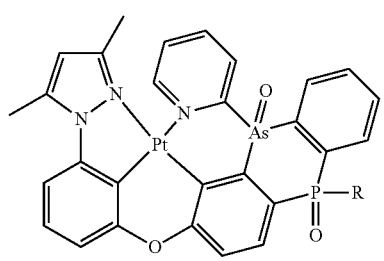
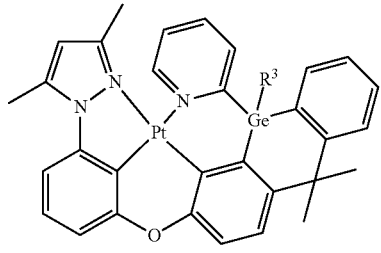
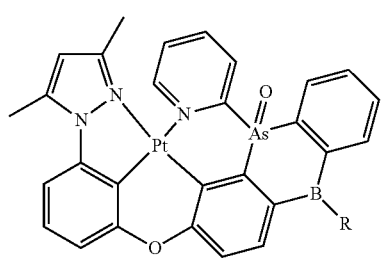
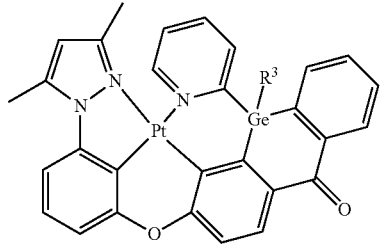
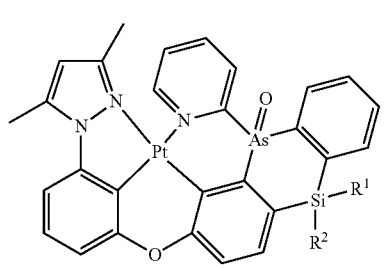
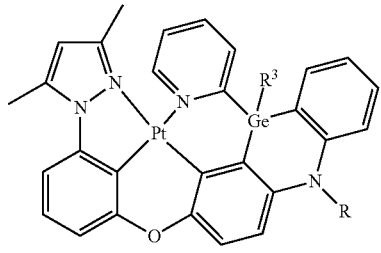
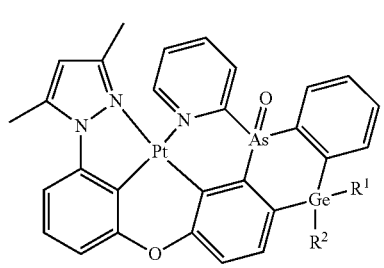

Structures 4
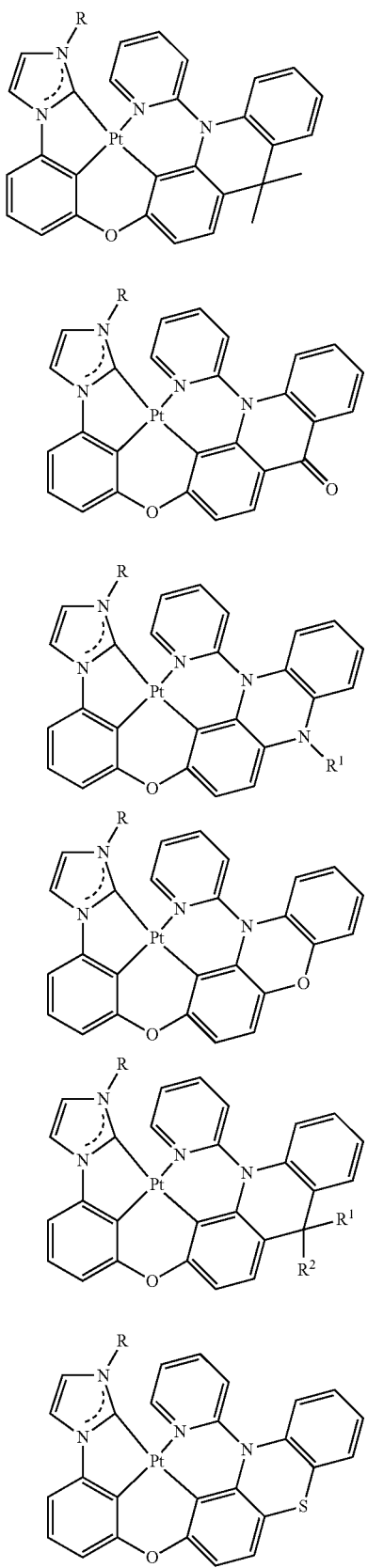
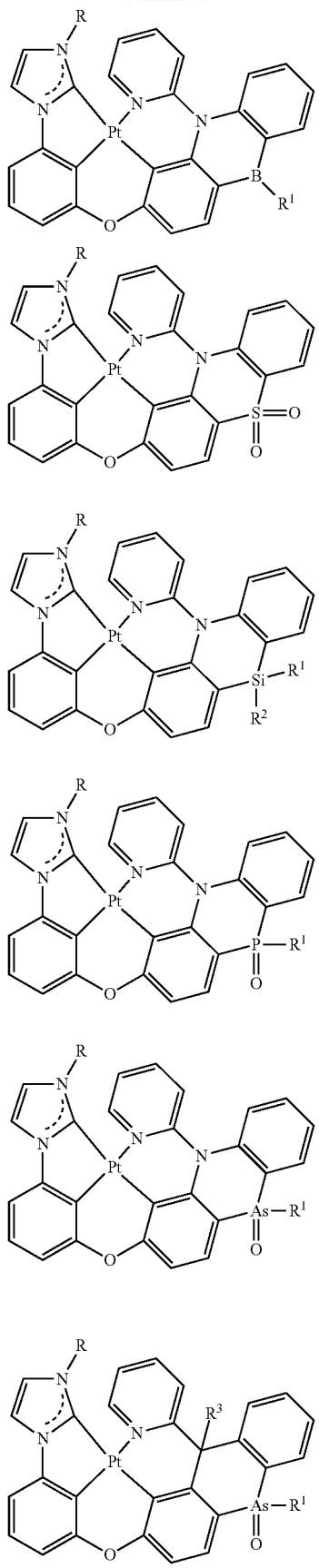

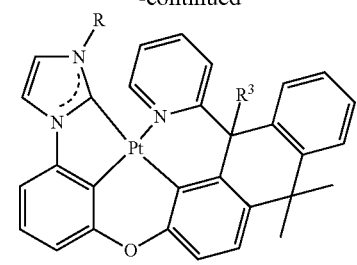
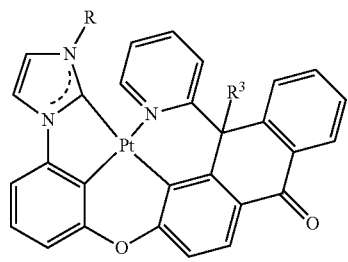
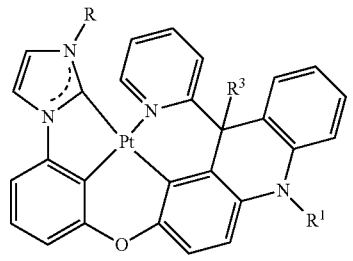
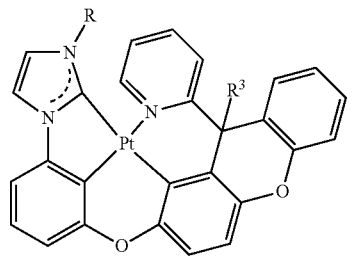
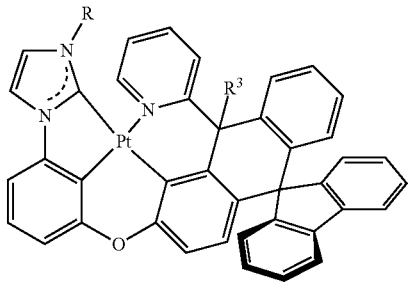
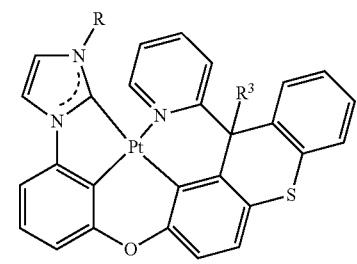
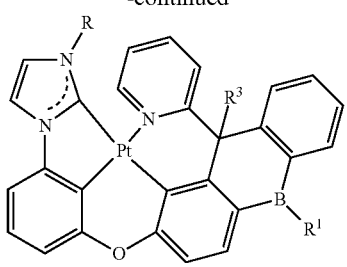
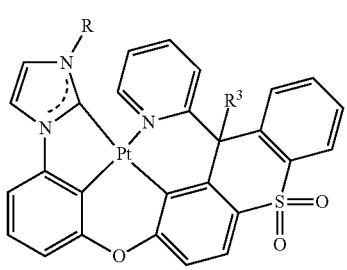
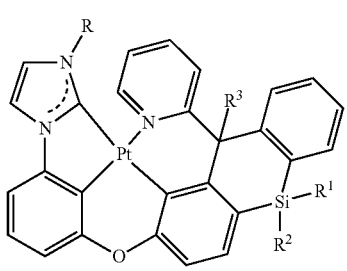
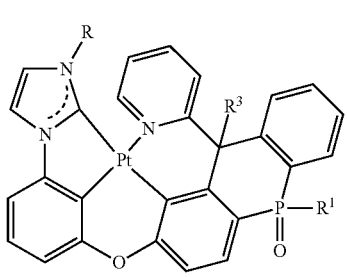
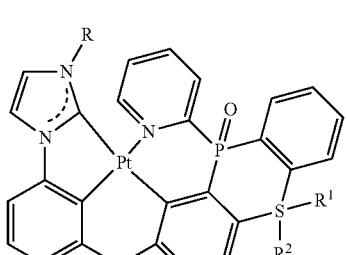
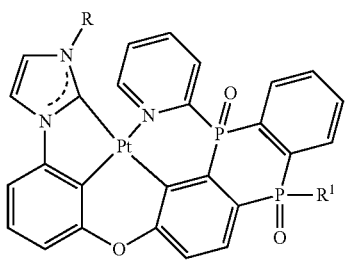

89
-continued
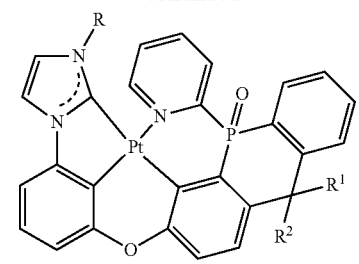
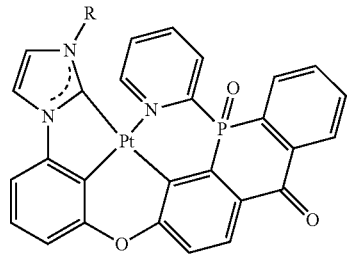
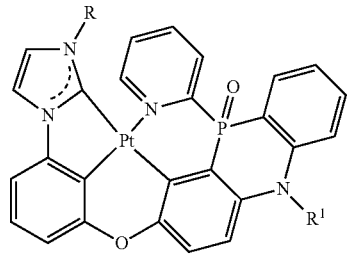
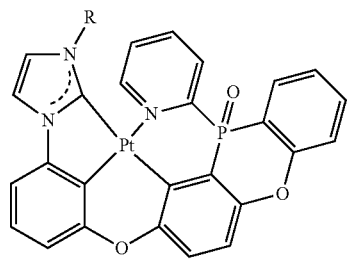
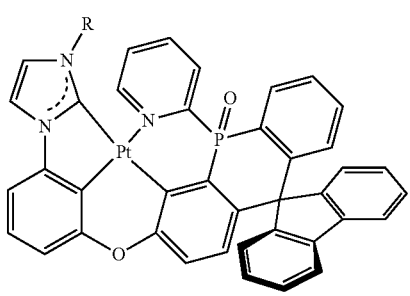
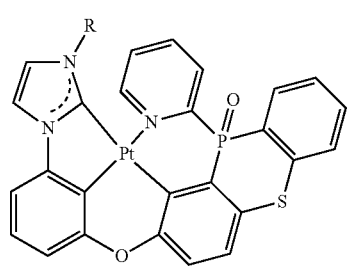
90
-continued
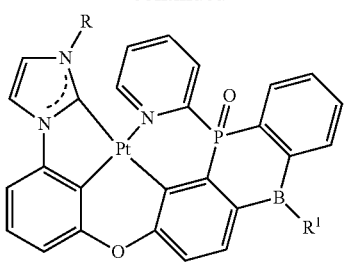
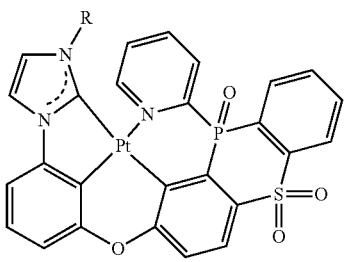
Structures 5
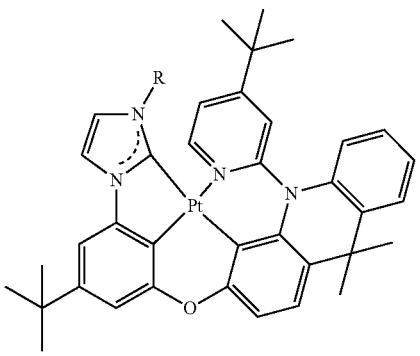
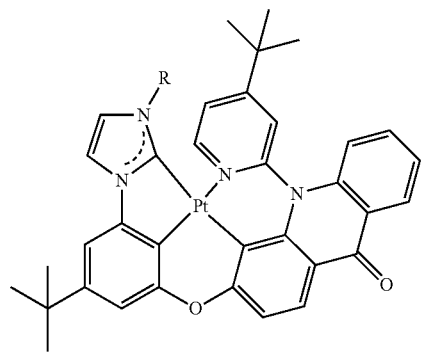
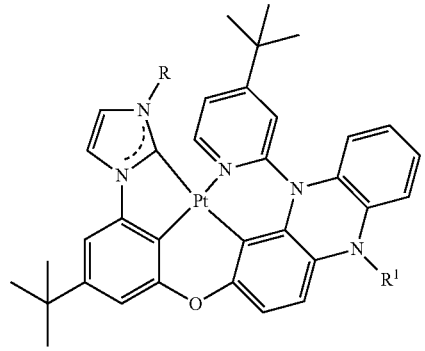

| 91 -continued | 92 -continued |
|---|---|
| 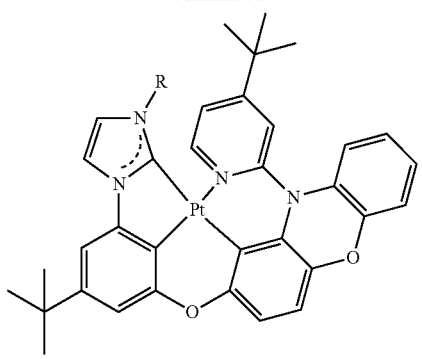 | 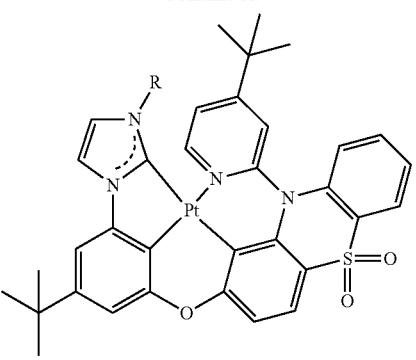 |
| 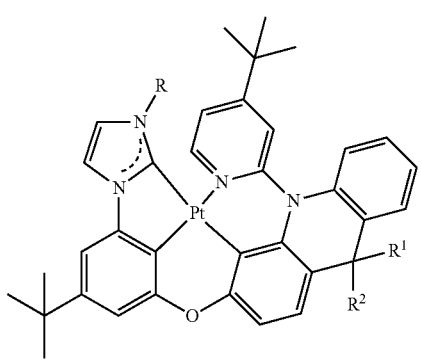 | 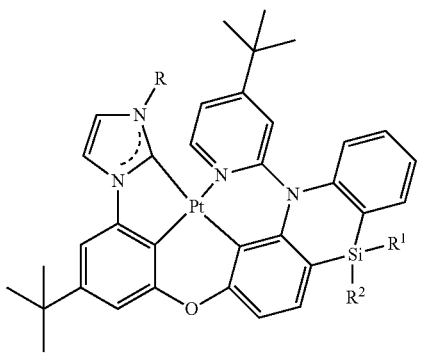 |
| 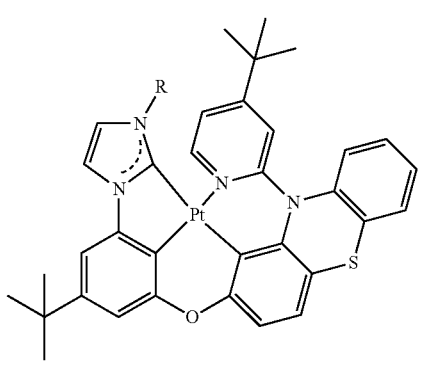 | 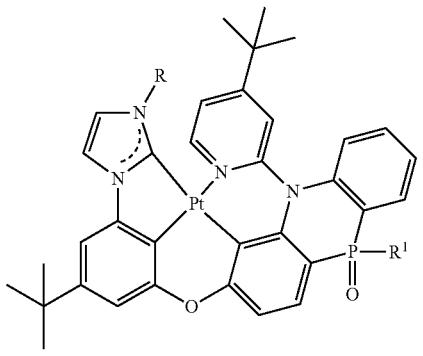 |
| 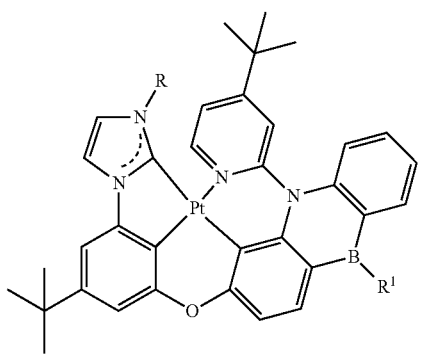 | 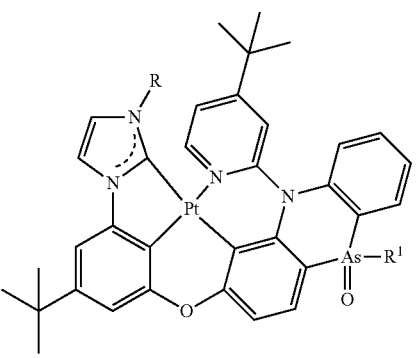 |

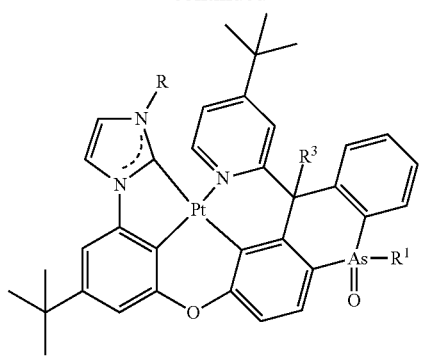
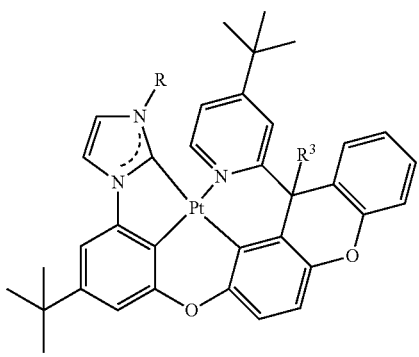
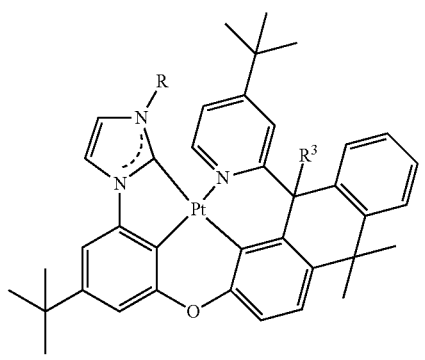
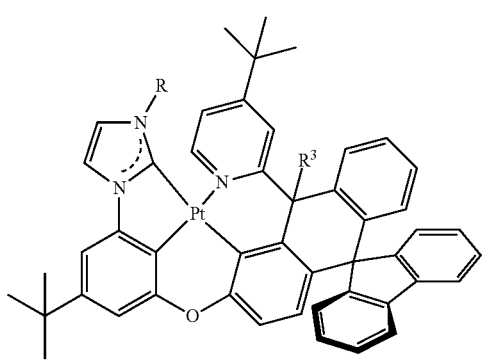
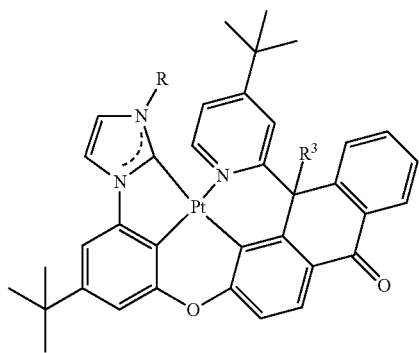
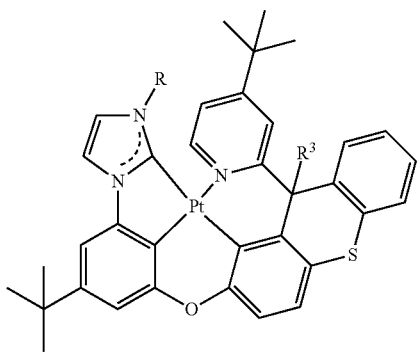
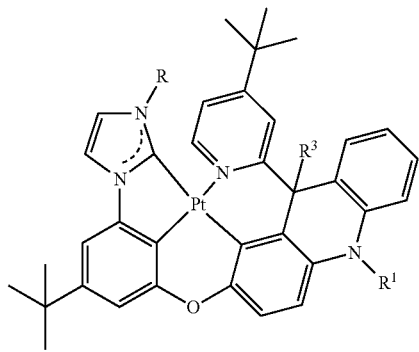
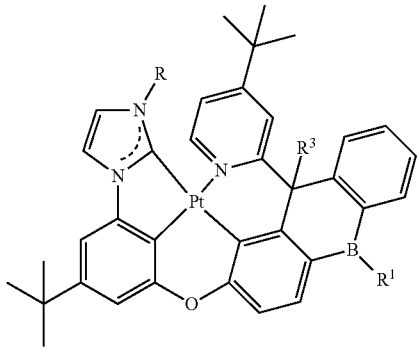

95
-continued
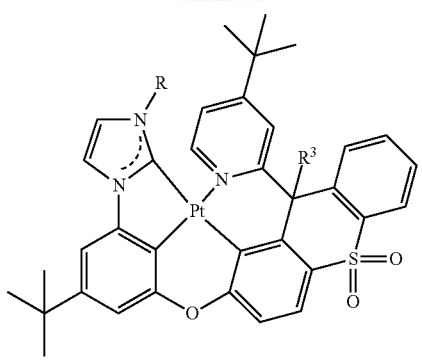
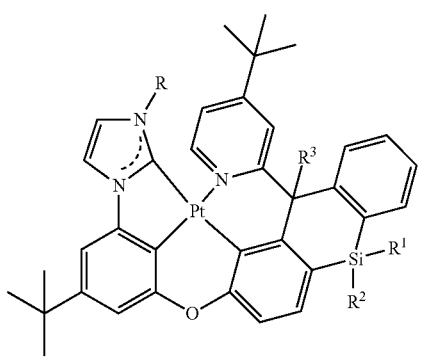
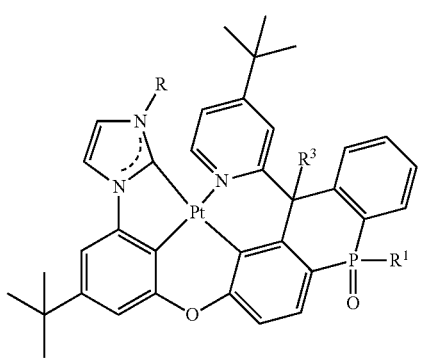
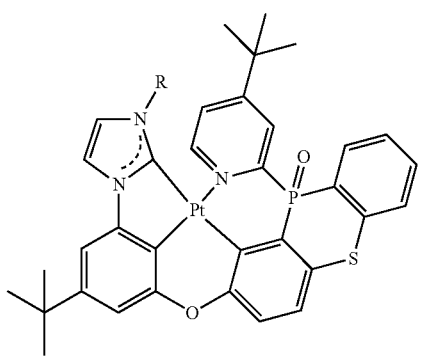
96
-continued
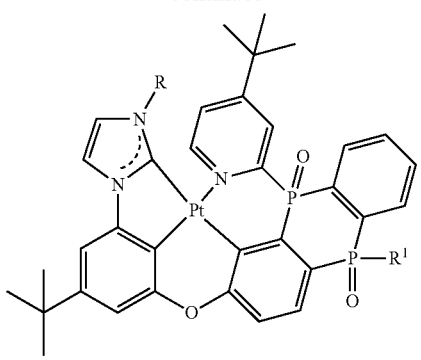
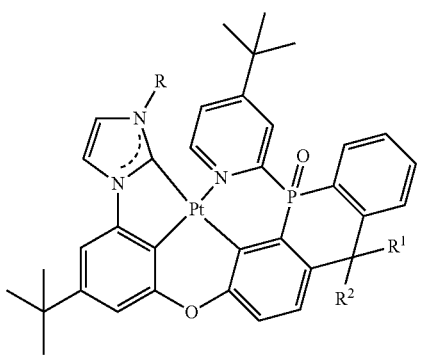
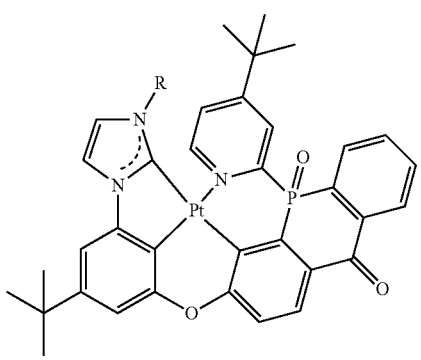
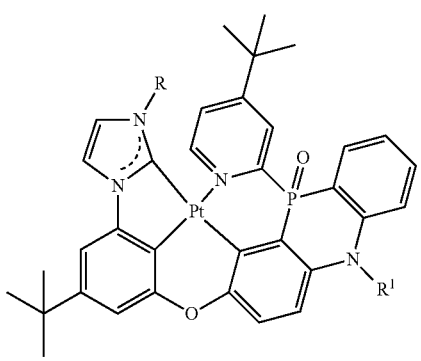

97
-continued
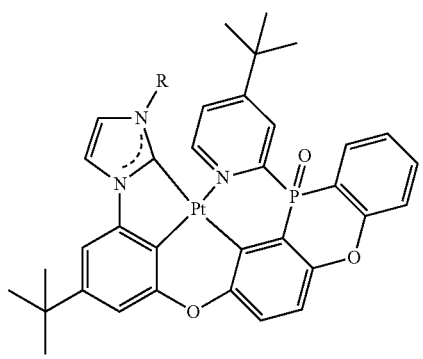
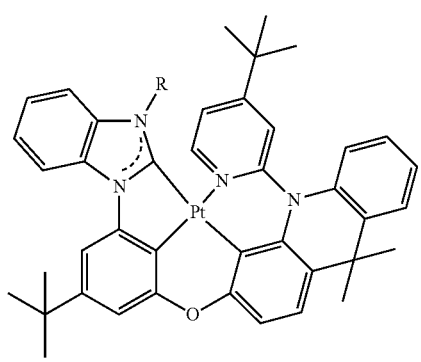
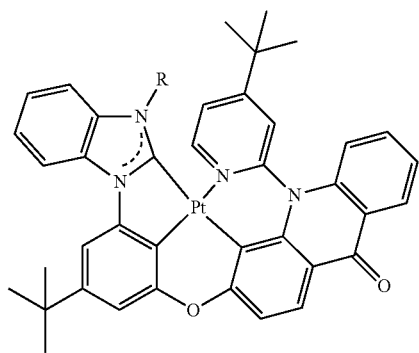
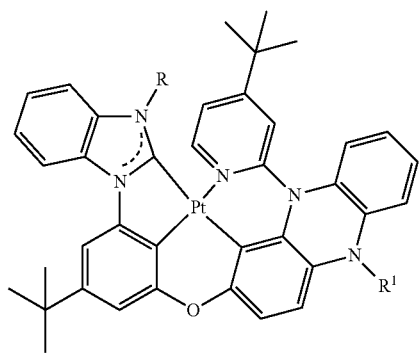
98
-continued
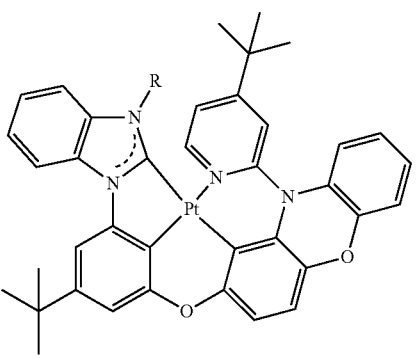
Structures 6
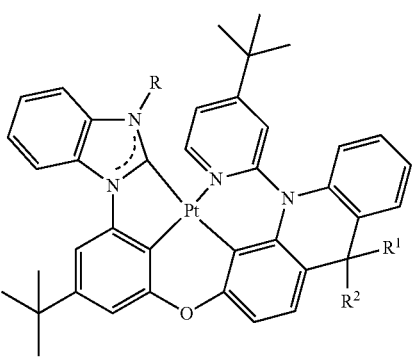
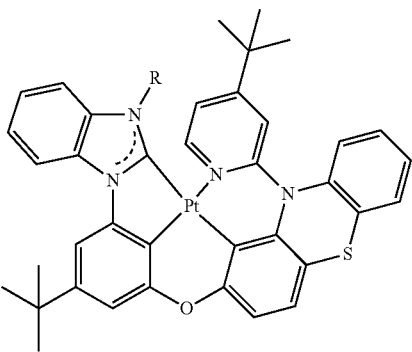
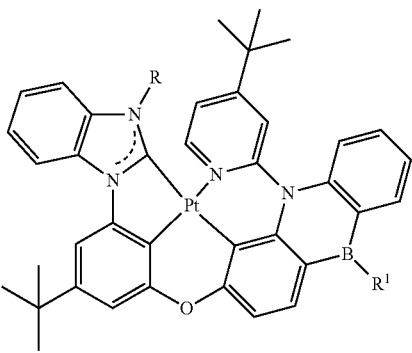

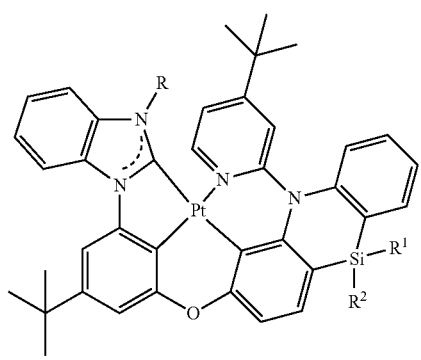

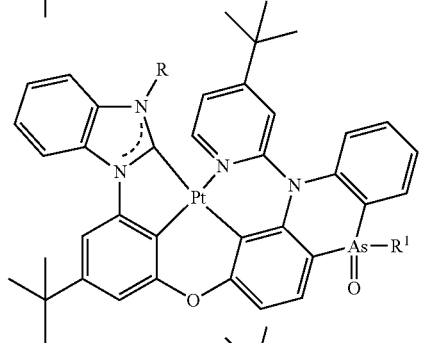
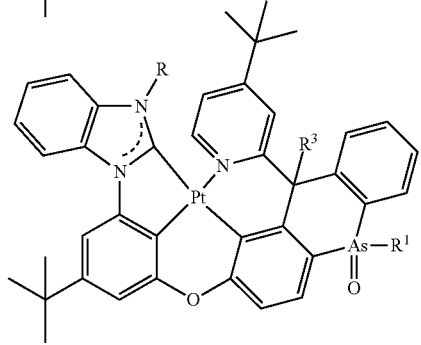
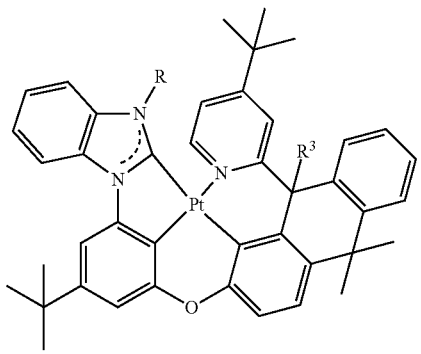
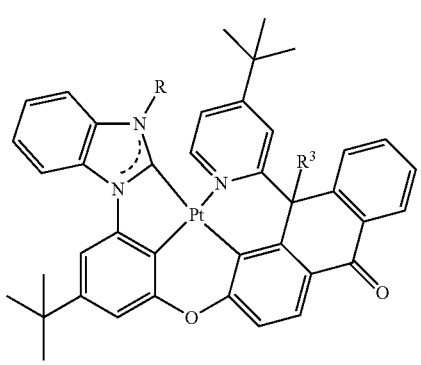
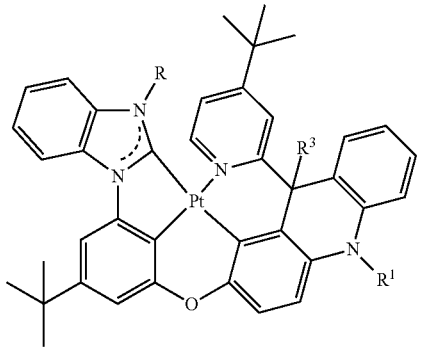
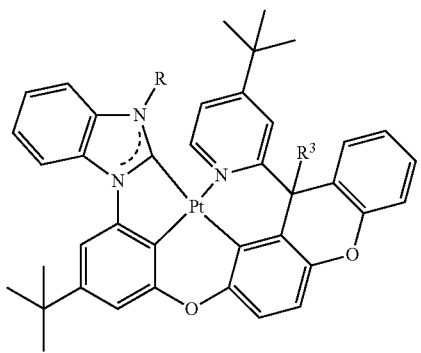

101
-continued
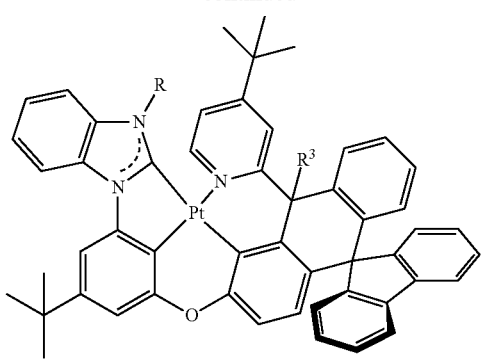
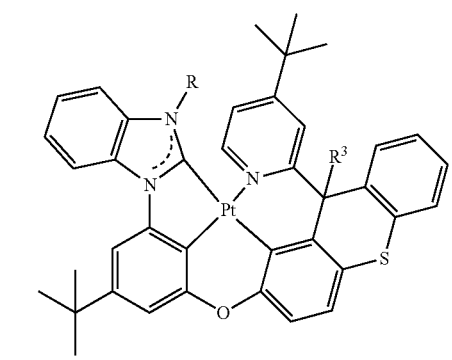
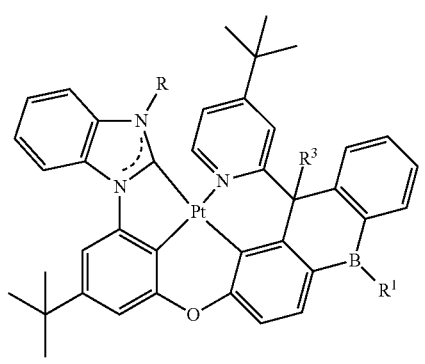
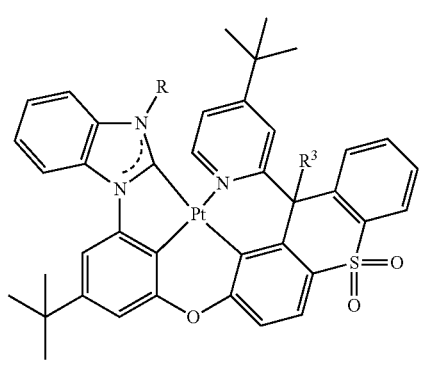
102
-continued
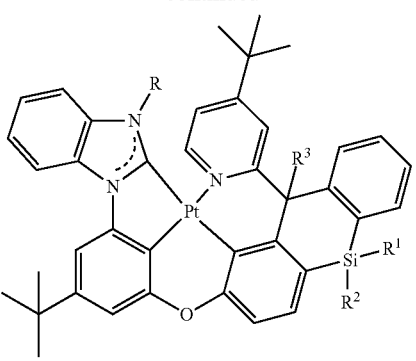
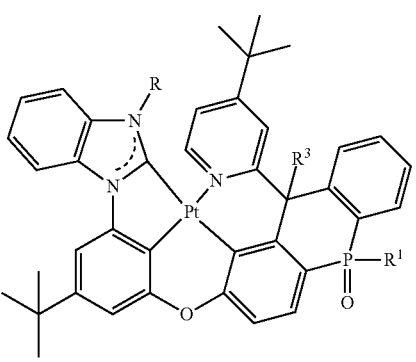
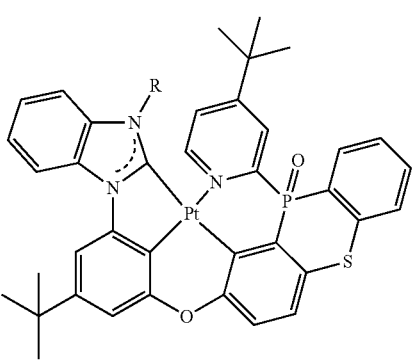
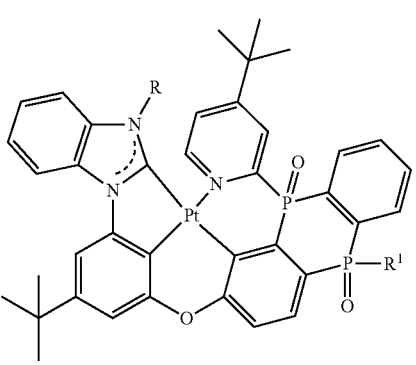

Structures 7
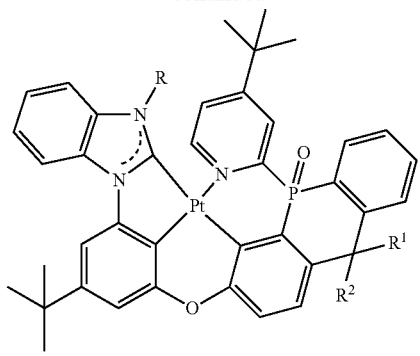
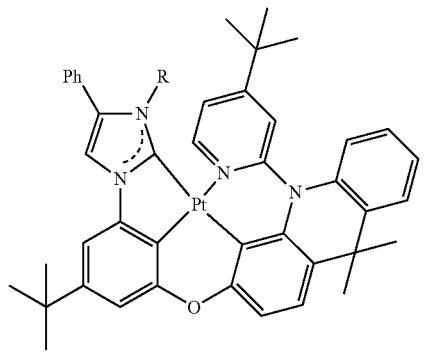
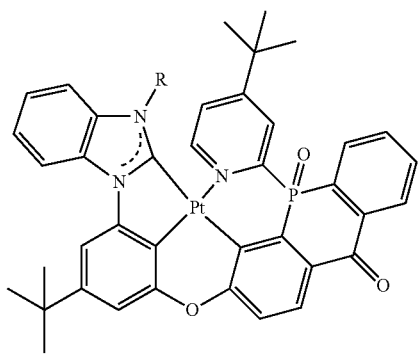
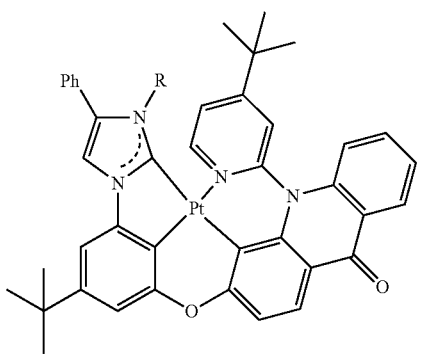
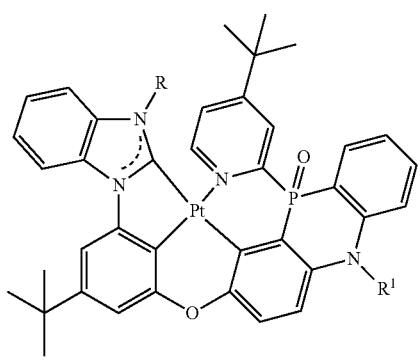
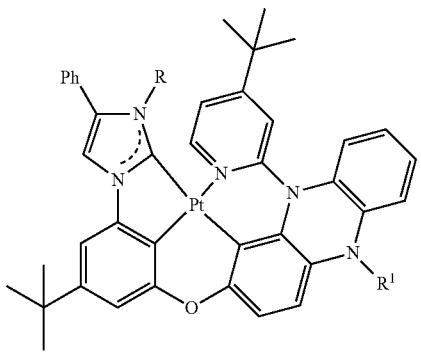
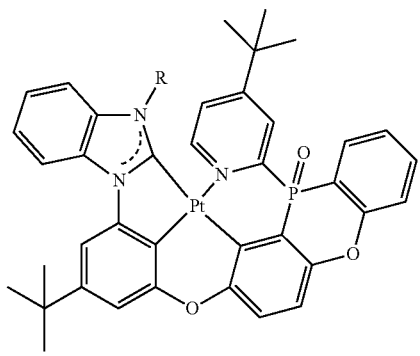

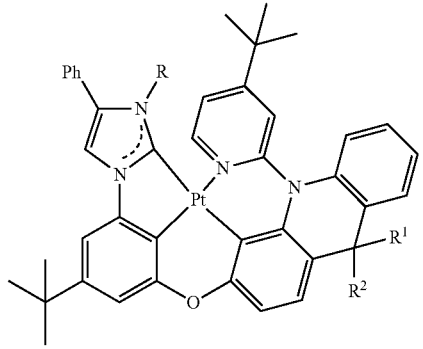
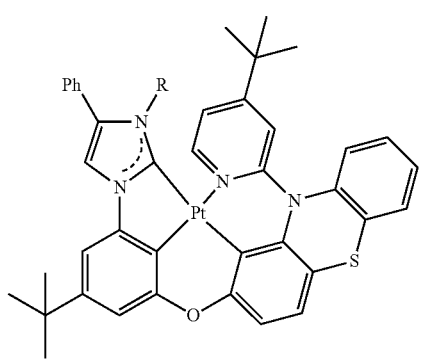
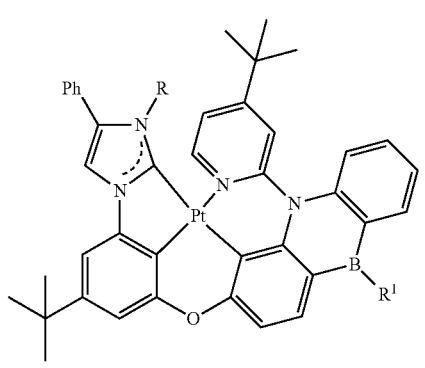
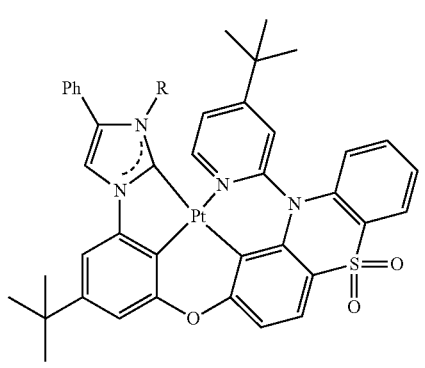
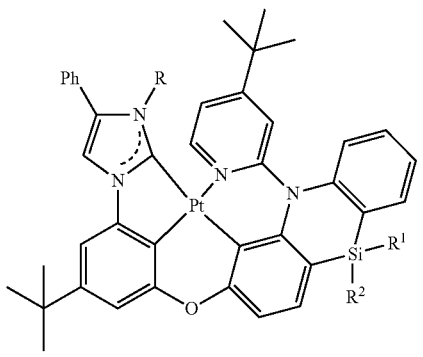
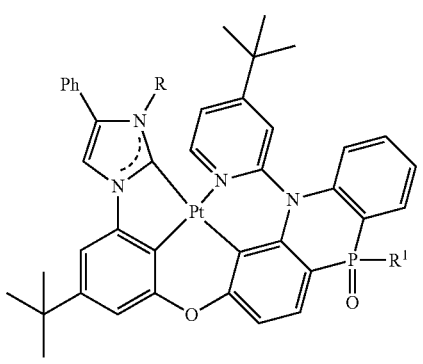
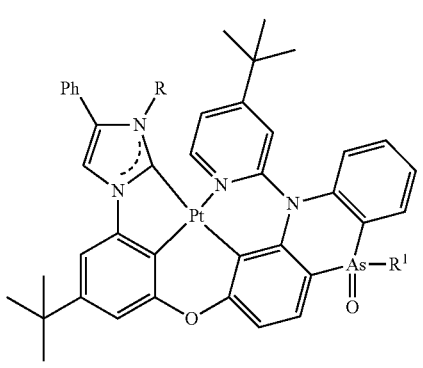
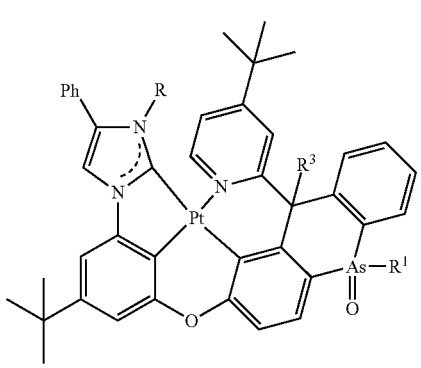

107
-continued
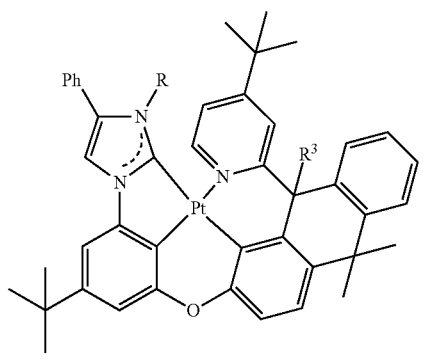
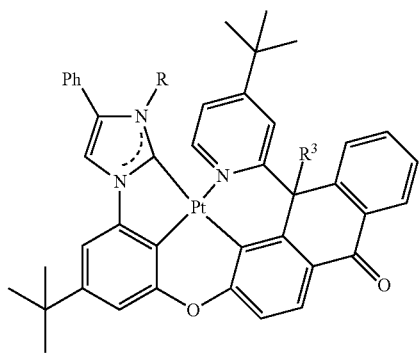
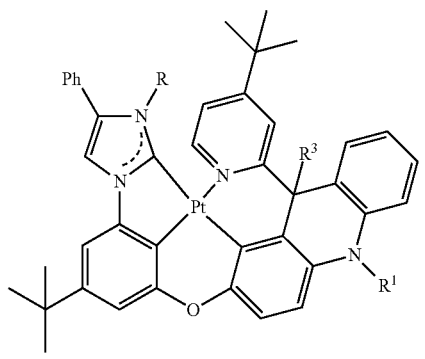
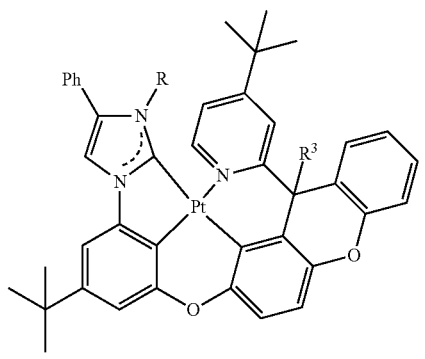
108
-continued
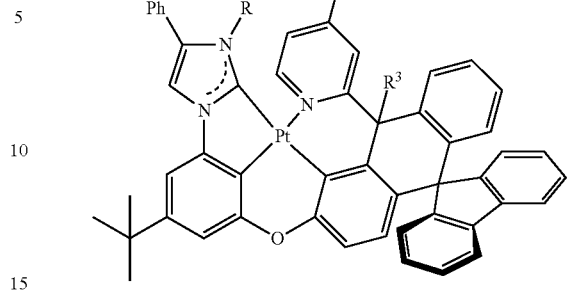
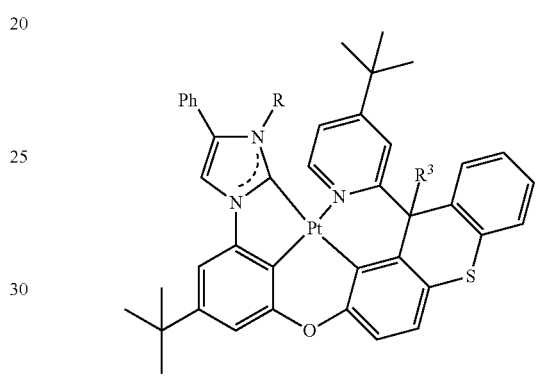
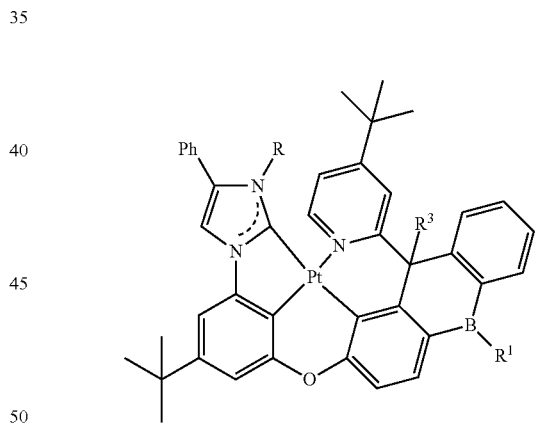
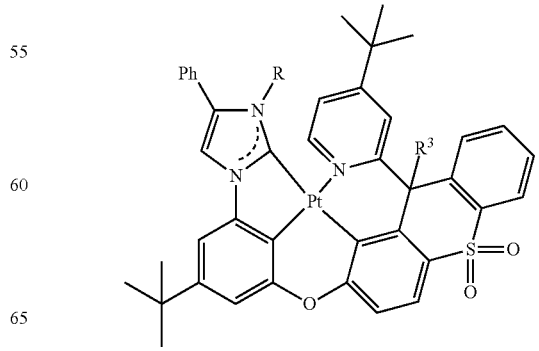

109
-continued
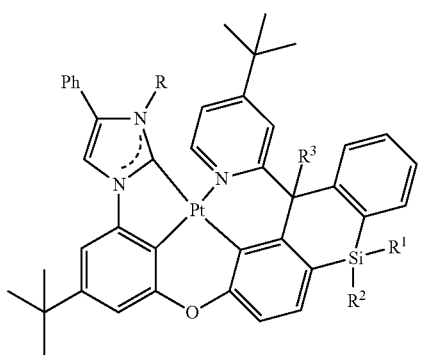
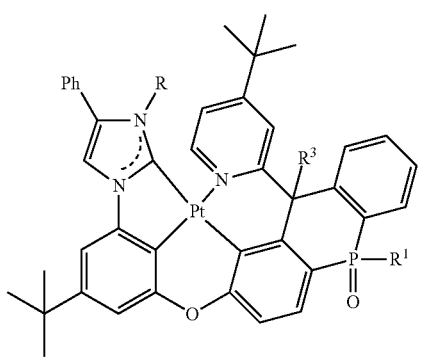
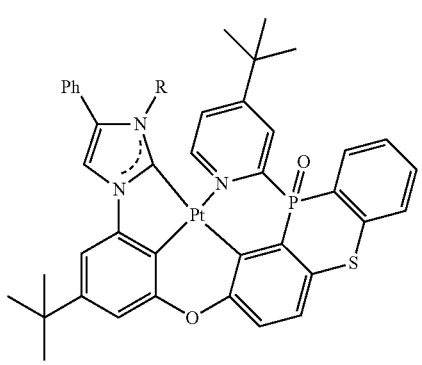
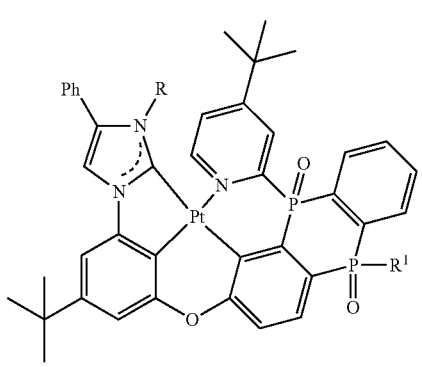
110
-continued
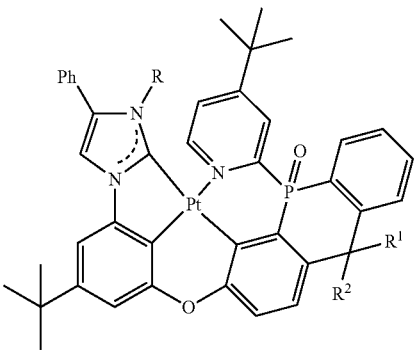
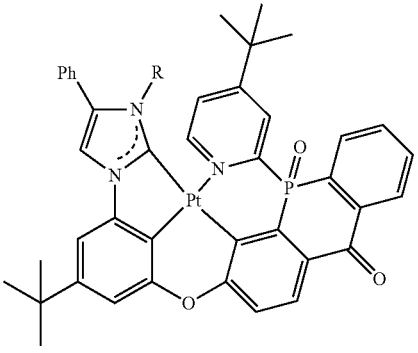
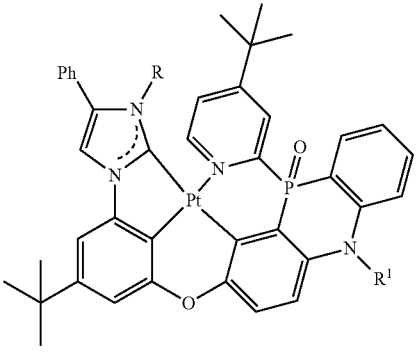
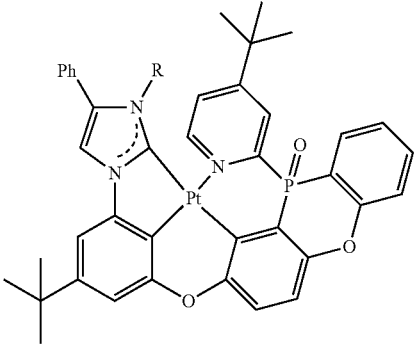

Structures 8
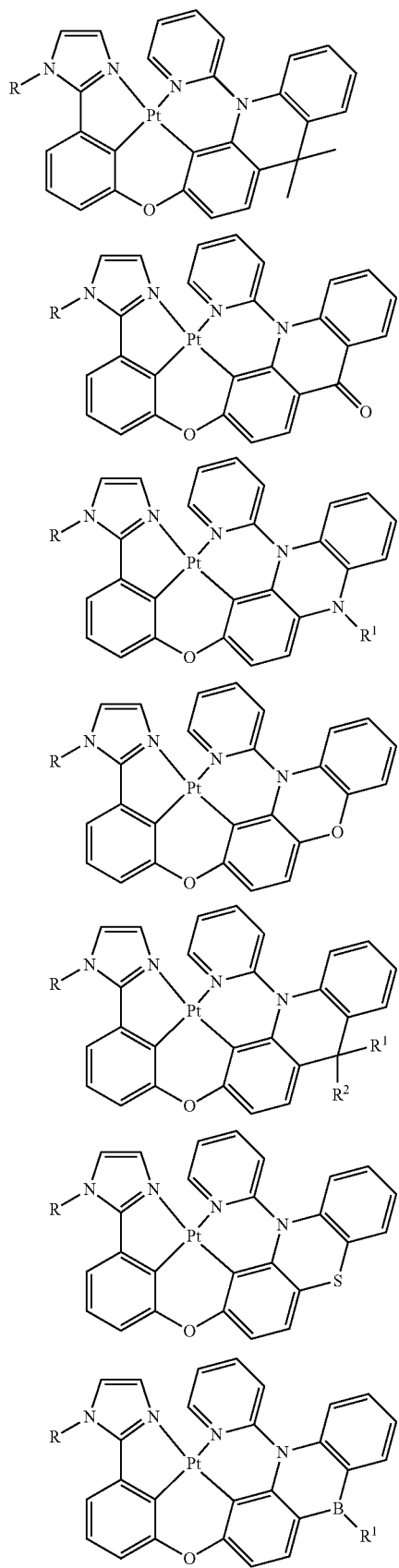
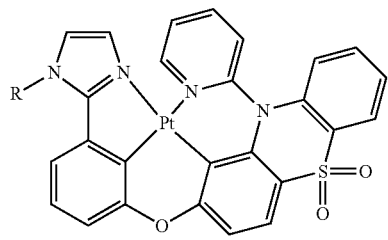
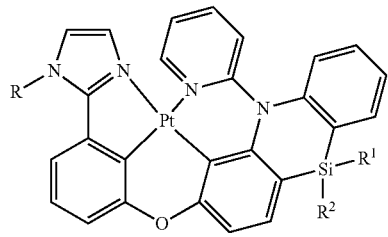
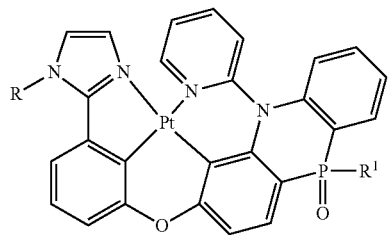
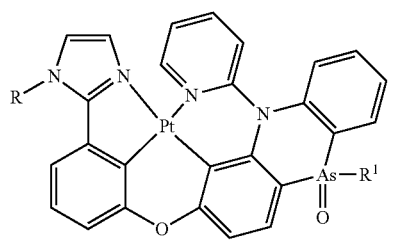
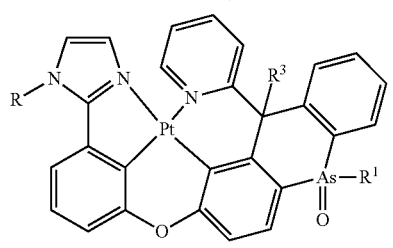
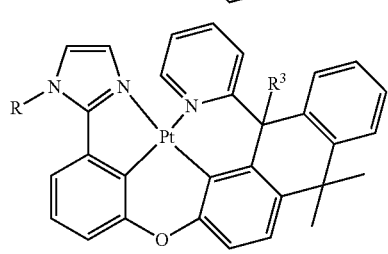
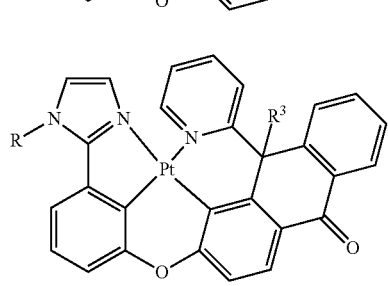

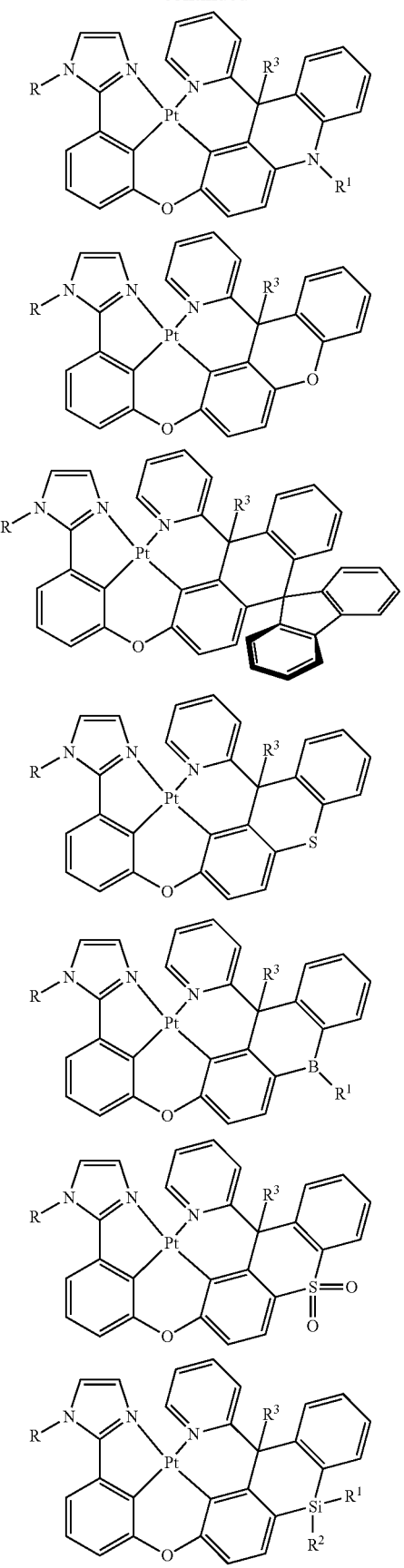
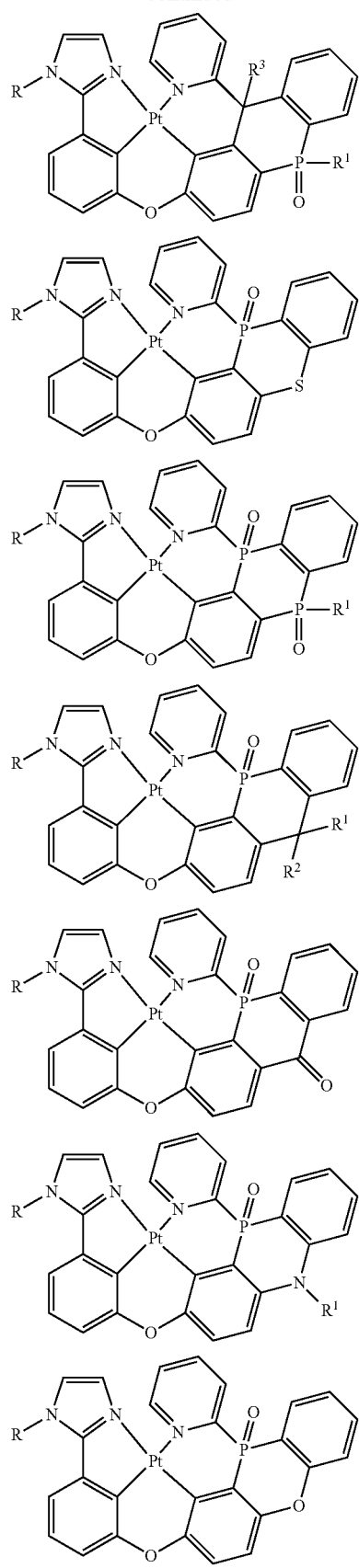

Structures 9
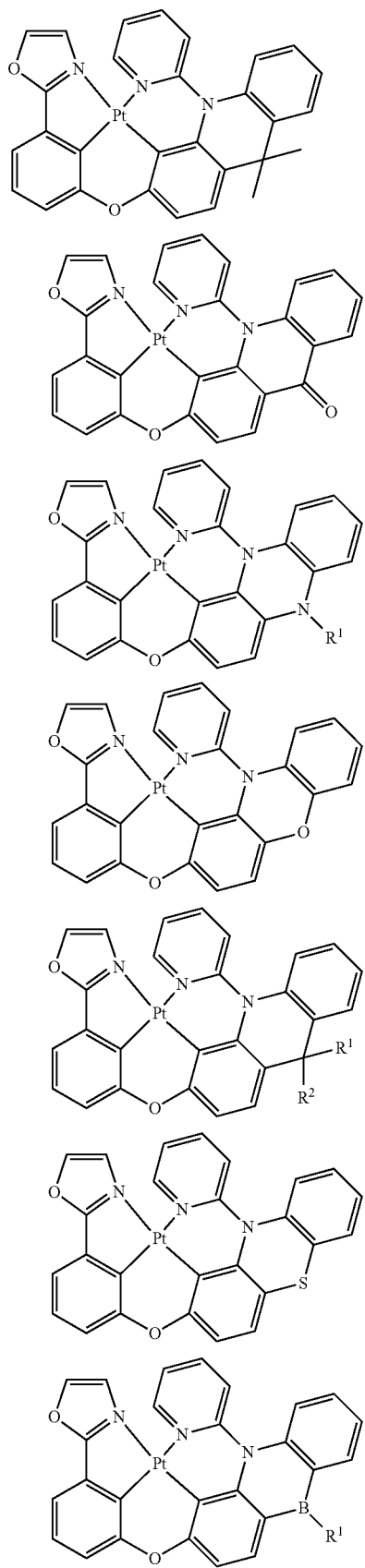
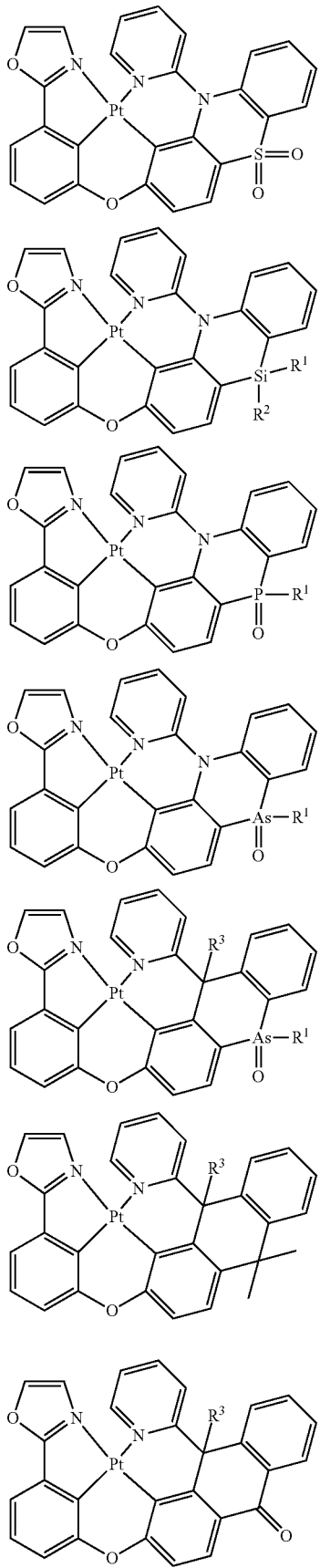

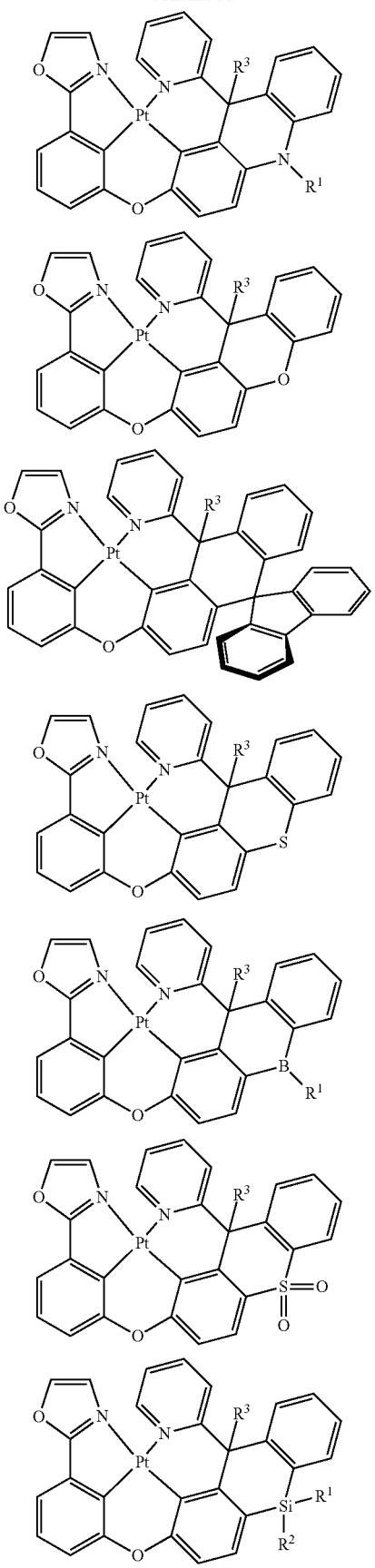
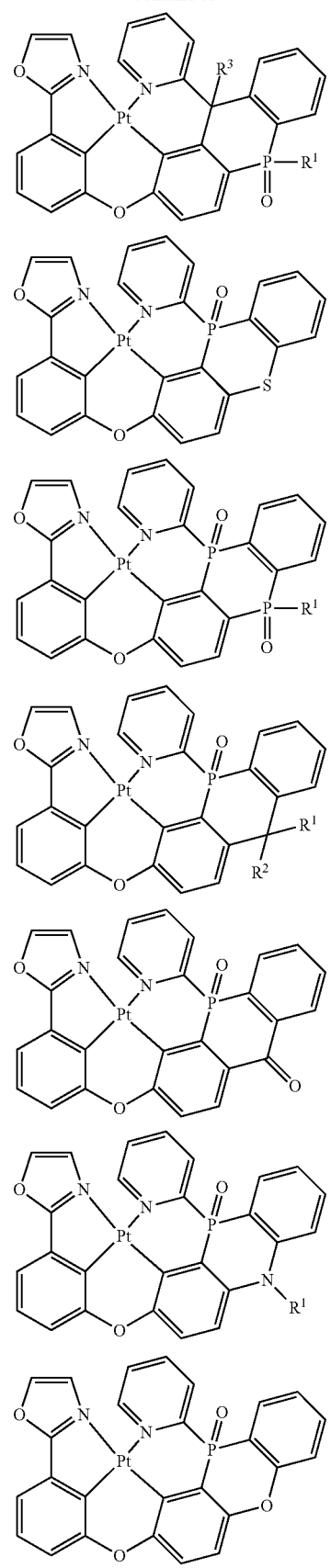

Structures 10
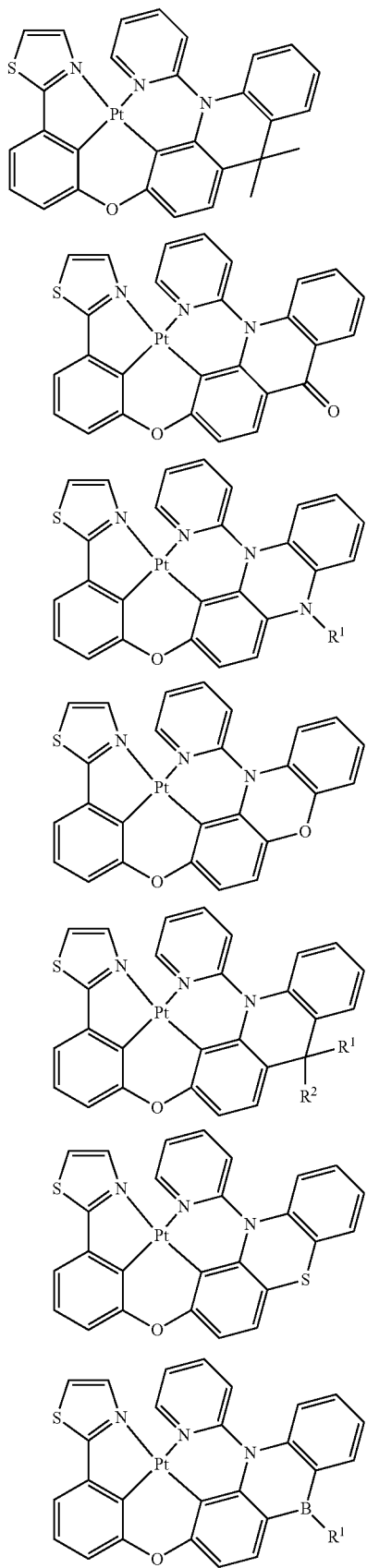

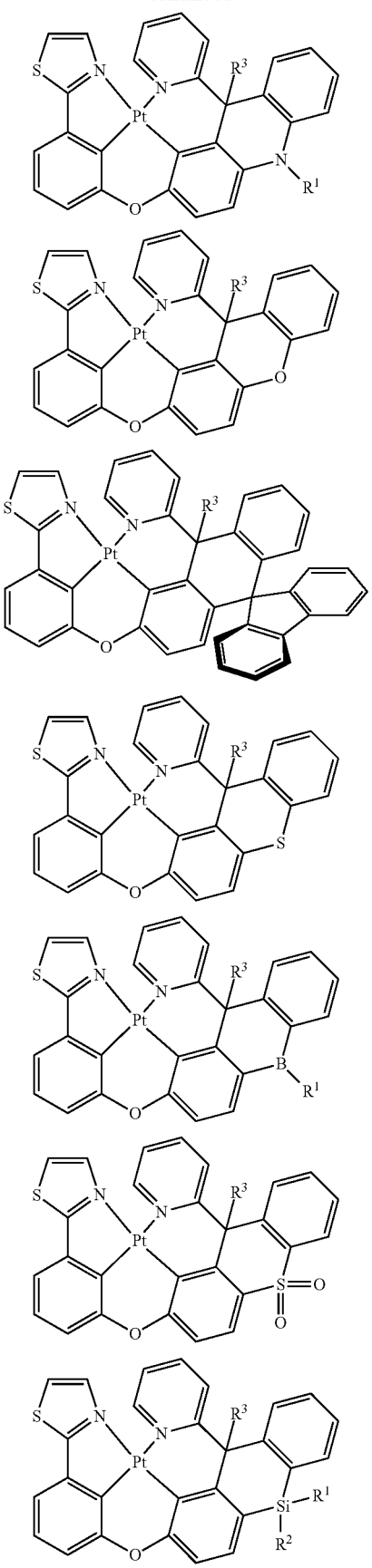
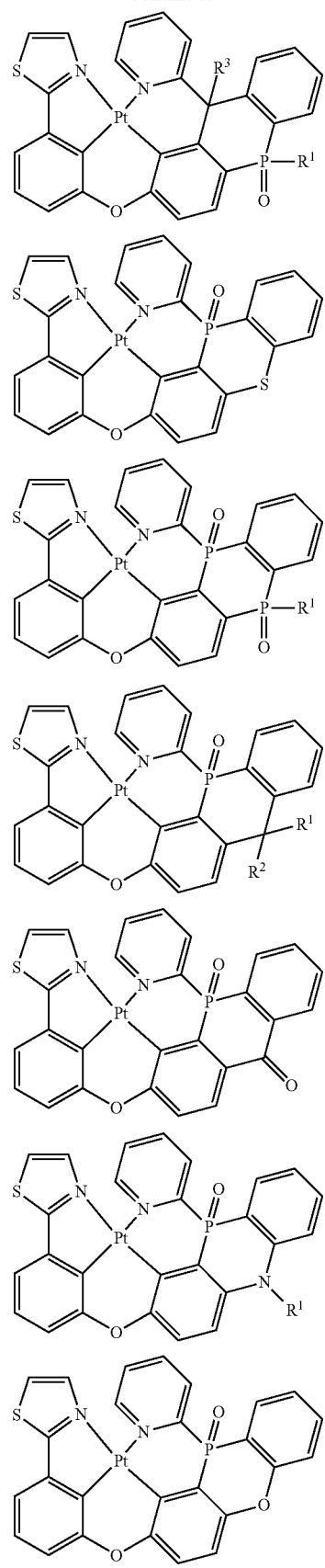

Structures 11
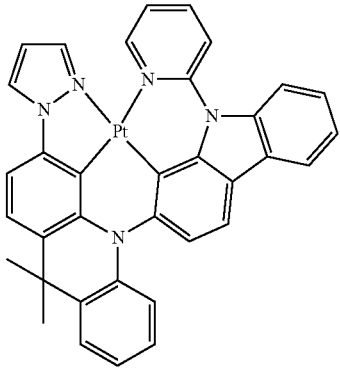
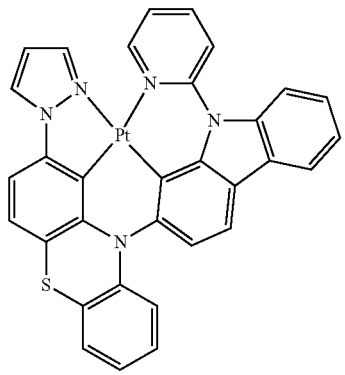
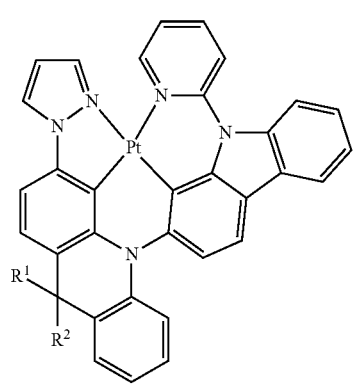
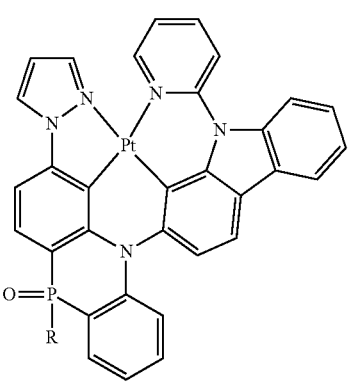
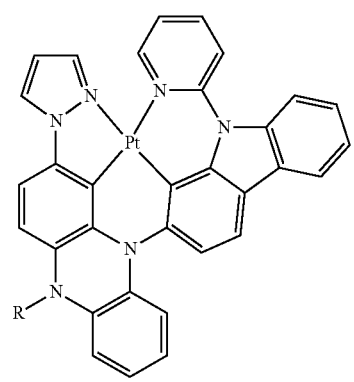
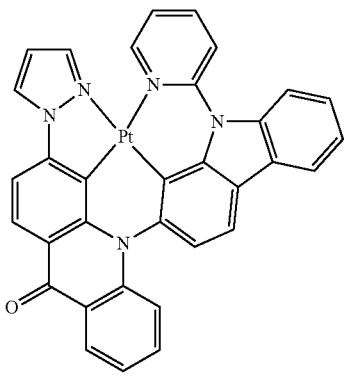
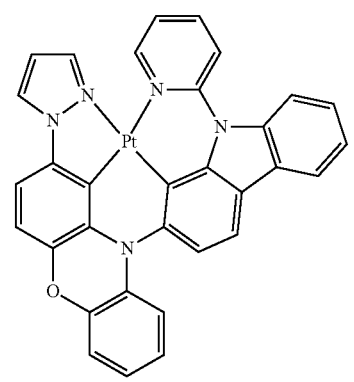
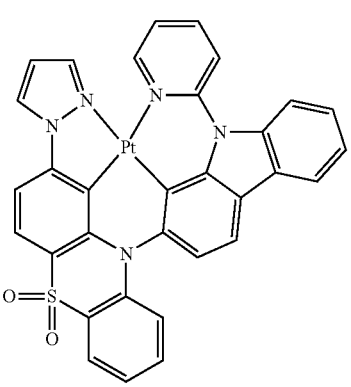

125
-continued
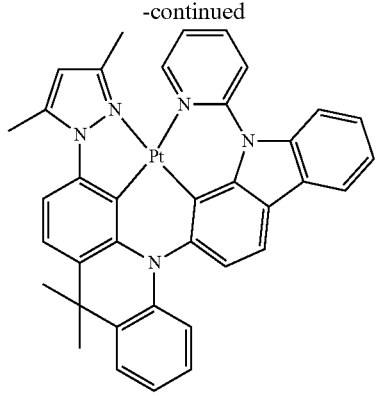
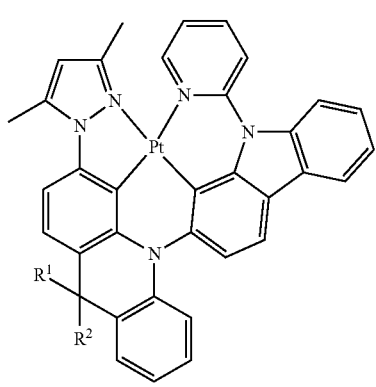
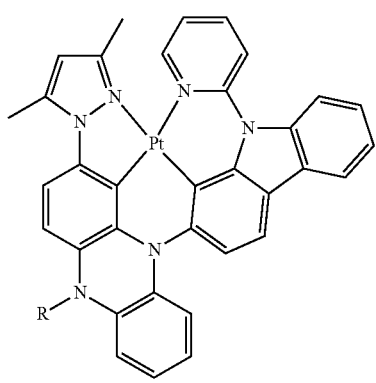
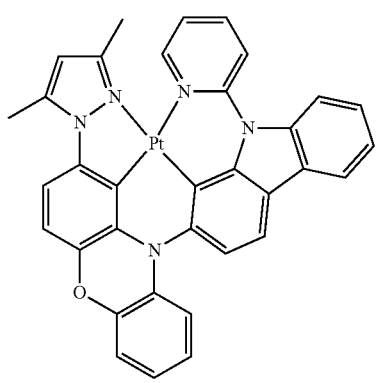
126
-continued
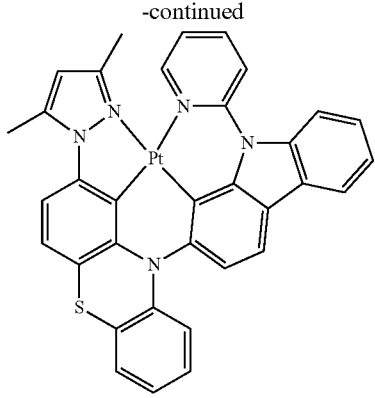
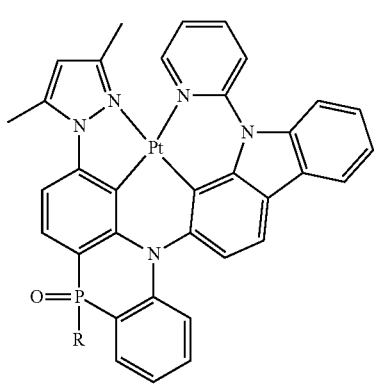
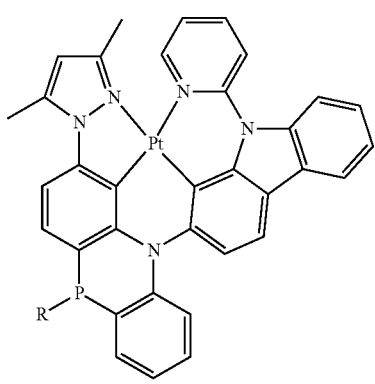
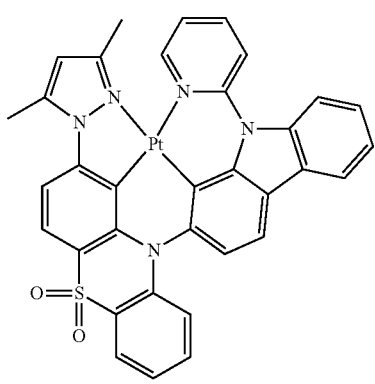

127
-continued
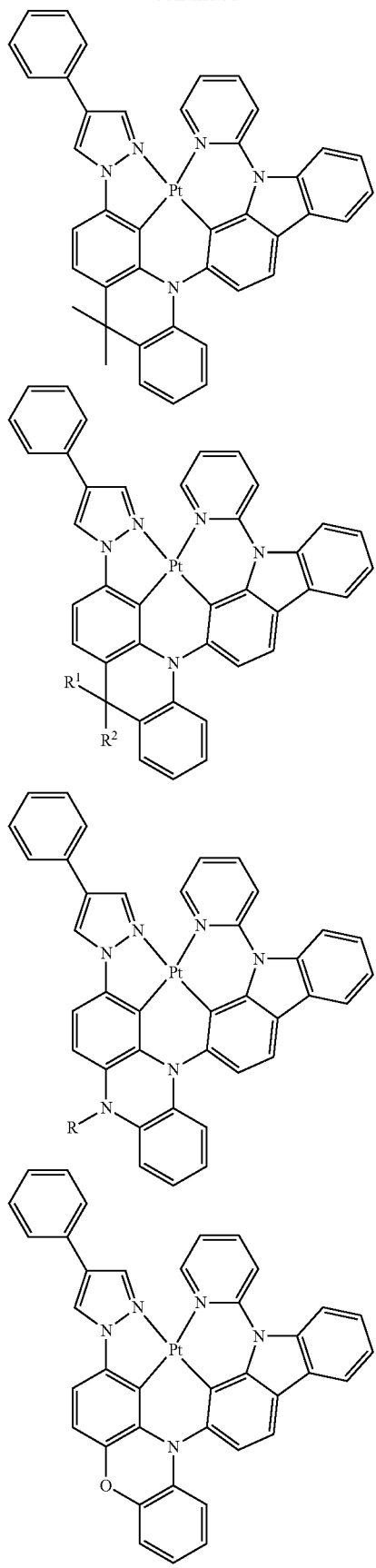
128
-continued
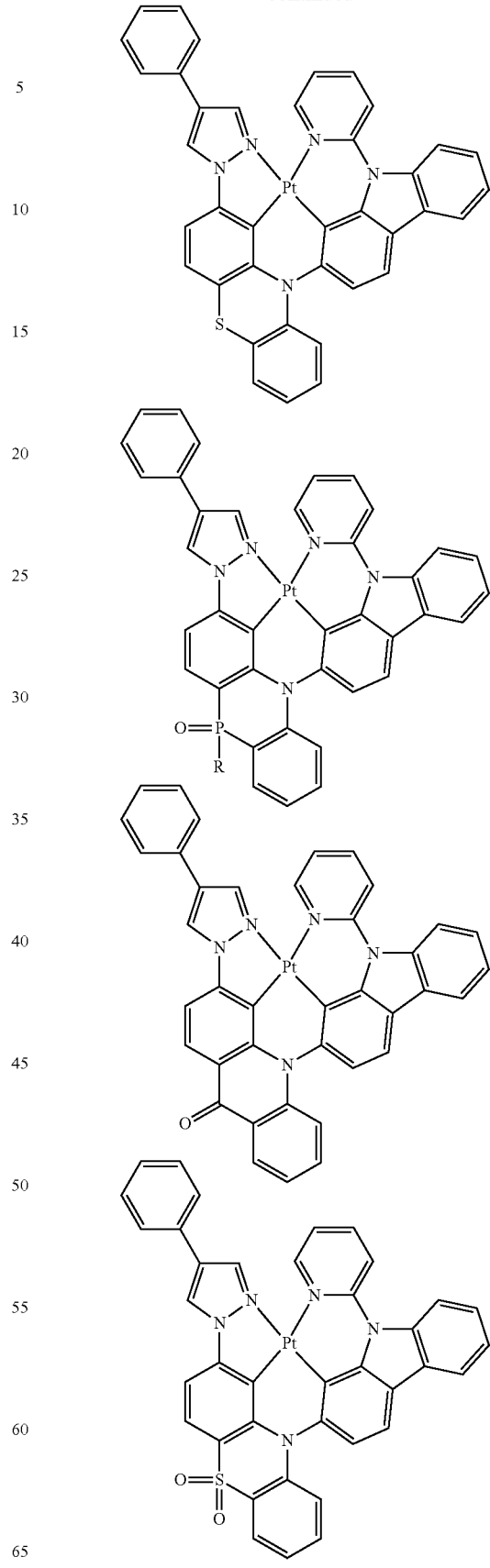

Structures 12
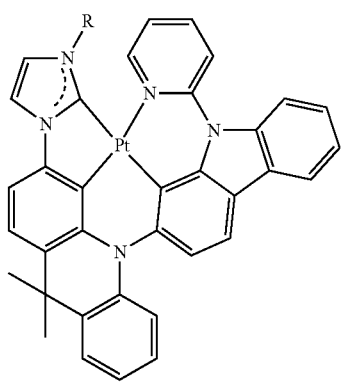
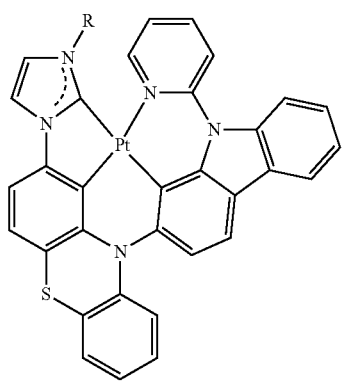
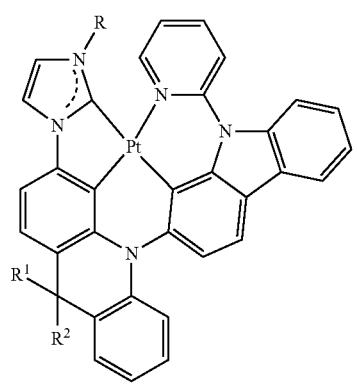
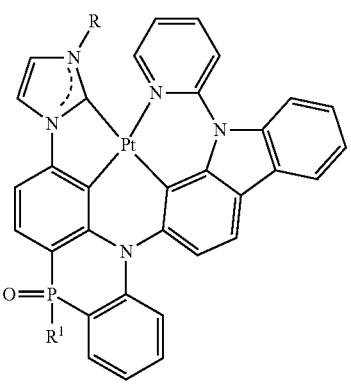
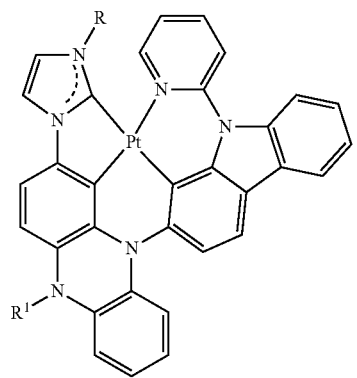
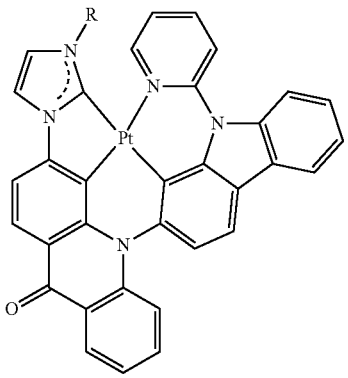
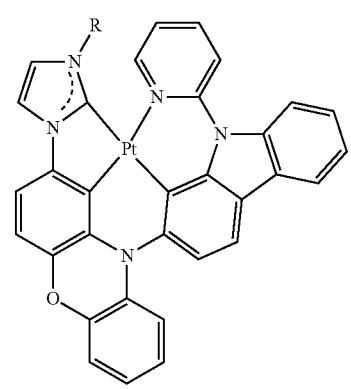
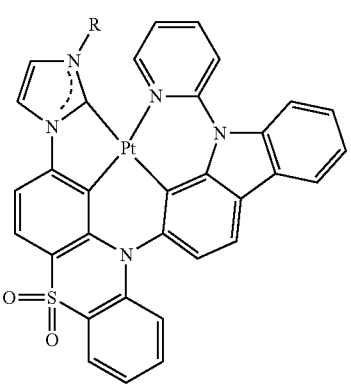

131
-continued
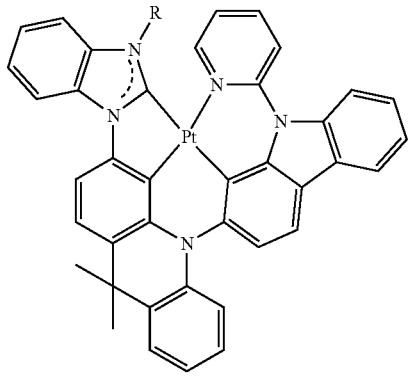
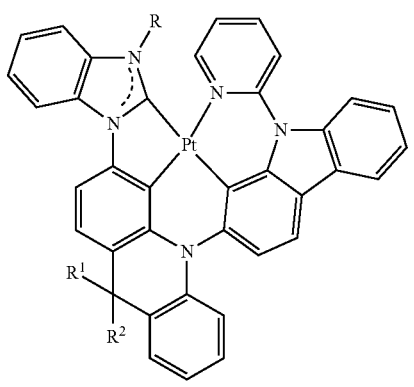
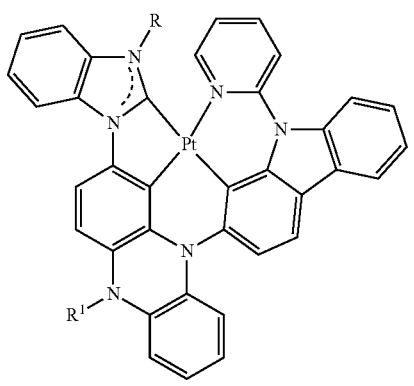
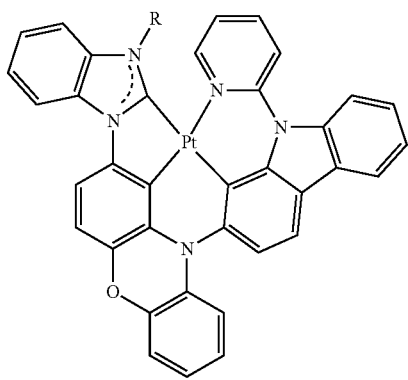
132
-continued
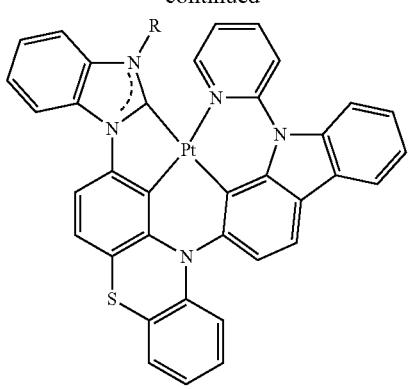
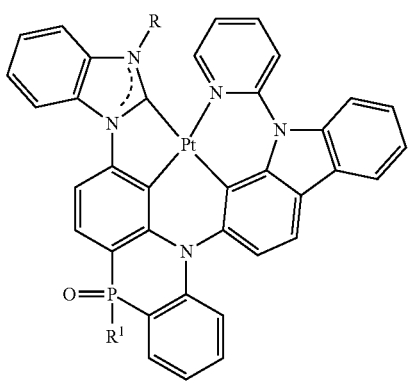
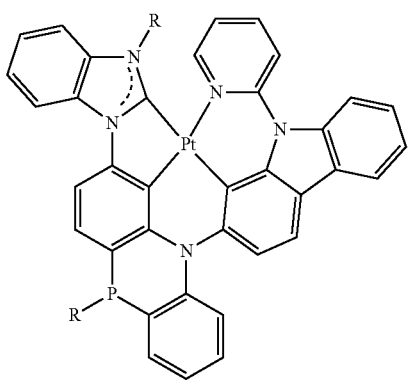
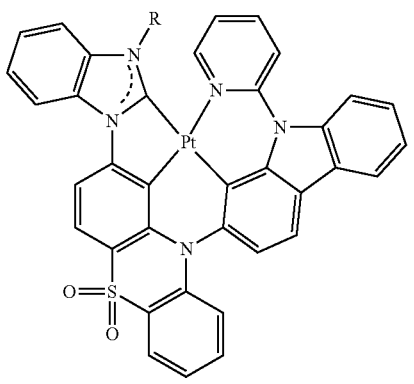

133
-continued
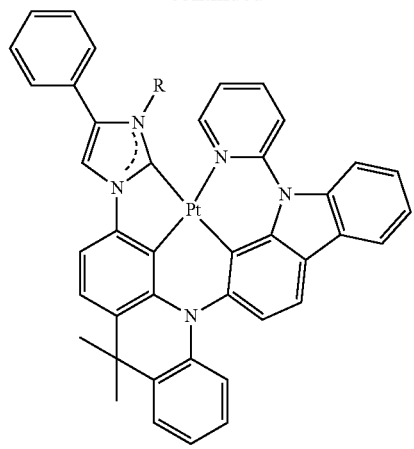
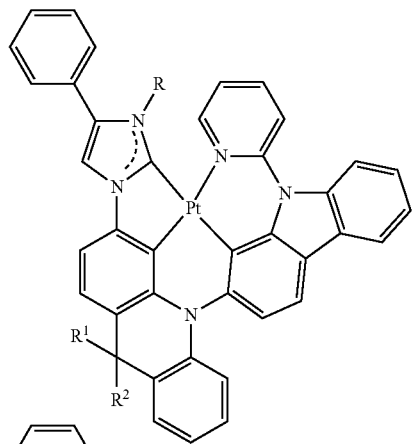
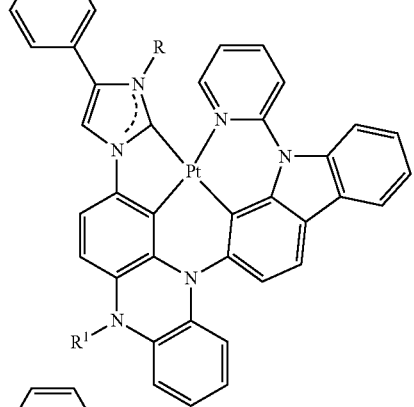
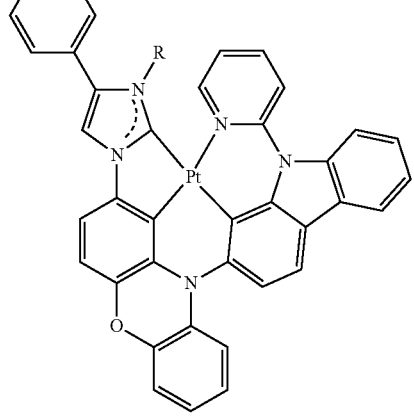
134
-continued
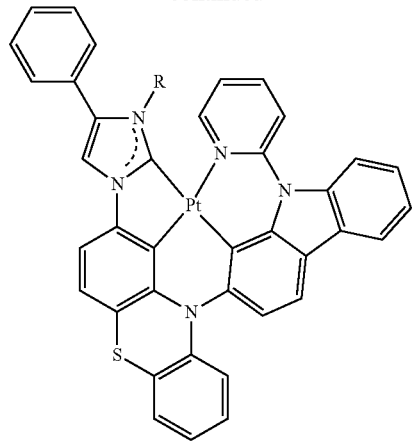
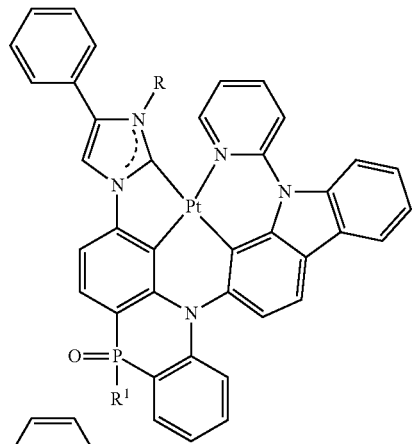
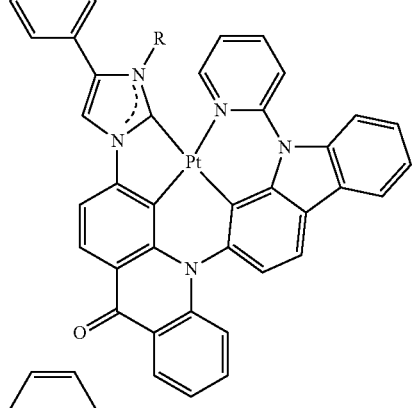
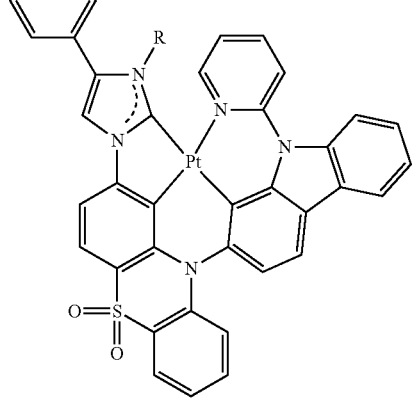

Structures 13
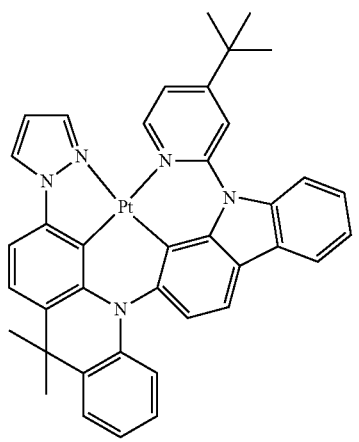
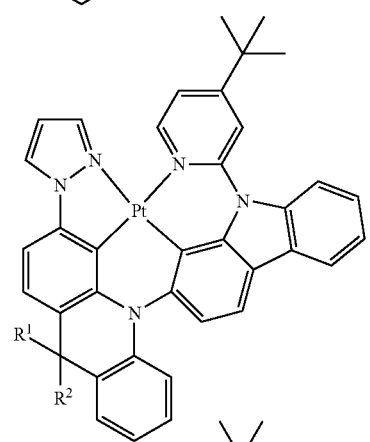
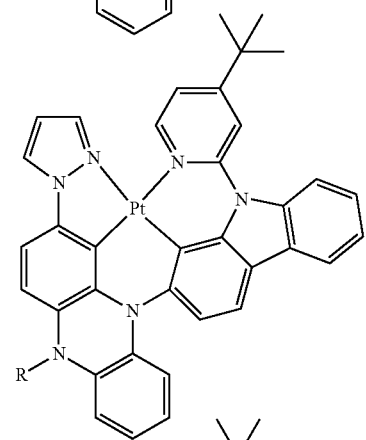
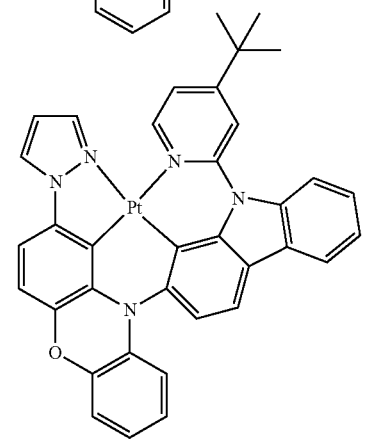
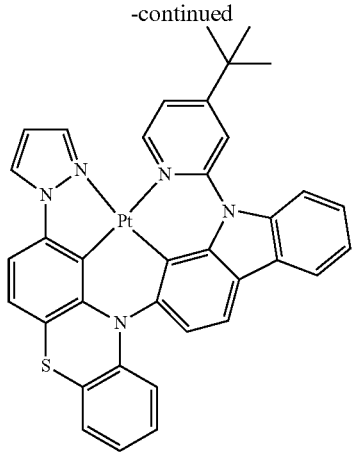
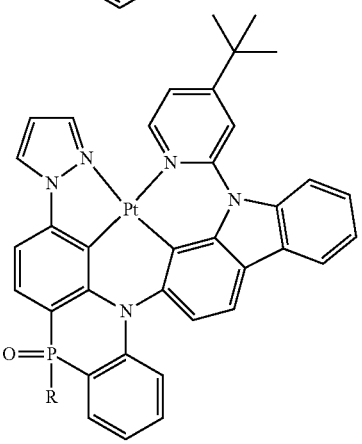
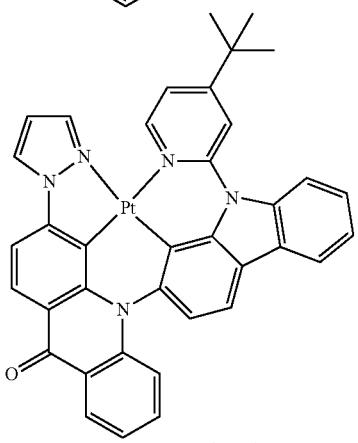
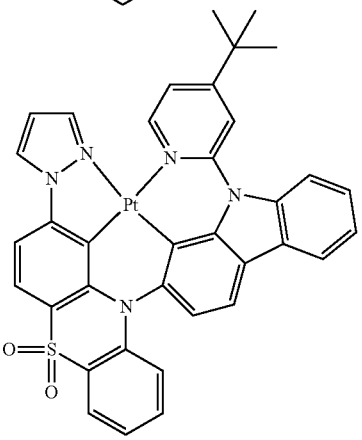

137
-continued
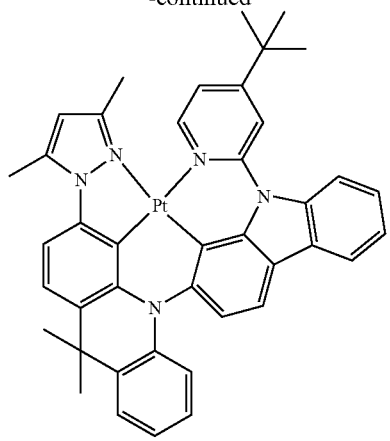
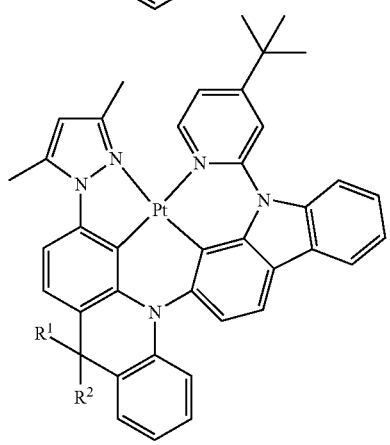
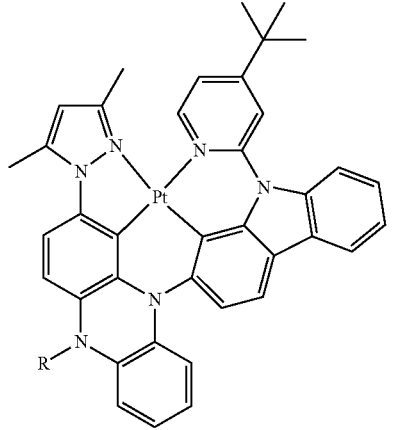
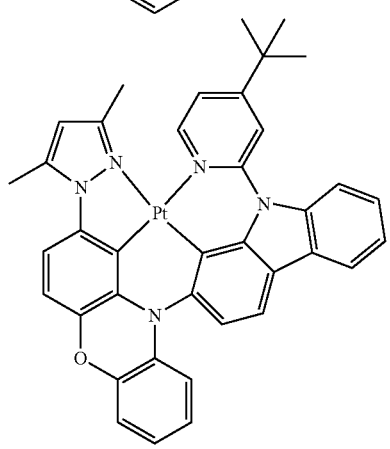
138
-continued
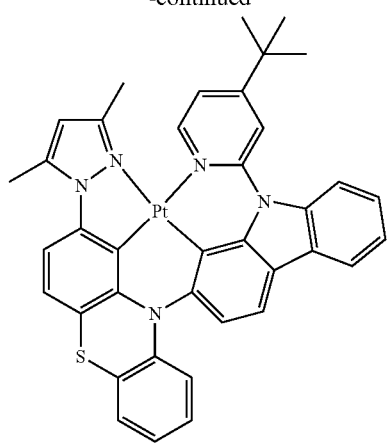
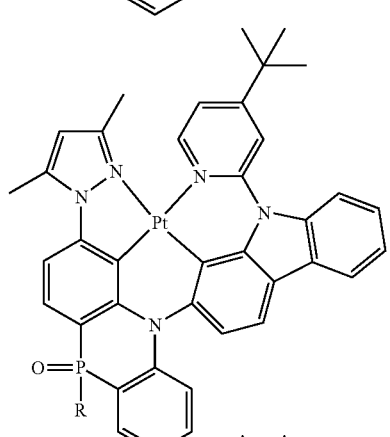

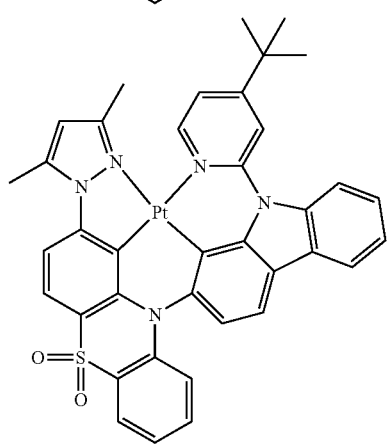

139
-continued
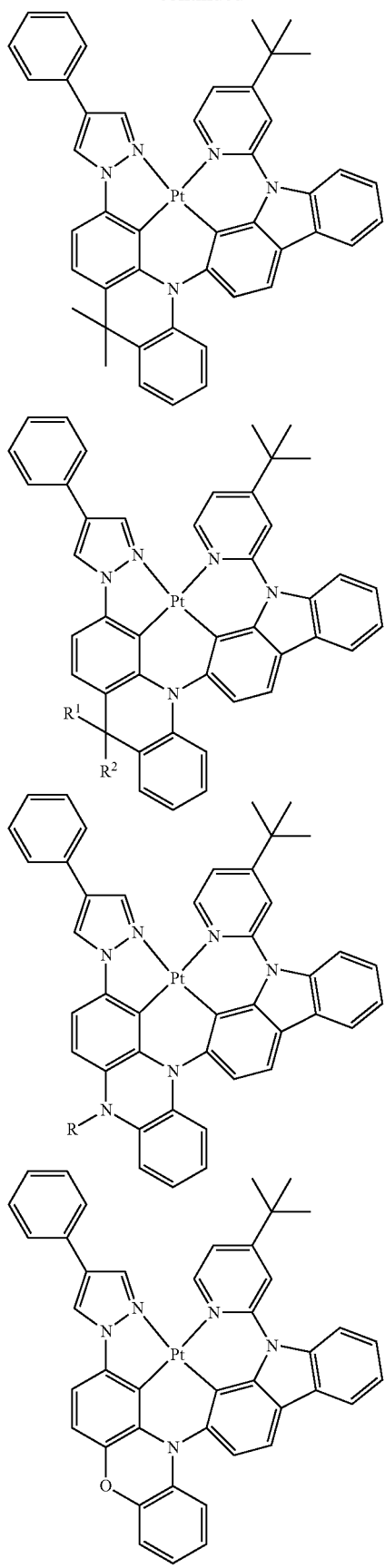
140
-continued
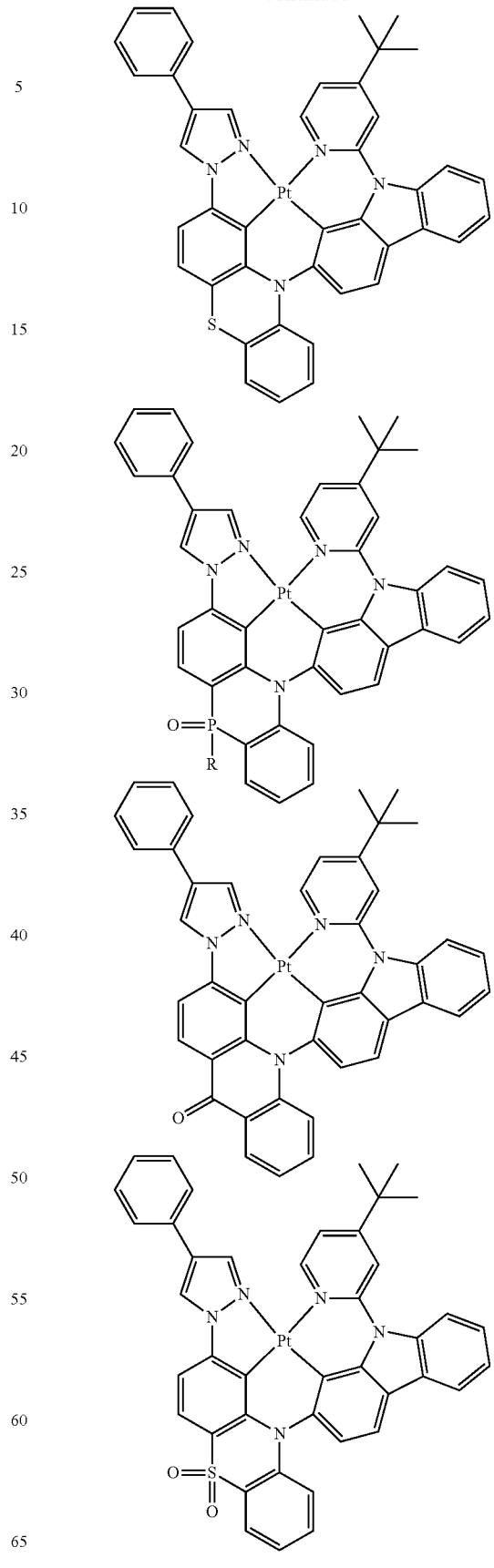

Structures 14
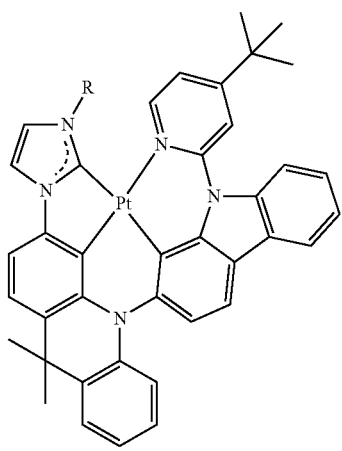
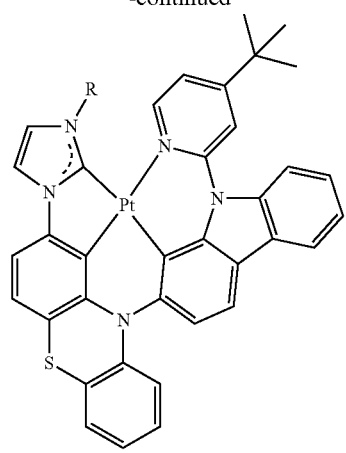
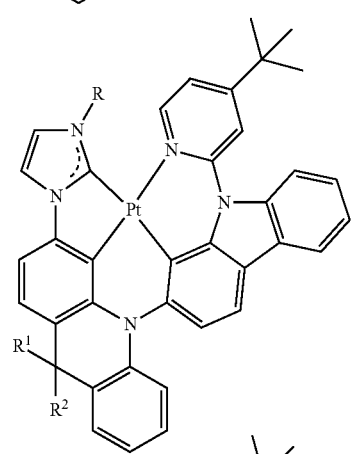
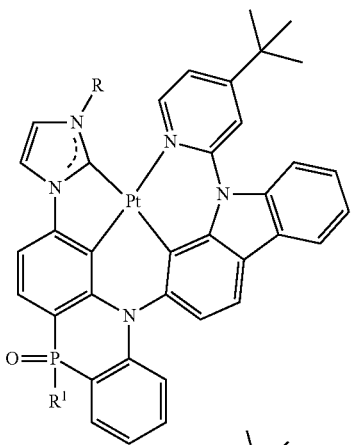
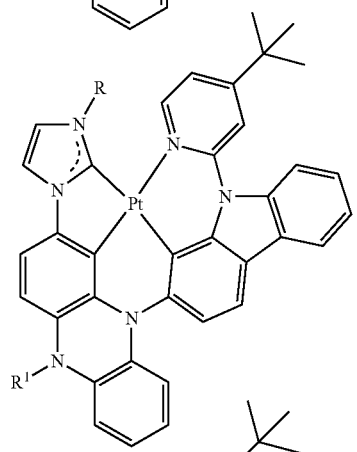
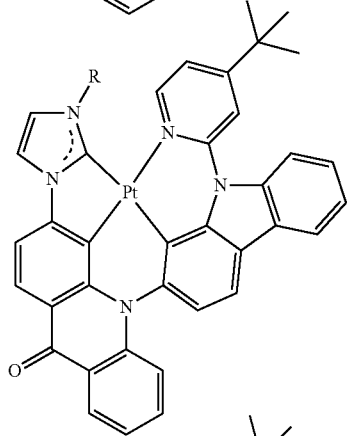
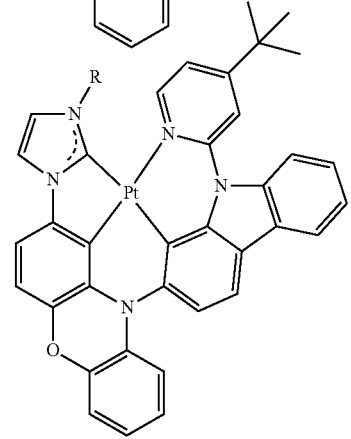
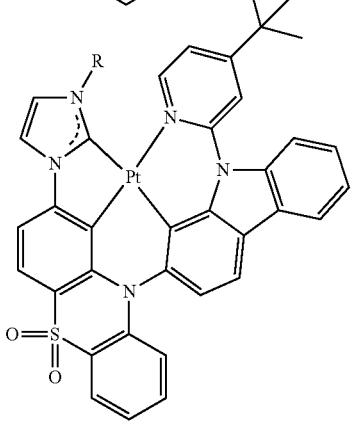

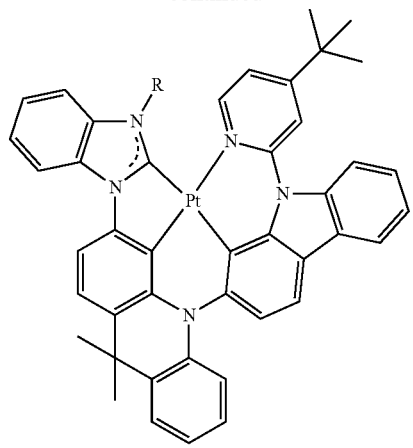
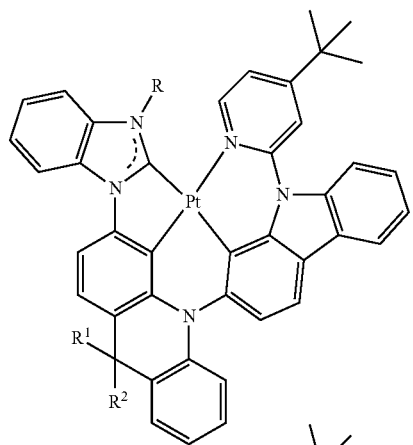
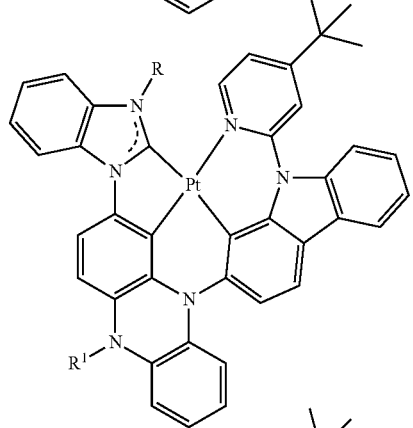
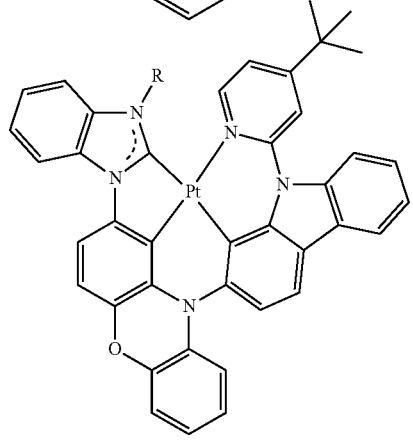
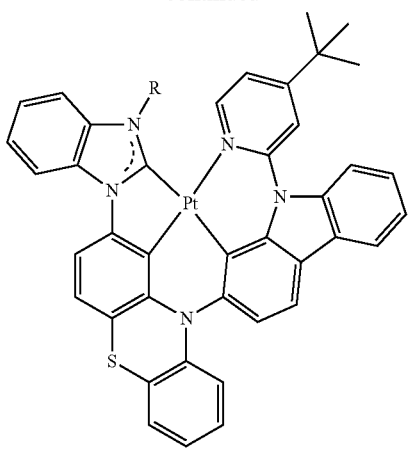
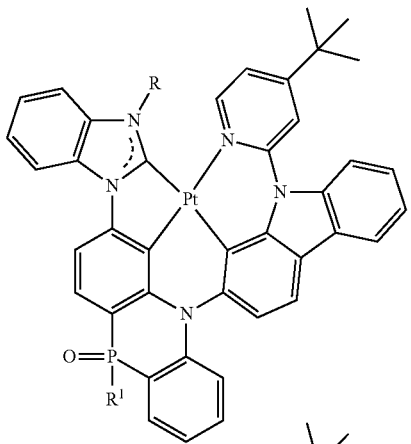
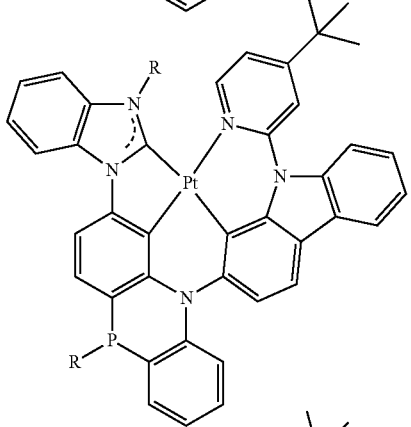
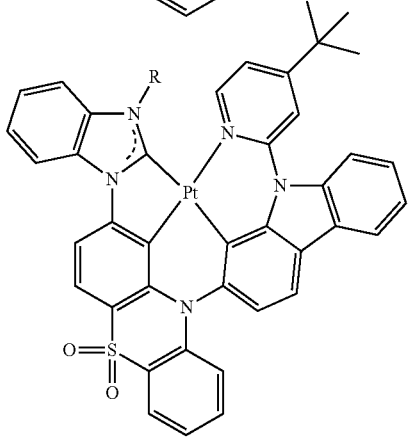

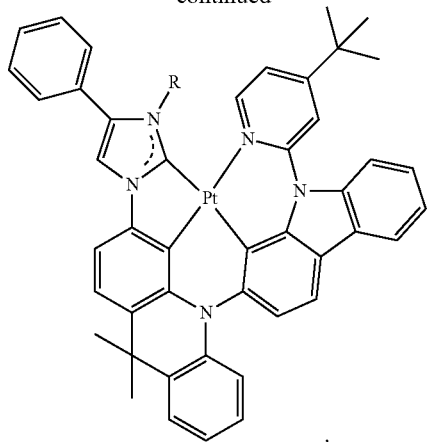
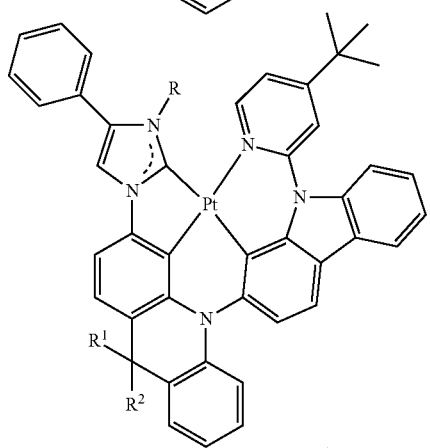
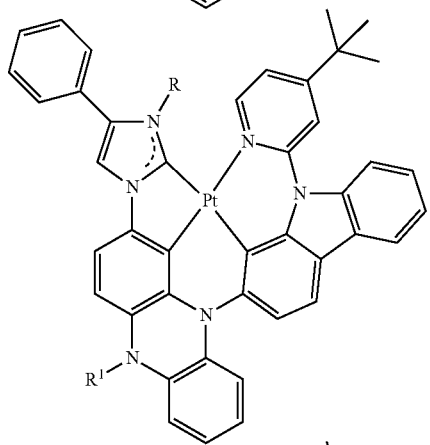
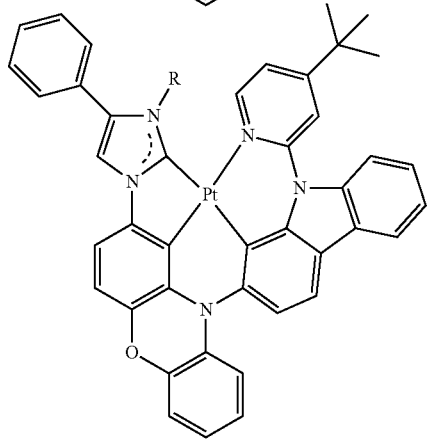
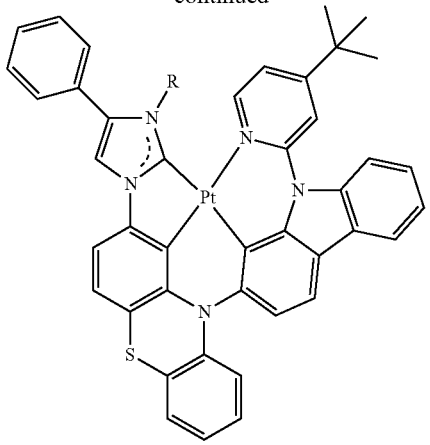
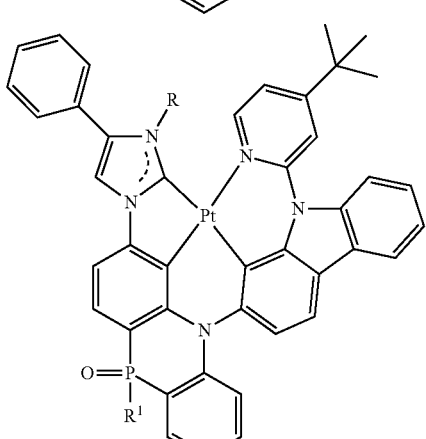
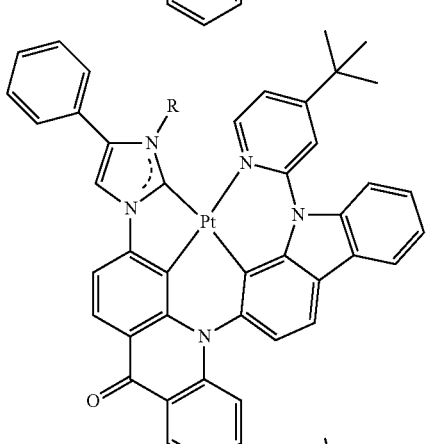
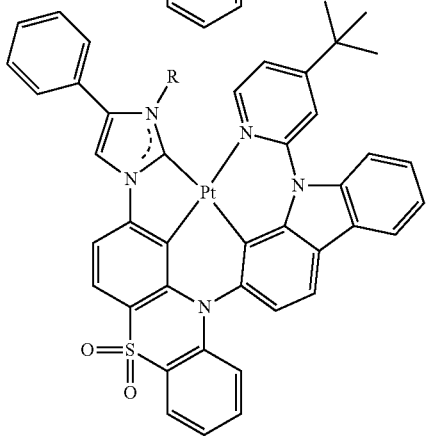

Structures 15
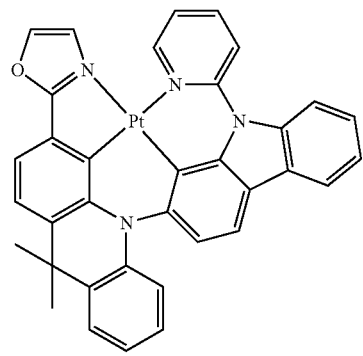
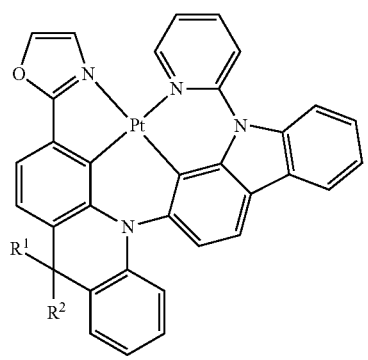
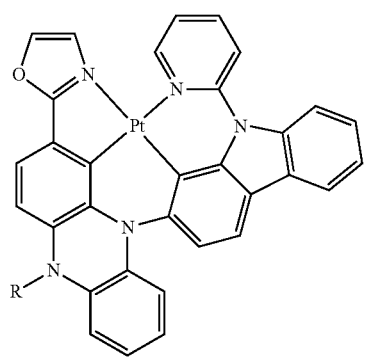
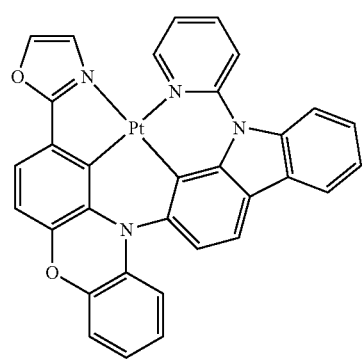
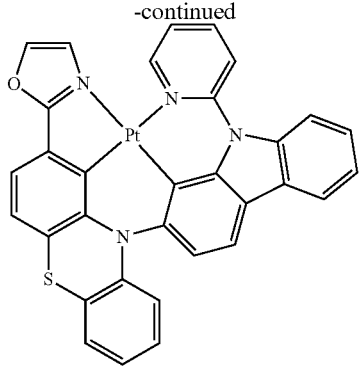
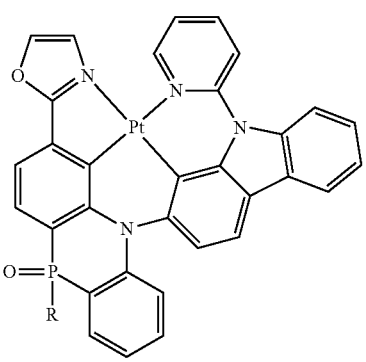
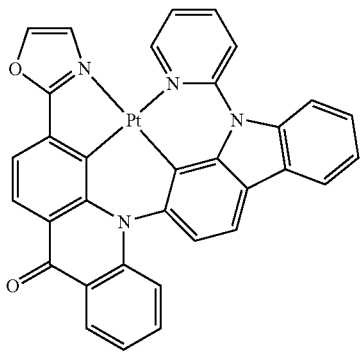
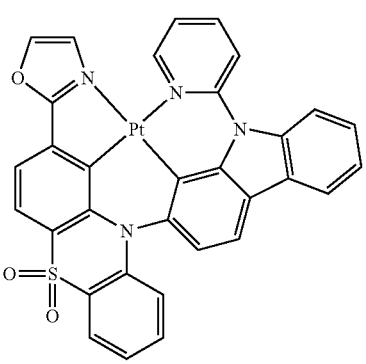

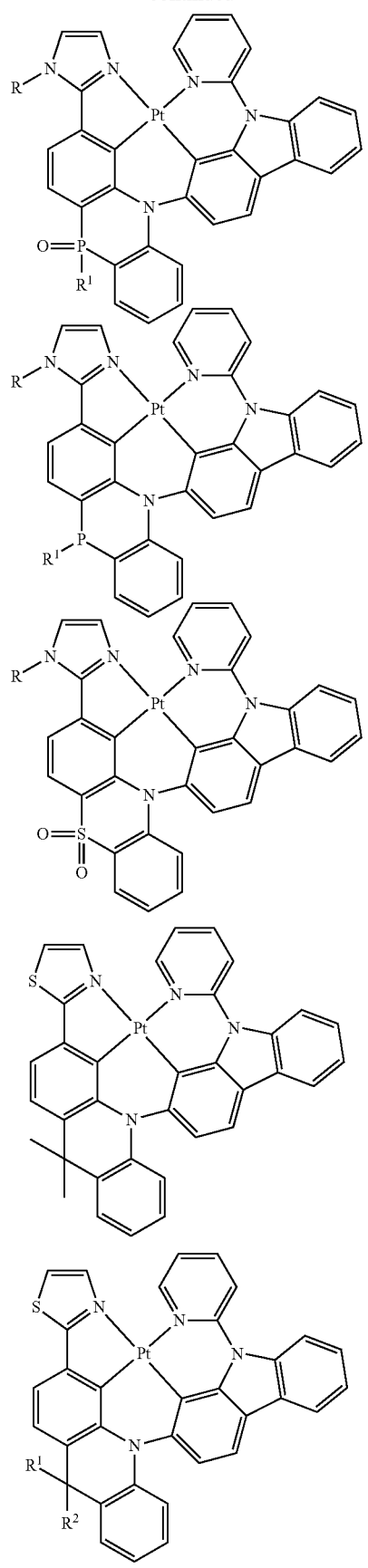

151
-continued
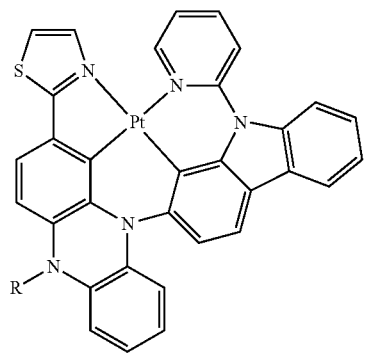
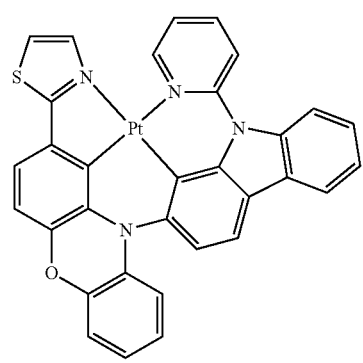
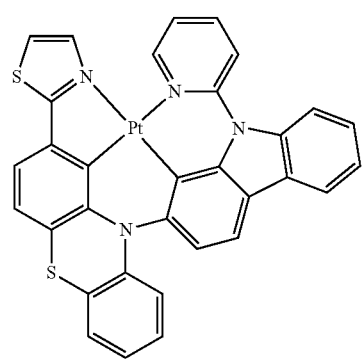
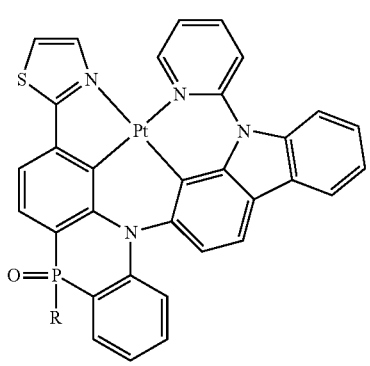
152
-continued
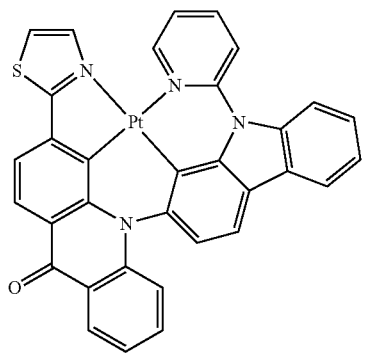
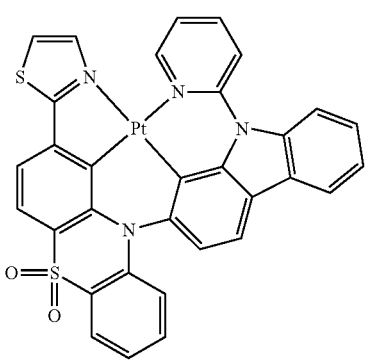
Structures 16
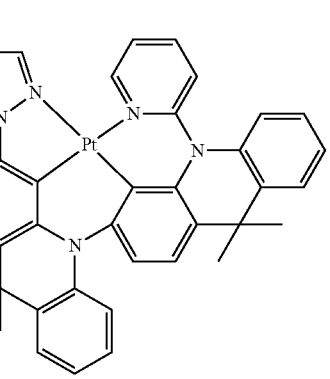
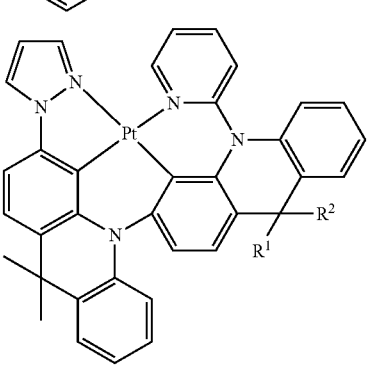

153
-continued
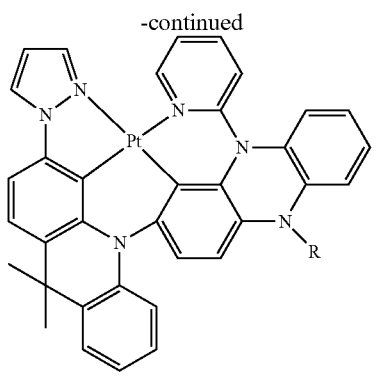
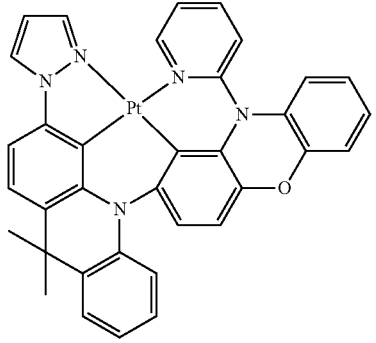
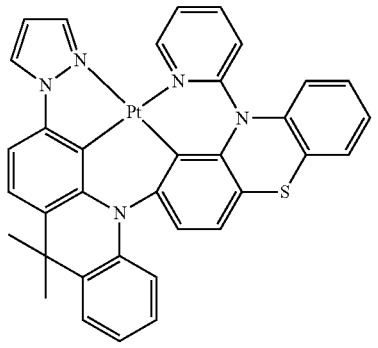
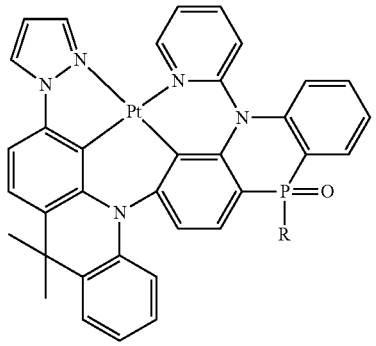
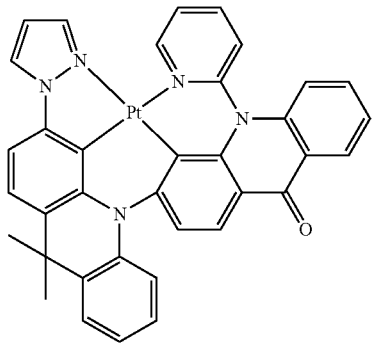
154
-continued
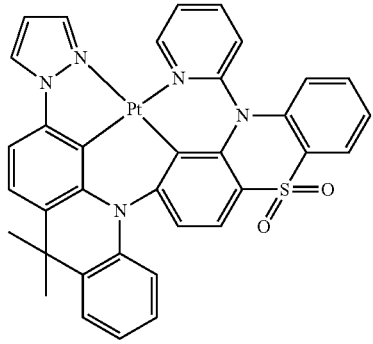
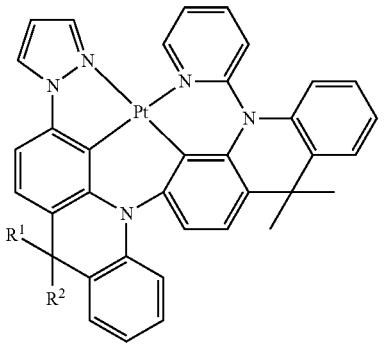
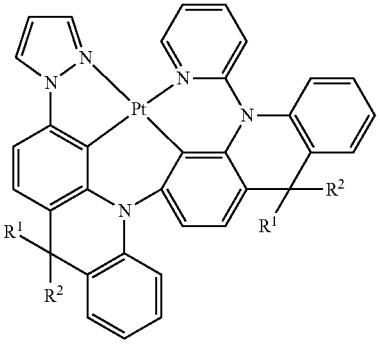
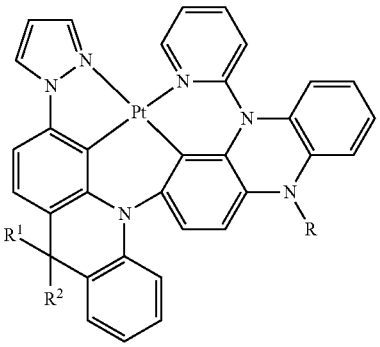
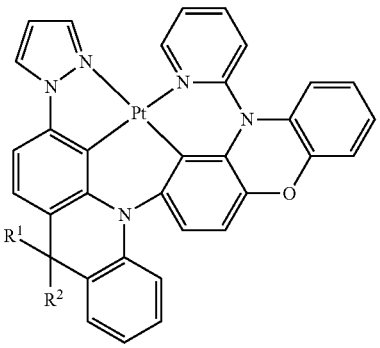

155
-continued
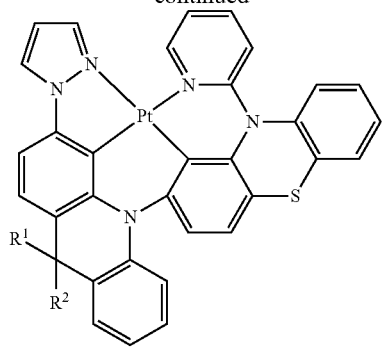
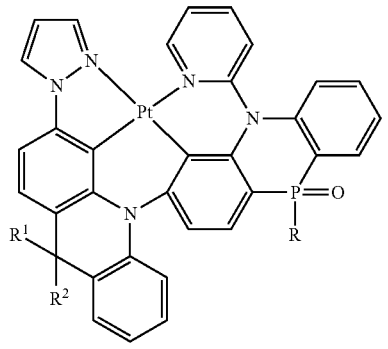
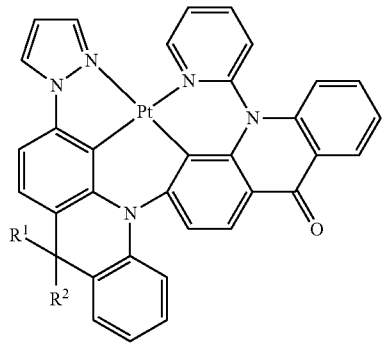
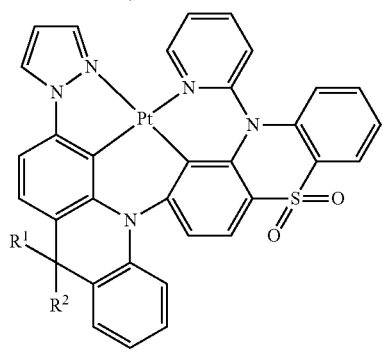
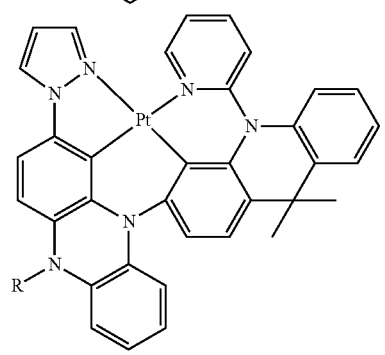
156
-continued
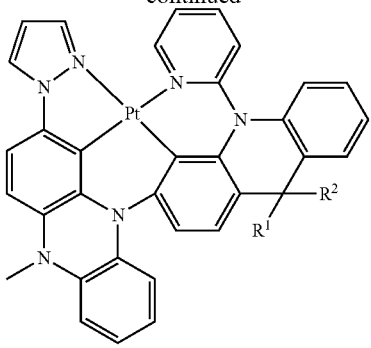
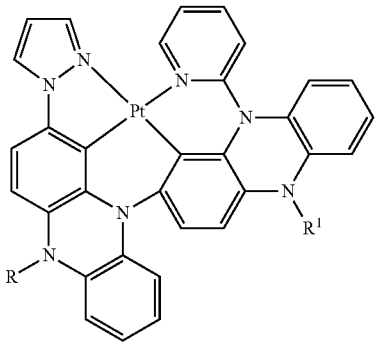
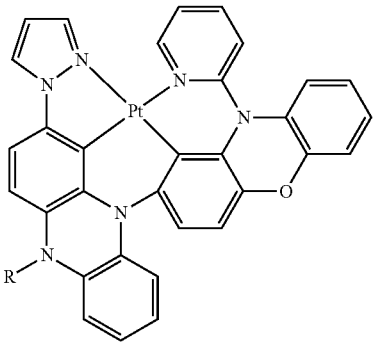
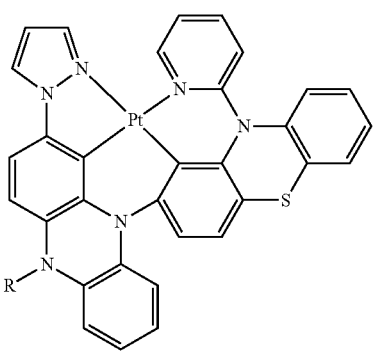
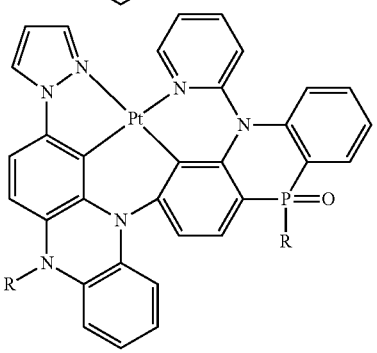

157
-continued
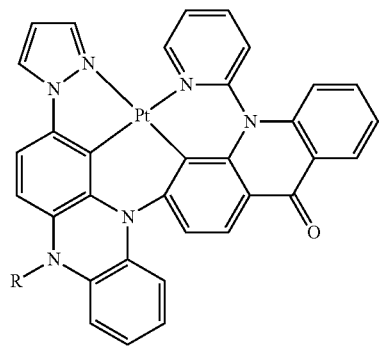
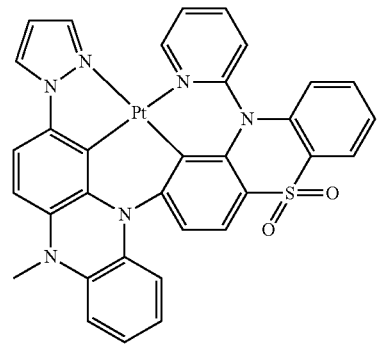
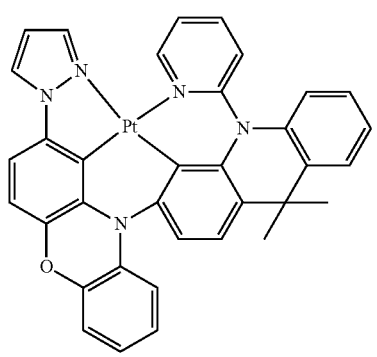
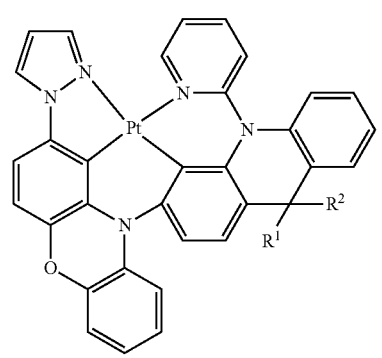
158
-continued
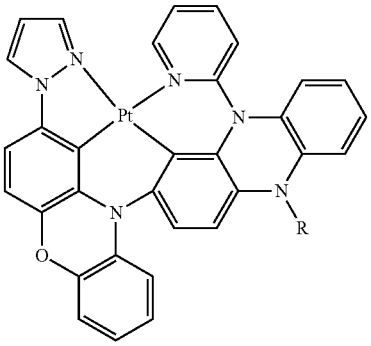
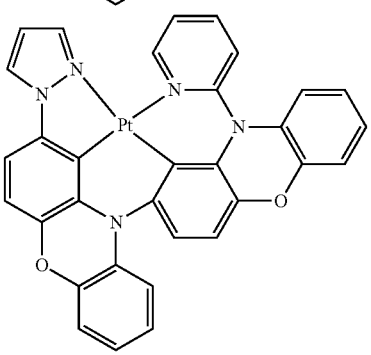
Structures 17
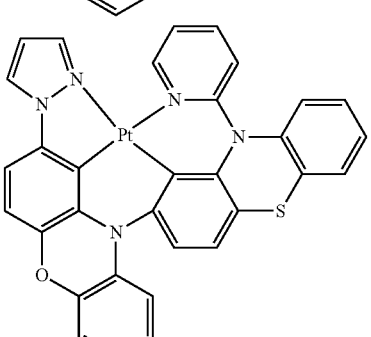
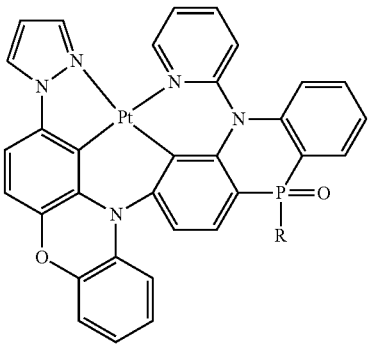
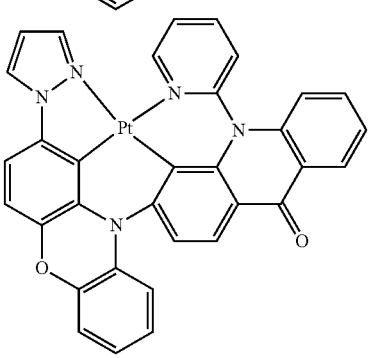

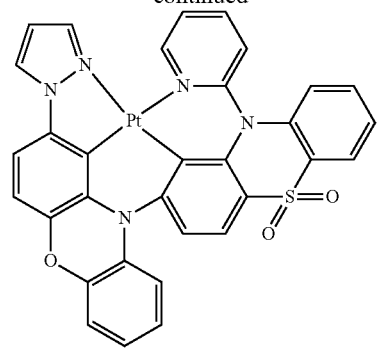
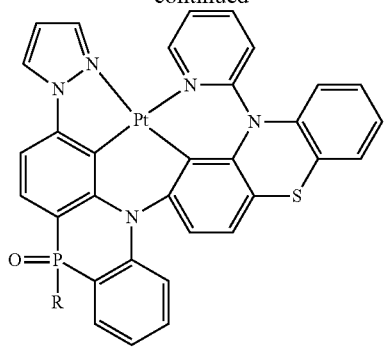
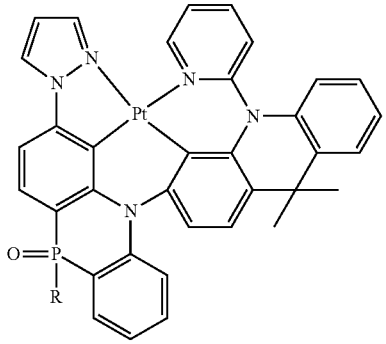
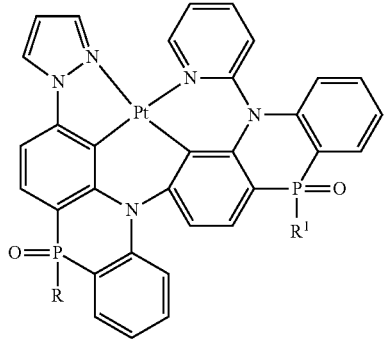
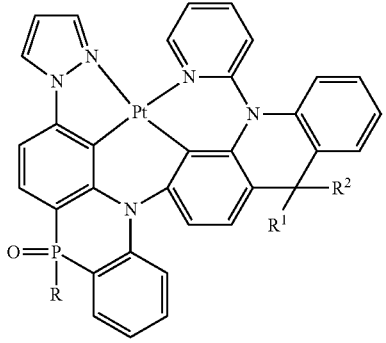
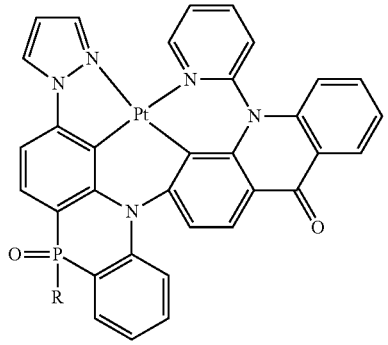
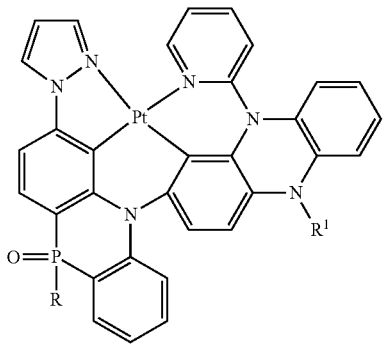
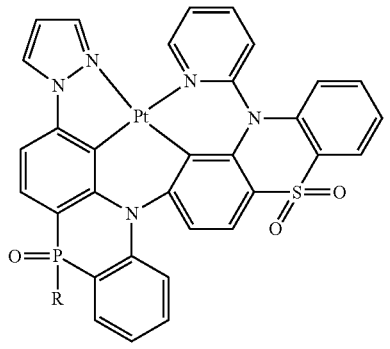
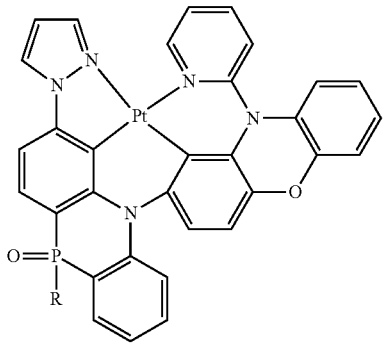
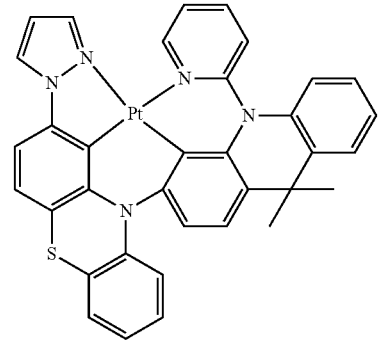

-continued
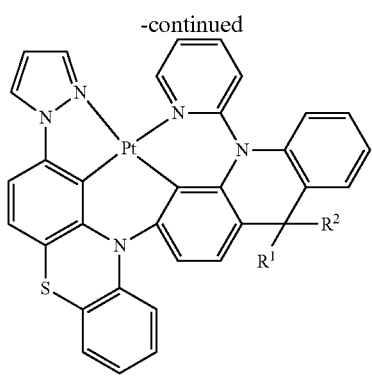
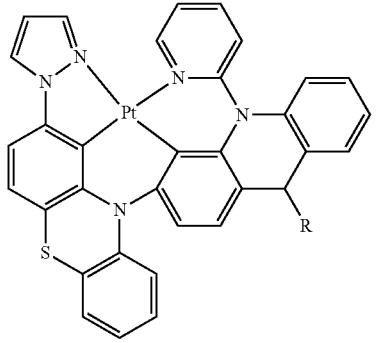
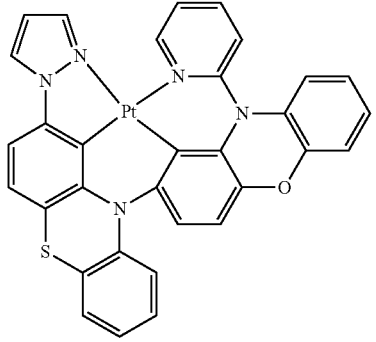
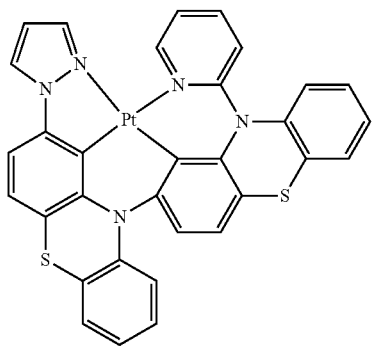
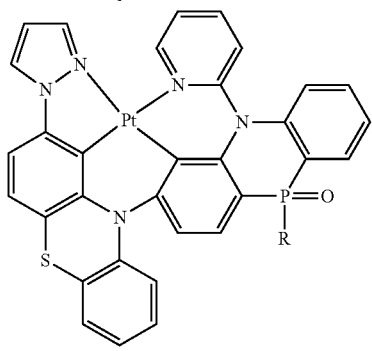
-continued
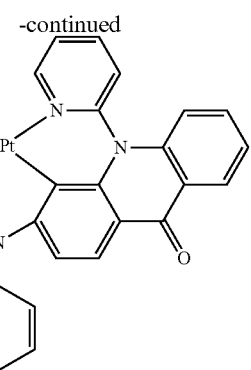
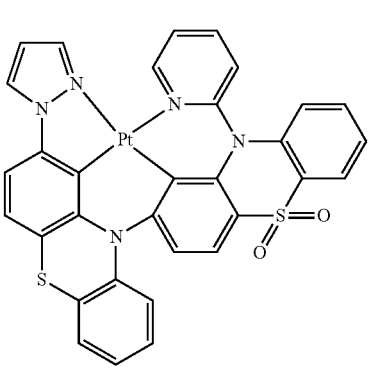
Structure 18
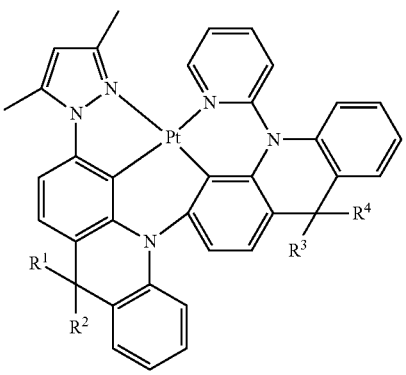
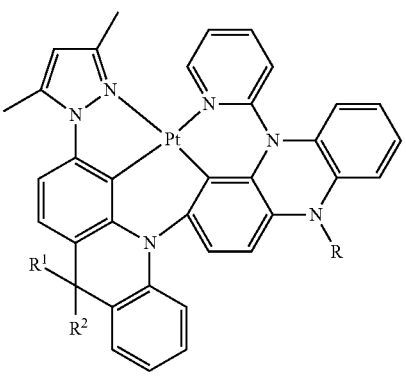

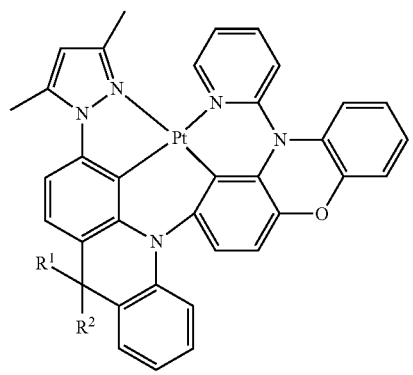
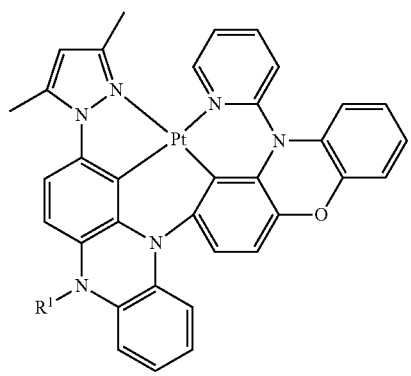
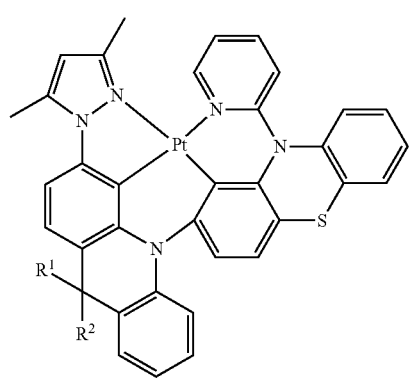
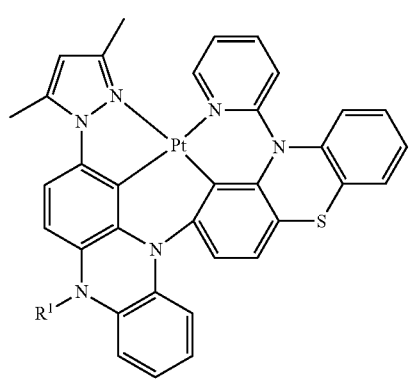
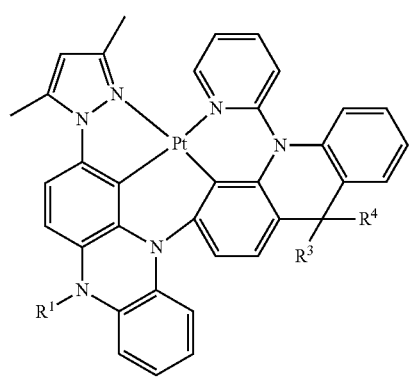
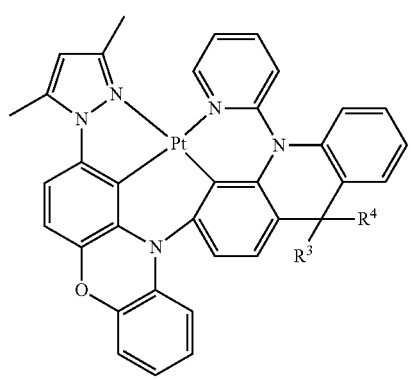
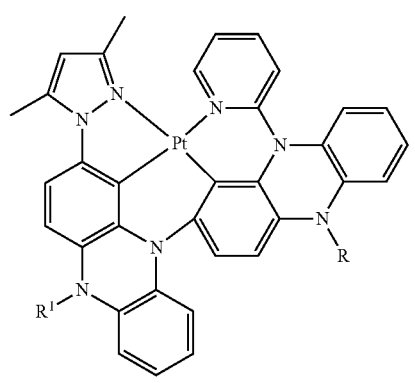
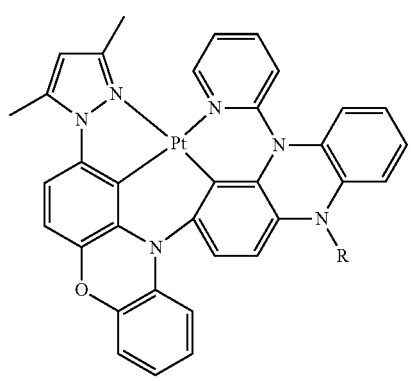

165
-continued
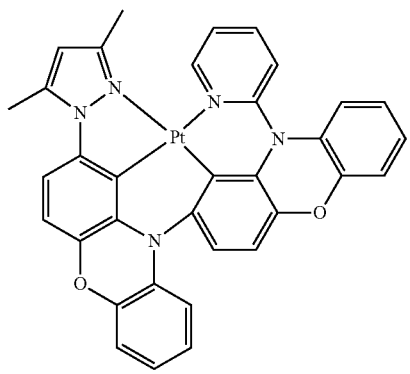
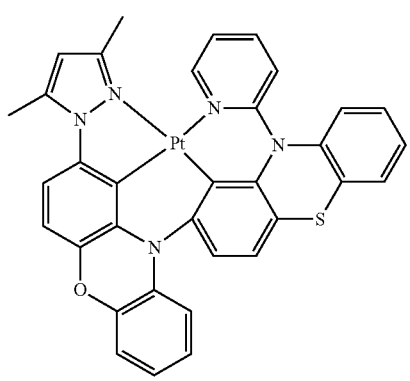
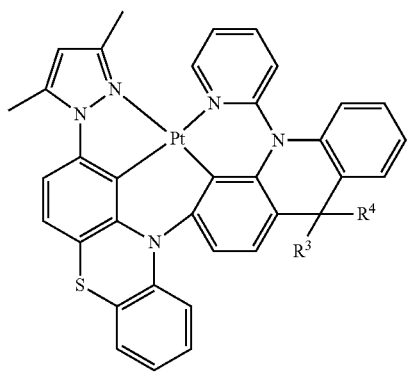
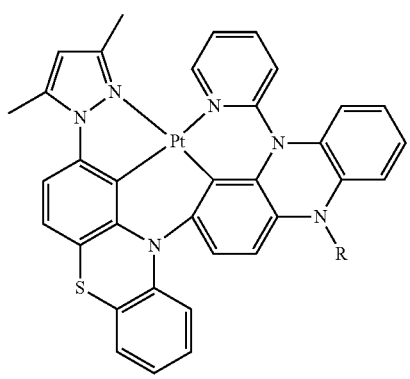
166
-continued
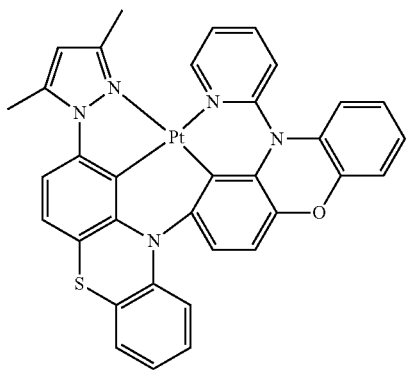
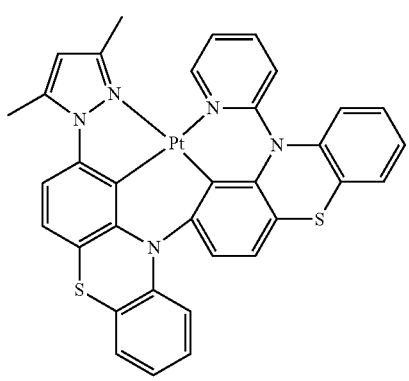
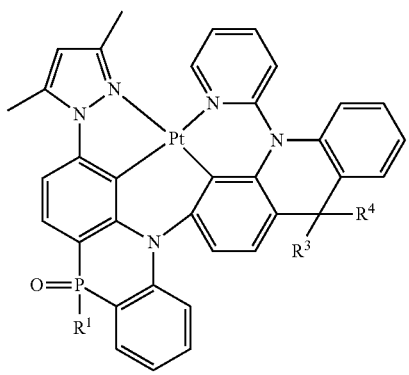
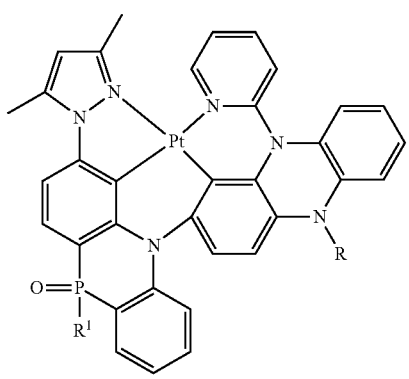

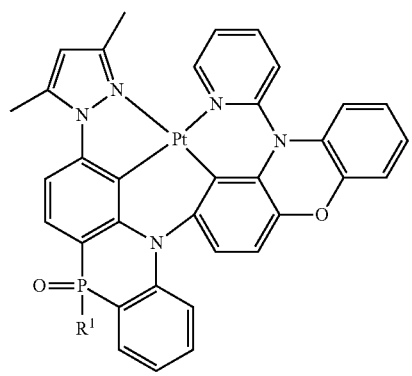
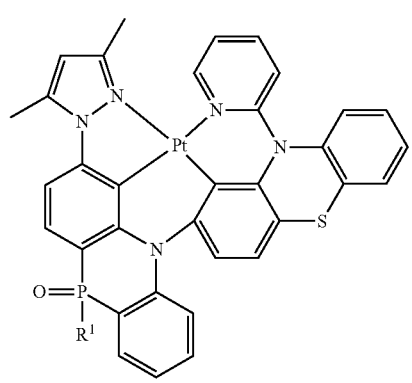
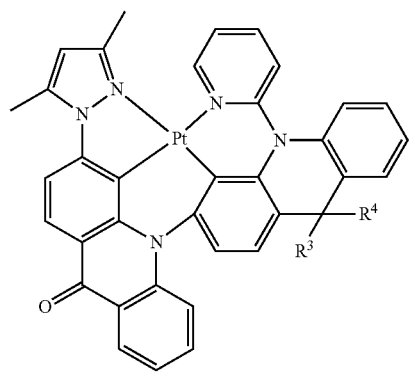
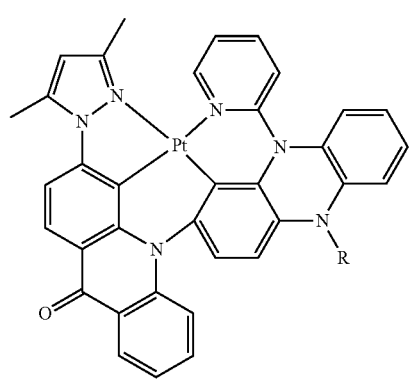
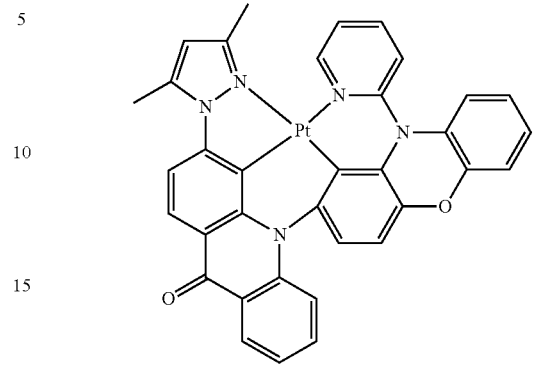
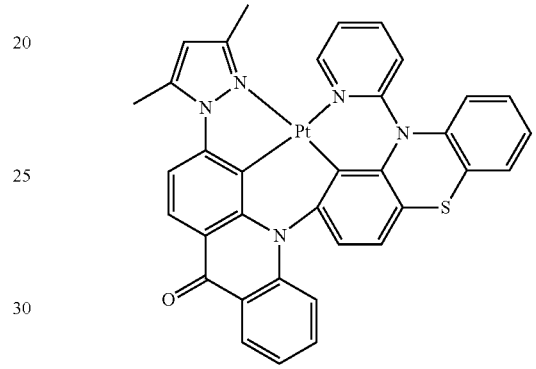
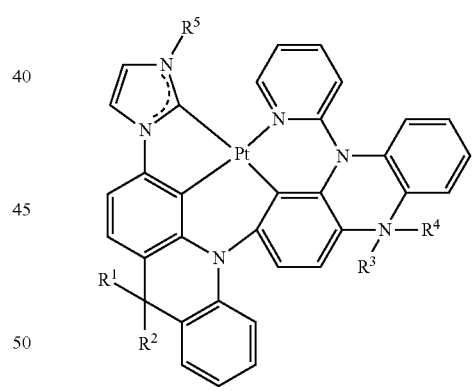
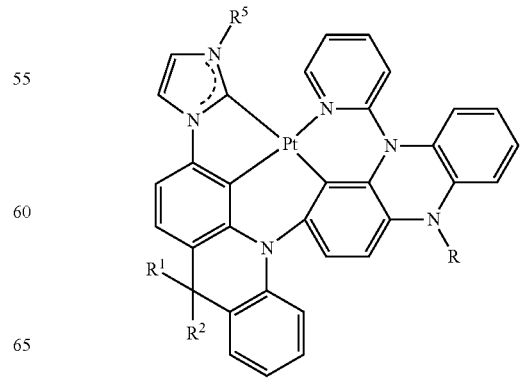
Structures 19

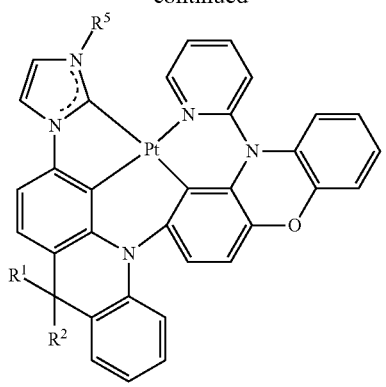
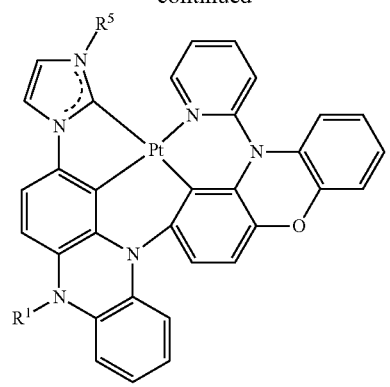
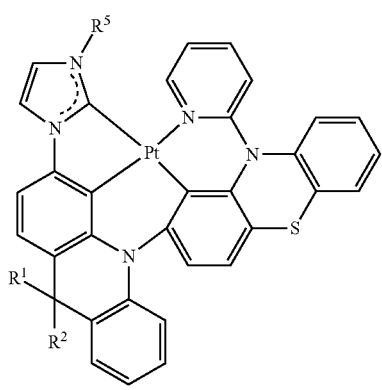
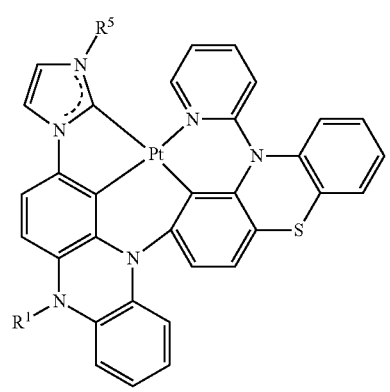
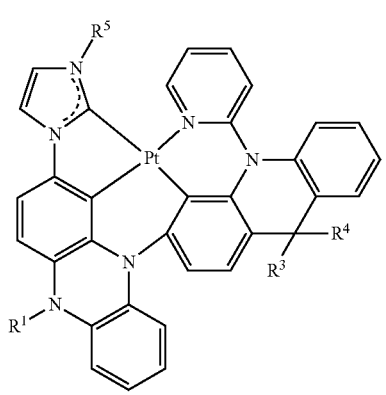
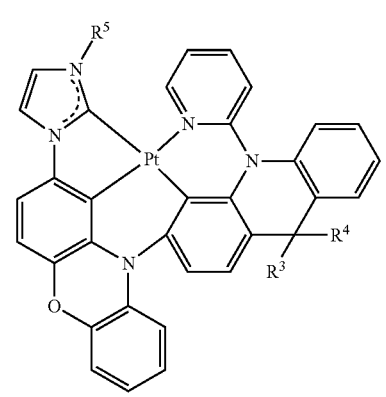
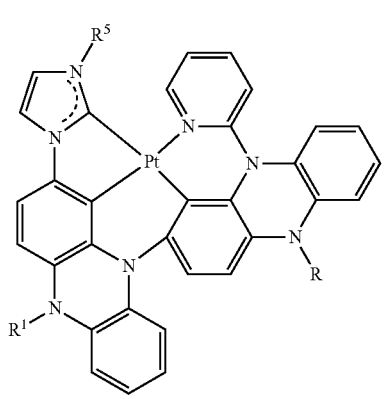
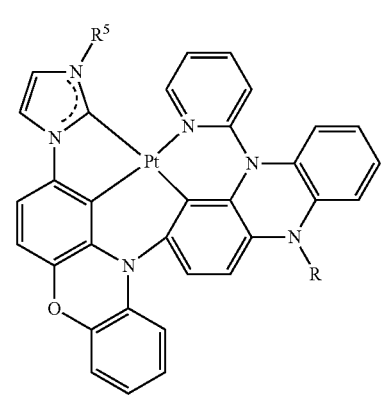

171
-continued
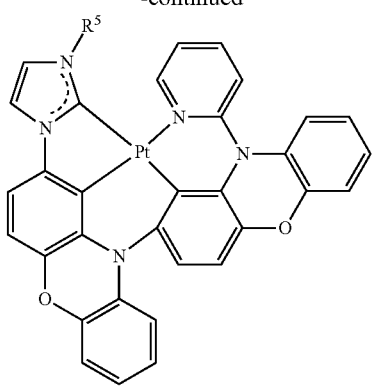
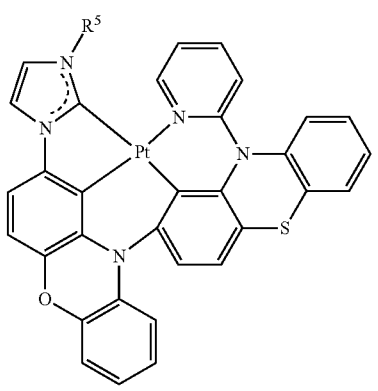
172
-continued
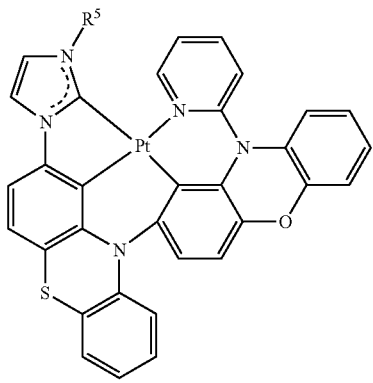
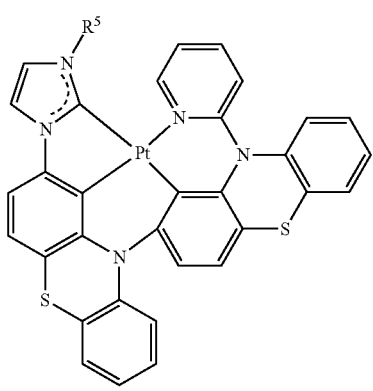
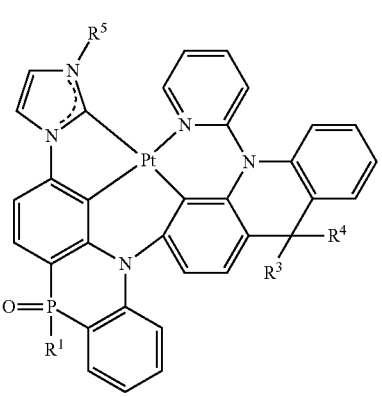
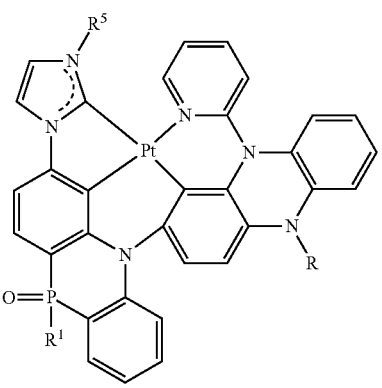

173
-continued
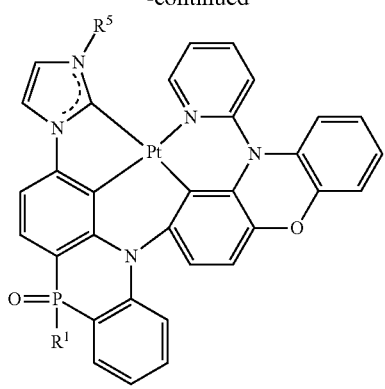
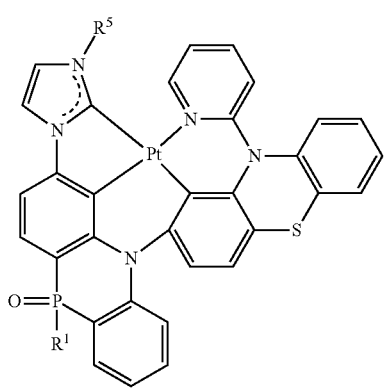
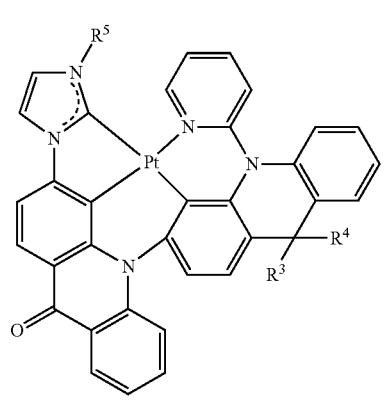
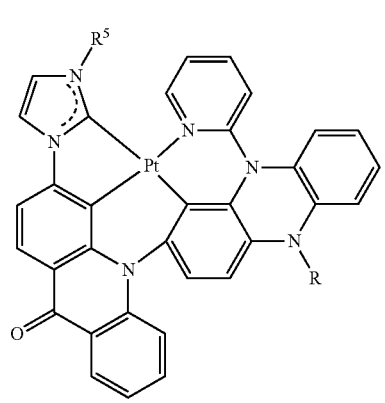
174
-continued
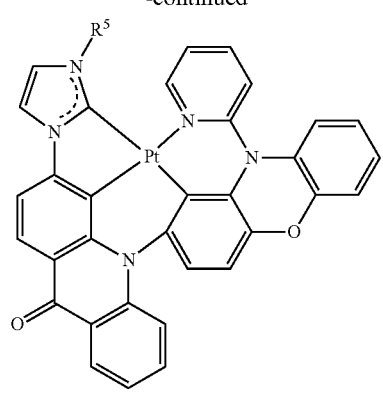
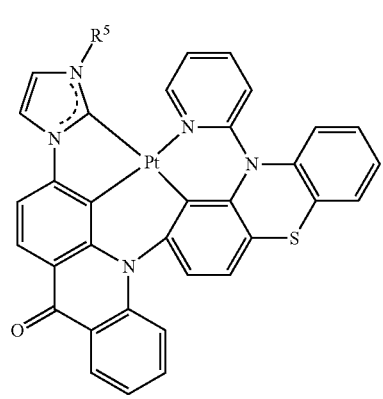
Structures 20
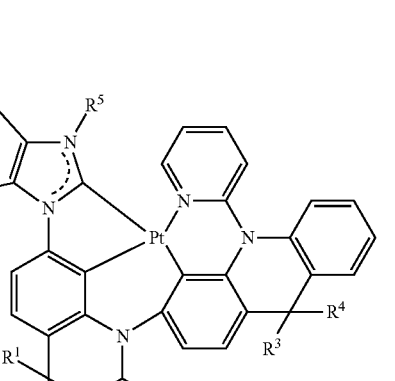
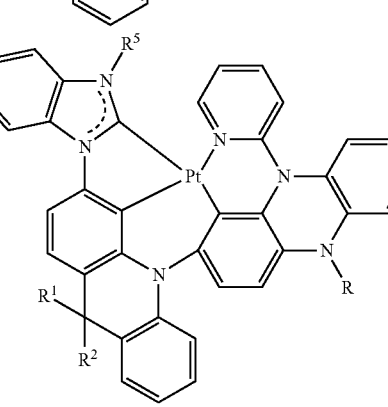

-continued
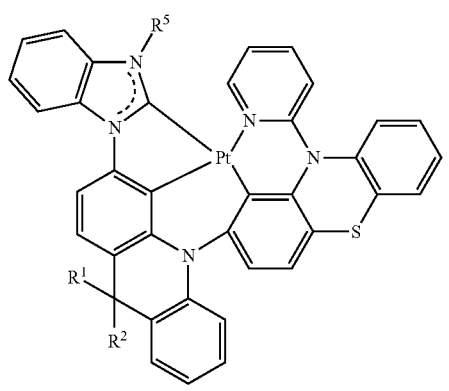
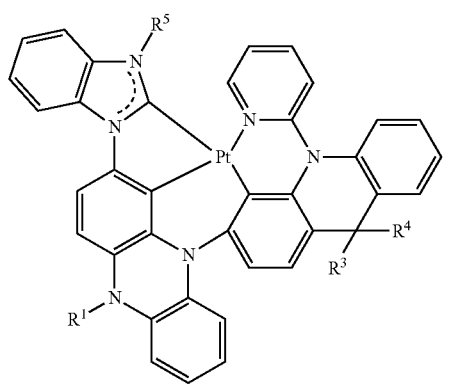
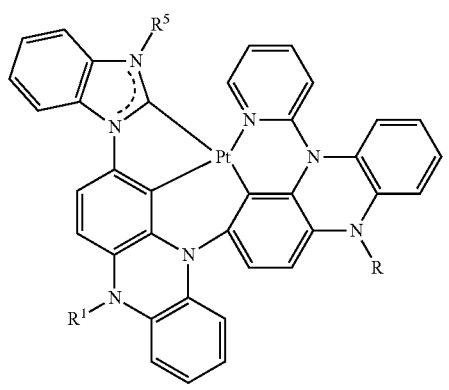
-continued
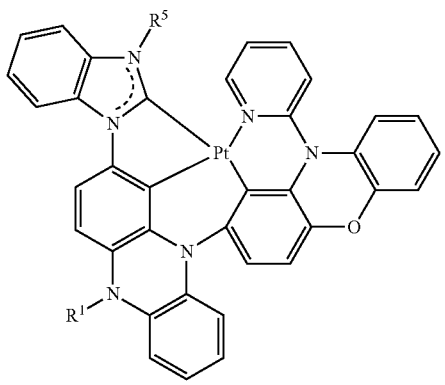
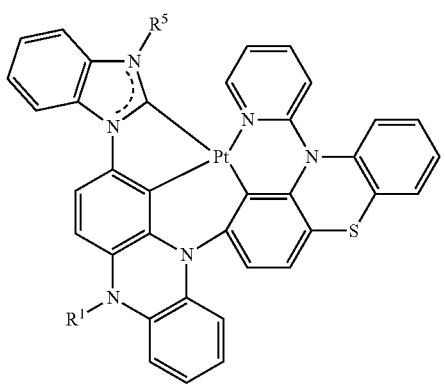
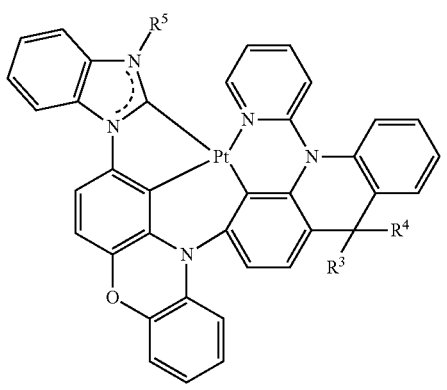
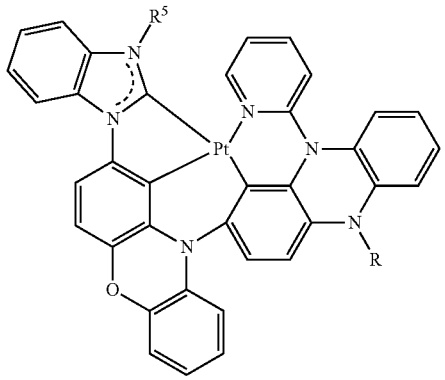

177
-continued
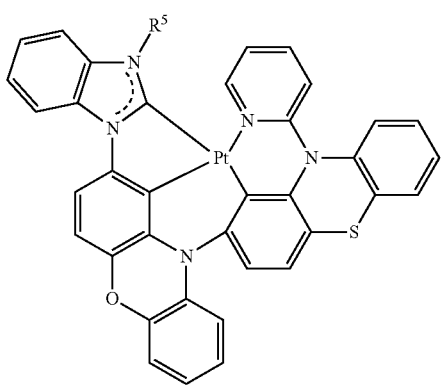
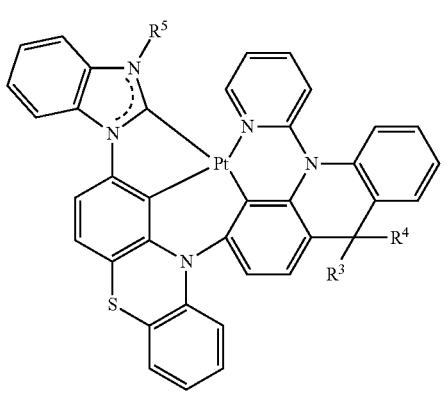
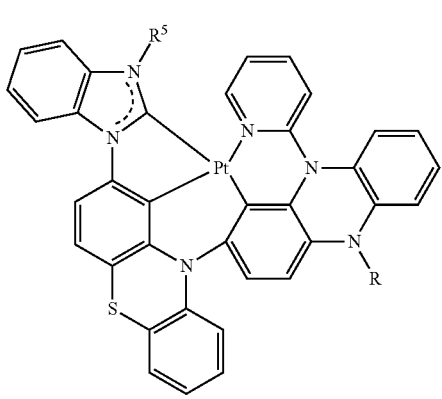
178
-continued
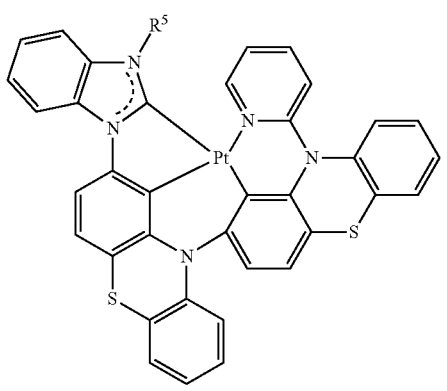
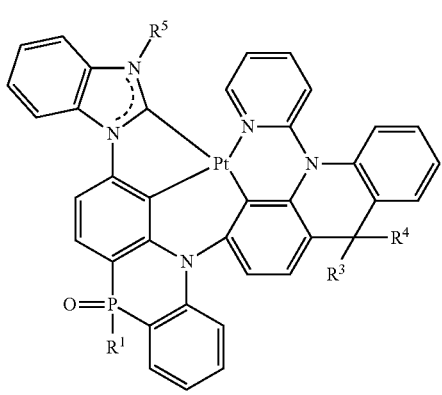
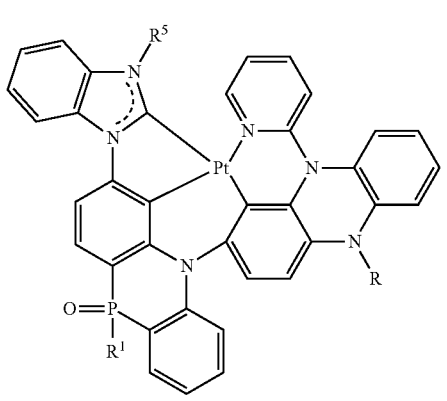

179
-continued
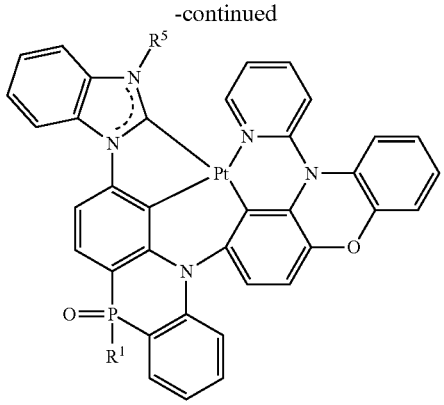
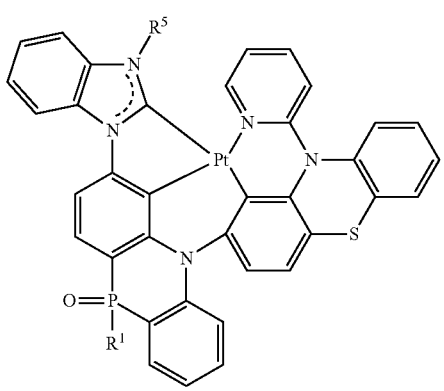
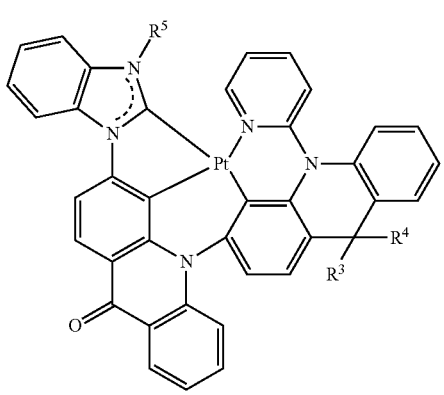
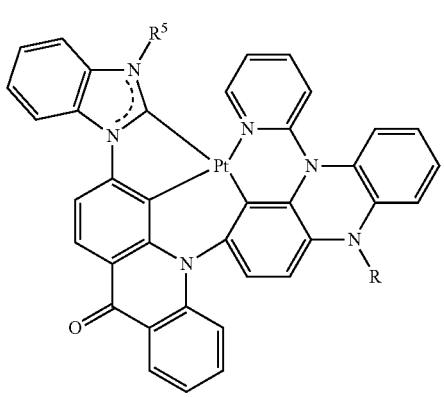
180
-continued
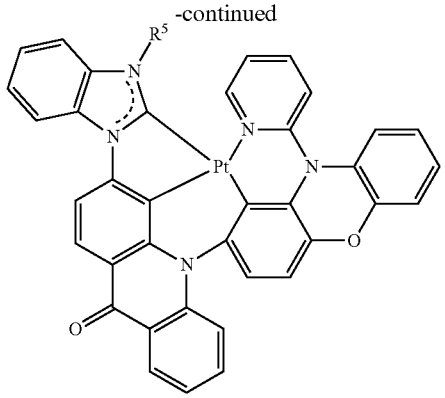
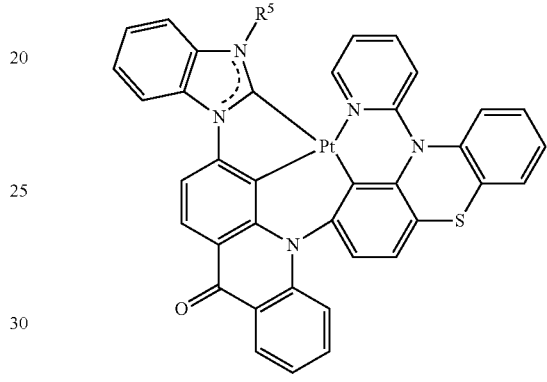
Structures 21
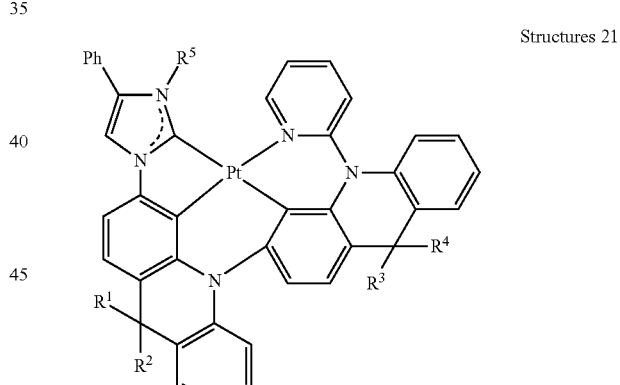
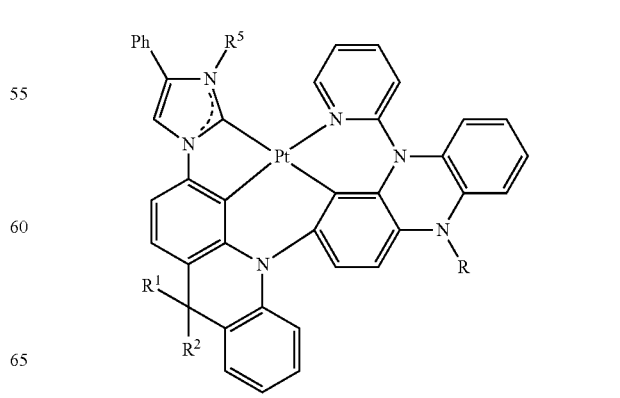

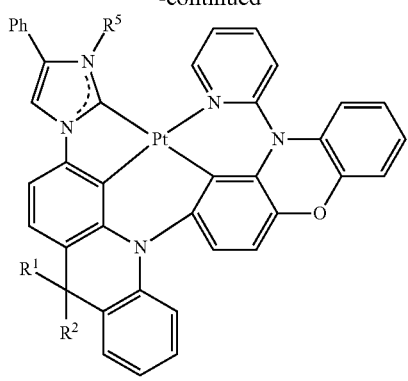
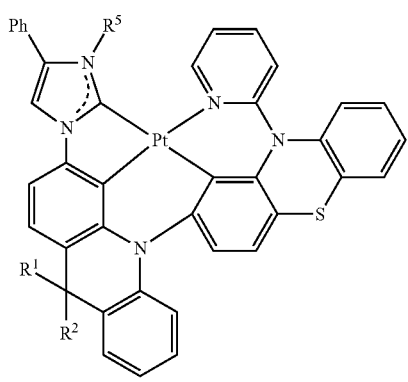
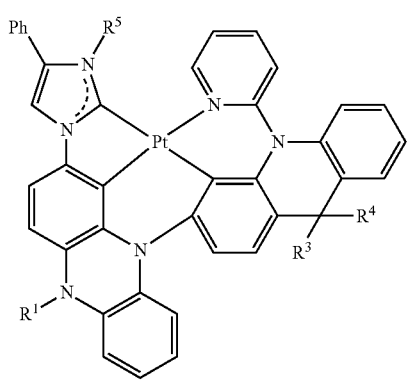
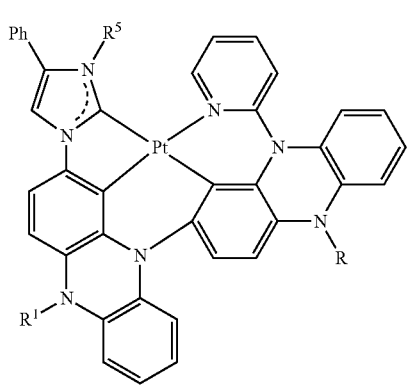
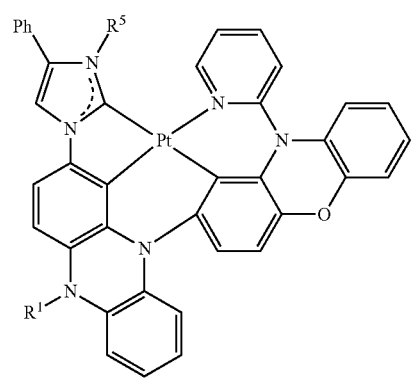
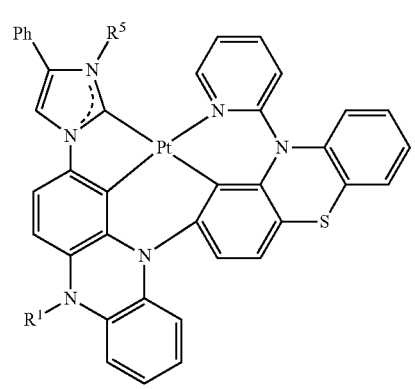
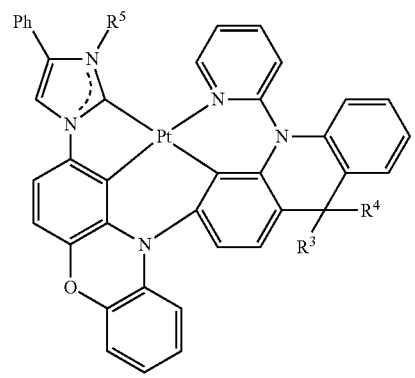
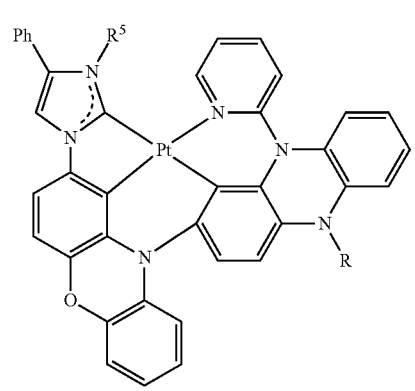

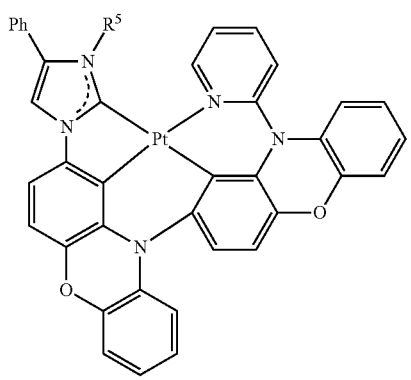
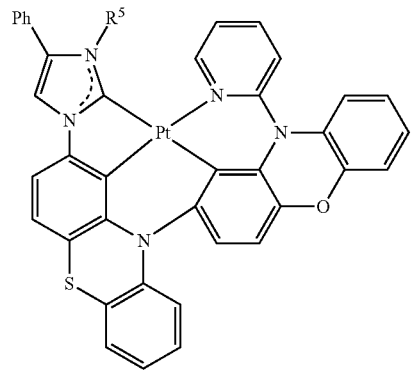
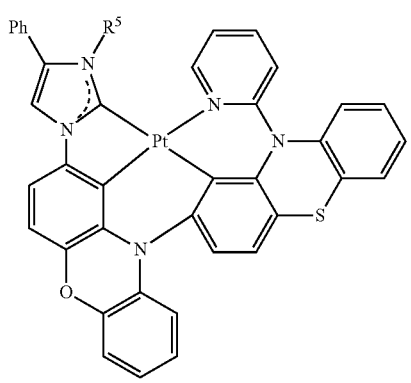
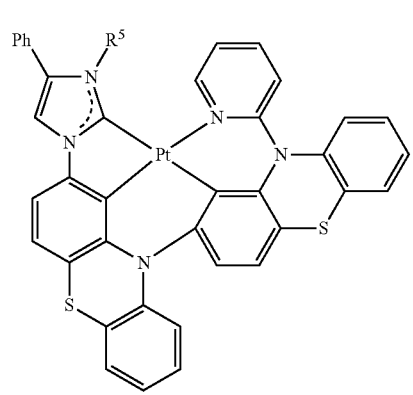
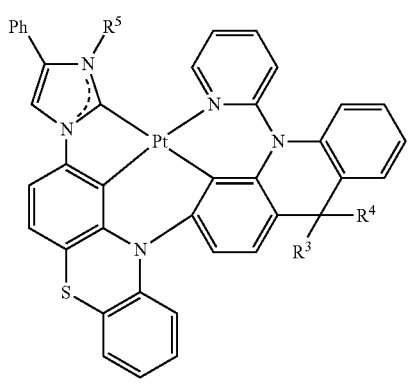
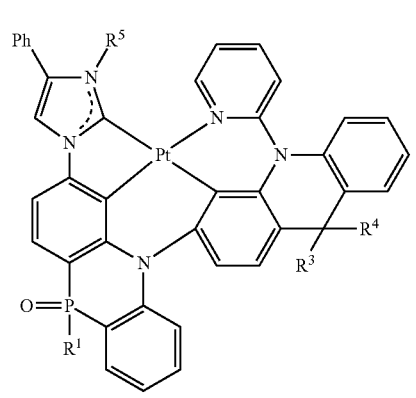
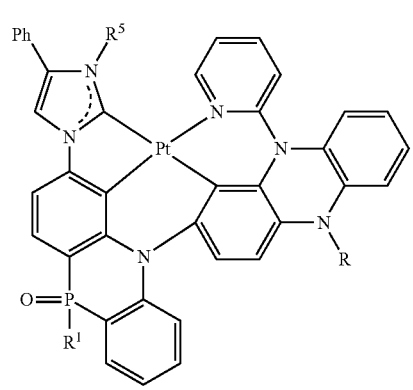

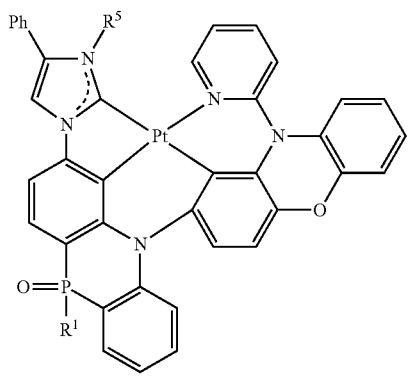
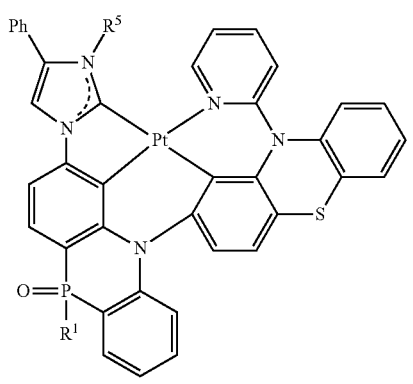
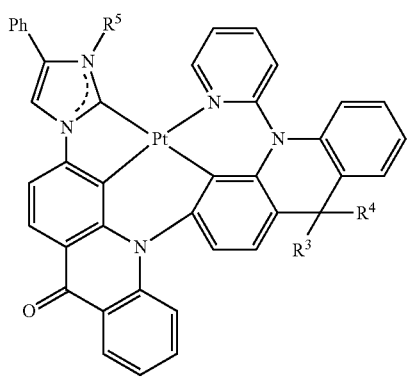
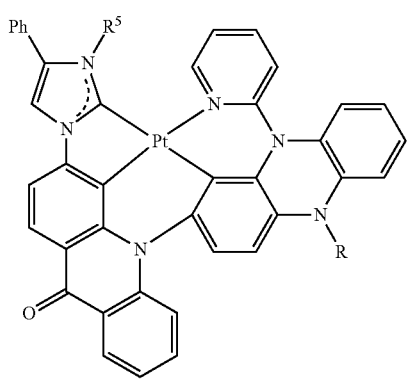
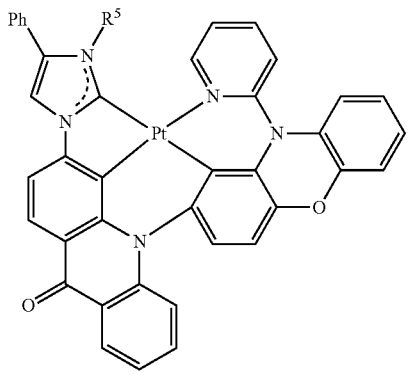
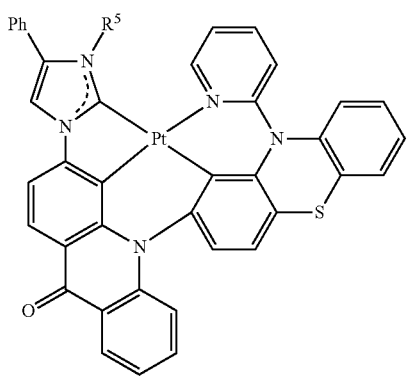
Structure 22
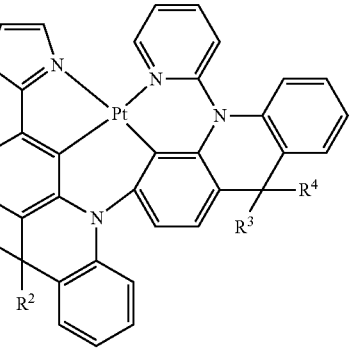
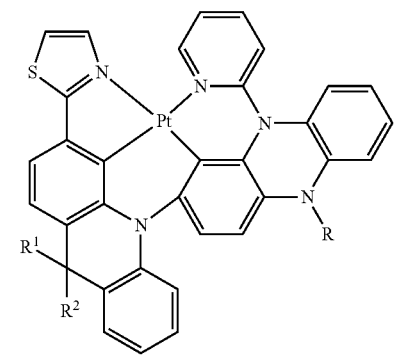

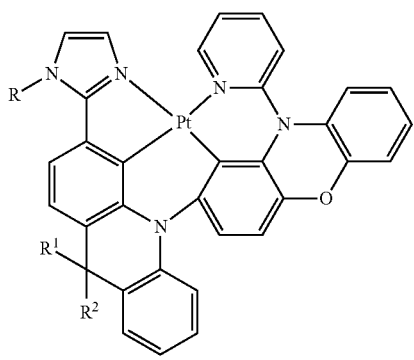
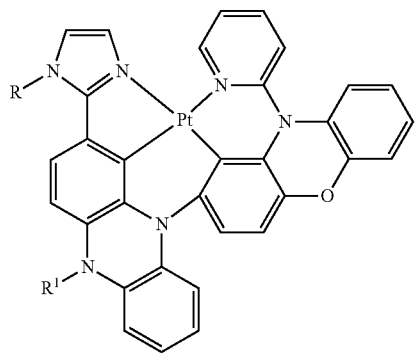
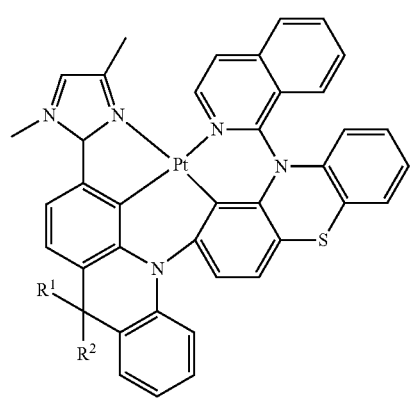
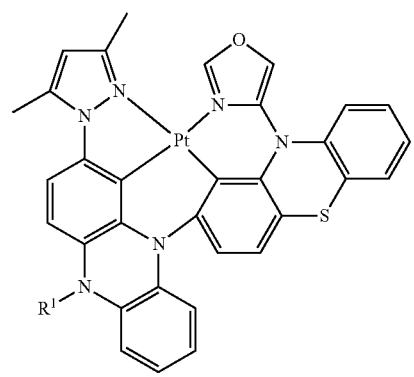
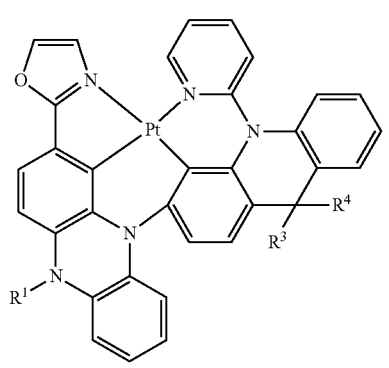
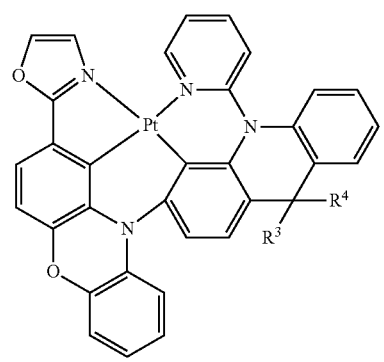
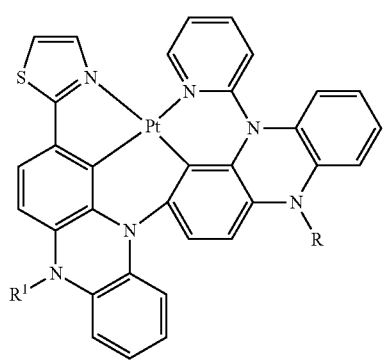
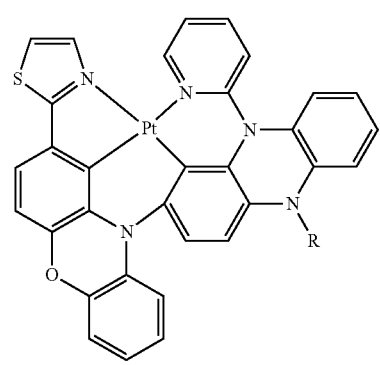

-continued
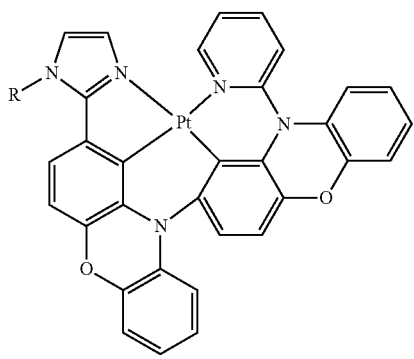
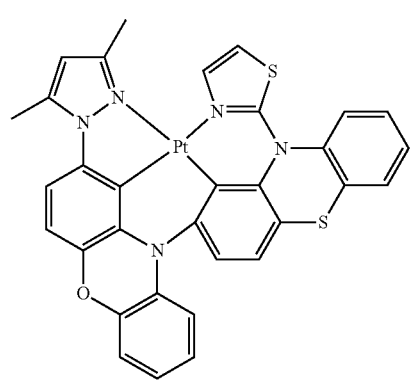
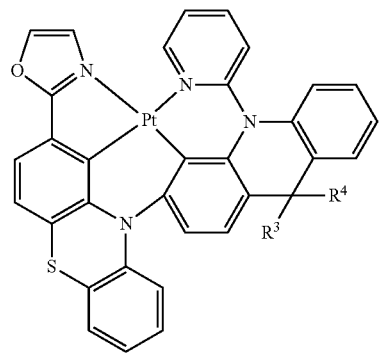
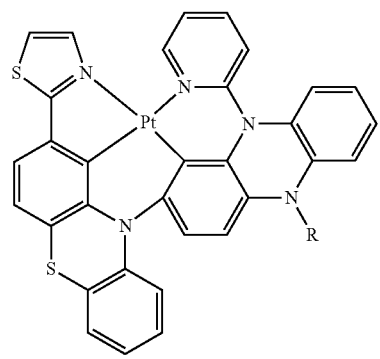
-continued
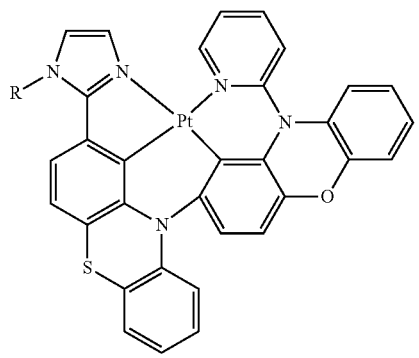
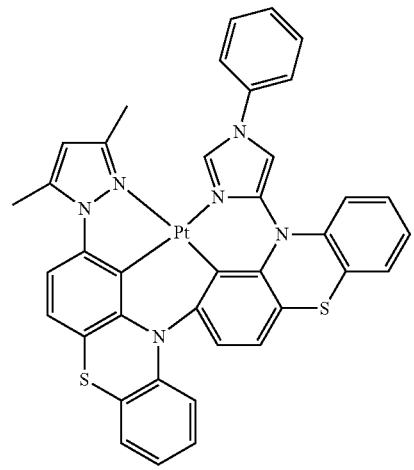
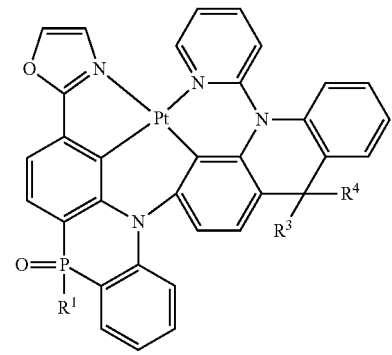
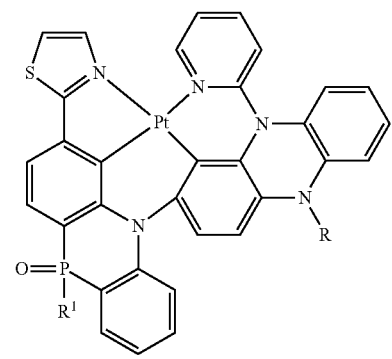

191
-continued
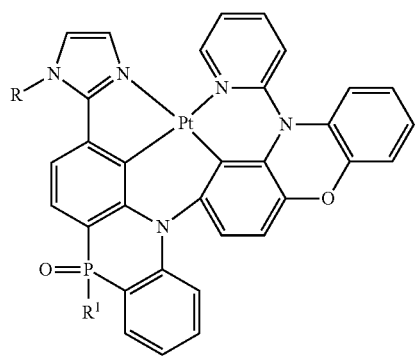
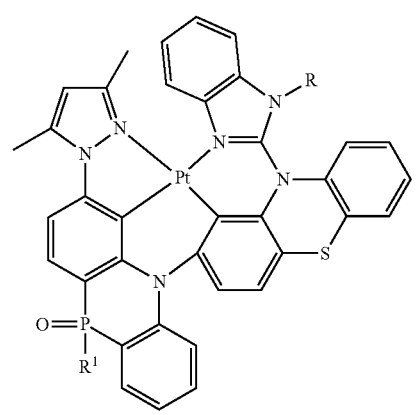
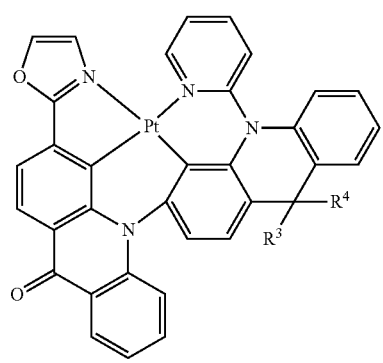
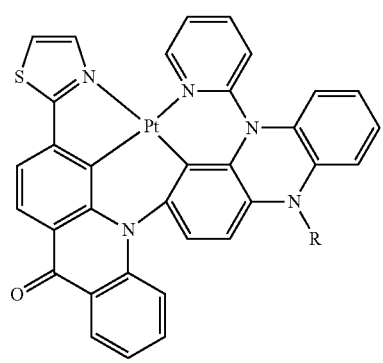
192
-continued
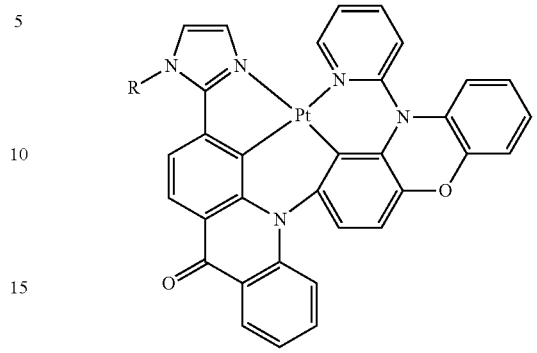
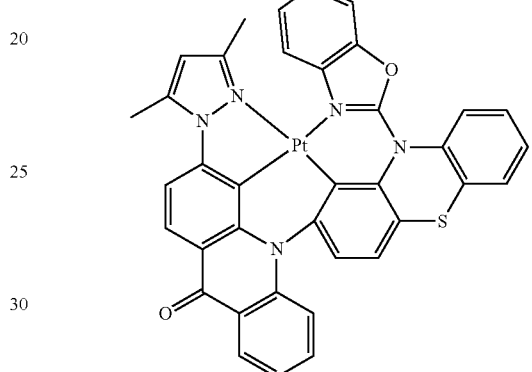
Structures 23
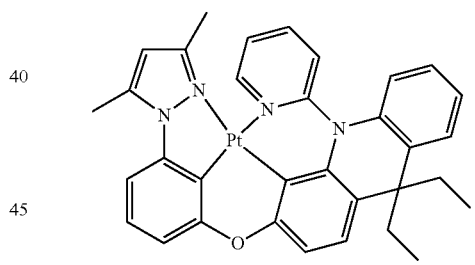
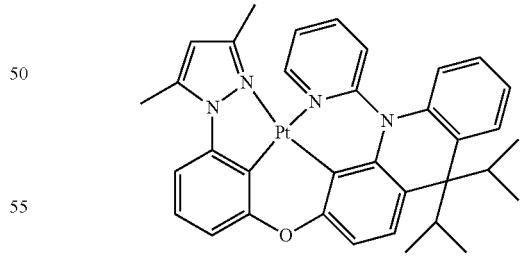
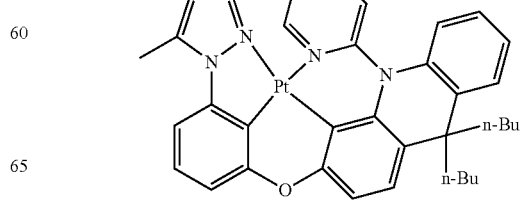

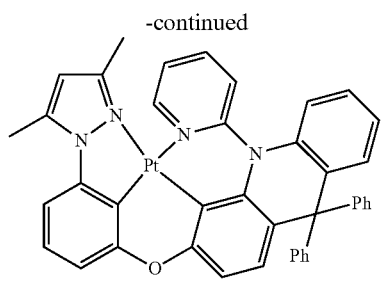
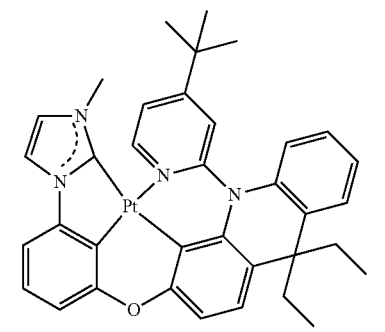
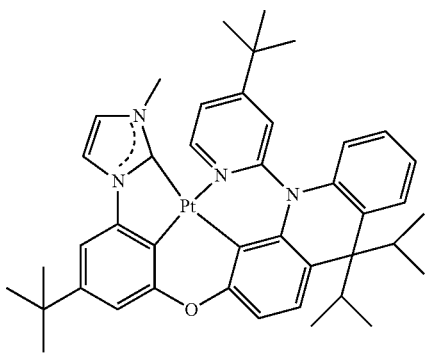
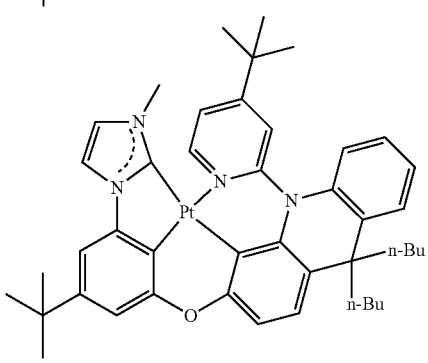
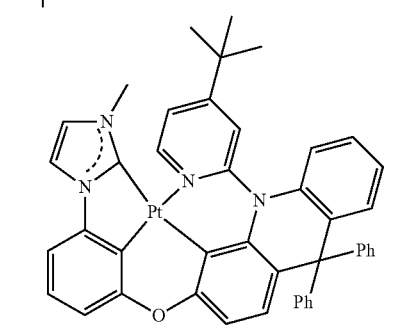
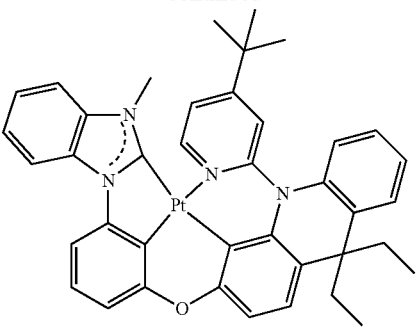
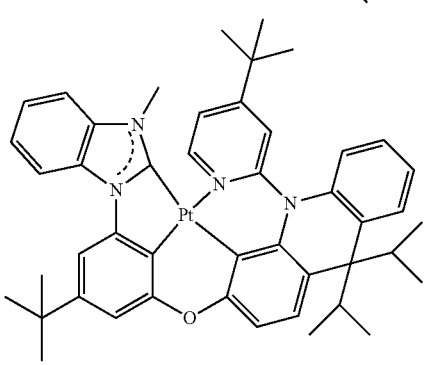
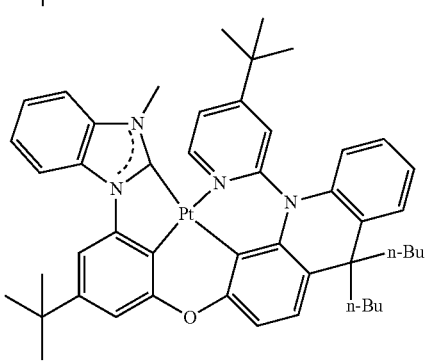
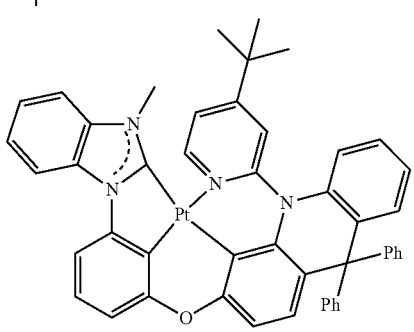
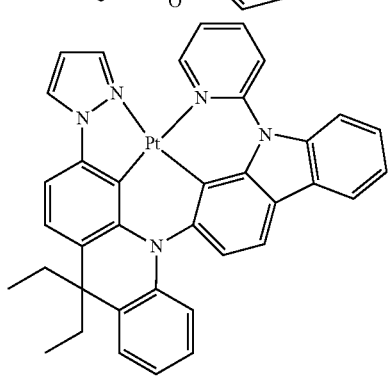

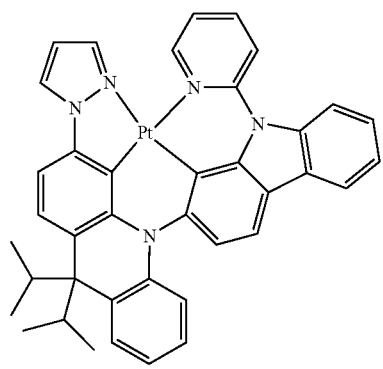
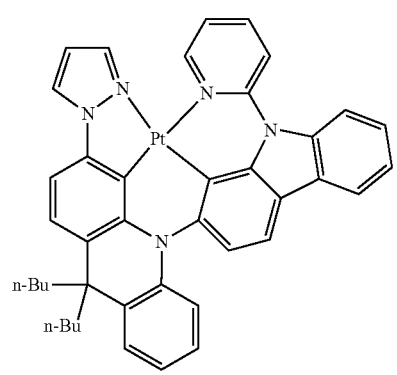
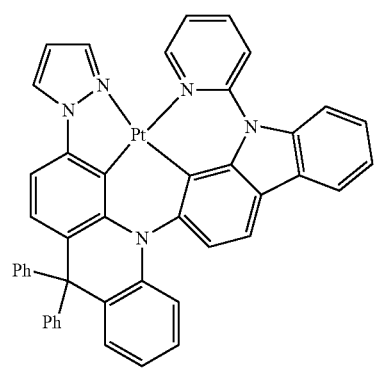
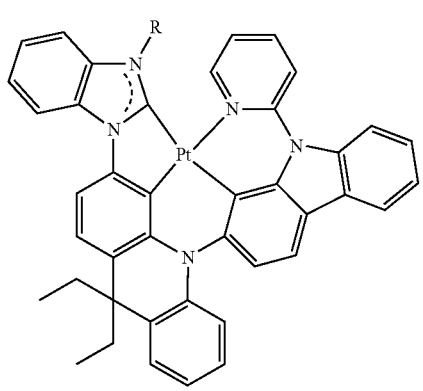
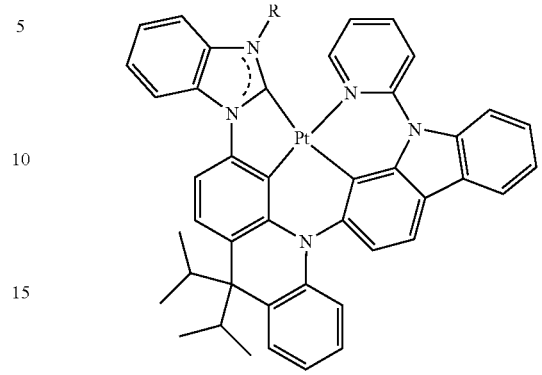
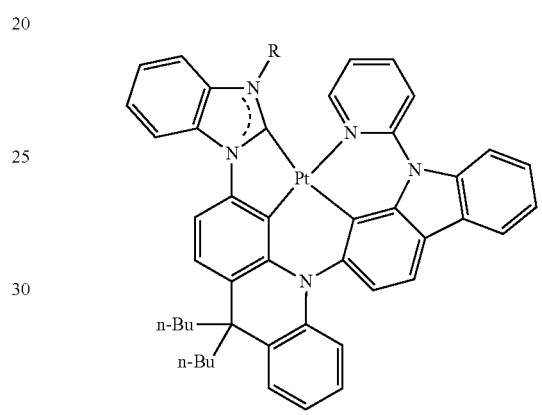
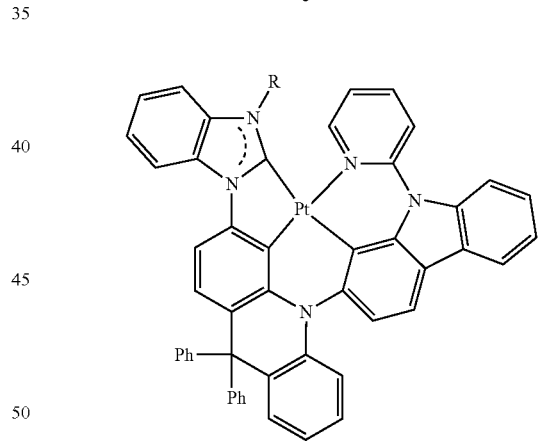
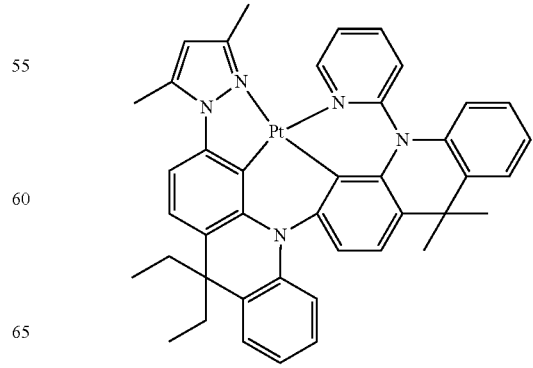

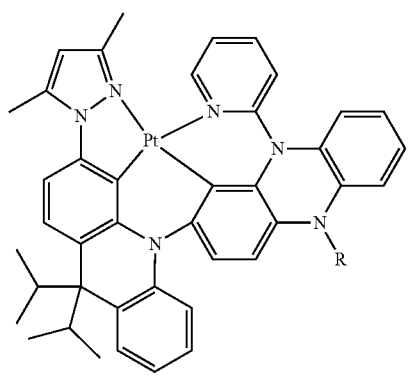
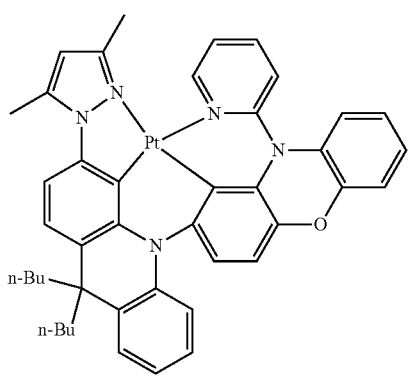
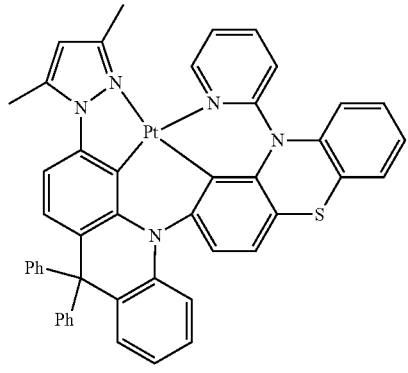
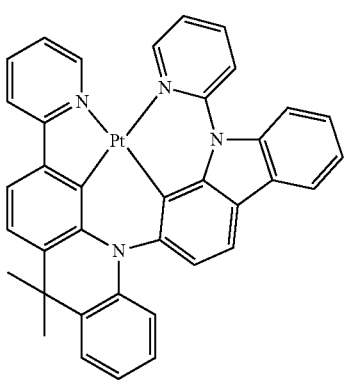
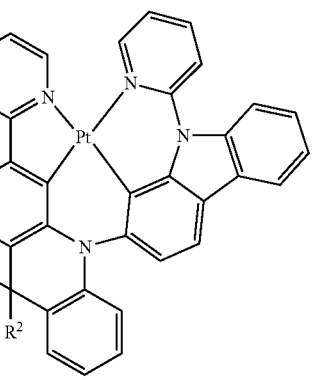
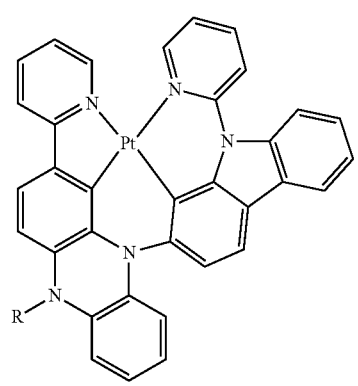
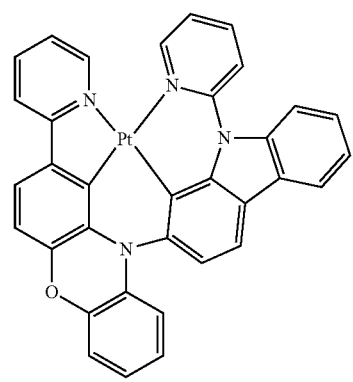
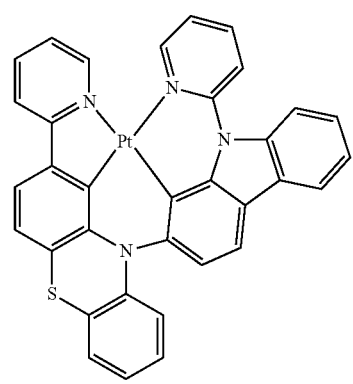
Structures 24

199
-continued
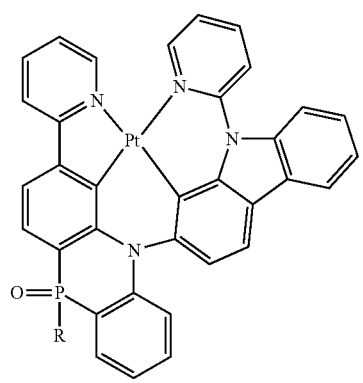
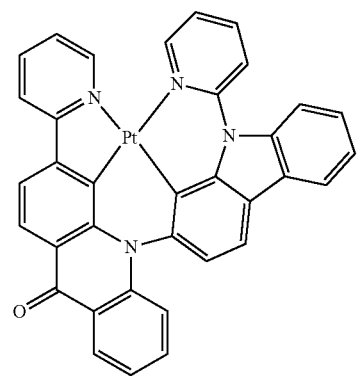
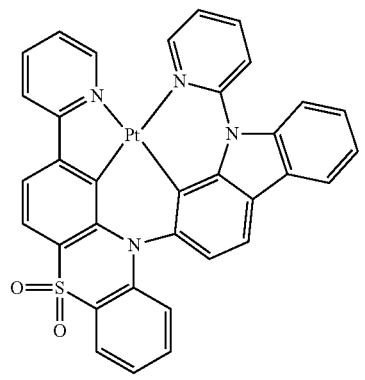
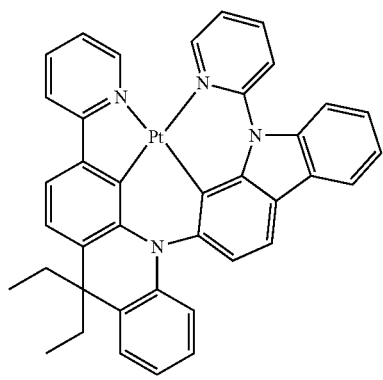
200
-continued
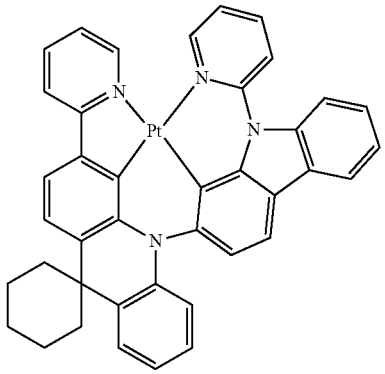
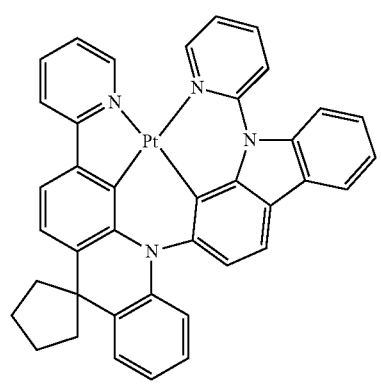
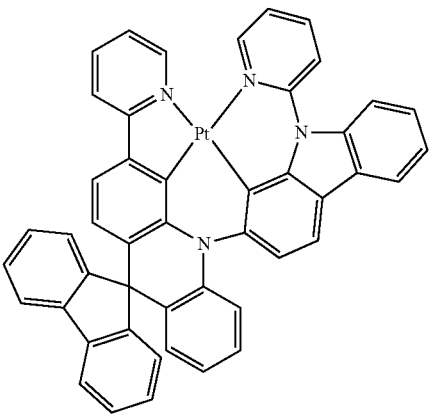
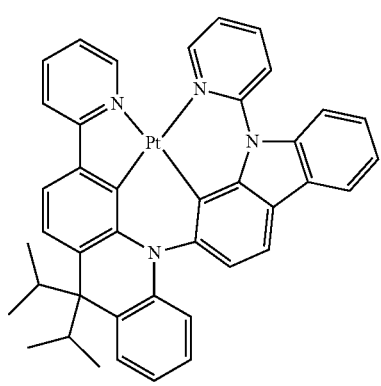

201
-continued
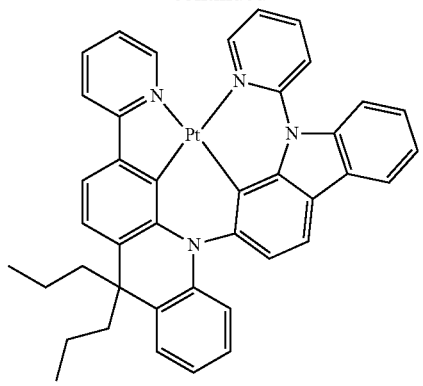
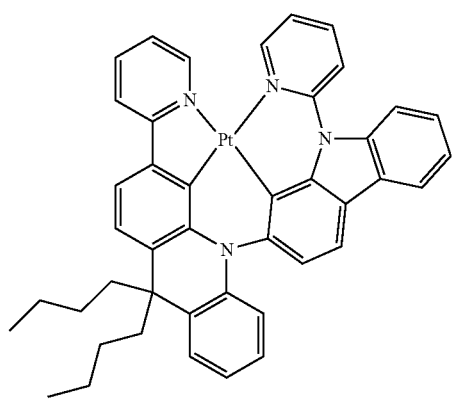
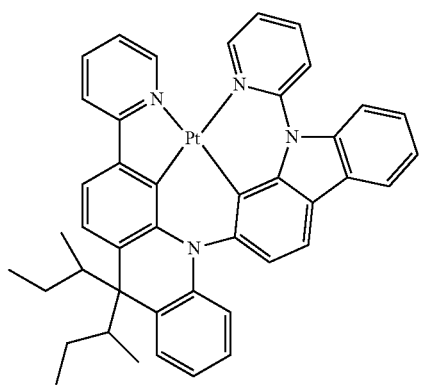
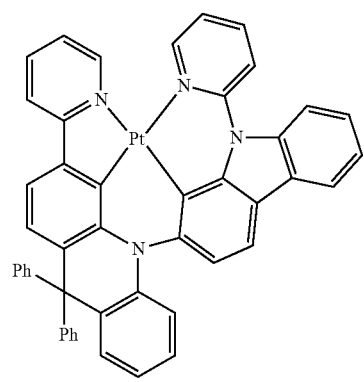
202
-continued
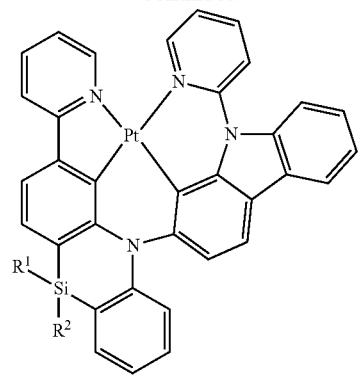
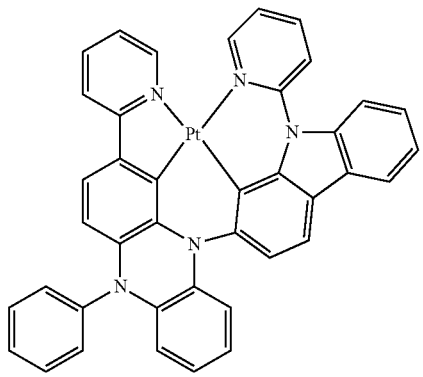
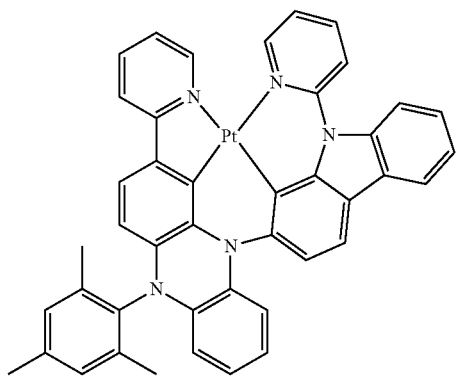
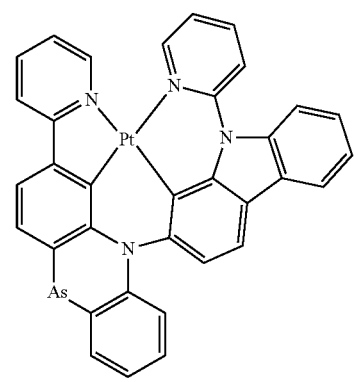

203
-continued
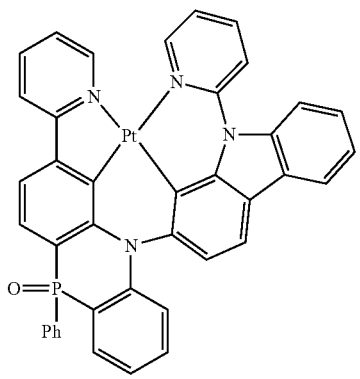
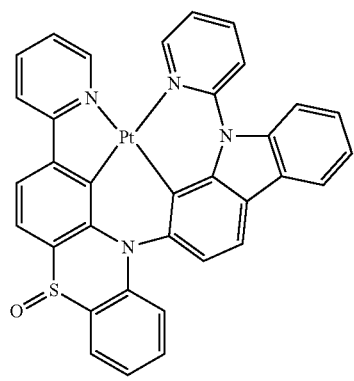
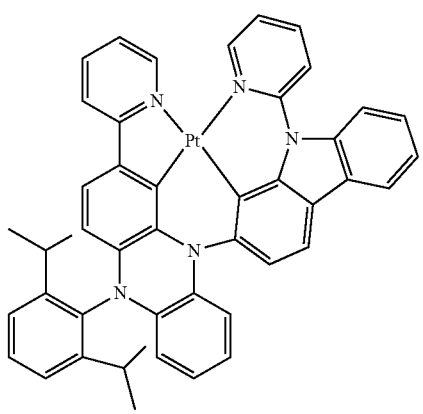
Structures 25
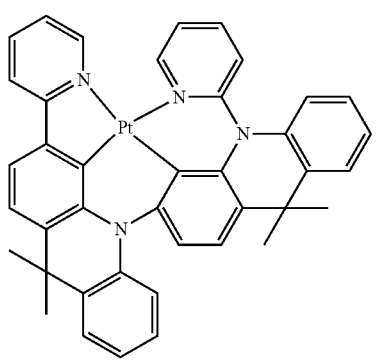
204
-continued
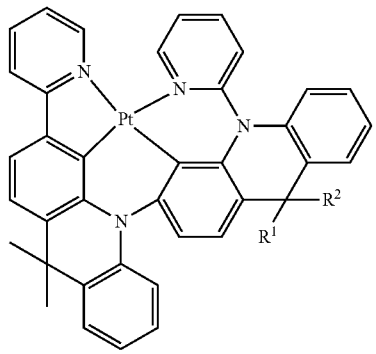
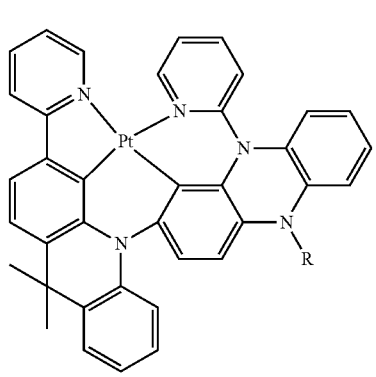
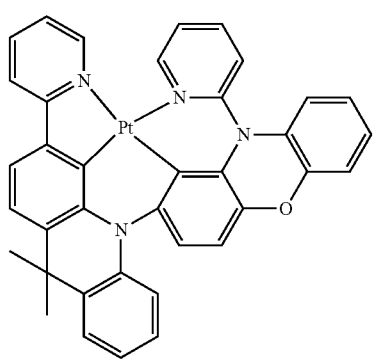
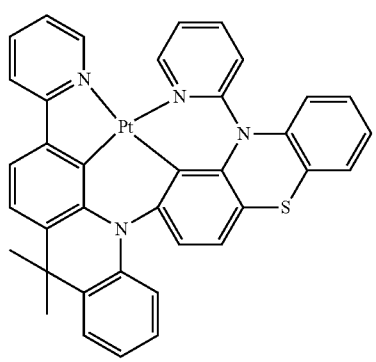

205
-continued
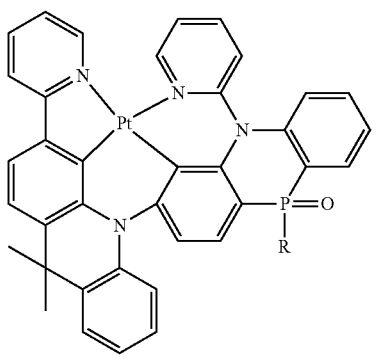
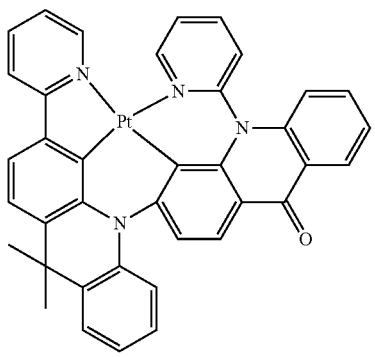
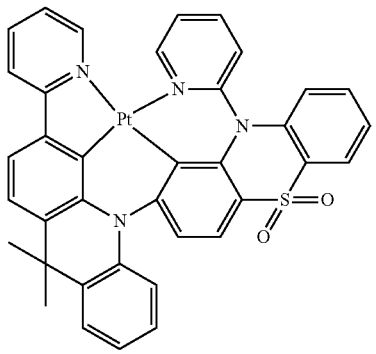
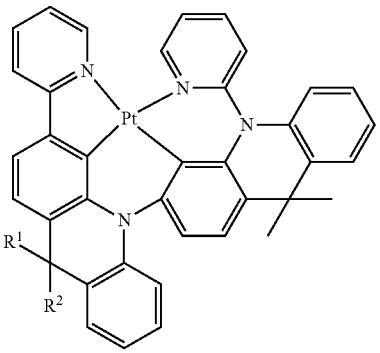
206
-continued
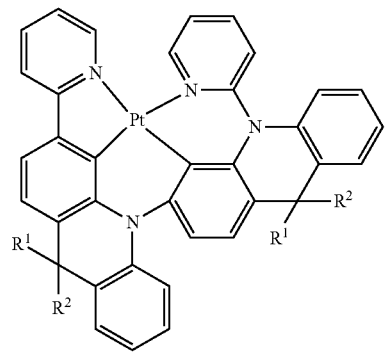
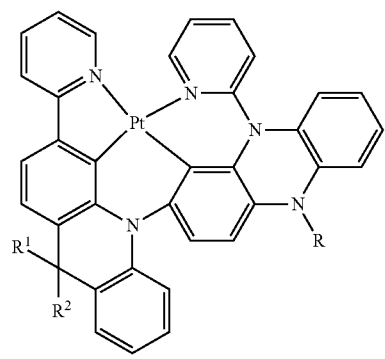
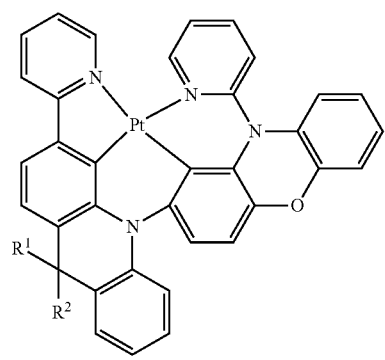
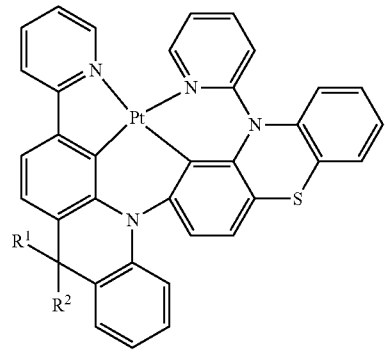

207
-continued
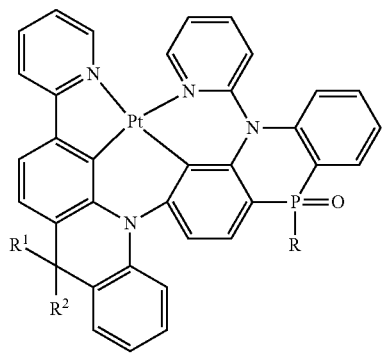
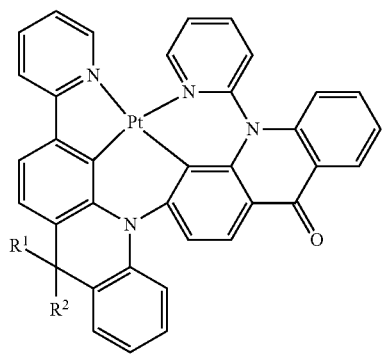
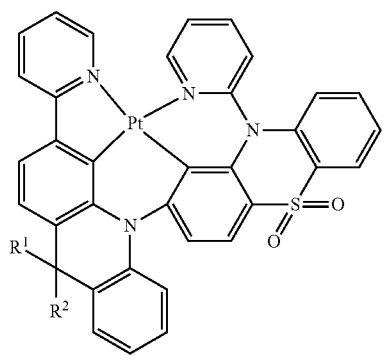
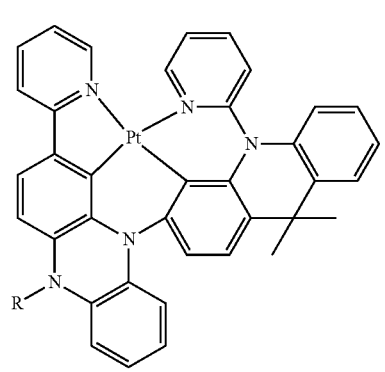
208
-continued
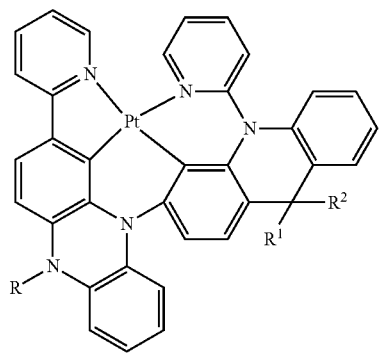
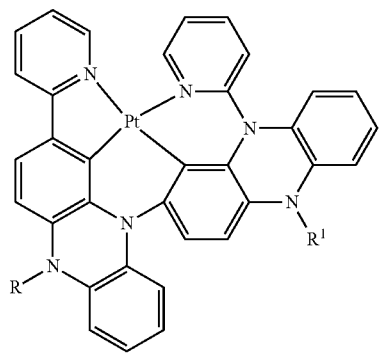
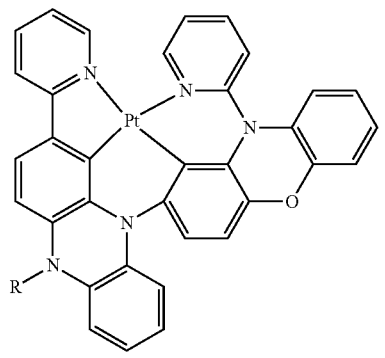
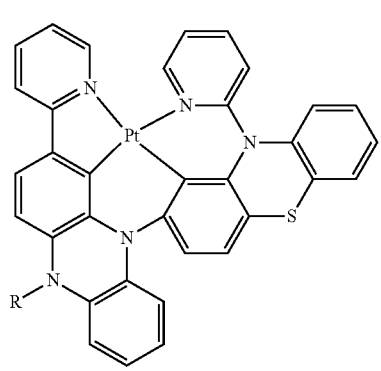

-continued
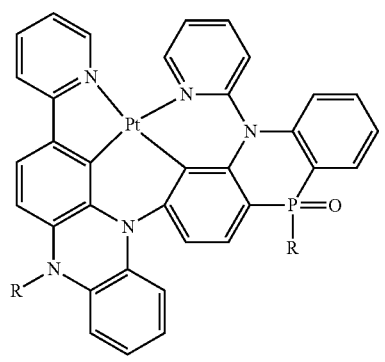
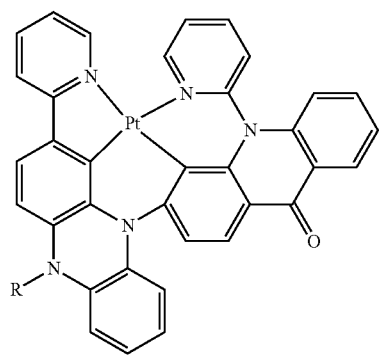
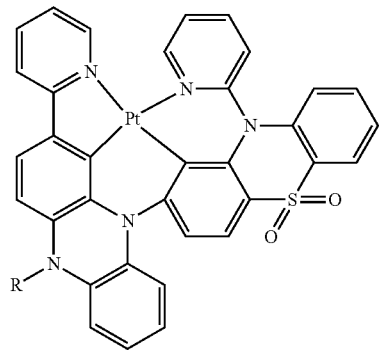
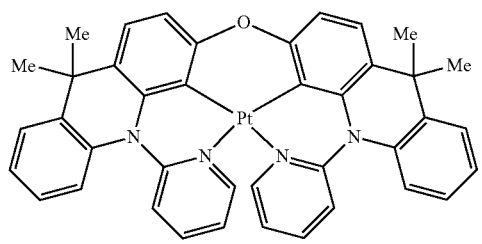
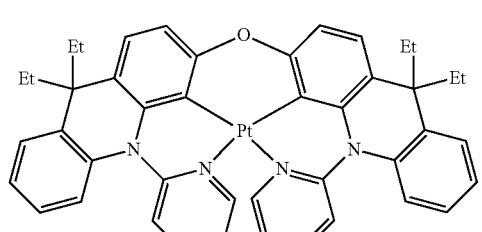
-continued
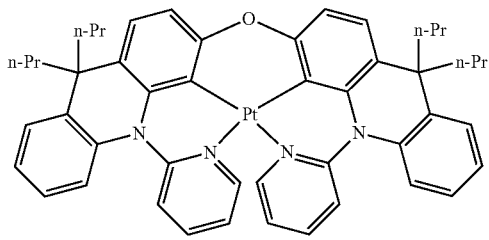
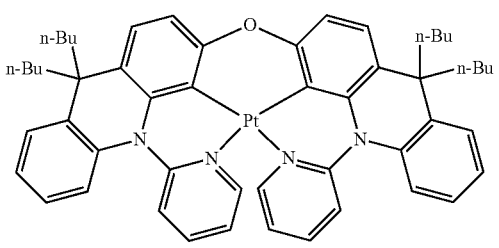
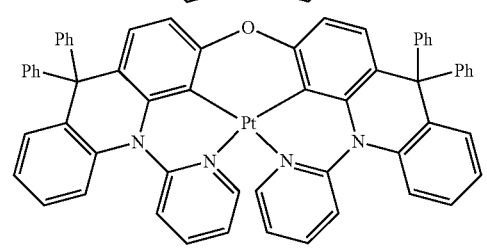
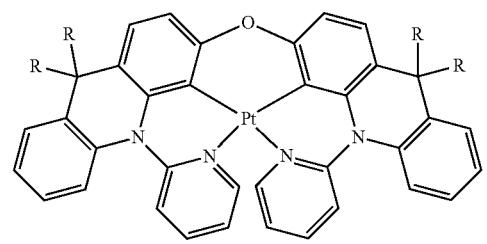
Structures 26
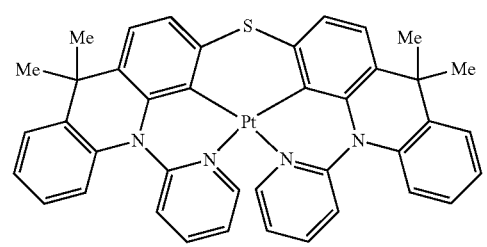
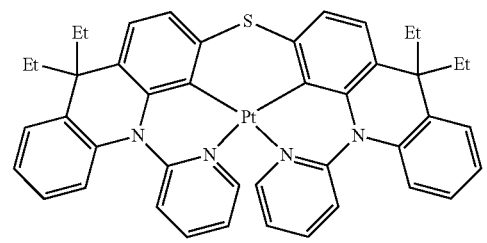
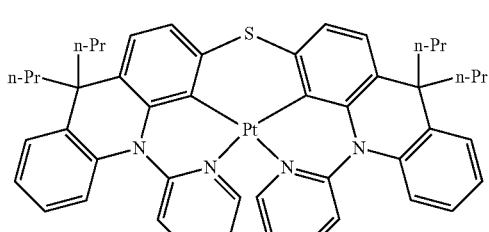

211
-continued
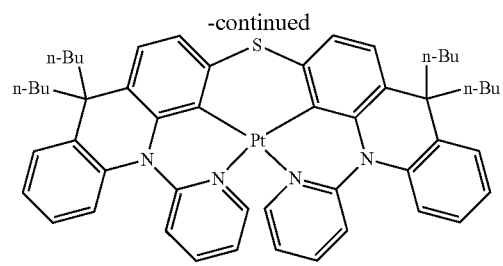
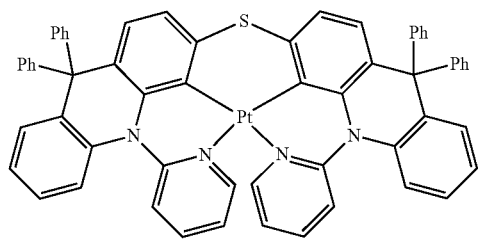
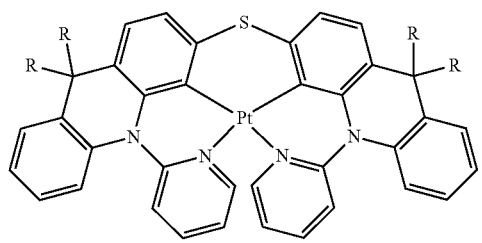
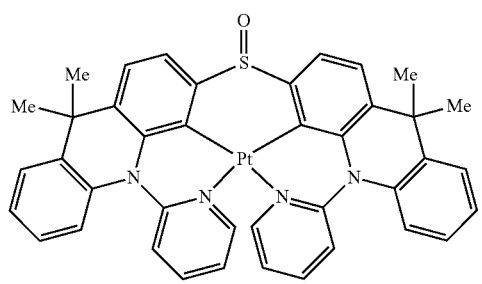
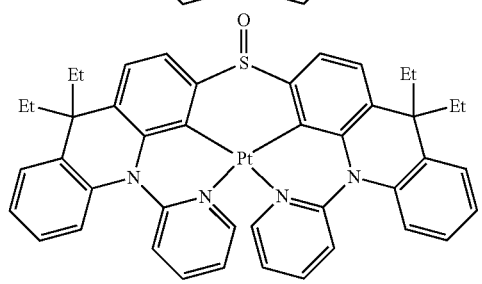
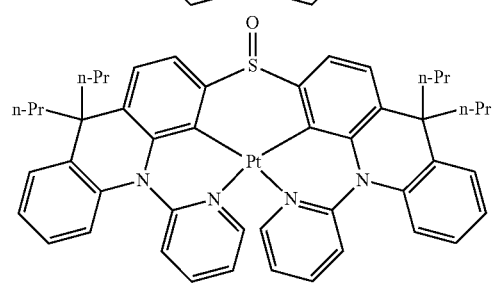
212
-continued
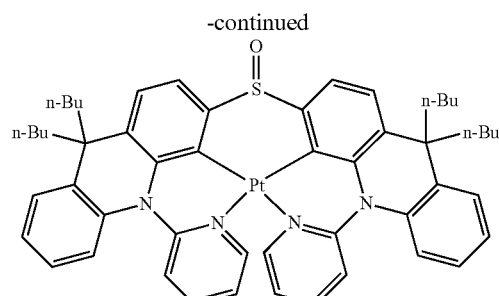
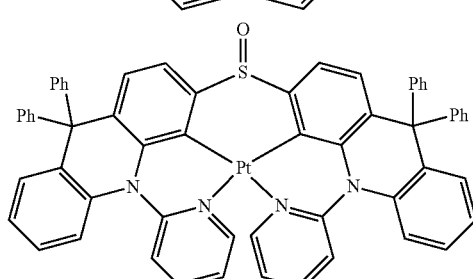
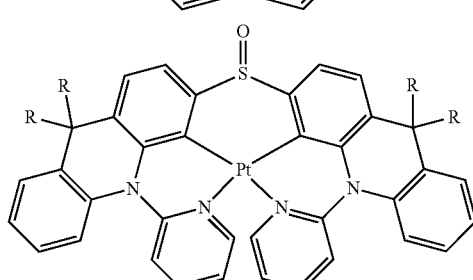
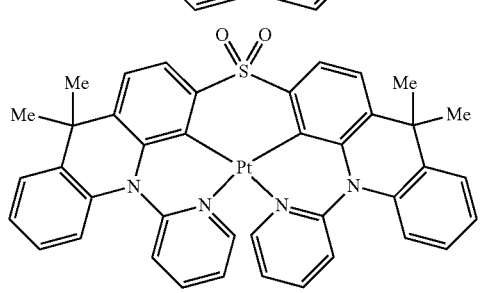
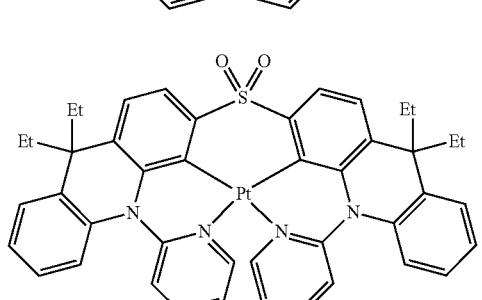
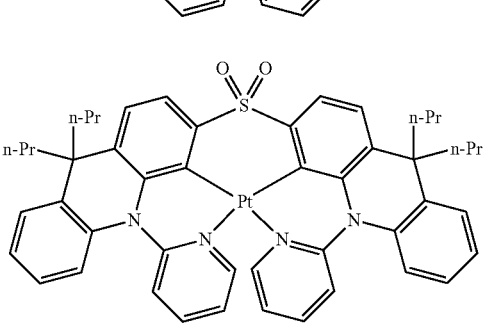

213
-continued
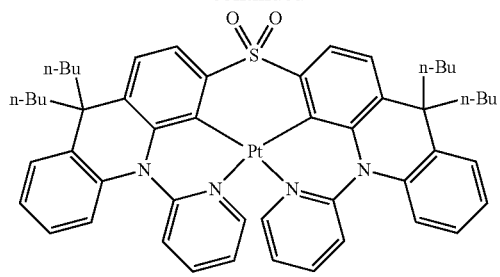
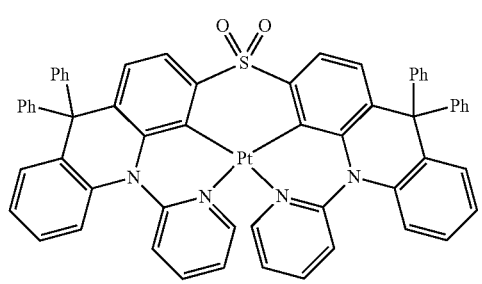
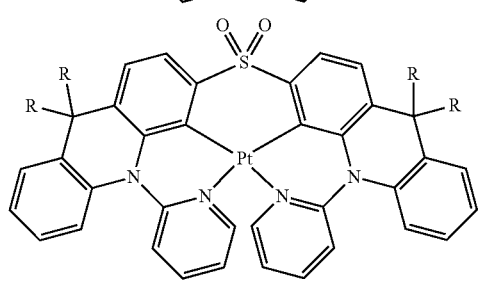
Structures 27
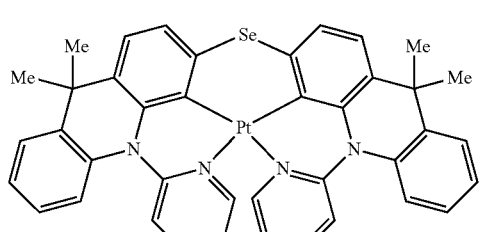
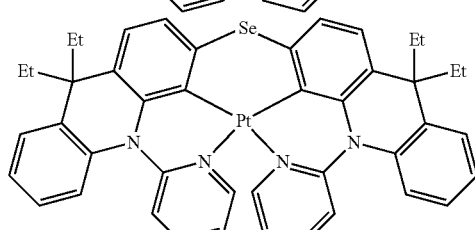
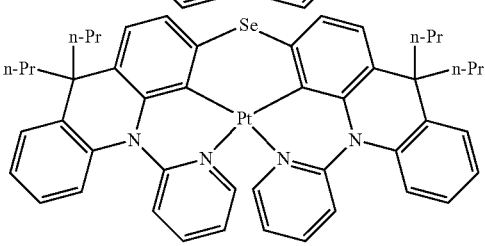
214
-continued
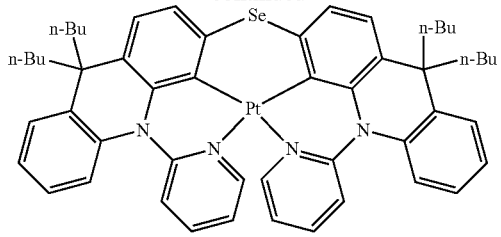
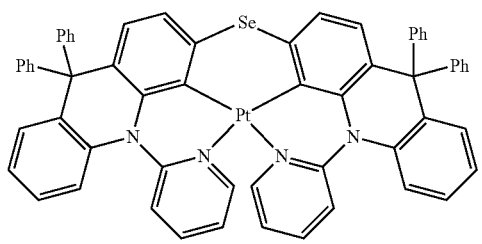
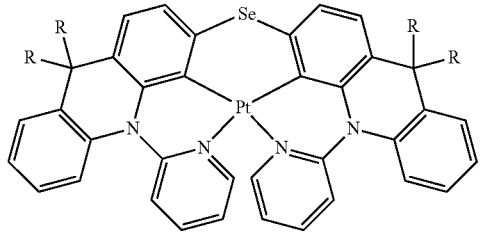

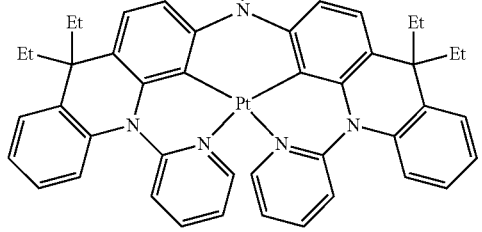
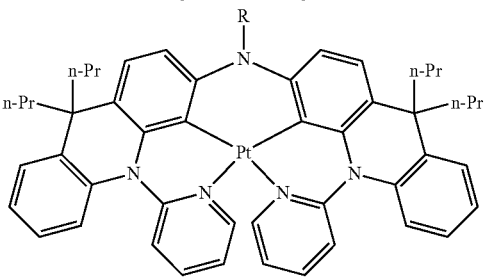

215
-continued
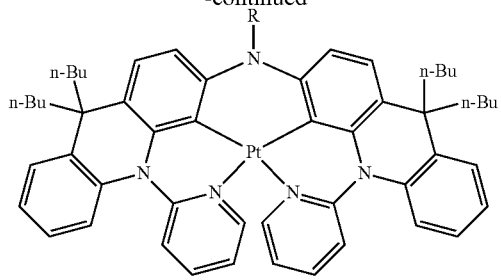
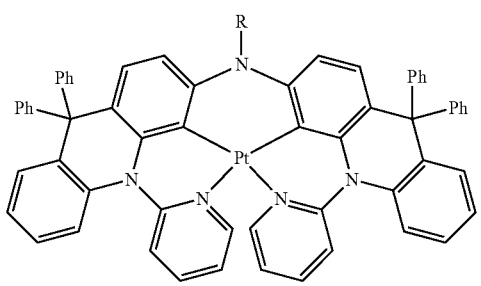
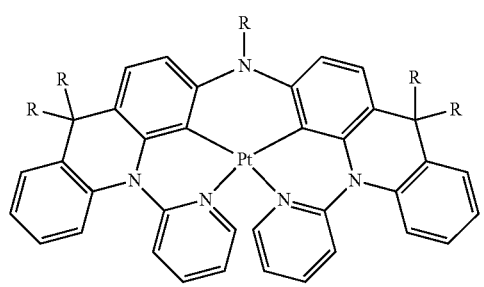
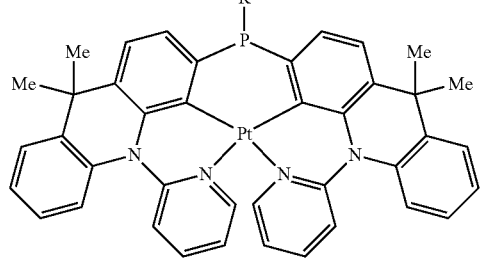
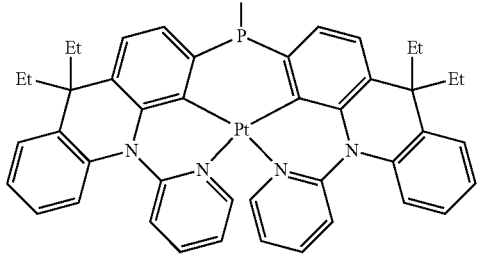
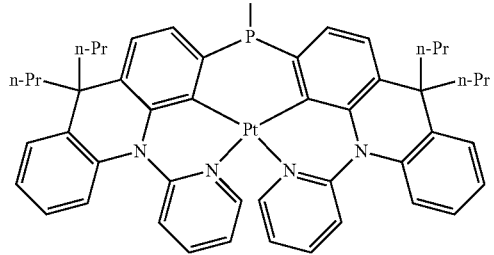
216
-continued
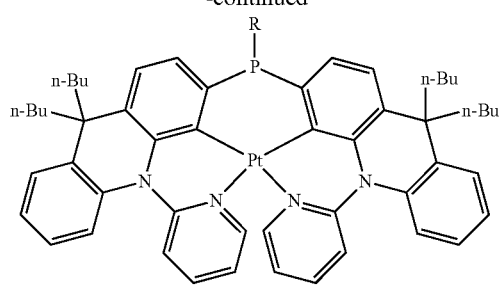
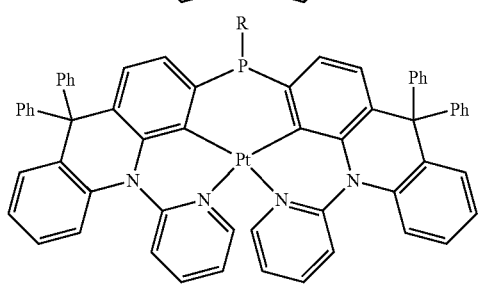
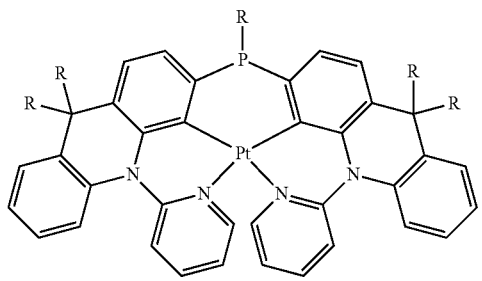
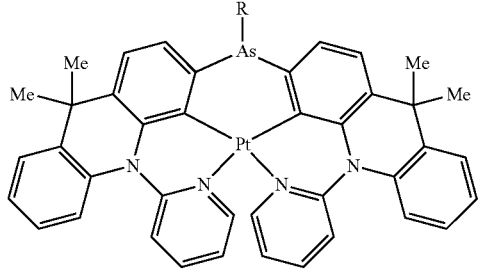
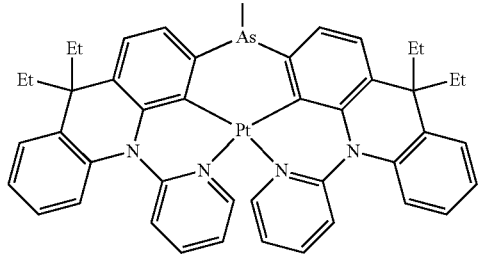
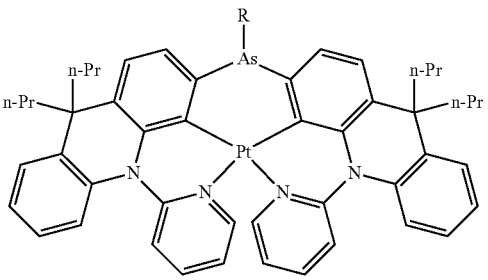

217
-continued
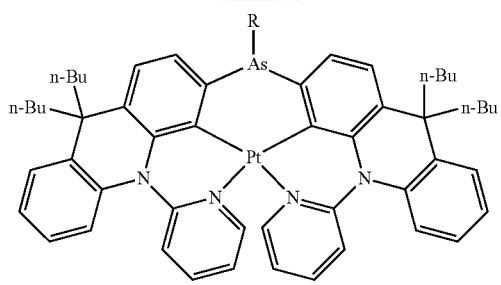
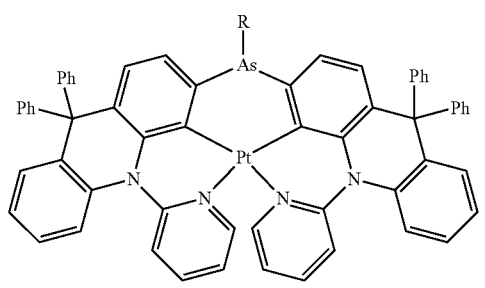
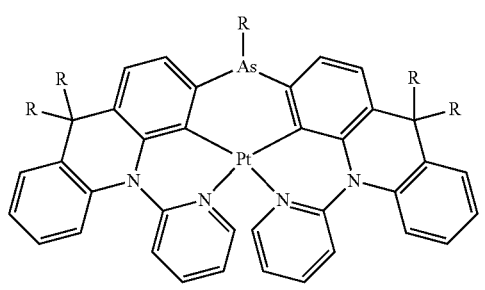
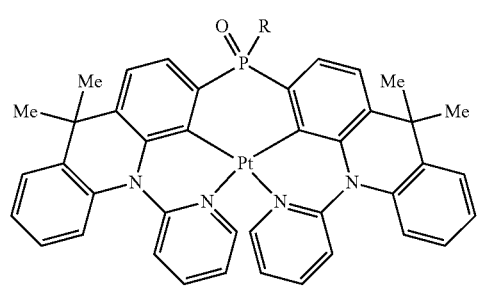
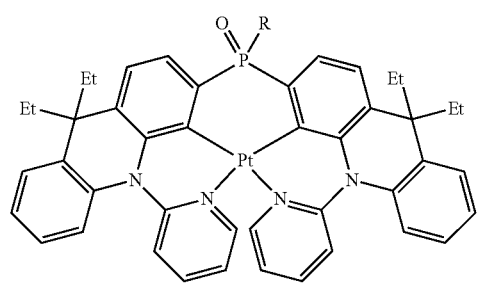
218
-continued
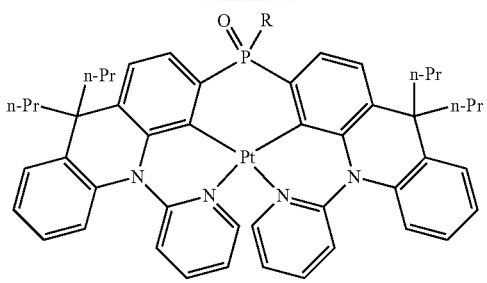
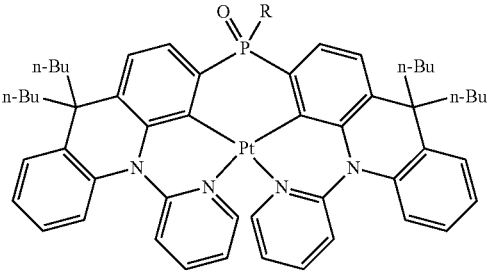
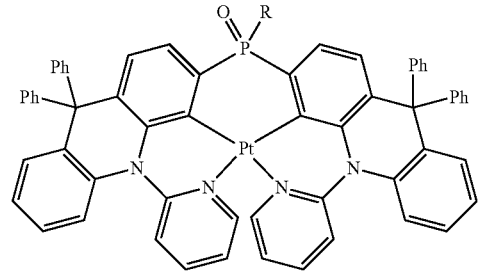
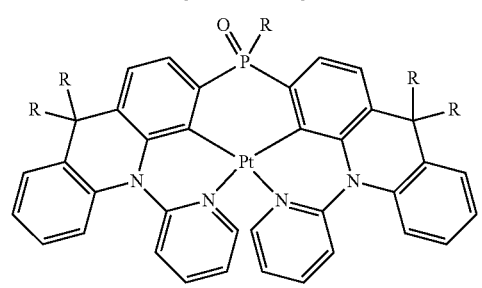
Structures 28
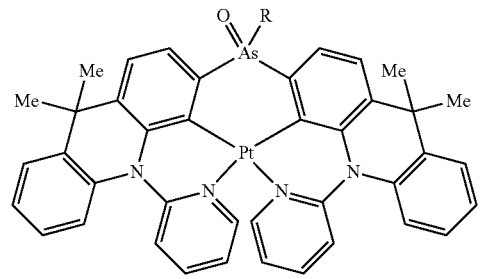
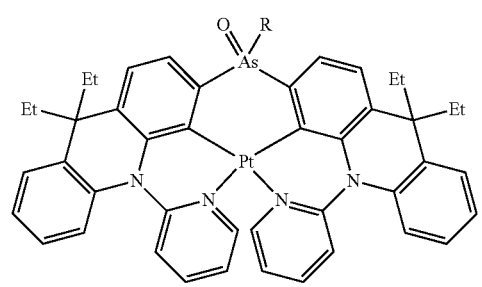

219
-continued
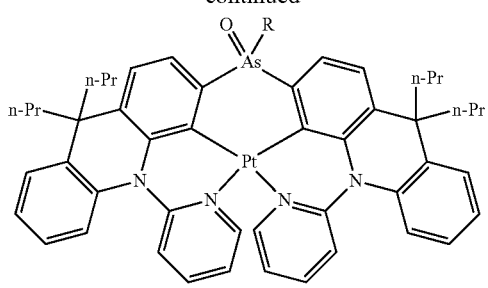
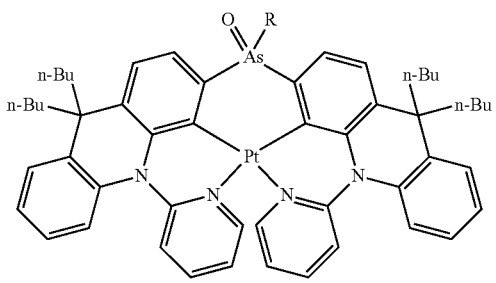
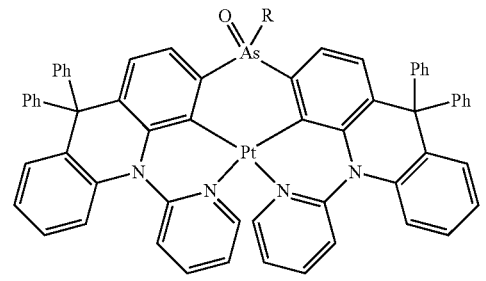
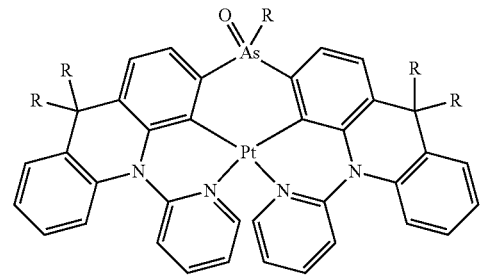
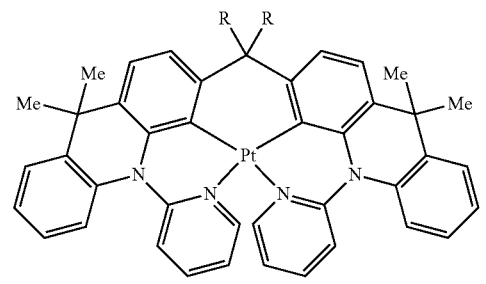
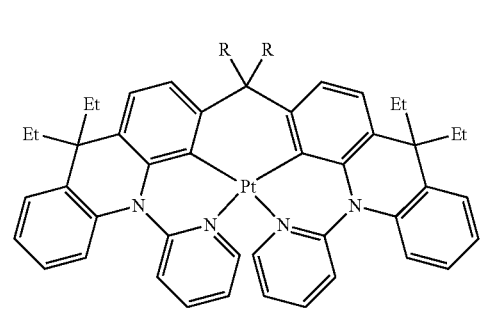
220
-continued
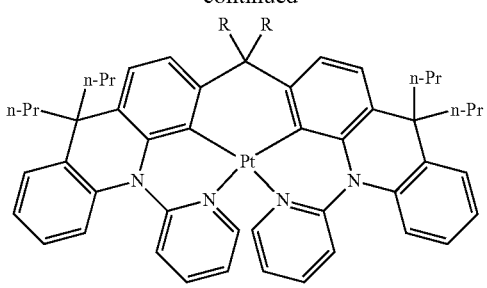
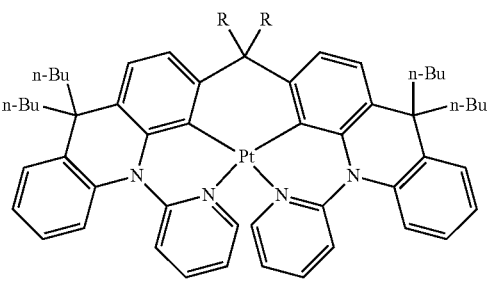
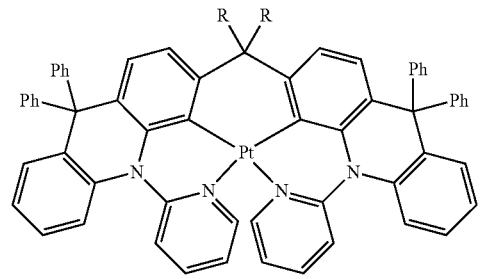
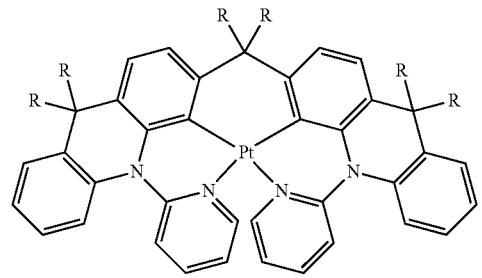
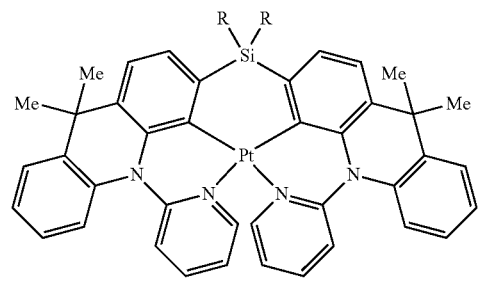
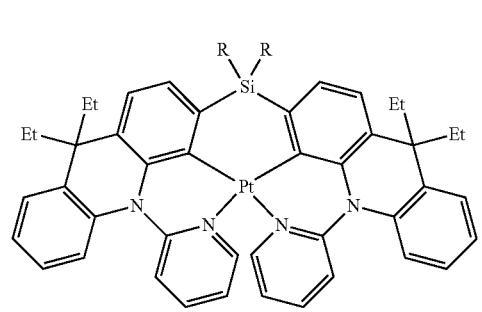

221
-continued
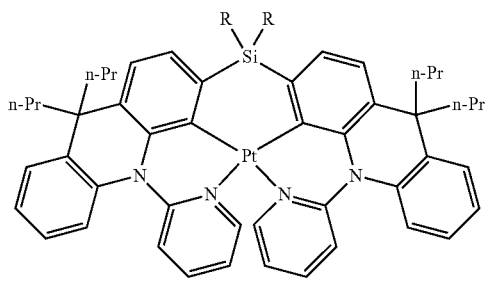
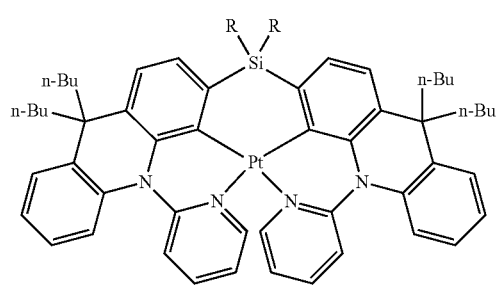
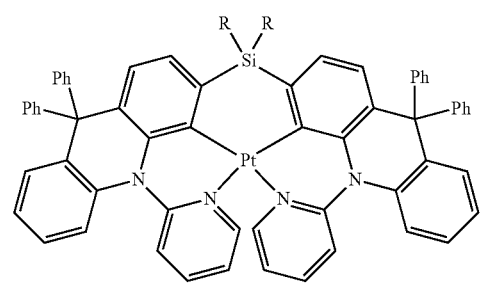
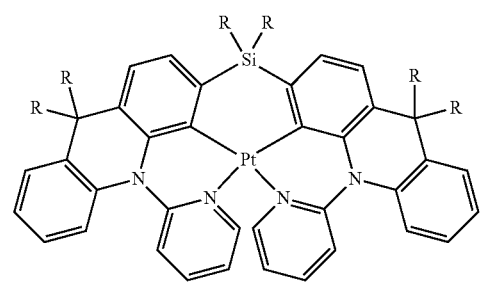
Structures 29
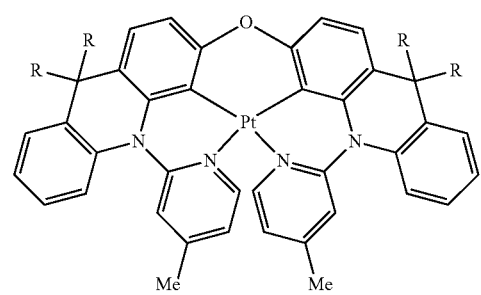
222
-continued
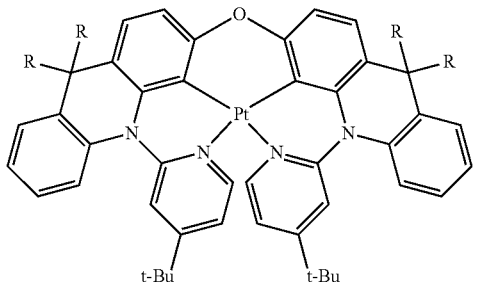
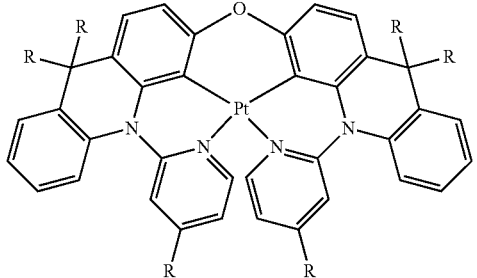
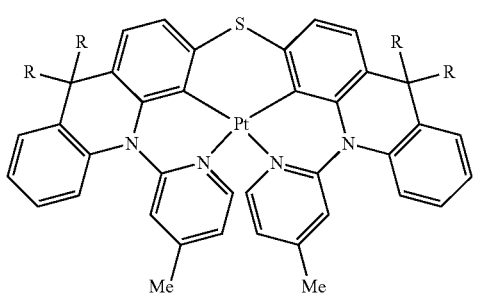
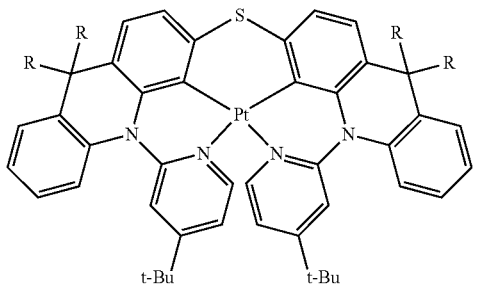
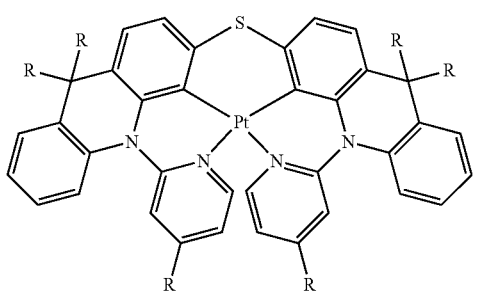

223
-continued
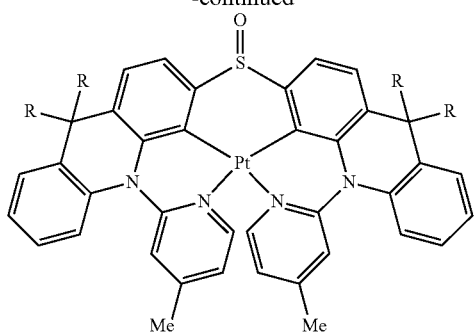
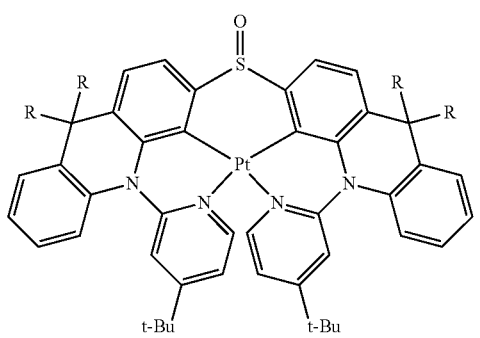
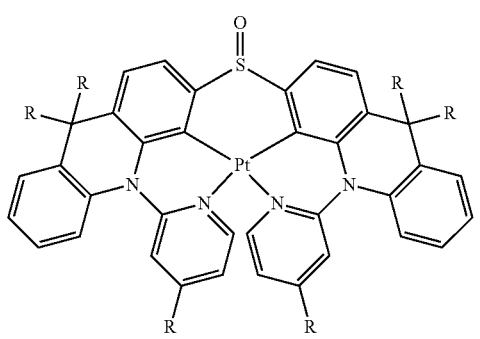
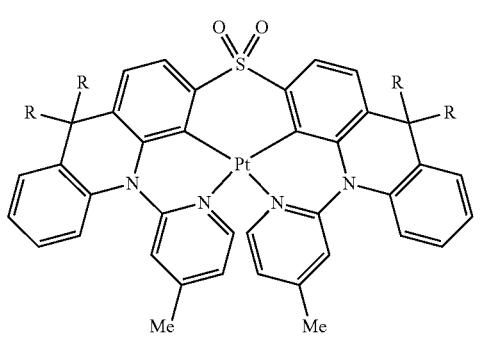
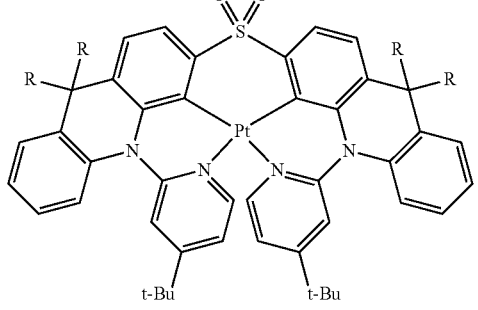
224
-continued
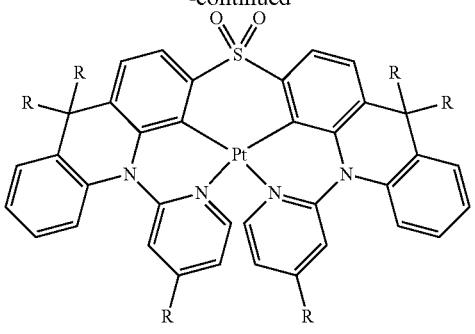
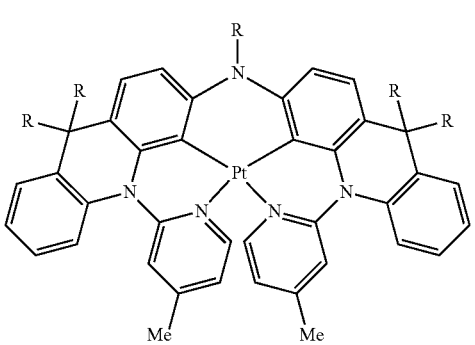
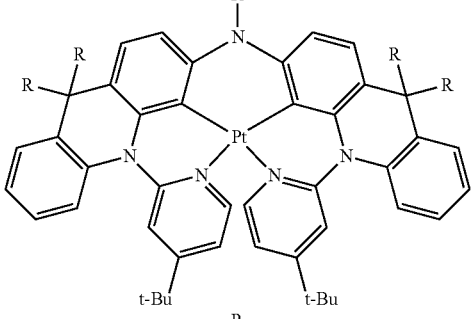
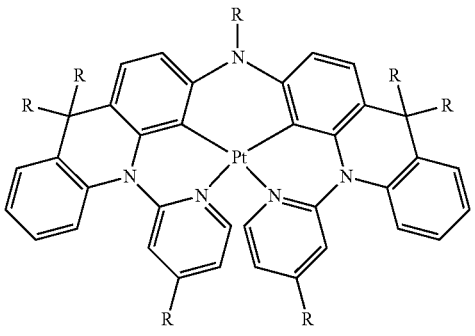
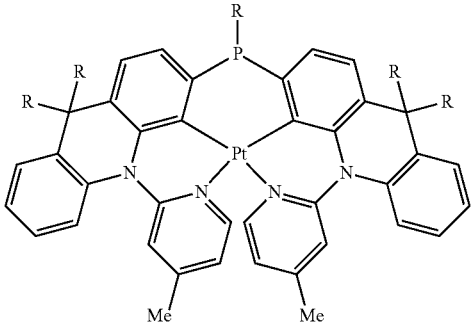

225
-continued
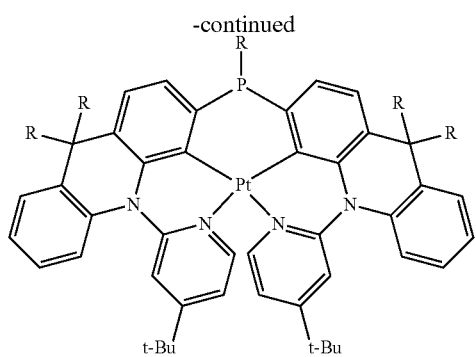
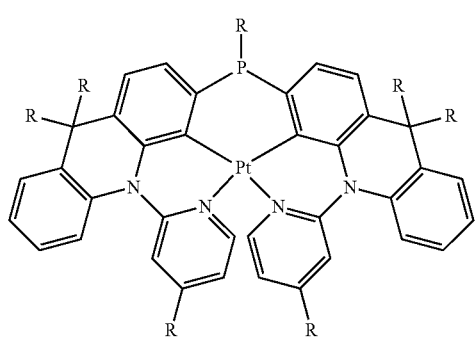
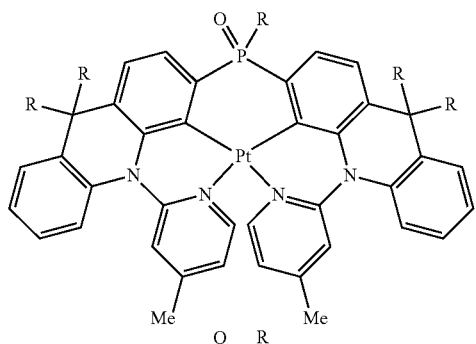
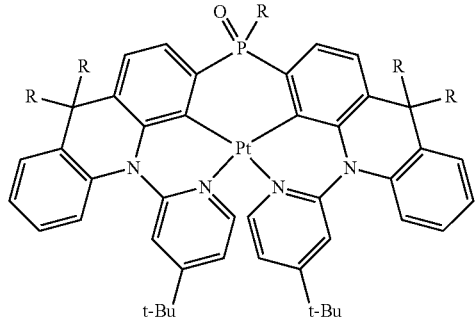
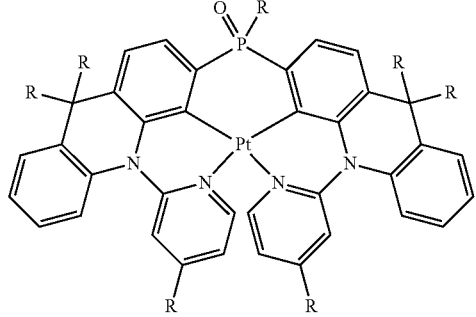
226
Structures 30
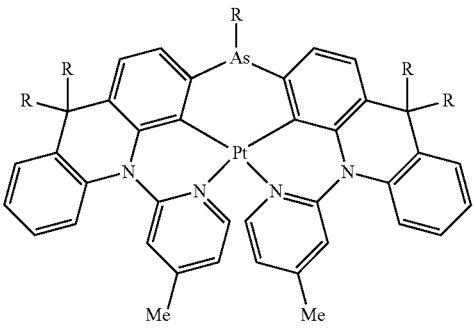
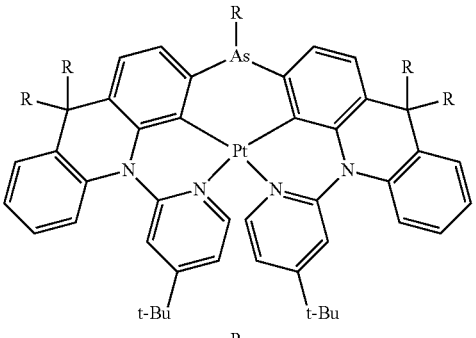
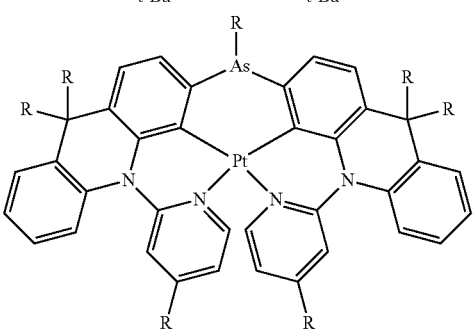
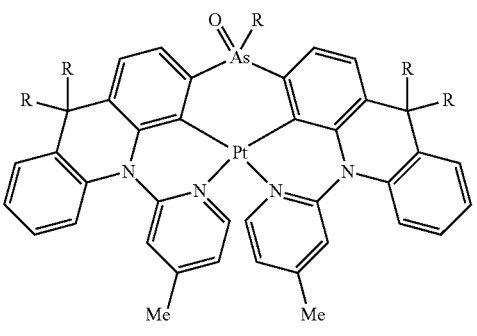
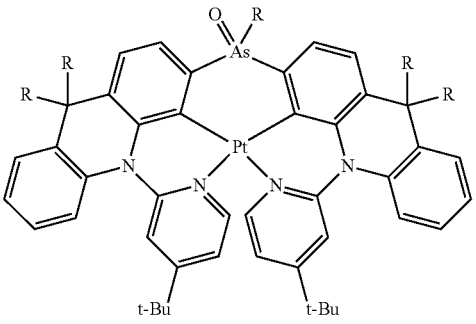

227
-continued
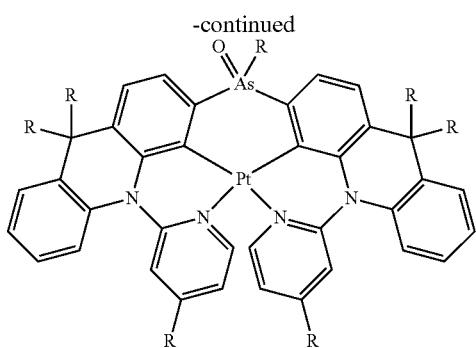
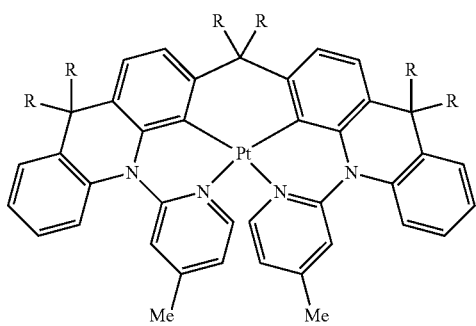
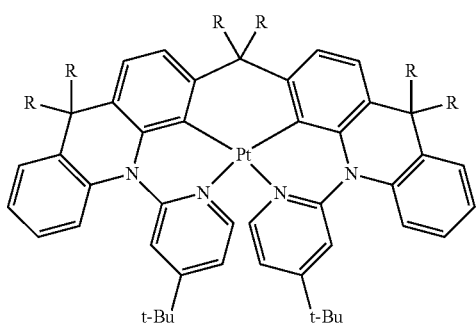
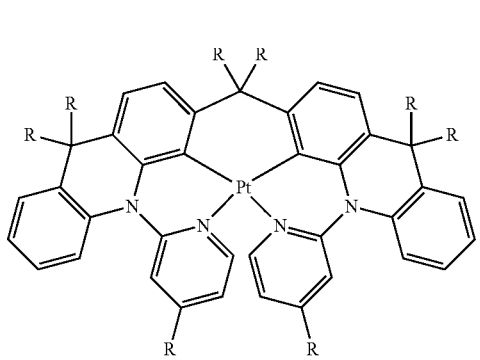
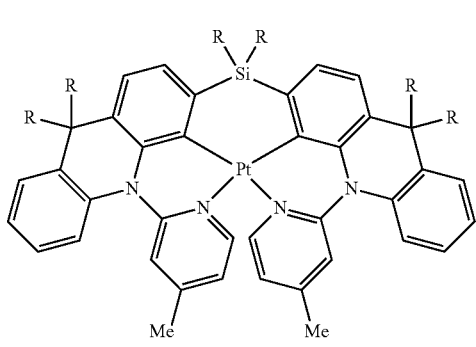
228
-continued
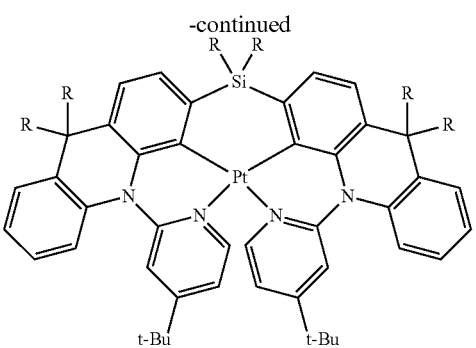
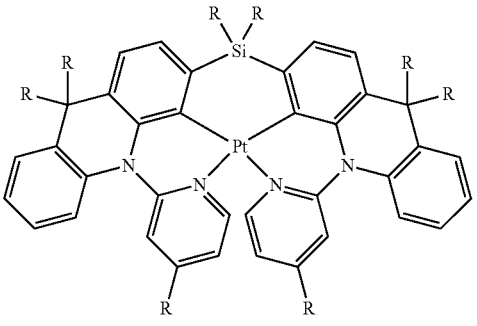
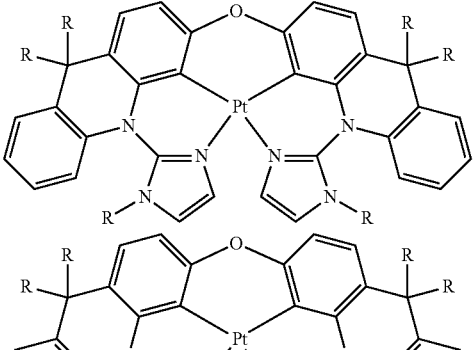
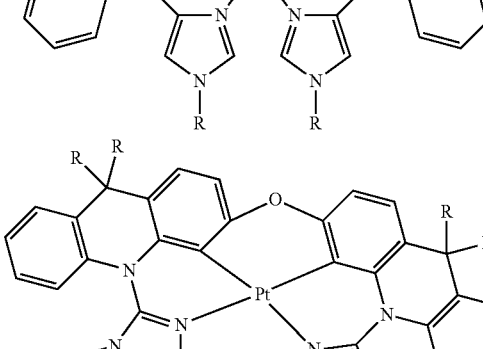
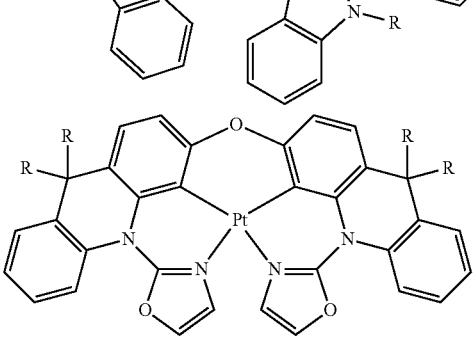

229
-continued
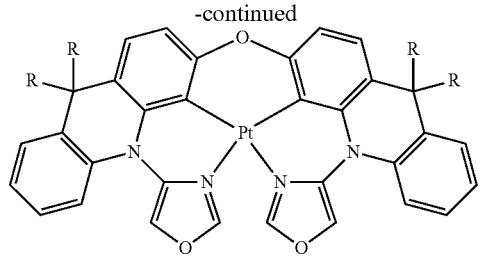
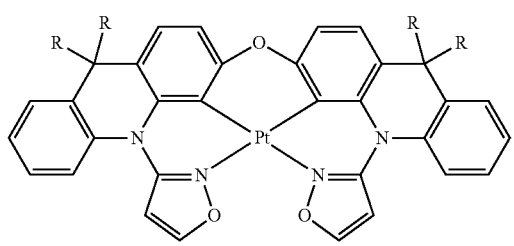
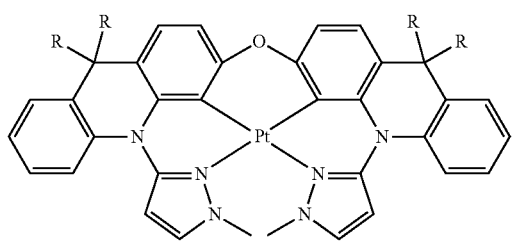
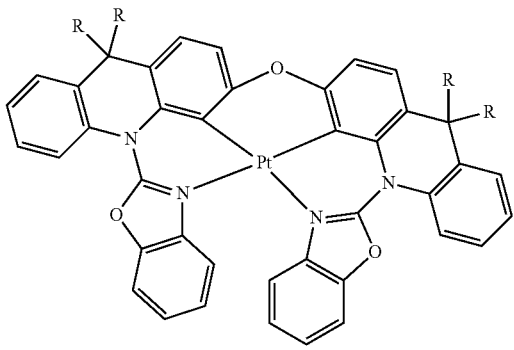
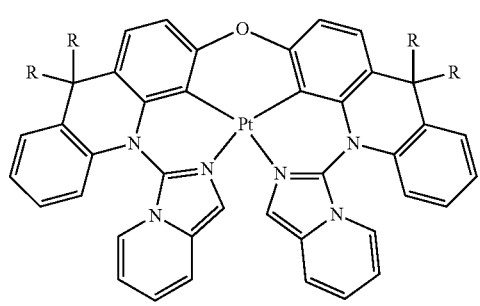
230
Structures 31
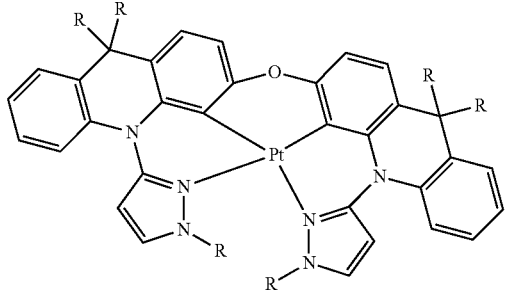
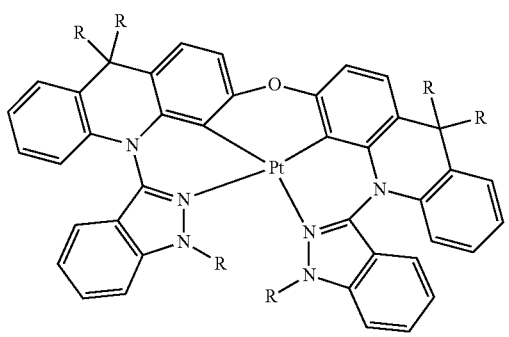
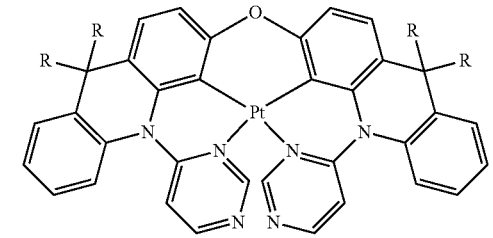
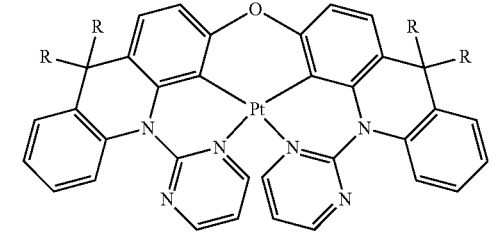
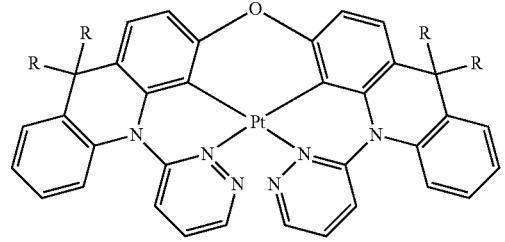
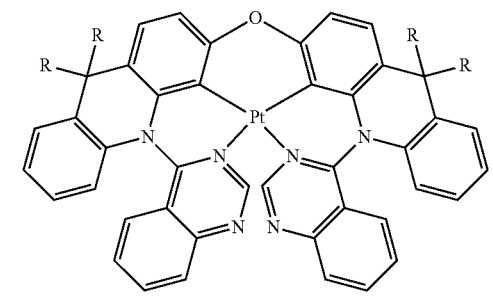

231
-continued
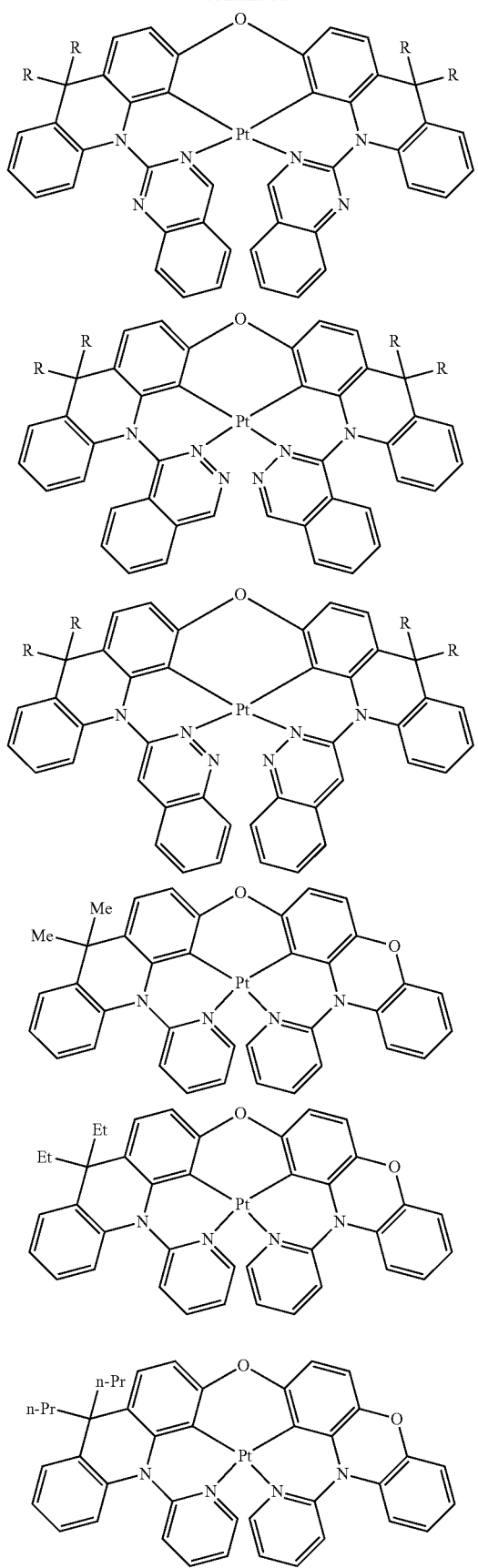
232
-continued
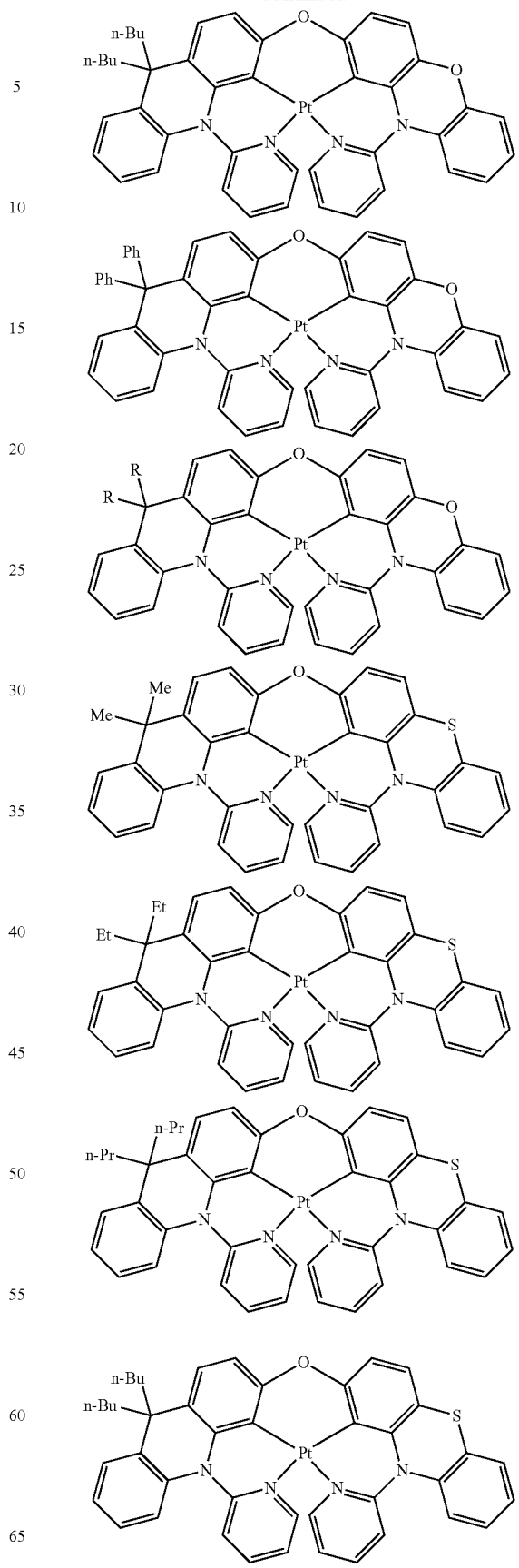

233
-continued
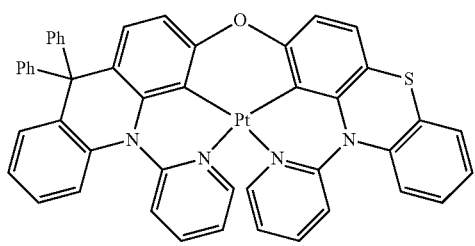
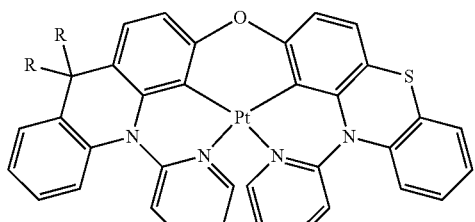
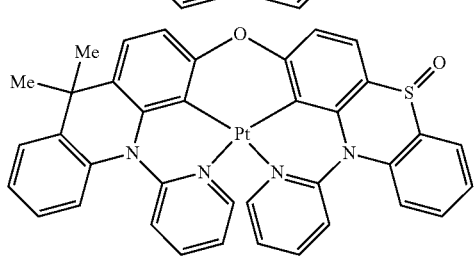
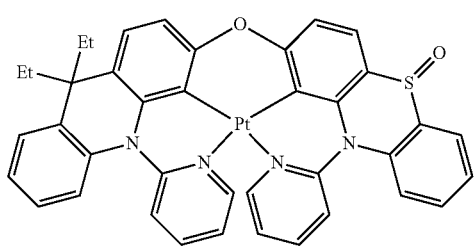
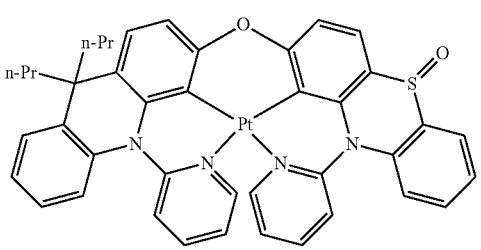
234
-continued
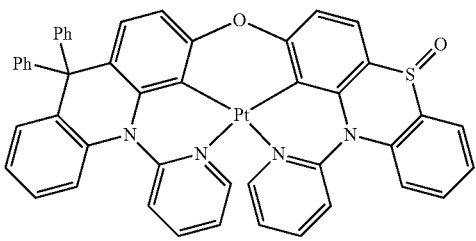
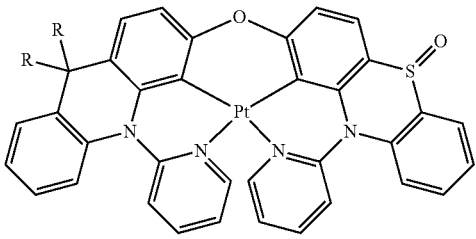
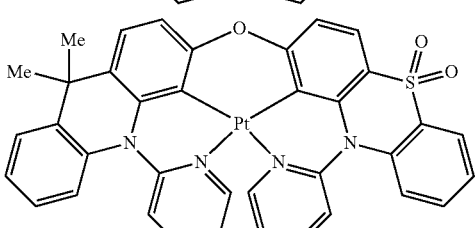
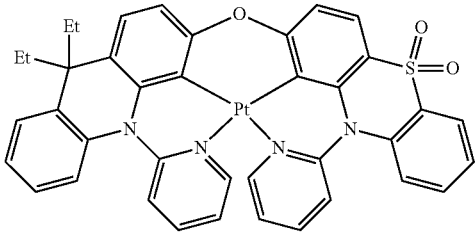
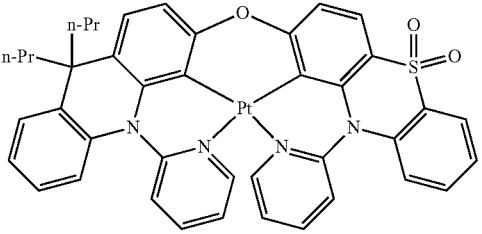
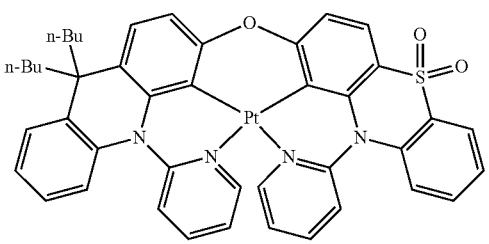
Structures 32
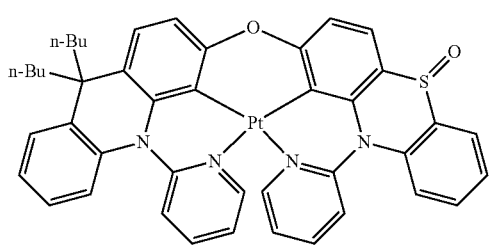
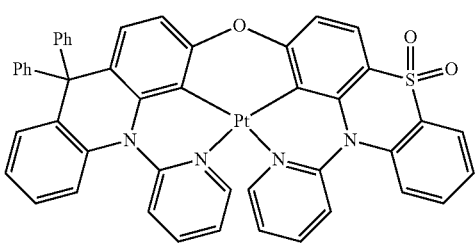

235
-continued
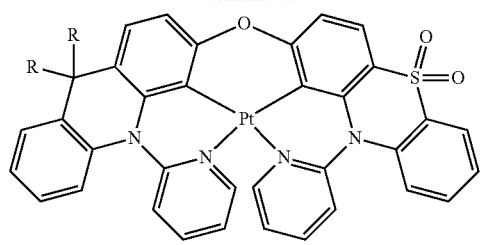
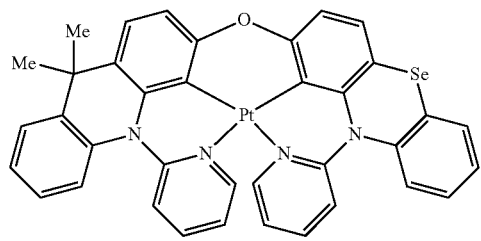
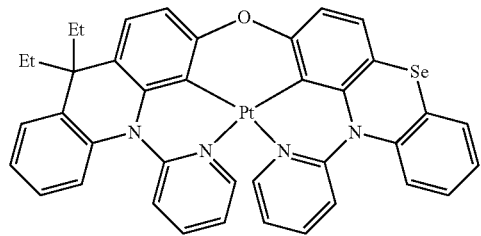
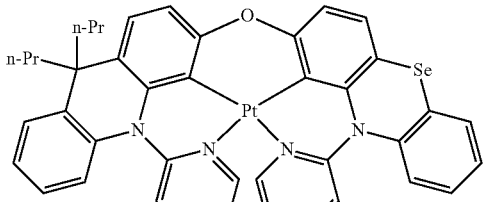
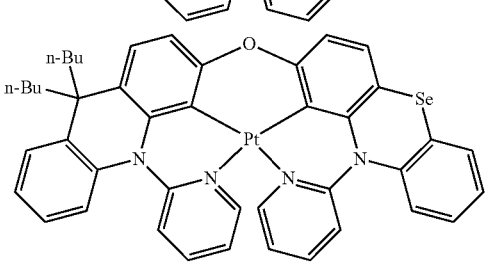
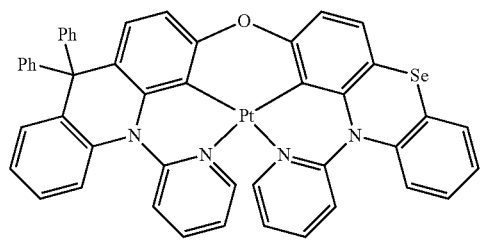
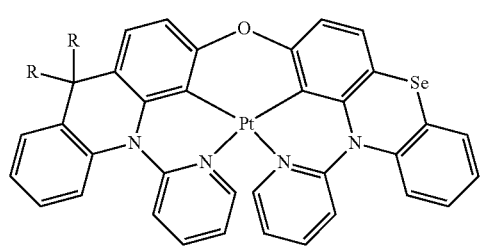
236
-continued
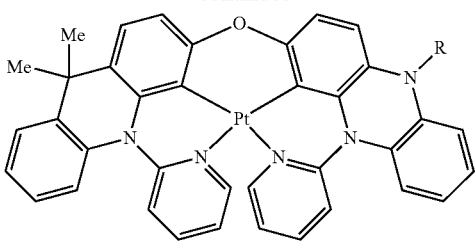
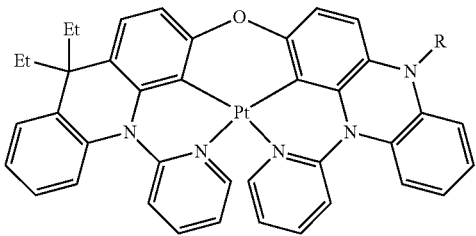
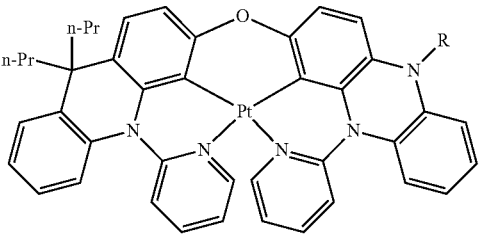
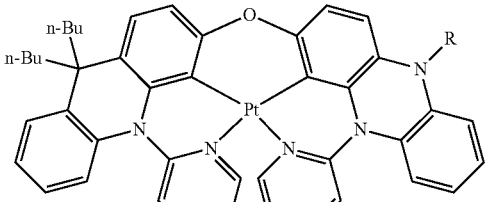
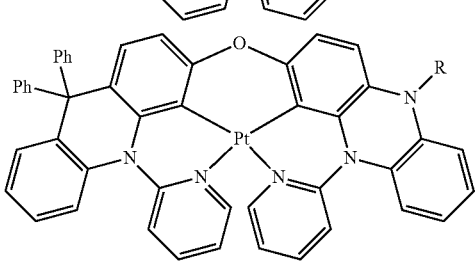
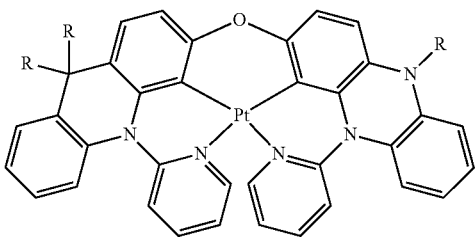
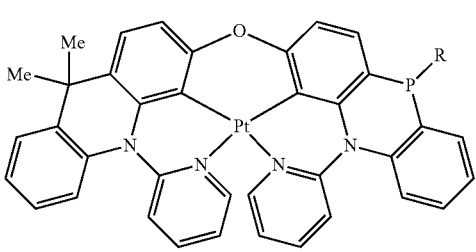

237
-continued
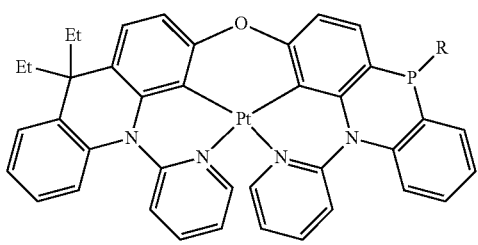
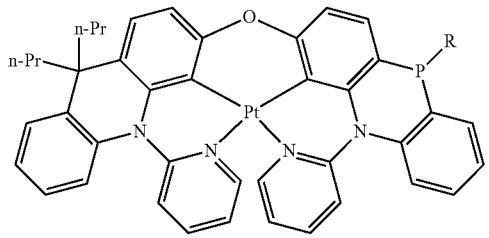
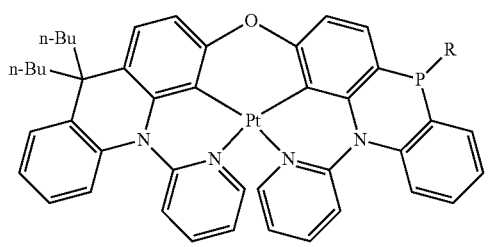
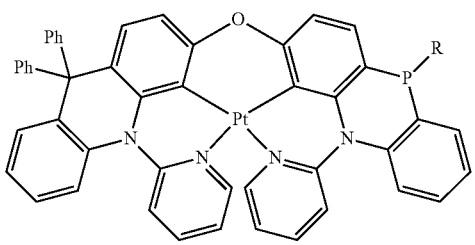
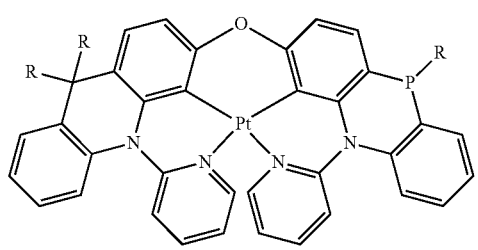
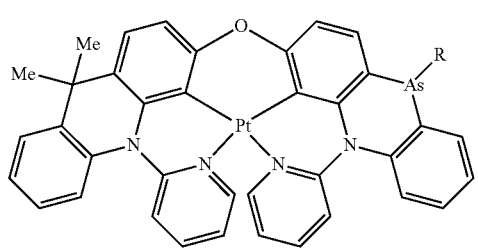
Structures 33
238
-continued
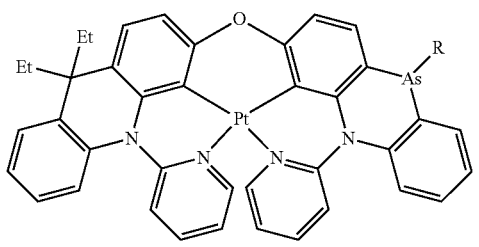
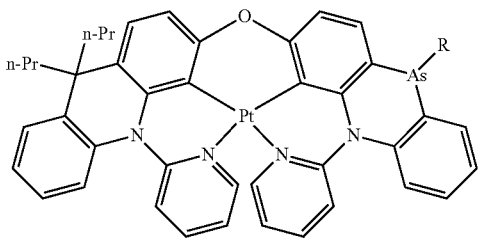
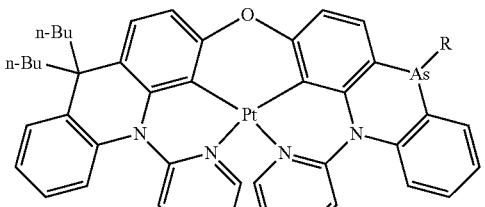
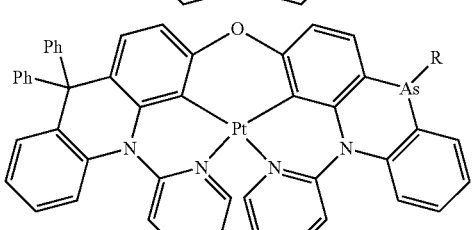
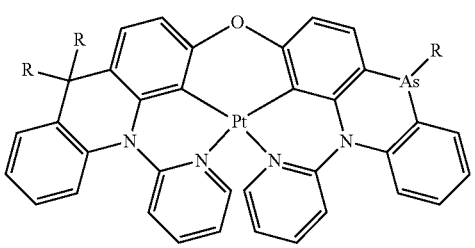
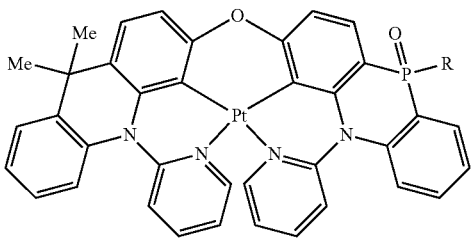
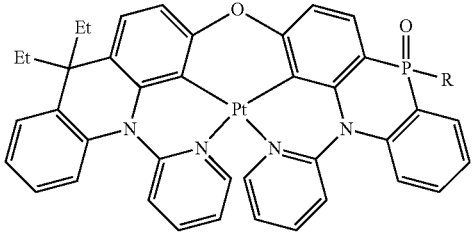

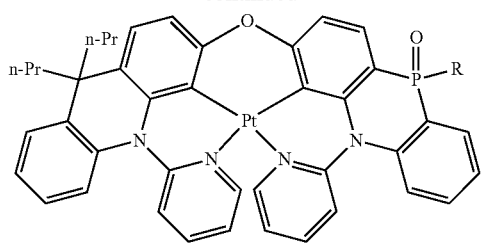
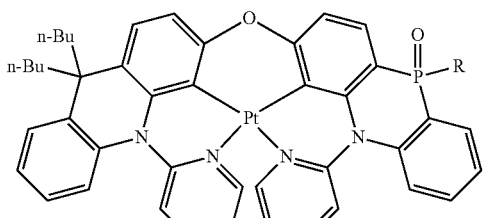
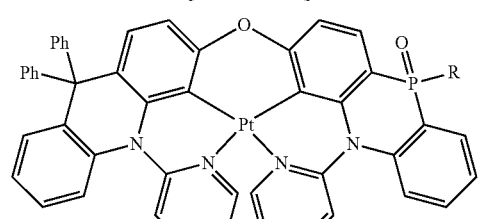
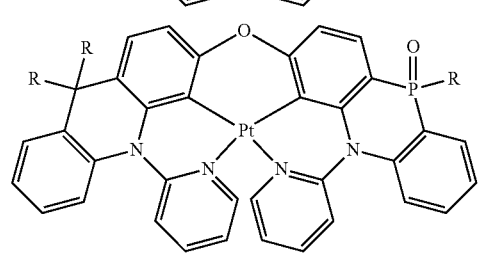
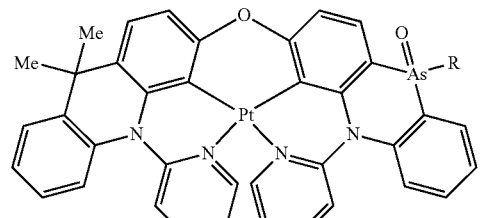
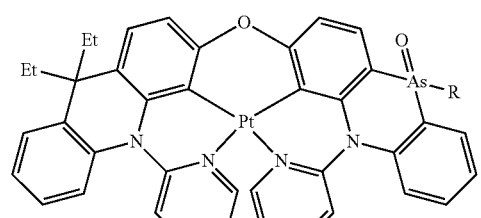
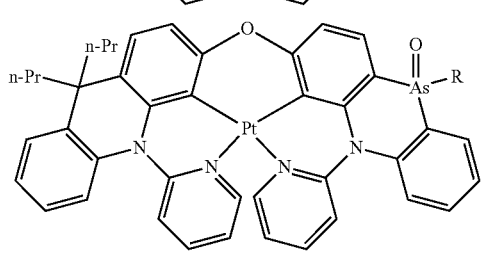
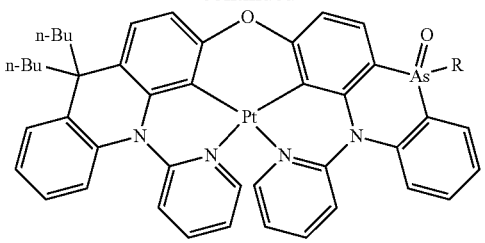
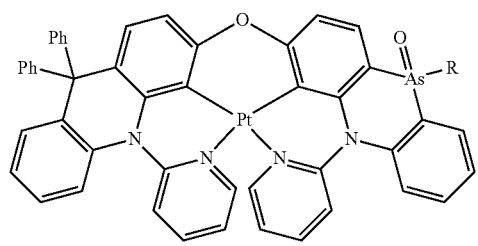
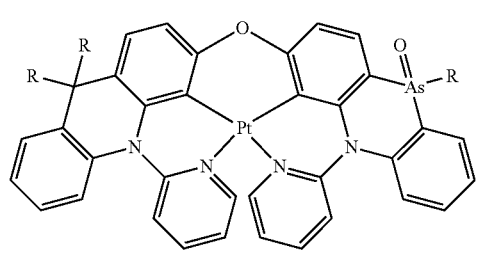
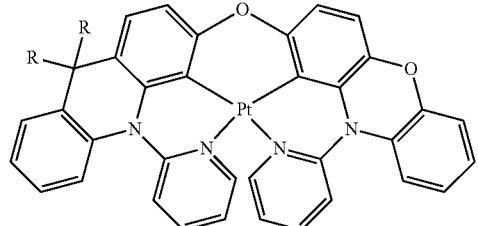
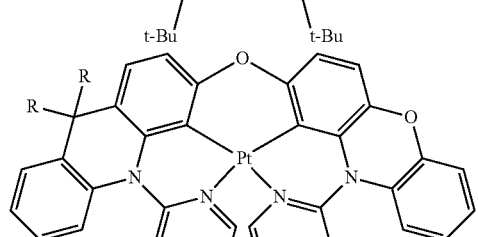
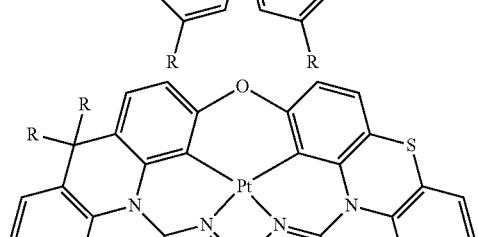

Structures 34
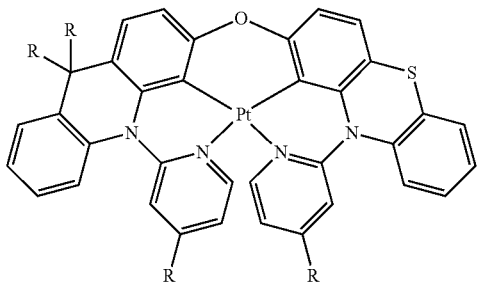
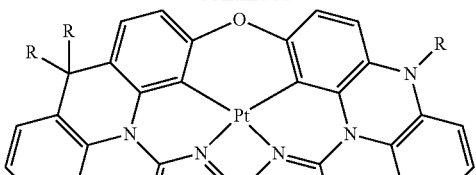
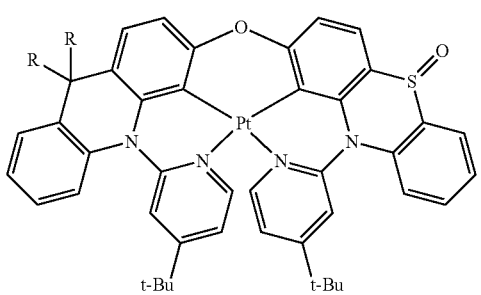
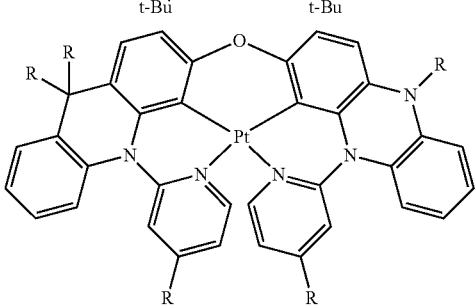
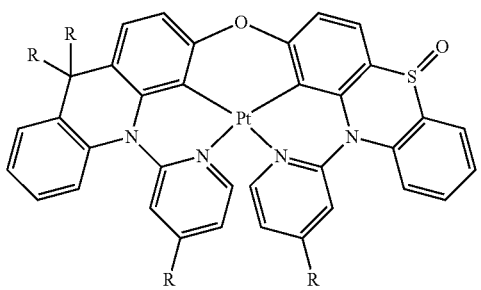
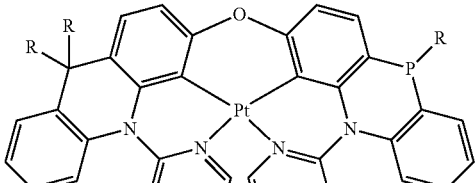
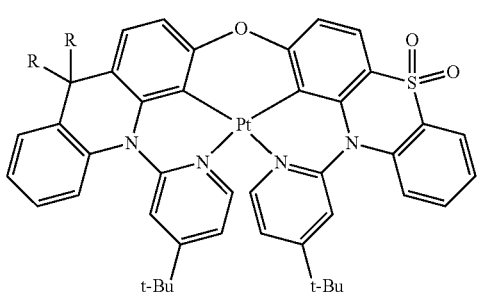
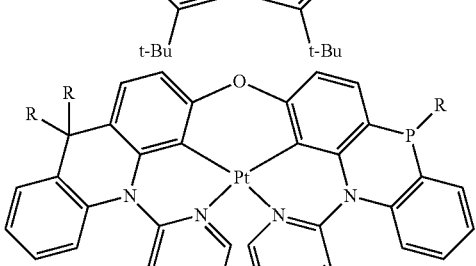
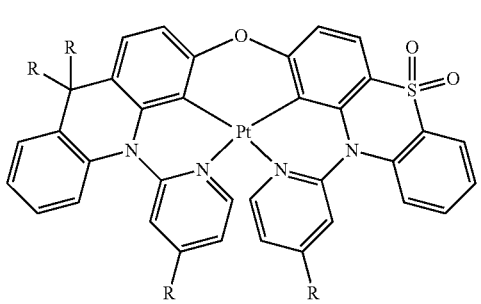
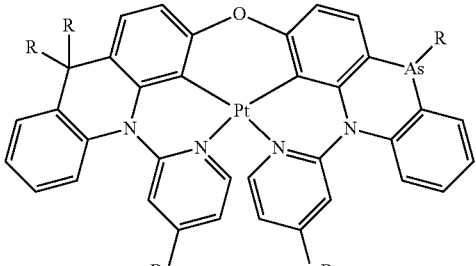
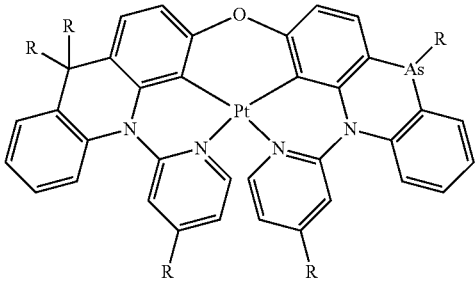

-continued
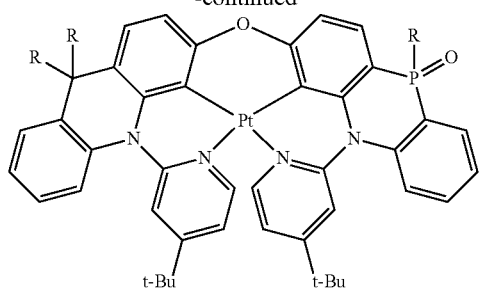
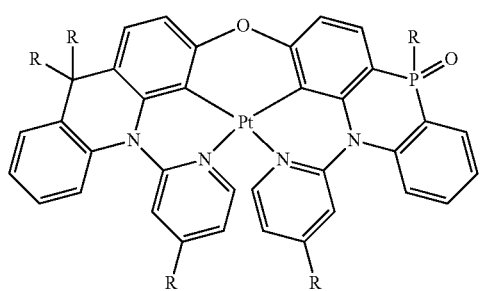
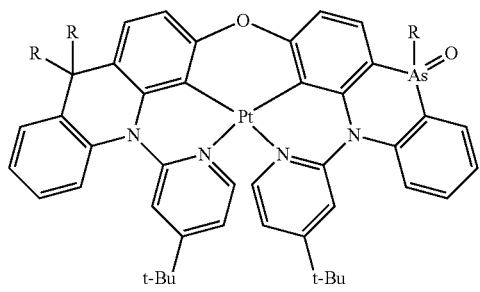
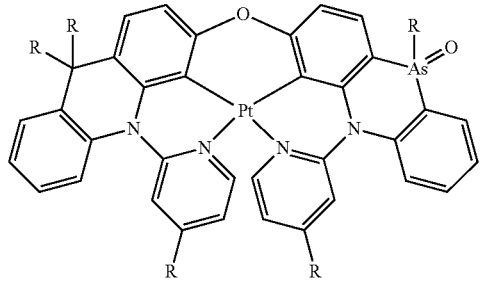
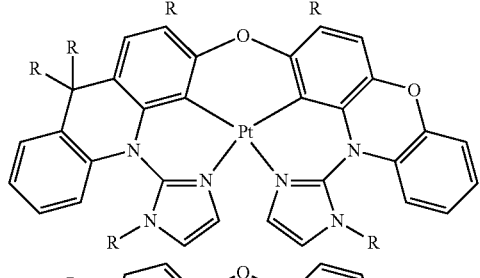
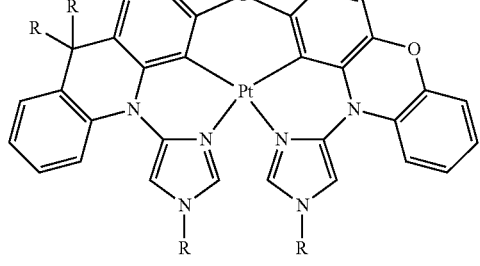
-continued
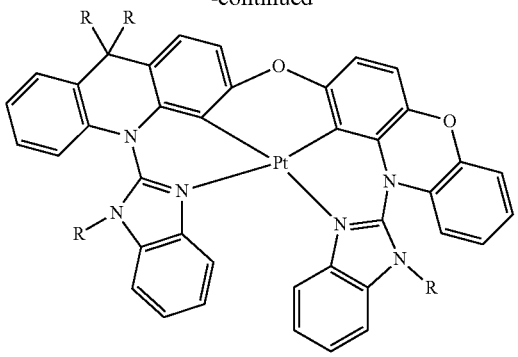
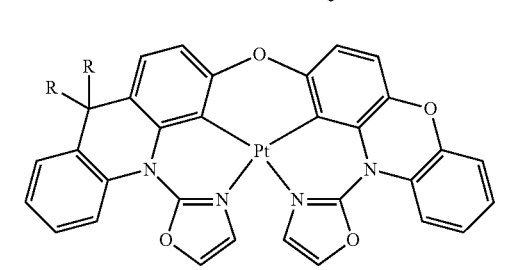
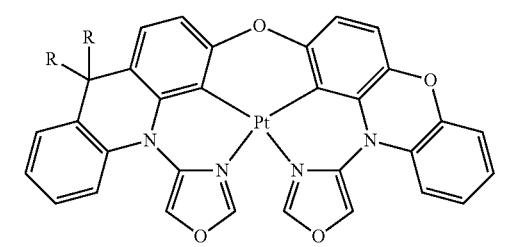
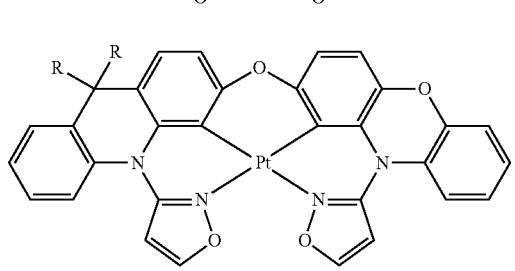
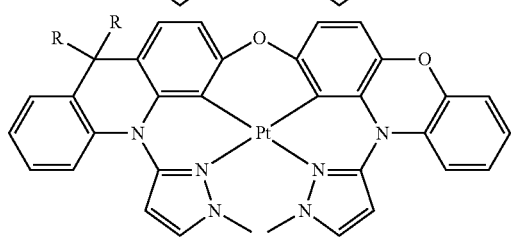
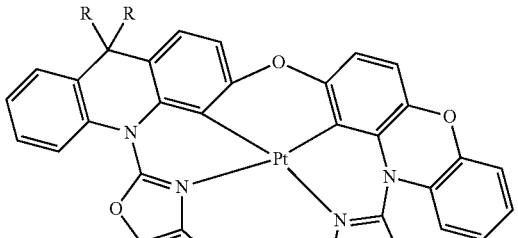
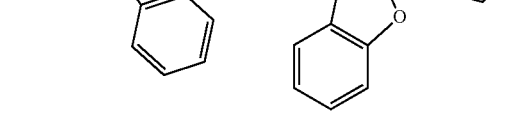

245
-continued
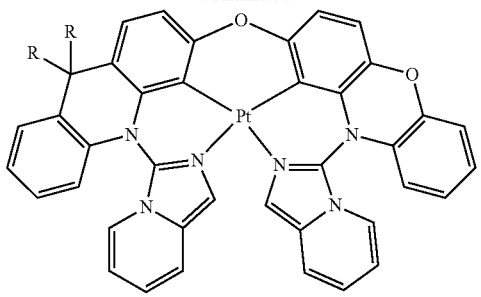
Structures 35
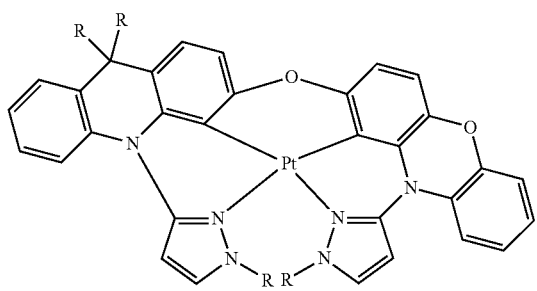
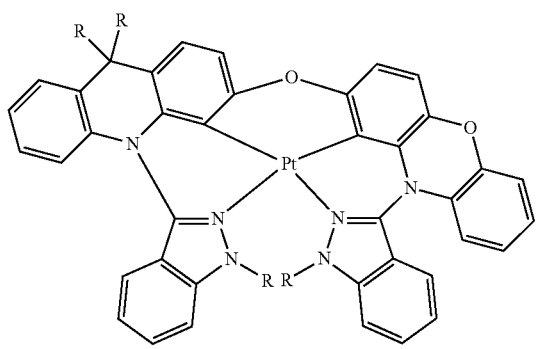
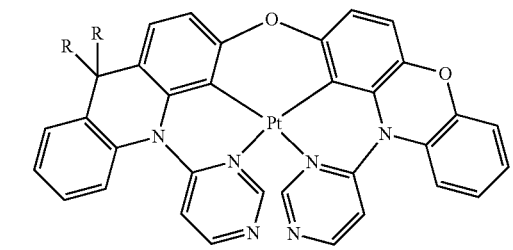
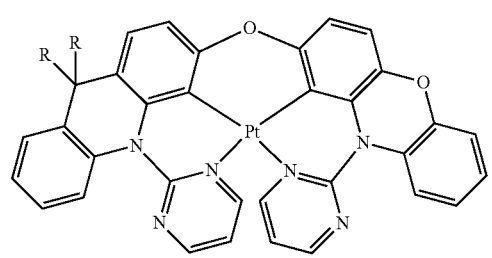
246
-continued
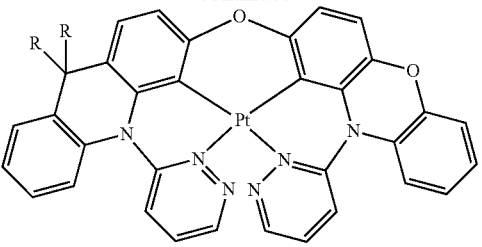
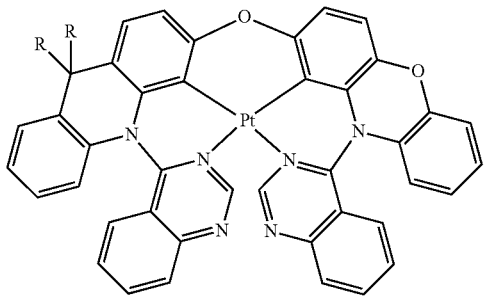
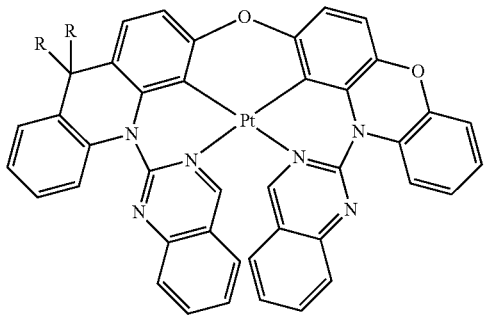
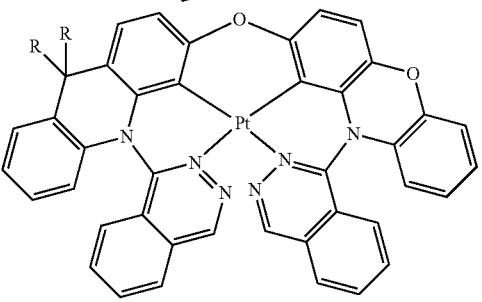
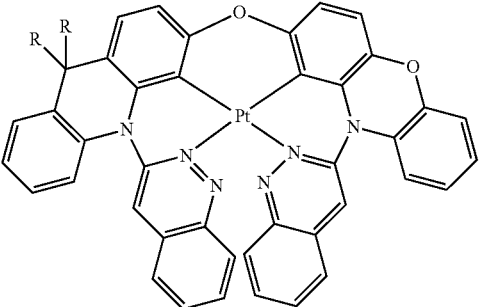
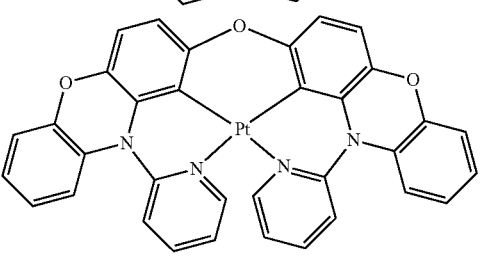

247
-continued
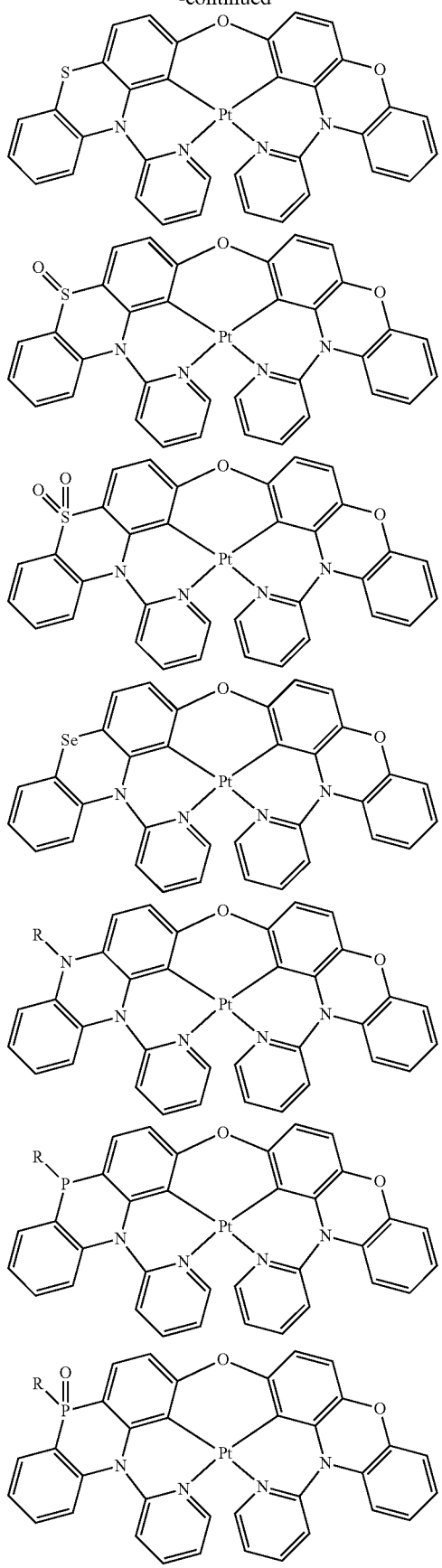
248
-continued
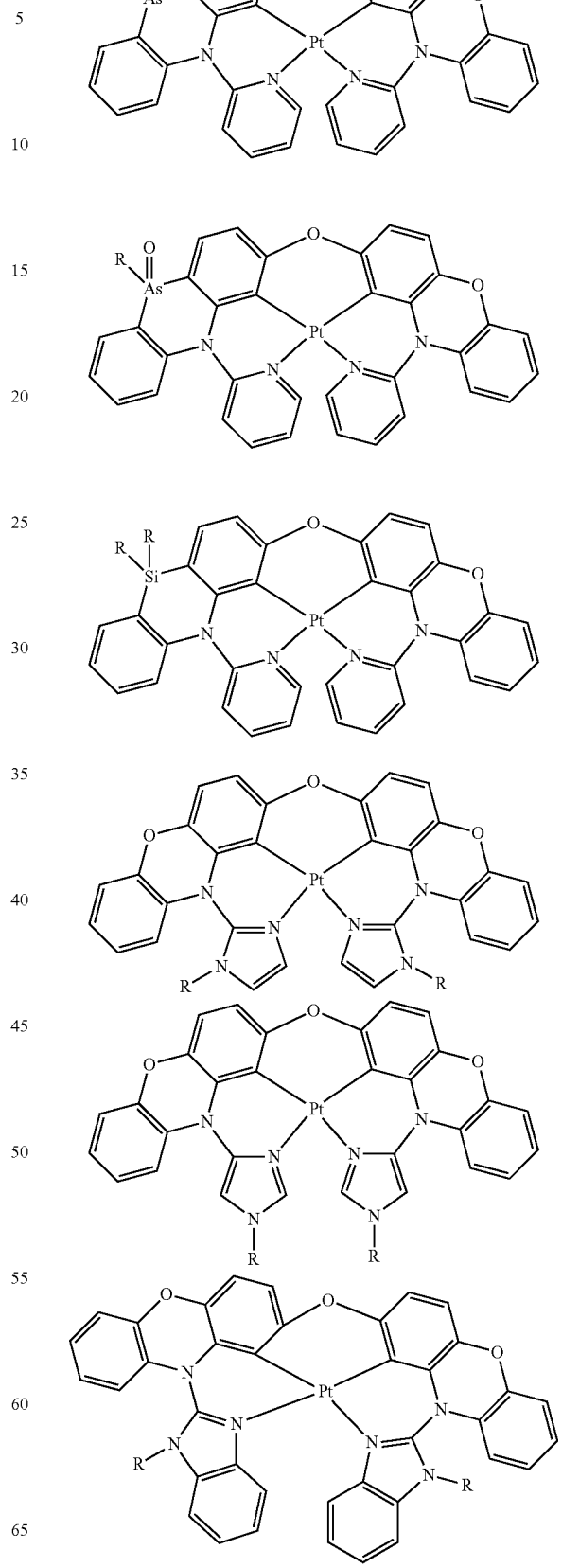

249
-continued
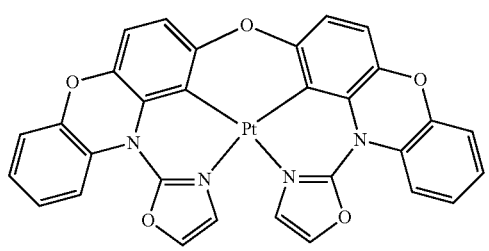
250
-continued
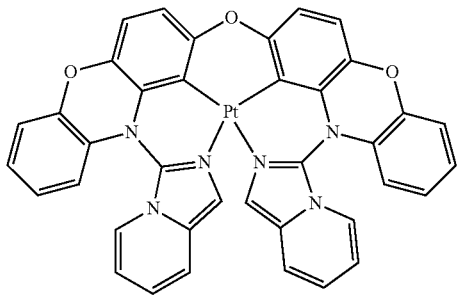
Structures 36
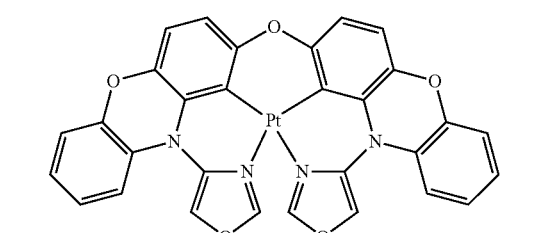
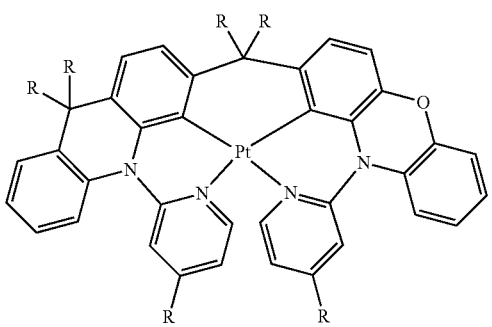
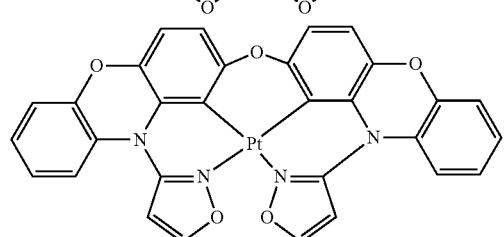
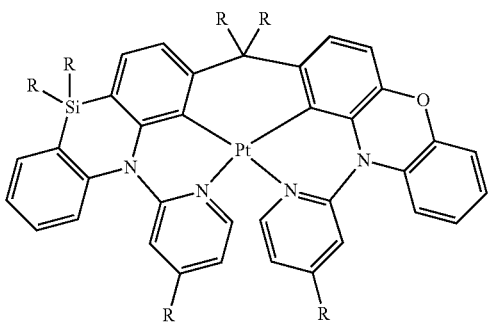
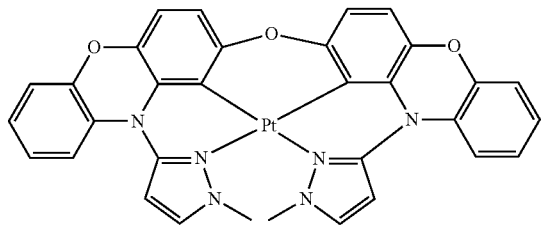
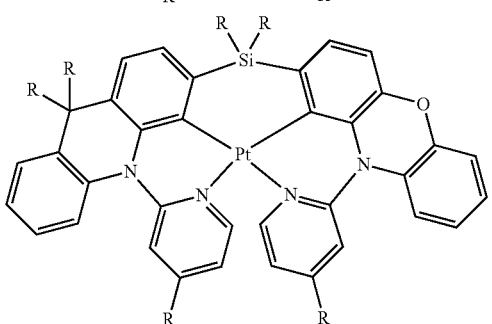
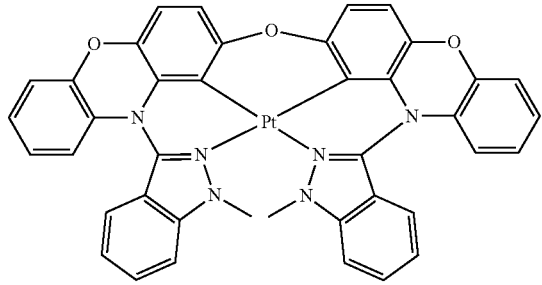
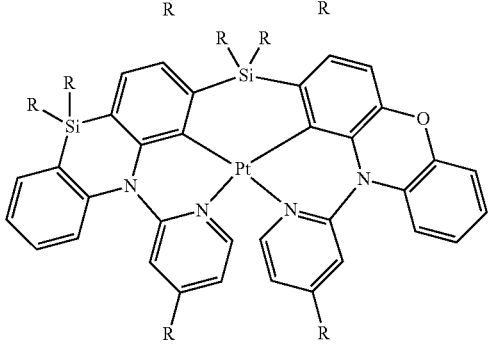
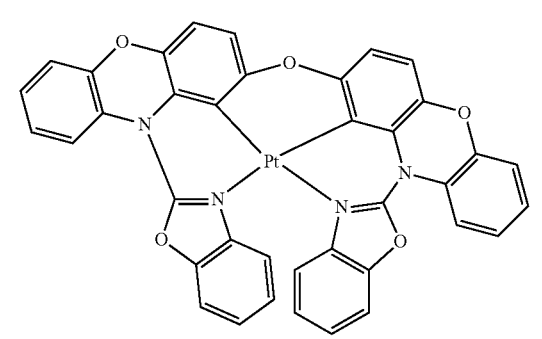

251
-continued
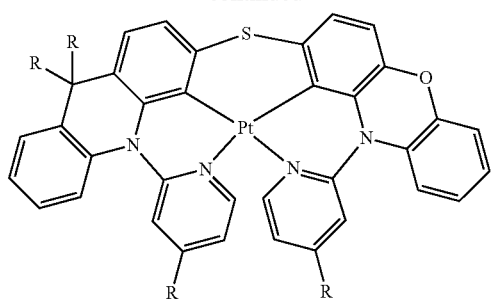
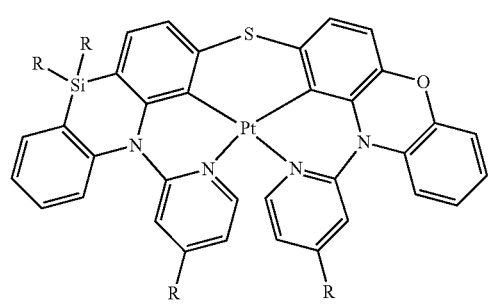
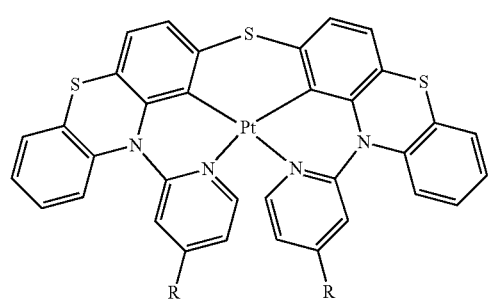
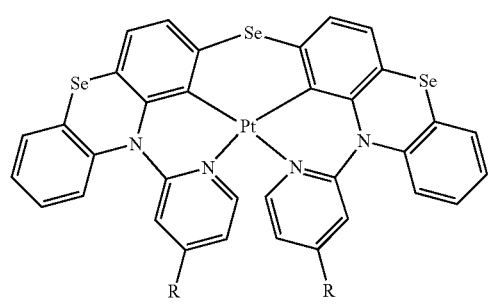
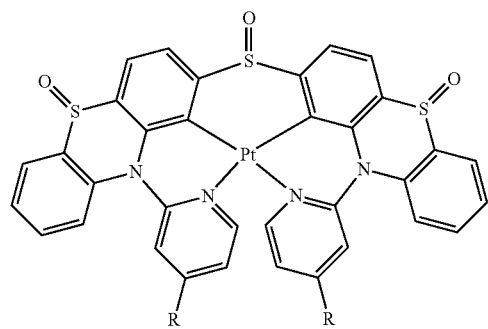
252
-continued
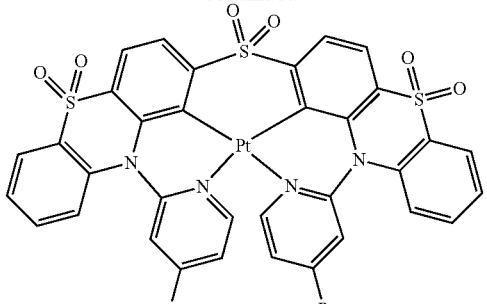
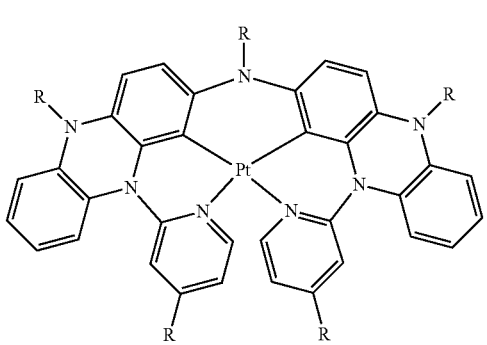
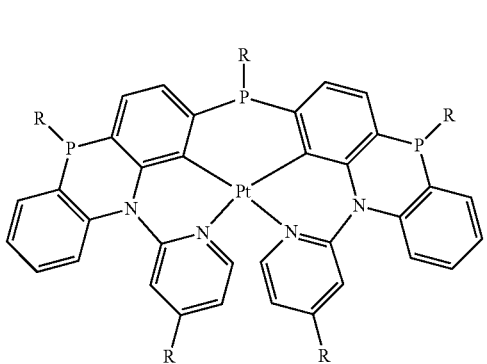
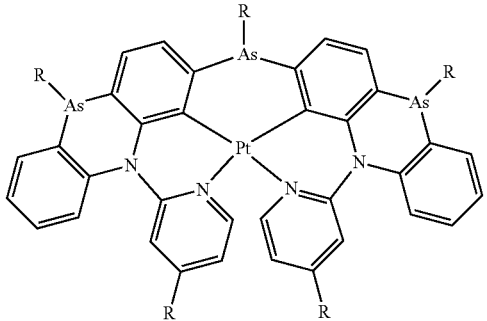
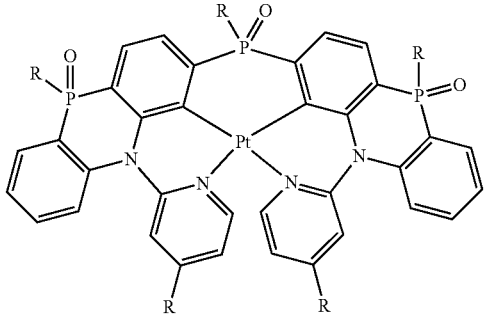

253
-continued
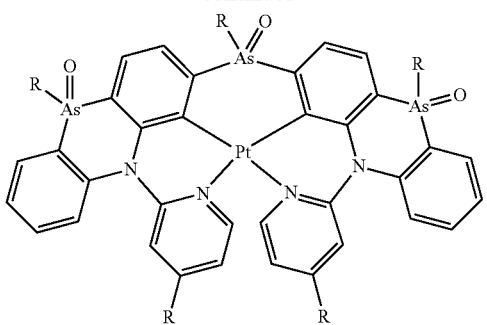
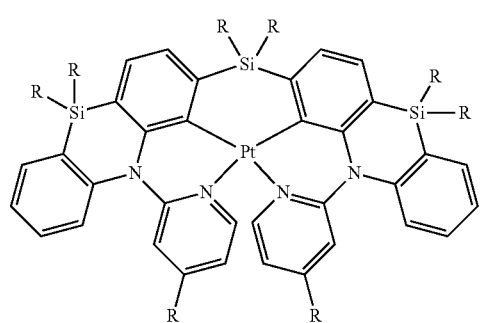
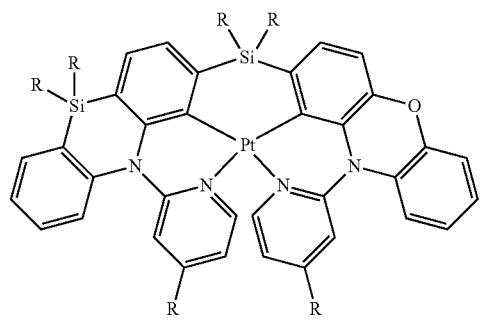
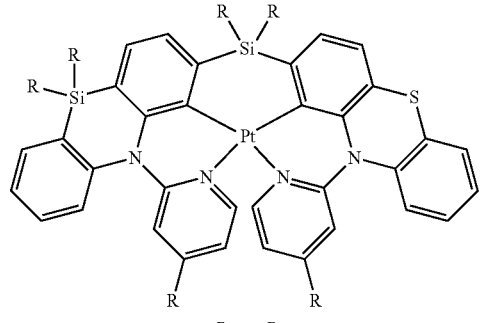
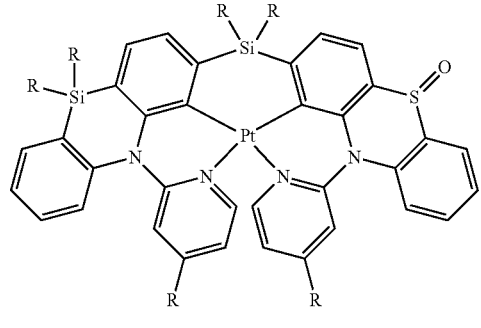
254
-continued
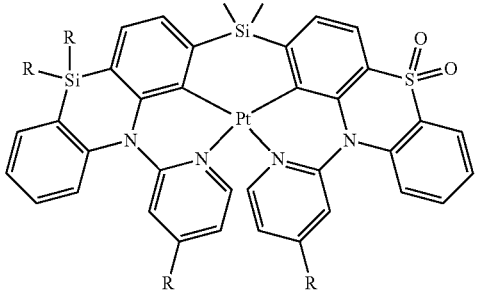
Structures 37
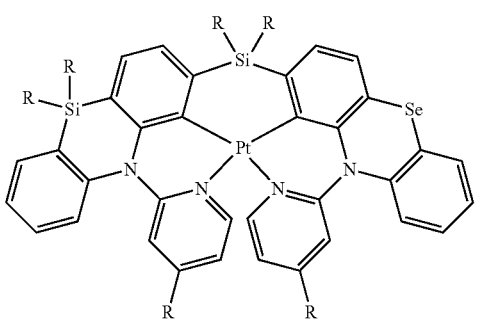
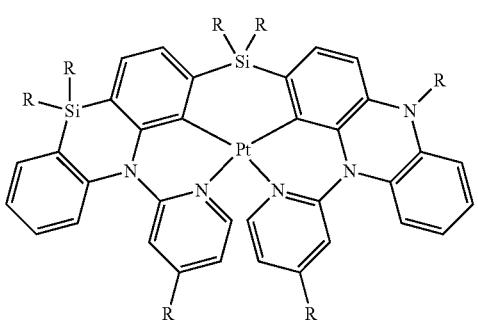
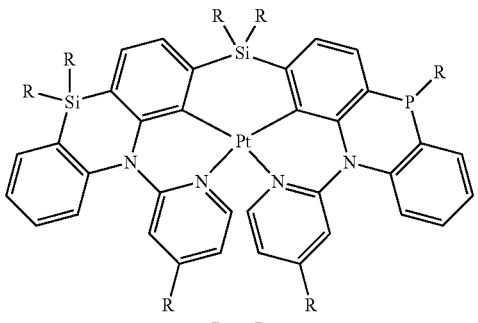
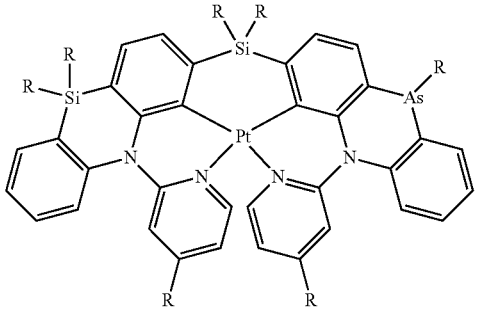

255
-continued
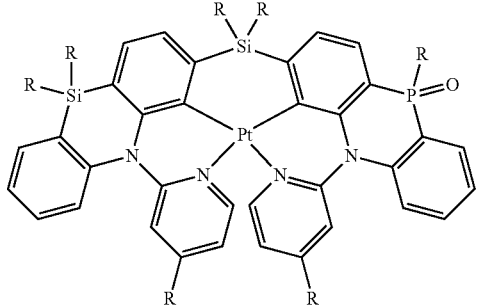
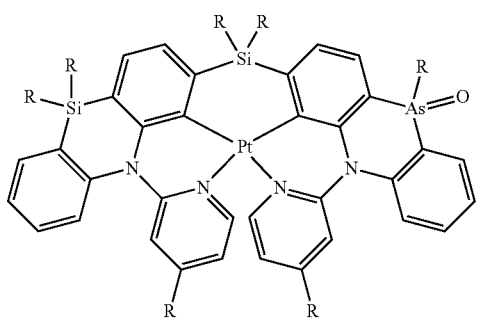
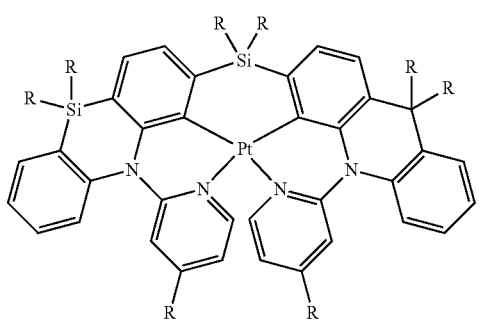
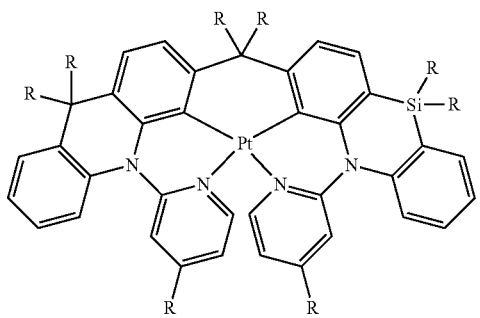
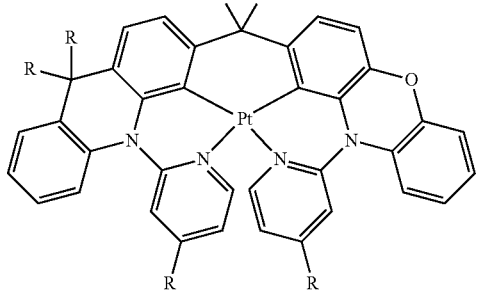
256
-continued
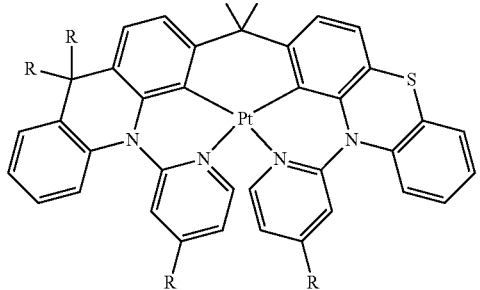
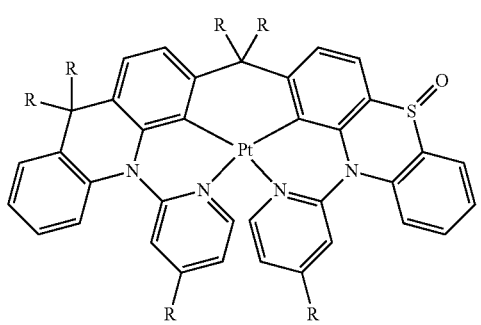
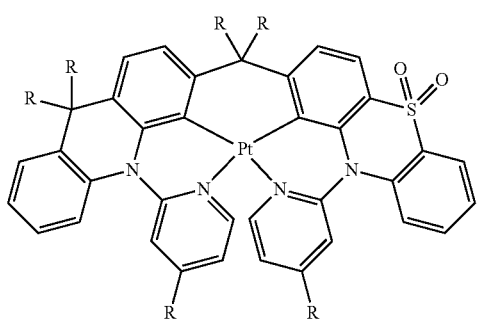
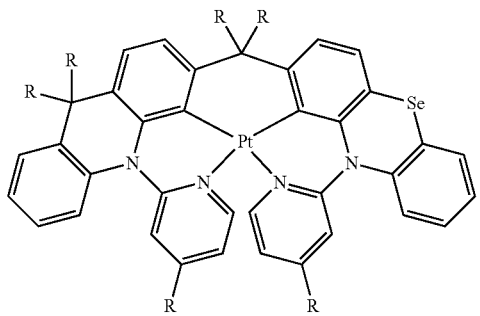
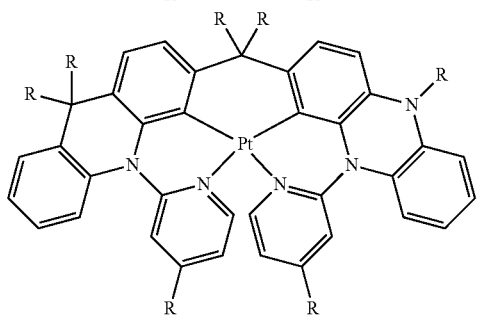

257
-continued
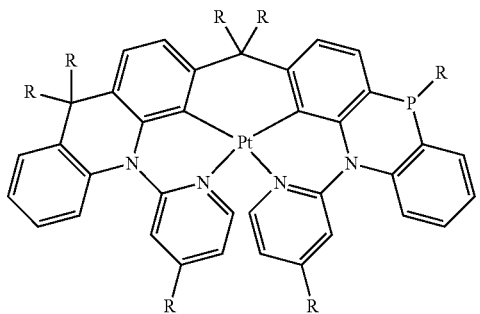
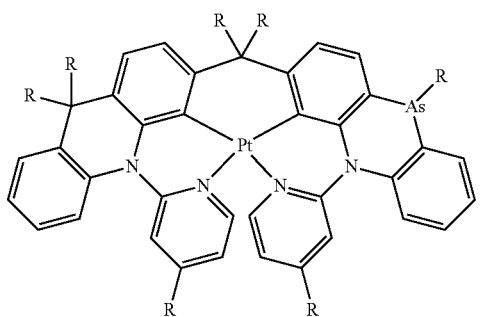
Structures 38
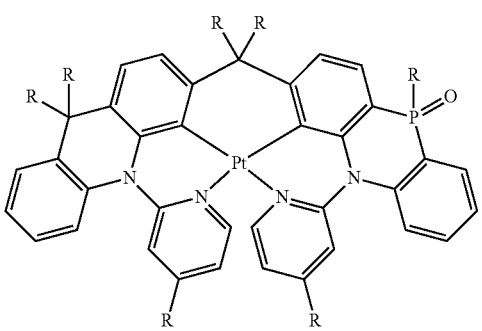
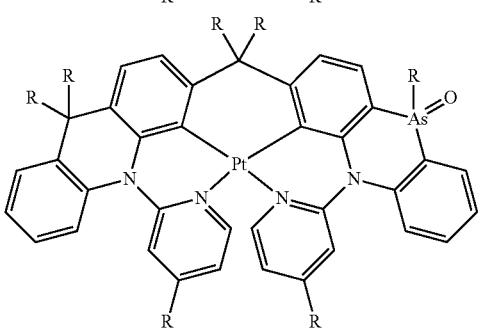
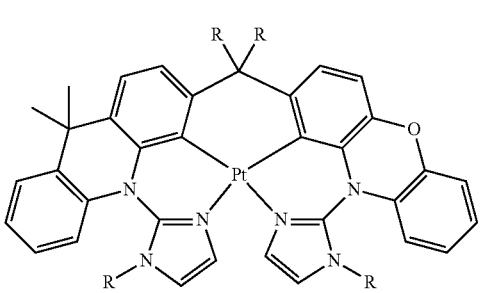
258
-continued
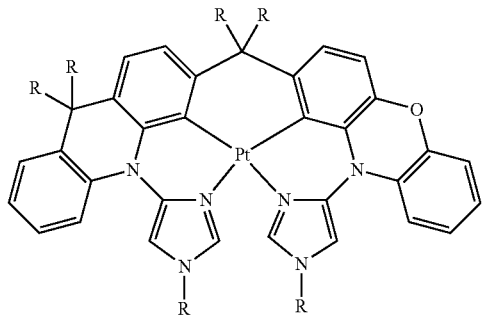
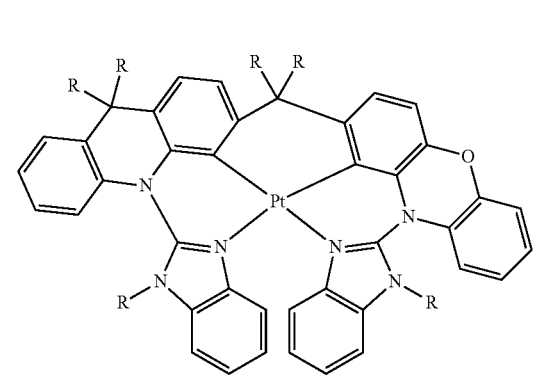
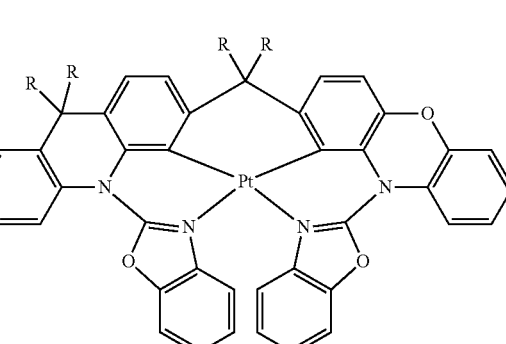
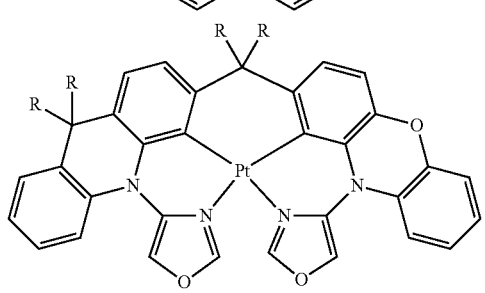

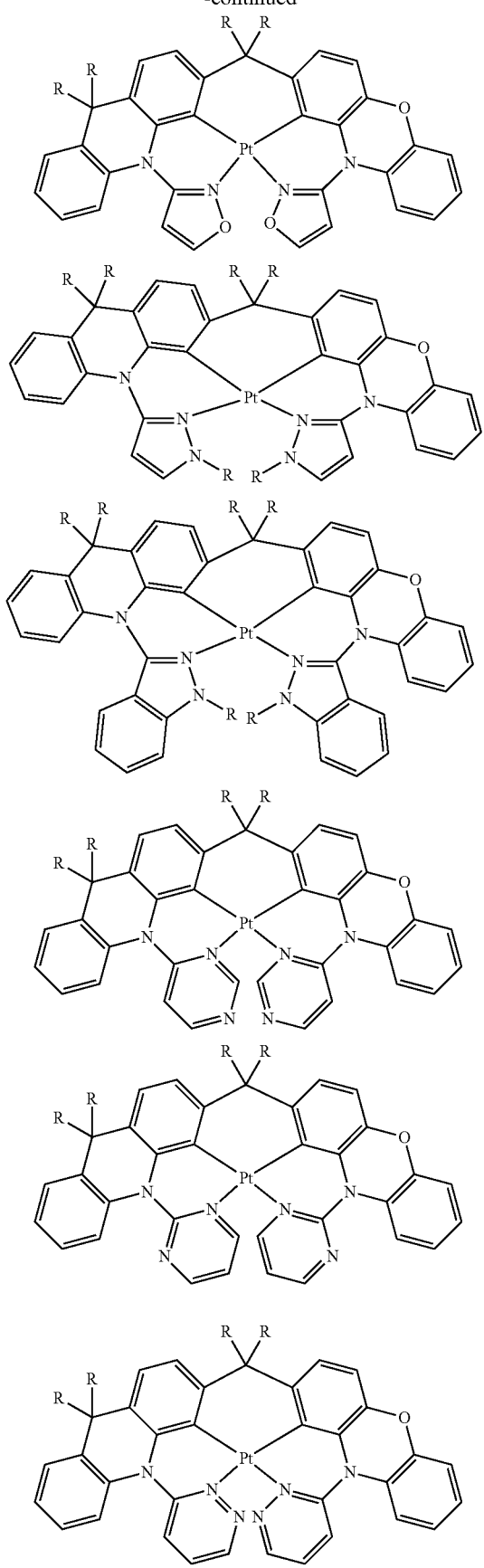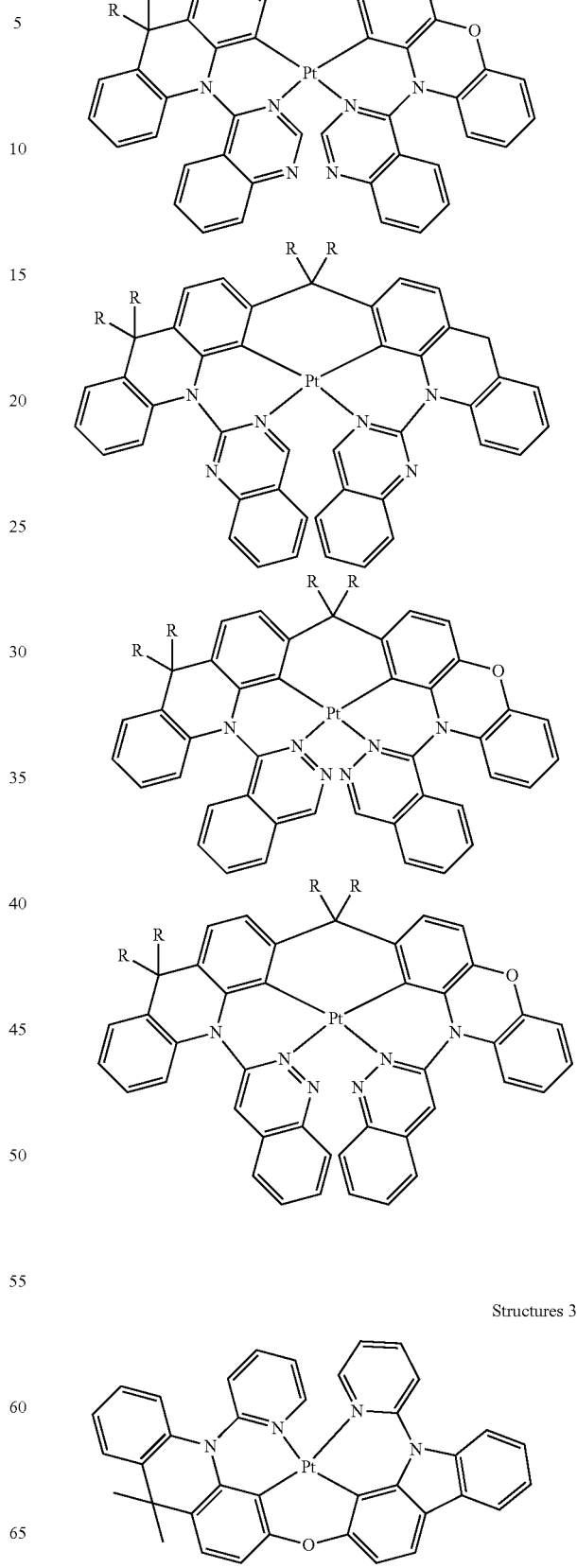
Structures 39

-continued
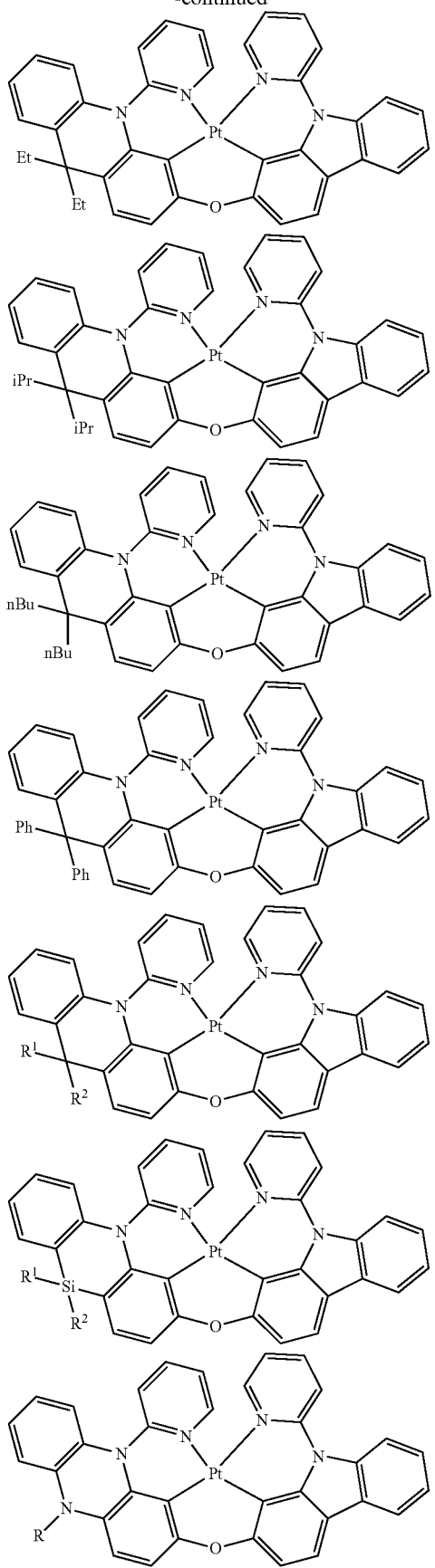
-continued
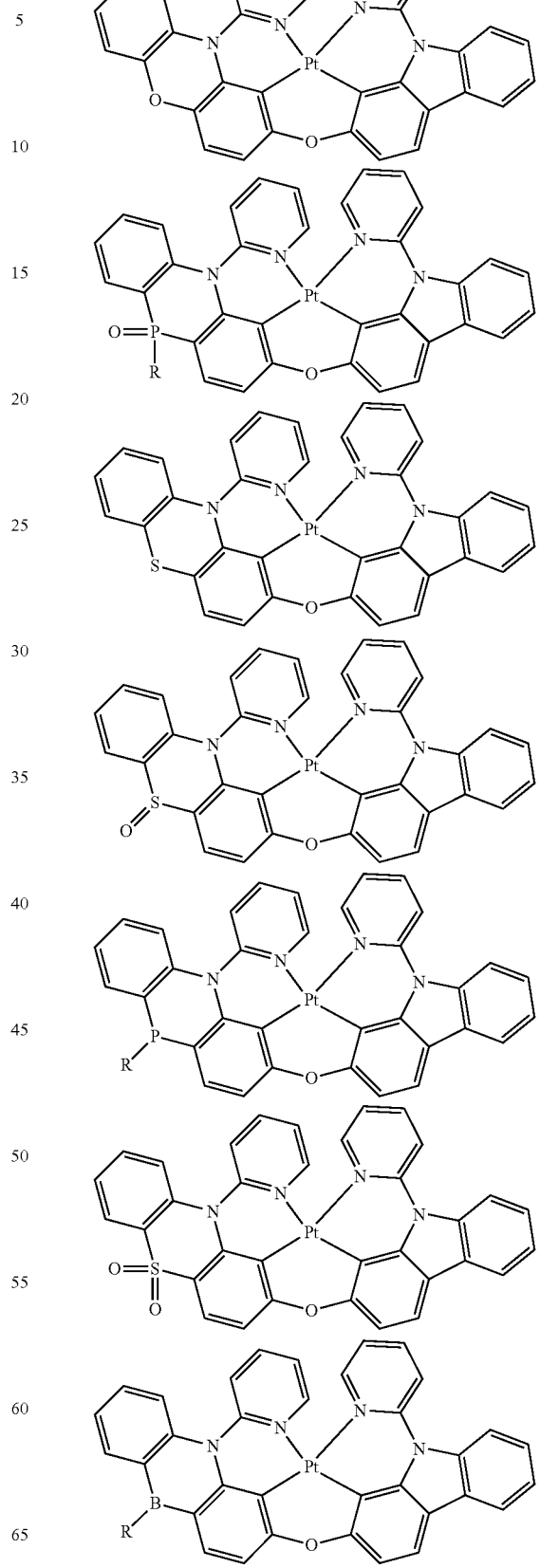

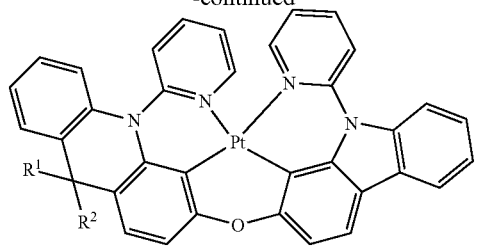
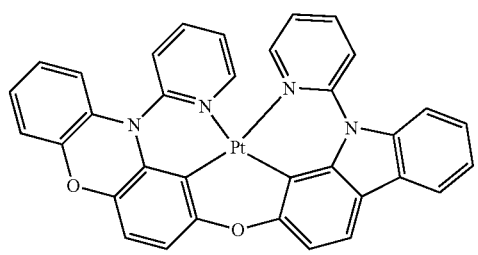
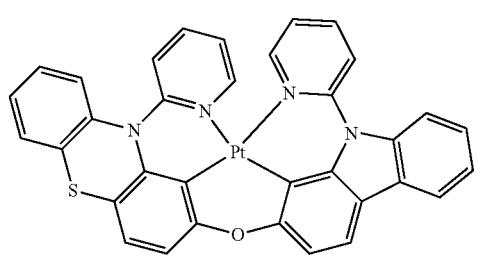
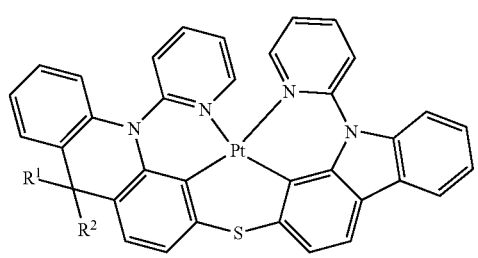
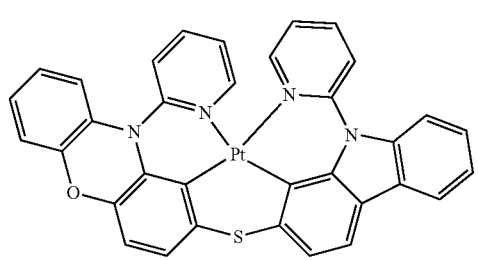
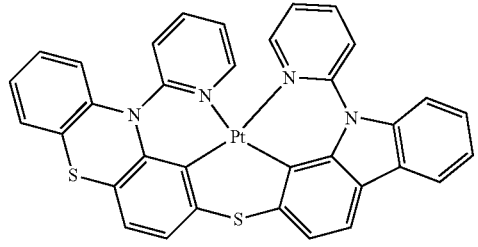
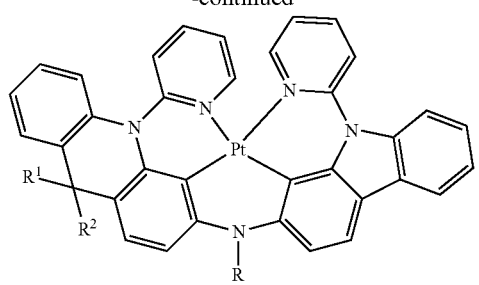
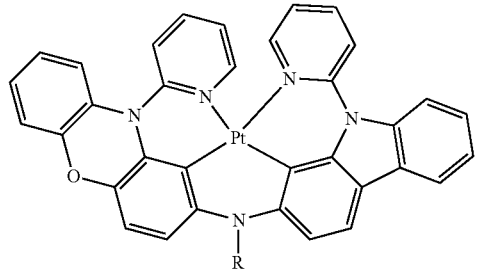
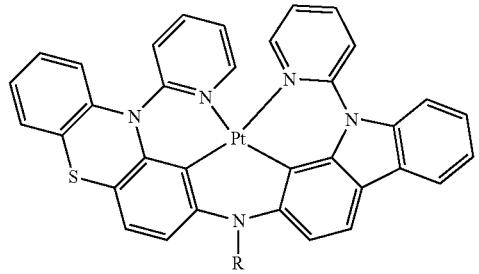
Structures 40
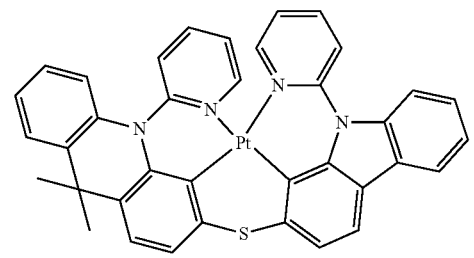
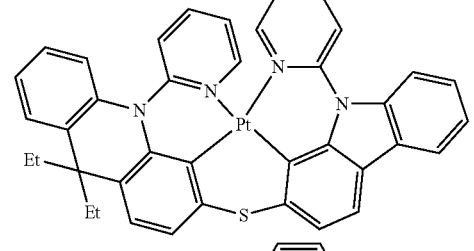
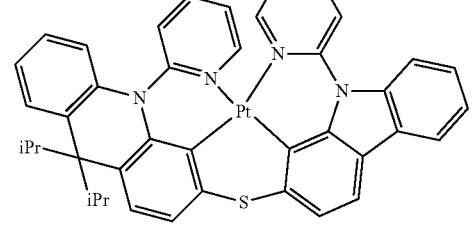

265
-continued
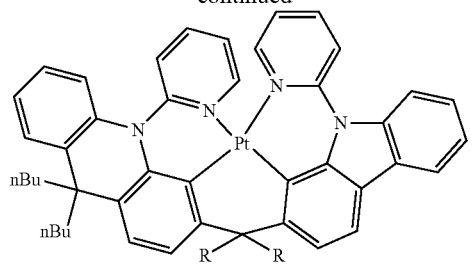
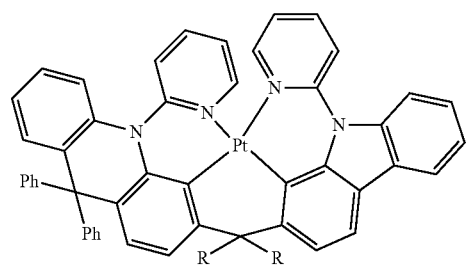
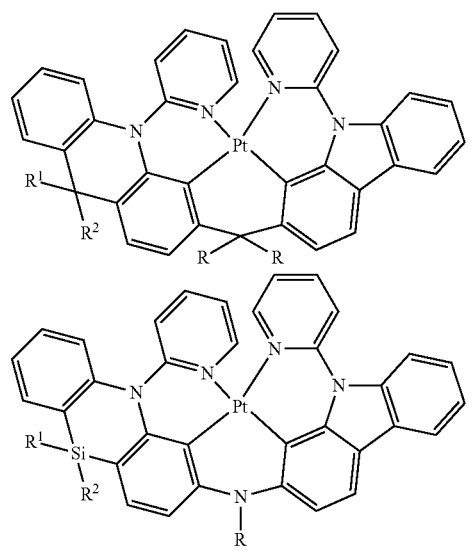
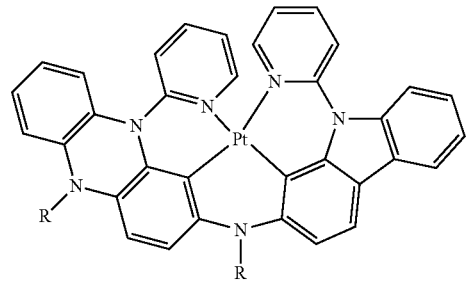
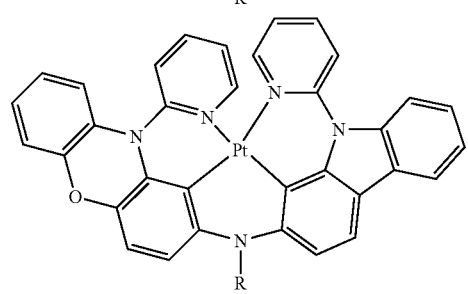
266
-continued
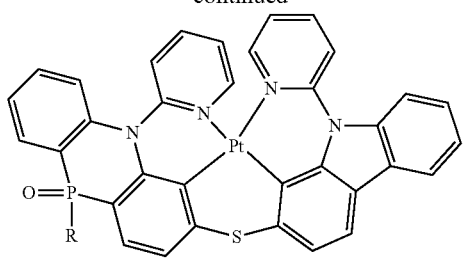
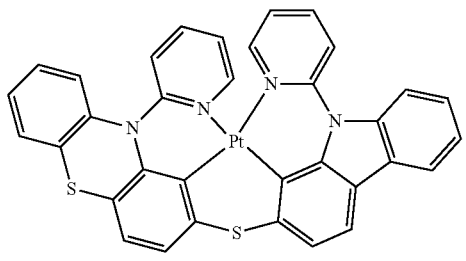
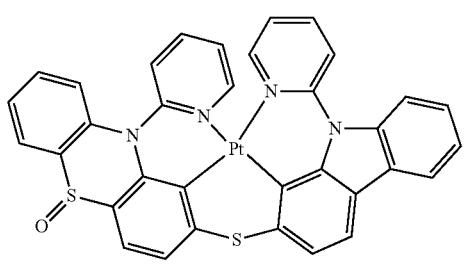
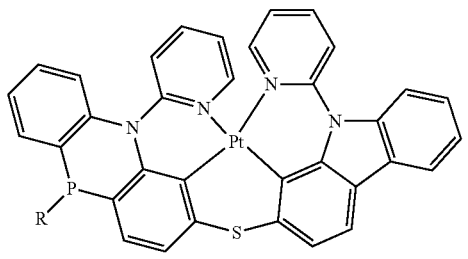
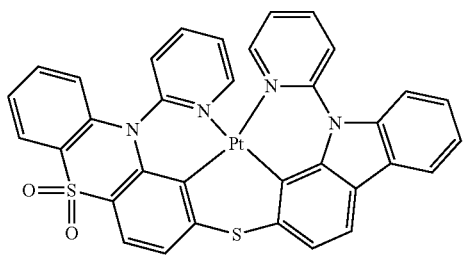
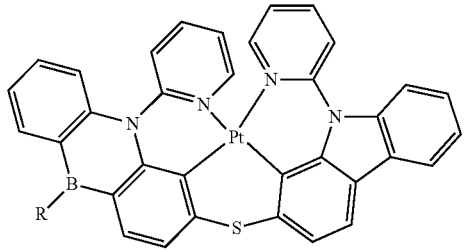

267
-continued
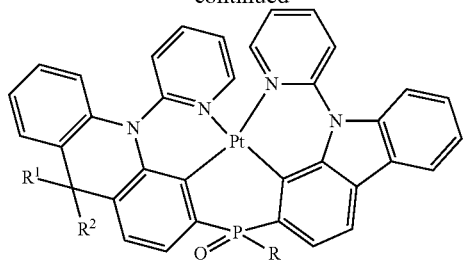
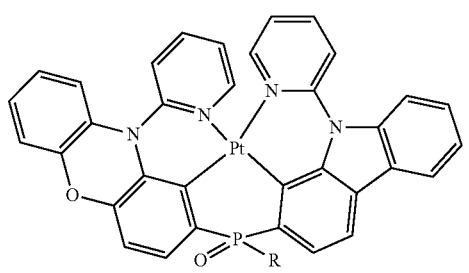
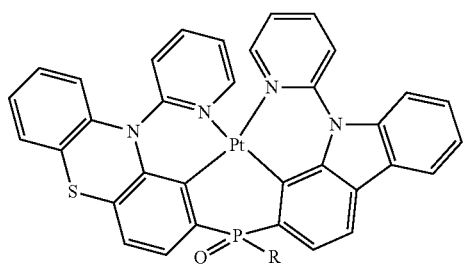
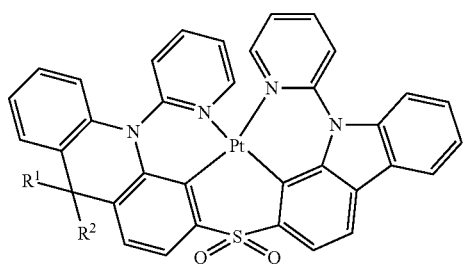
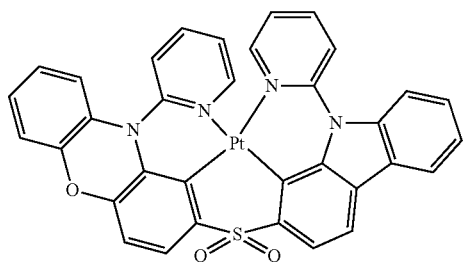
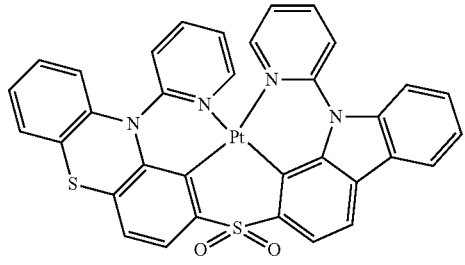
268
-continued
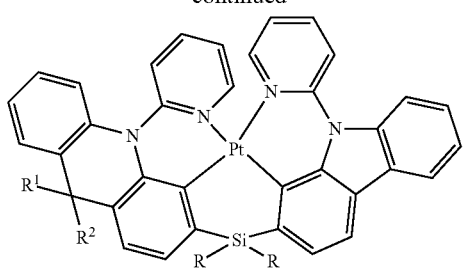
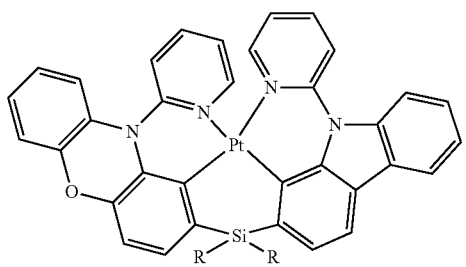
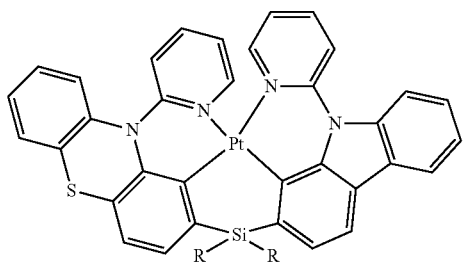
Structures 41
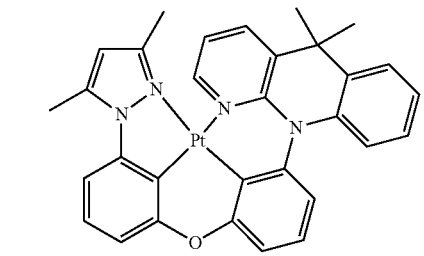
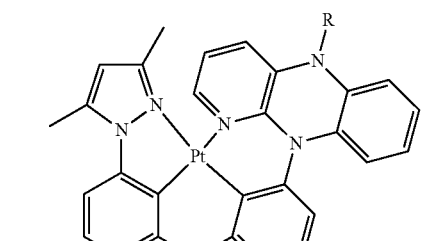
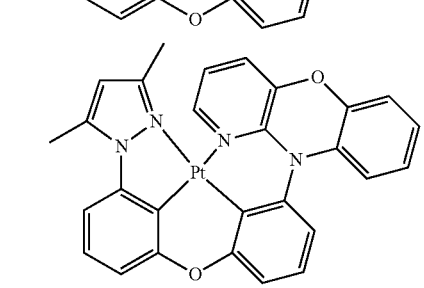

269
-continued
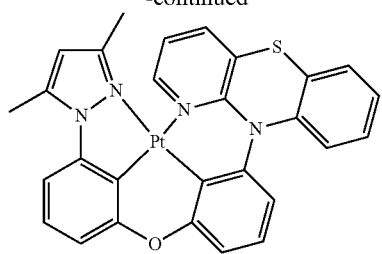
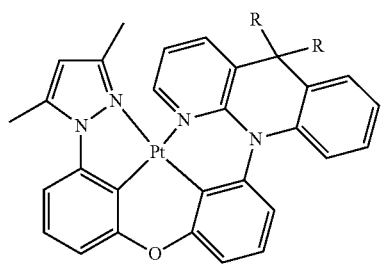
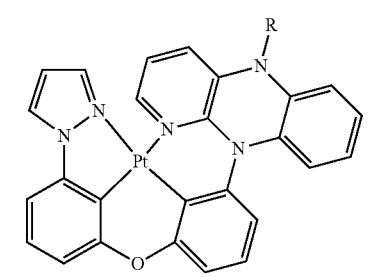
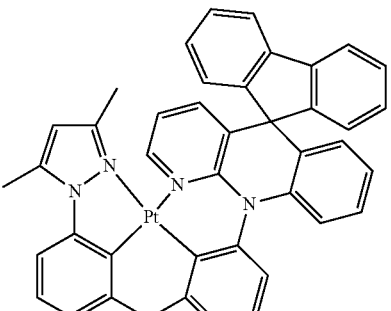
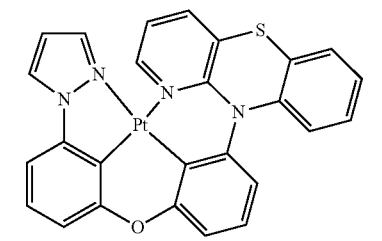
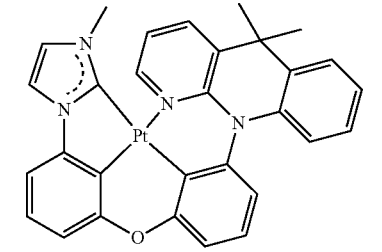
270
-continued
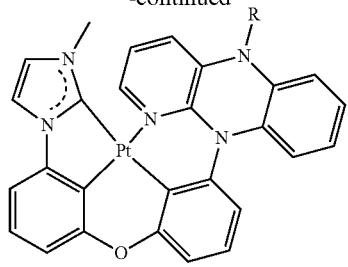
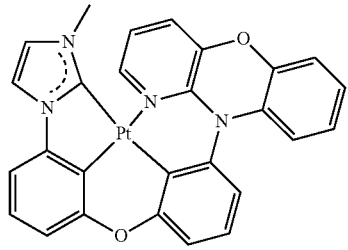
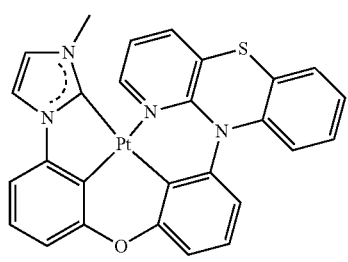
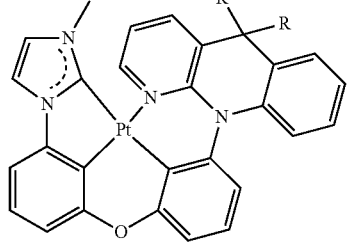
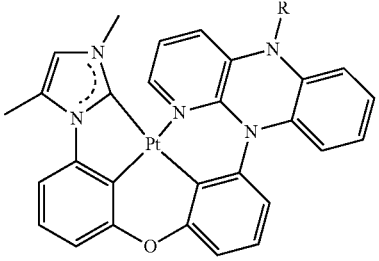
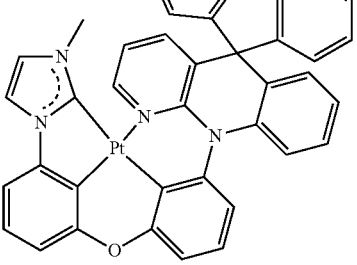

271
-continued
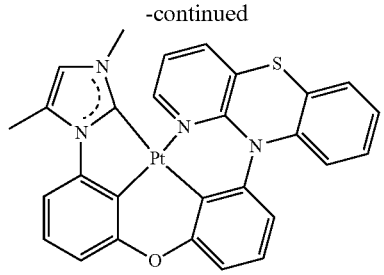
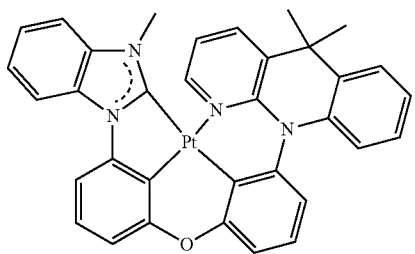
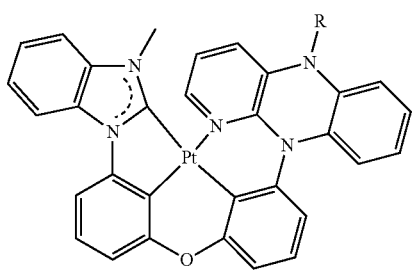
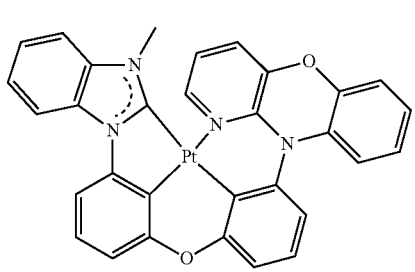
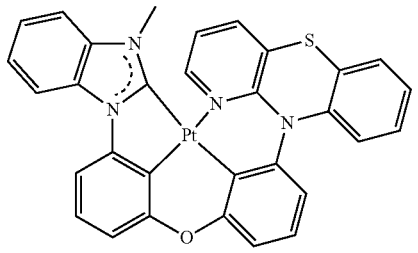
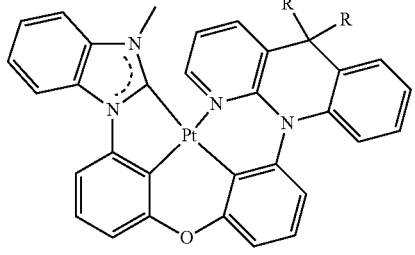
272
-continued
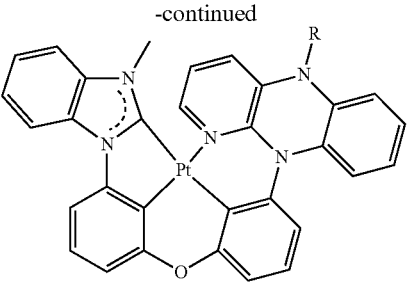
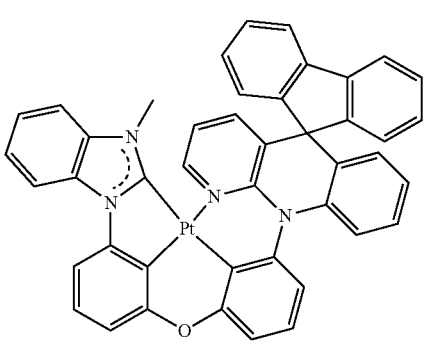
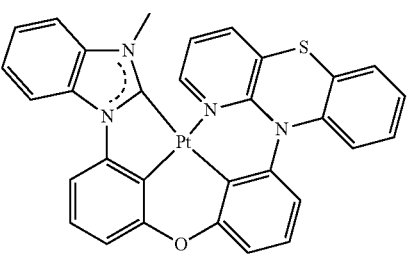
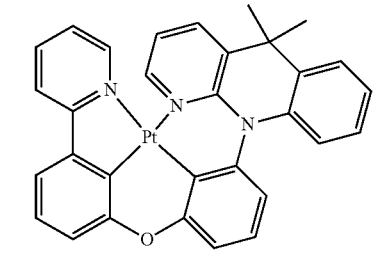
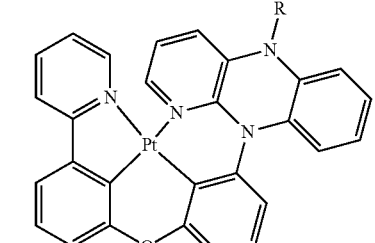
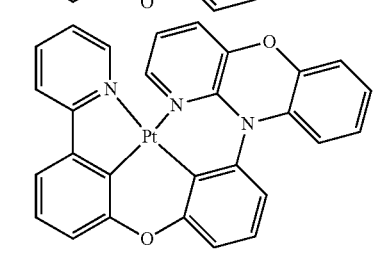

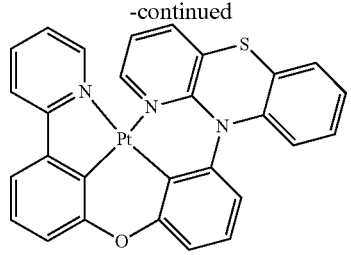
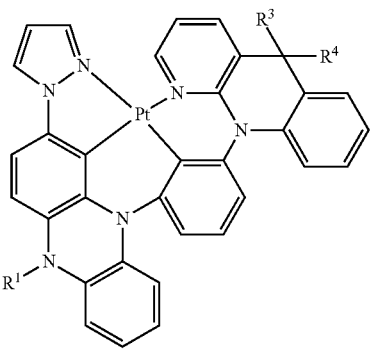
Structures 42
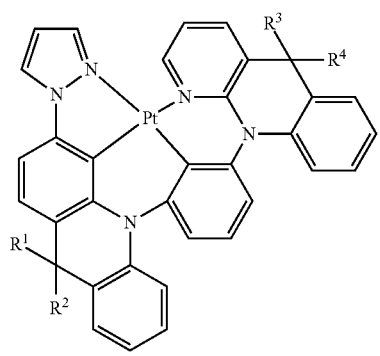
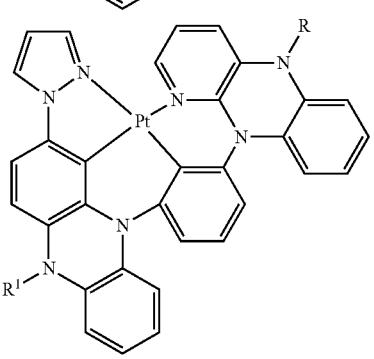
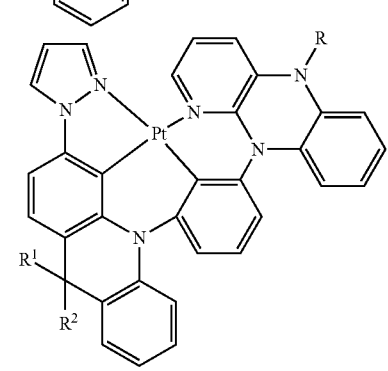
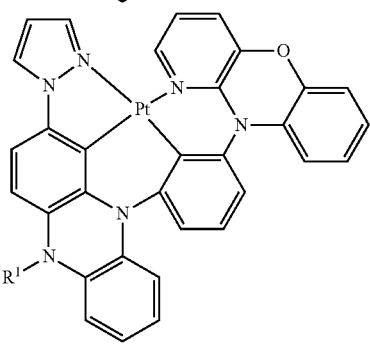
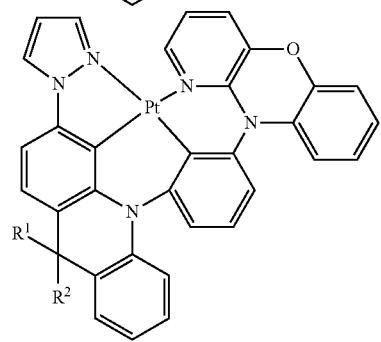
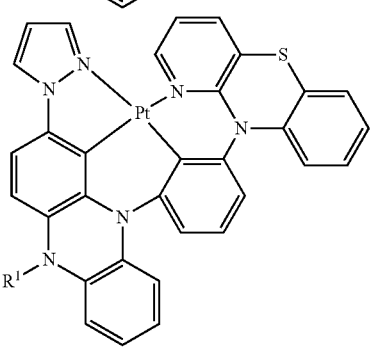
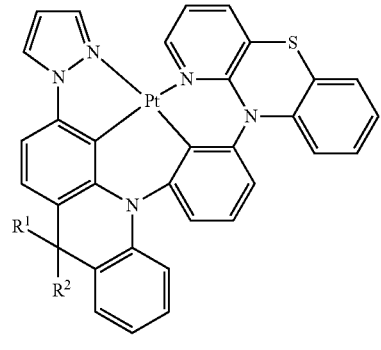
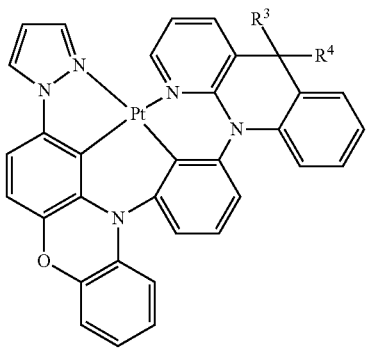

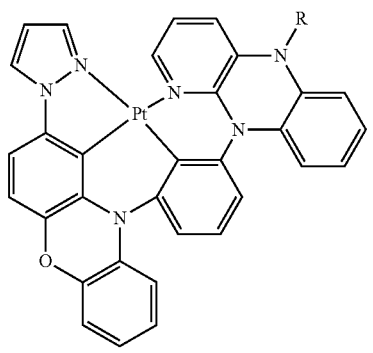
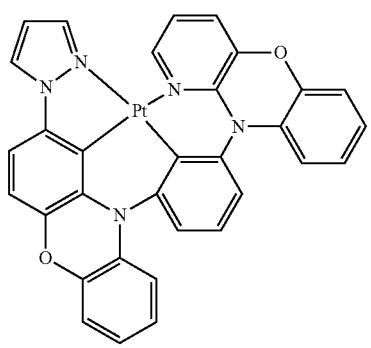
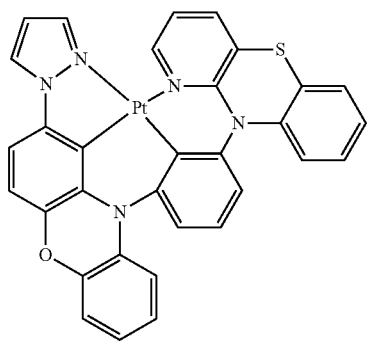
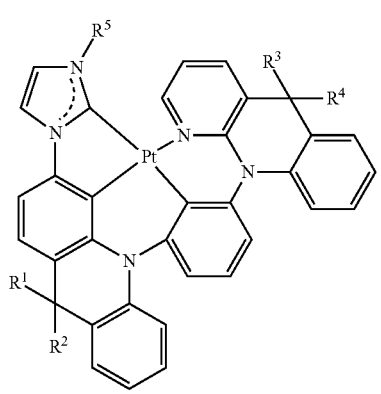
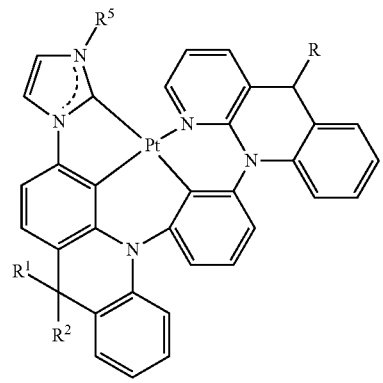
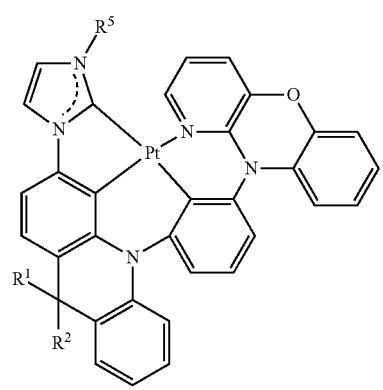
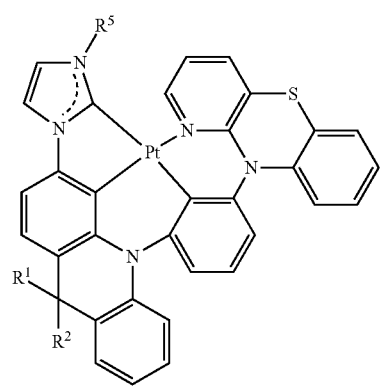
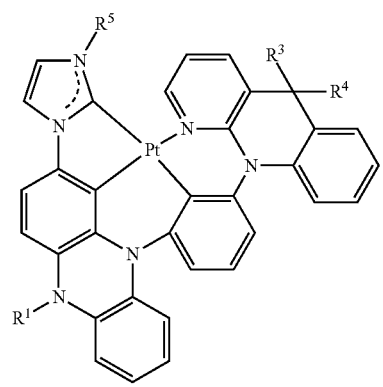

277
-continued
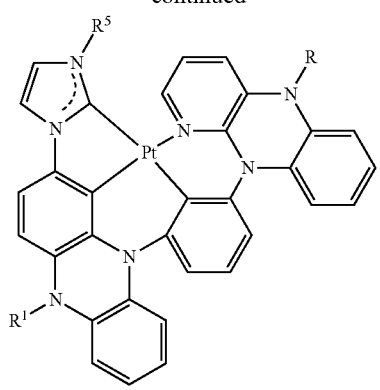
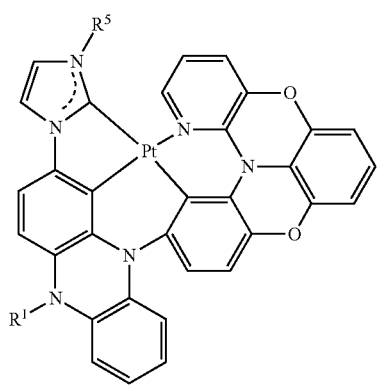
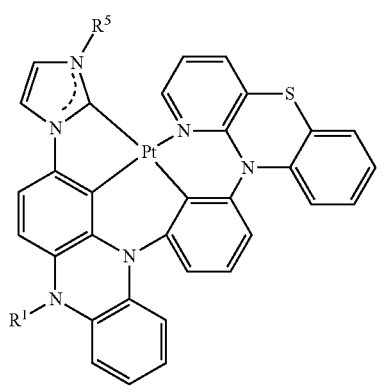
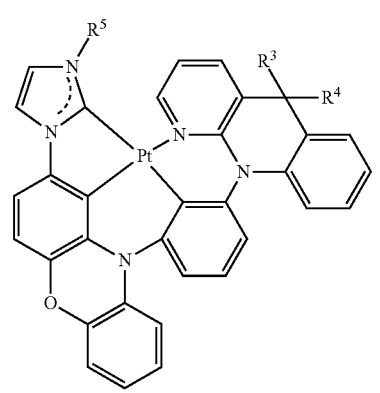
278
-continued
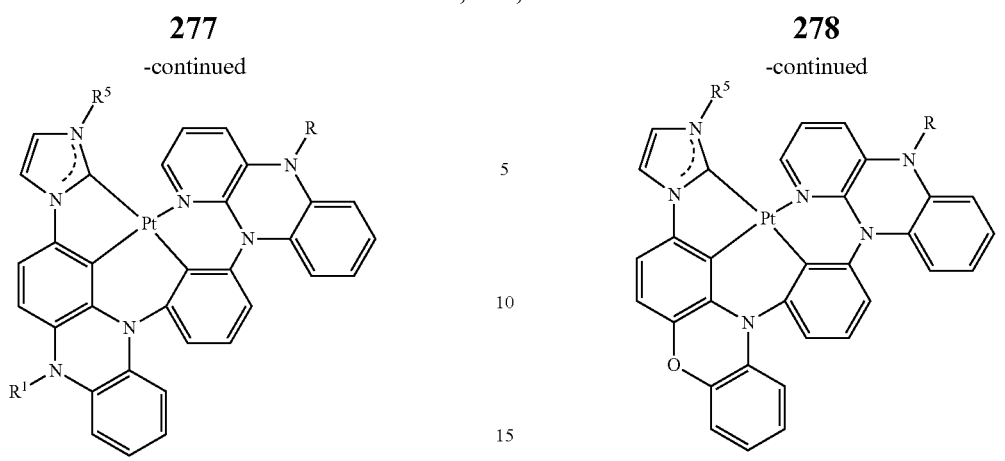
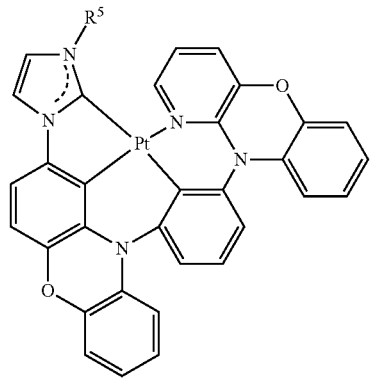
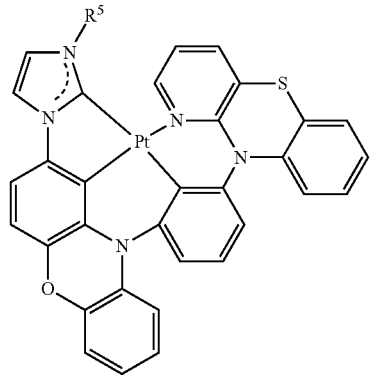
Structures 43
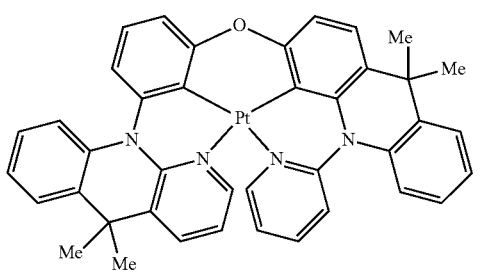

279
-continued
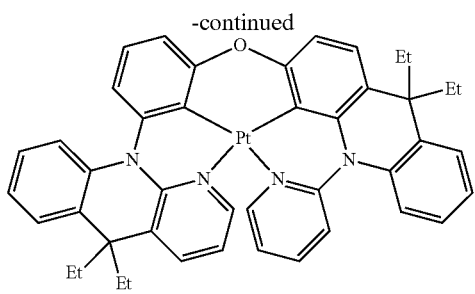
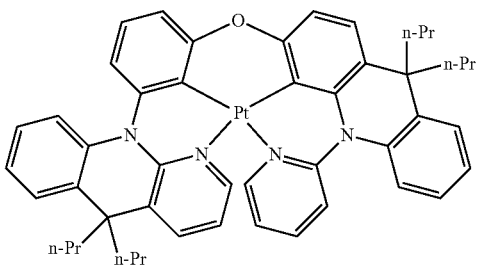
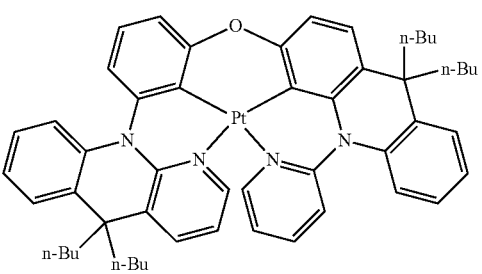
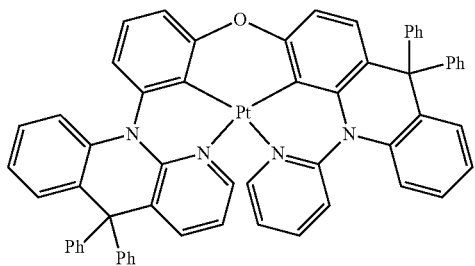
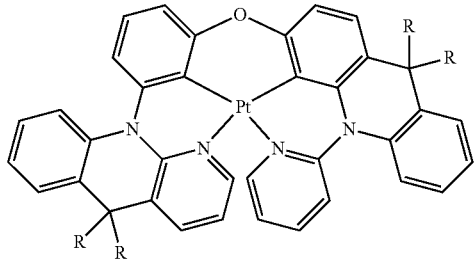
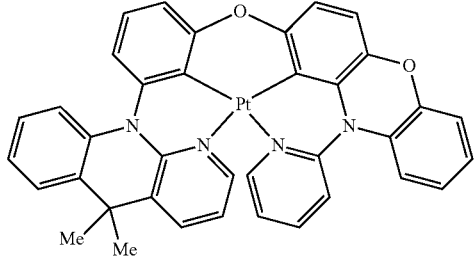
280
-continued
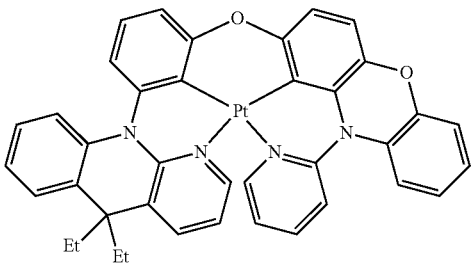
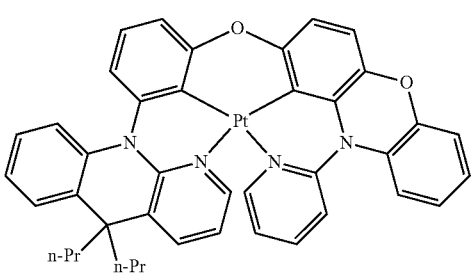
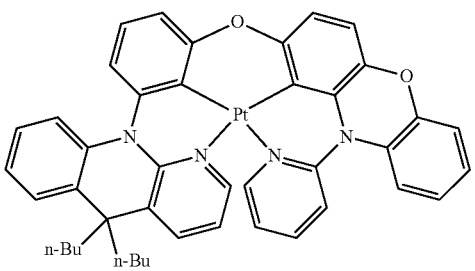
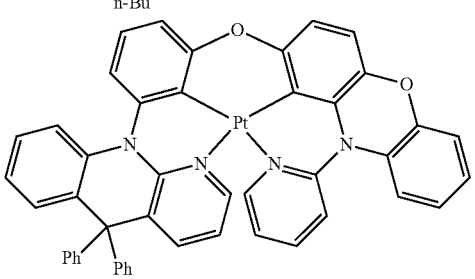
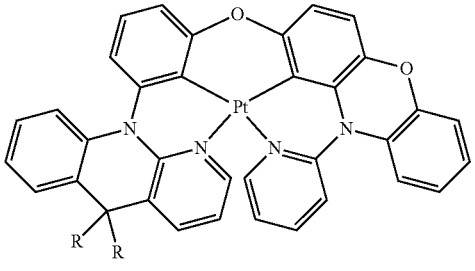
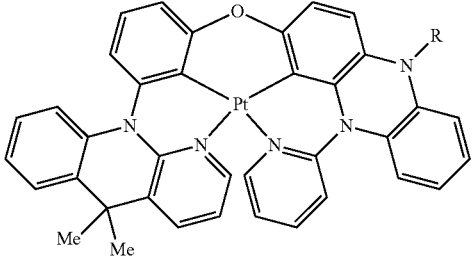

281
-continued
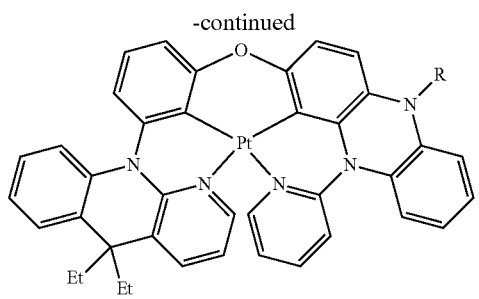
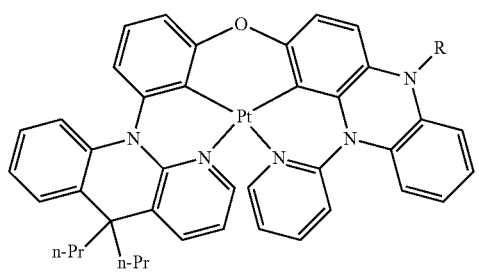
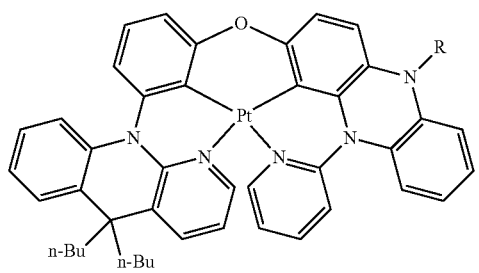
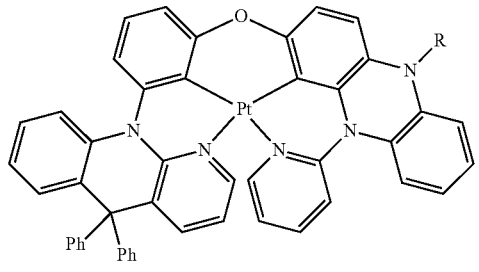
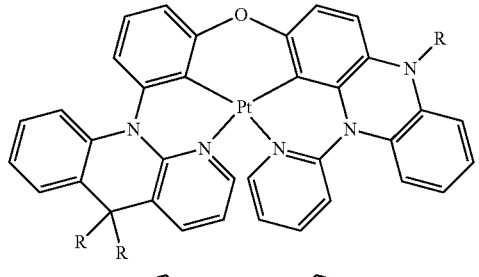
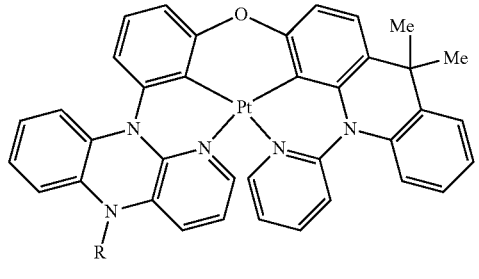
282
-continued
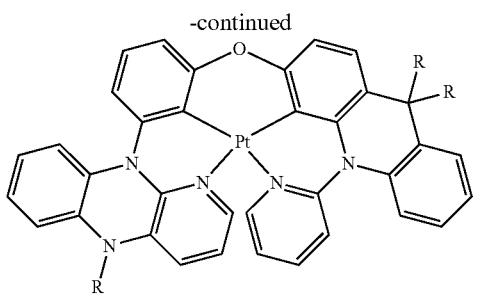
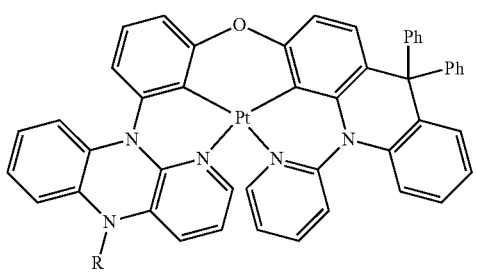
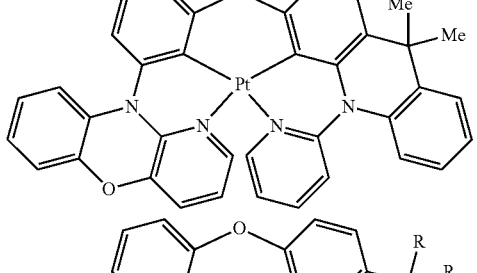
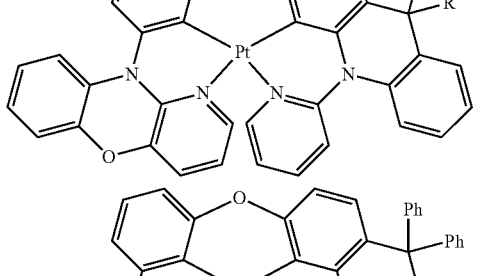
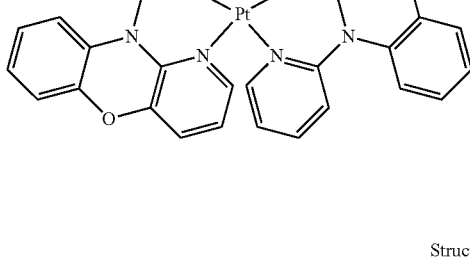
Structures 44
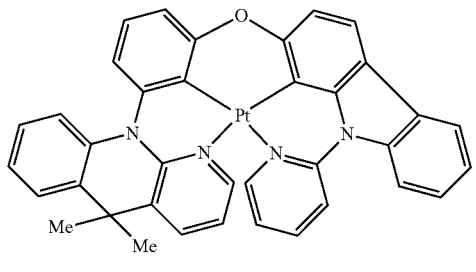

283
-continued
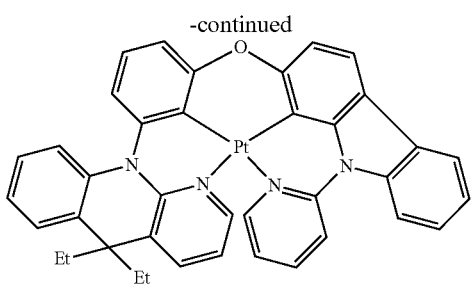
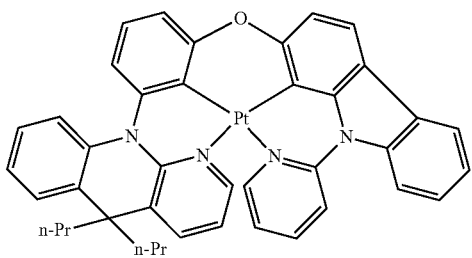
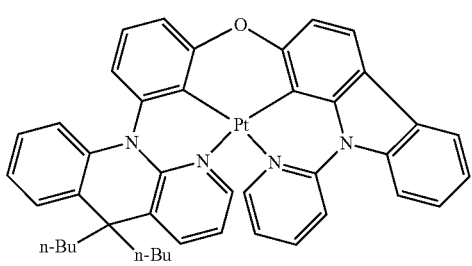
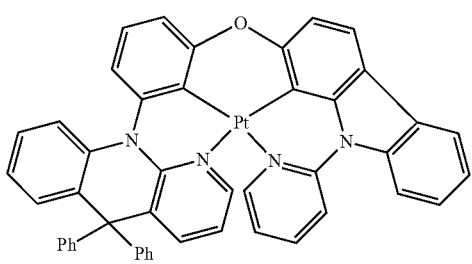
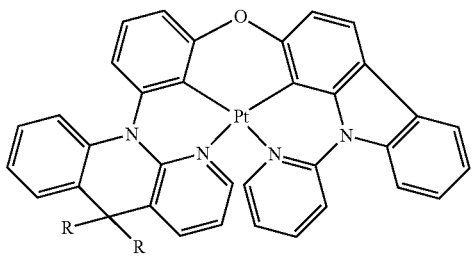
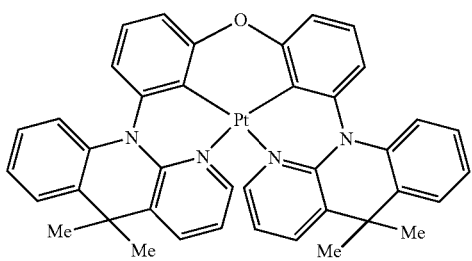
284
-continued
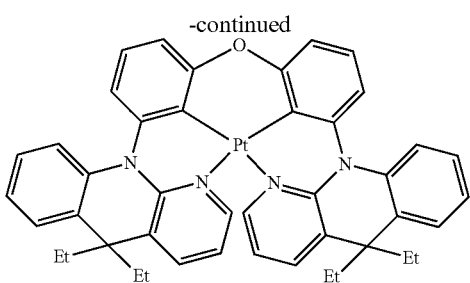
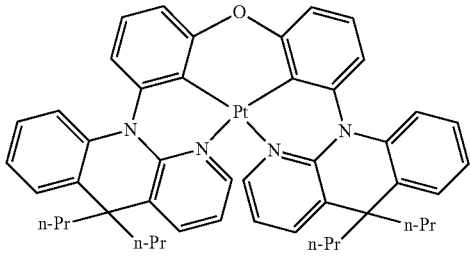
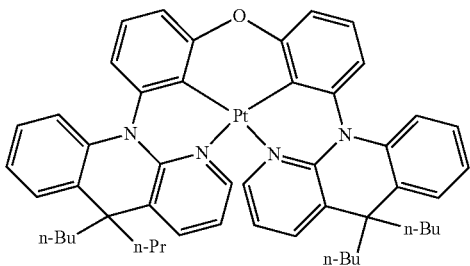
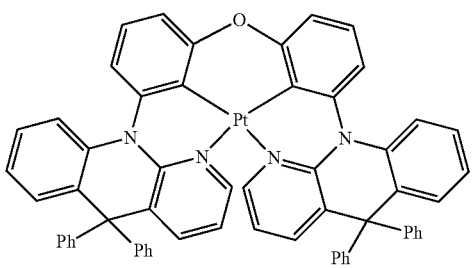
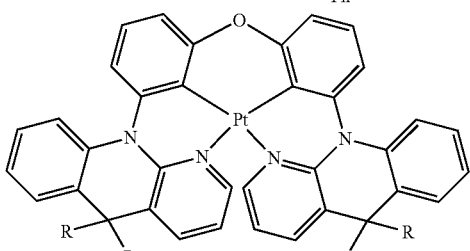
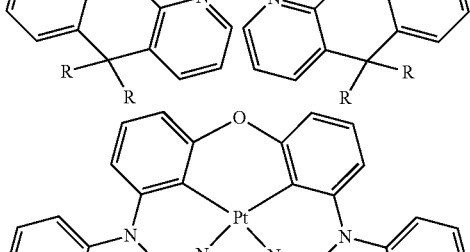

-continued

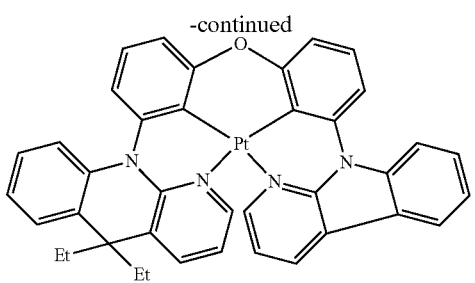
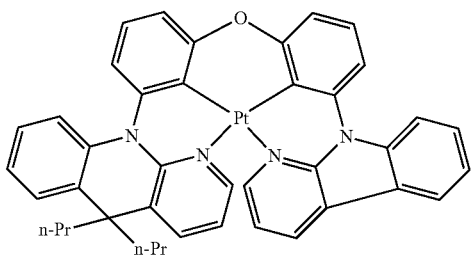
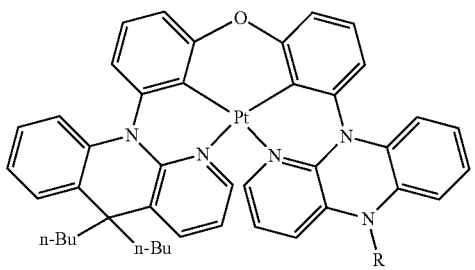
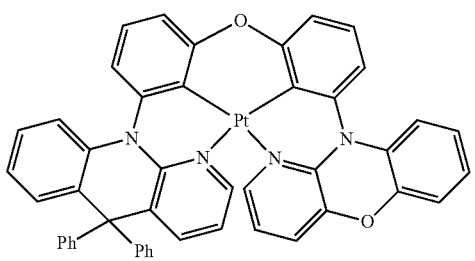
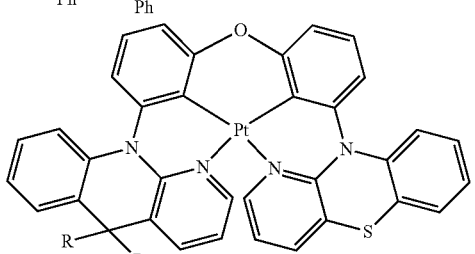
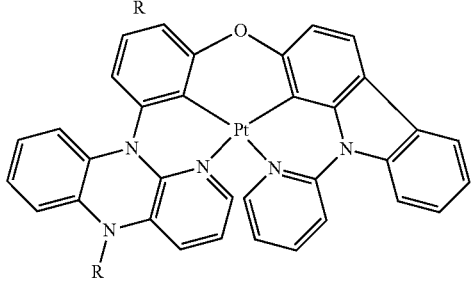

-continued

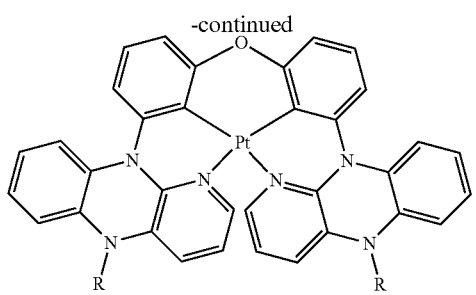
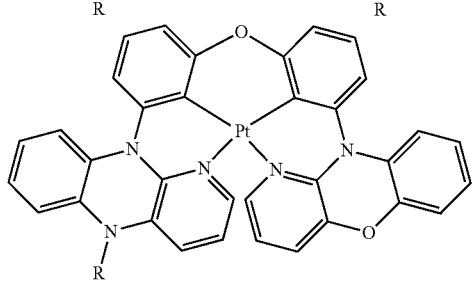
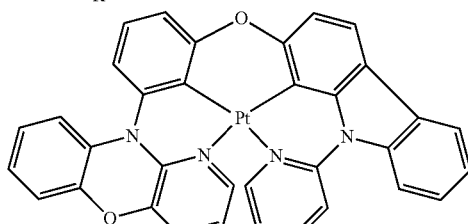
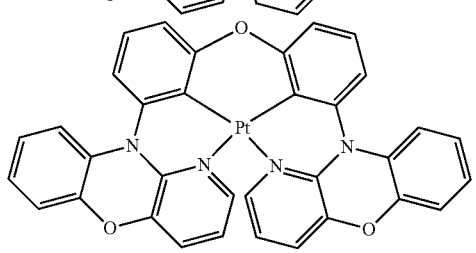
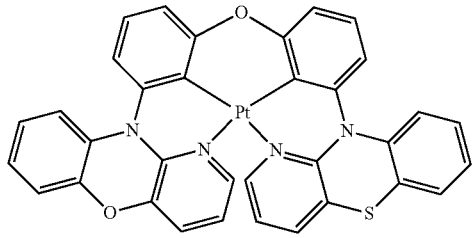

In the compounds shown in Structures 1-44, each of R, $R^1$, $R^2$, $R^3$, $R^4$, $R^5$, and R″ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In another aspect, each of R, $R^1$, $R^2$, $R^3$, and $R^4$ is independently hydrogen, halogen, hydroxyl, thiol, nitro, cyano; substituted or unsubstituted aryl, cycloalkyl, cycloalkenyl, heterocyclyl, heteroaryl, alkyl, alkenyl, alkynyl, or amino. In another aspect, each of R, R, $R^1$, $R^2$, $R^3$, and $R^4$ is independently hydrogen; substituted or unsubstituted aryl, cycloalkyl, cycloalkenyl, heterocyclyl, heteroaryl, alkyl, alkenyl, or alkynyl.

2. Devices

Also disclosed herein are devices including one or more of the compounds disclosed herein.

The compounds disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by reference.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane (δ=0.00 ppm) as internal reference; $^{13}$C NMR spectra were recorded with CDCl$_3$ (δ=77.00 ppm) as internal reference. If DMSO-d$_6$ was used as solvent, $^1$H NMR spectra were recorded with residual H$_2$O (δ=3.33 ppm) as internal reference; $^{13}$C NMR spectra were recorded with DMSO-d$_6$ (δ=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

General Synthetic Routes

A general synthesis for the compounds disclosed herein includes:

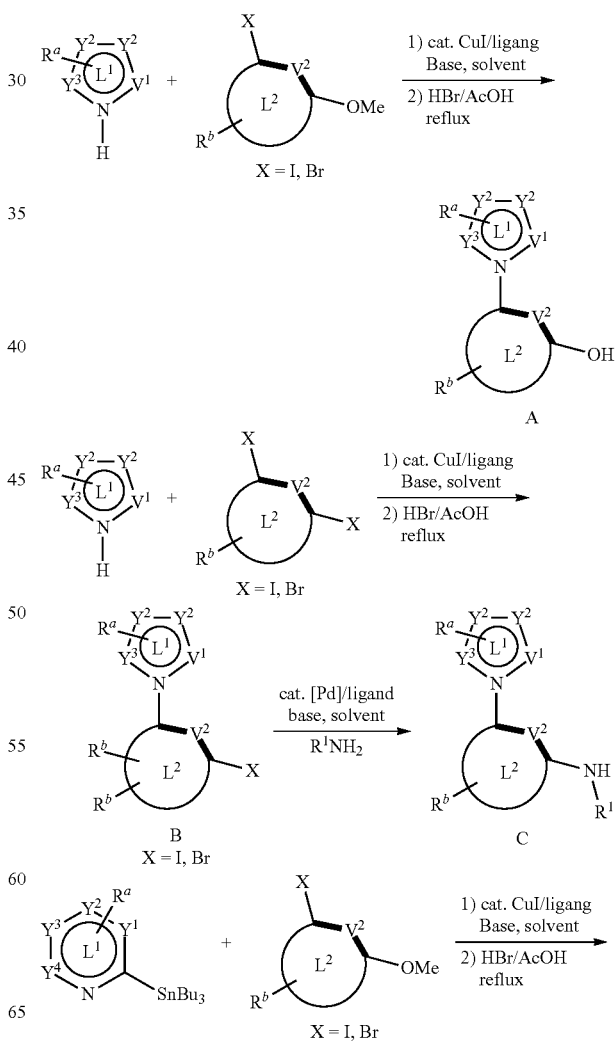

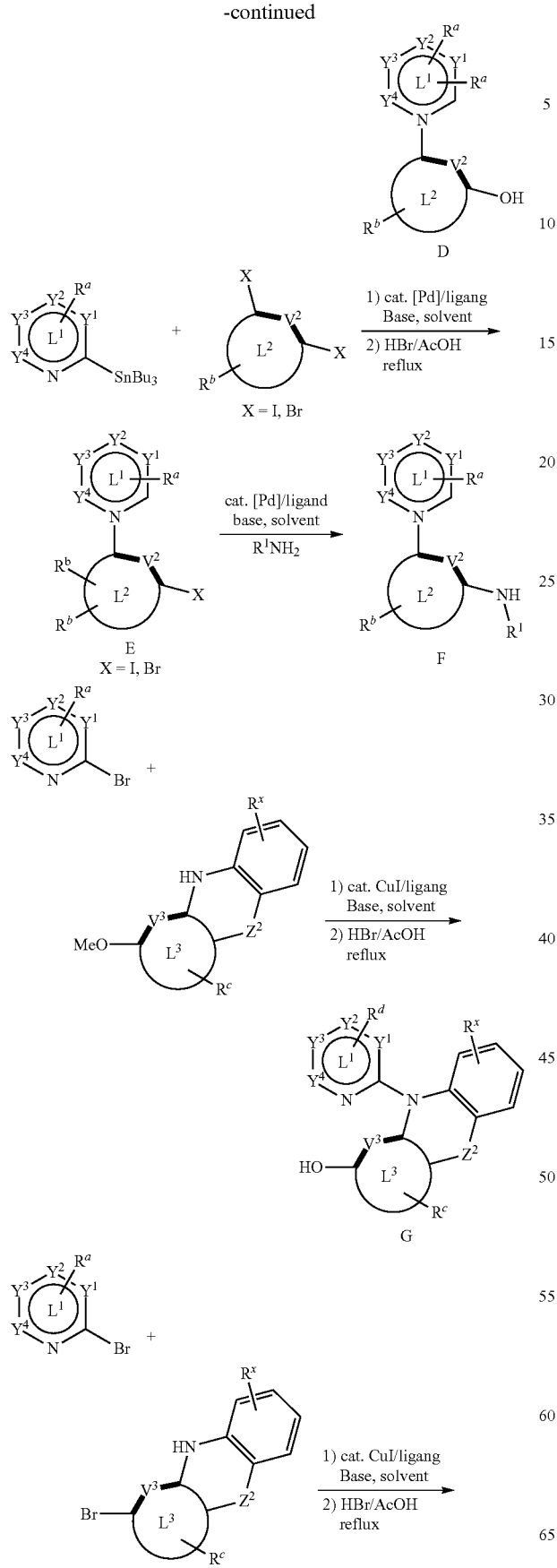
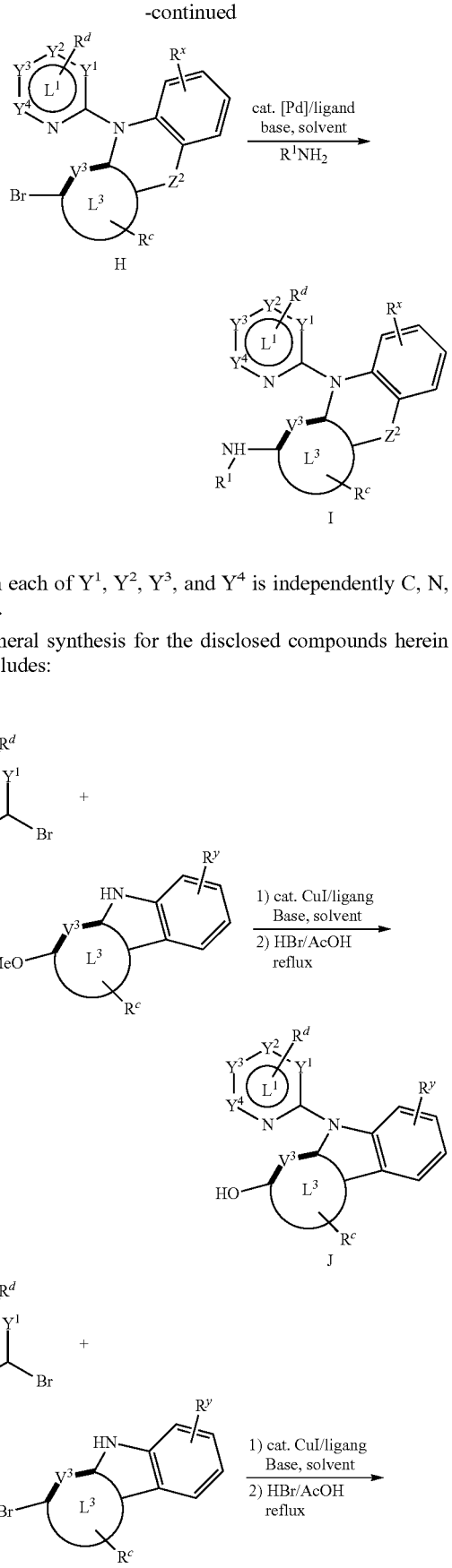
wherein each of $Y^1$, $Y^2$, $Y^3$, and $Y^4$ is independently C, N, O, or S.
A general synthesis for the disclosed compounds herein also includes:

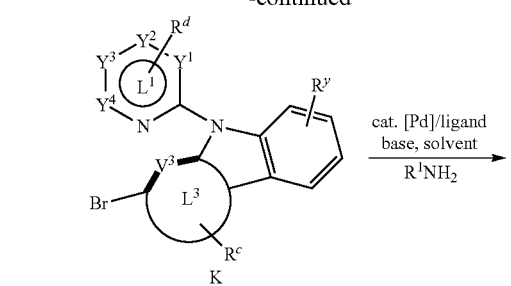
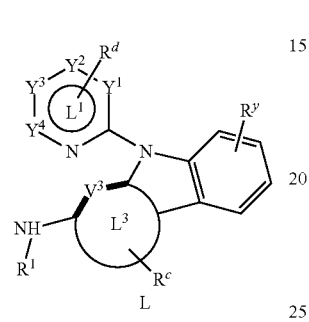
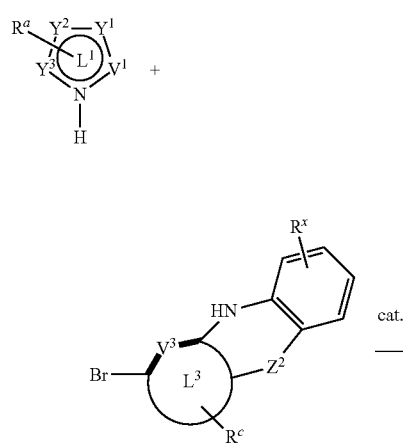
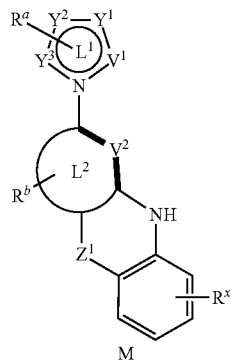
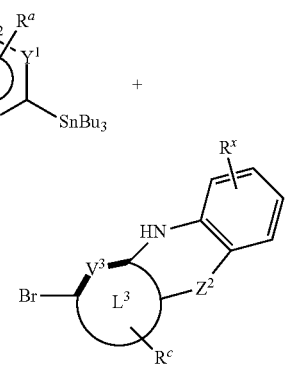
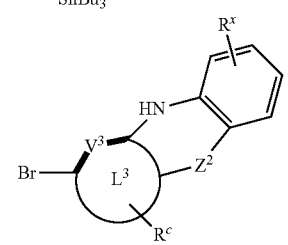
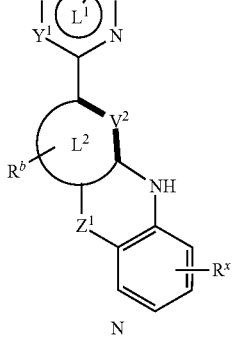
wherein each of $Y^1$, $Y^2$, $Y^3$, and $Y^4$ is independently C, N, O, or S.
A general synthesis for the disclosed compounds herein also includes:
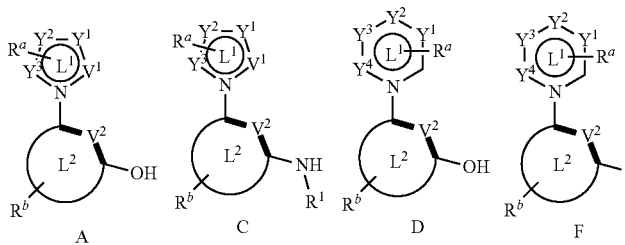
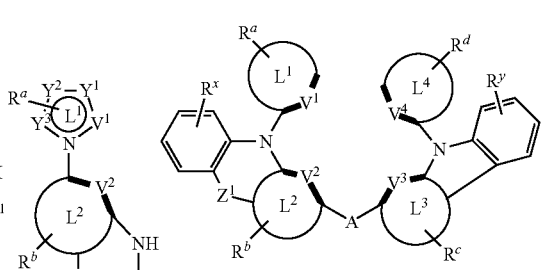
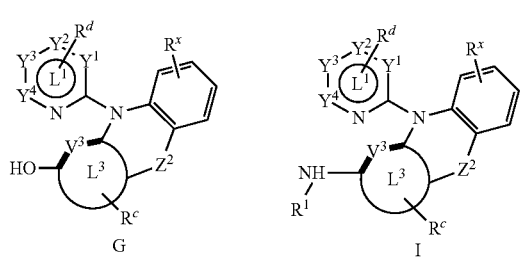

-continued
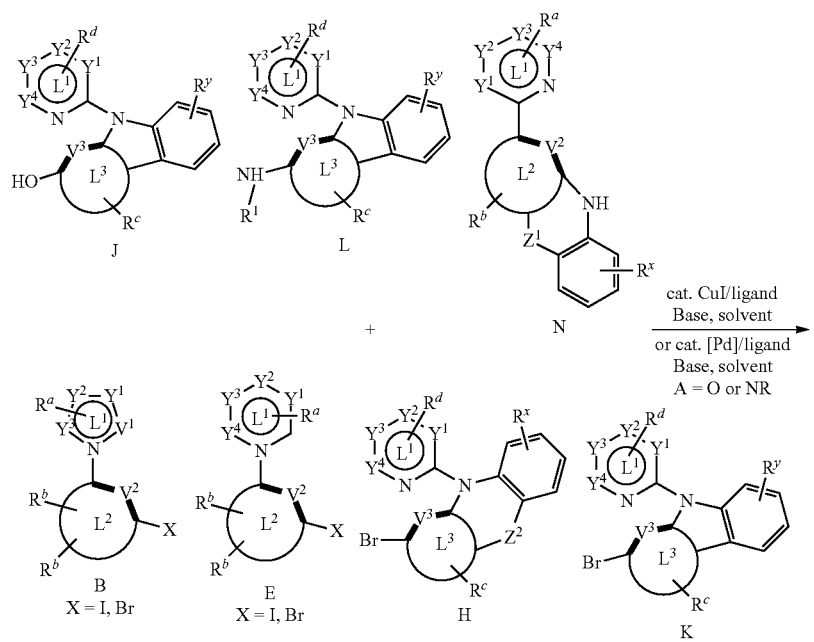
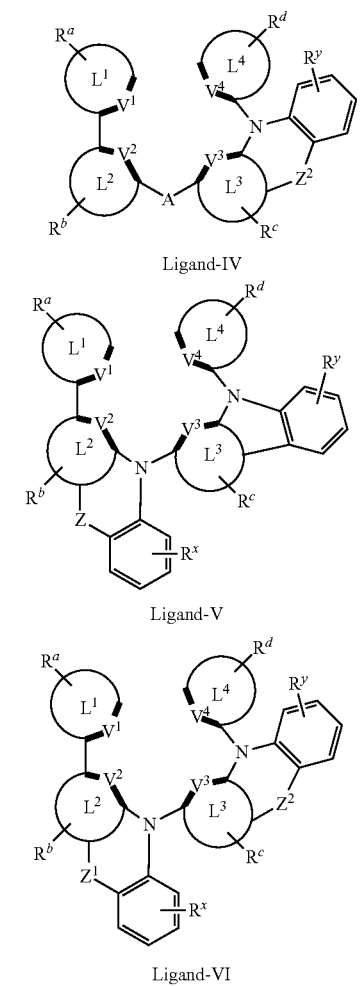
wherein each of $Y^1$, $Y^2$, $Y^3$, and $Y^4$ is independently C, N, O, or S.
A general synthesis for the disclosed compounds herein also includes:
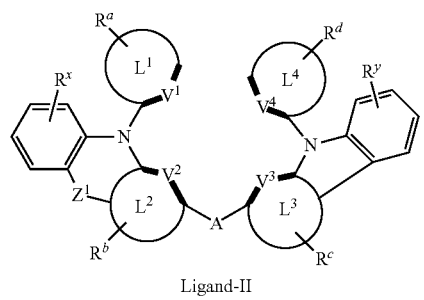
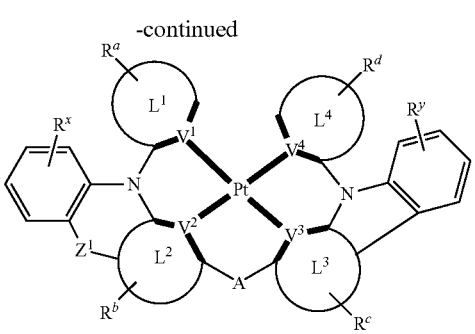
-continued
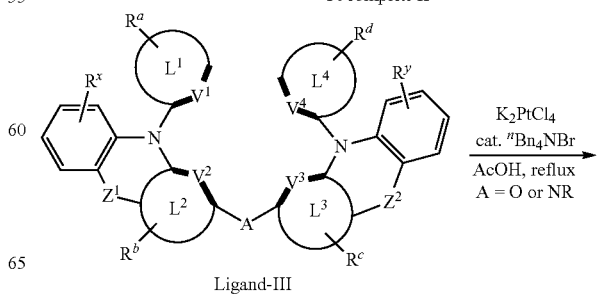

-continued
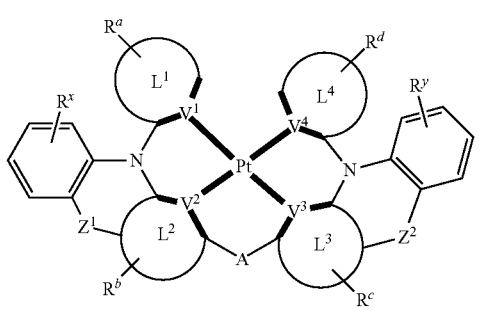
Pt complex-III
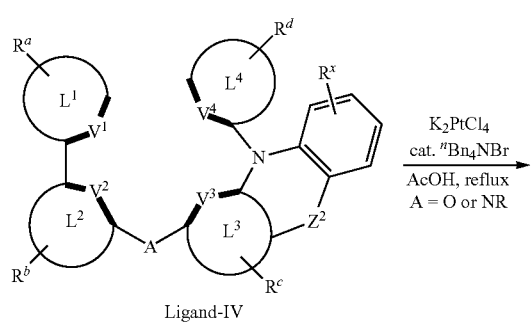
Ligand-IV
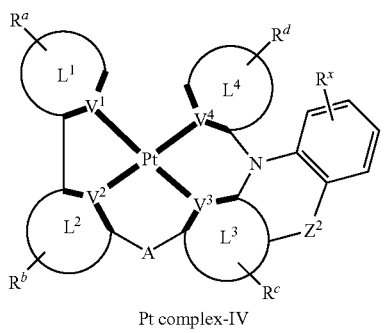
Pt complex-IV
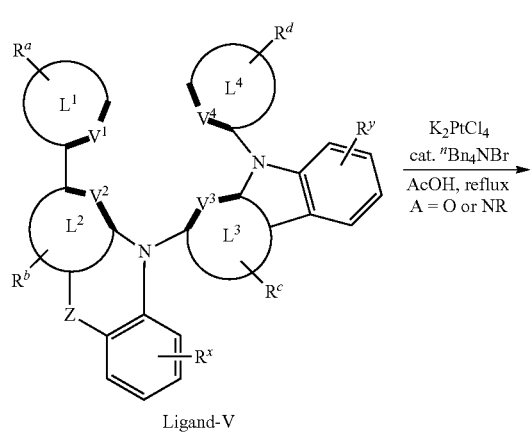
Ligand-V
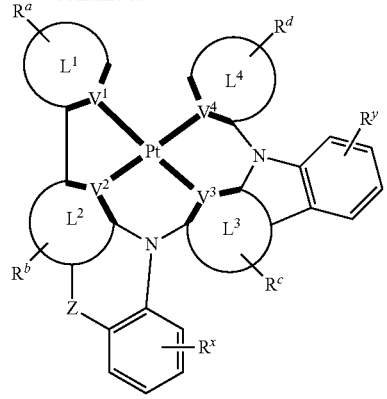
Pt complex-V
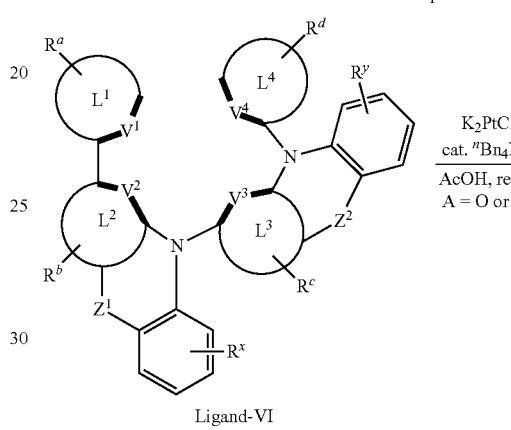
Ligand-VI
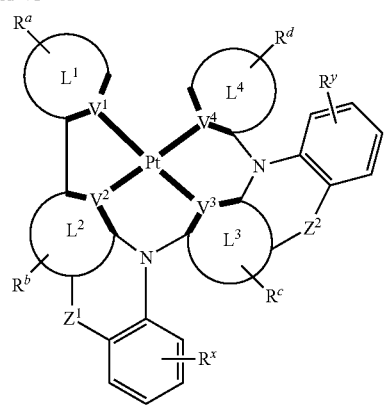
Pt complex-VI
1. Example 1
Platinum complex PtN'1N was prepared according to the following scheme:
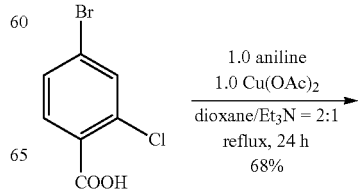

-continued

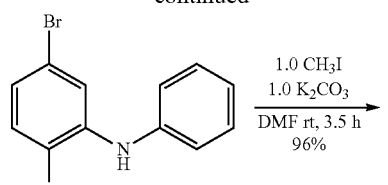

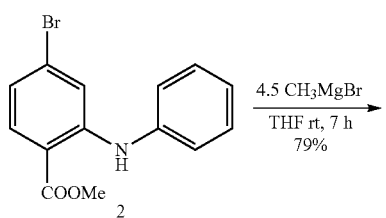

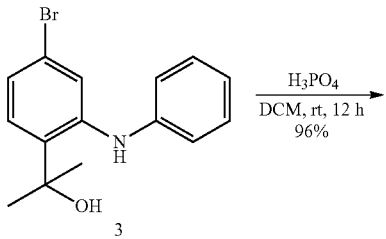

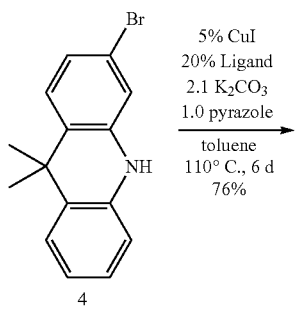

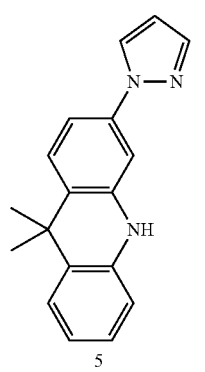

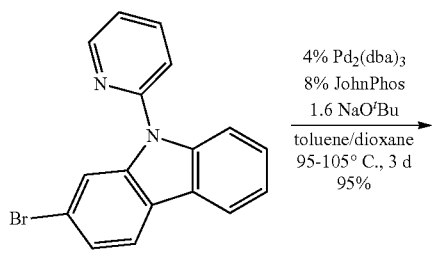

-continued

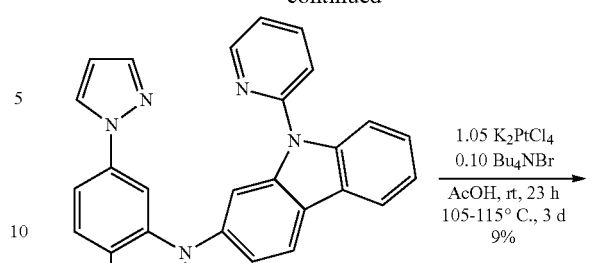

Ligand N'1N

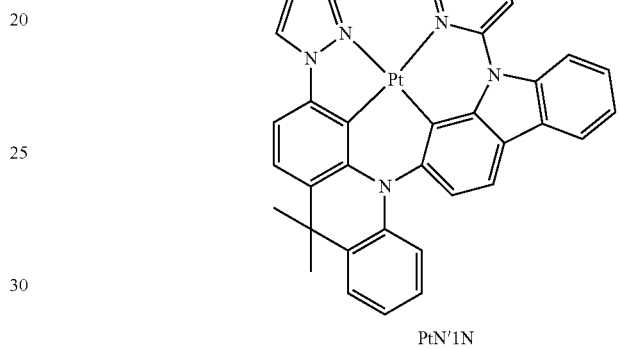

PtN'1N

Synthesis of 4-bromo-2-(phenylamino)benzoic acid 1

[Structure of 4-bromo-2-(phenylamino)benzoic acid]

Cu(OAc)$_2$ (5.55 g, 30 mmol, 1.0 eq) was added to a solution of 4-bromo-2-chlorobenzoic acid (7.07 g, 30 mmol, 1.0 eq) and aniline (2.74 mL, 30 mmol, 1.0 eq) in dioxane (80 mL) and Et$_3$N (40 mL) under an atmosphere of nitrogen. Then the mixture refluxed for 24 hours, cooled down to ambient temperature, the solvent was removed and the residue was diluted with ethyl acetate. The mixture was acidified with 1M HCl. The organic layer was separated and dried over sodium sulfate, filtered and washed with ethyl acetate. The filtrate was concentrated and the residue was purified through column chromatography on silica gel using dichloromethane and methanol (40:1-30:1) as eluent to obtain the desired product 6.00 g in 68% yield (purity was about 85% from $^1$H NMR) with two impurities. $^1$H NMR (CDCl$_3$, 500 MHz): δ 6.86 (dd, J=9.0, 2.0 Hz, 1H), 7.19 (t, 7.5 Hz, 1H), 7.23-7.27 (m, 2H), 7.31 (d, J=1.0 Hz, 1H), 7.40 (t, J=7.5 Hz, 2H), 7.86 (d, J=8.5 Hz, 1H), 9.36 (s, 1H).

Synthesis of methyl 4-bromo-2-(phenylamino)benzoate 2

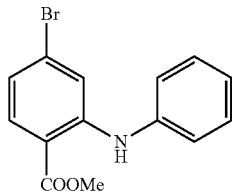 [SMILES: COC(=O)c1ccc(Br)cc1Nc1ccccc1]

K$_2$CO$_3$ (276 mg, 2.0 mmol, 1.0 eq) and MeI (125 uL, 2.0 mmol, 1.0 eq) were added to a solution of 4-bromo-2-(phenylamino)benzoic acid 1 (584 mg, 2.0 mmol, 1.0 eq) in DMF (10 mL) respectively. Then the mixture was stirred at room temperature for 3.5 hours and monitored by TLC until the reaction was complete. The mixture was diluted with water and then extracted with ethyl acetate, dried over sodium sulfate, filtered and washed with ethyl acetate. The filtrate was concentrated and the residue was purified through column chromatography on silica gel using hexane and ethyl acetate (10:1) as eluent to obtain the desired product as a yellow solid 588 mg in 96% yield with a small amount of impurities. $^1$H NMR (DMSO-d$_6$, 400 MHz): δ 3.86 (s, 3H), 6.95-6.97 (m, 1H), 7.16-7.20 (m, 2H), 7.28 (d, J=8.0 Hz, 2H), 7.42 (t, J=7.6 Hz, 2H), 7.81 (dd, J=8.8, 1.2 Hz, 1H), 9.36 (s, 1H).

Synthesis of 2-(4-bromo-2-(phenylamino)phenyl)propan-2-ol 3

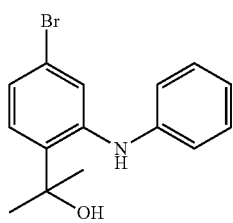 [SMILES: CC(C)(O)c1ccc(Br)cc1Nc1ccccc1]

MeMgBr (48.38 mL, 48.38 mmol, 4.5 eq, 1.0 M in THF) was added slowly to a solution of 4-bromo-2-(phenylamino)benzoate 2 (3.29 g, 11.75 mmol, 1.0 eq) in THF (20 mL) at room temperature under an atmosphere of nitrogen. Then the mixture was stirred at room temperature for 7 hours and monitored by TLC until the reaction was complete. The mixture was quenched with a saturated solution of NH$_4$Cl in water and then extracted with ethyl acetate, dried over sodium sulfate, filtered and washed with ethyl acetate. The filtrate was concentrated and the residue was purified through column chromatography on silica gel using hexane and ethyl acetate (20:1-10:1) as eluent to obtain the desired product as a yellow solid 3.13 g in 79% yield with a small amount of impurities. $^1$H NMR (DMSO-d$_6$, 400 MHz): δ 1.52 (s, 6H), 6.90 (s, 1H), 6.91-6.97 (m, 2H), 7.05 (d, J=8.0 Hz, 2H), 7.18 (d, J=7.6 Hz, 1H), 7.27-7.32 (m, 3H), 9.36 (s, 1H).

Synthesis of 3-bromo-9,9-dimethyl-9,10-dihydroacridine 4

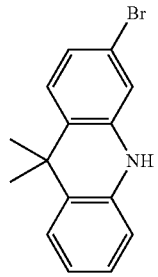 [SMILES: CC1(C)c2ccccc2Nc2cc(Br)ccc21]

H$_3$PO$_4$ (7 mL, 85%) was added to a solution of 2-(4-bromo-2-(phenylamino)phenyl)propan-2-ol 3 (488 mg, 1.44 mmol) in DCM (20 mL) at room temperature. Then the mixture was stirred at room temperature for 12 hours and monitored by TLC until the reaction was complete. The mixture was quenched with water and then extracted with ethyl acetate. The combined organic layer was dried over sodium sulfate, filtered and washed with ethyl acetate. The filtrate was concentrated and the residue was purified through column chromatography on silica gel using hexane and ethyl acetate (20:1) as eluent to obtain the desired product as a yellow sticky liquid 441 mg in 96% yield with a small amount of impurities. $^1$H NMR (DMSO-d$_6$, 400 MHz): δ 1.47 (s, 6H), 6.75-6.79 (m, 1H), 6.82-6.86 (m, 1H), 6.91-6.93 (m, 2H), 7.05-7.09 (m, 1H), 7.29 (d, J=8.0 Hz, 1H), 7.35 (d, J=7.6 Hz, 1H), 9.00 (s, 1H).

Synthesis of 9,9-dimethyl-3-(1H-pyrazol-1-yl)-9,10-dihydroacridine 5

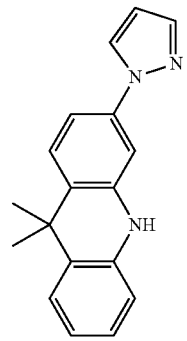 [SMILES: CC1(C)c2ccccc2Nc2cc(-n3cccn3)ccc21]

3-bromo-9,9-dimethyl-9,10-dihydroacridine 4 (1.60 g, 5.0 mmol, 1.0 eq), pyrazole (340 mg, 5.0 mmol, 1.0 eq), CuI (48 mg, 0.25 mmol, 0.05 eq), K$_2$CO$_3$ (1.45 g, 10.5 mmol, 2.1 eq) and trans-1,2-cyclohexanediamine (142 mg, 1.0 mmol, 0.2 eq) were added to a dry pressure tube equipped with a magnetic stir bar. Then the tube was taken into a glove box and solvent toluene (5 mL) was added. The mixture was bubbled with nitrogen for 5 minutes and then the tube was sealed. The tube was taken out of the glove box and the mixture was stirred in an oil bath at 105-115° C. for 6 days. Then the mixture was cooled down to ambient temperature. The solvent was removed and the residue was purified through column chromatography on silica gel using hexane and ethyl acetate (10:1-5:1) as eluent to obtain the pure desired product as a yellow solid 1.16 g in 76% yield. $^1$H NMR (DMSO-d$_6$, 400 MHz): δ 1.51 (s, 6H), 6.51 (t, J=2.0

Hz, 1H), 6.78 (d, J=8.0 Hz, 1H), 6.82 (td, J=8.0, 1.6 Hz, 1H), 7.07 (dd, J=7.6, 1.6 Hz, 1H), 7.19 (dd, J=8.0, 2.0 Hz, 1H), 7.26 (d, J=2.8 Hz, 1H), 7.36 (d, J=7.6 Hz, 1H), 7.43 (d, J=8.4 Hz, 1H), 7.71 (d, J=1.6 Hz, 1H), 8.35 (d, J=2.4 Hz, 1H), 9.06 (s, 1H).

Synthesis of 9,9-dimethyl-3-(1H-pyrazol-1-yl)-10-(9-(pyridin-2-yl)-9H-carbazol-2-yl)-9,10-dihydroacridine Ligand N'1N

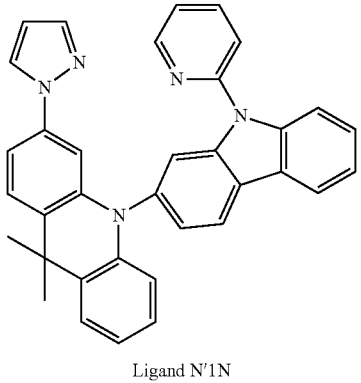 [SMILES: CC1(C)c2ccccc2N(c2ccc3c4ccccc4n(-c4ccccn4)c3c2)c2cc(-n3cccn3)ccc21]

Ligand N'1N 9,9-dimethyl-3-(1H-pyrazol-1-yl)-9,10-dihydroacridine 5 (614 mg, 2.0 mmol, 1.0 eq), 2-bromo-9-(pyridin-2-yl)-9H-carbazole (776 mg, 2.4 mmol, 1.2 eq), Pd$_2$(dba)$_3$ (73 mg, 0.08 mmol, 0.04 eq), XPhos (48 mg, 0.16 mmol, 0.08 eq) and $^t$BuONa (308 mg, 3.2 mmol, 1.6 eq) were added to a dry pressure tube equipped with a magnetic stir bar. The tube was then taken into a glove box and dry solvent toluene (8 mL) and dioxane (8 mL) were added. The tube was sealed and taken out of the glove box. The mixture was stirred at 95-105° C. in an oil bath for three days, cooled to ambient temperature. The solvent was evaporated under reduced pressure and the residue was purified through column chromatography on silica gel using hexane and ethyl acetate (10:1-5:1) as eluent to obtain the desired product Ligand N'1N as a white solid 1.04 g in 95% yield. $^1$H NMR (DMSO-d$_6$, 400 MHz): δ 1.67 (s, 6H), 6.20 (d, J=8.0 Hz, 1H), 6.37 (t, J=1.6 Hz, 1H), 6.75 (d, J=2.0 Hz, 1H), 6.90-6.97 (m, 2H), 7.27-7.33 (m, 2H), 7.42-7.54 (m, 4H), 7.58 (t, J=8.4 Hz, 2H), 7.81 (d, J=8.0 Hz, 1H), 7.82 (s, 1H), 7.85 (d, J=8.0 Hz, 1H), 8.05-8.10 (m, 1H), 8.23 (d, J=2.4 Hz, 1H), 8.39 (d, J=7.6 Hz, 1H), 8.59 (d, J=8.0 Hz, 1H), 8.67 (d, J=2.8 Hz, 1H).

Synthesis of platinum(II)-9,9-dimethyl-3-(1H-pyrazol-1-yl)-10-(9-(pyridin-2-yl)-9H-carbazol-2-yl)-9,10-dihydroacridine PtN'1N

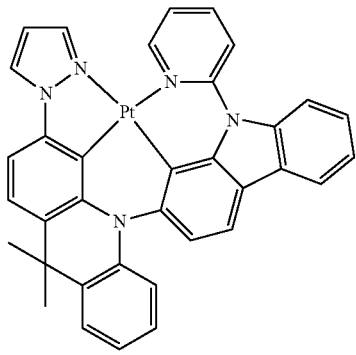

Figure 2:
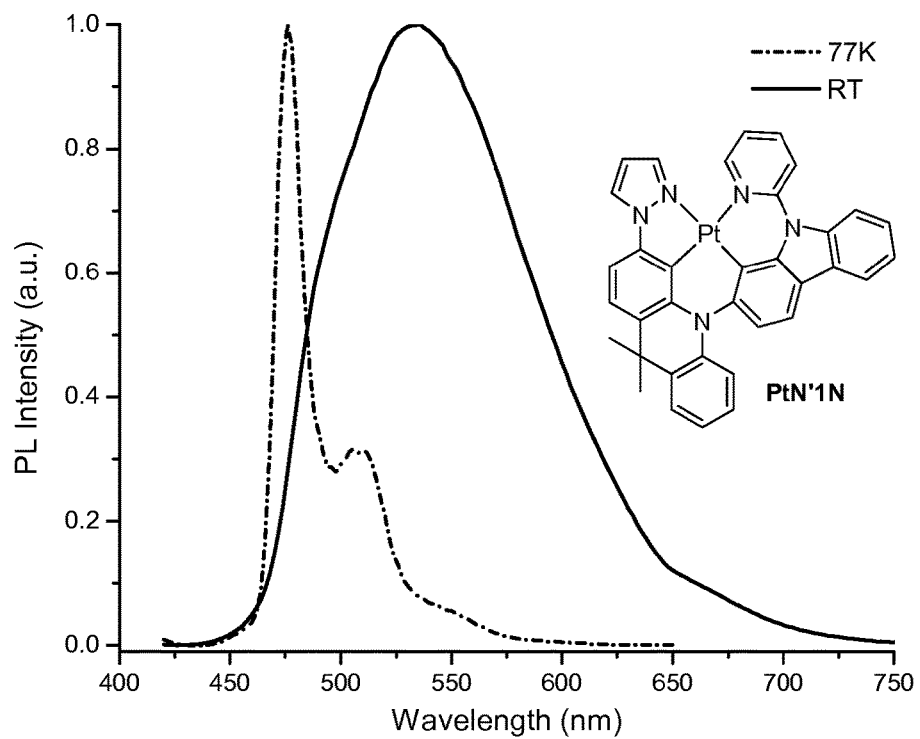
FIG. 2 shows emission spectra of PtN'1N in $CH_2Cl_2$ at room temperature and in 2-methyltetrahydrofuran at 77K, in accordance with various aspects of the present disclosure.

PtN'1N 9,9-dimethyl-3-(1H-pyrazol-1-yl)-10-(9-(pyridin-2-yl)-9H-carbazol-2-yl)-9,10-dihydroacridine Ligand N'1N (1.02 g, 1.858 mmol, 1.0 eq), K$_2$PtCl$_4$ (817 mg, 1.95 mmol, 1.05 eq) and $^n$Bu$_4$NBr (61 mg, 0.19 mmol, 0.1 eq) were added to a three-neck flask equipped with a magnetic stir bar and a condenser. Then the flask was evacuated and backfilled with nitrogen, and this evacuation and back-fill procedure was repeated twice. Then solvent acetic acid (111 mL) was added under nitrogen atmosphere. The mixture was bubbled with nitrogen for 30 minutes stirred at room temperature for 23 hours, followed at 105-115° C. in an oil bath for another three days, cooled down to ambient temperature and water (222 mL) was added slowly. After stirring at room temperature for 10 minutes, the precipitate was filtered off and washed with water three times. Then the solid was dried in air under reduced pressure. The collected solid was purified through column chromatography on silica gel using dichloromethane as eluent to obtain the desired product PtN'1N as a yellow solid 122.6 mg in 9% yield. $^1$H NMR (DMSO-d$_6$, 400 MHz): δ 1.29 (s, 3H0, 1.90 (s, 3H), 6.82 (t, J=2.4 Hz, 1H), 6.99 (t, J=6.4 Hz, 1H), 7.05 (d, J=6.8 Hz, 1H), 7.10 (d, J=8.0 Hz, 1H), 7.19 (d, J=8.4 Hz, 1H), 7.25 (d, J=8.0 Hz, 1H), 7.38 (t, J=7.2 Hz, 1H), 7.41-7.49 (m, 4H), 7.73 (d, J=8.4 Hz, 1H), 8.03 (d, J=2.4 Hz, 1H), 8.08 (t, J=8.4 Hz, 2H), 8.21-8.28 (m, 2H), 8.81 (d, J=2.8 Hz, 1H), 9.26 (d, J=5.2 Hz, 1H). Emission spectra of PtN'1N at room temperature in CH$_2$Cl$_2$ and at 77K in 2-methyltetrahydrofuran are shown in FIG. 2.

2. Example 2

Platinum complex PtN'1N-tBu was prepared according to the following scheme:

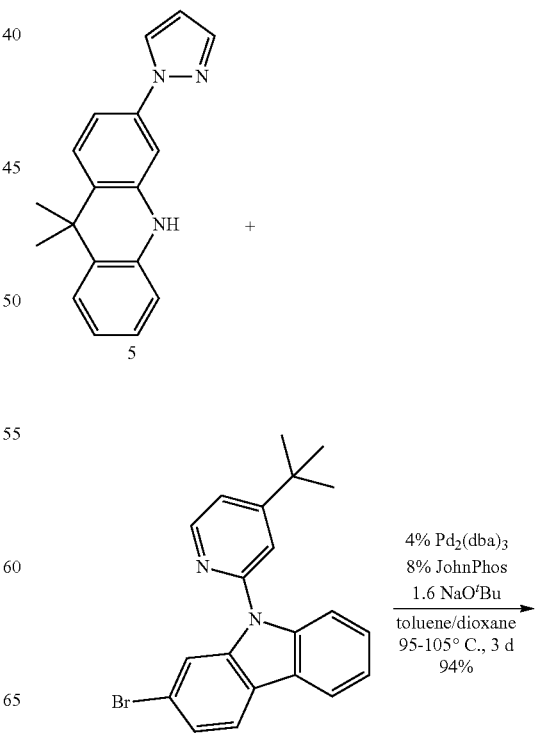

-continued

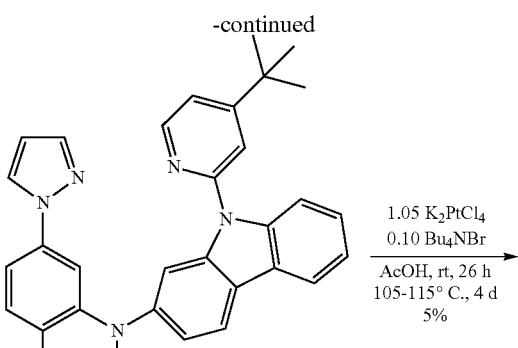

Ligand N'1N—tBu 1.05 K₂PtCl₄
0.10 Bu₄NBr
───────────→
AcOH, rt, 26 h
105-115° C., 4 d
5%

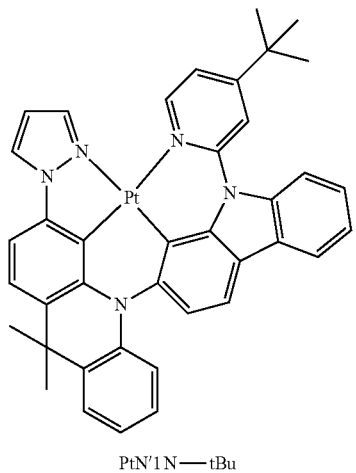

PtN'1N—tBu

Synthesis of 10-(9-(4-tert-butylpyridin-2-yl)-9H-carbazol-2-yl)-9,9-dimethyl-3-(1H-pyrazol-1-yl)-9,10-dihydroacridine Ligand N'1N-tBu

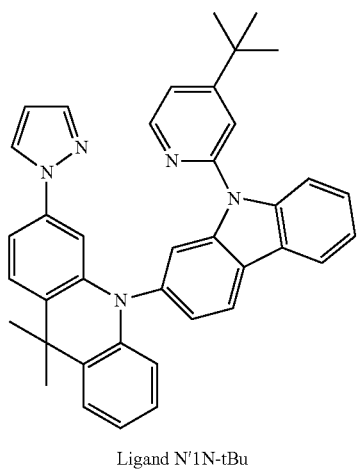 [SMILES: CC(C)(C)c1ccnc(-n2c3ccccc3c3ccc(N4c5ccccc5C(C)(C)c5ccc(-n6cccn6)cc54)cc32)c1]

Ligand N'1N-tBu 9,9-Dimethyl-3-(1H-pyrazol-1-yl)-9,10-dihydroacridine 5 (560 mg, 1.82 mmol, 1.0 eq), 2-bromo-9-(4-tert-butylpyridin-2-yl)-9H-carbazole (826 mg, 2.18 mmol, 1.2 eq), Pd₂(dba)₃ (67 mg, 0.073 mmol, 0.04 eq), JohnPhos (45 mg, 0.15 mmol, 0.08 eq) and ᵗBuONa (280 mg, 2.91 mmol, 1.6 eq) were added to a dry pressure tube equipped with a magnetic stir bar. The tube was then taken into a glove box and dry solvent toluene (8 mL) and dioxane (8 mL) were added. The tube was sealed and taken out of the glove box. The mixture was stirred at 95-105° C. in an oil bath for three days, cooled to ambient temperature. The solvent was evaporated under reduced pressure and the residue was purified through column chromatography on silica gel using hexane and ethyl acetate (10:1-6:1) as eluent to obtain the desired product Ligand N'1N-tBu as a white solid 1.03 g in 94% yield. ¹H NMR (DMSO-d₆, 500 MHz): δ 1.24 (s, 9H), 1.64 (s, 6H), 6.23 (dd, J=8.0, 2.0 Hz, 1H), 6.35 (t, J=1.5 Hz, 1H), 6.79 (d, J=2.5 Hz, 1H), 6.89-6.96 (m, 2H), 7.27 (dd, J=8.5, 2.0 Hz, 1H), 7.32 (dd, J=8.0, 1.5 Hz, 1H), 7.40-7.44 (m, 2H), 7.46 (d, J=1.5 Hz, 1H), 7.50 (dd, J=7.5, 1.5 Hz, 1H), 7.54-7.58 (m, 2H), 7.68 (d, J=1.0 Hz, 1H), 7.74 (d, J=1.0 Hz, 1H), 7.81 (d, J=8.0 Hz, 1H), 8.23 (d, J=2.0 Hz, 1H), 8.38 (d, J=7.5 Hz, 1H), 8.55 (d, J=5.0 Hz, 1H), 8.57 (d, J=8.0 Hz, 1H).

Synthesis of 10-(9-(4-tert-butylpyridin-2-yl)-9H-carbazol-2-yl)-9,9-dimethyl-3-(1H-pyrazol-1-yl)-9,10-dihydroacridine PtN'1N-tBu

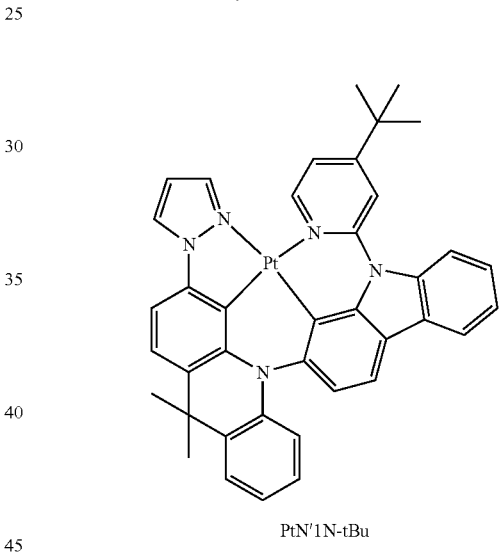

Figure 3:
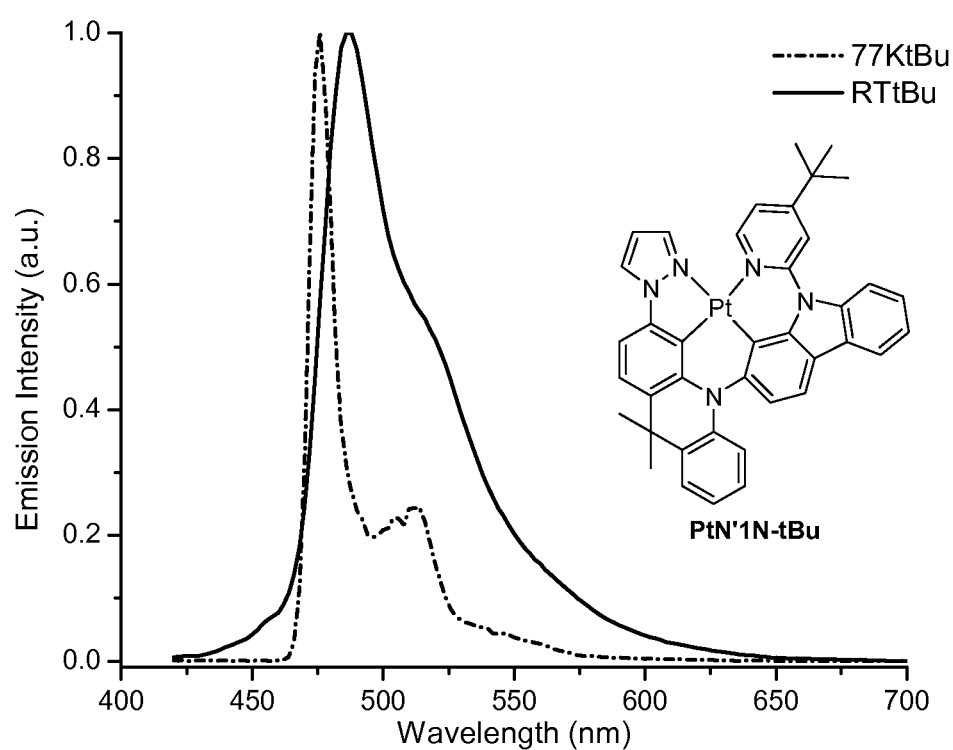
FIG. 3 shows emission spectra of PtN'1N-tBu in $CH_2Cl_2$ at room temperature and in 2-methyltetrahydrofuran at 77K, in accordance with various aspects of the present disclosure.
Figure 5:
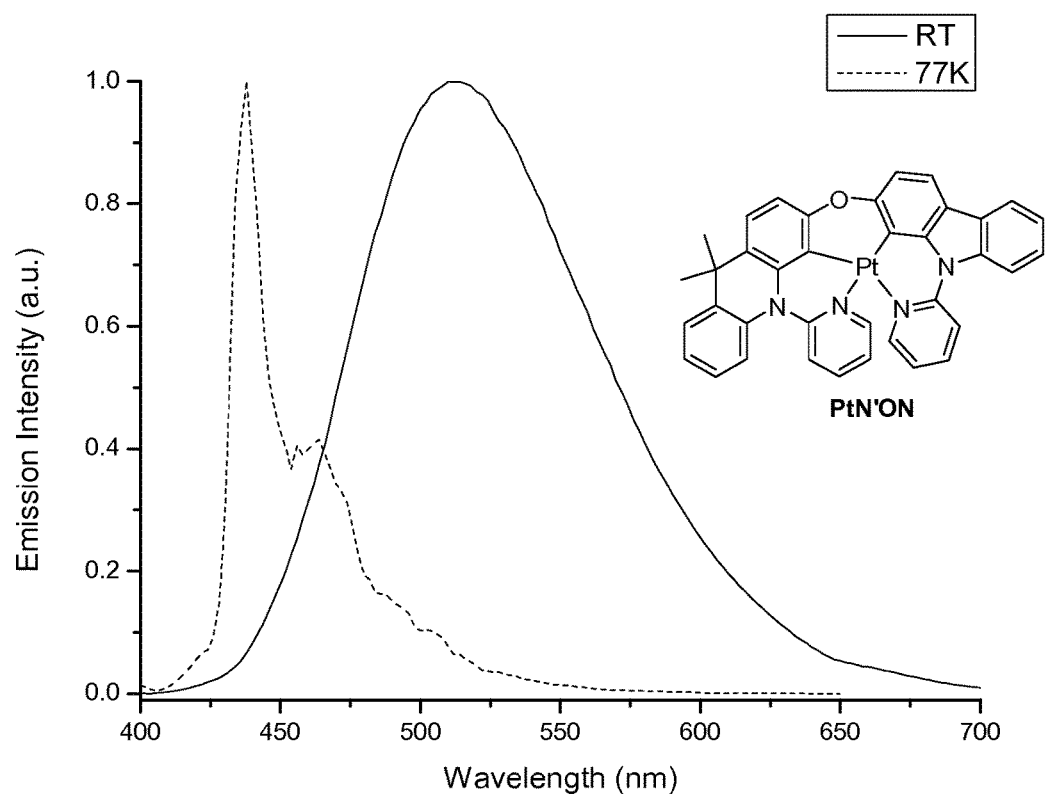
FIG. 5 shows emission spectra of PtN'ON in $CH_2Cl_2$ at room temperature and in 2-methyltetrahydrofuran at 77K, in accordance with various aspects of the present disclosure.

PtN'1N-tBu 10-(9-(4-Tert-butylpyridin-2-yl)-9H-carbazol-2-yl)-9,9-dimethyl-3-(1H-pyrazol-1-yl)-9,10-dihydroacridine Ligand N'1N-tBu (1.02 g, 1.68 mmol, 1.0 eq), K₂PtCl₄ (742 mg, 1.77 mmol, 1.05 eq) and ⁿBu₄NBr (55 mg, 0.17 mmol, 0.1 eq) were added to a three-neck flask equipped with a magnetic stir bar and a condenser. Then the flask was evacuated and backfilled with nitrogen, this evacuation and back-fill procedure was repeated for another twice. Then solvent acetic acid (101 mL) was added under nitrogen atmosphere. The mixture was bubbled with nitrogen for 30 minutes stirred at room temperature for 26 hours, followed at 105-115° C. in an oil bath for another four days, cooled down to ambient temperature and water (202 mL) was added slowly. After stirring at room temperature for 10 minutes, the precipitate was filtered off and washed with water three times. Then the solid was dried in air under reduced pressure. The collected solid was purified through column chromatography on silica gel using hexane/dichloromethane (1:1) as eluent to obtain the desired product PtN'1N-tBu as a yellow solid 63 mg in 5% yield. ¹H NMR (DMSO-d₆, 400 MHz): δ 1.30 (s, 3H), 1.40 (s, 9H), 1.91 (s, 3H), 6.82 (t, J=2.4 Hz, 1H), 6.98-7.09 (m, 3H), 7.20 (d, J=8.4 Hz, 1H), 7.25 (d, J=8.0 Hz, 1H), 7.39 (t, J=7.6 Hz, 1H), 7.43-7.51 (m, 4H), 7.73 (d, J=8.0 Hz, 1H), 8.05 (d, J=2.4 Hz, 1H), 8.08 (d, J=8.4 Hz, 1H), 8.11 (d, J=8.0 Hz, 1H), 8.15 (s, 1H), 8.82 (d, J=2.8 Hz, 1H), 9.16 (d, J=6.4 Hz, 1H). Emission spectra of PtN'1N-tBu at room temperature in CH$_2$Cl$_2$ and at 77K in 2-methyltetrahydrofuran are shown in FIG. 3. A comparison of the spectra of PtN'1N and PtN'1N-tBu at room temperature in CH$_2$Cl$_2$ and at 77K in 2-methyltetrahydrofuran is shown in FIG. 5.

3. Example 3

Platinum complex PtN'ON was prepared according to the following scheme:

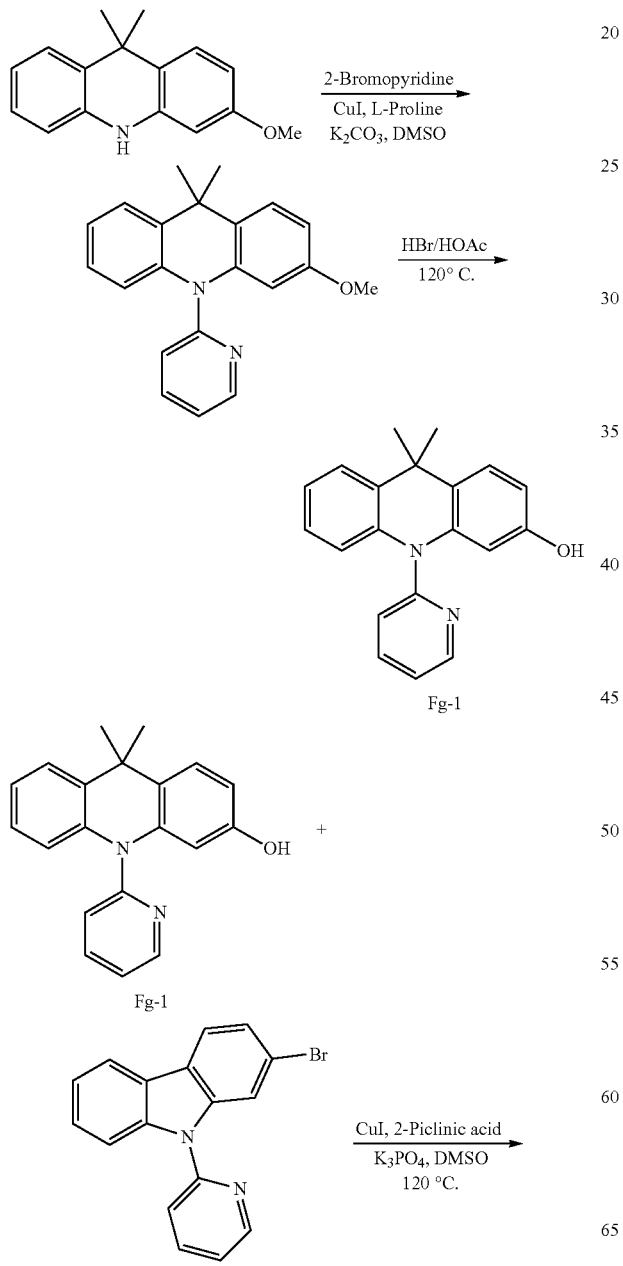

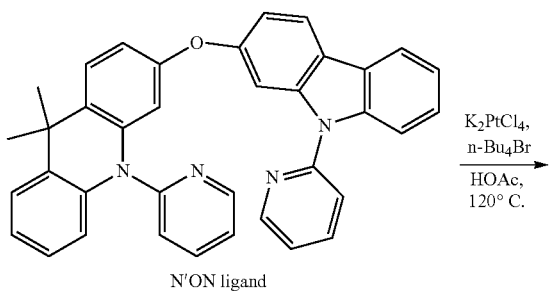

Synthesis of 3-methoxy-9,9-dimethyl-10-(pyridin-2-yl)-9,10-dihydroacridine

The synthesis of Fg-1 started from a known compound 3-methoxy-9,9-dimethyl-9,10-dihydroacridine: to a solution of 3-methoxy-9,9-dimethyl-9,10-dihydroacridine (694 mg, 2.9 mmol) in toluene (15 mL) were added 2-bromopyridine (1.375 g), Pd$_2$(dba)$_3$ (133 mg), JohnPhos (87 mg), and t-BuONa (418 mg) under the protection of N$_2$. The mixture was heated to reflux for 2 days. The mixture was then cooled to room temperature and filtered through a short pad of silica gel. The filtrate was concentrated under reduced pressure. Purification by flash column chromatography on silica gel (hexane/ethyl acetate) gave the 3-methoxy-9,9-dimethyl-10-(pyridin-2-yl)-9,10-dihydroacridine (752 mg, yield 82%). $^1$H NMR (DMSO-d$_6$, 400 MHz): δ 8.75-8.69 (m, 1 H), 8.05 (td, J=7.9, 2.0 Hz, 1 H), 7.53-7.37 (m, 4 H), 7.05-6.93 (m, 2 H), 6.58 (dd, J=8.8, 2.3 Hz, 1 H), 6.38 (dd, J=8.1, 1.5 Hz, 1 H), 5.94 (d, J=2.4 Hz, 1 H), 3.58 (s, 3 H), 1.57 (s, 6 H).

Synthesis of 9,9-dimethyl-10-(pyridin-2-yl)-9,10-dihydroacridin-3-ol Fg-1

Synthesis of platinum(II)-9,9-dimethyl-10-(pyridin-2-yl)-3-(9-(pyridin-2-yl)-9H-carbazol-2-yloxy)-9,10-dihydroacridine PtN'ON

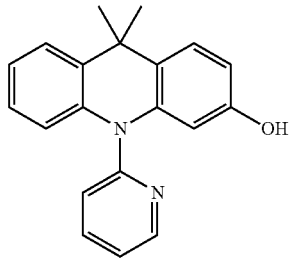 [SMILES: CC1(C)c2ccccc2N(c2ccccn2)c2cc(O)ccc21]

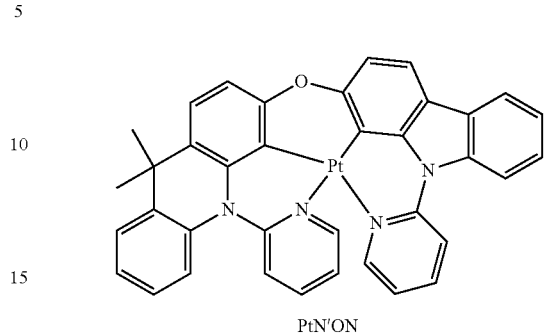

PtN'ON

To a solution of 3-methoxy-9,9-dimethyl-10-(pyridin-2-yl)-9,10-dihydroacridine (728 mg, 2.3 mmol) in acetic acid (10 mL) was added hydrobromic acid (2 mL, 48%). The mixture was heated to 120° C. and maintained at this temperature for 24 hours. The mixture was cooled to room temperature and neutralized with sodium carbonate (to pH 7), extracted with ethyl acetate. The combined organic phase was dried with anhydrous $Na_2SO_4$. Further purification by flash column chromatography on silica gel (hexane/ethyl acetate) gave 9,9-dimethyl-10-(pyridin-2-yl)-9,10-dihydroacridin-3-ol (661 mg, yield 95%. Fg-1) $^1$H NMR (DMSO-$d_6$, 400 MHz): δ 9.06 (s, 1 H), 8.76-8.70 (m, 1 H), 8.10-8.03 (m, 1 H), 7.53-7.43 (m, 2 H), 7.40 (d, J=7.8 Hz, 1 H), 7.02-6.90 (m, 2 H), 6.38 (dd, J=8.2, 2.3 Hz, 1 H), 6.33 (dd, J=8.0, 1.2 Hz, 1 H), 5.82 (d, J=2.4 Hz, 1 H), 1.55 (s, 6 H).

Figure 4:
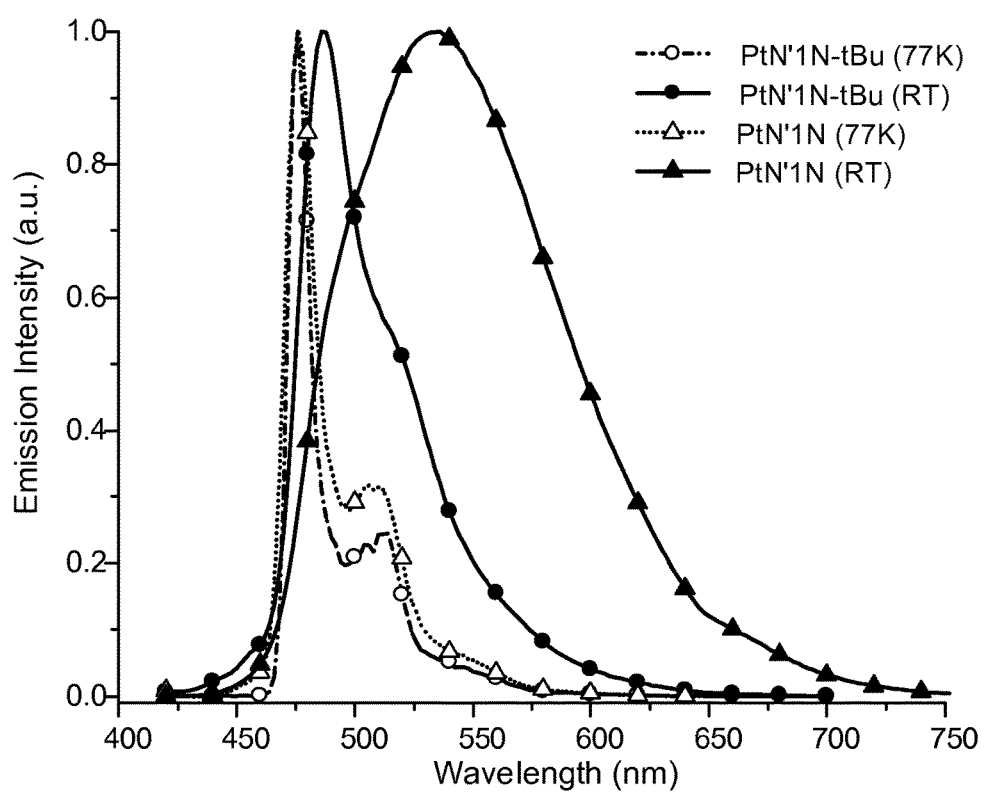
FIG. 4 shows the comparison of emission spectra of PtN'1N and PtN'1N-tBu in $CH_2Cl_2$ at room temperature and in 2-methyltetrahydrofuran at 77K, in accordance with various aspects of the present disclosure.

To an oven-dried flask were added N'ON ligand (229 mg, 0.42 mmol), $K_2PtCl_4$ (183 mg, 0.441 mmol), and n-$Bu_4$NBr (14 mg, 0.042 mmol). The flask was evacuated and back-filled with $N_2$, followed by the addition of HOAc (21 mL, 0.05 M) under the protection of $N_2$. The mixture was then heated to 120° C. and maintained at this temperature. After 3 days, the mixture was cooled to room temperature and concentrated under reduced pressure. Purification by flash column chromatography on silica gel (DCM/Hexane=1/1 to 2/1) gave PtN'ON as a light yellow solid (210 mg, 68% yield). $^1$H NMR (DMSO-$d_6$, 400 MHz): δ 8.74 (dd, J=5.9, 1.4 Hz, 1 H), 8.70 (d, J=5.9 Hz, 1 H), 8.20 (d, J=3.9 Hz, 2 H), 8.17 (d, J=7.3 Hz, 1H), 8.05 (d, J=8.2 Hz, 1 H), 8.02-7.96 (m, 1 H), 7.91 (d, J=8.3 Hz, 1 H), 7.58 (dd, J=7.5, 2.0 Hz, 1 H), 7.51 (dd, J=7.7, 1.9 Hz, 1 H), 7.48-7.43 (m, 1 H), 7.40 (t, J=6.8 Hz, 1 H) 7.35-7.25 (m, 4 H), 7.22-7.15 (m, 2 H), 7.12 (d, J=7.8 Hz, 1 H), 6.92 (d, J=8.3 Hz, 1 H), 1.90 (s, 3 H), 1.27 (s, 3 H). Emission spectra of PtN'ON at room temperature in $CH_2Cl_2$ and at 77K in 2-methyltetrahydrofuran are shown in FIG. 4.

4. Example 4

Platinum complex PtON'1 were prepared according to the following scheme:

Synthesis of 9,9-dimethyl-10-(pyridin-2-yl)-3-(9-(pyridin-2-yl)-9H-carbazol-2-yloxy)-9,10-dihydroacridine N'ON ligand

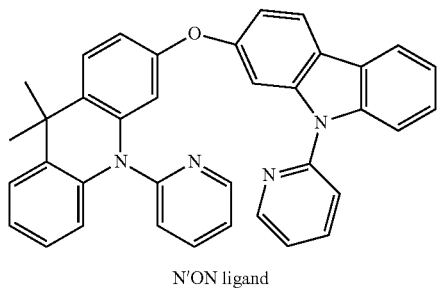 [SMILES: CC1(C)c2ccccc2N(c2ccccn2)c2cc(Oc3ccc4c5ccccc5n(-c5ccccn5)c4c3)ccc21]

N'ON ligand

To a solution of Fg-1 (302 mg, 1 mmol) in DMSO (5 mL) were added 2-bromo-9-(pyridin-2-yl)-9H-carbazole (388 mg, 1.2 mmol), CuI (19 mg, 0.1 mmol), 2-picolinic acid (25 mg, 0.2 mmol), and $K_3PO_4$ (318 mg, 1.5 mmol) under the protection of $N_2$. The mixture was heated to 100° C. and maintained at this temperature for 2 days. The reaction was cooled to room temperature and 20 mL $H_2O$ was then added. The mixture was extracted with ethyl acetate. The combined organic phase was dried with anhydrous $Na_2SO_4$. Further purification by flash column chromatography on silica gel (hexane/ethyl acetate) gave the N'ON ligand (318 mg, 58% yield).

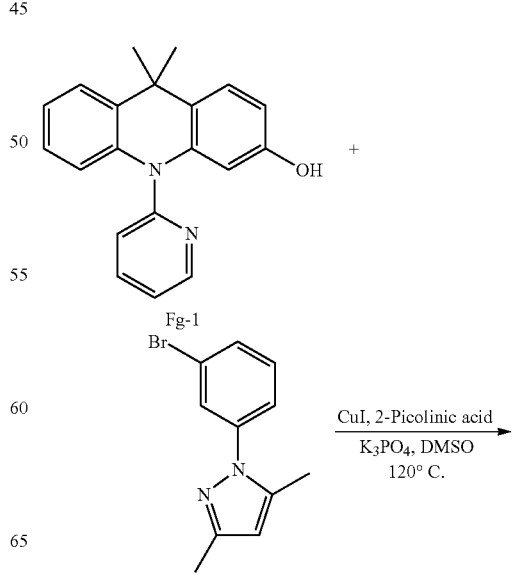

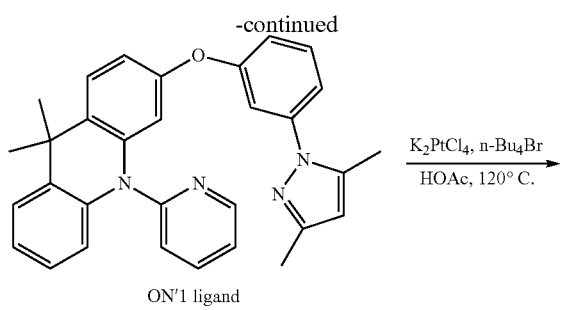

ON'1 ligand

K₂PtCl₄, n-Bu₄Br
HOAc, 120° C.

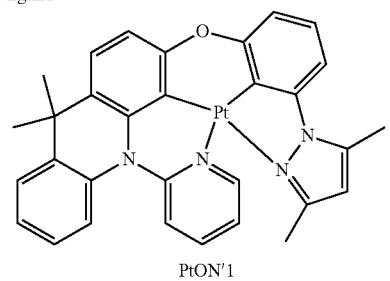

PtON'1

Synthesis of 3-(3-(3,5-dimethyl-1H-pyrazol-1-yl)phenoxy)-9,9-dimethyl-10-(pyridin-2-yl)-9,10-dihydroacridine ON'1 ligand

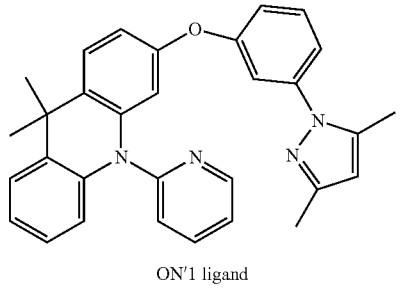 [SMILES: Cc1cc(C)n(-c2cccc(Oc3ccc4c(c3)N(c3ccccn3)c3ccccc3C4(C)C)c2)n1]

ON'1 ligand

To a solution of Fg-1 (302 mg, 1 mmol) in DMSO (5 mL) were added 1-(3-bromophenyl)-3,5-dimethyl-1H-pyrazole (301 mg, 1.2 mmol), CuI (19 mg, 0.1 mmol), 2-picolinic acid (25 mg, 0.2 mmol), and K₃PO₄ (318 mg, 1.5 mmol) under the protection of N₂. The mixture was heated to 100° C. and maintained at this temperature for 2 days. The reaction was cooled to room temperature and 20 mL was then added. The mixture was extracted with ethyl acetate and dried with anhydrous Na₂SO₄. Further purification by flash column chromatography on silica gel (hexane/ethyl acetate) gave the N'ON ligand (246 mg, 52% yield).

Synthesis of platinum(II)-3-(3-(3,5-dimethyl-1H-pyrazol-1-yl)phenoxy)-9,9-dimethyl-10-(pyridin-2-yl)-9,10-dihydroacridine PtON'1

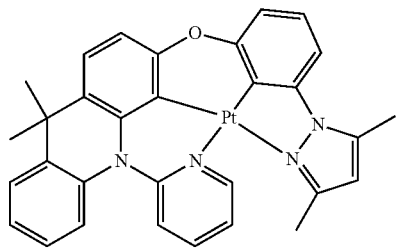

PtON'1

To an oven-dried flask were added ON'1 ligand (227 mg, 0.48 mmol), K₂PtCl₄ (227 mg, 0.504 mmol), and n-Bu₄NBr (15 mg, 0.048 mmol). The flask was evacuated and backfilled with N₂, followed by the addition of HOAc (24 mL, 0.05 M) under the protection of N₂. The mixture was then heated to 120° C. and maintained at this temperature. After 3 days, the mixture was cooled to room temperature and concentrated under reduced pressure. Purification by flash column chromatography on silica gel (DCM/Hexane=1/1 to 2/1) gave PtON'1 as a light yellow solid (205 mg, 64% yield). ¹H NMR (DMSO-d₆, 400 MHz): δ 8.98-8.91 (m, 1 H), 7.96-7.89 (m, 1 H), 7.59-7.52 (m, 1 H), 7.30-7.10 (m, 8 H), 6.90 (d, J=8.3 Hz, 1 H), 6.86 (d, J=7.8 Hz, 1 H), 6.38 (s, 1 H), 2.72 (s, 3 H), 2.26 (s, 3 H), 1.87 (s, 3 H), 1.22 (s, 3 H).

5. Example 5

Platinum complex PtON"1 can be prepared according to the following scheme:

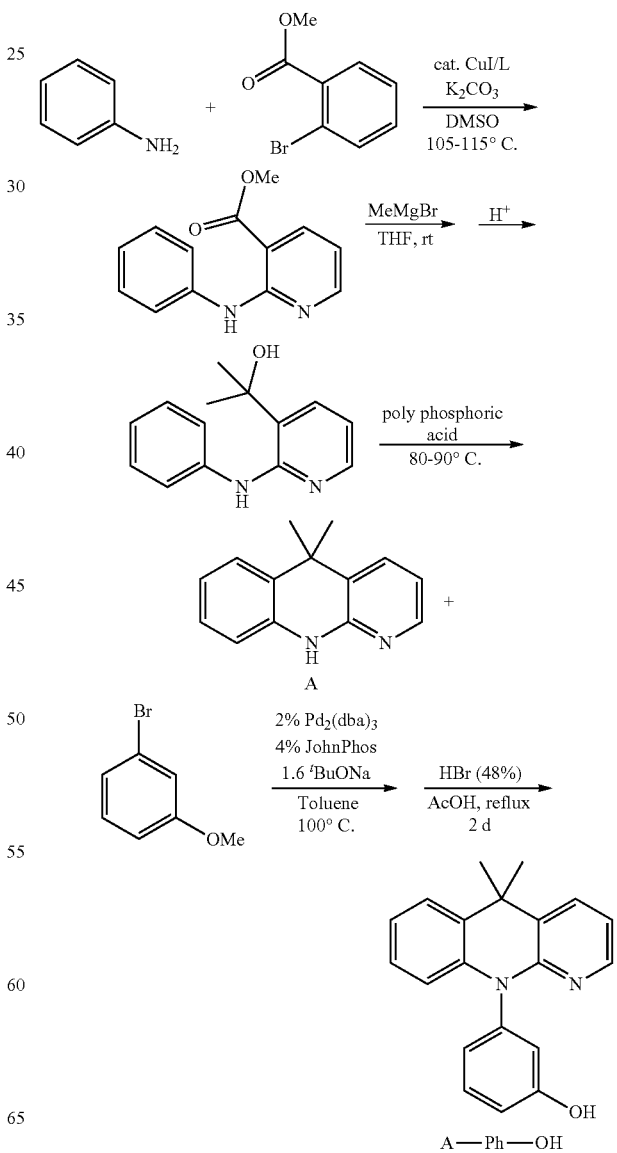

A—Ph—OH

311
-continued
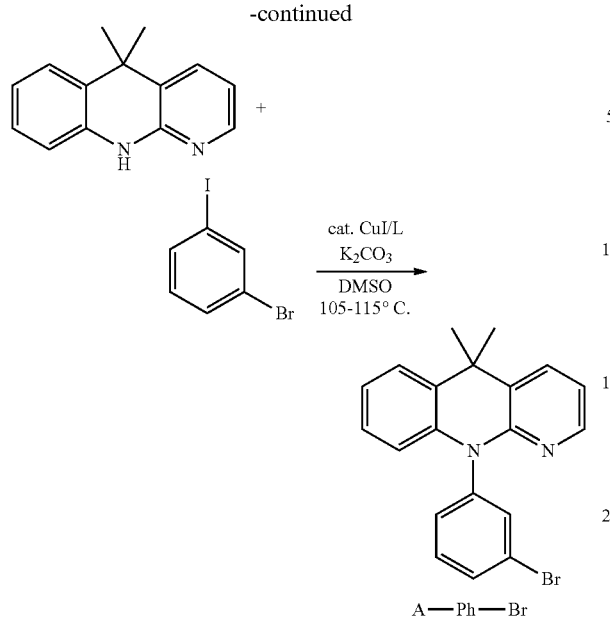
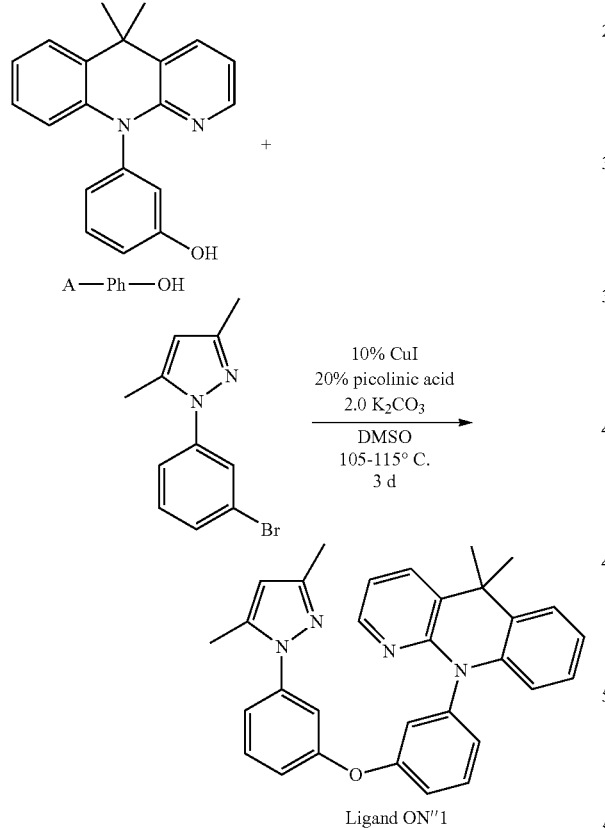
312
-continued
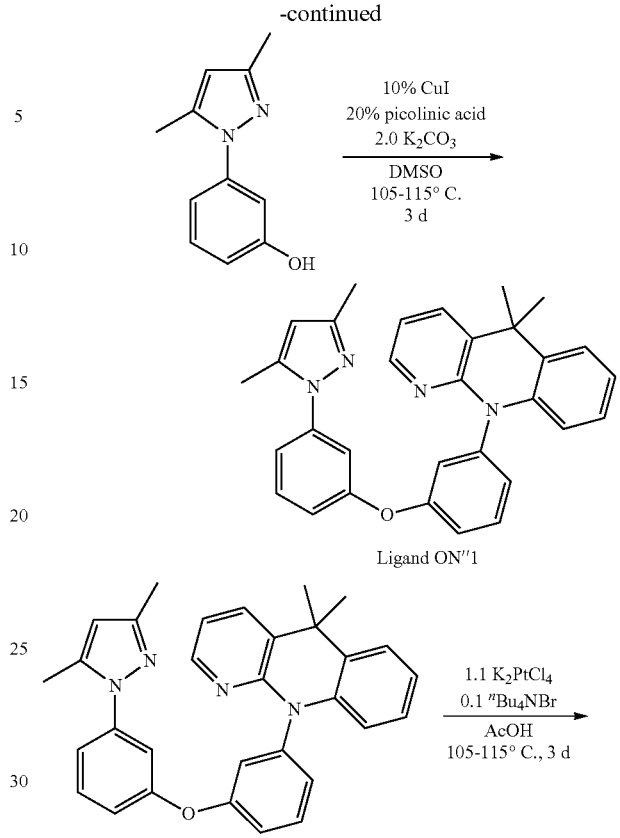
6. Example 6
Platinum complex PtNON″ was prepared according to the following scheme:
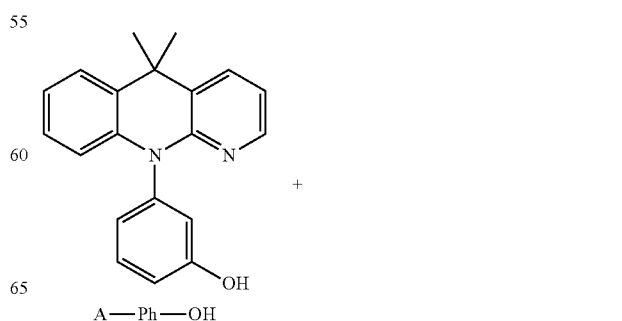

313
-continued
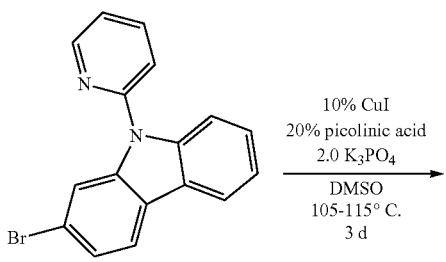
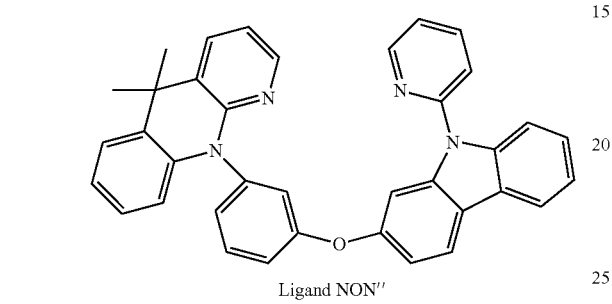
Ligand NON″
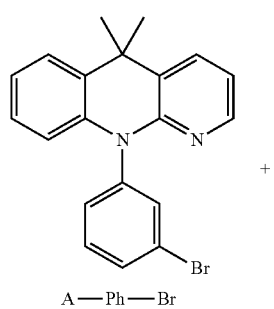
A—Ph—Br
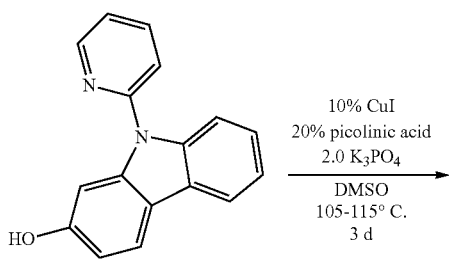
Ligand NON″
314
7. Example 7
Platinum complex PtN′ON″ was prepared according to the following scheme:
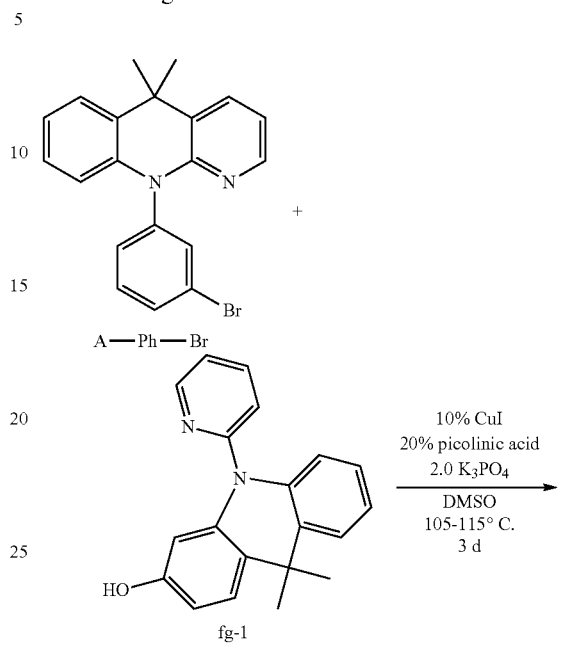
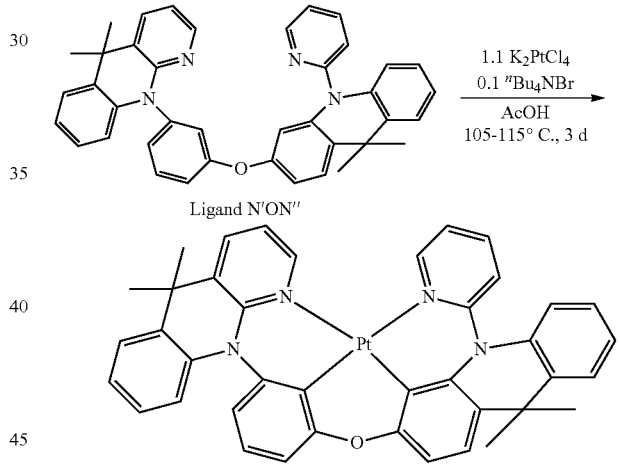
PtN′ON″
8. Example 8
Platinum complex PtN′ON″ can be prepared according to the following scheme:
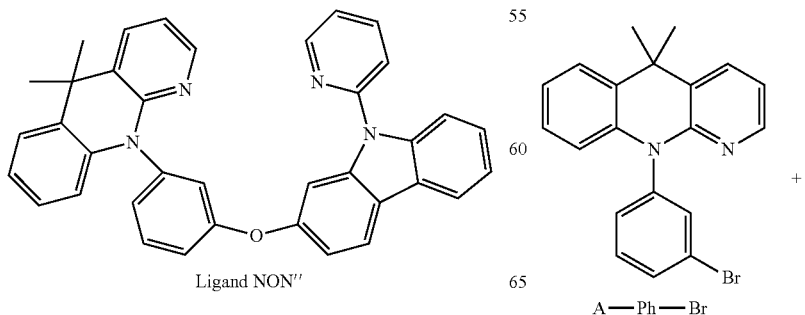
A—Ph—Br 315
-continued

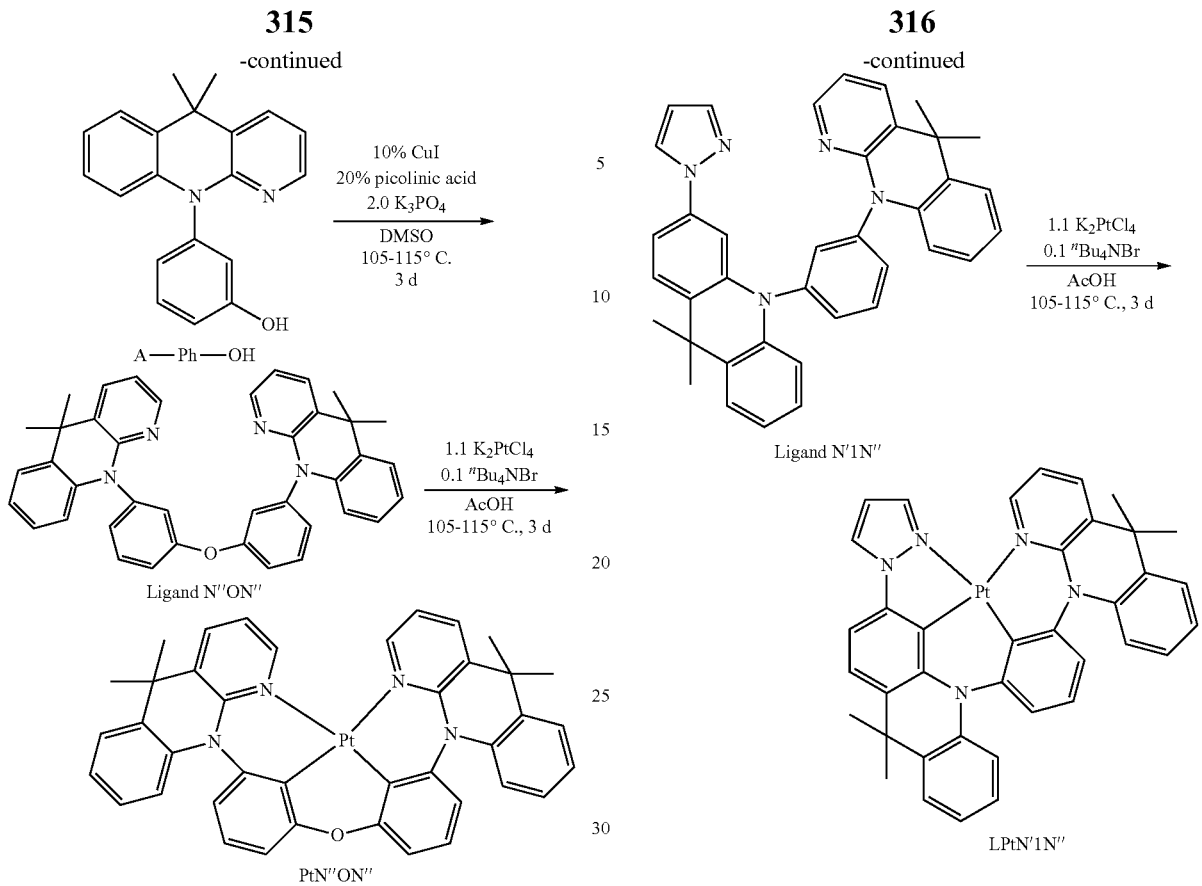

9. Example 9

Platinum complex PtN'1N" can be prepared according to the following scheme:

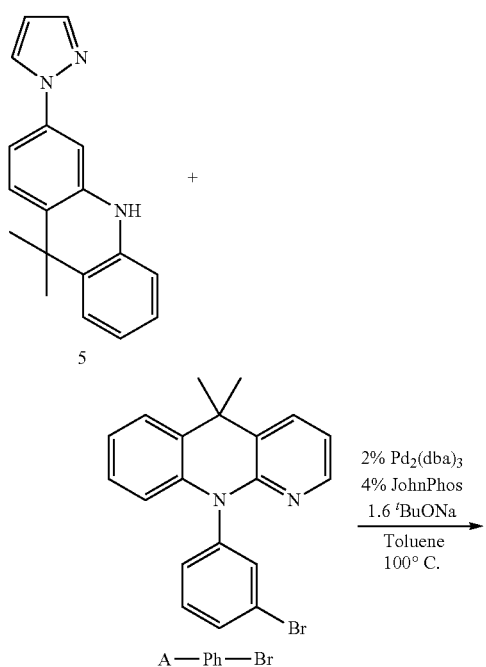

316
-continued

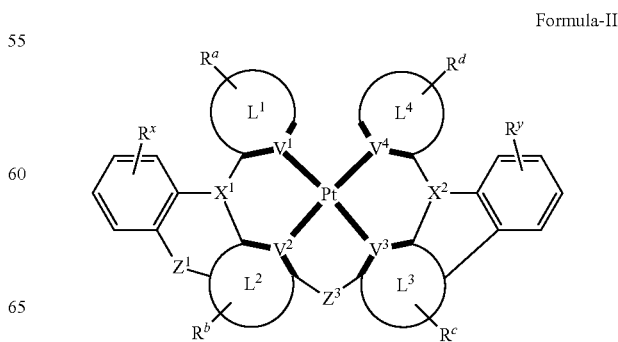

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A compound of Formula II, Formula IV, Formula VI, Formula VII, Formula VIII, Formula IX, Formula X, or Formula XI:

Formula-IV
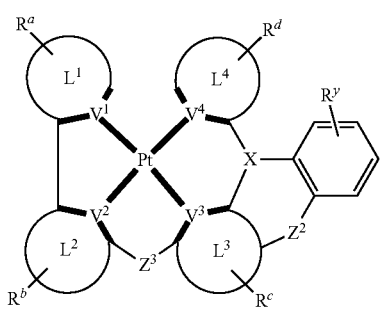

Formula-V
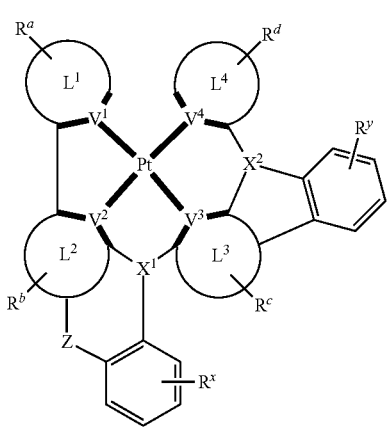

Formula-VI
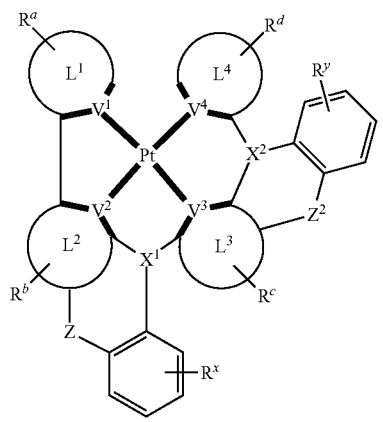

Formula-VII
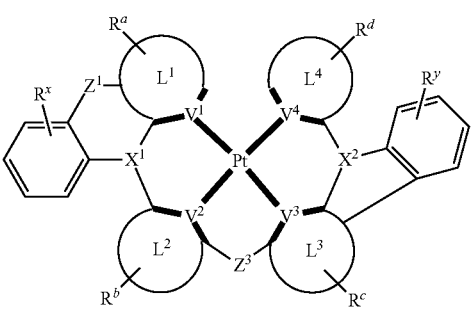

Formula-VIII
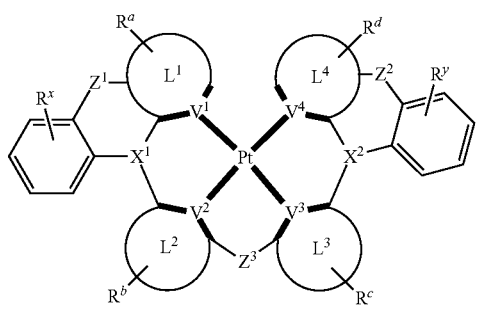

Formula-IX
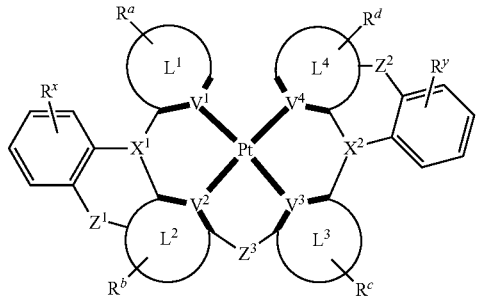

Formula-X
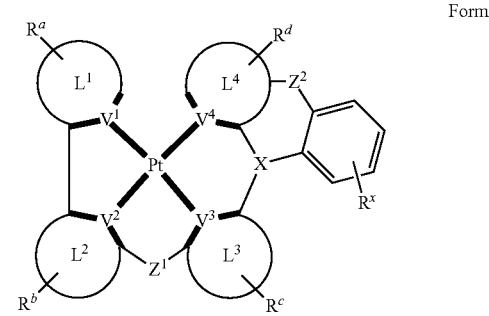

Formula-XI
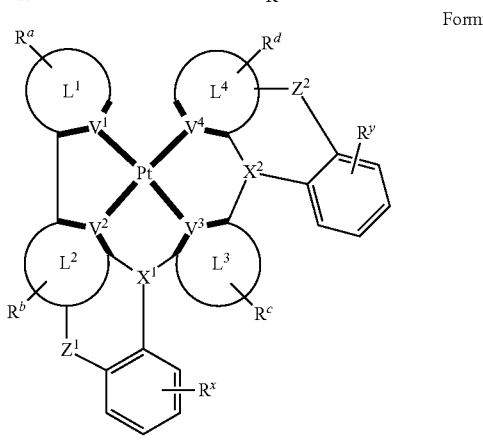

wherein:
each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene,
each of $V^1$, $V^2$, $V^3$, and $V^4$ is coordinated with Pt and is independently N, C, P, B, or Si,
each of $R^a$, $R^b$, $R^c$, and $R^d$ is independently present or absent, and if present each of $R^a$, $R^b$, $R^c$, and $R^d$ independently represents mono-, di-, or tri-substitutions, and each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of X, $X^1$, and $X^2$ is independently CH, $CR^1$, SiH, $SiR^1$, GeH, $GeR^1$, N, P, P=O, As, As=O, B, Bi, or Bi=O;

each of $Z^1$, $Z^2$, and $Z^3$ is independently $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$;

each of $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; and each of $R^x$ and $R^y$ is independently present or absent, and if present each of $R^x$ and $R^y$ independently represents mono-, di-, or tri-substitutions, and each of $R^x$ and $R^y$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

2. The compound of claim 1, wherein the compound has a neutral charge.

3. The compound of claim 1, wherein each of

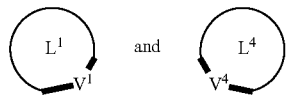

is independently selected from the following structures:

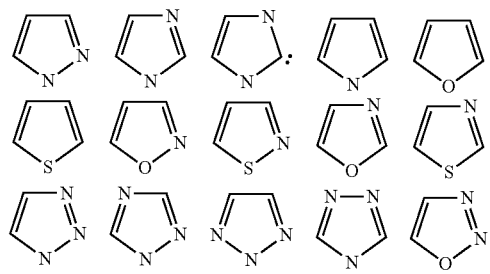

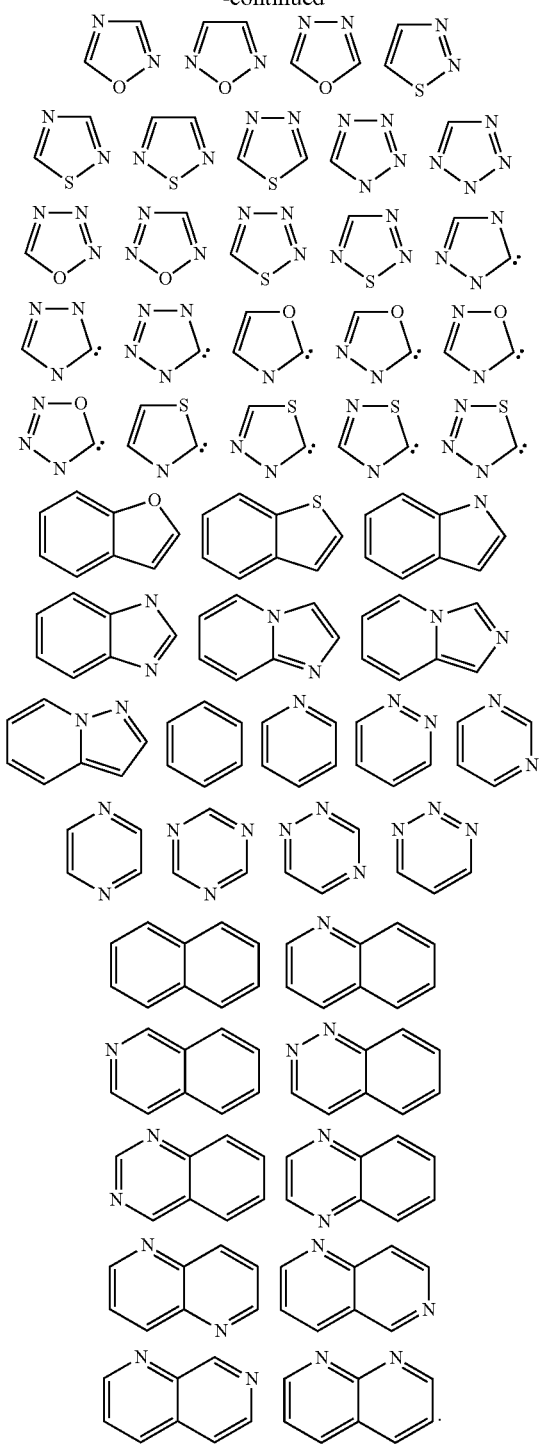

4. The compound of claim 1, wherein each of

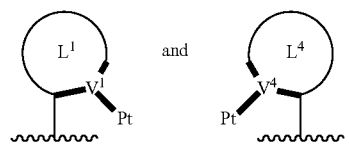

is independently selected from the following structures:
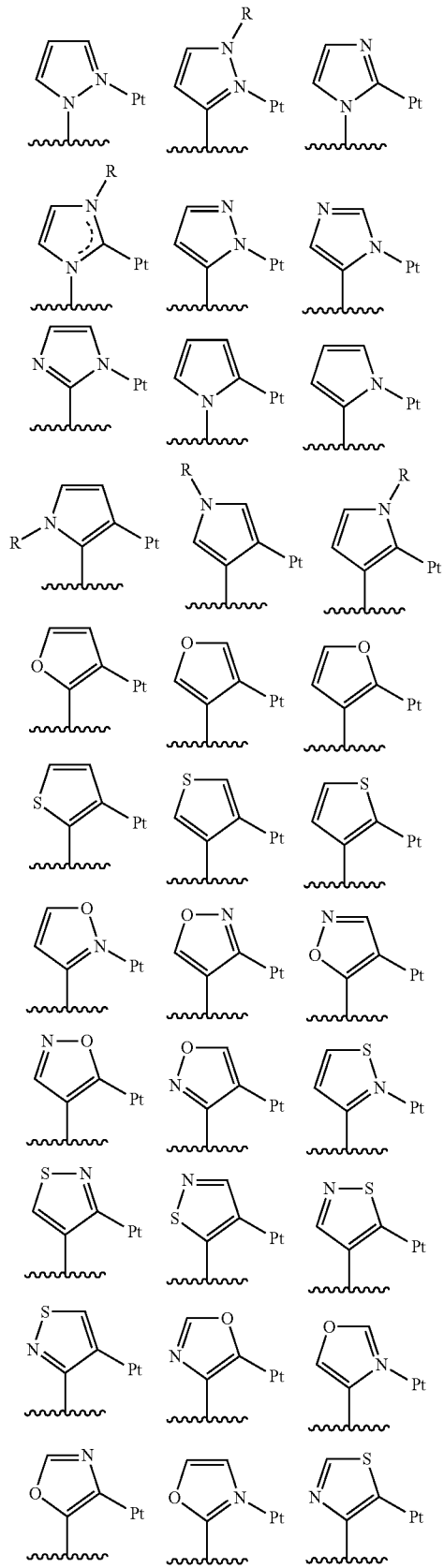
-continued
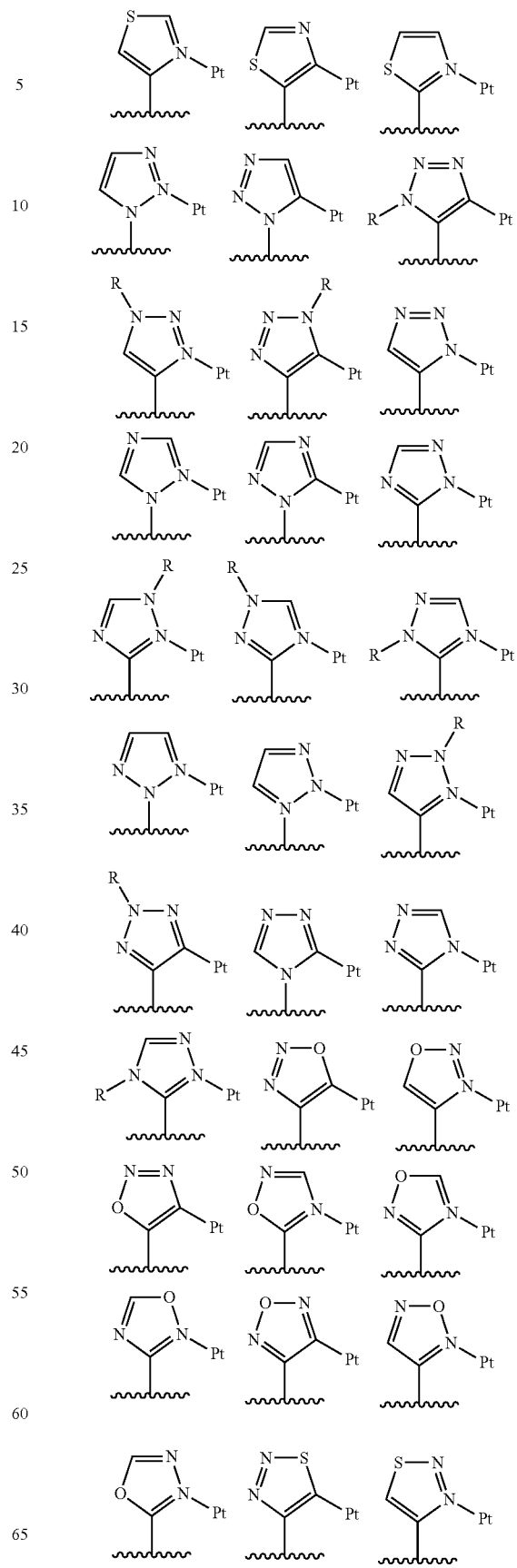

323
-continued
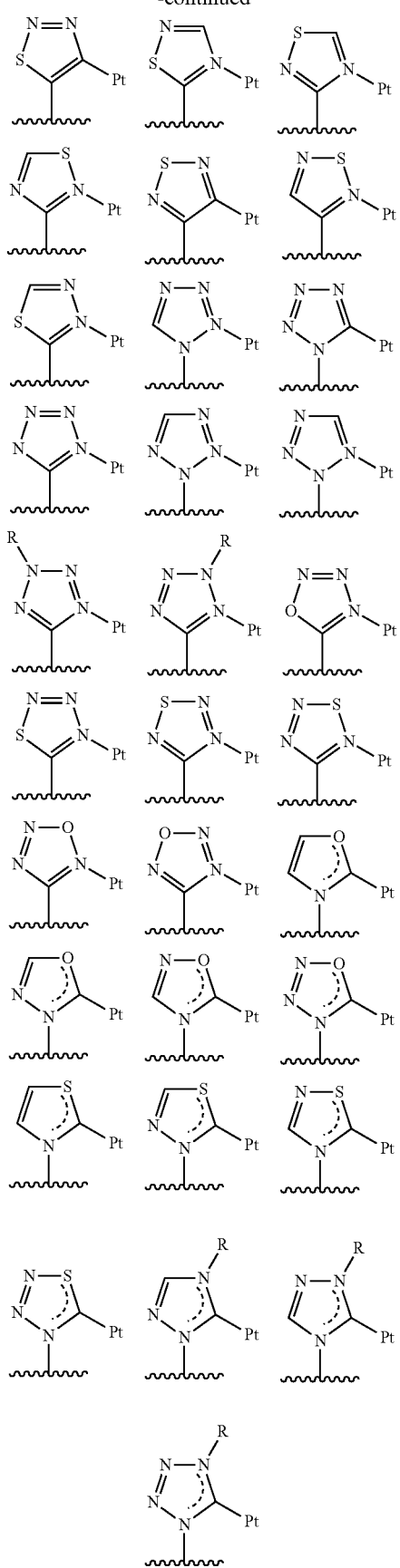
324
-continued
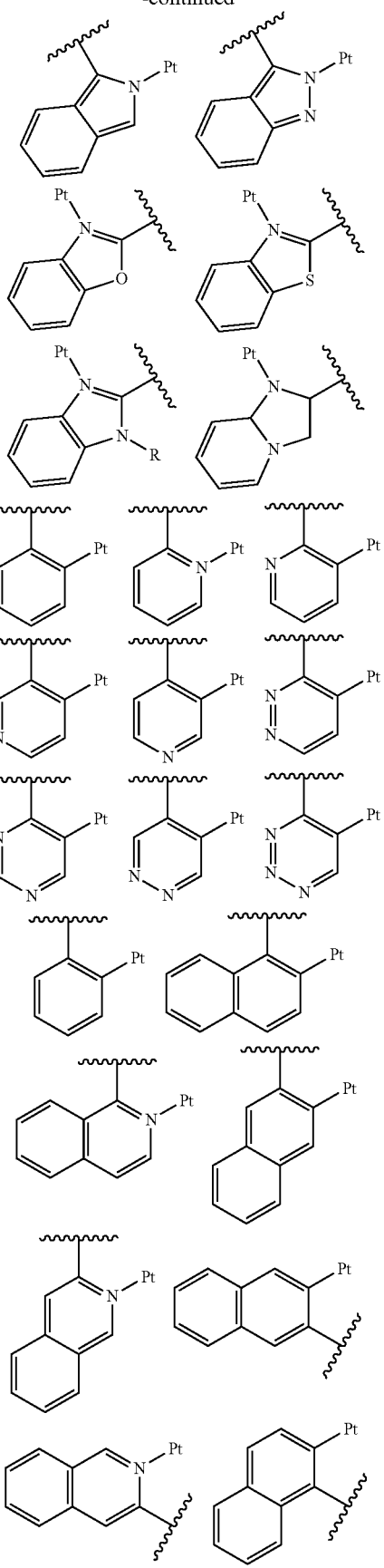

-continued

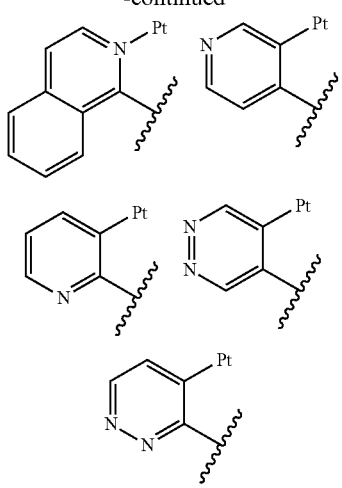

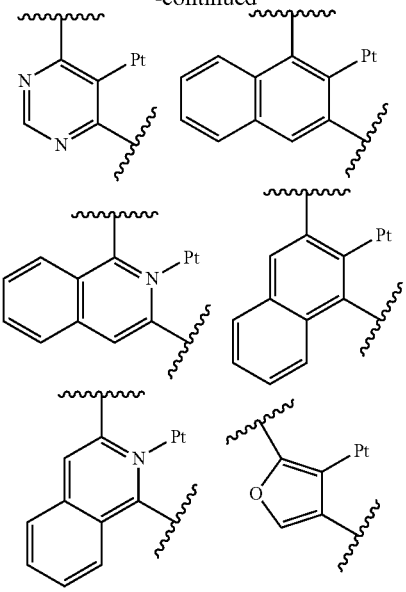

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

5. The compound of claim 1, wherein each of

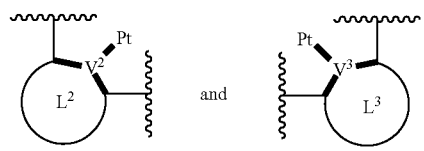

and independently selected from the following structures:

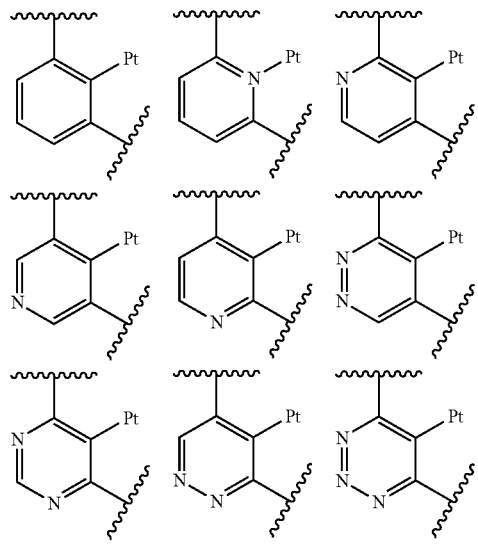

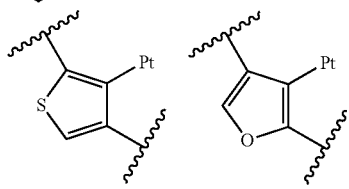

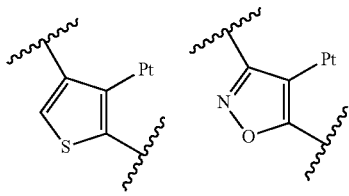

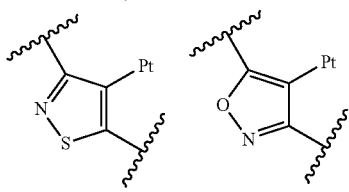

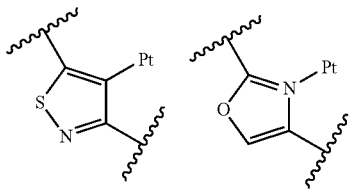

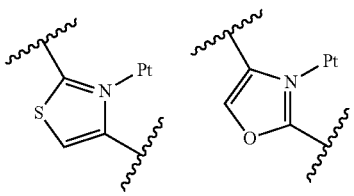

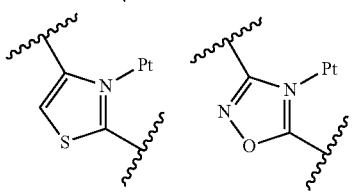

-continued

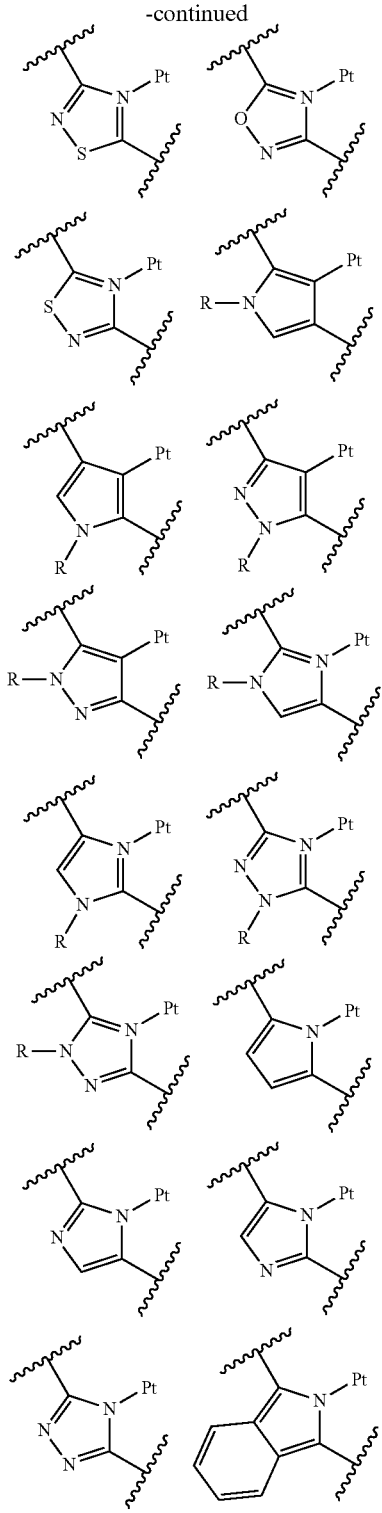

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

6. The compound of claim 1, wherein each of

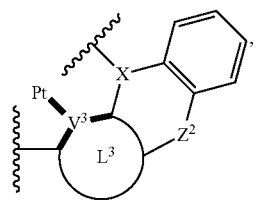

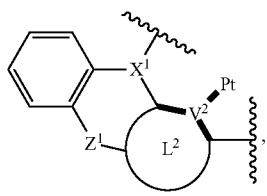

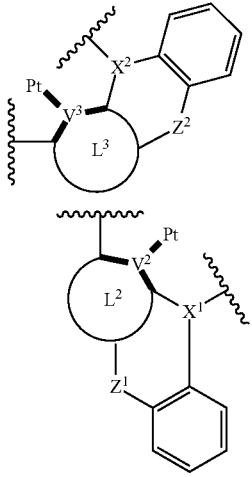

and is independently selected from the following structures:

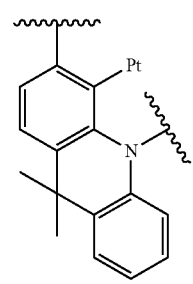

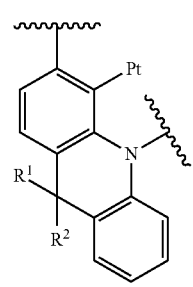

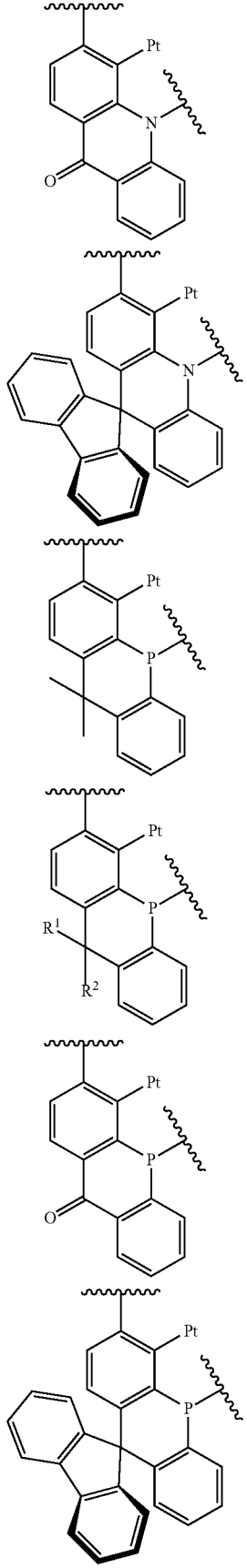
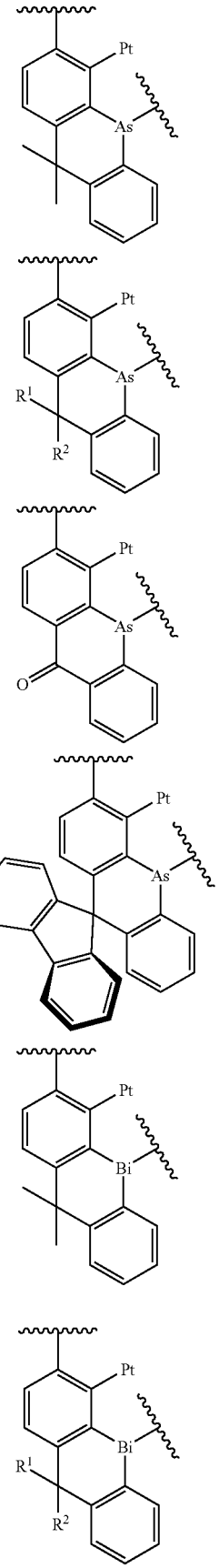

331
-continued
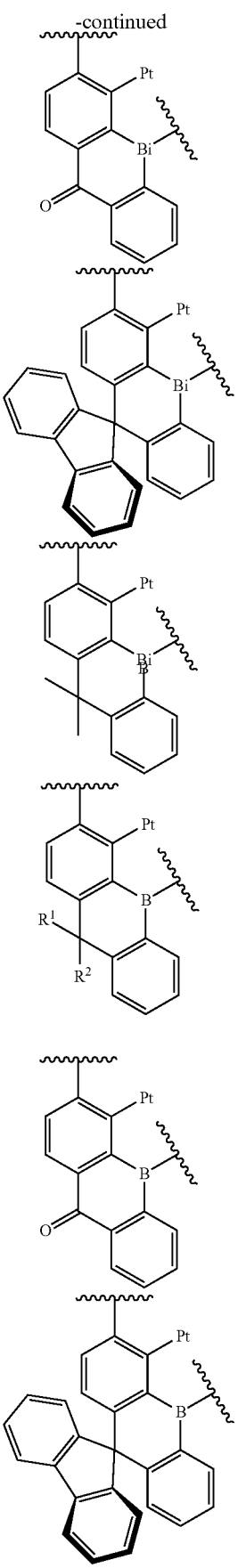
332
-continued
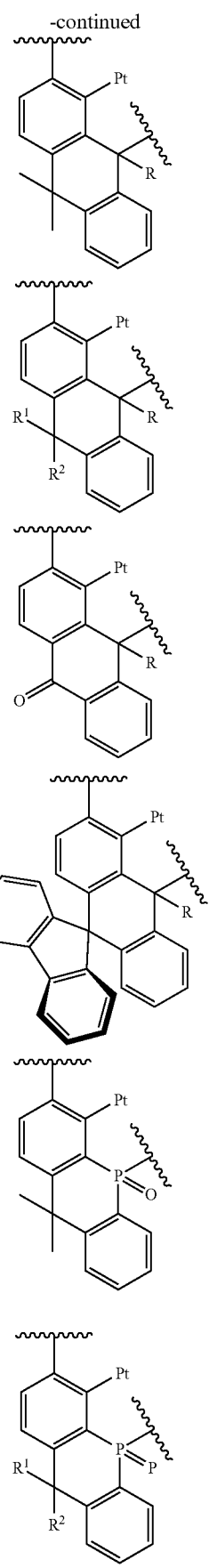

333
-continued
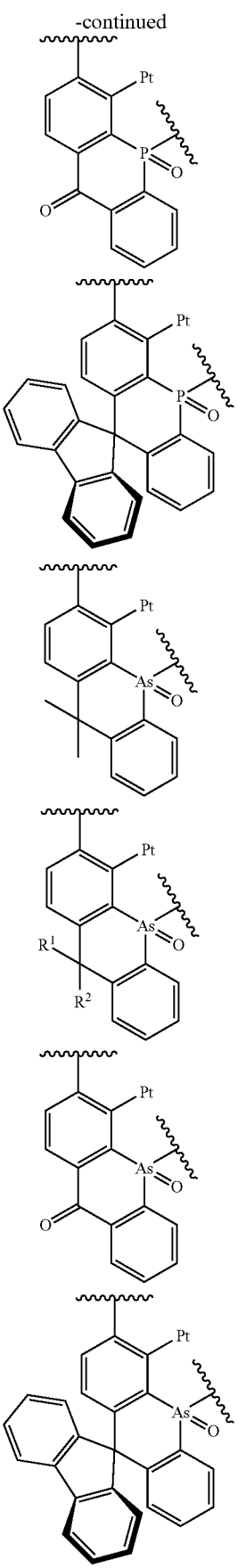
334
-continued
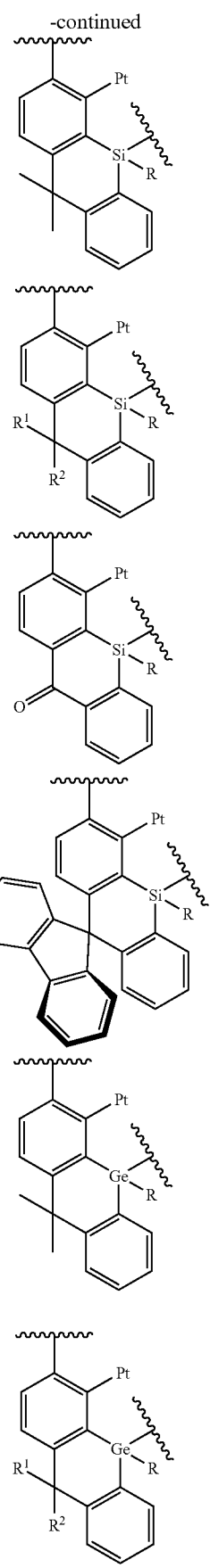

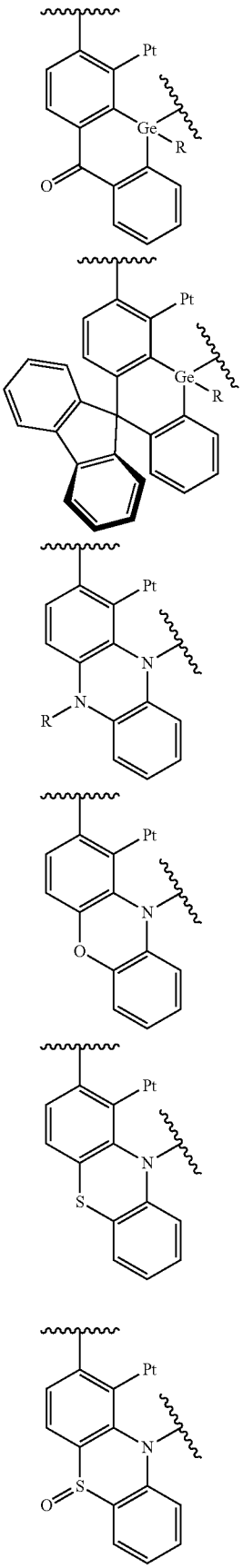
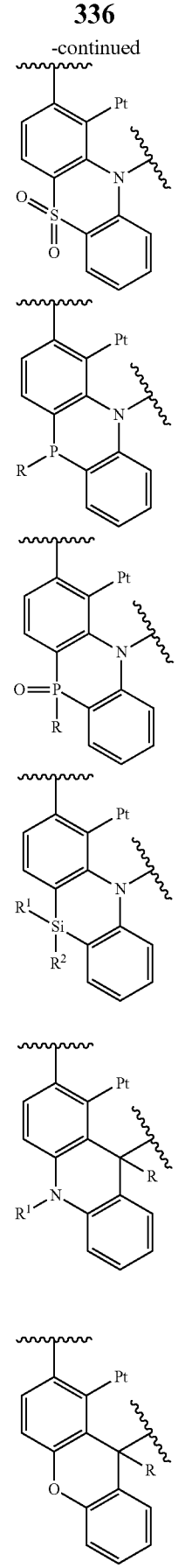

337
-continued
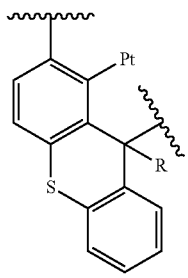
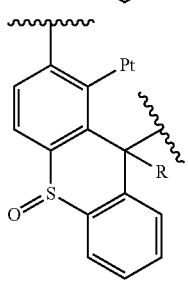
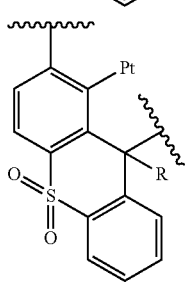
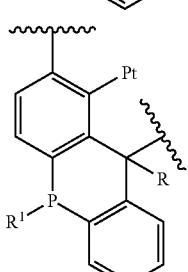
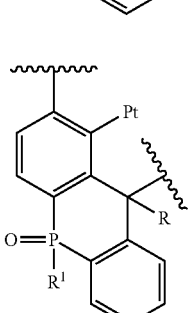
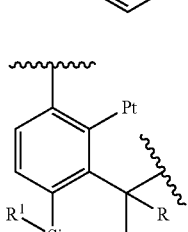
338
-continued
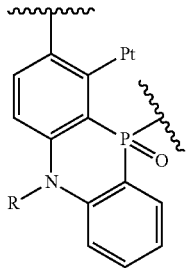
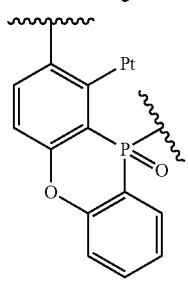
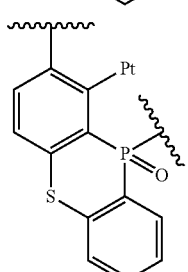
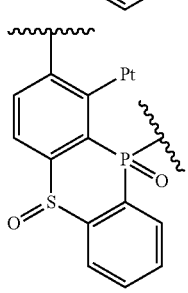
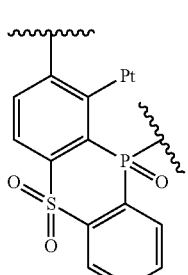
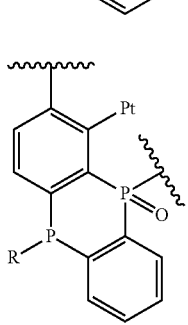

-continued
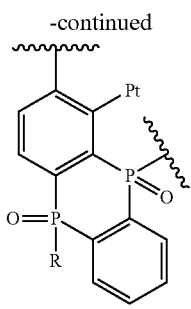
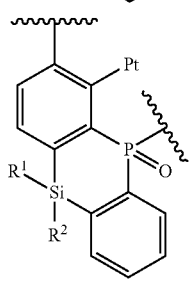
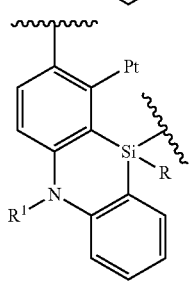
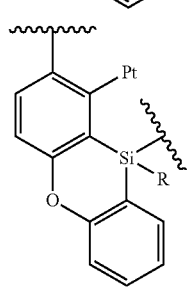
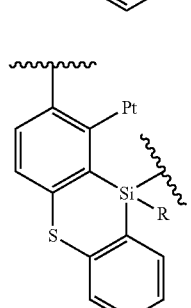
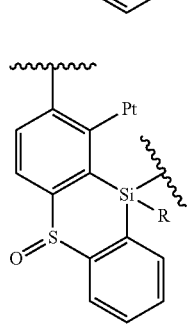
-continued
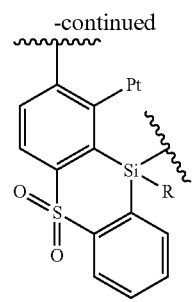
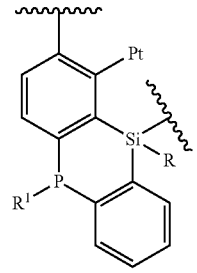
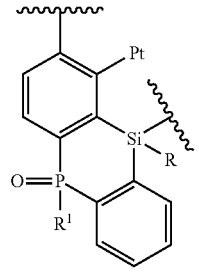
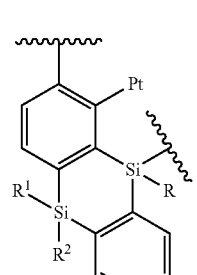
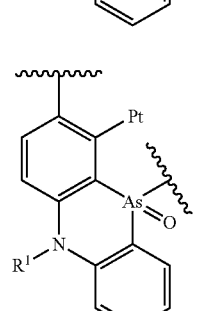
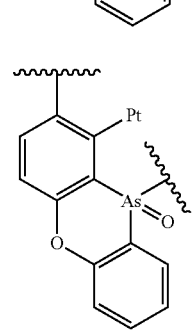

341
-continued
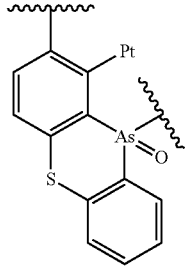
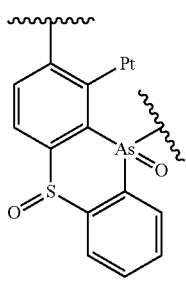
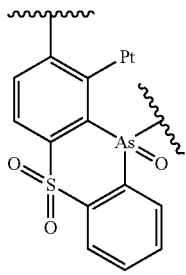
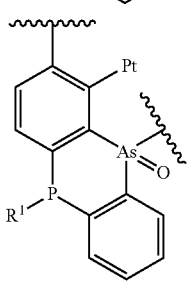
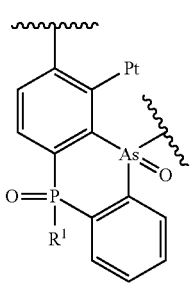
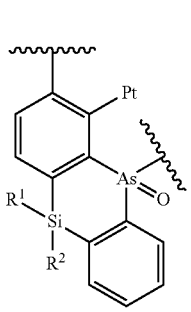
342
-continued
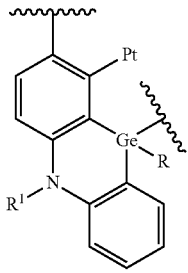
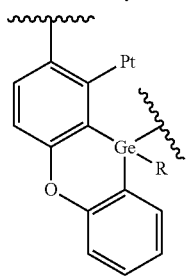
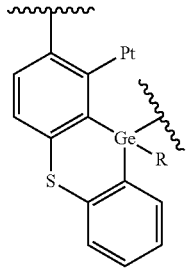
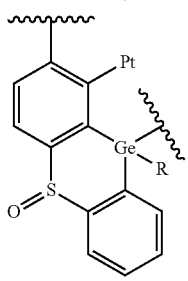
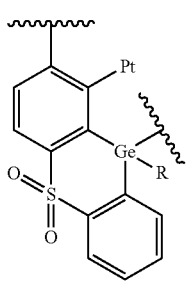
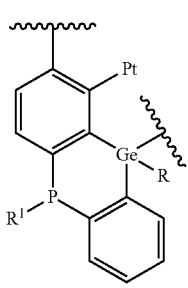

343
-continued
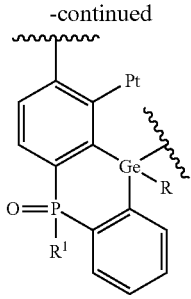
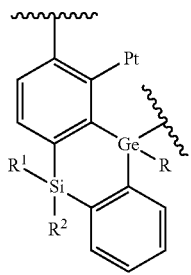
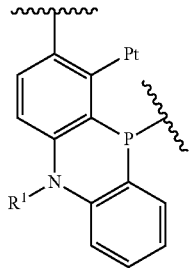
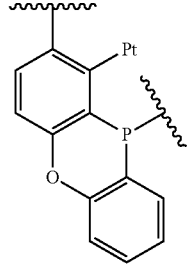
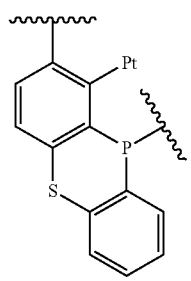
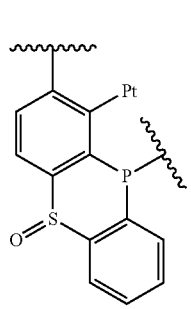
344
-continued
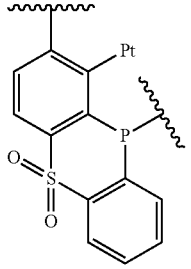
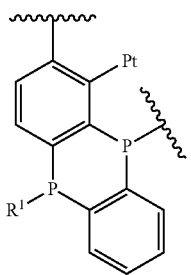
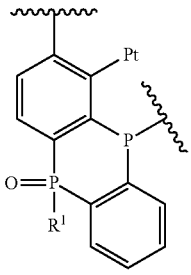
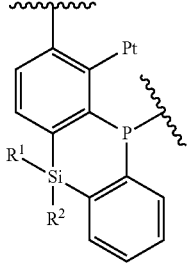
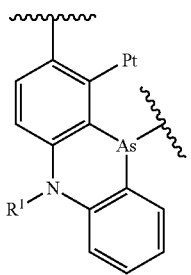
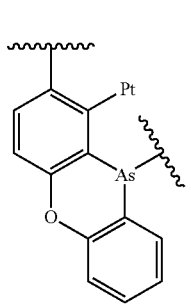

345
-continued
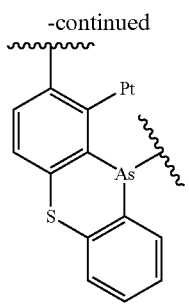
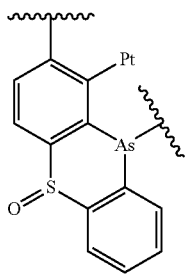
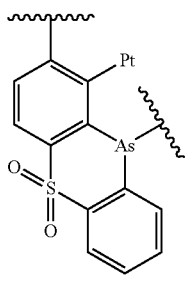
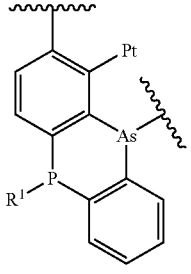
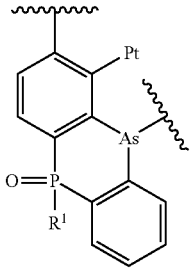
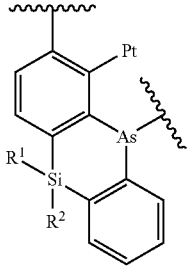
346
-continued
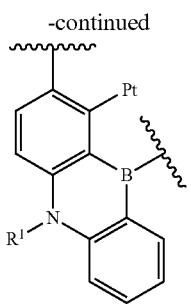
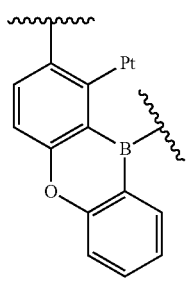
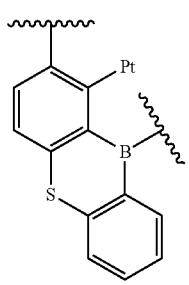
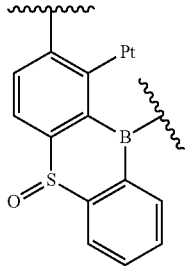
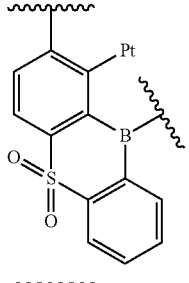
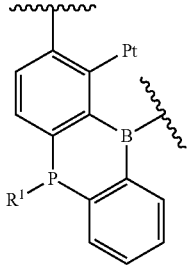

-continued
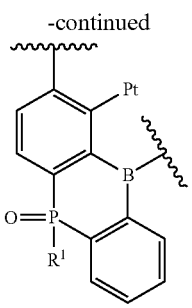
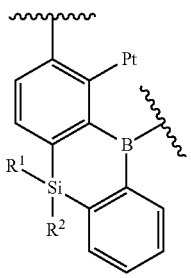
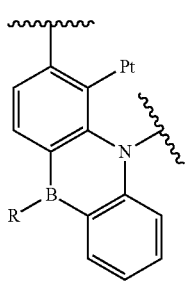
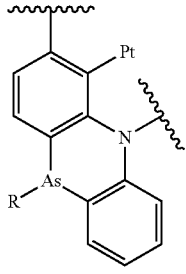
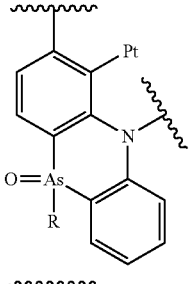
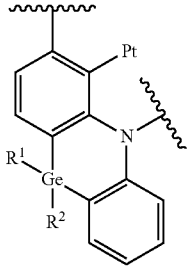
-continued
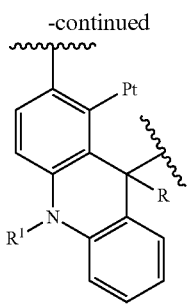
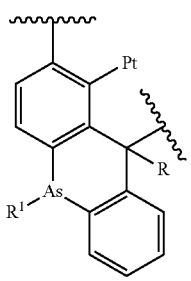
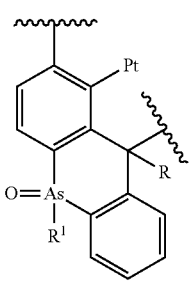
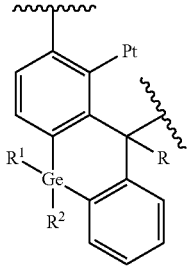
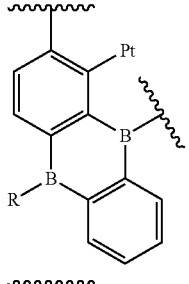
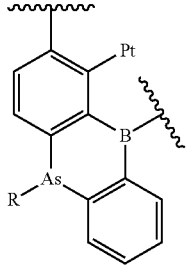

349
-continued
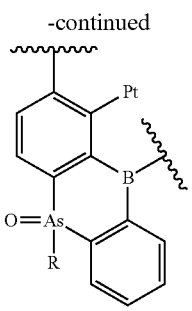
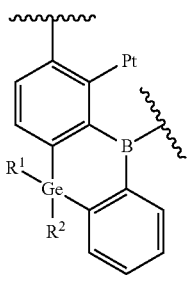
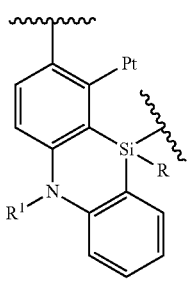
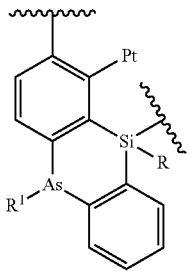
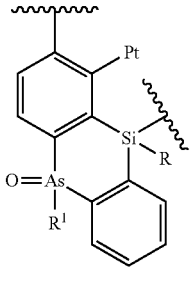
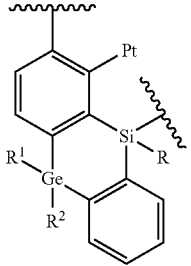
350
-continued
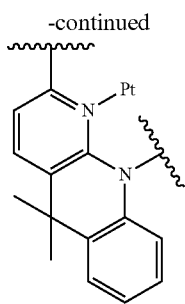
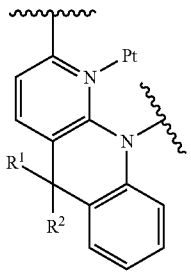
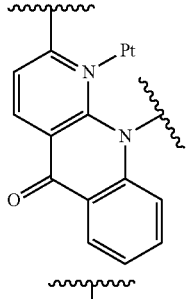
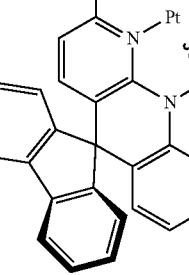
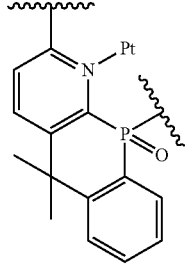
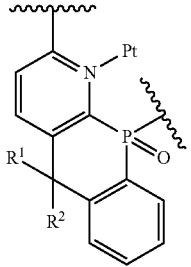

351
-continued
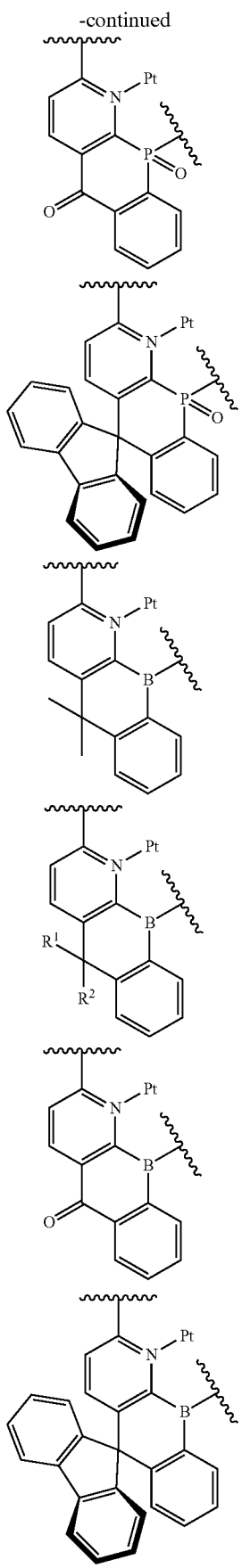
352
-continued
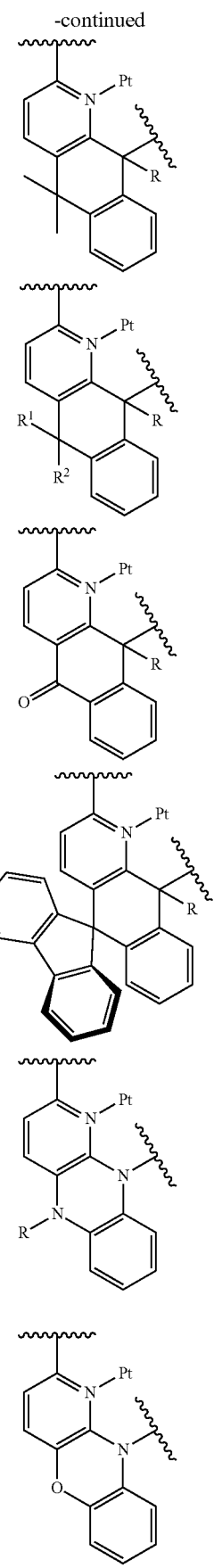

353
-continued
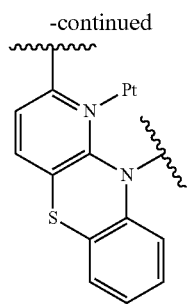
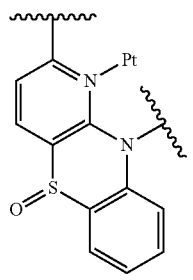
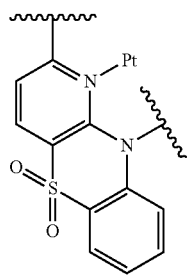
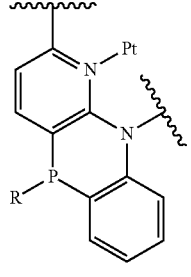
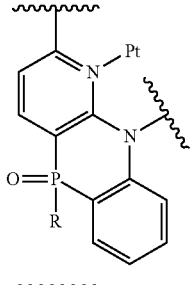
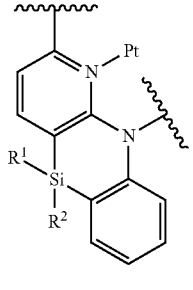
354
-continued
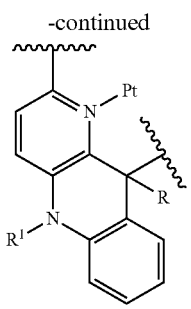
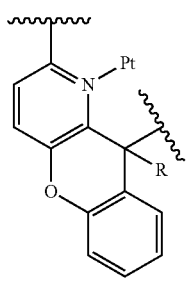
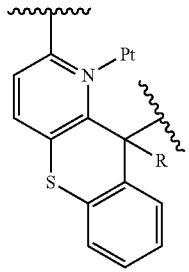
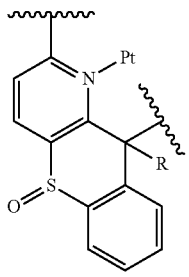
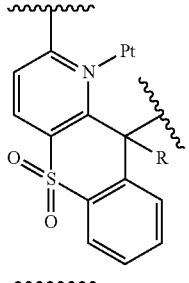
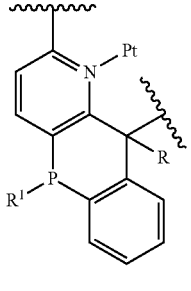

355
-continued
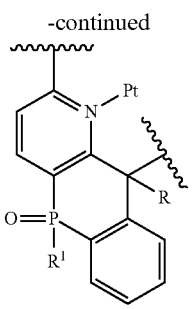
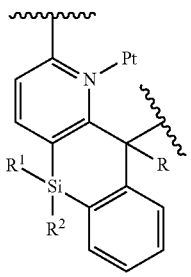
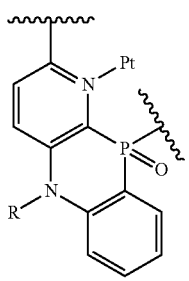
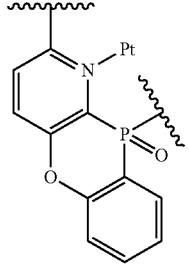
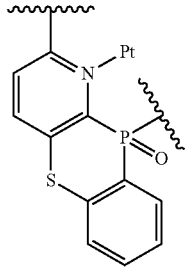
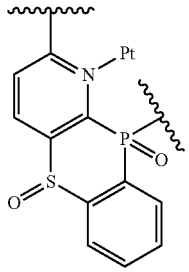
356
-continued
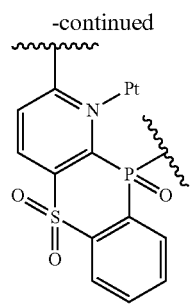
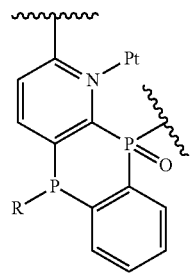
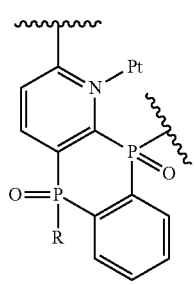
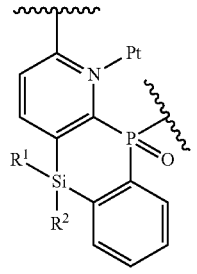
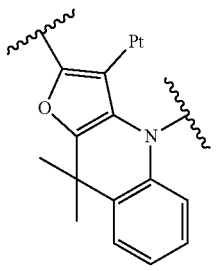
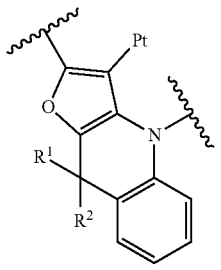

357
-continued
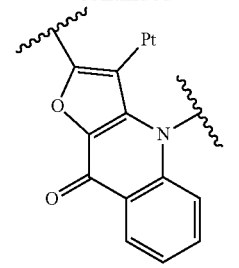
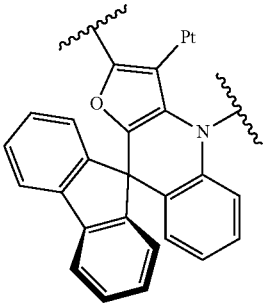
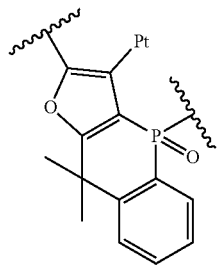
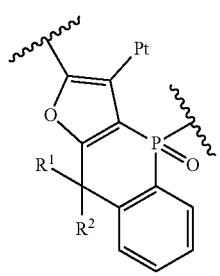
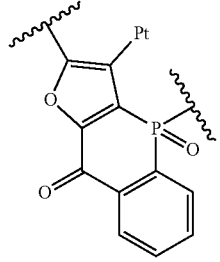
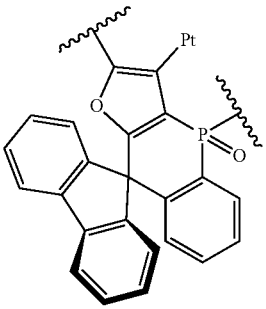
358
-continued
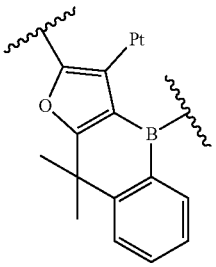
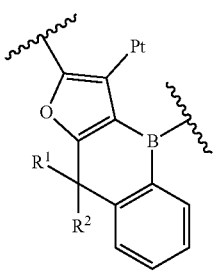
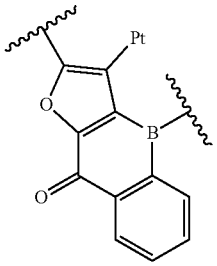
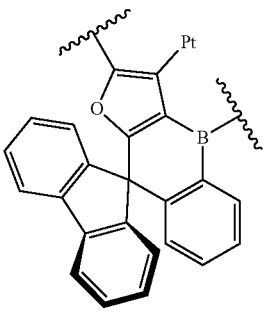
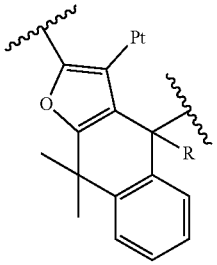
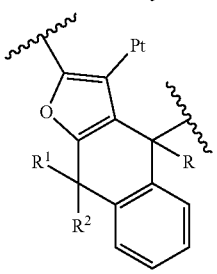

359
-continued
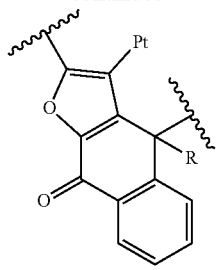
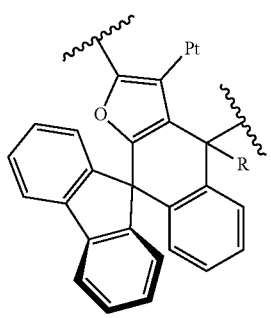
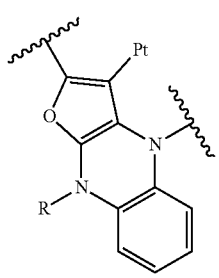
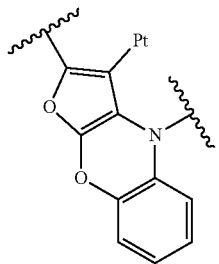
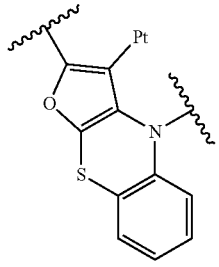
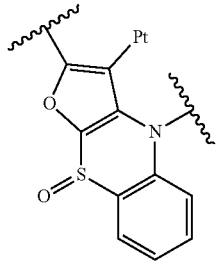
360
-continued
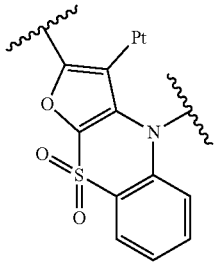
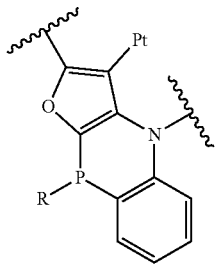
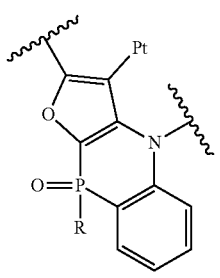
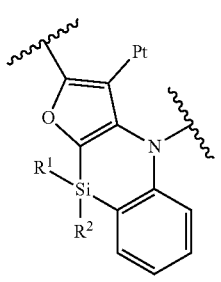
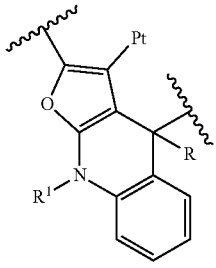
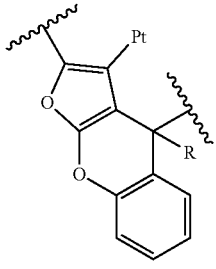

361
-continued
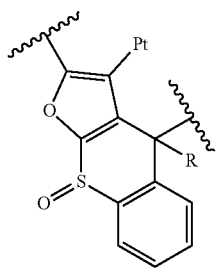
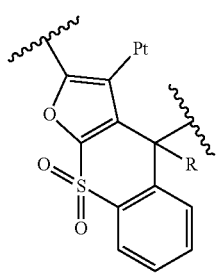
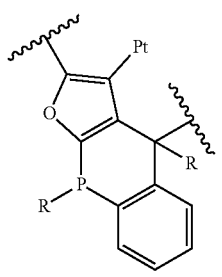
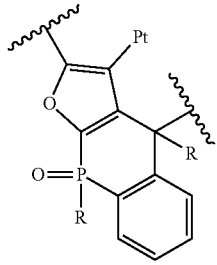
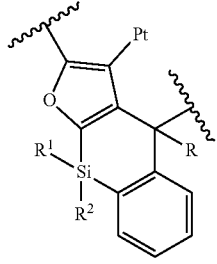
362
-continued
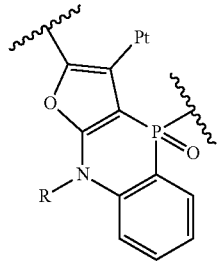
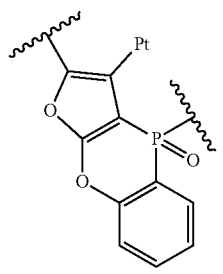
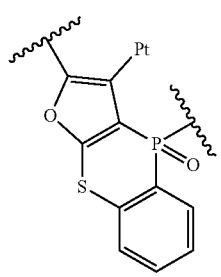
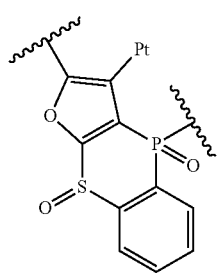
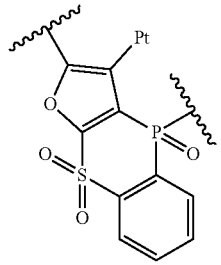
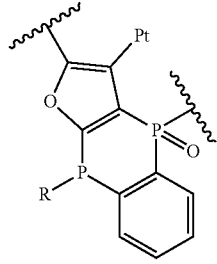

363
-continued

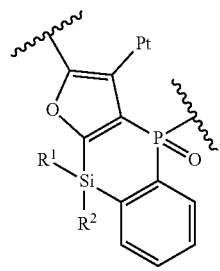
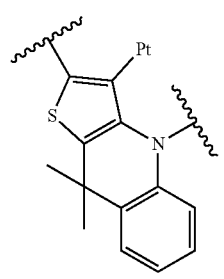
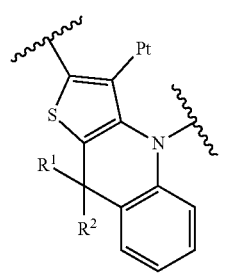
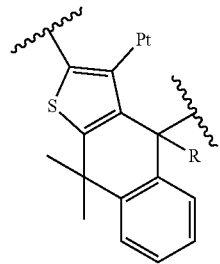
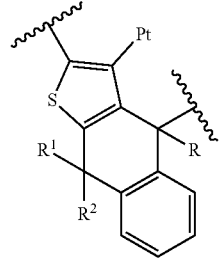
364
-continued
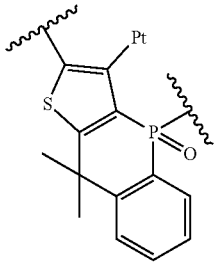
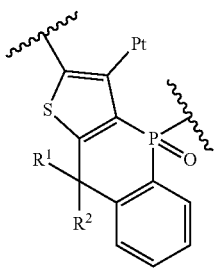
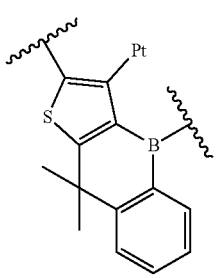
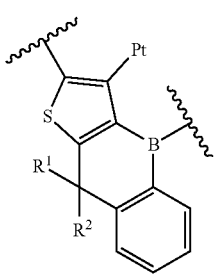
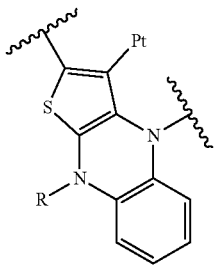
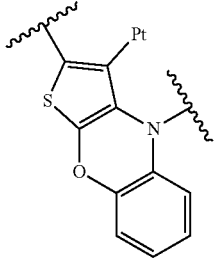

365
-continued

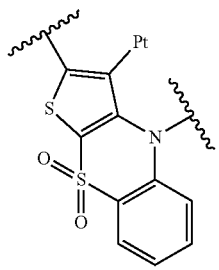
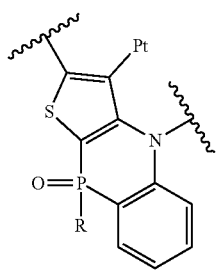
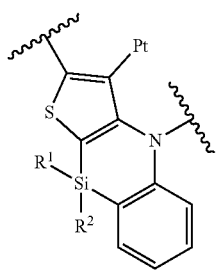
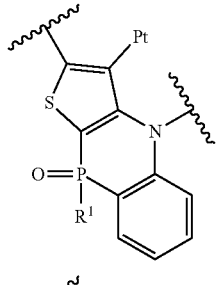
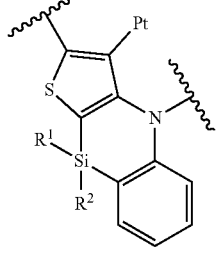
366
-continued
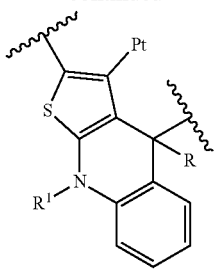
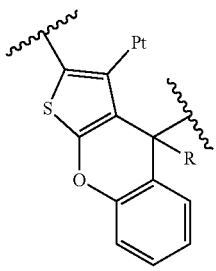
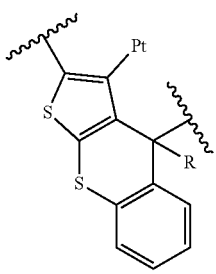
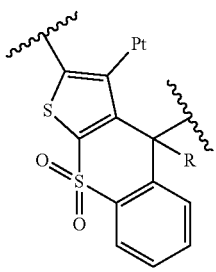
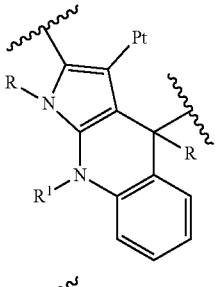
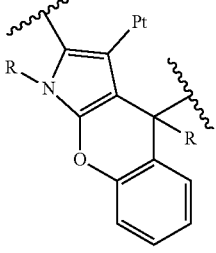

367
-continued
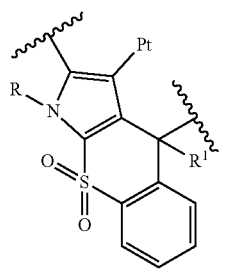
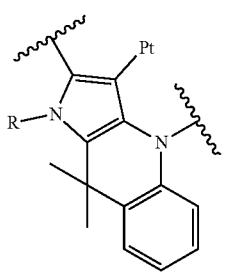
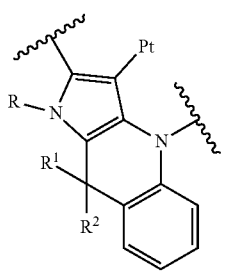
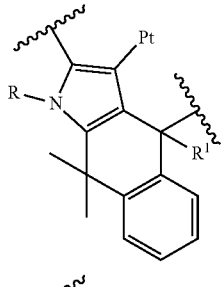
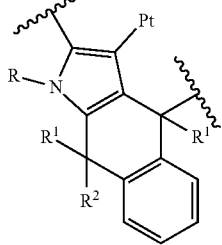
368
-continued

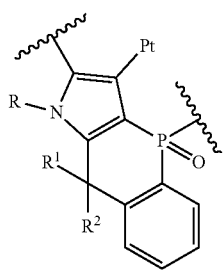
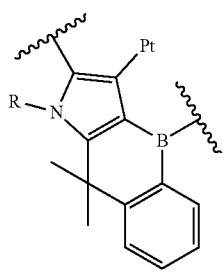
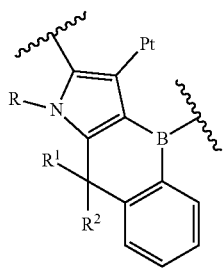
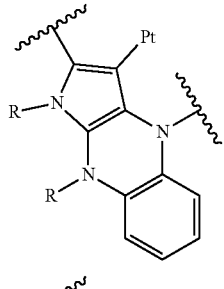
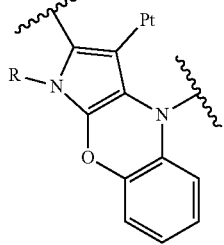

369
-continued
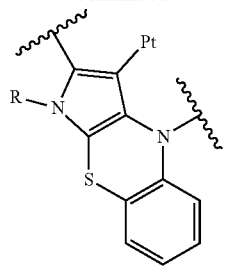
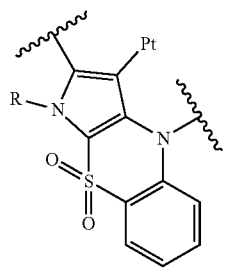
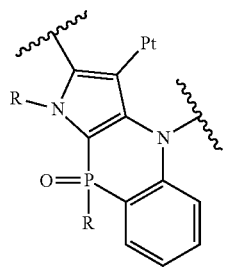
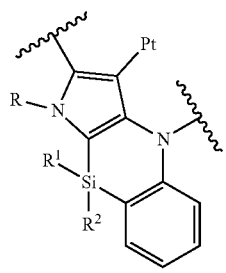
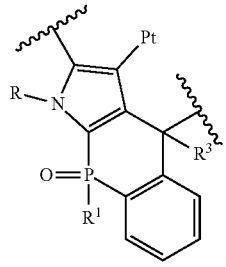
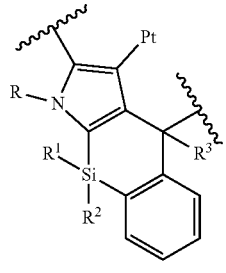
370
-continued
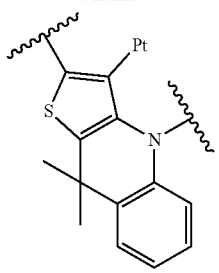
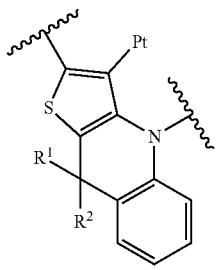
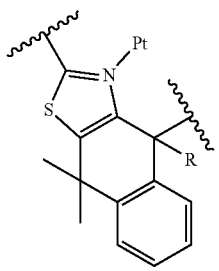
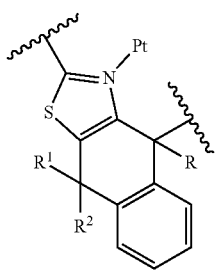
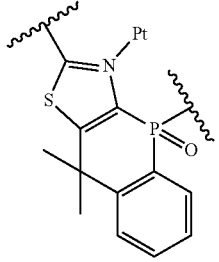
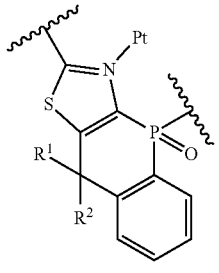

371
-continued
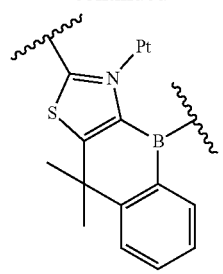
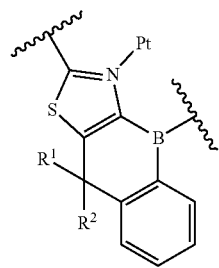
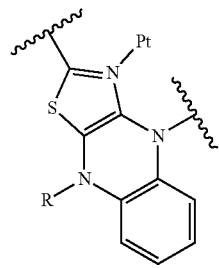
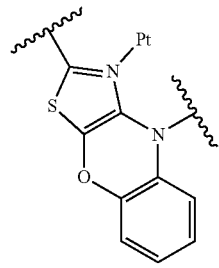
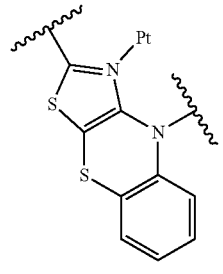
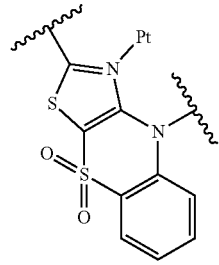
372
-continued
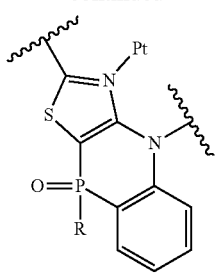
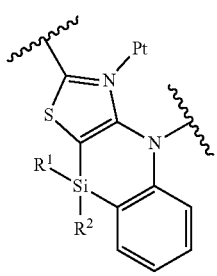
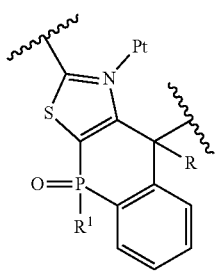
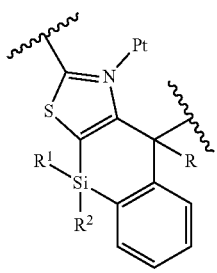
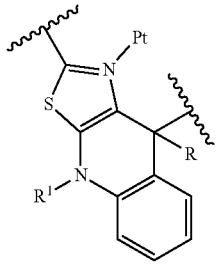
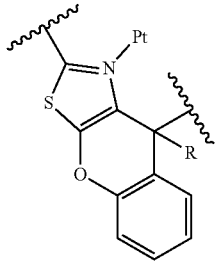

373
-continued
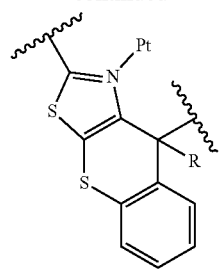
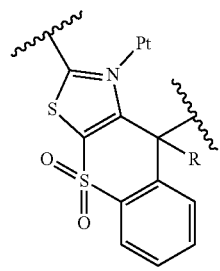
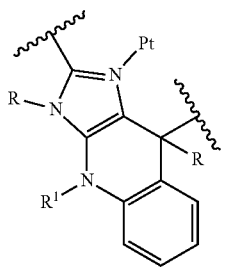
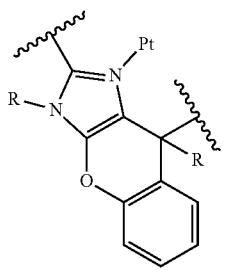
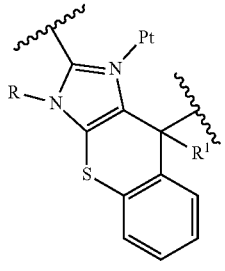
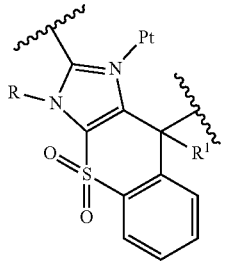
374
-continued
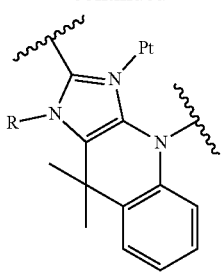
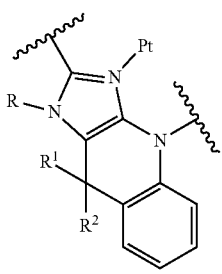
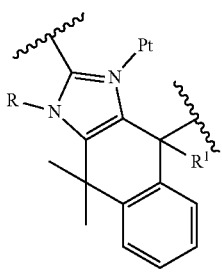
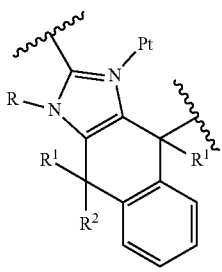
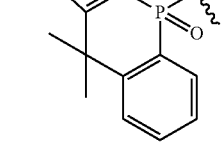
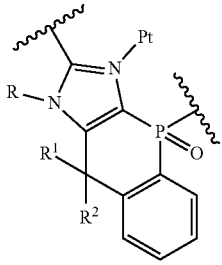

375
-continued
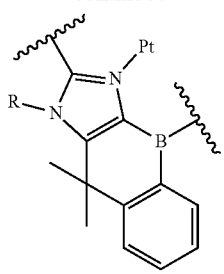
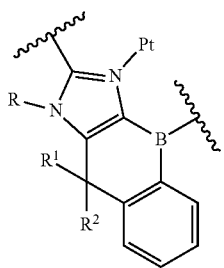
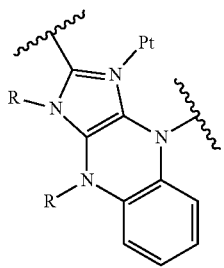
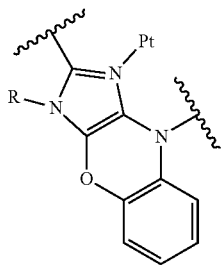
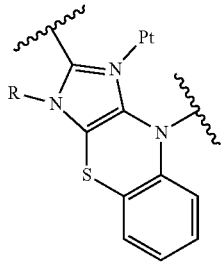
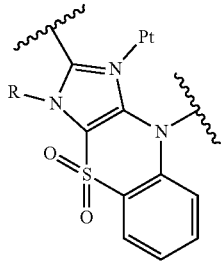
376
-continued
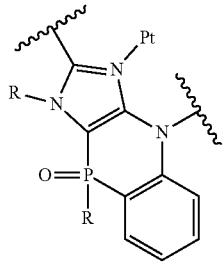
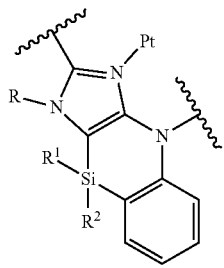
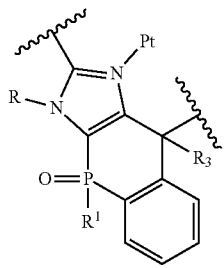
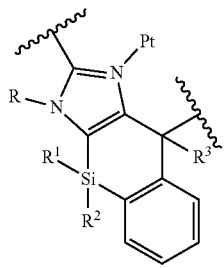
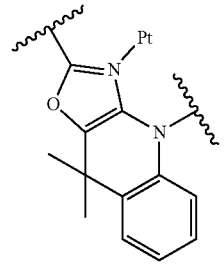
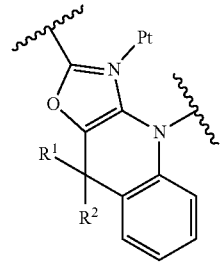

377
-continued
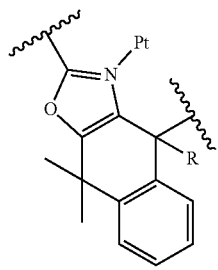
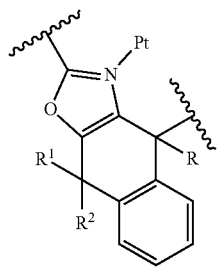
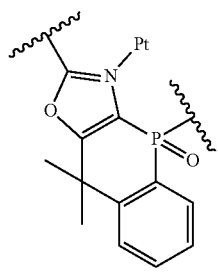
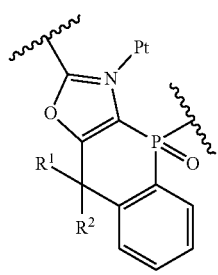
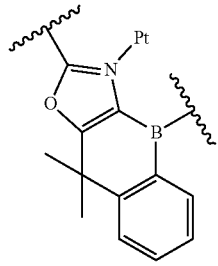
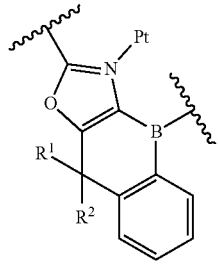
378
-continued
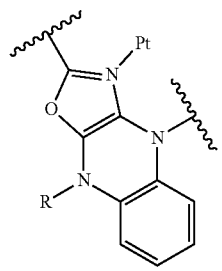
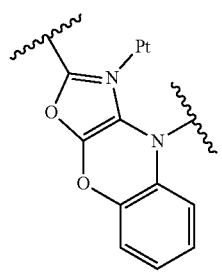
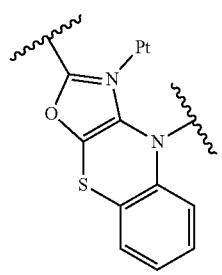
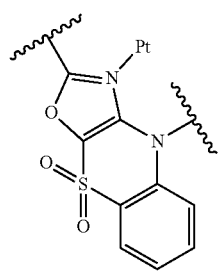
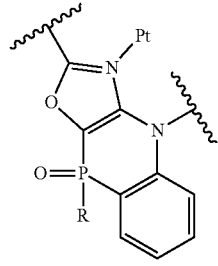
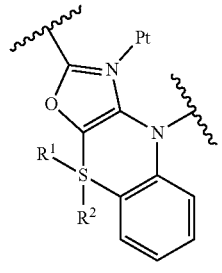

-continued
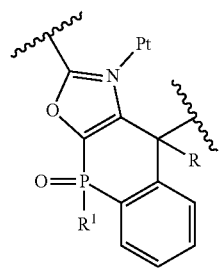
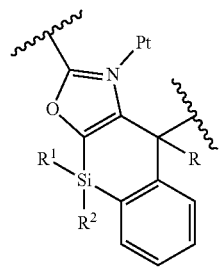
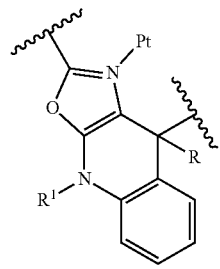
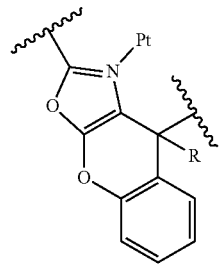
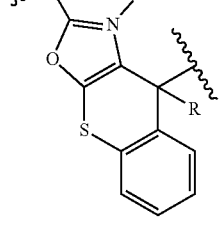
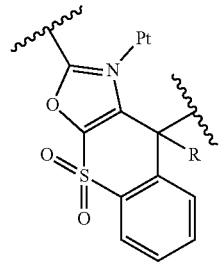
-continued
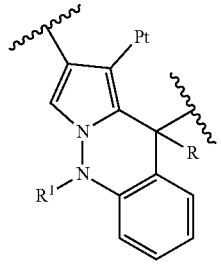
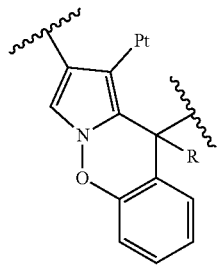
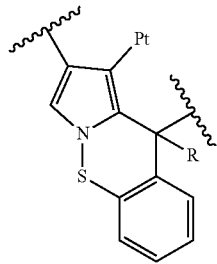
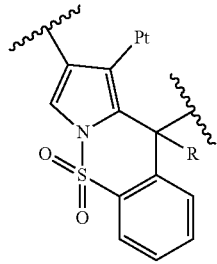
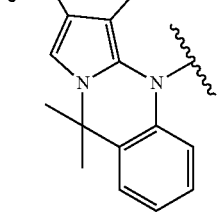
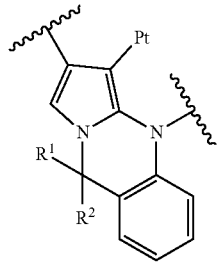

381
-continued
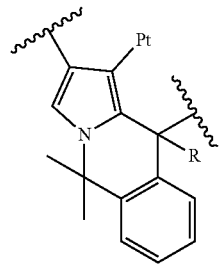
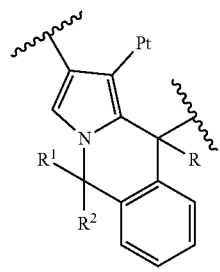
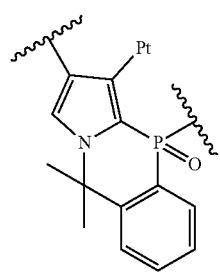
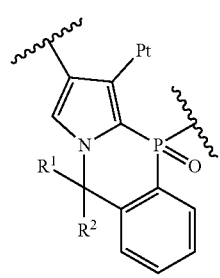
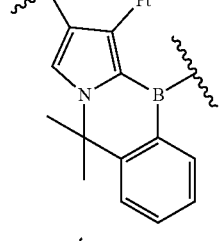
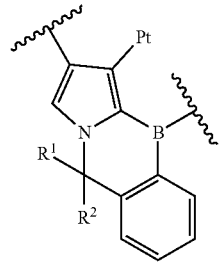
382
-continued
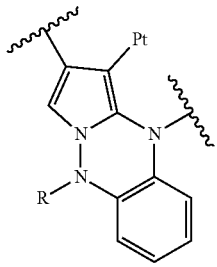
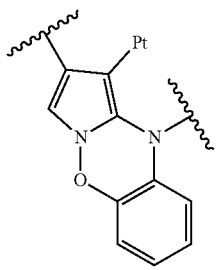
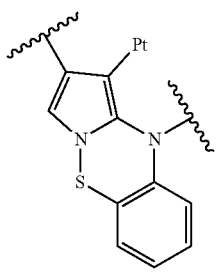
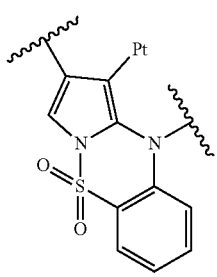
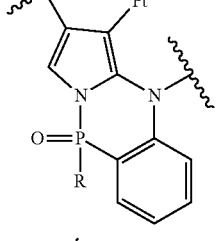
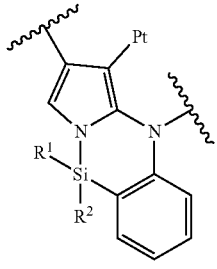

383
-continued
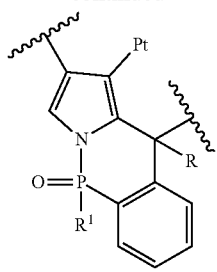
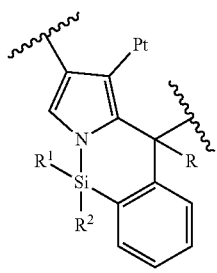
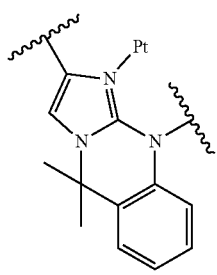
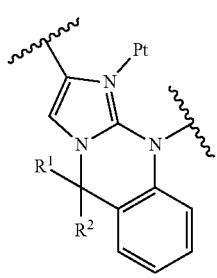
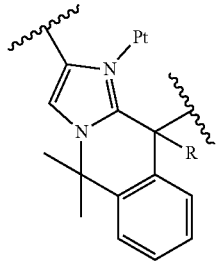
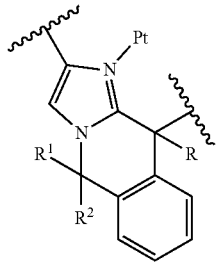
384
-continued
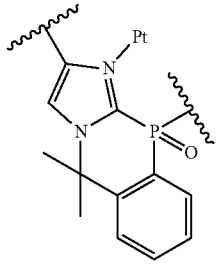
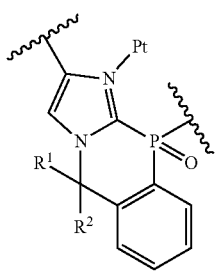
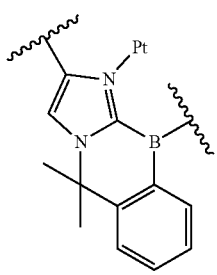
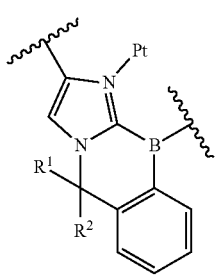
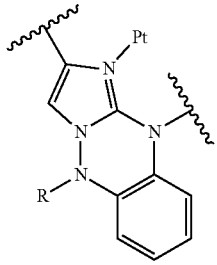
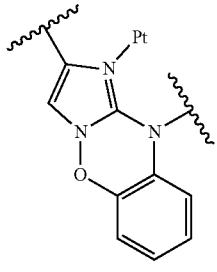

-continued

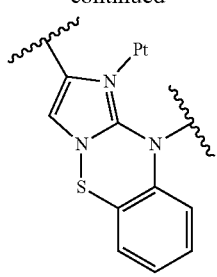
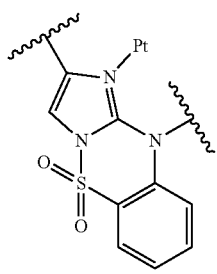
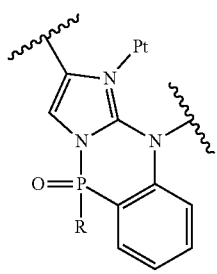
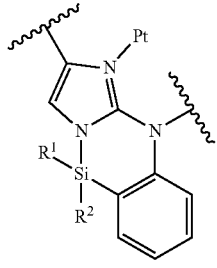
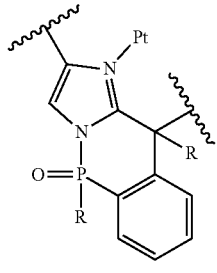
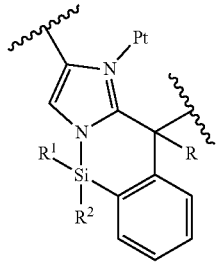

-continued

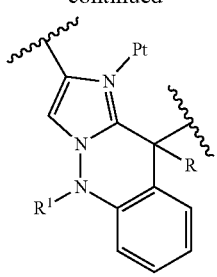
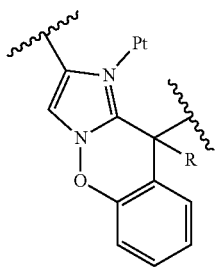
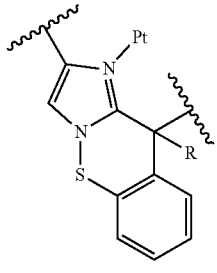
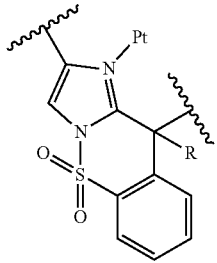

wherein each of R, $R^1$, and $^2$ is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

7. The compound of claim 1, wherein each of

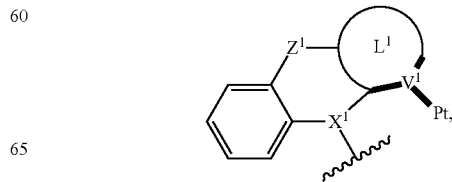

-continued
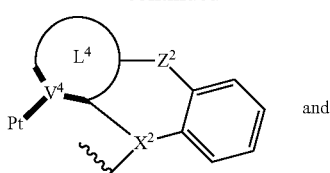
and
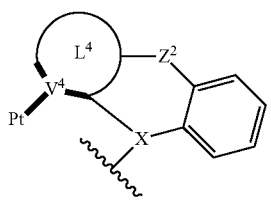
is independently one of the following structures:
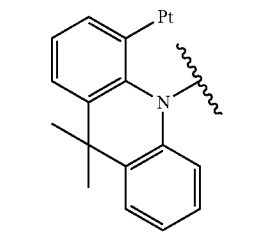
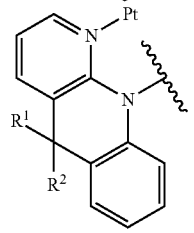
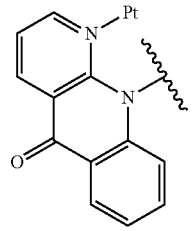
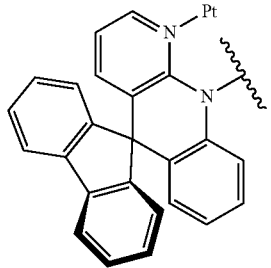
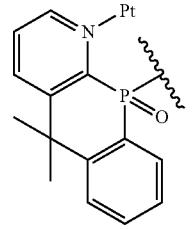
-continued
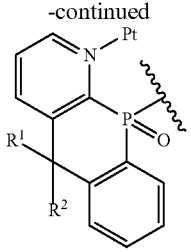
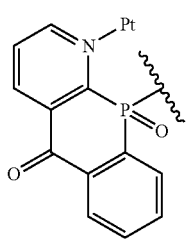
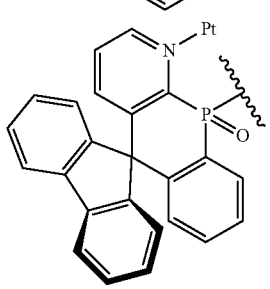
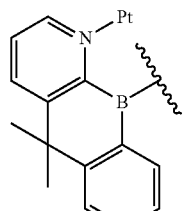
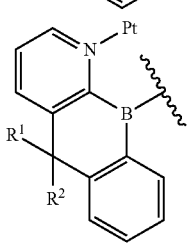
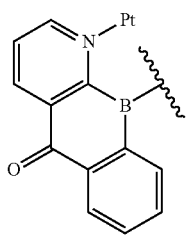
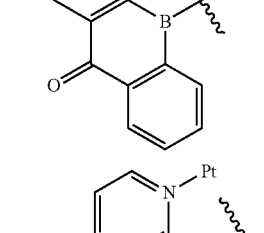
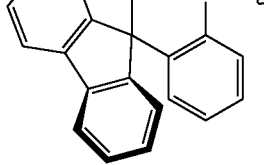

389
-continued
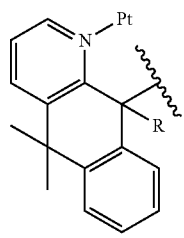
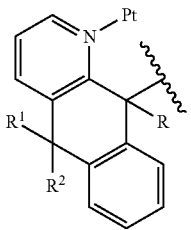
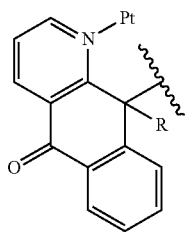
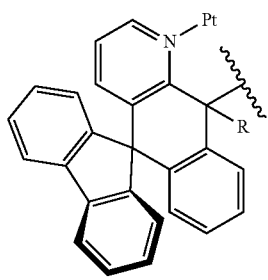
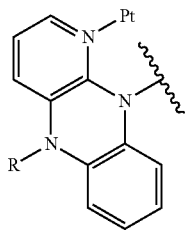
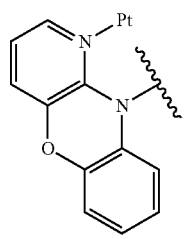
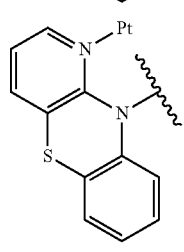
390
-continued
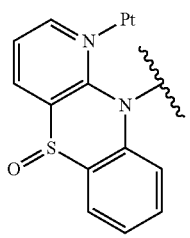
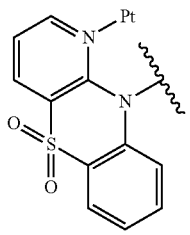
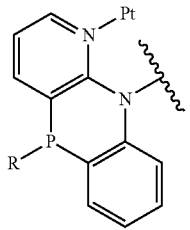
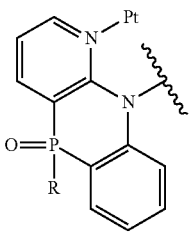
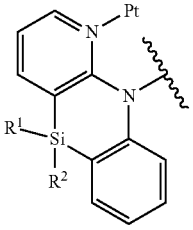
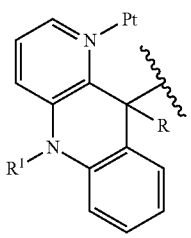
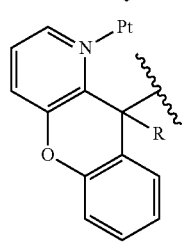

391
-continued
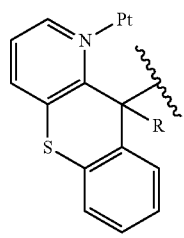
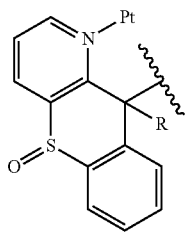
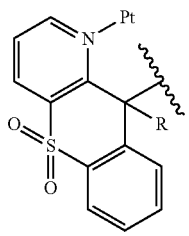
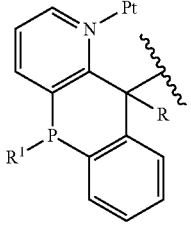
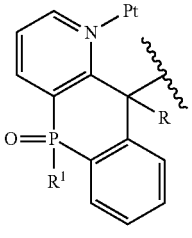
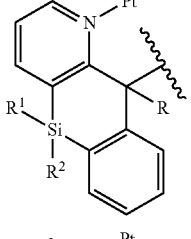
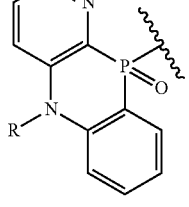
392
-continued
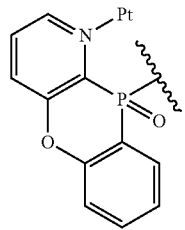
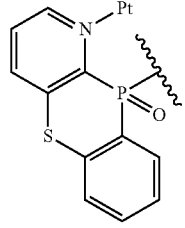
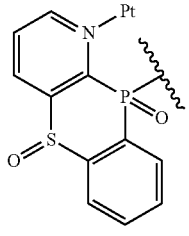
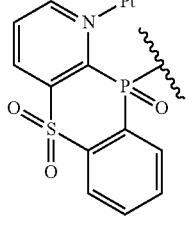
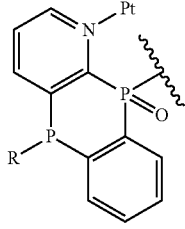
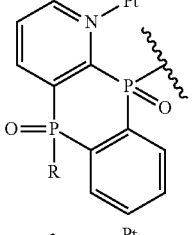
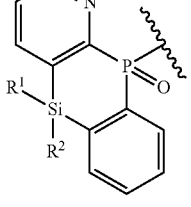

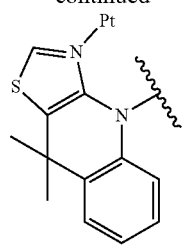
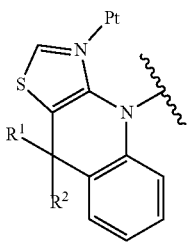
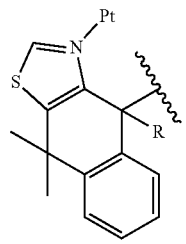
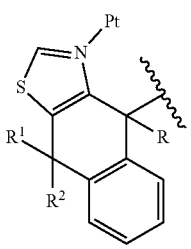
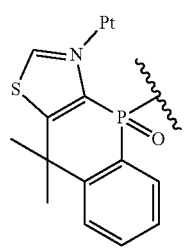
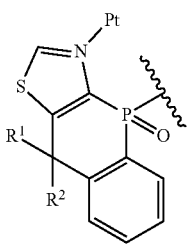
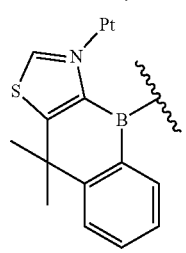
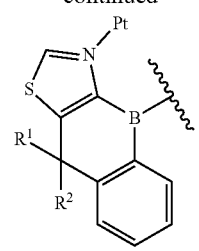
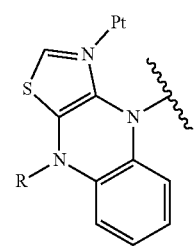
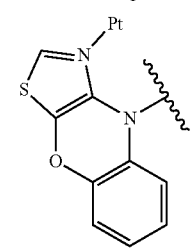
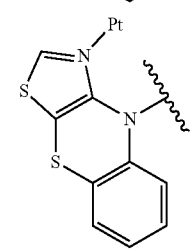
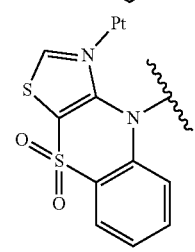
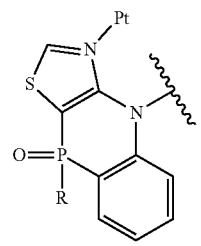
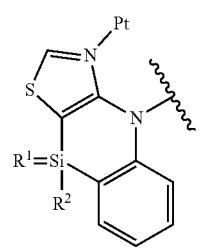

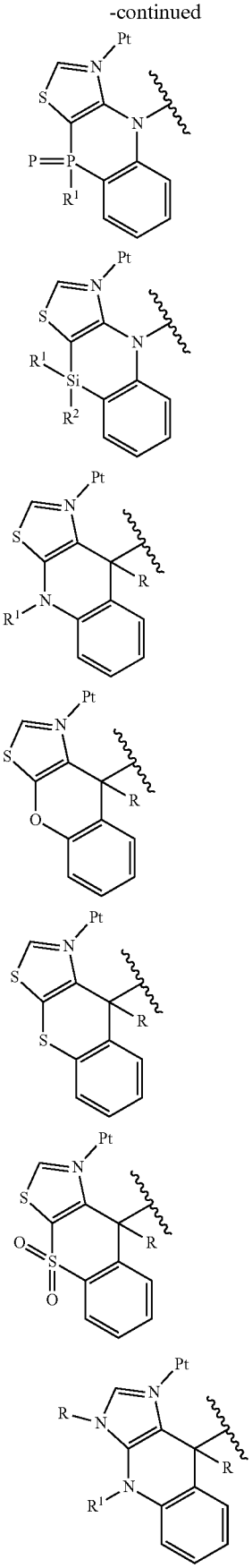
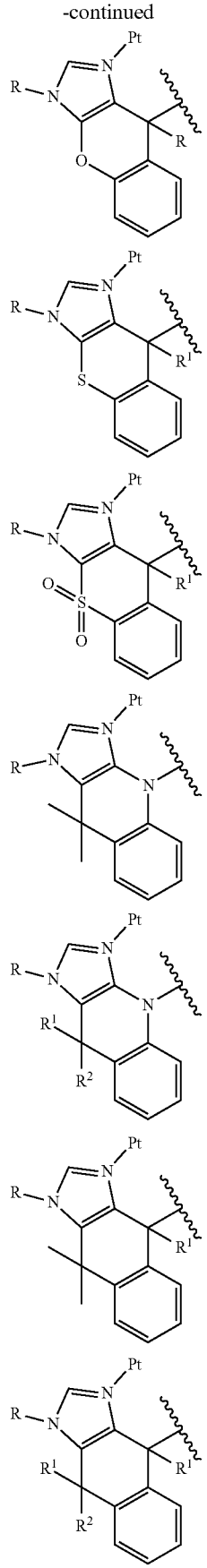

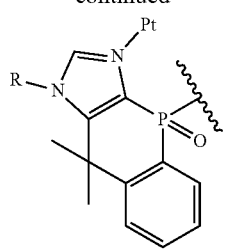
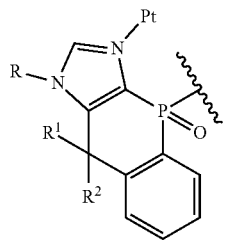
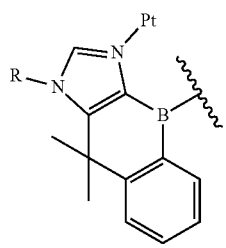
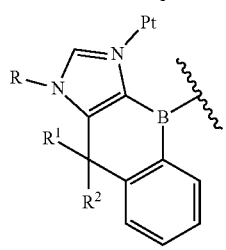
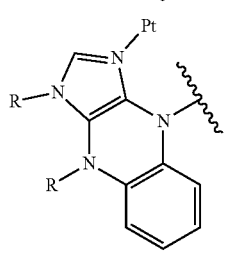
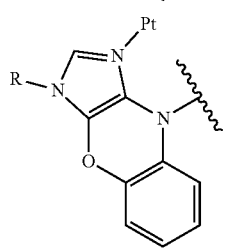
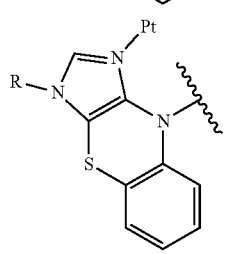
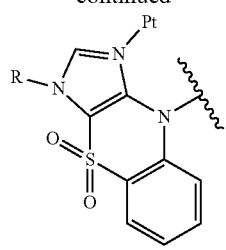
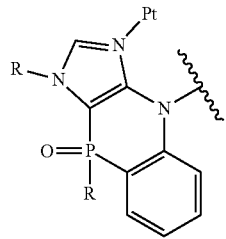
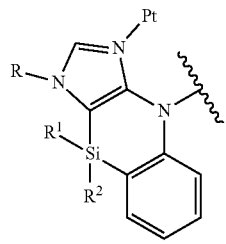
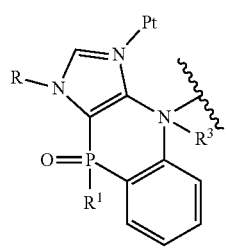
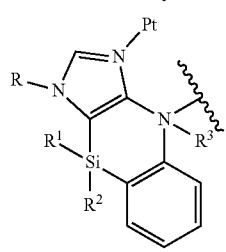
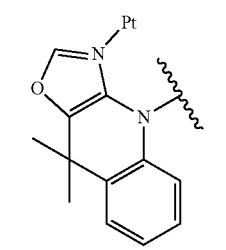
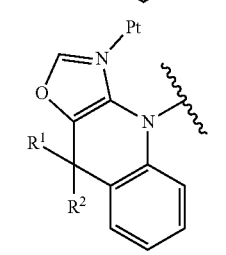

399
-continued
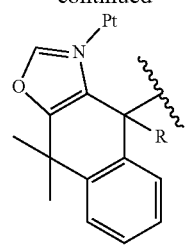
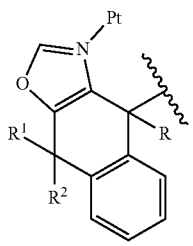
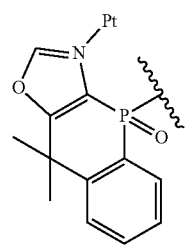
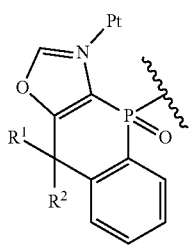
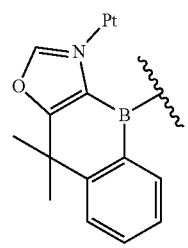
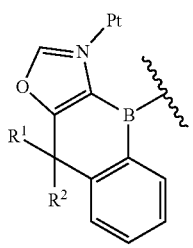
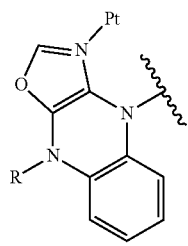
400
-continued
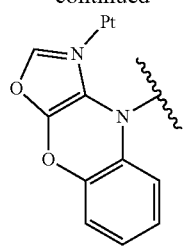
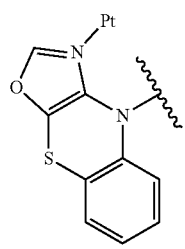
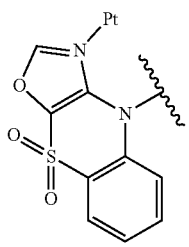
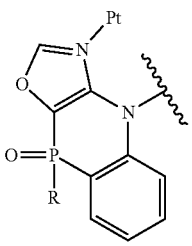
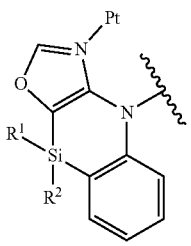
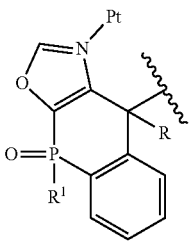
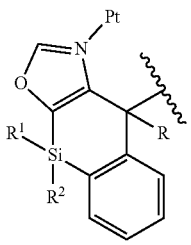

401
-continued
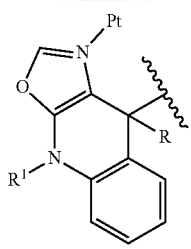
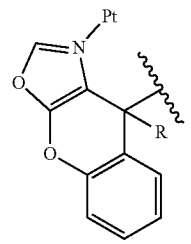
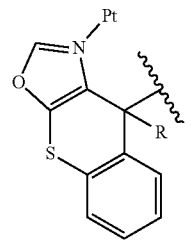
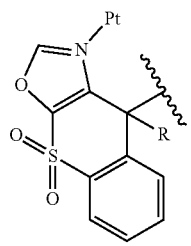
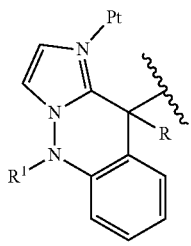
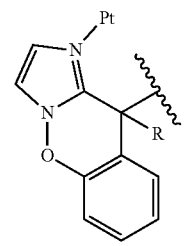
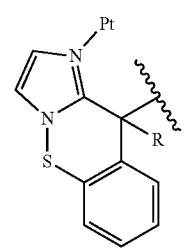
402
-continued
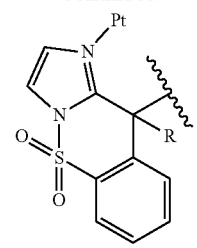
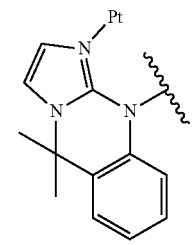
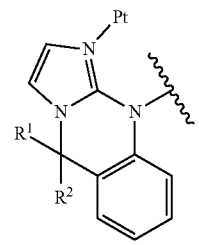
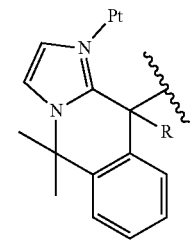
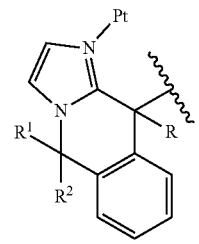
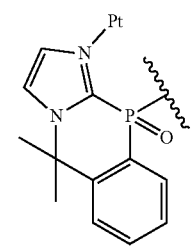
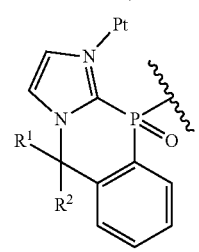

403

-continued

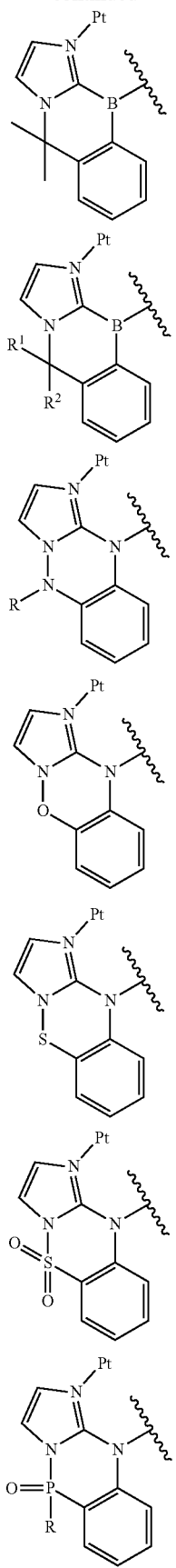

404

-continued

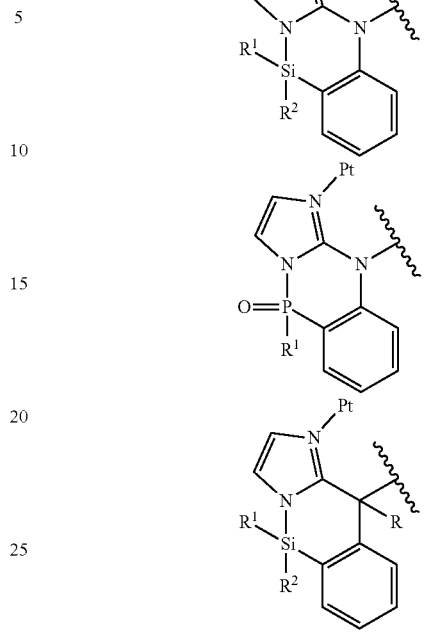

wherein R, R[1], and R[2] is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

8. The compound of claim 1, wherein polymeric comprises polyalkylene, polyester, or polyether.

9. The compound of claim 8, wherein polymeric comprises —$(CH_2O)_n$—$CH_3$, —$(CH_2CH_2O)_n$—$CH_3$, —$[CH_2CH(CH_3)]_n$—$CH_3$, —$[CH_2CH(COOCH_3)]_n$—$CH_3$, —$[CH_2CH(COOCH_2CH_3)]_n$—$CH_3$, or —$[CH_2CH(COO^tBu)]_n$—$CH_3$, where n is an integer.

10. An emitter comprising any one of the structures of Structures 1-10, Structures 16-23, Structures 25-38, and Structures 41-44 below:

Structures 1

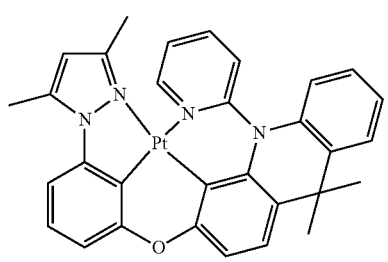

405
-continued
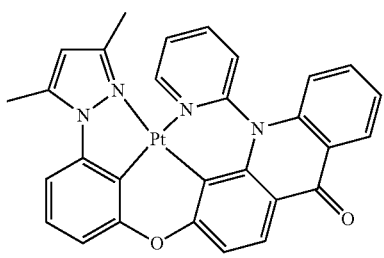
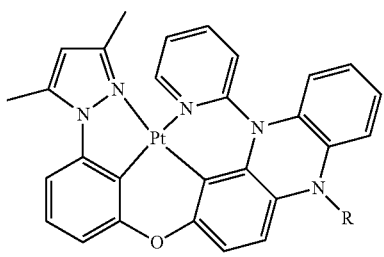
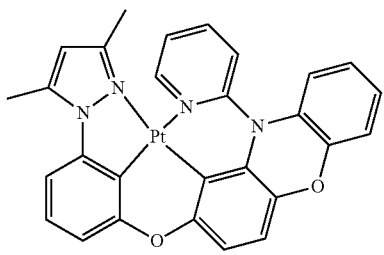
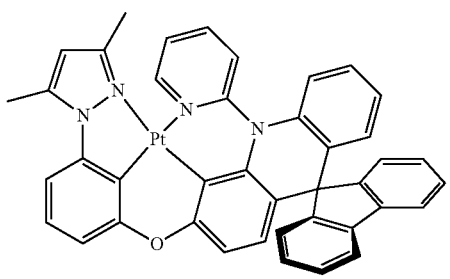
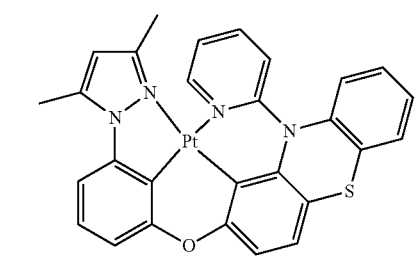
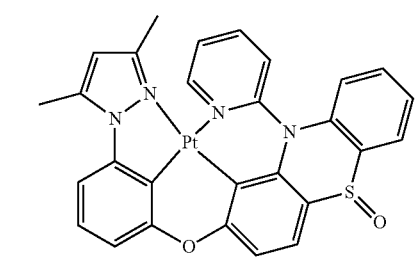
406
-continued
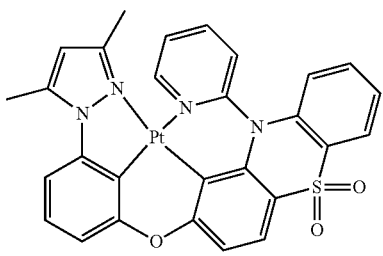
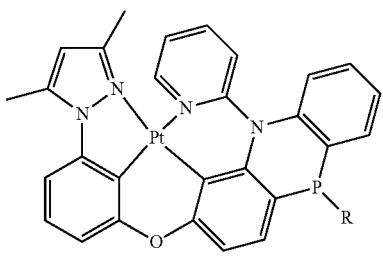
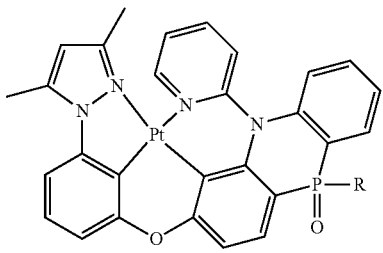
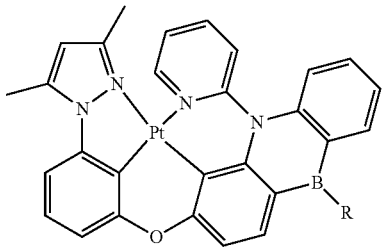
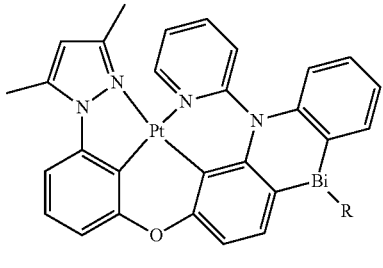
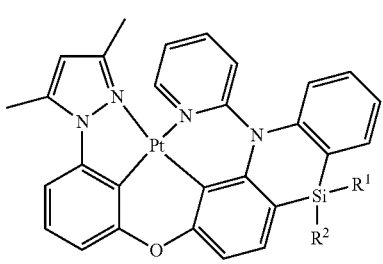

407
-continued
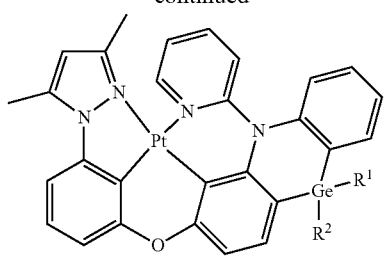
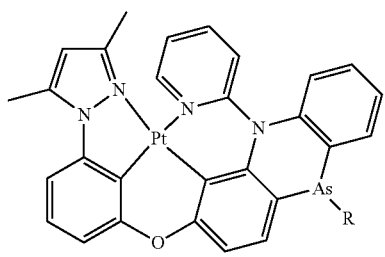
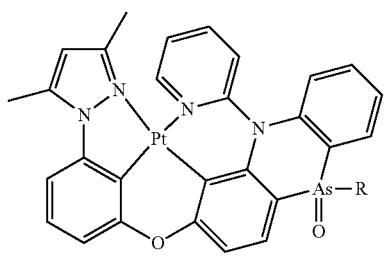
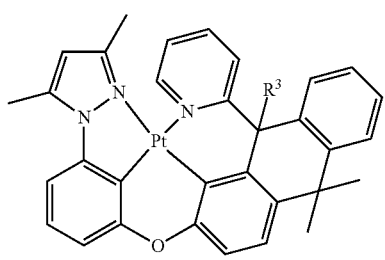
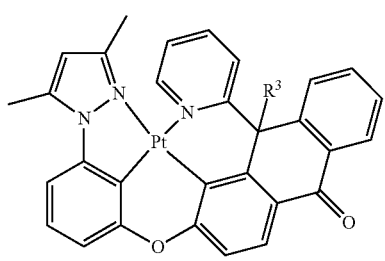
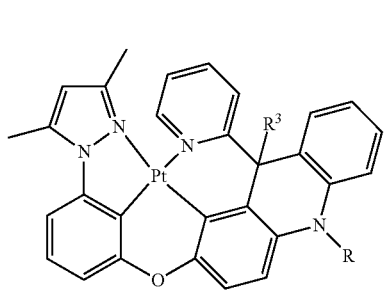
408
-continued
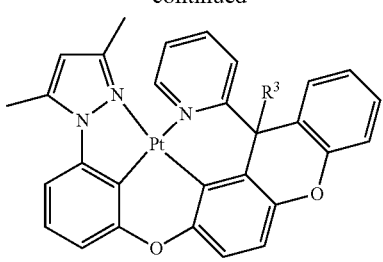
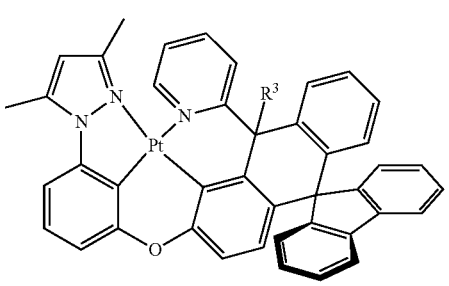
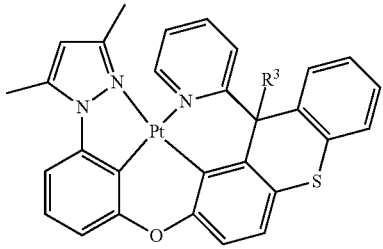
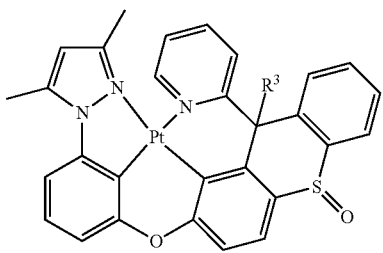
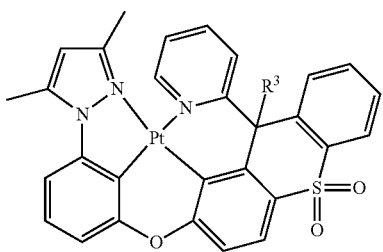
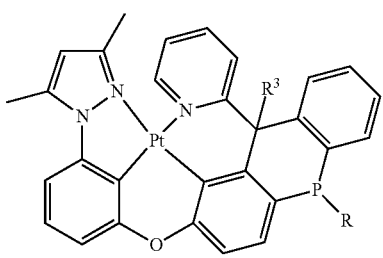

409
-continued
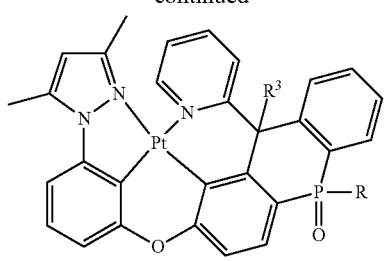
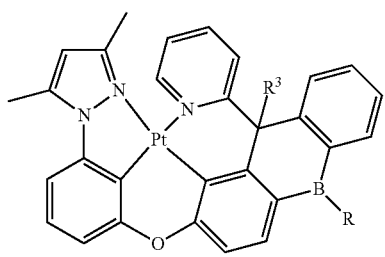
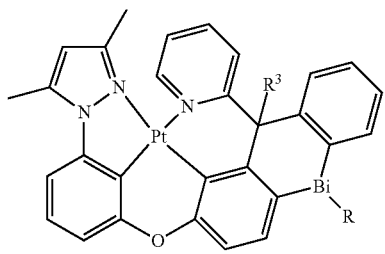
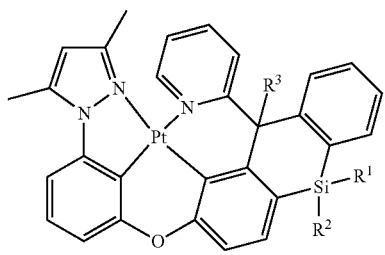
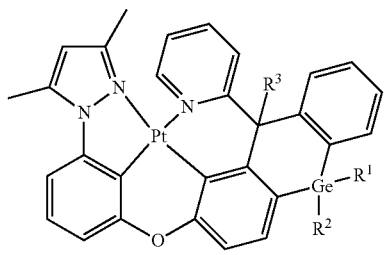
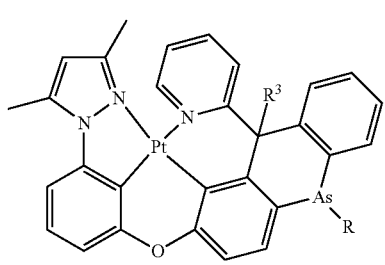
410
-continued
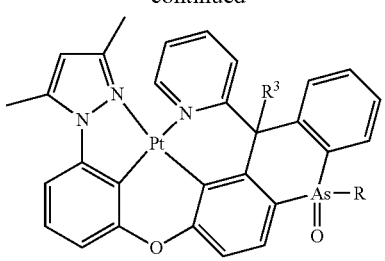
Structures 2
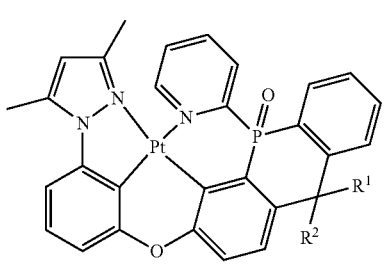
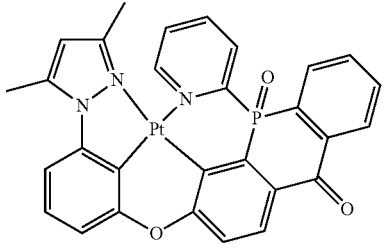
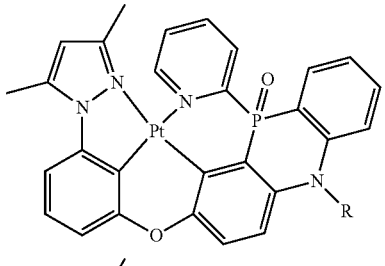
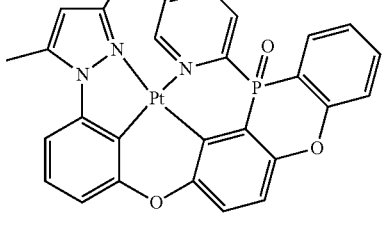
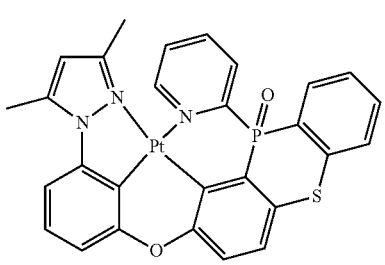

411
-continued
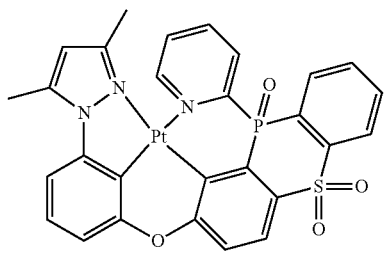
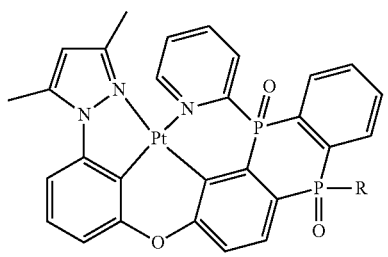
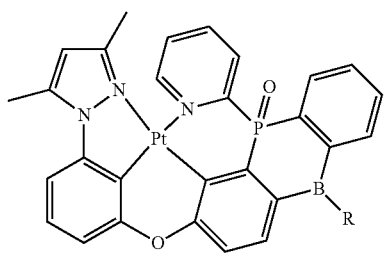
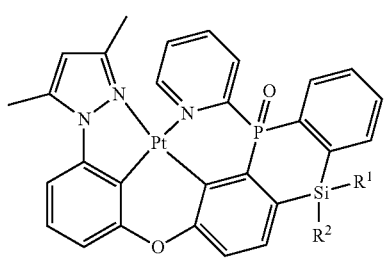
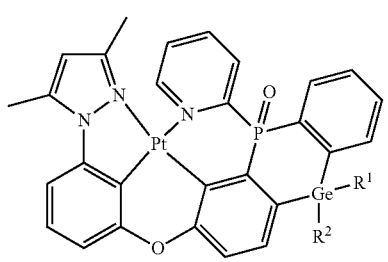
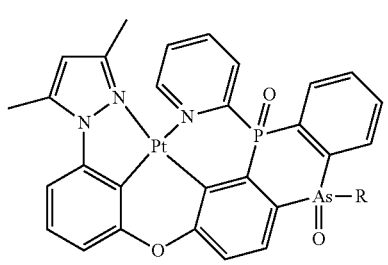
412
-continued
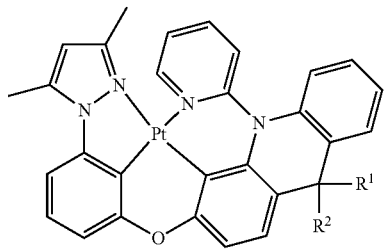
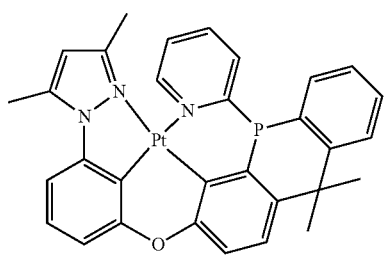
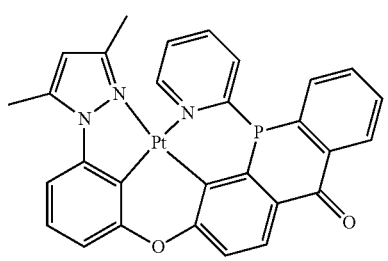
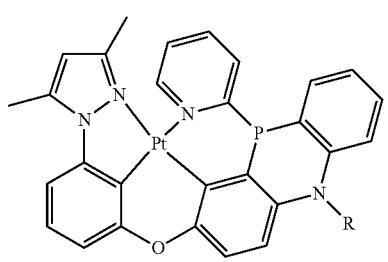
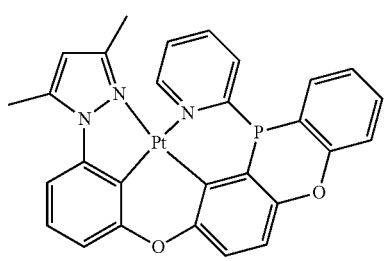
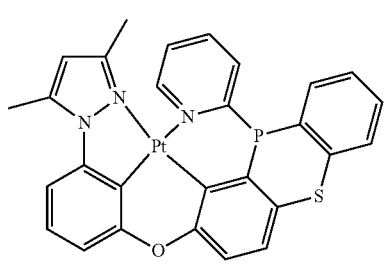

413
-continued
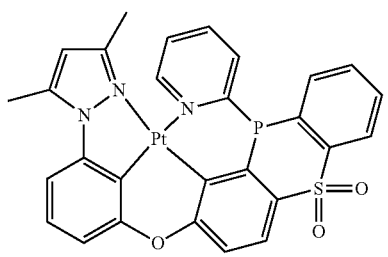
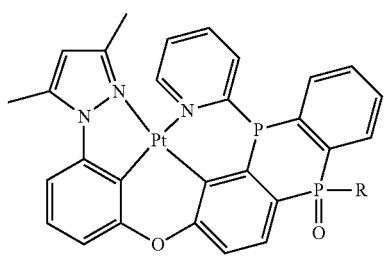
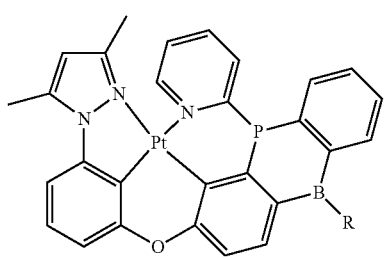
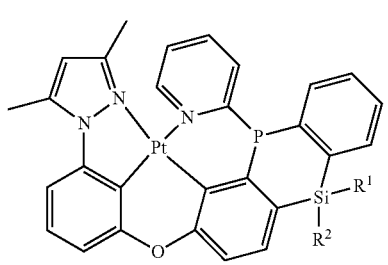
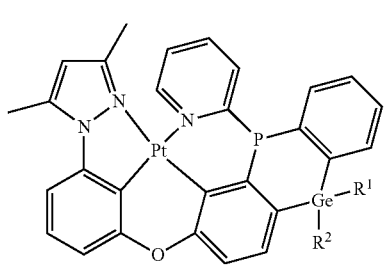
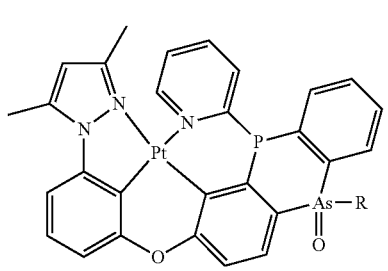
414
-continued
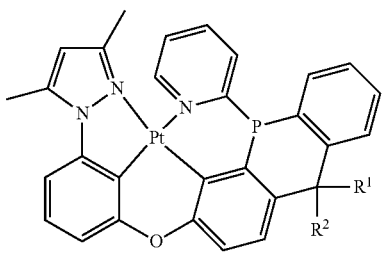
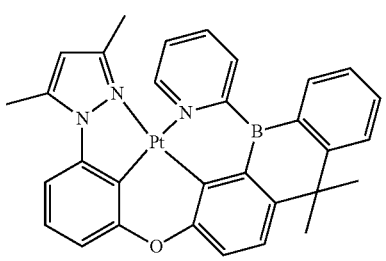
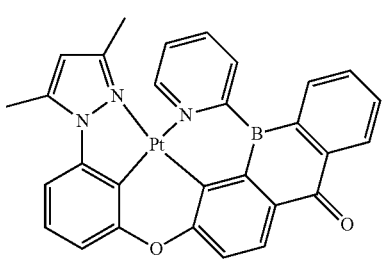
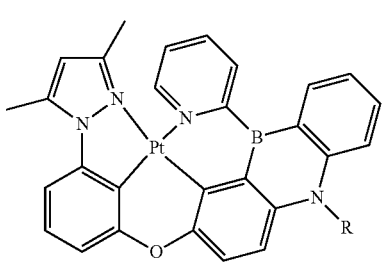
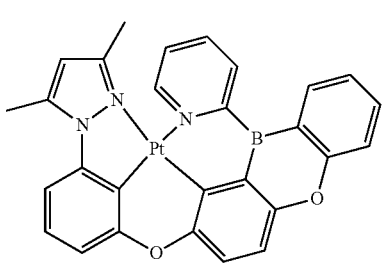
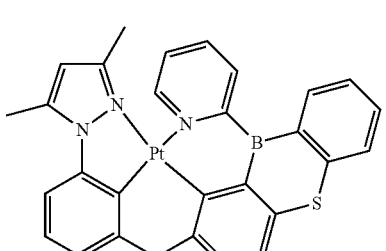

415
-continued
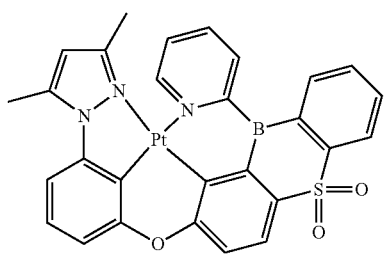
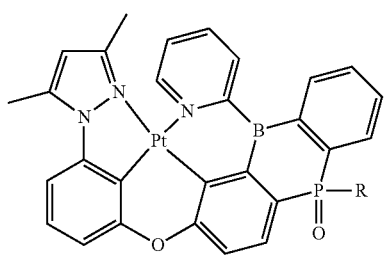
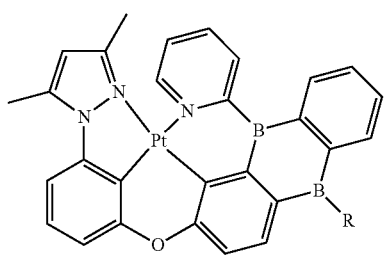
Structures 3
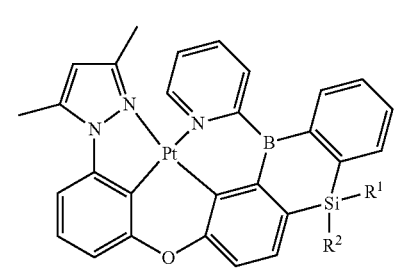
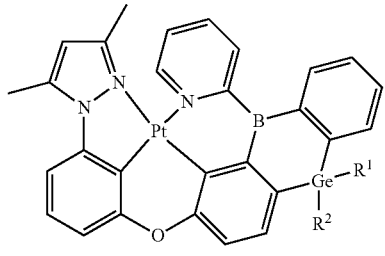
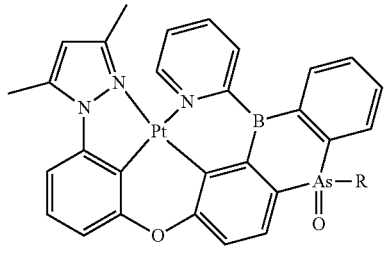
416
-continued
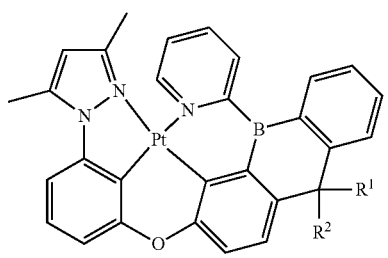
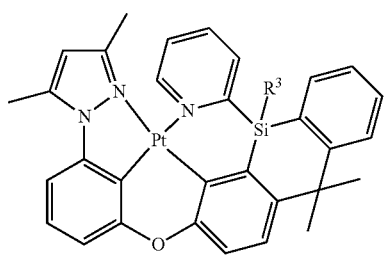
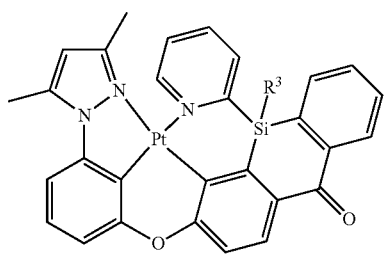
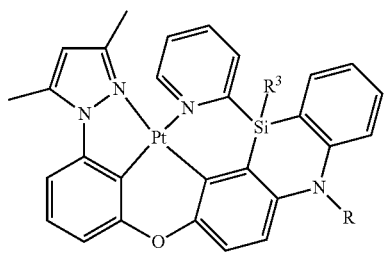
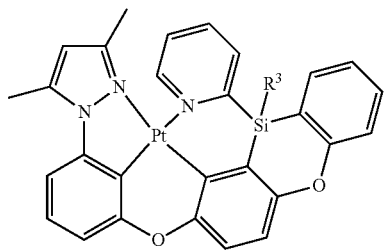
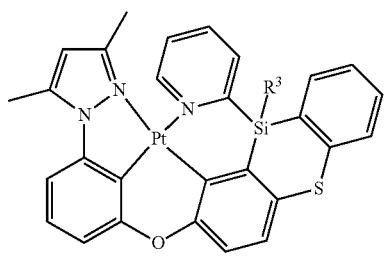

417
-continued
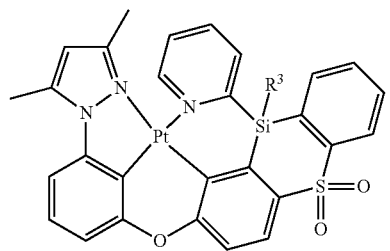
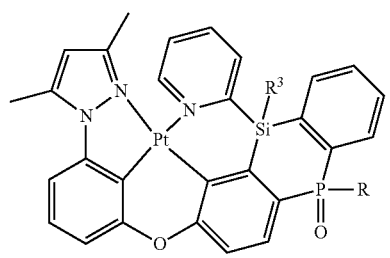
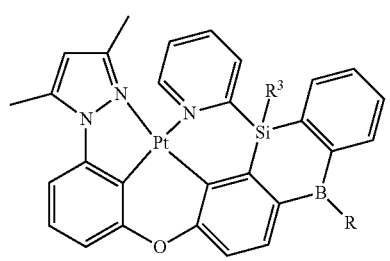
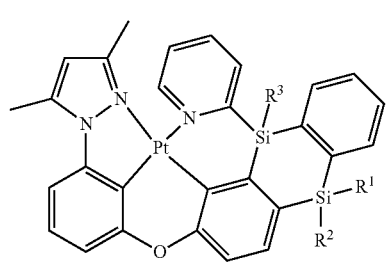
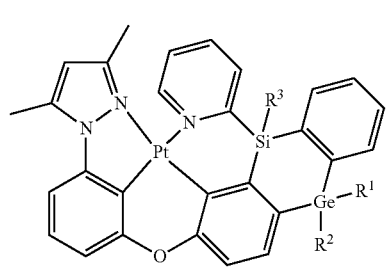
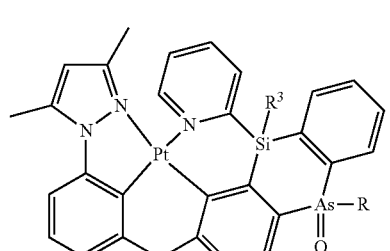
418
-continued
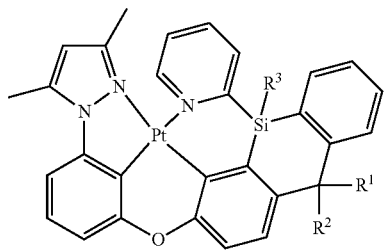
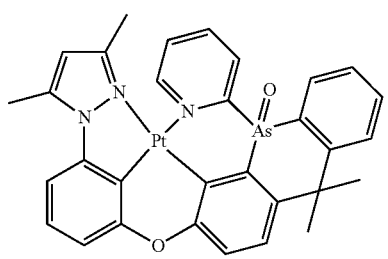
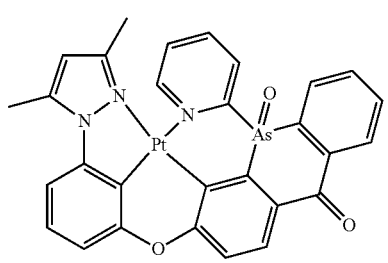
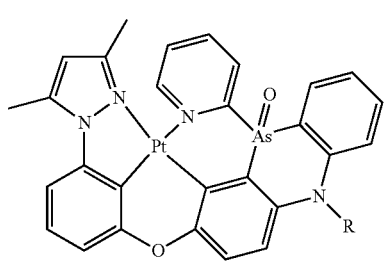
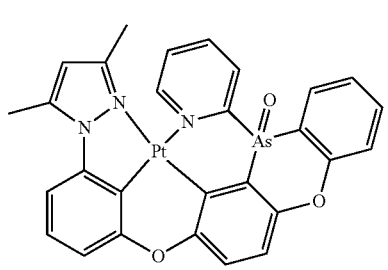
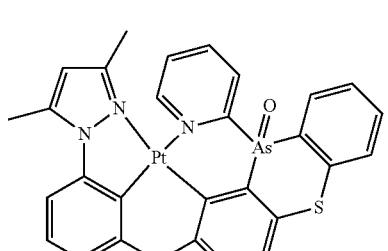

419
-continued
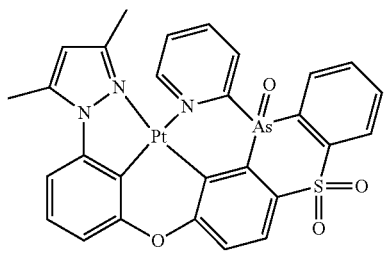
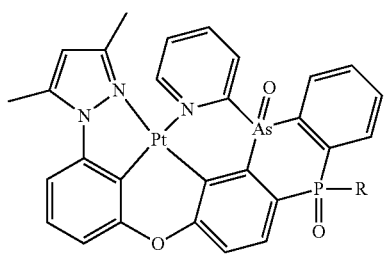
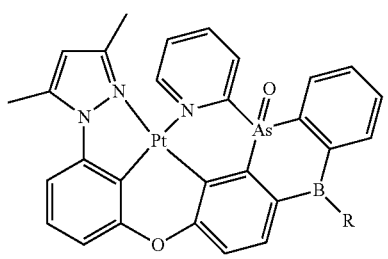
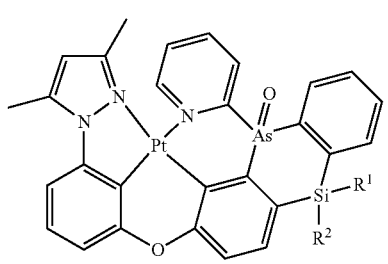
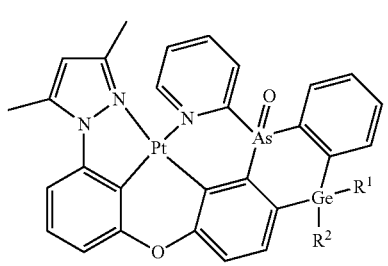
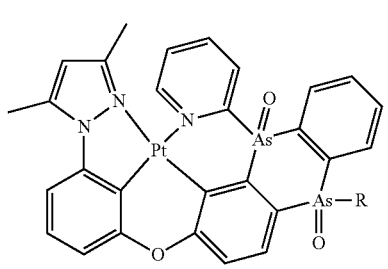
420
-continued
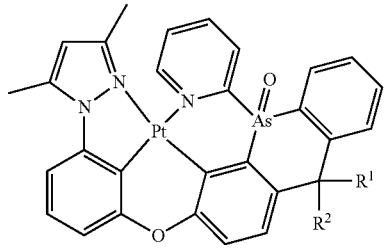
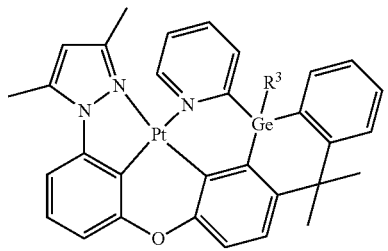
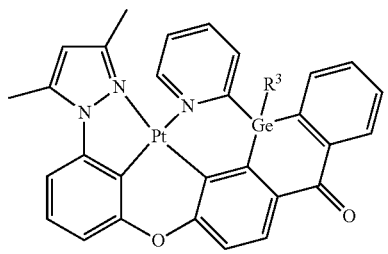
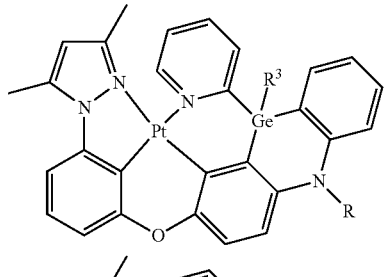
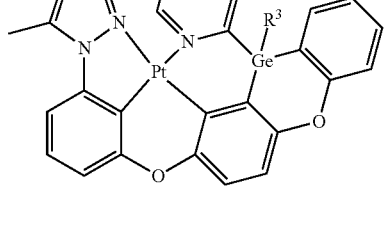
Structures 4
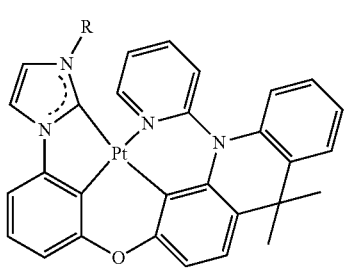

421
-continued
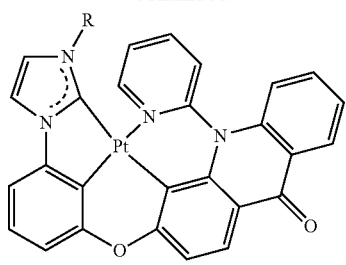
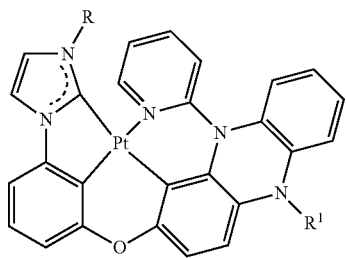
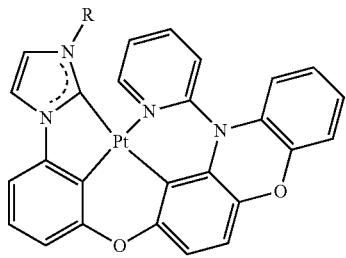
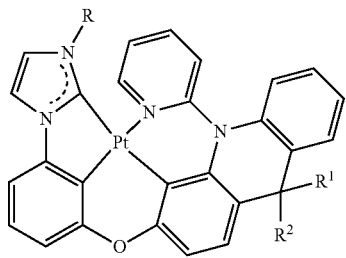
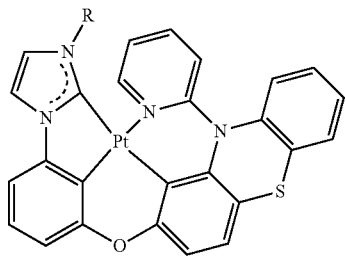
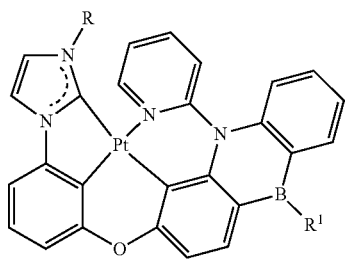
422
-continued
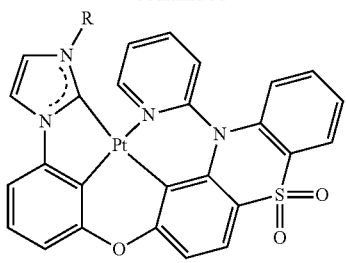
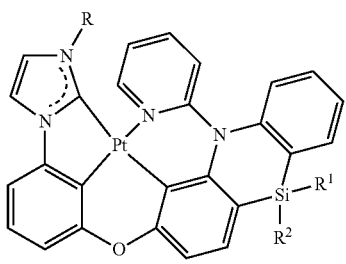
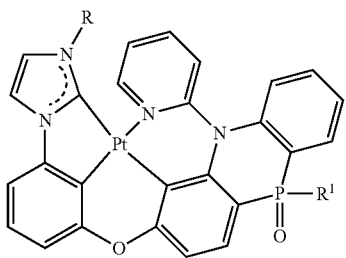
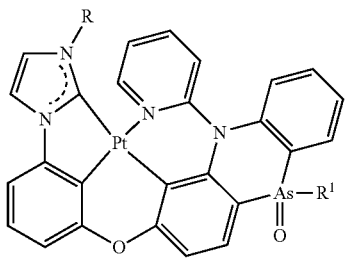
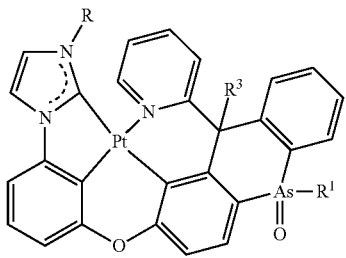
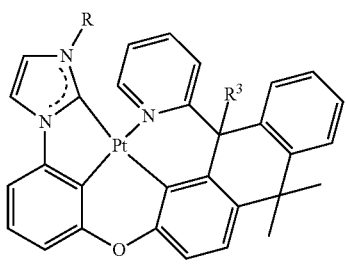

423
-continued
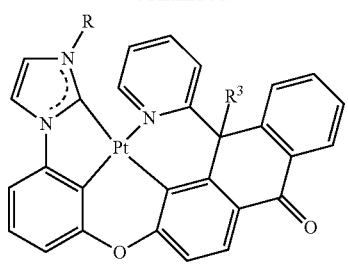
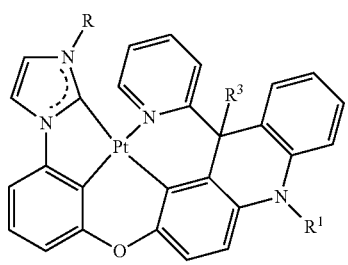
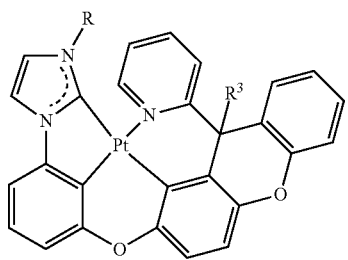
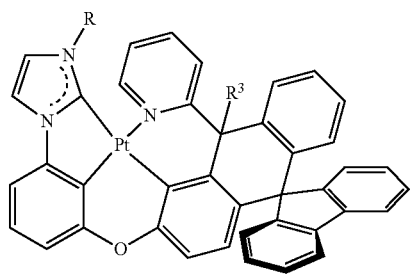
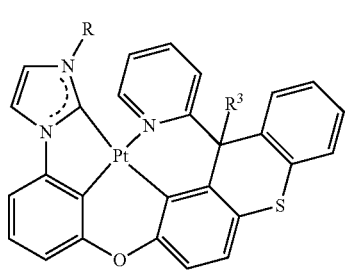
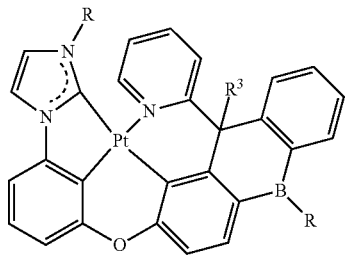
424
-continued
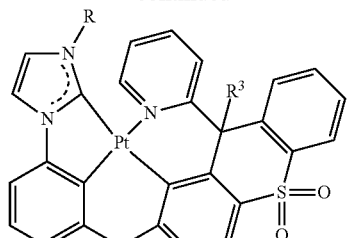
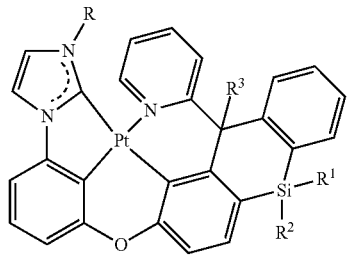
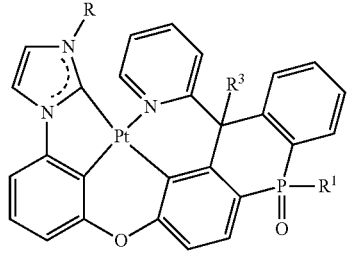
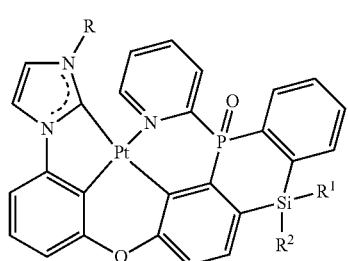
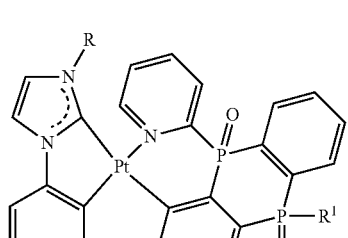
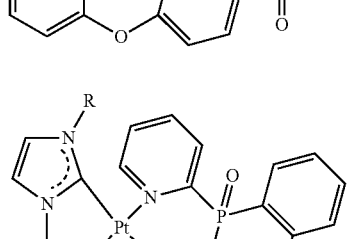

425
-continued
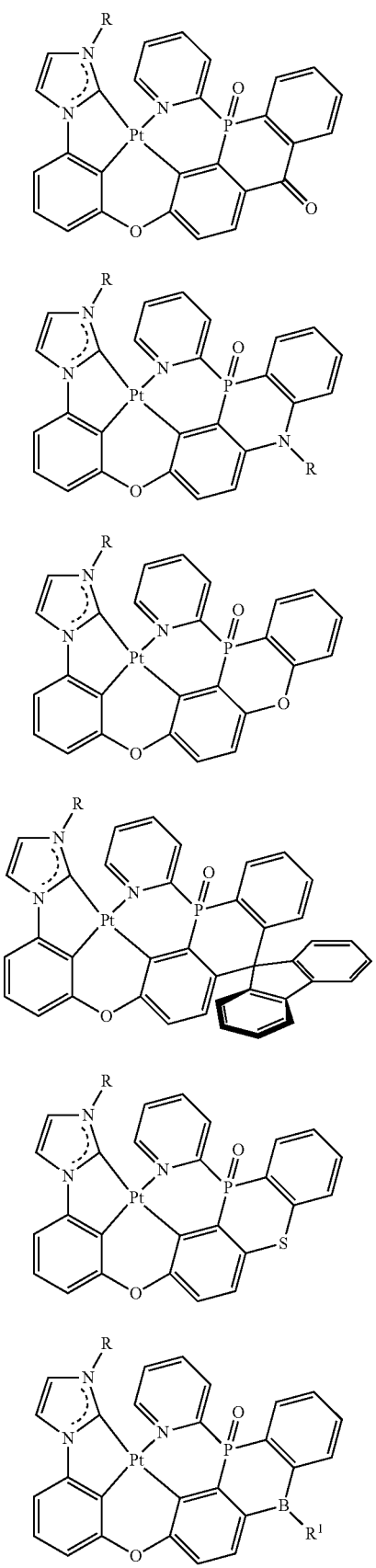
426
-continued
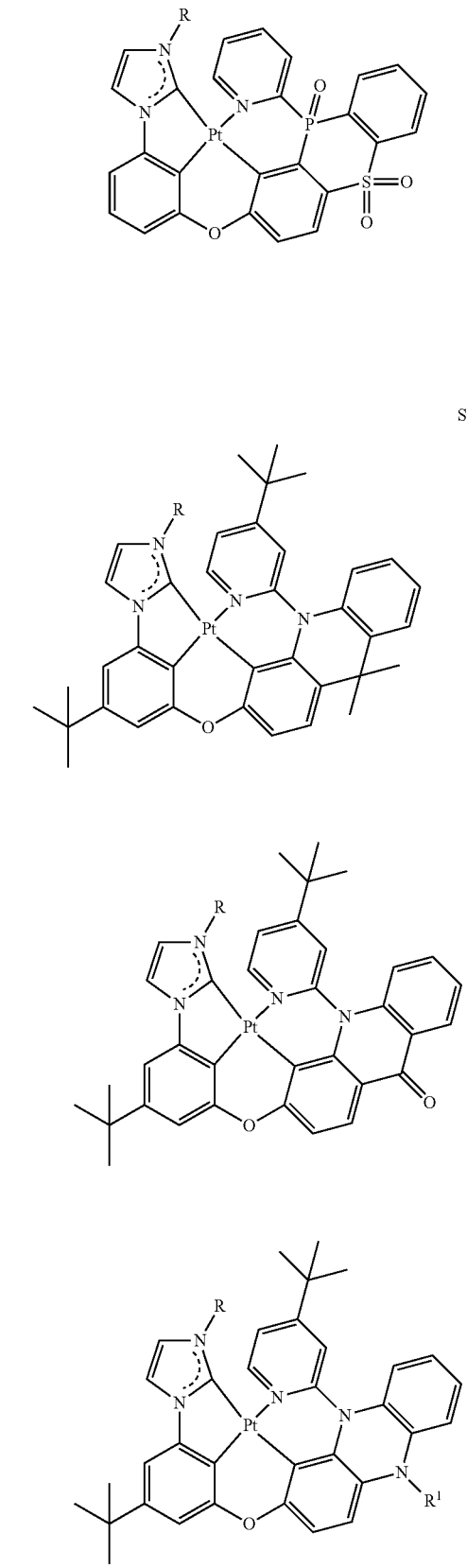
Structures 5

427
-continued
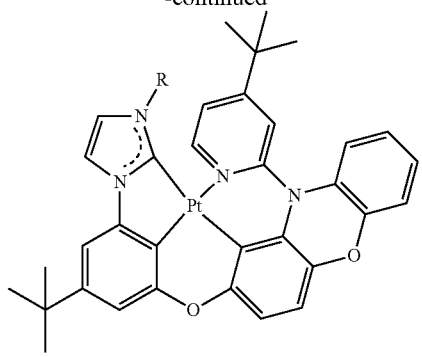
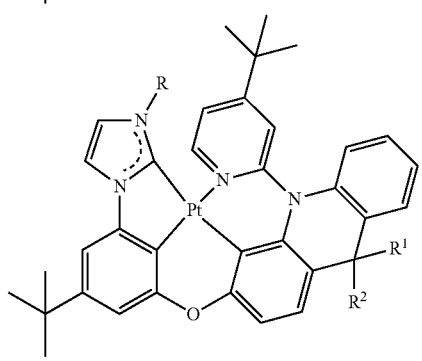
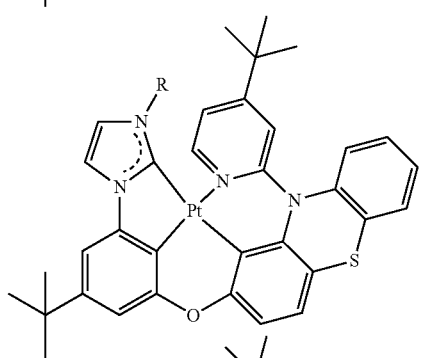
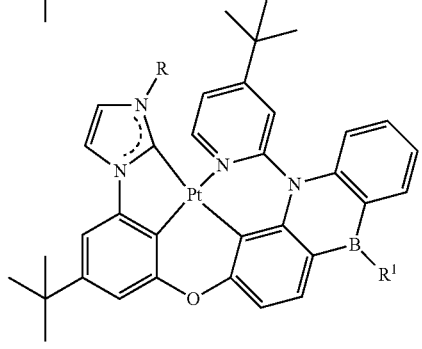
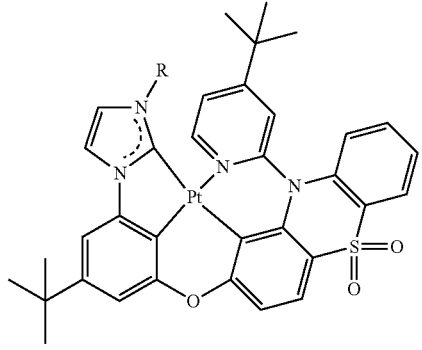
428
-continued
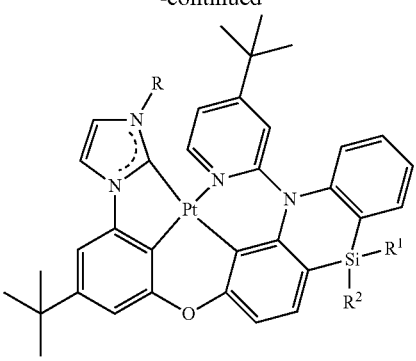
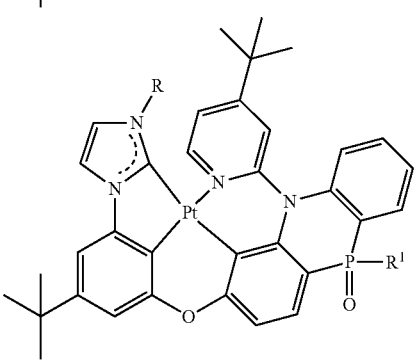
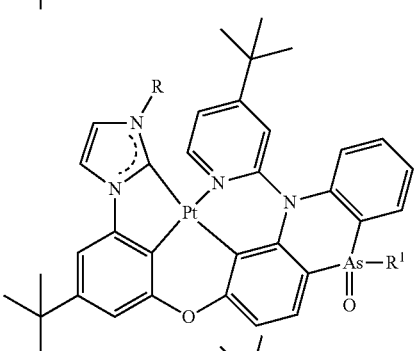
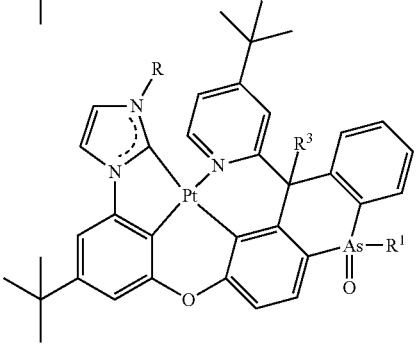
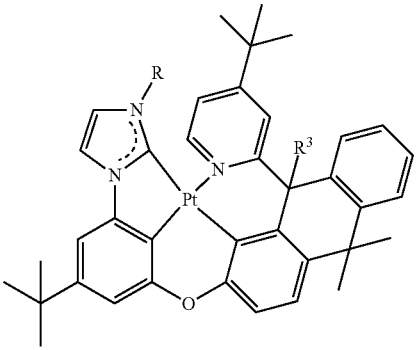

429
-continued
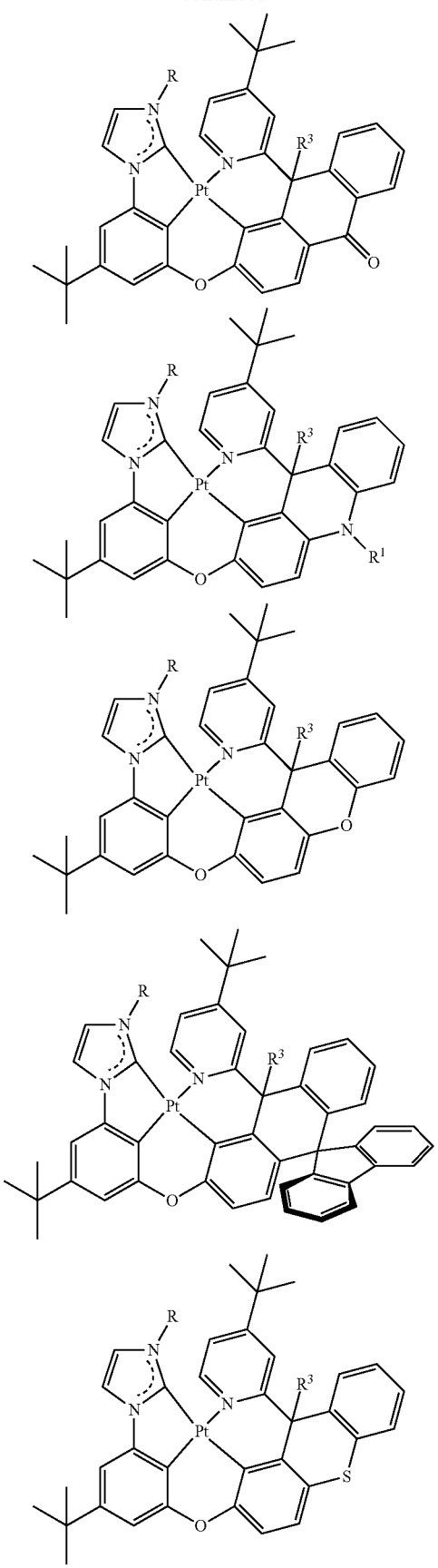
430
-continued
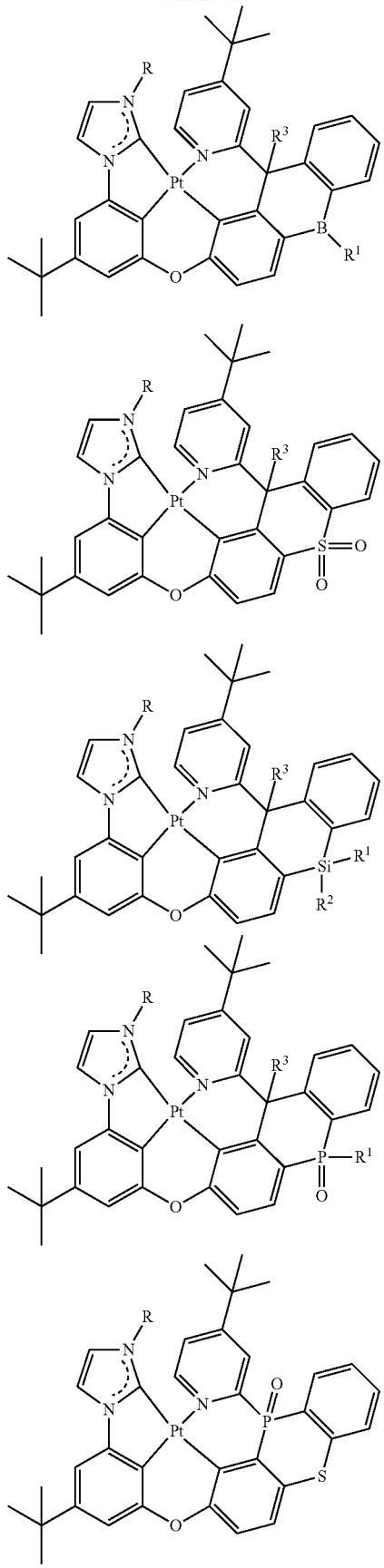

431
-continued
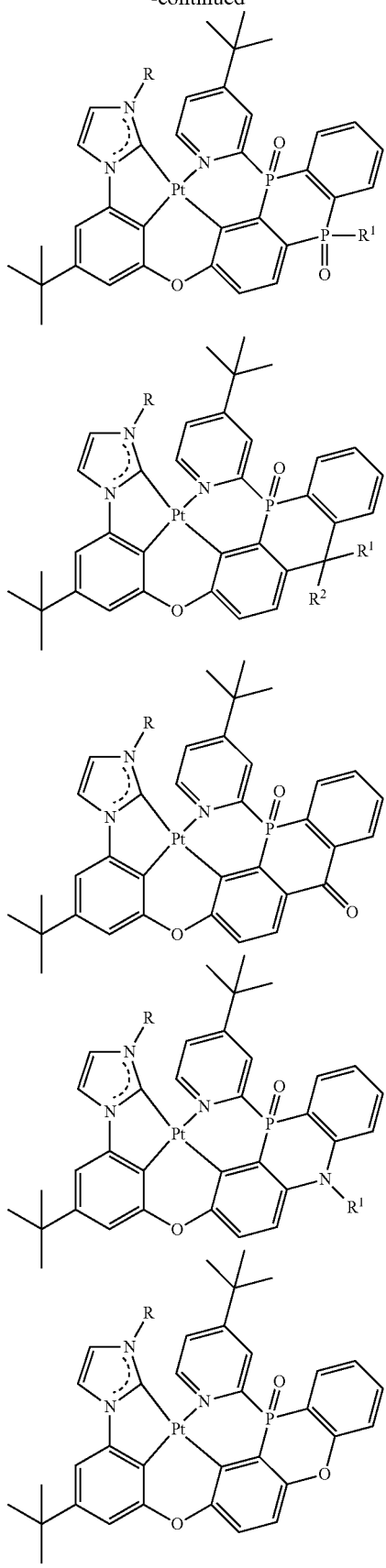
432
Structures 6
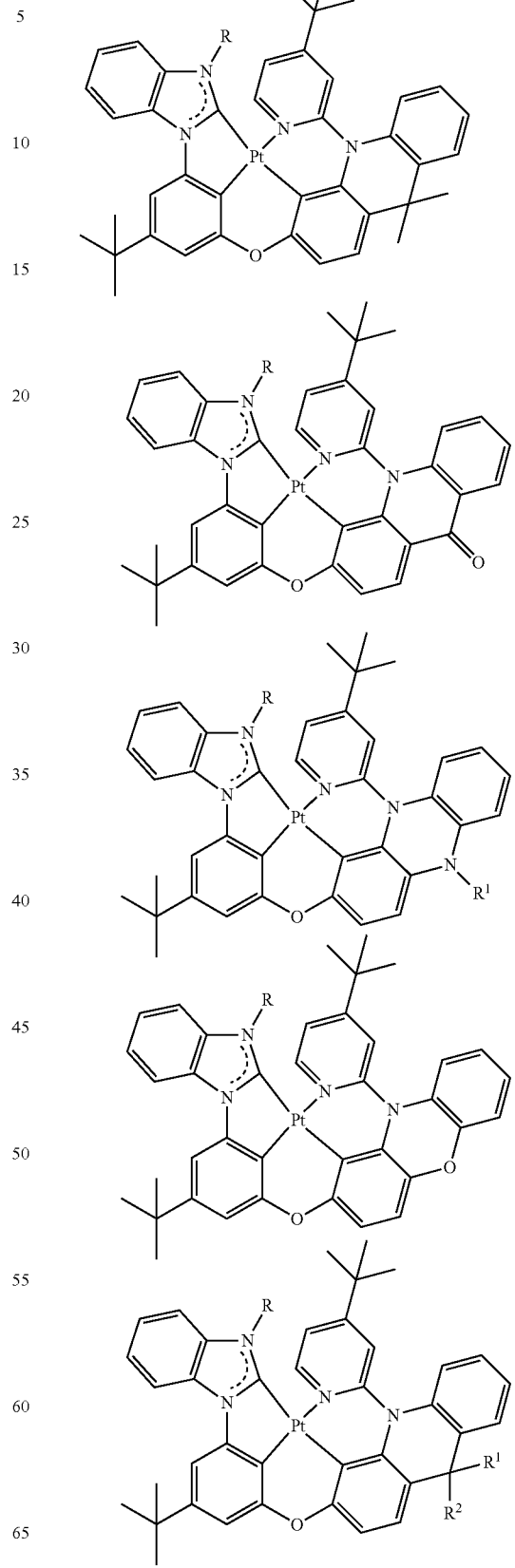

433
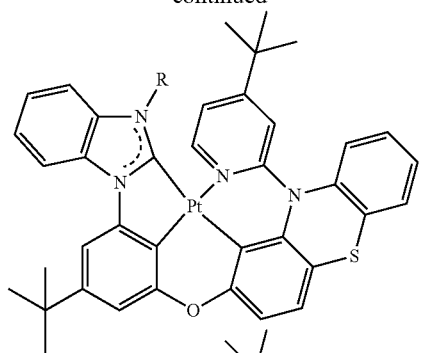
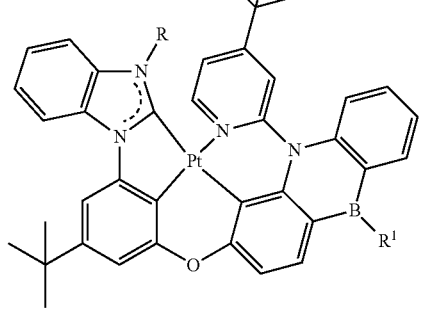
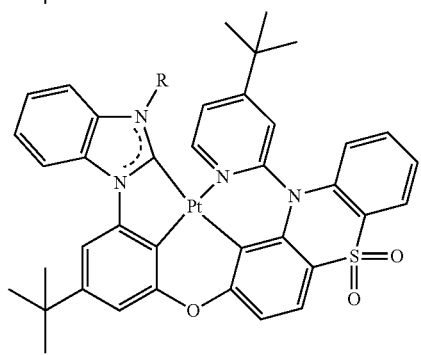
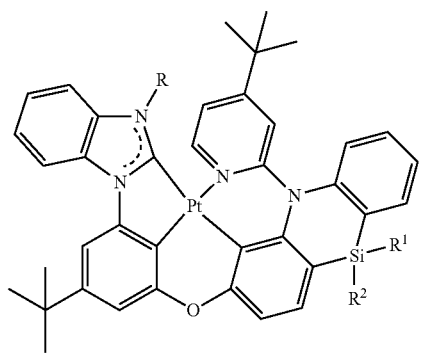
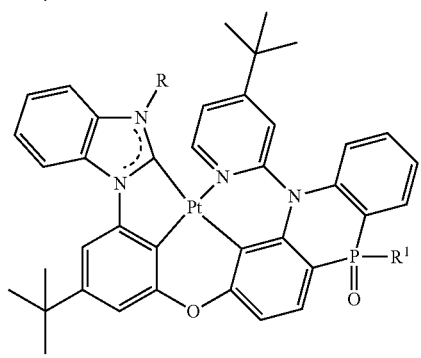
434
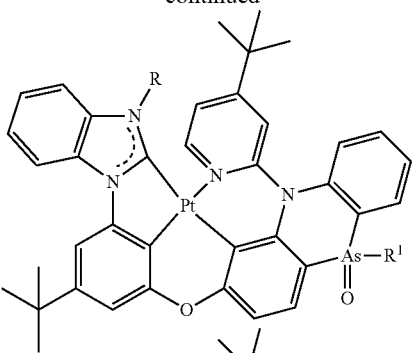
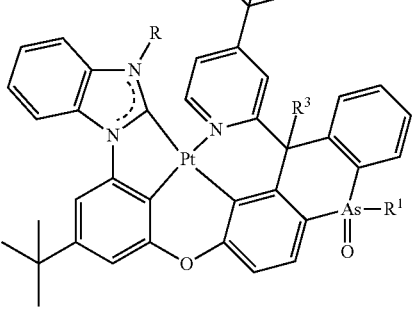
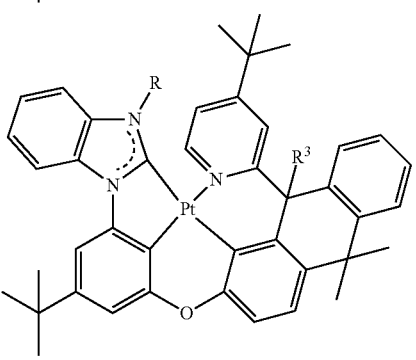
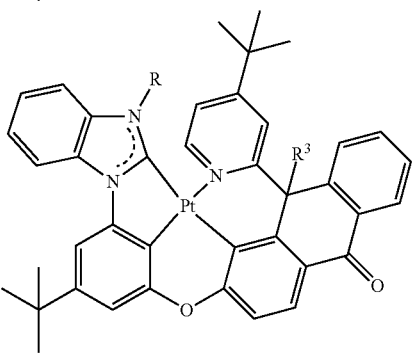
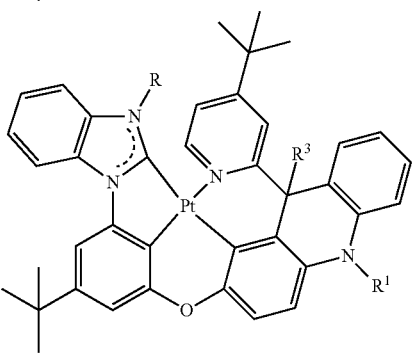

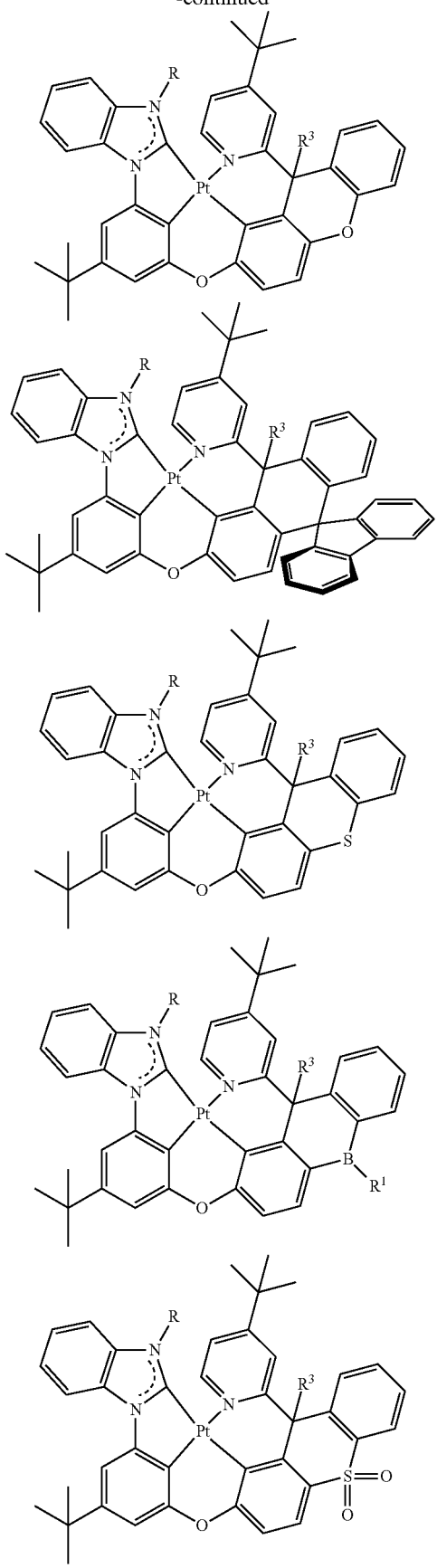
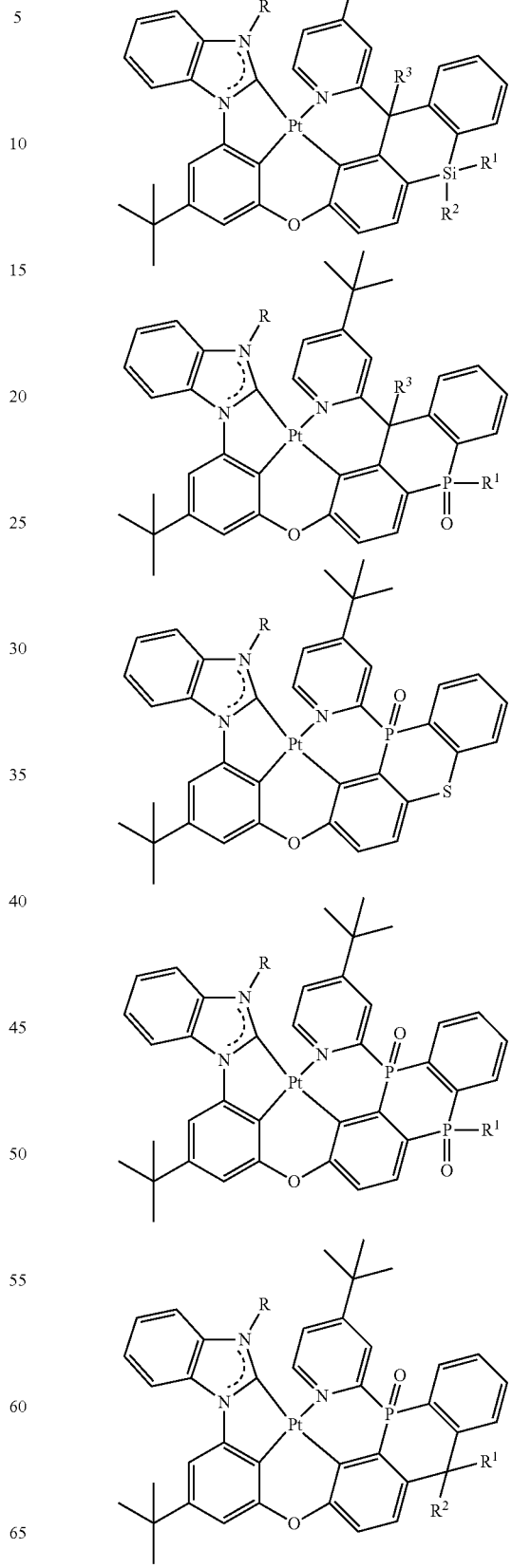

437
-continued
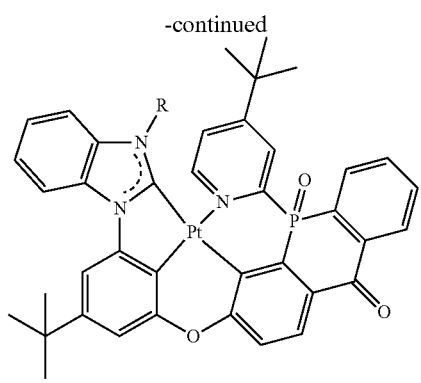
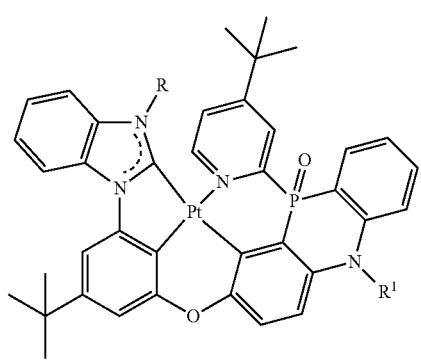
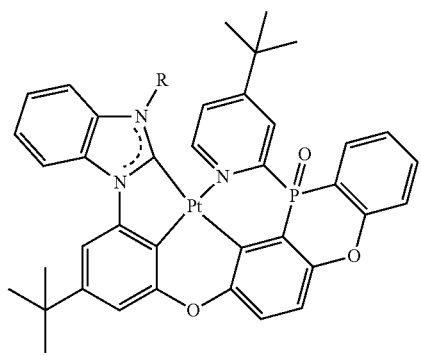
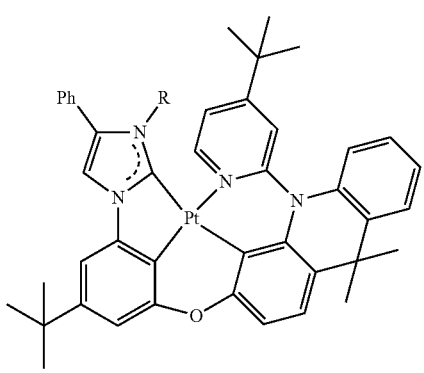
438
-continued
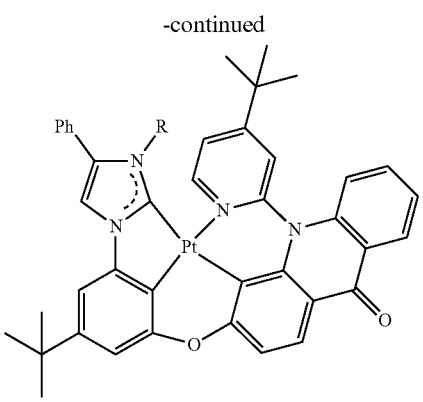
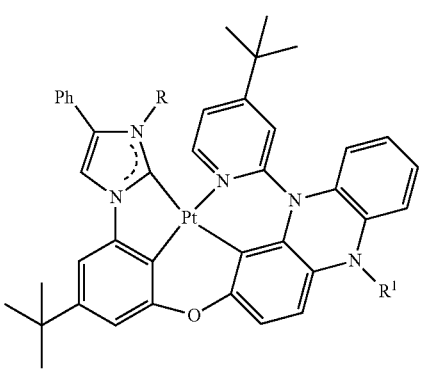
Structures 7
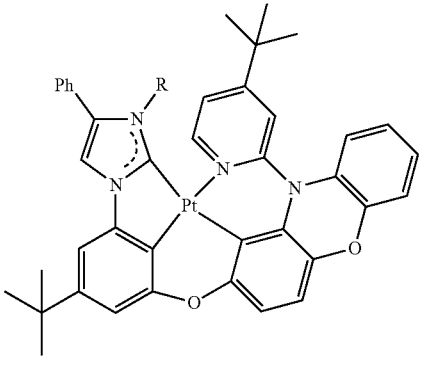
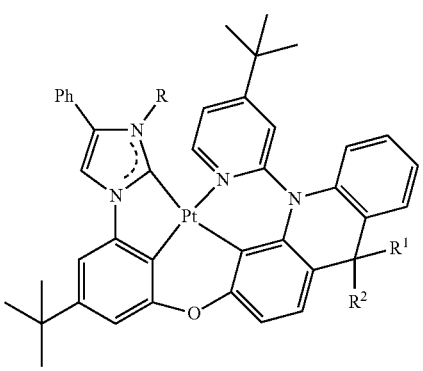

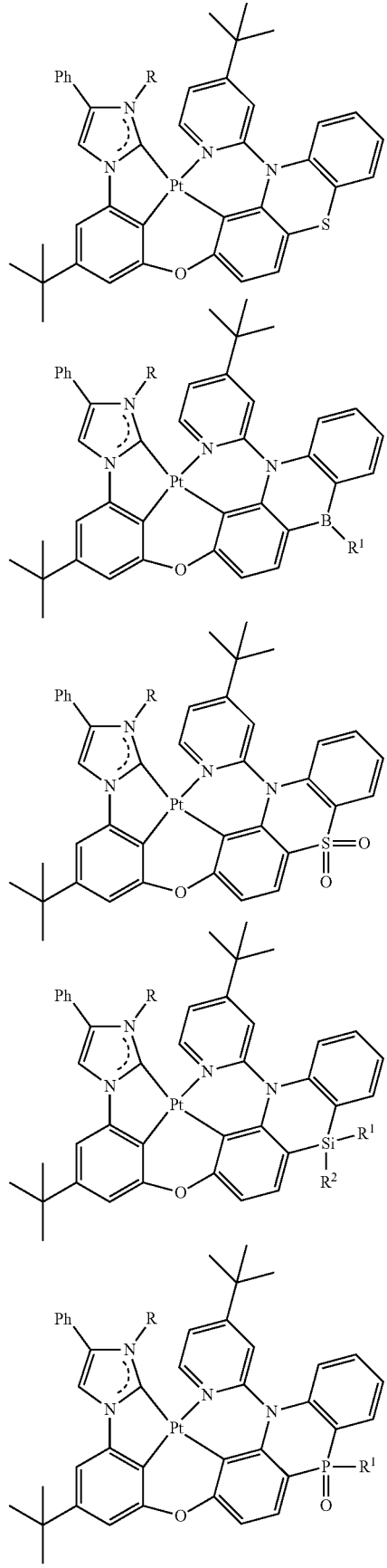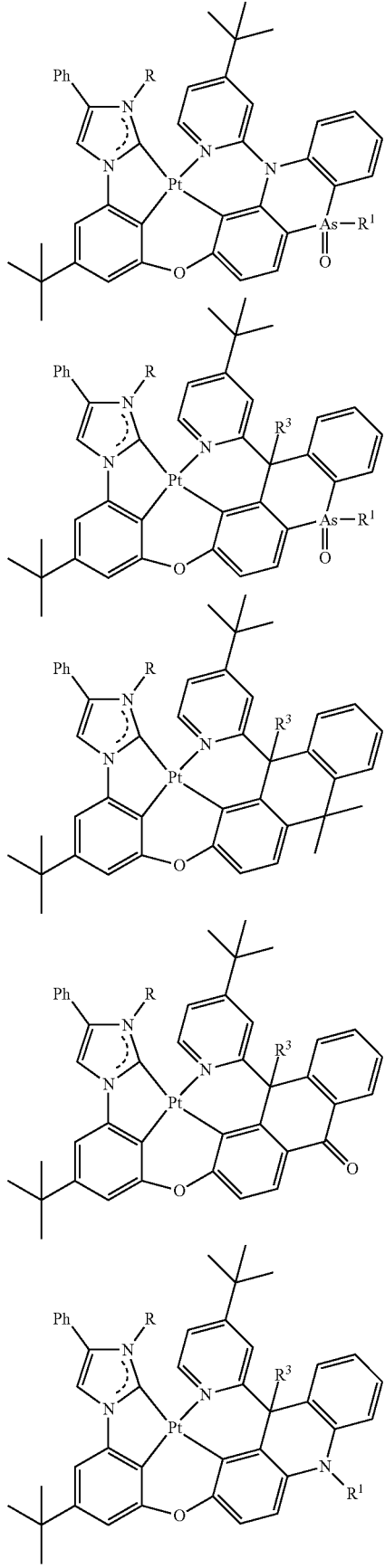

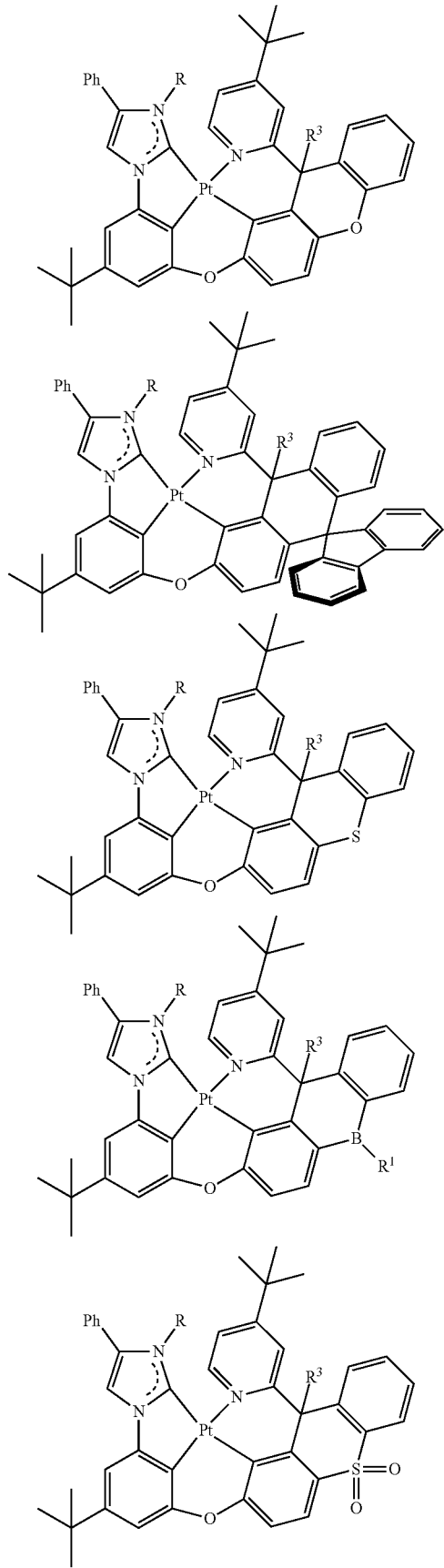
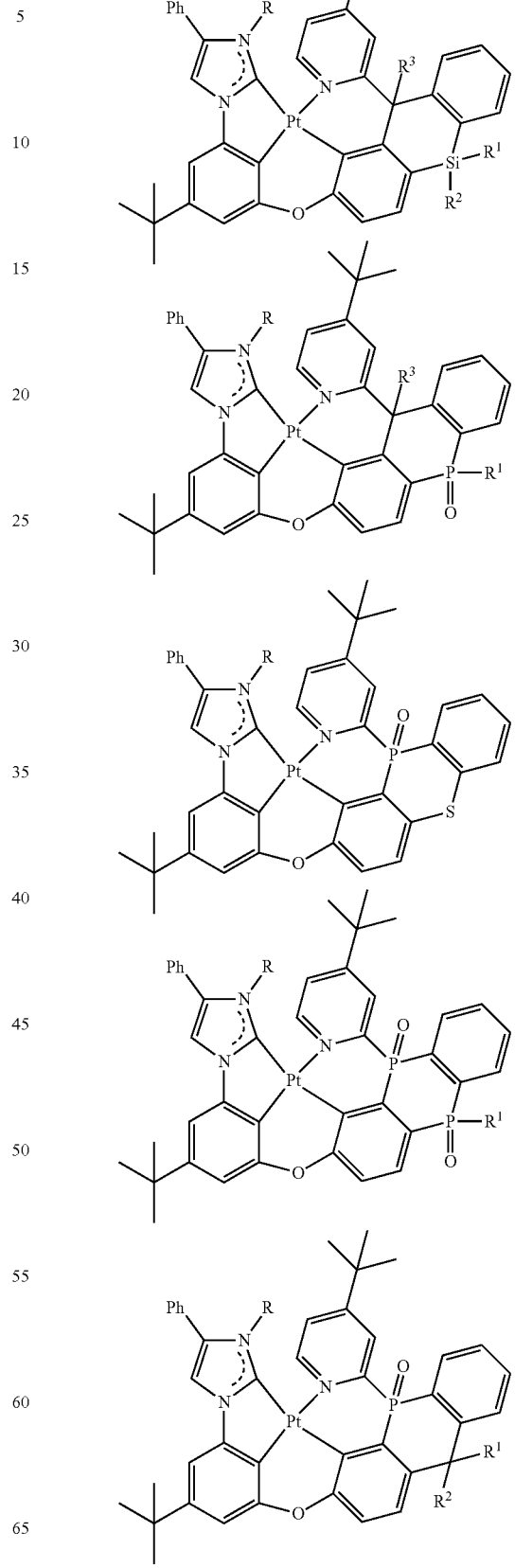

-continued
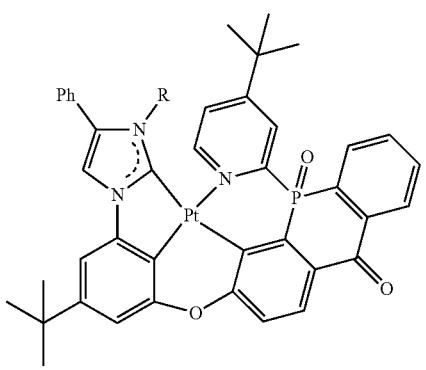
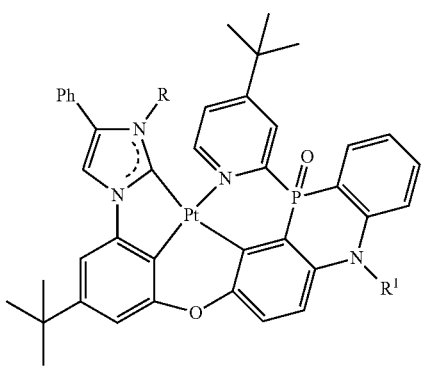
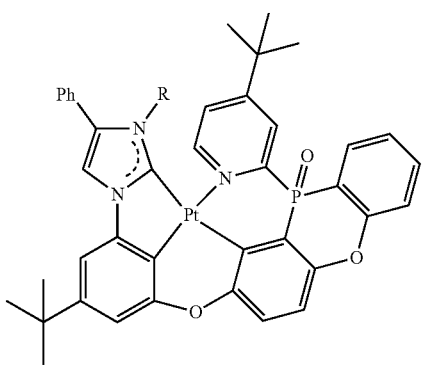
Structures 8
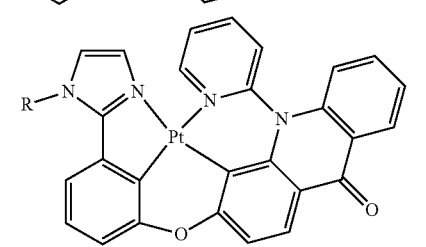
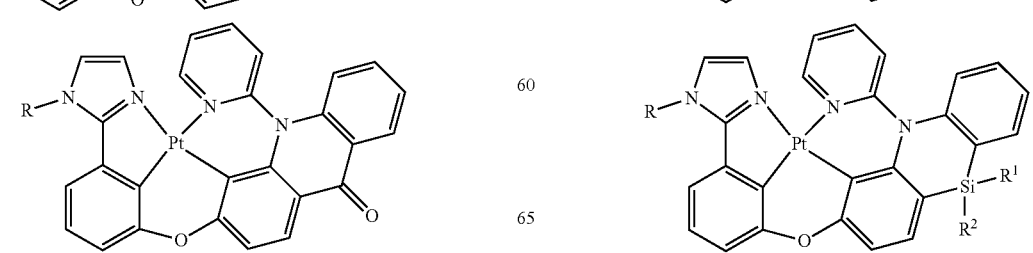
-continued
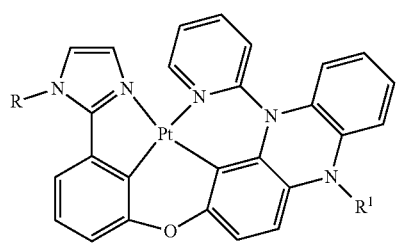
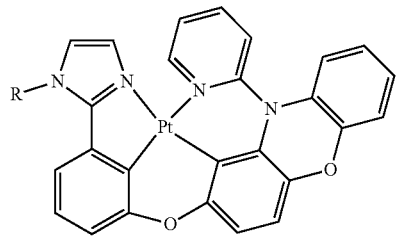
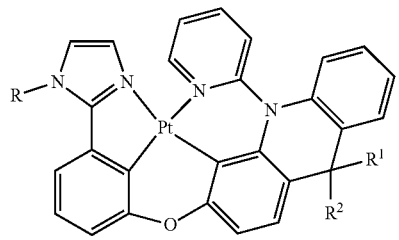
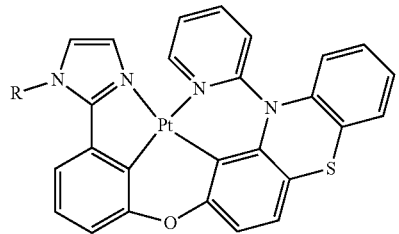
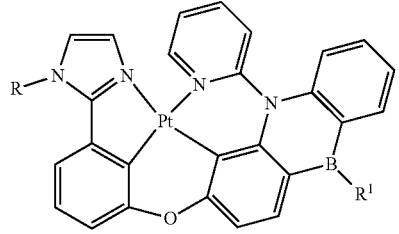
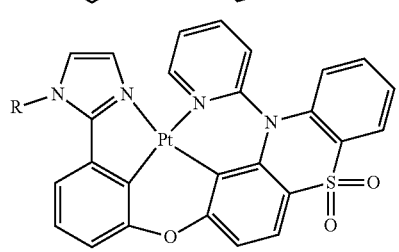
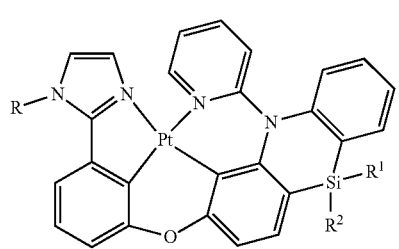

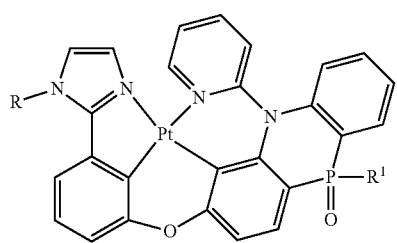
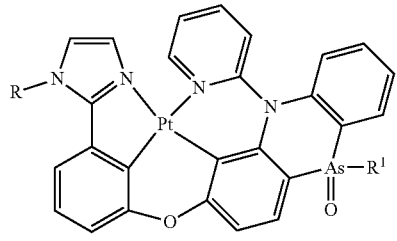
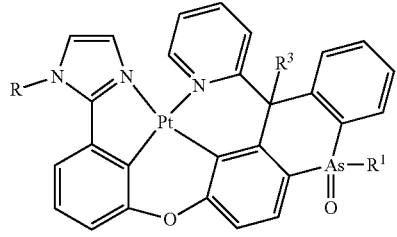
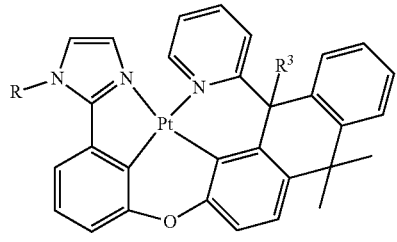
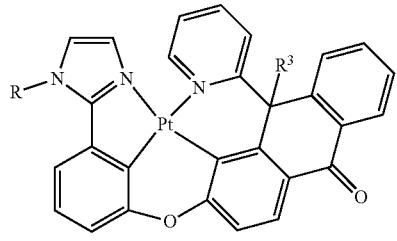
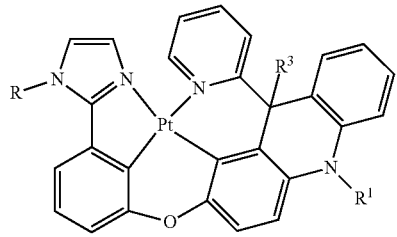
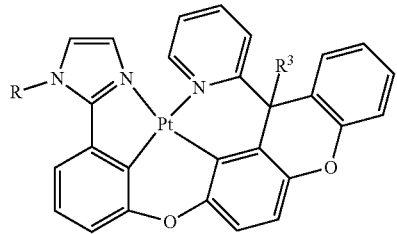
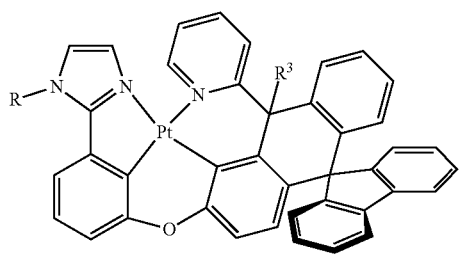
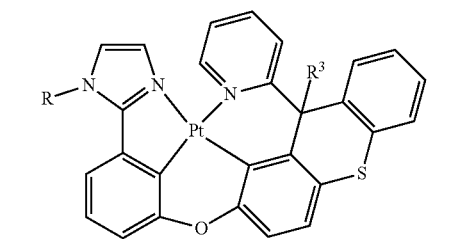
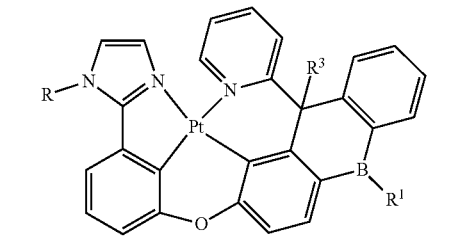
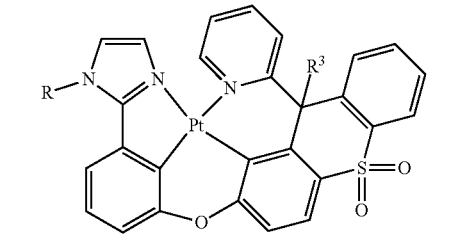
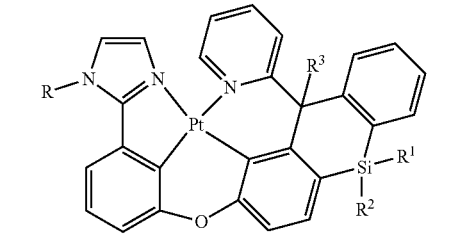
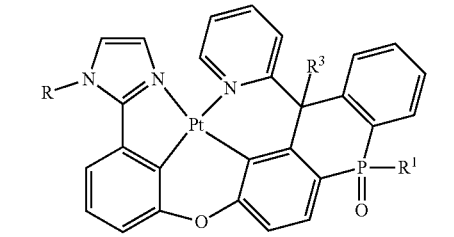
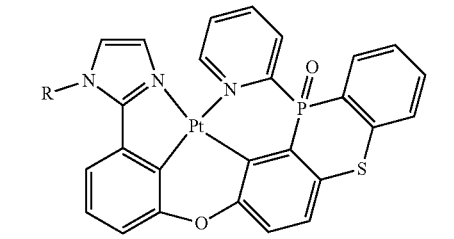

-continued
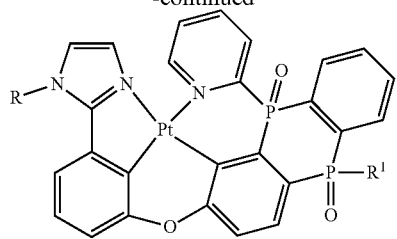
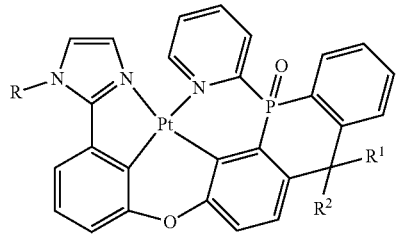
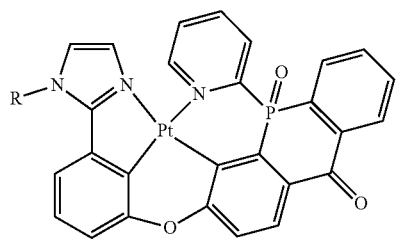
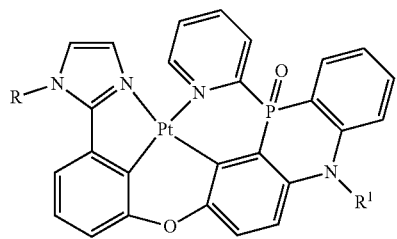
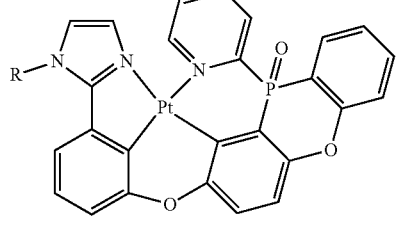
Structures 9
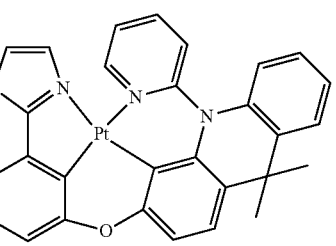
-continued
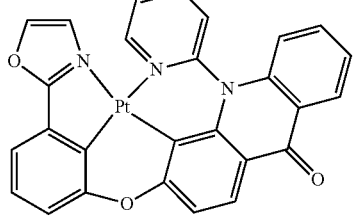
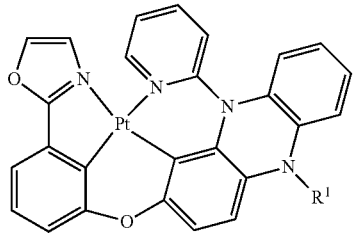
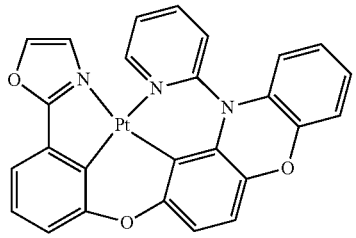
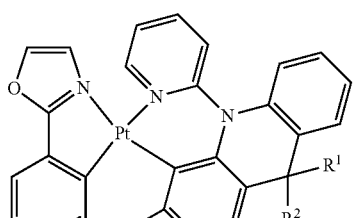
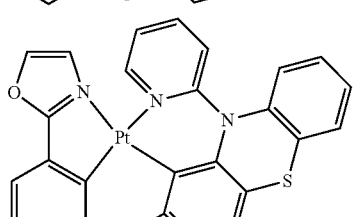
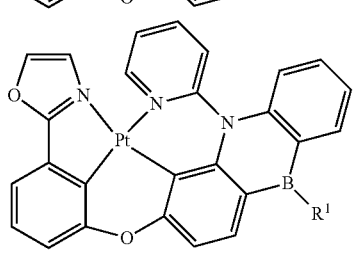
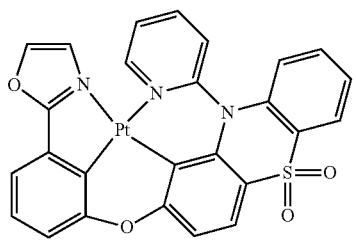

449
-continued
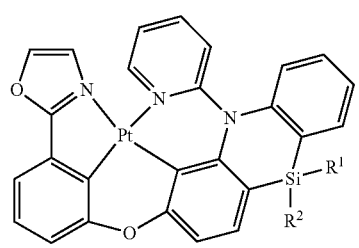
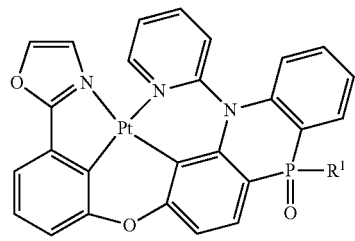
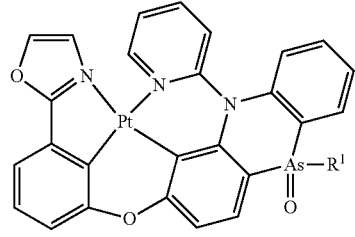
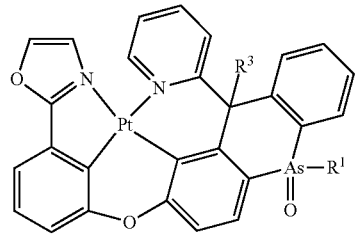
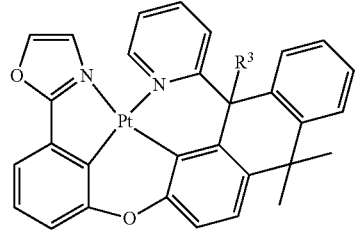
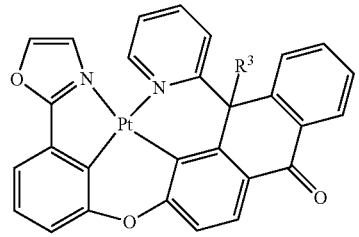
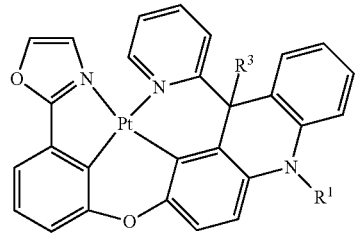
450
-continued
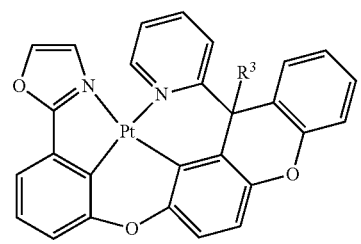
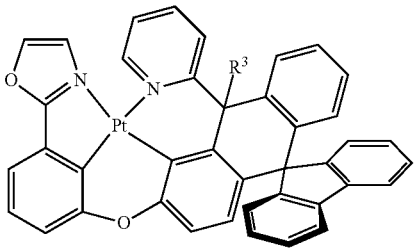
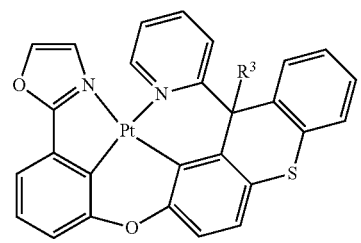
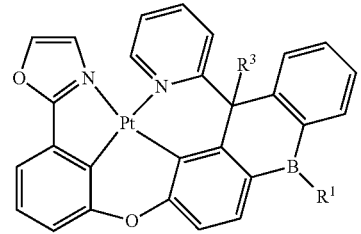
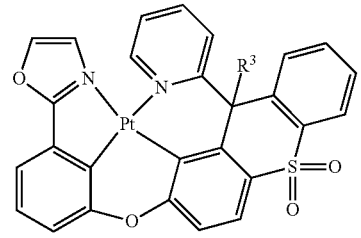
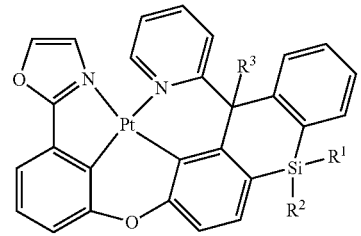
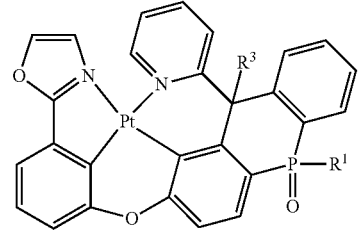

451
-continued
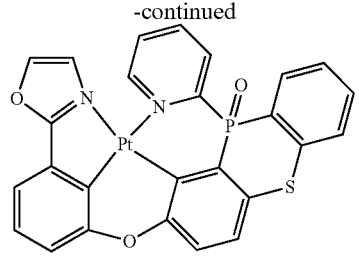
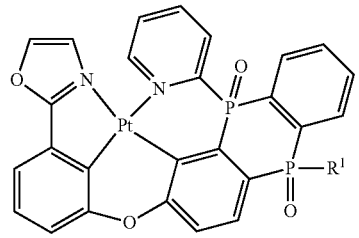
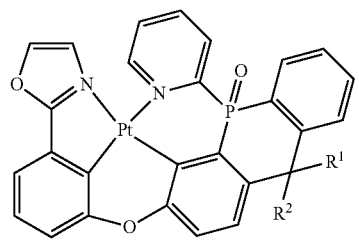
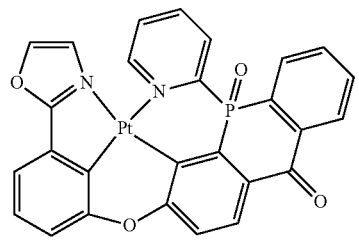
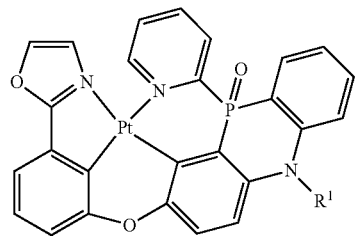
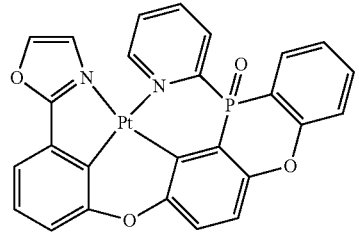
452
Structures 10
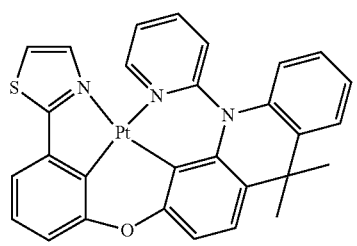
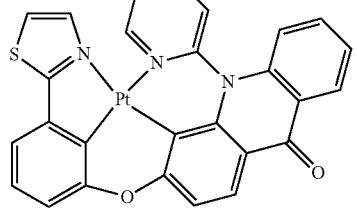
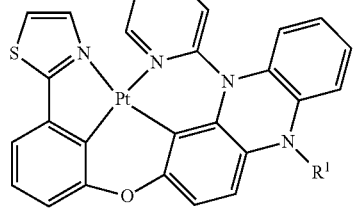
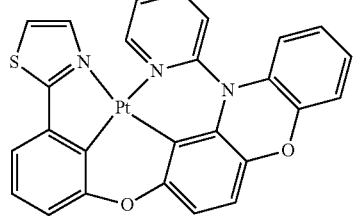
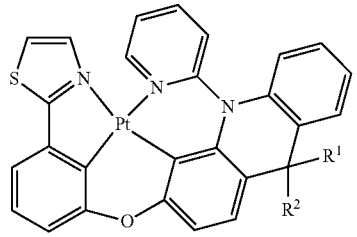
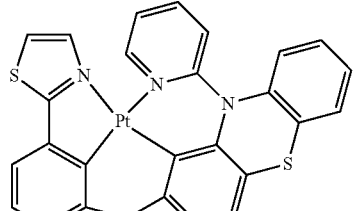
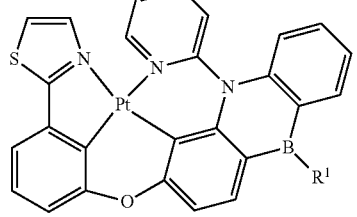

453
-continued
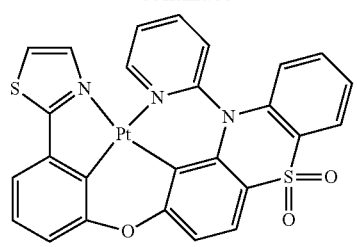
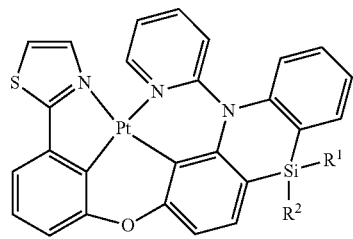
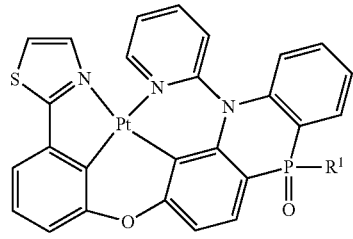
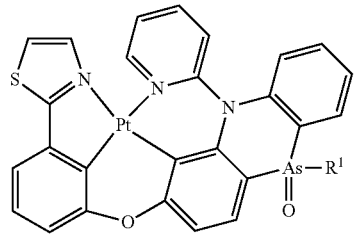
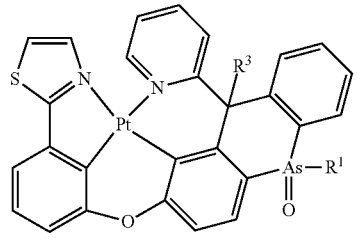
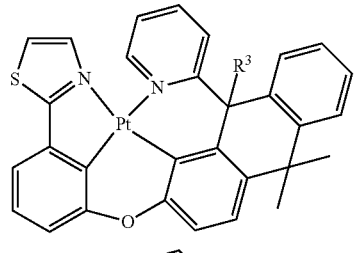
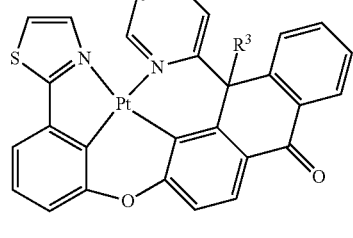
454
-continued
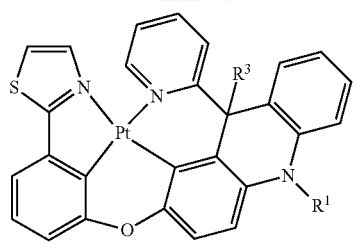
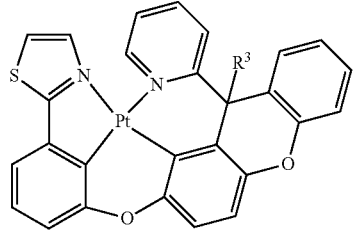
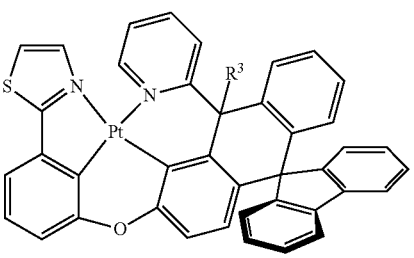
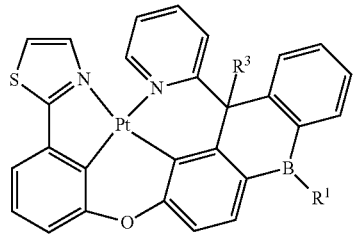
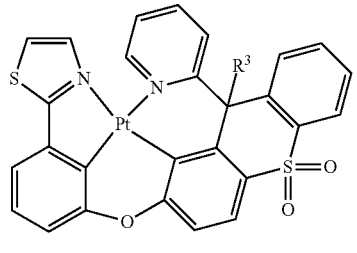
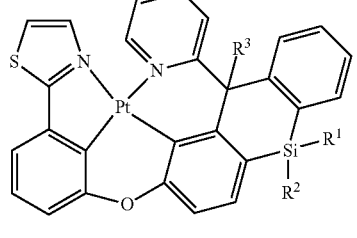

Structures 16
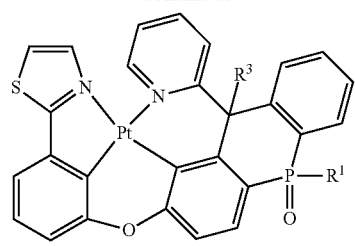
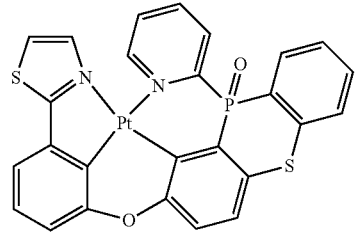
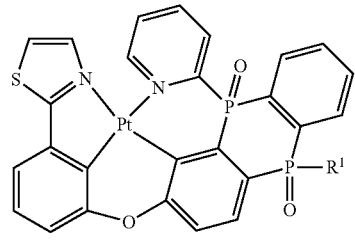
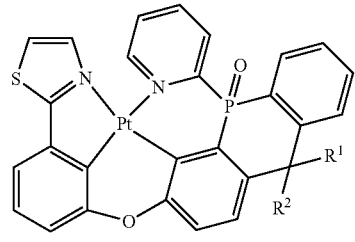
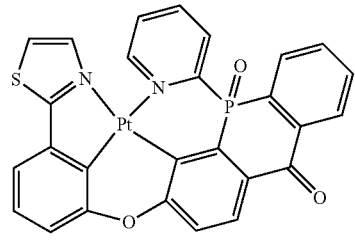
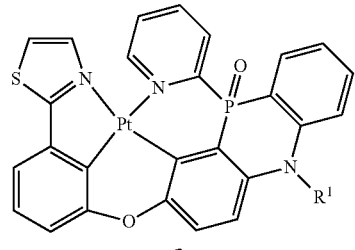
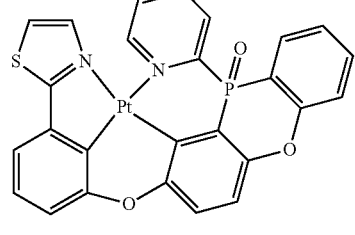
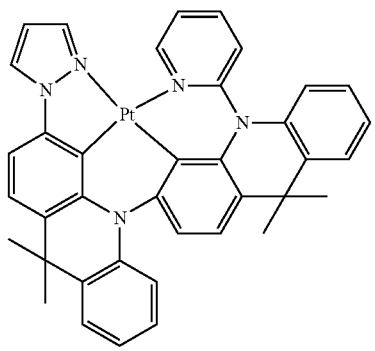
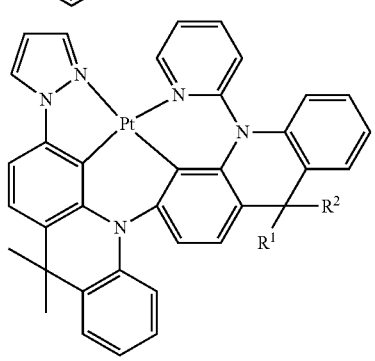
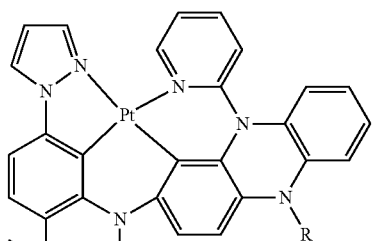
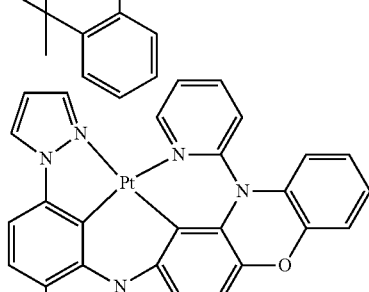
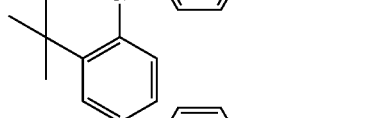
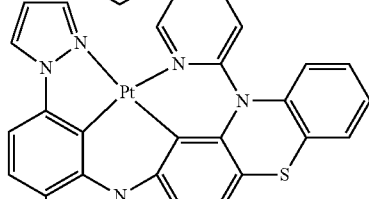
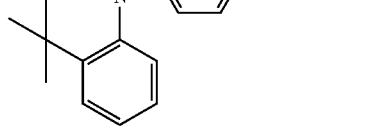

457
-continued
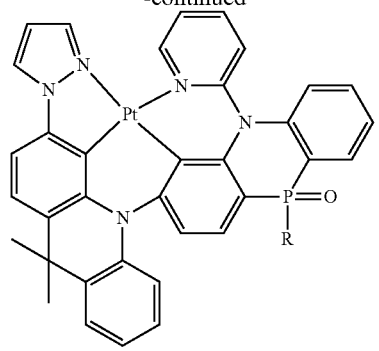
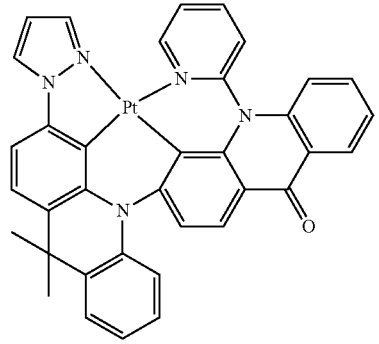
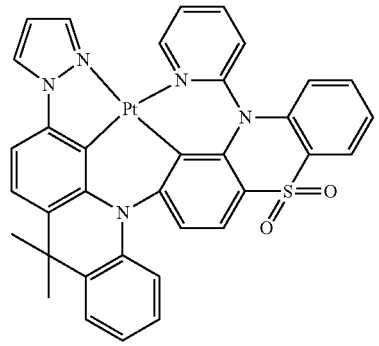
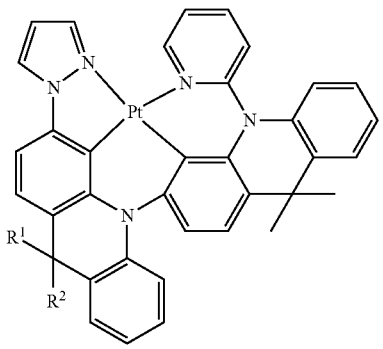
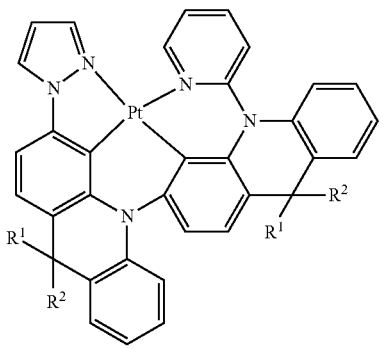
458
-continued
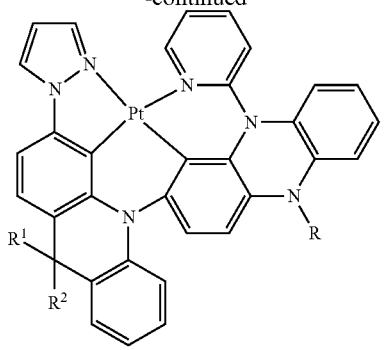
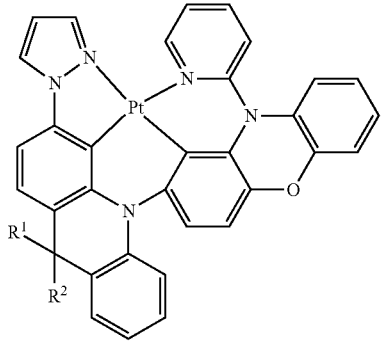
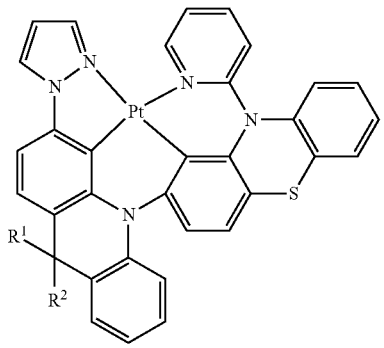
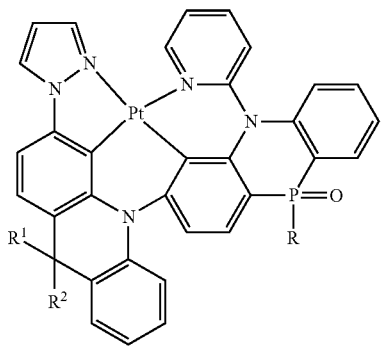
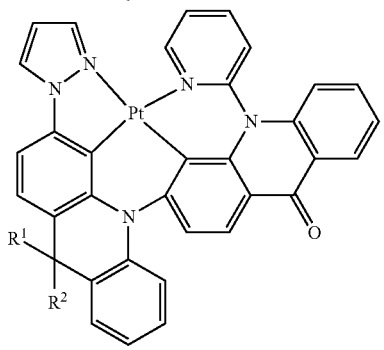

459
-continued
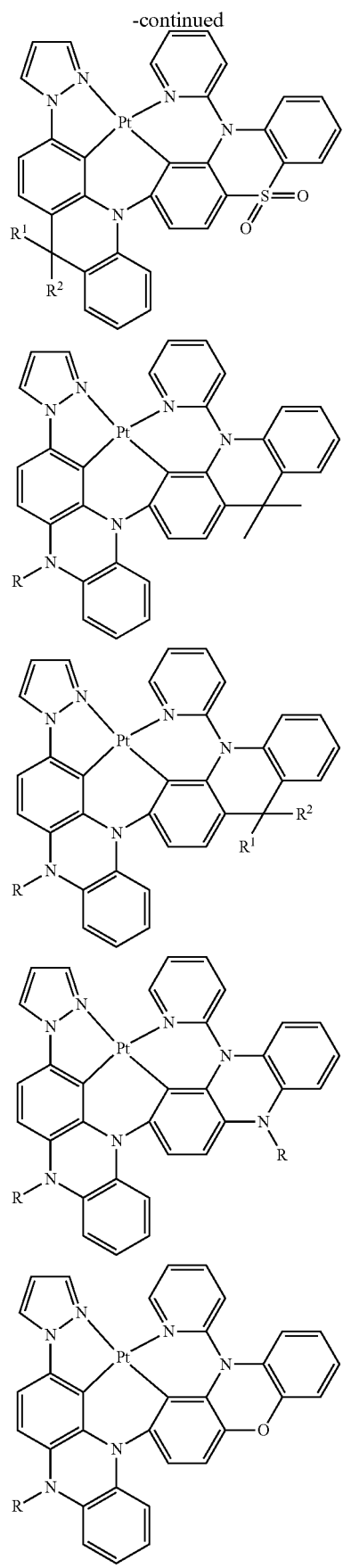
460
-continued
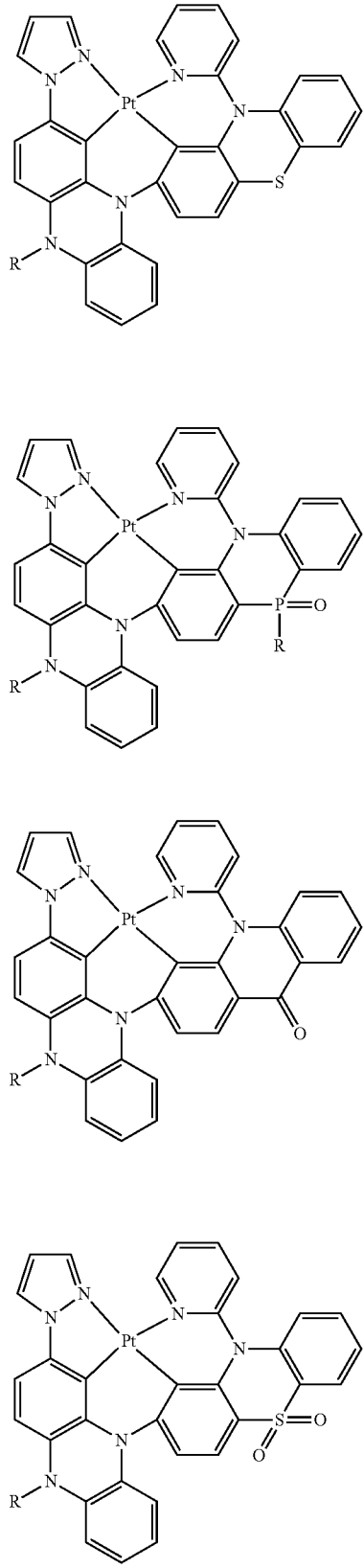

Structures 17
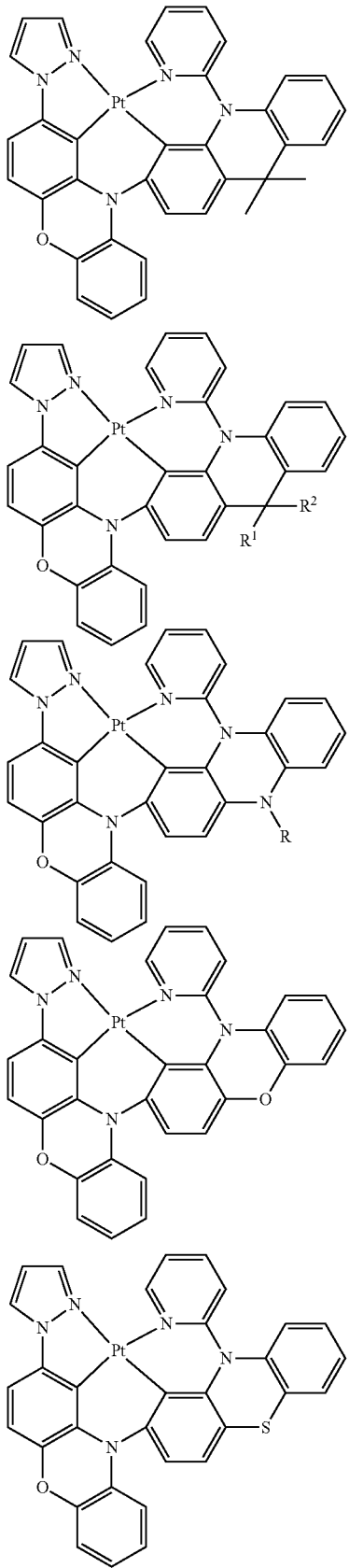
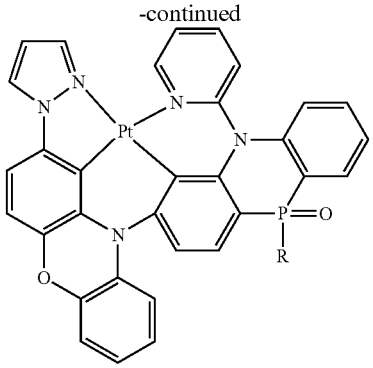
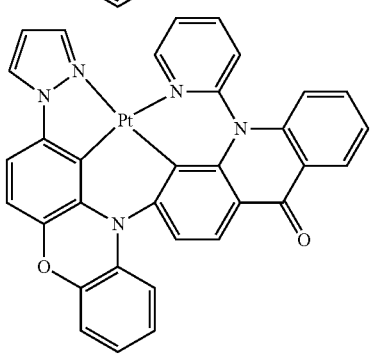
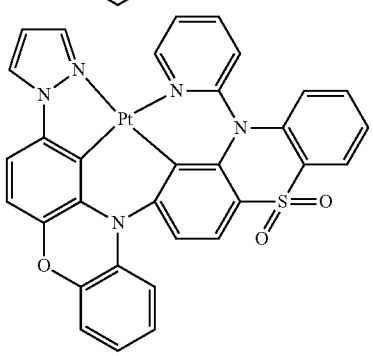
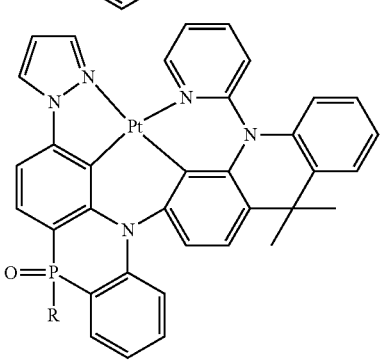
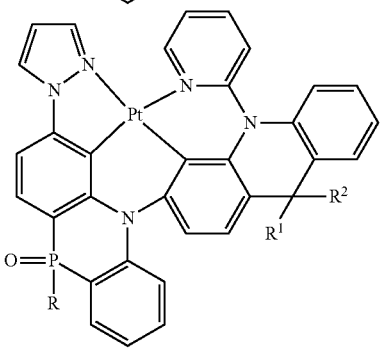

463
-continued
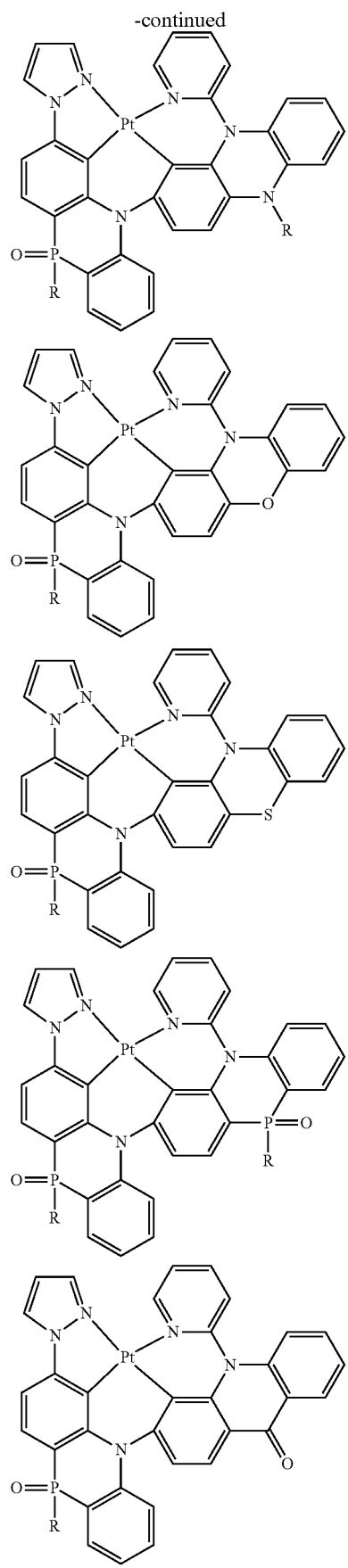
464
-continued
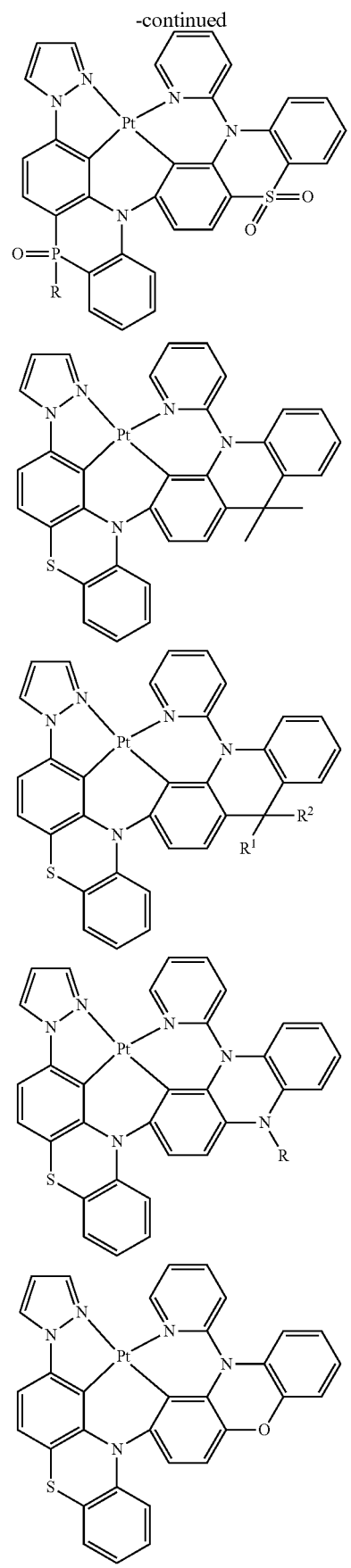

465
-continued
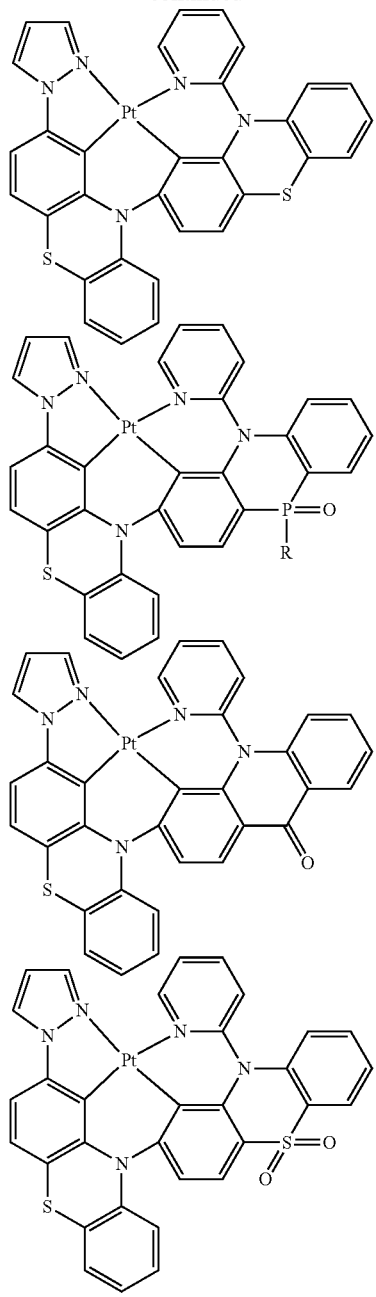
466
-continued
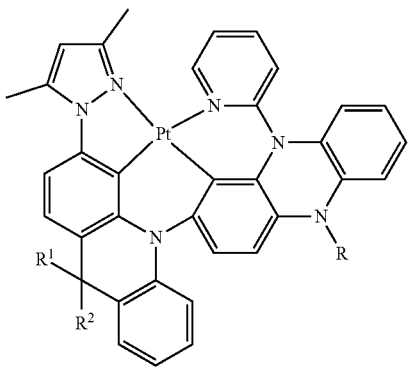
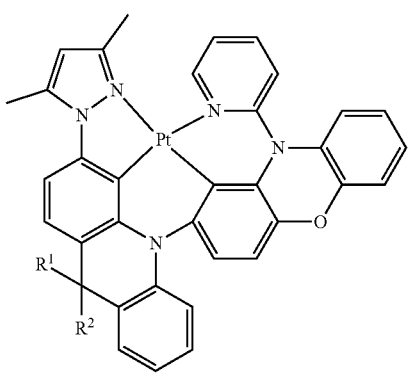
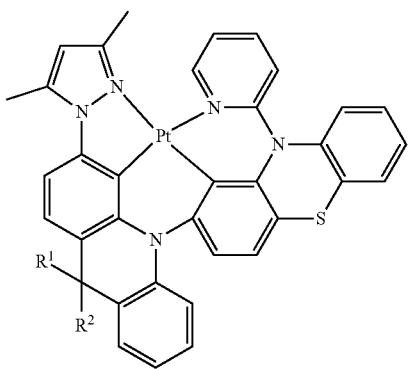
Structures 18
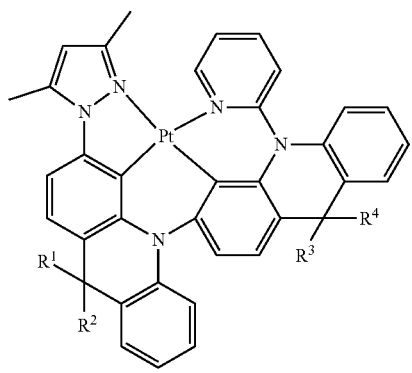
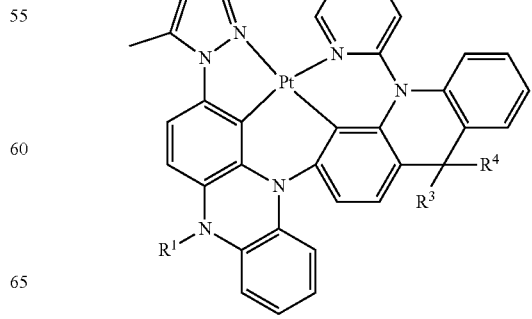

467
-continued
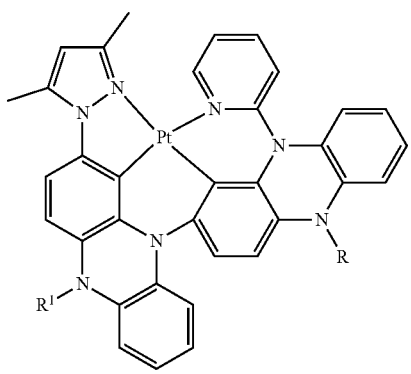
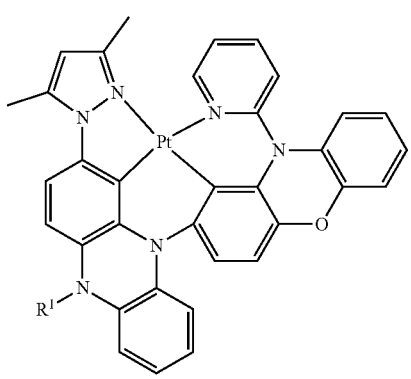
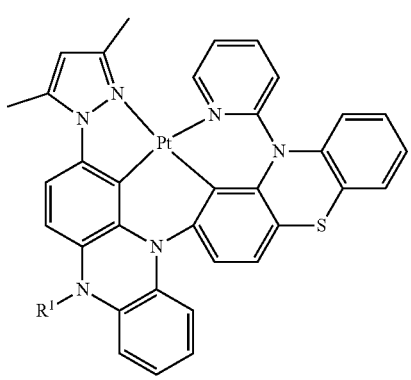
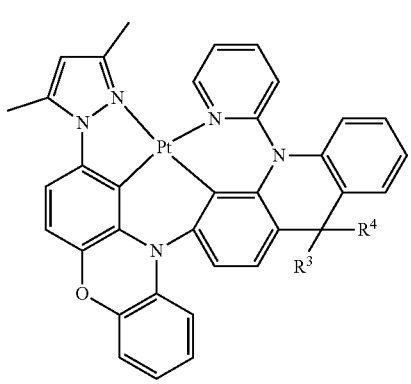
468
-continued
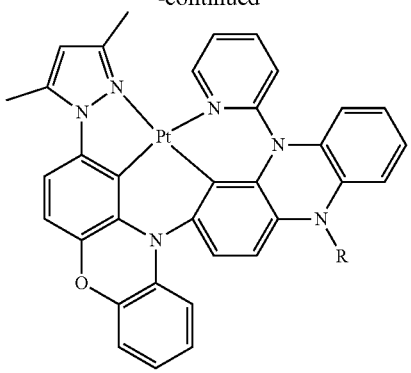
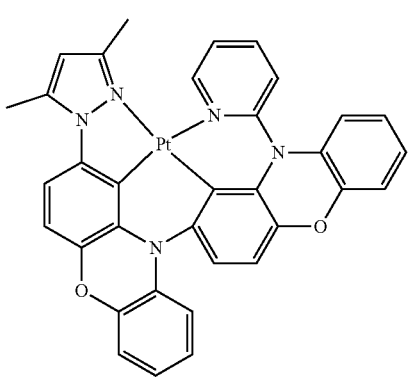
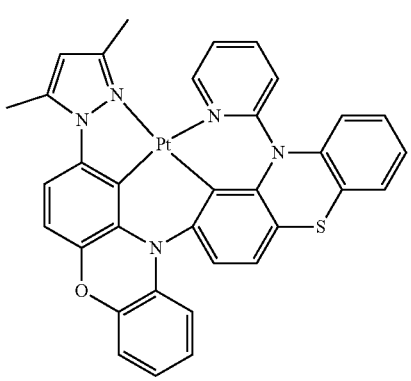
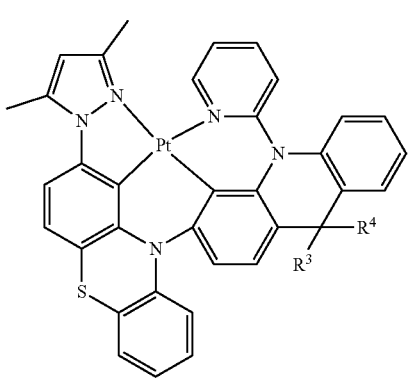

469
-continued
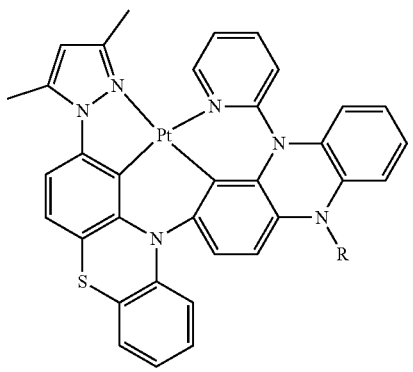
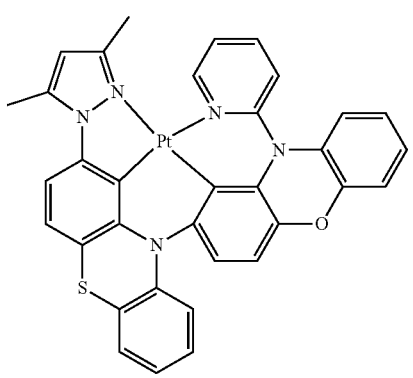
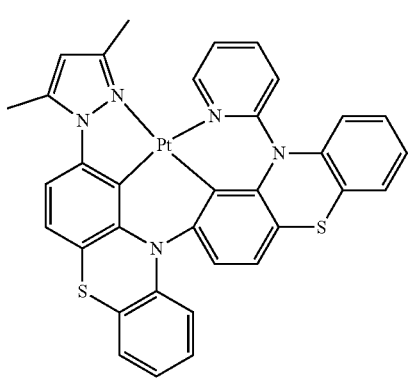
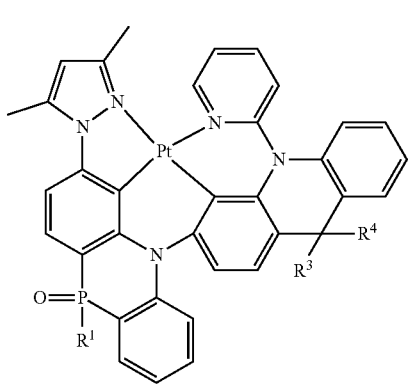
470
-continued
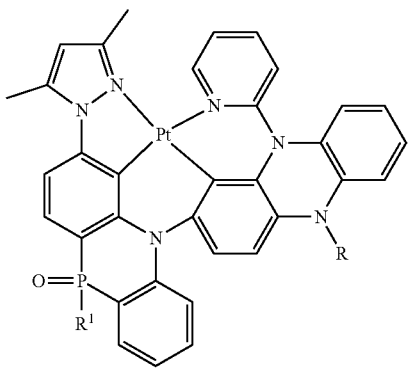
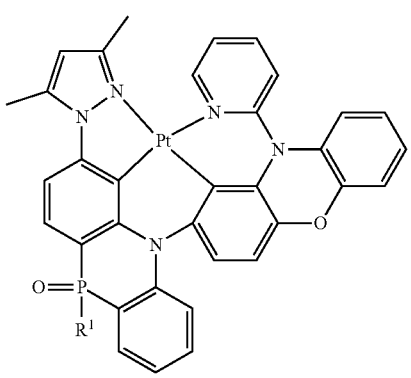
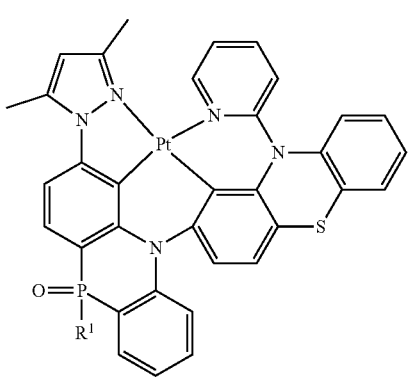
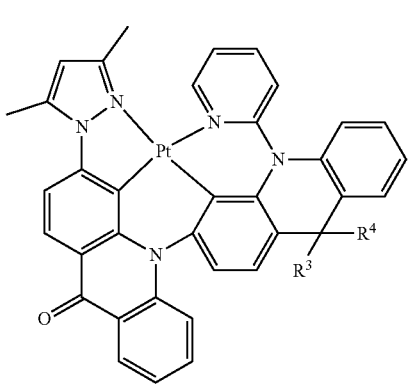

471
-continued
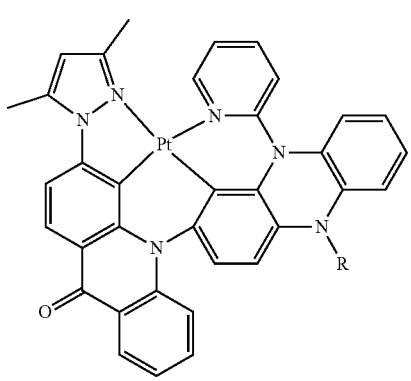
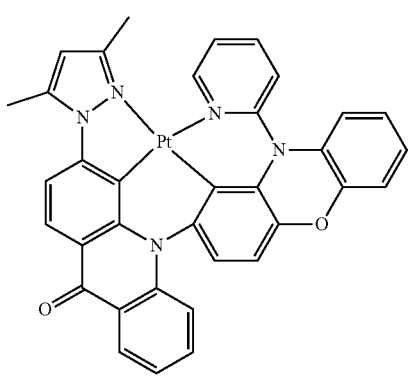
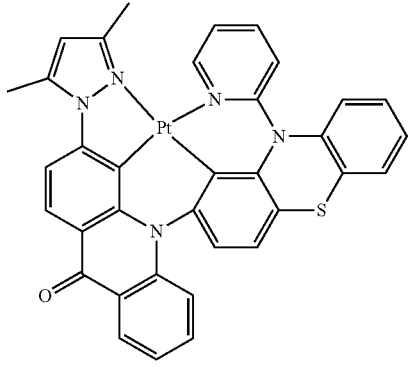
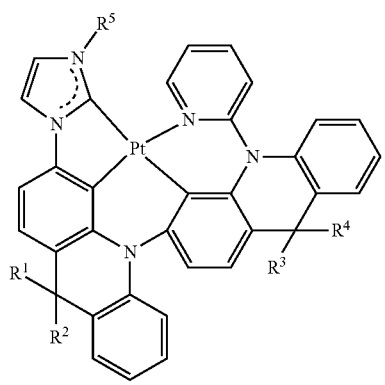
472
-continued
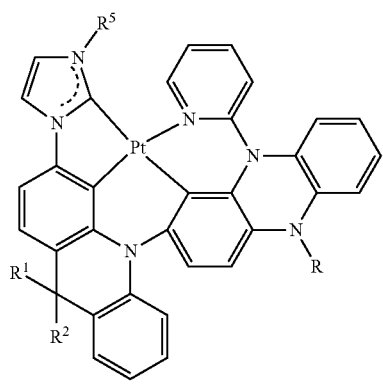
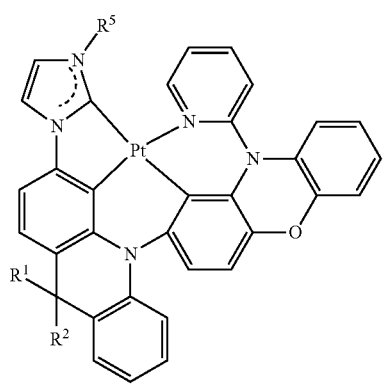
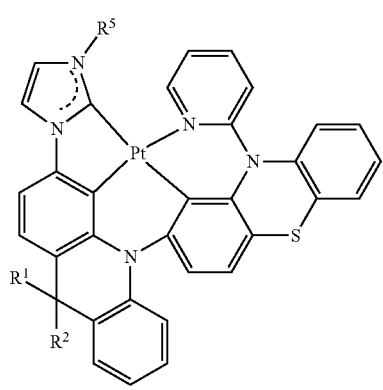
Structures 19
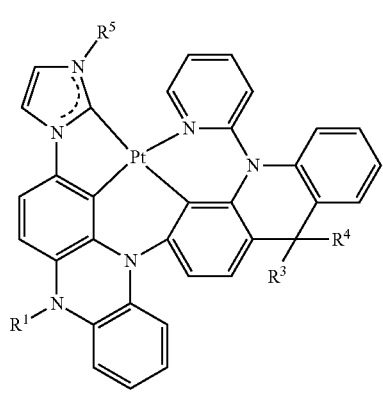

473
-continued
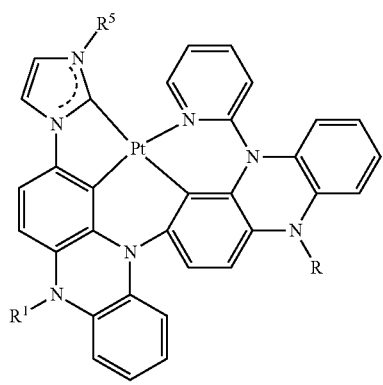
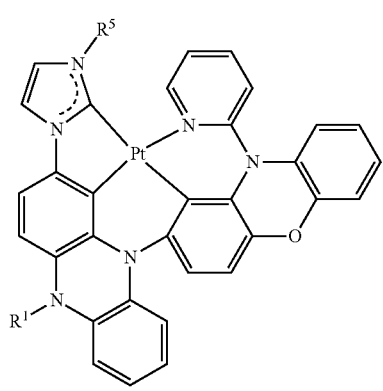
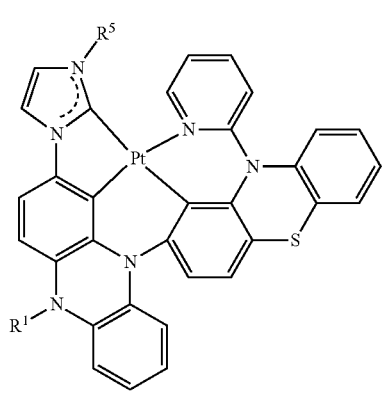
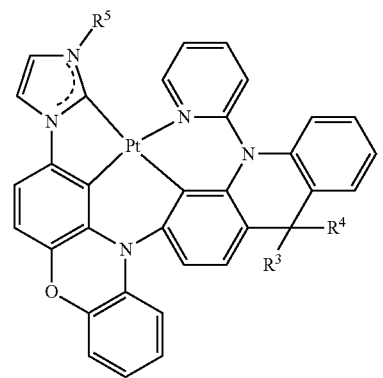
474
-continued
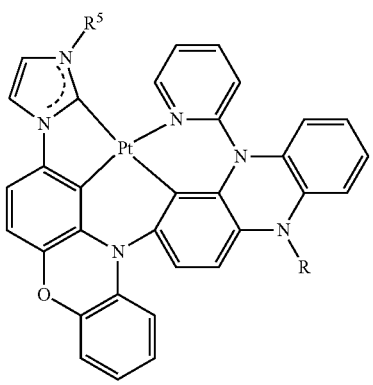
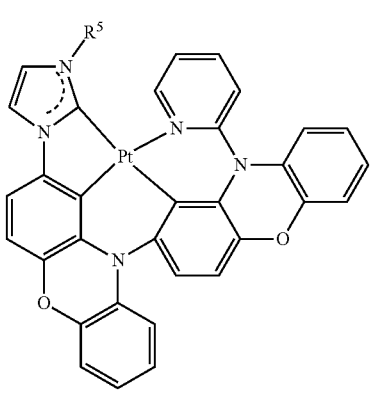
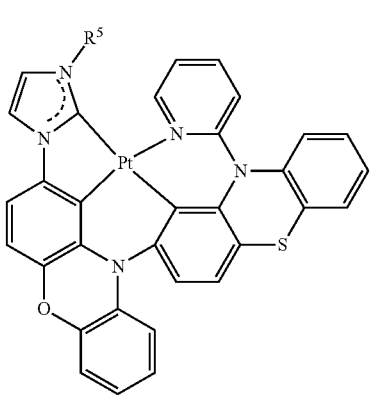
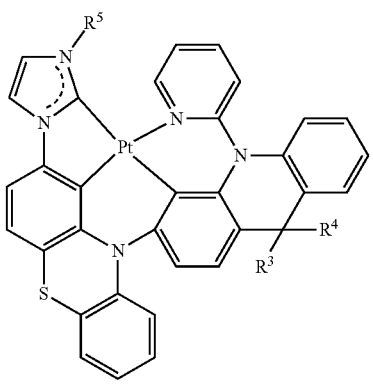

475
-continued
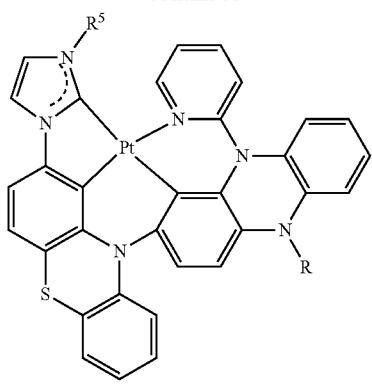
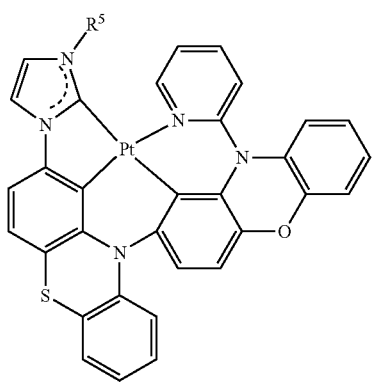
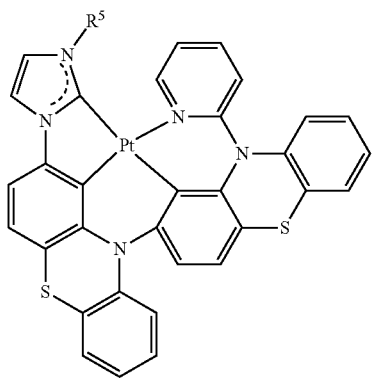
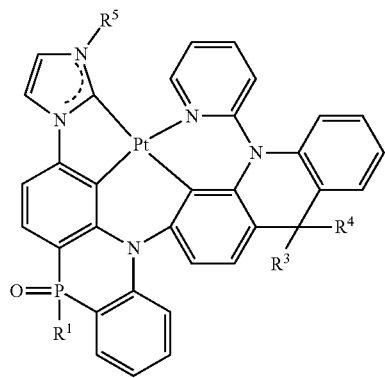
476
-continued
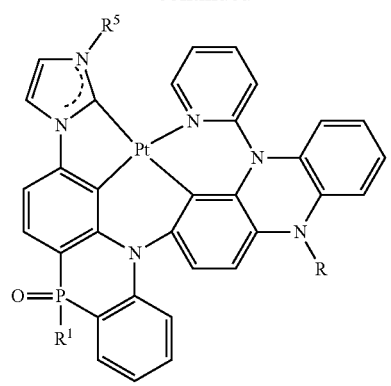
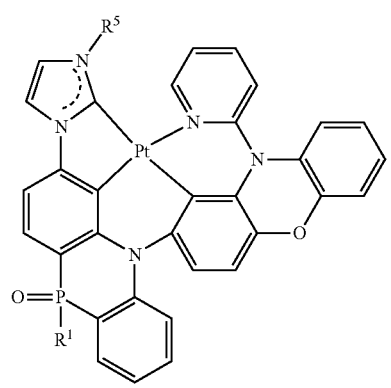
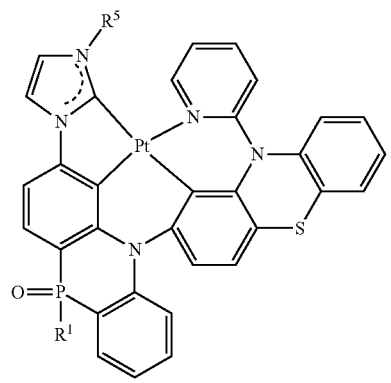
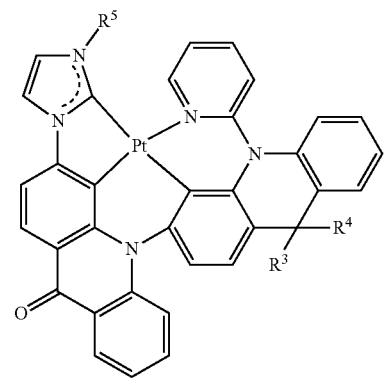

477
-continued
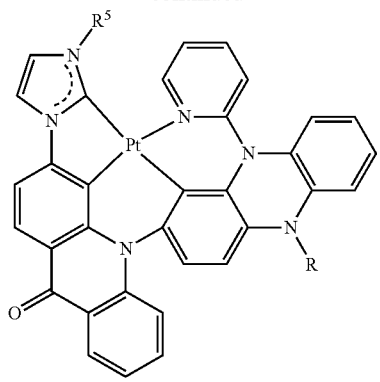
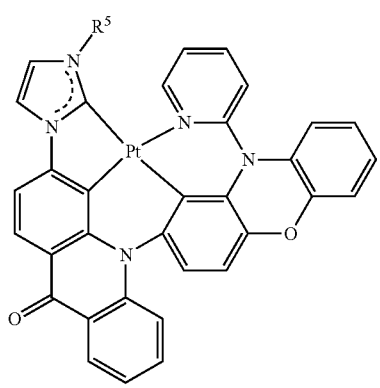
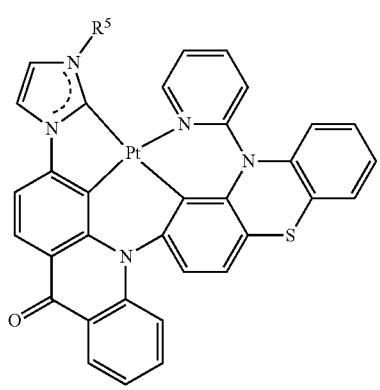
Structures 20
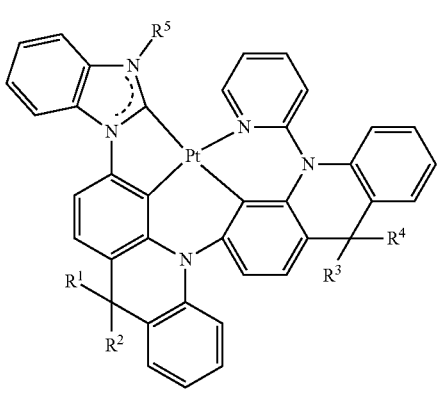
478
-continued
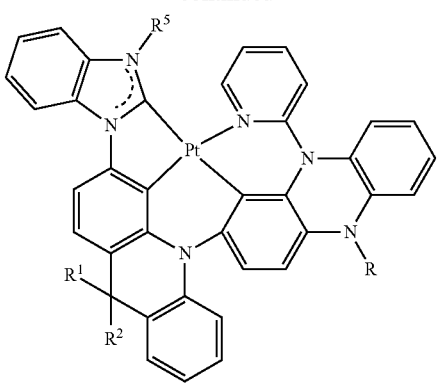
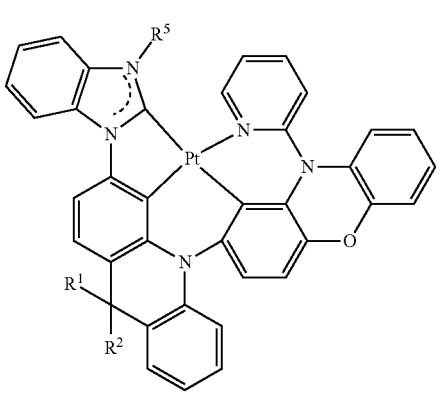
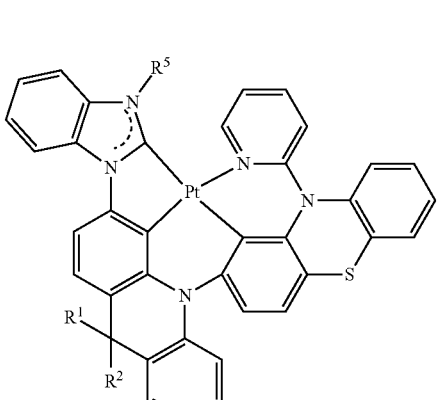
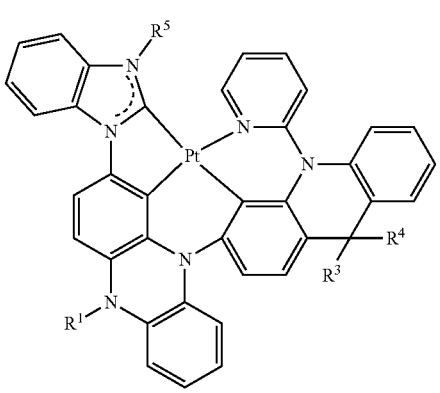

-continued
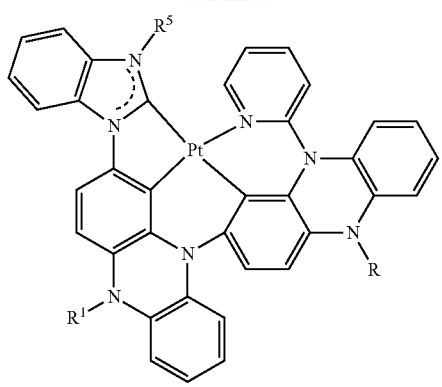
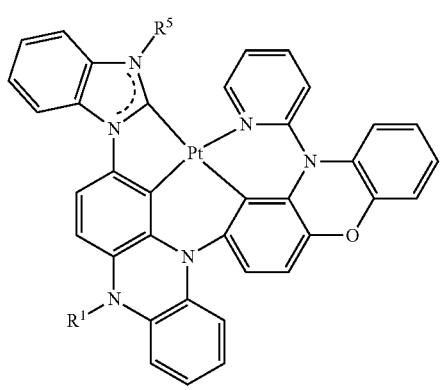
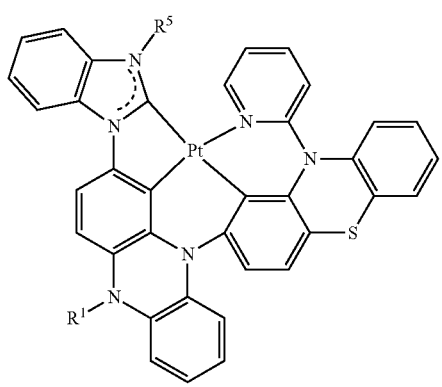
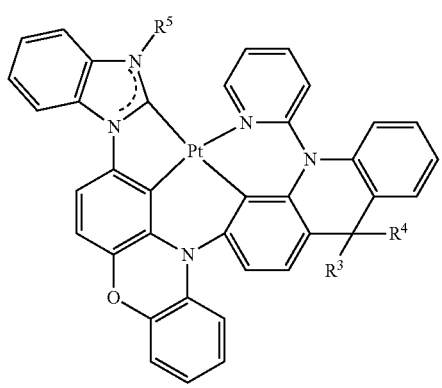
-continued
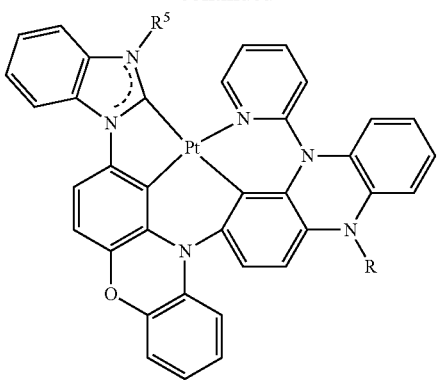
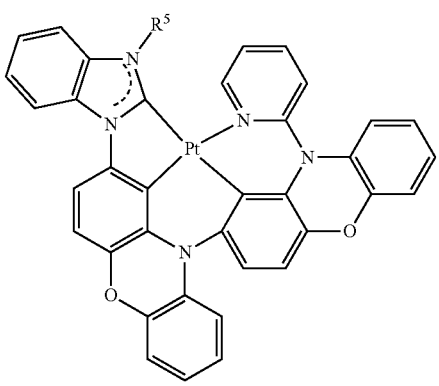
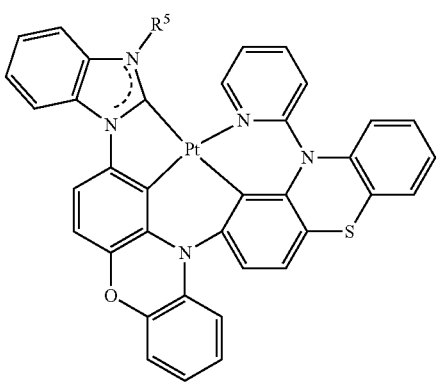
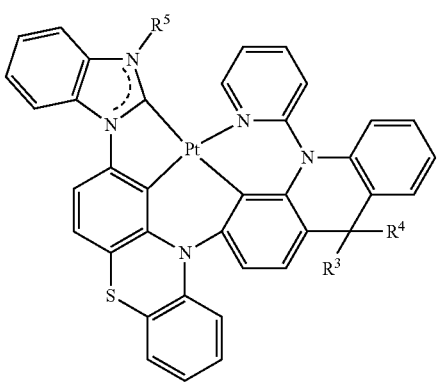

481
-continued
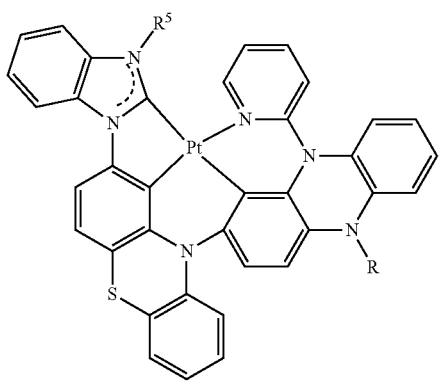
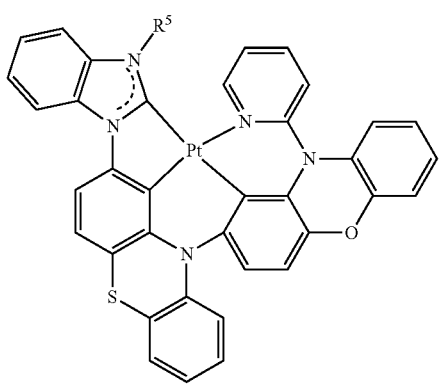
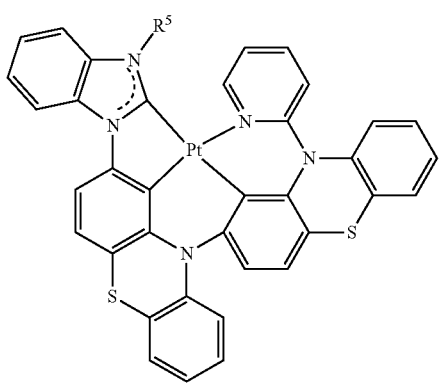
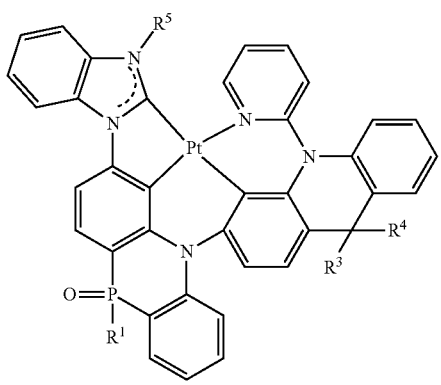
482
-continued
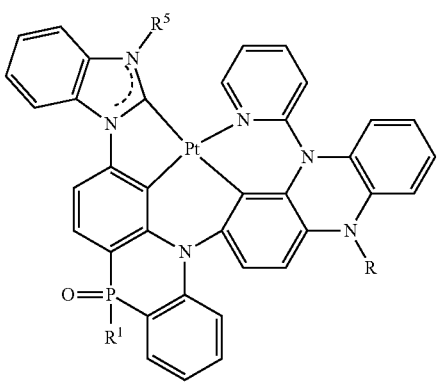
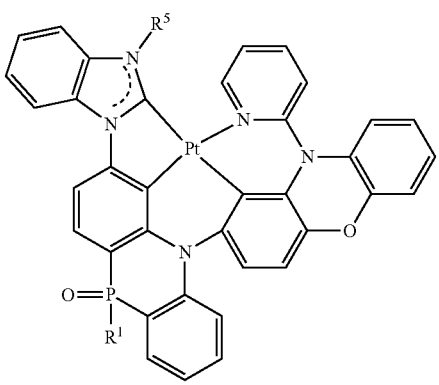
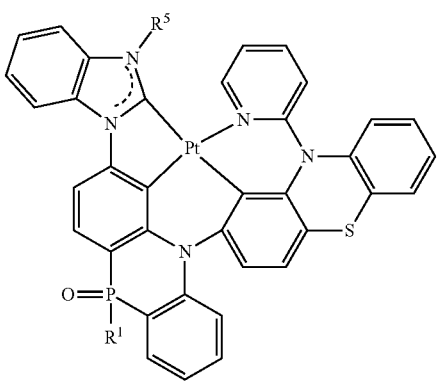
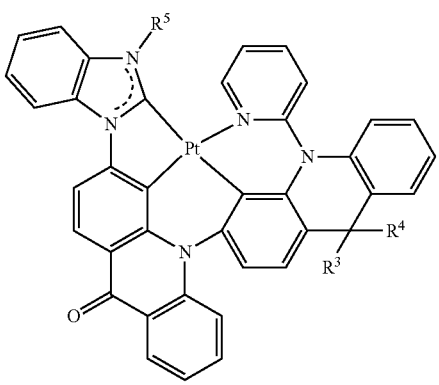

483
-continued
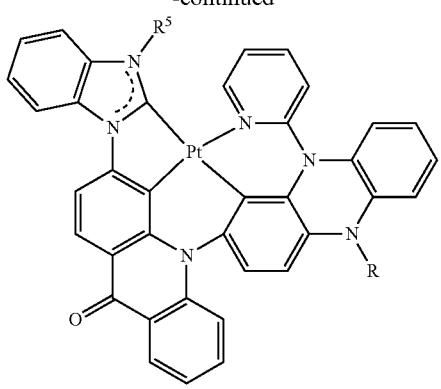
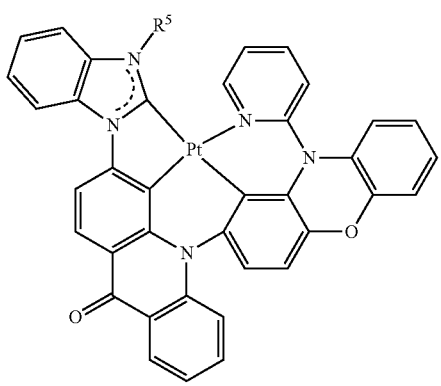
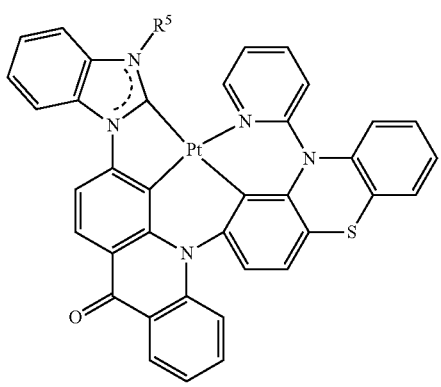
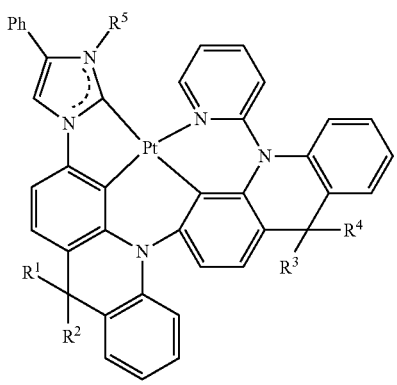
484
-continued
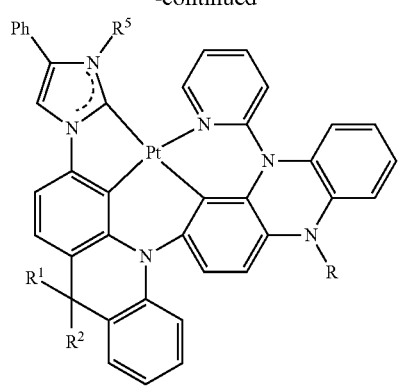
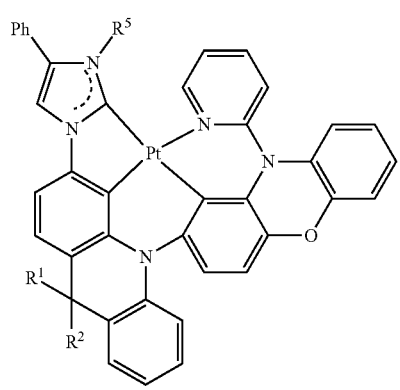
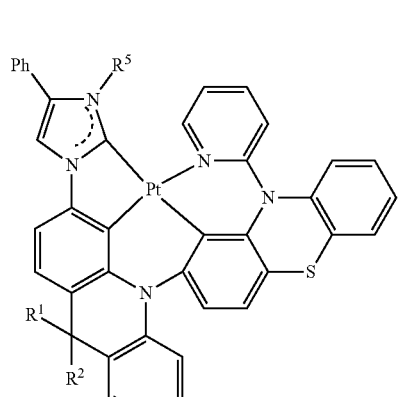
Structures 21
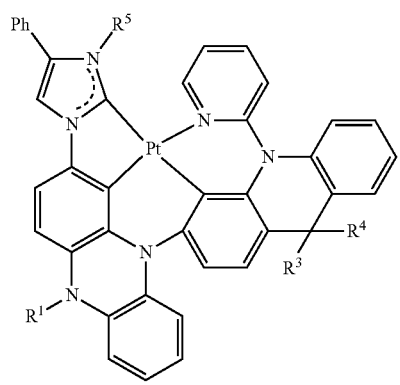

485
-continued
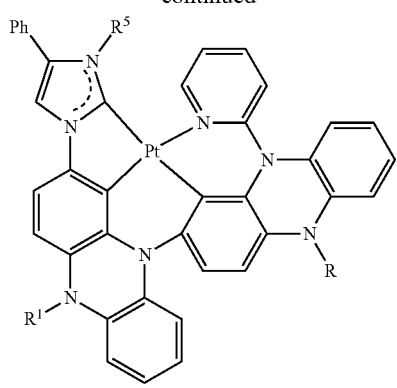
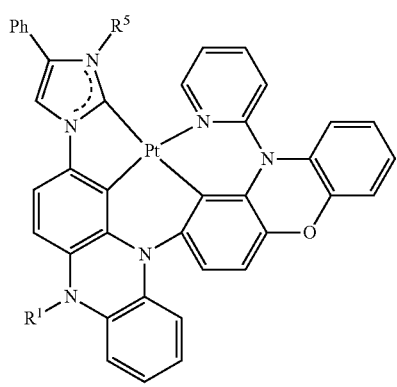
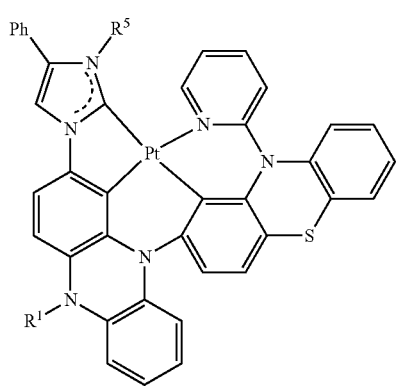
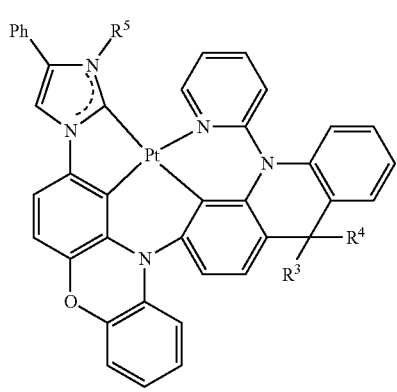
486
-continued
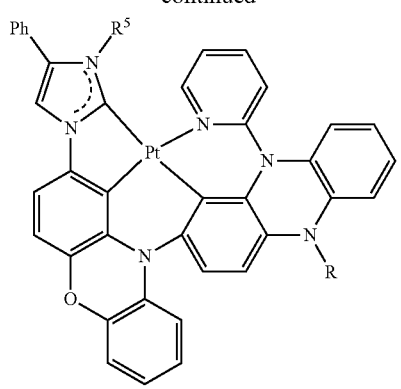
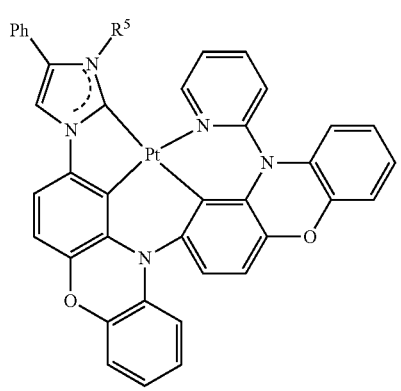
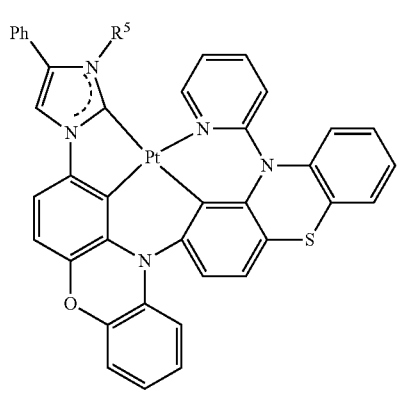
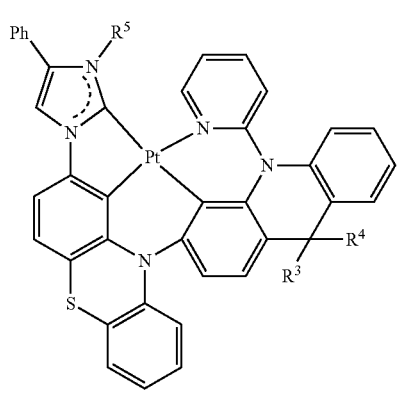

487
-continued
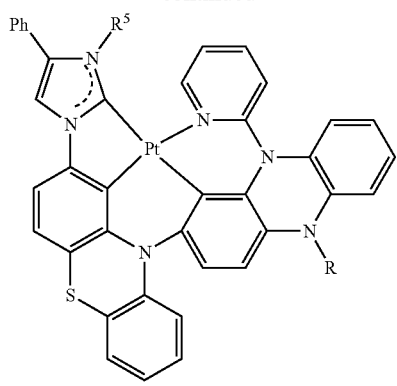
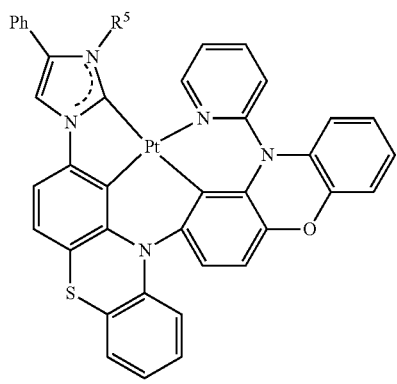
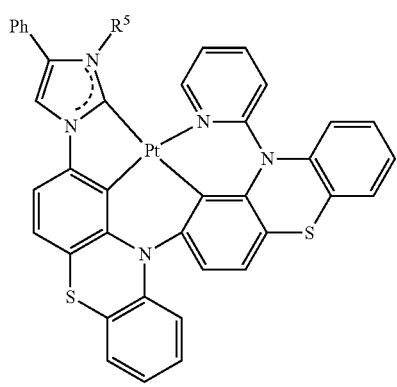
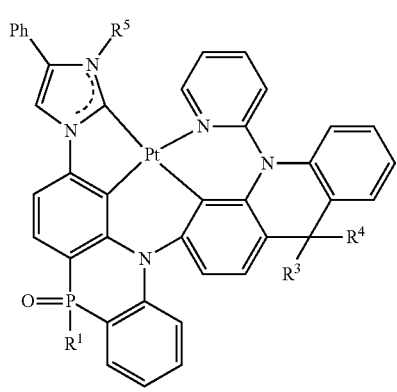
488
-continued
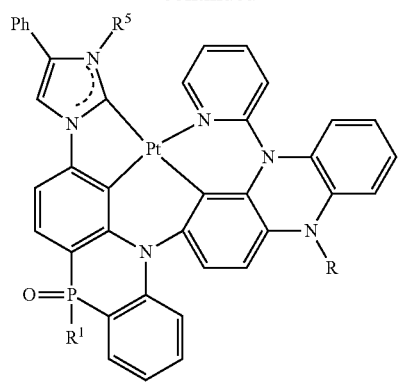
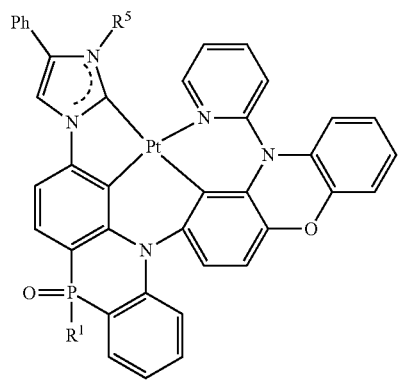
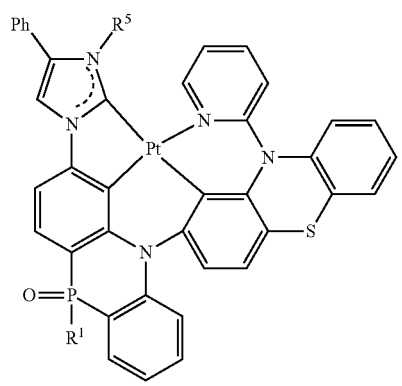
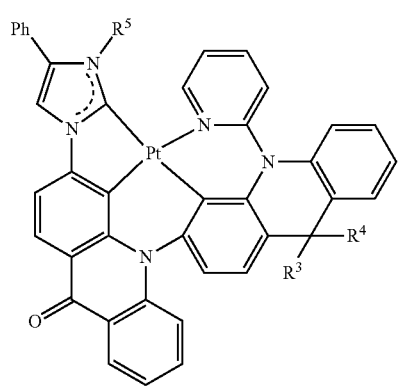

489
-continued
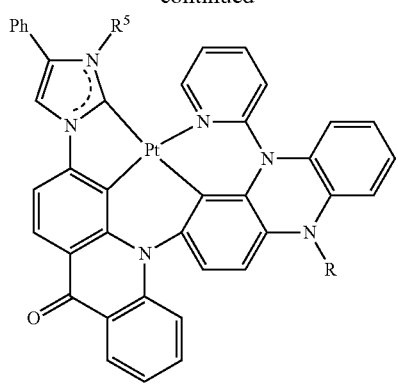
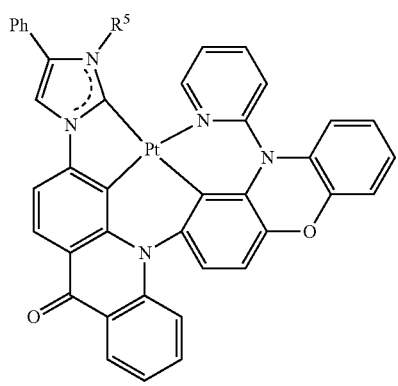
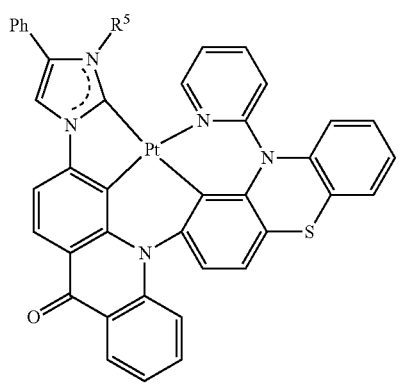
Structures 22
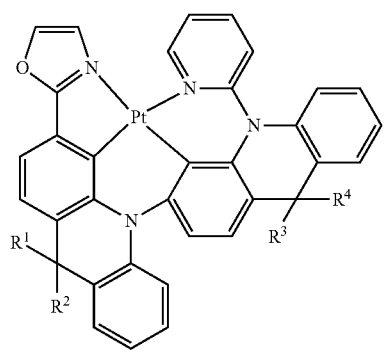
490
-continued
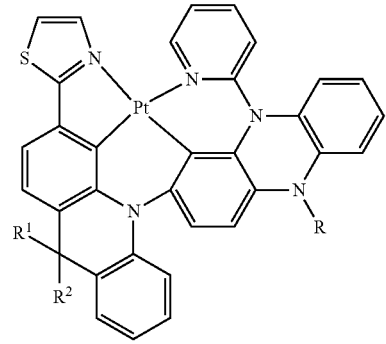
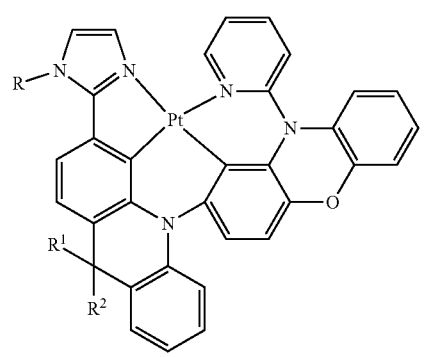
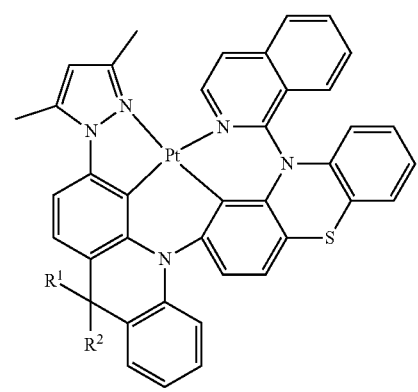
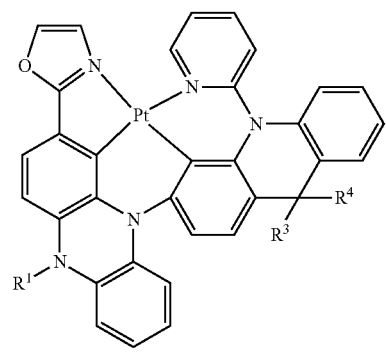

491
-continued
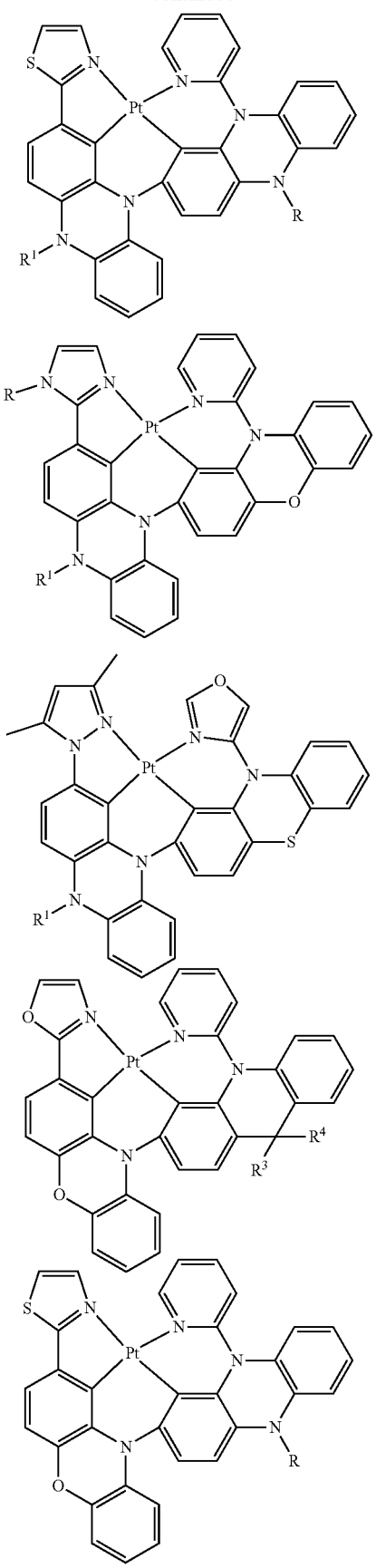
492
-continued
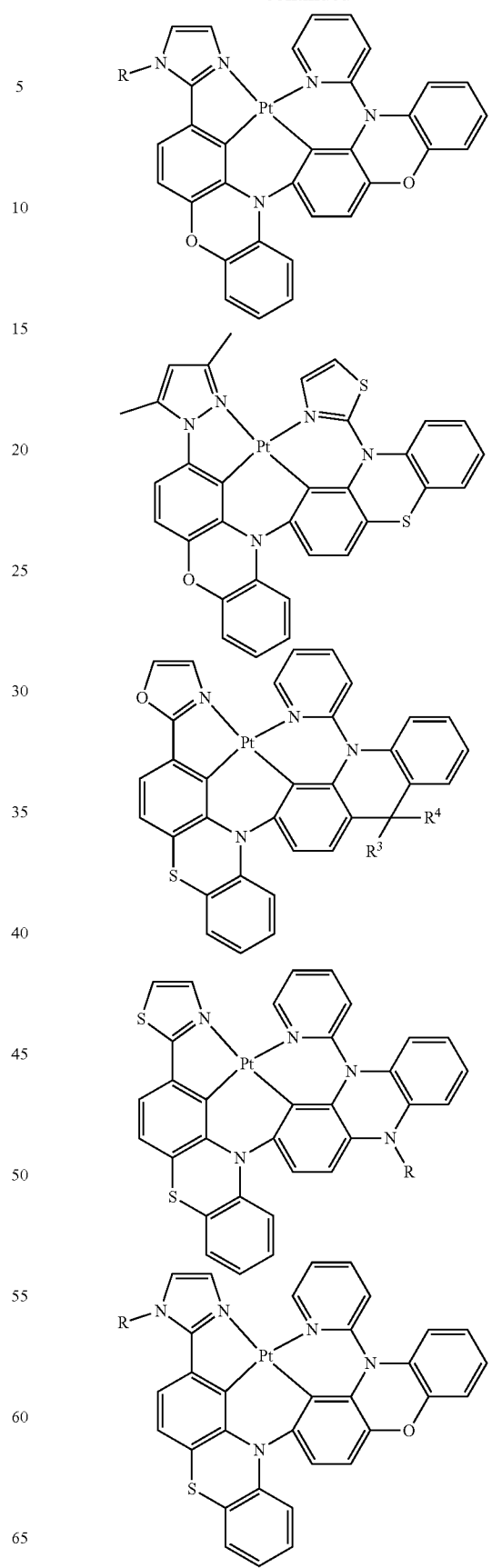

493
-continued
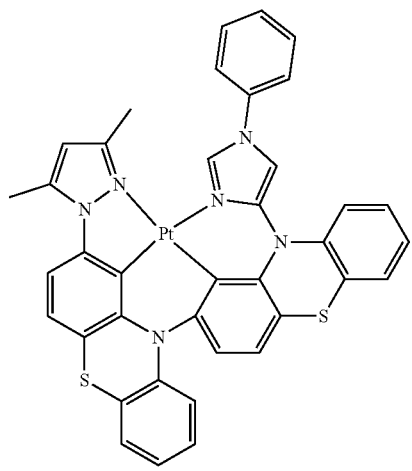
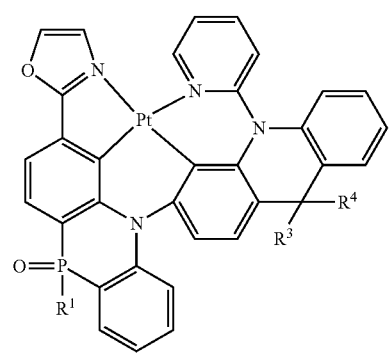
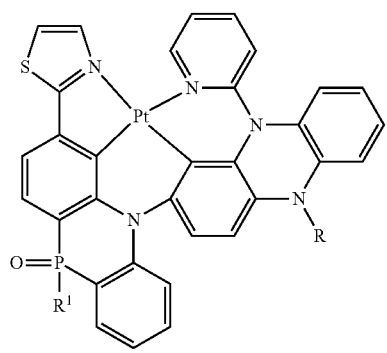
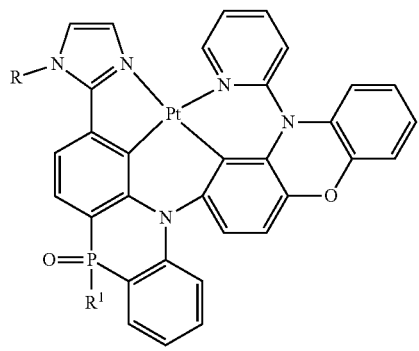
494
-continued
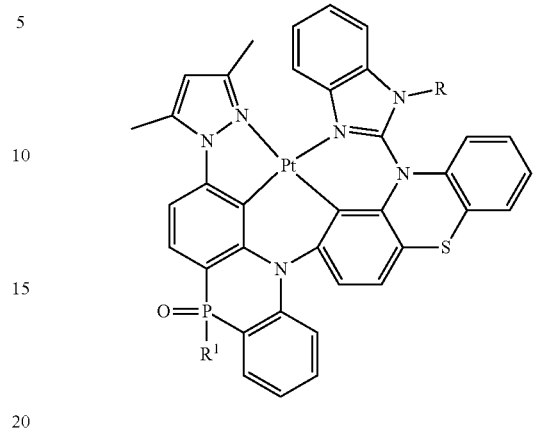
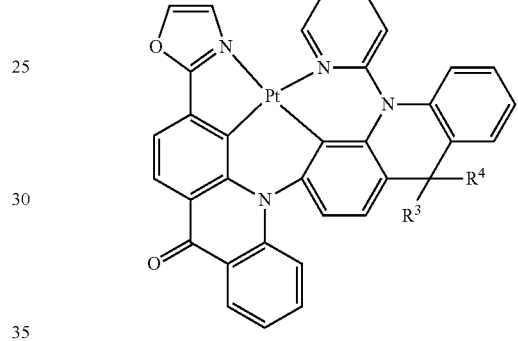
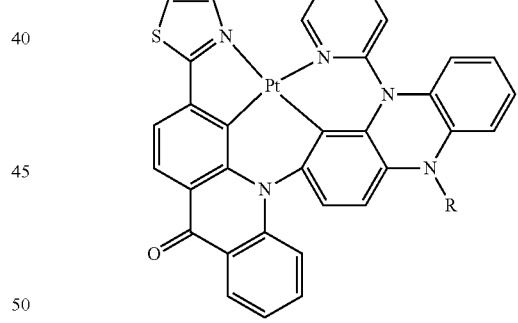
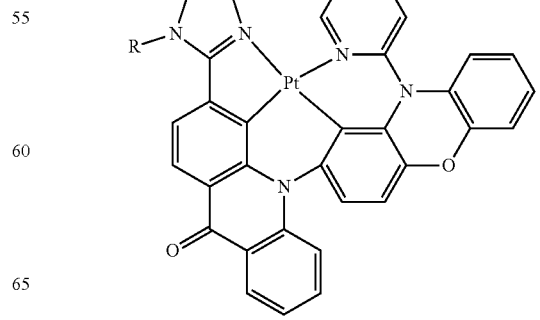

-continued
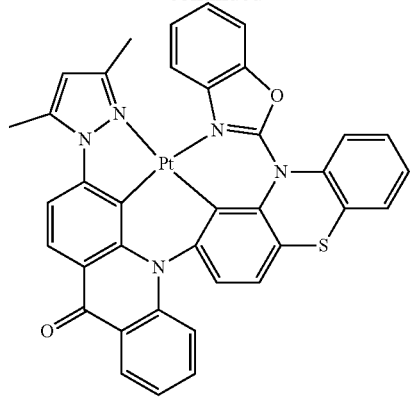
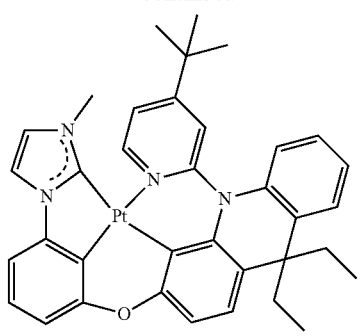
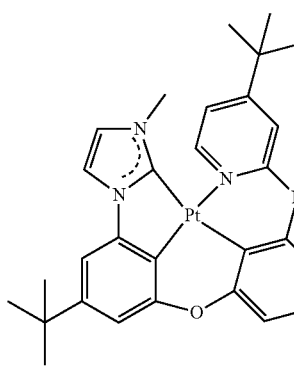
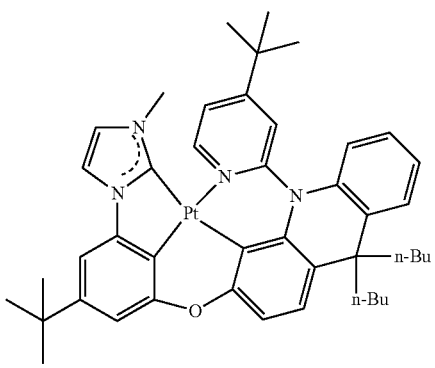
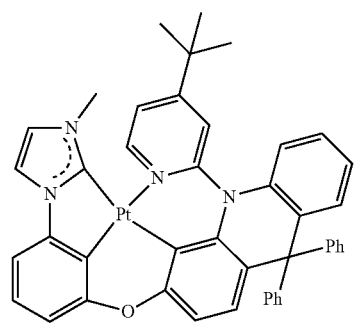
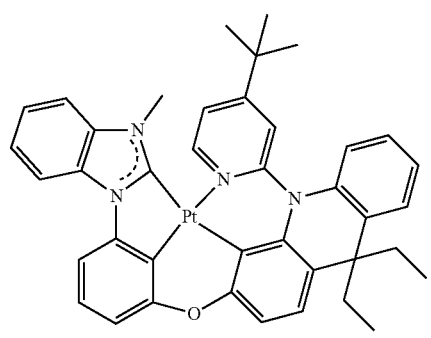

497
-continued
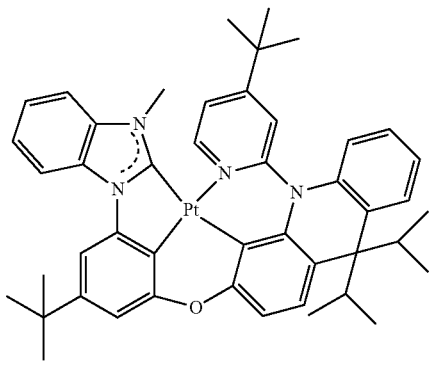
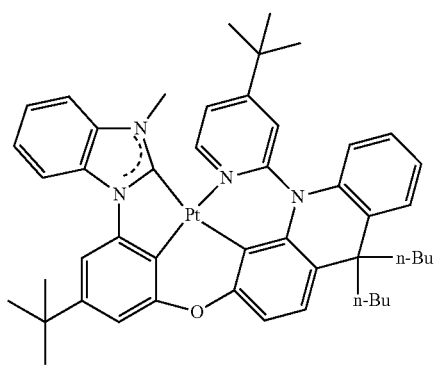
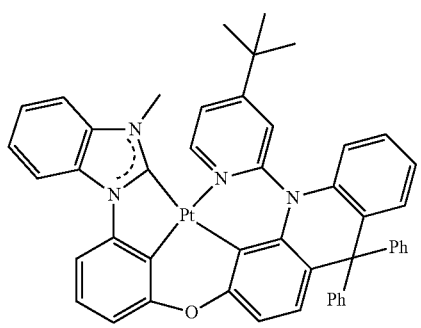
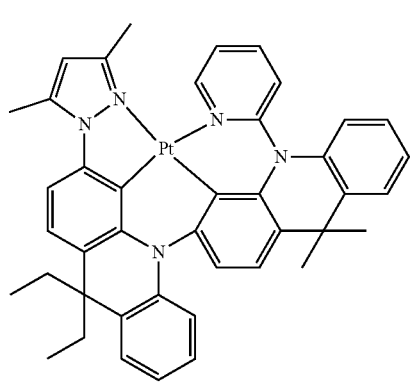
498
-continued
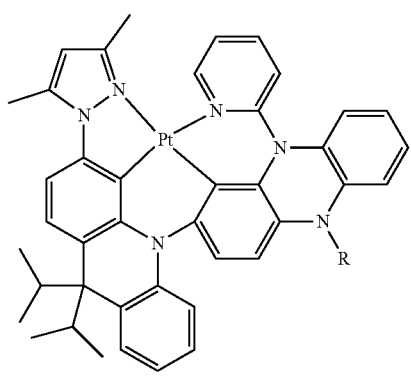
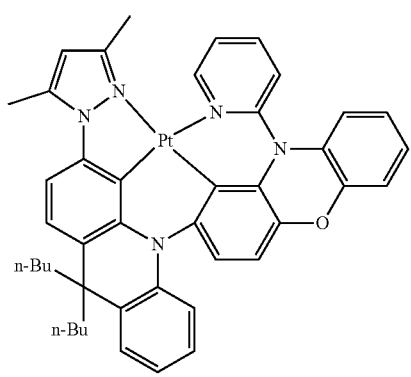
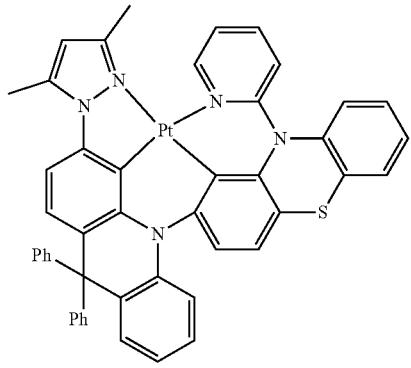
Structures 25
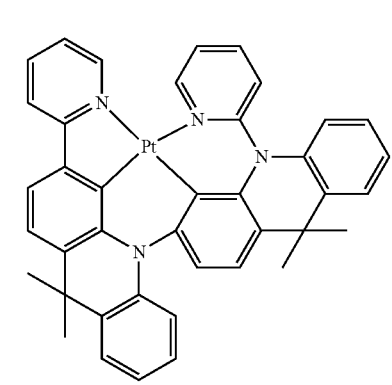

499
-continued
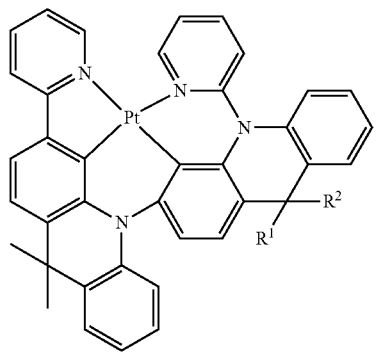
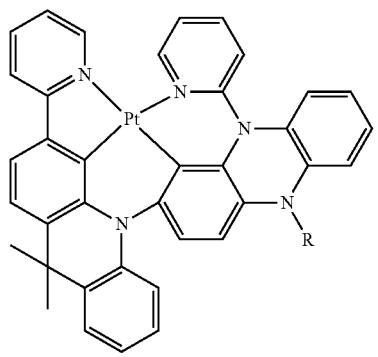
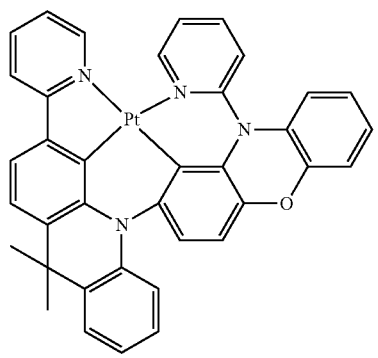
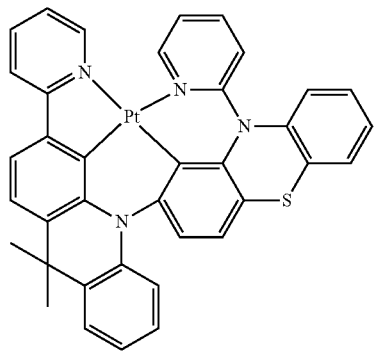
500
-continued
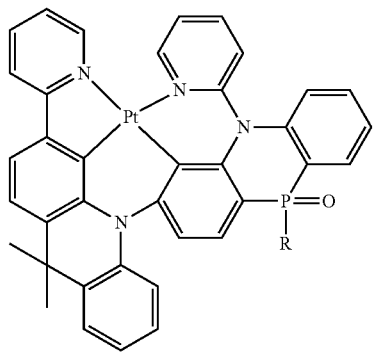
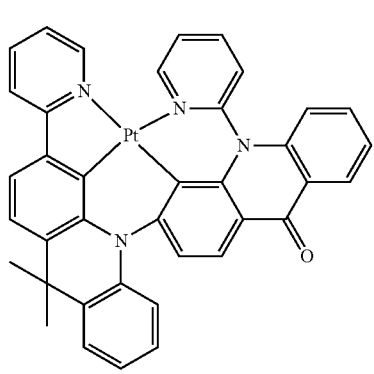
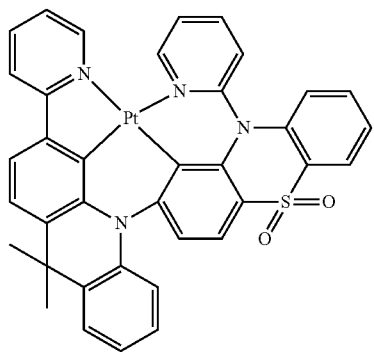
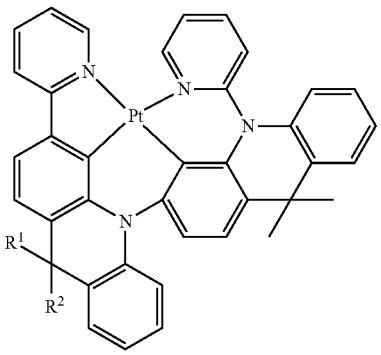

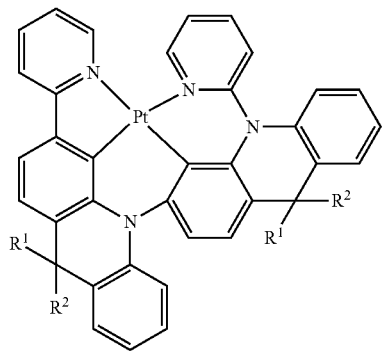
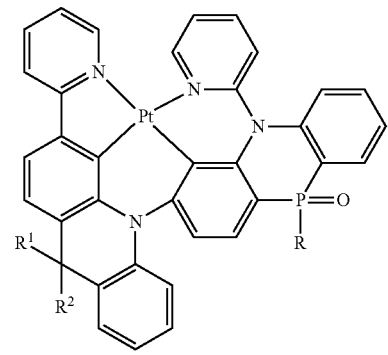
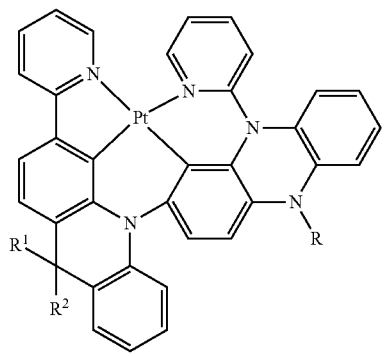
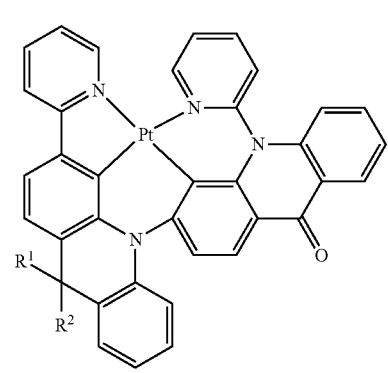
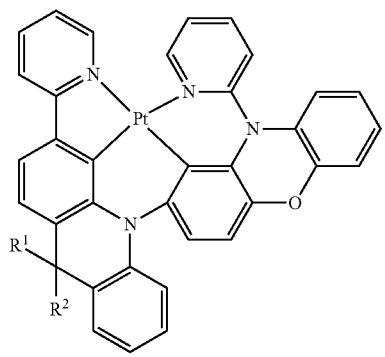
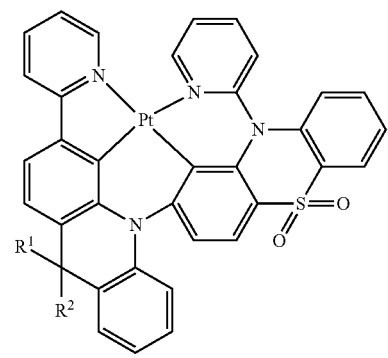
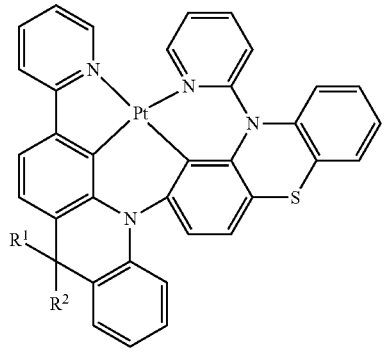
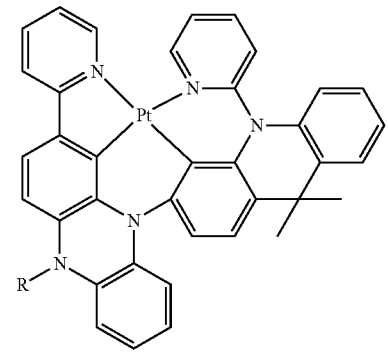

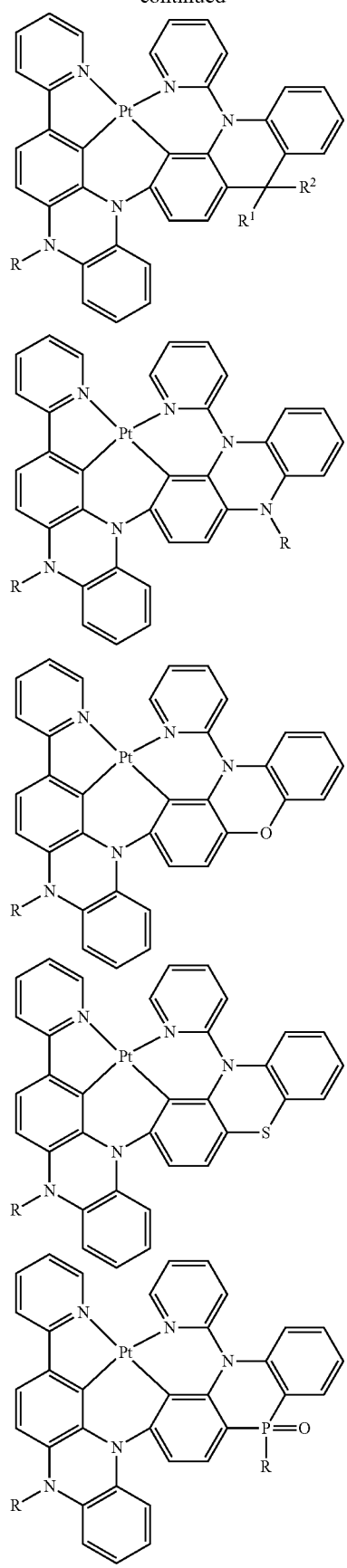
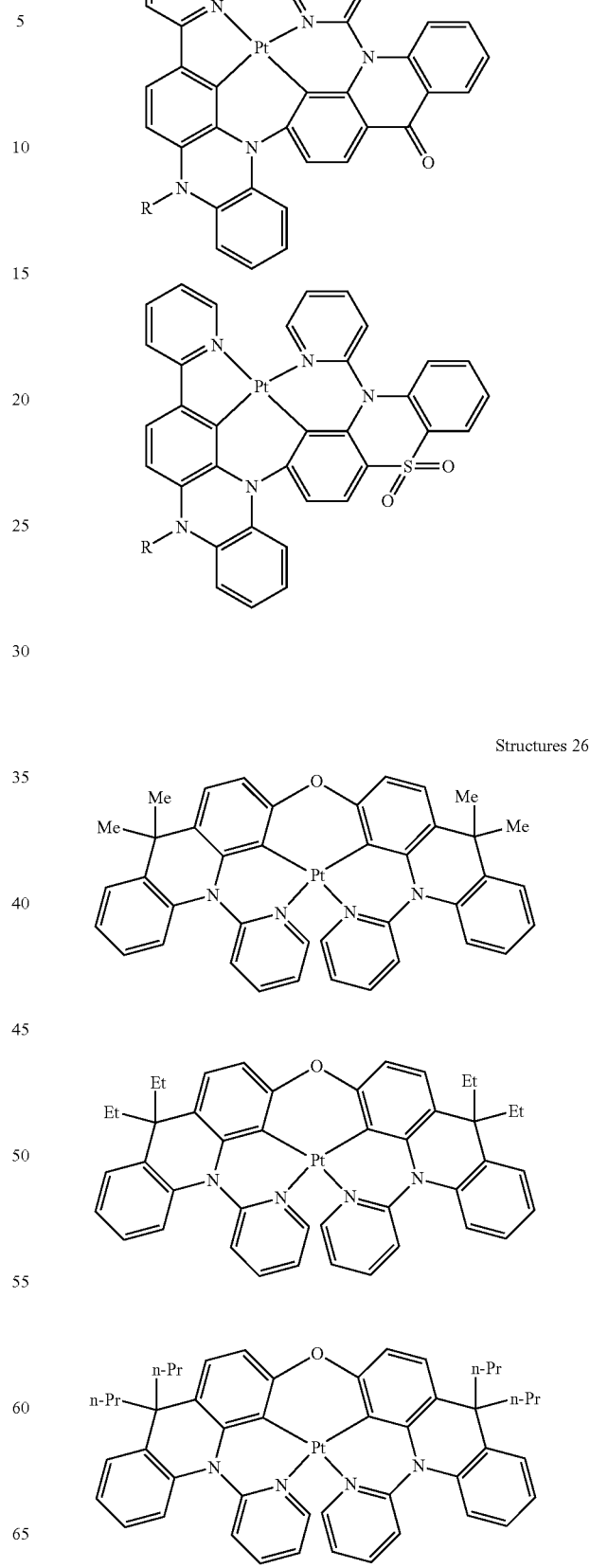

505
-continued
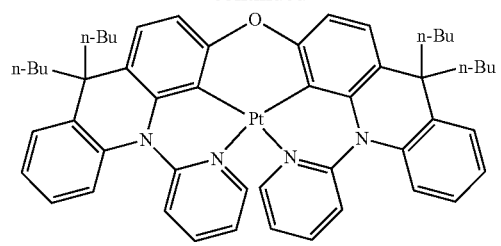
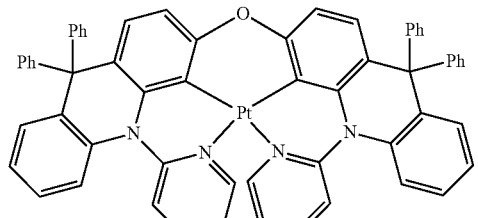
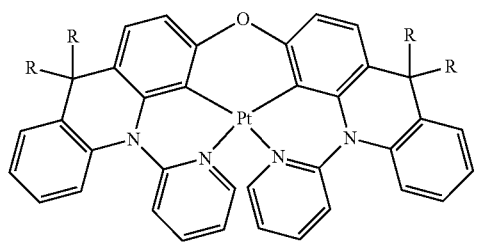
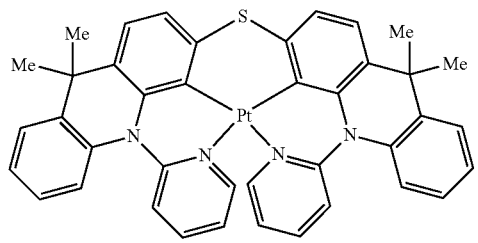
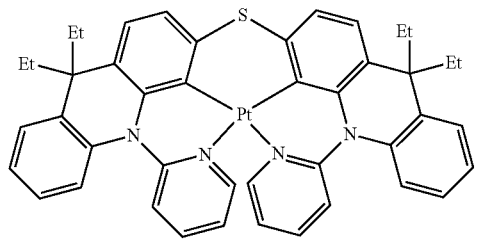
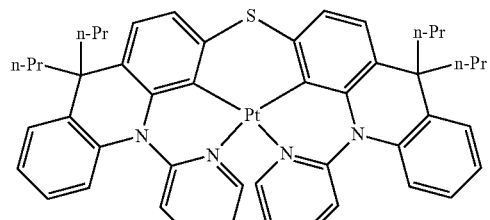
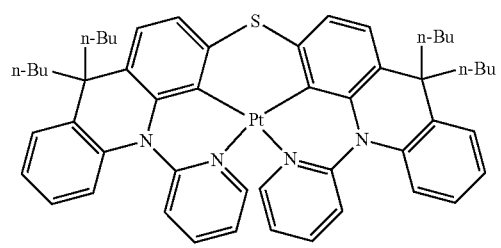
506
-continued
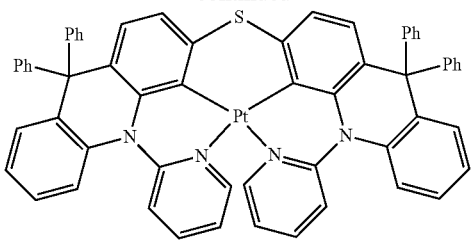
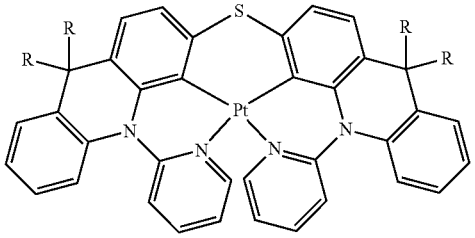
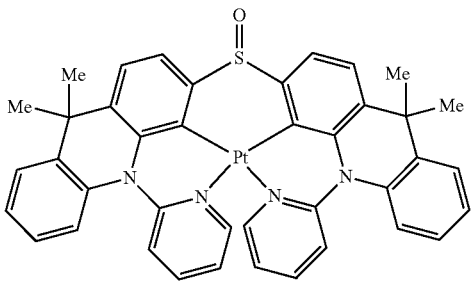
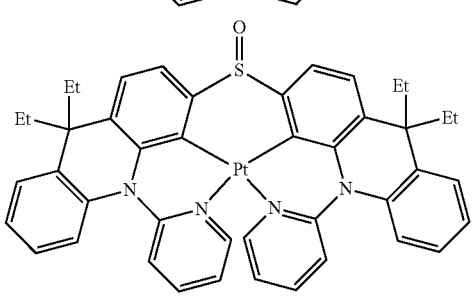
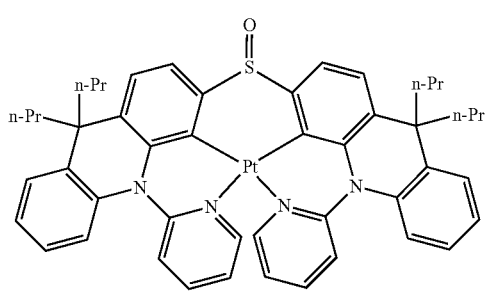
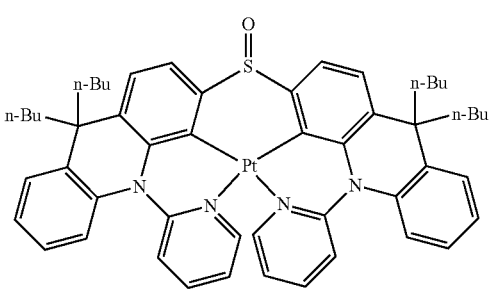

507
-continued
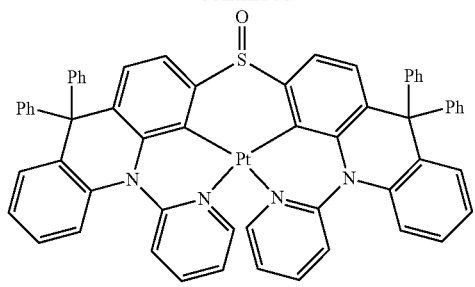
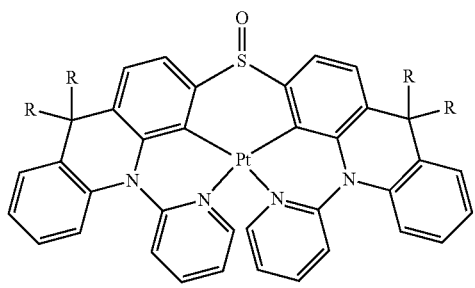
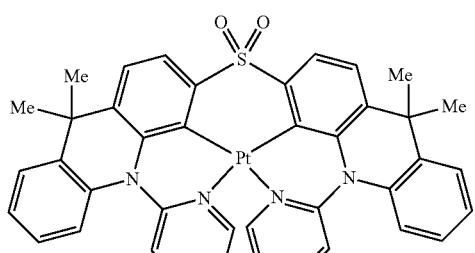
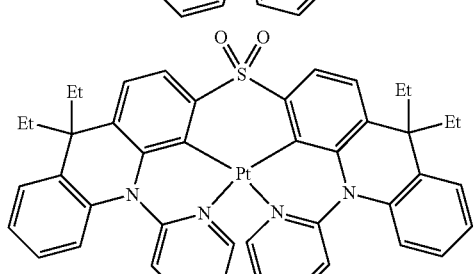
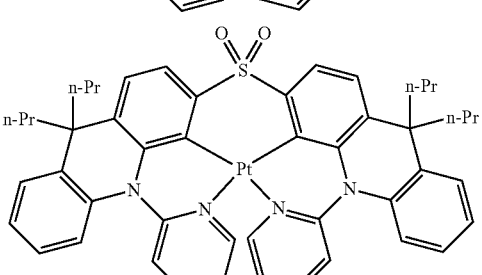
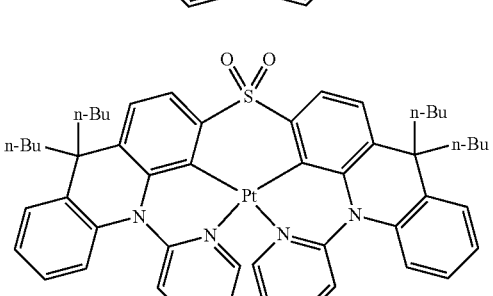
508
-continued
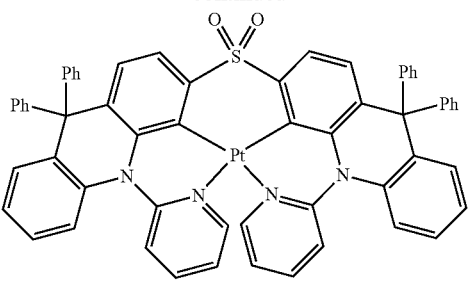
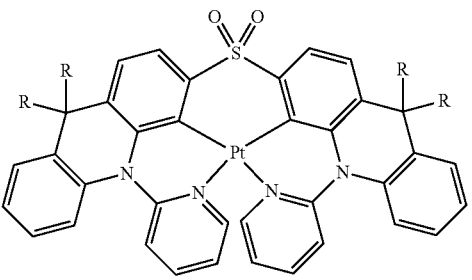
Structures 27
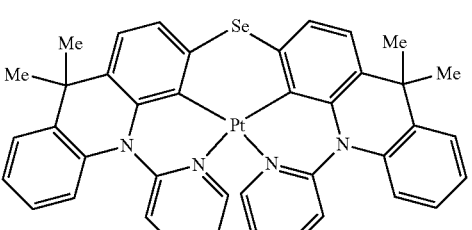
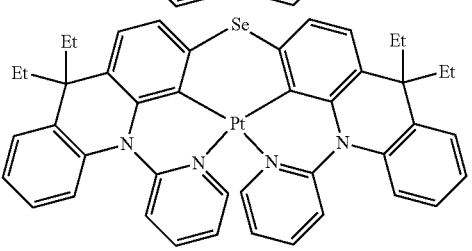
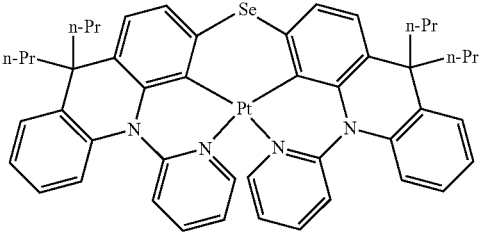
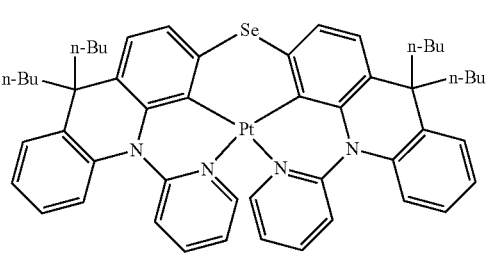

509
-continued
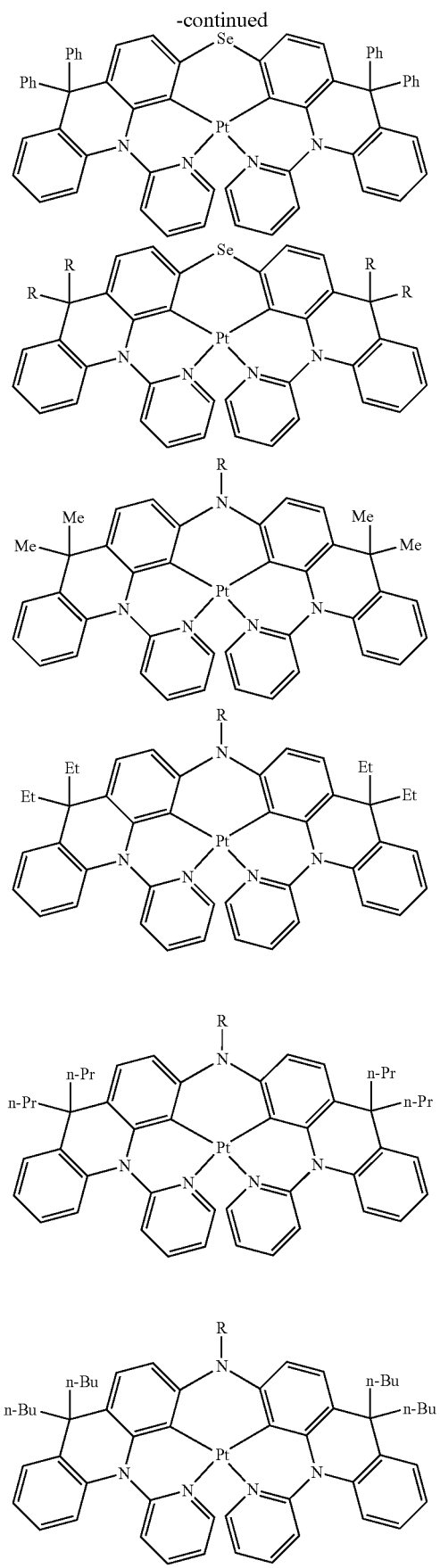
510
-continued
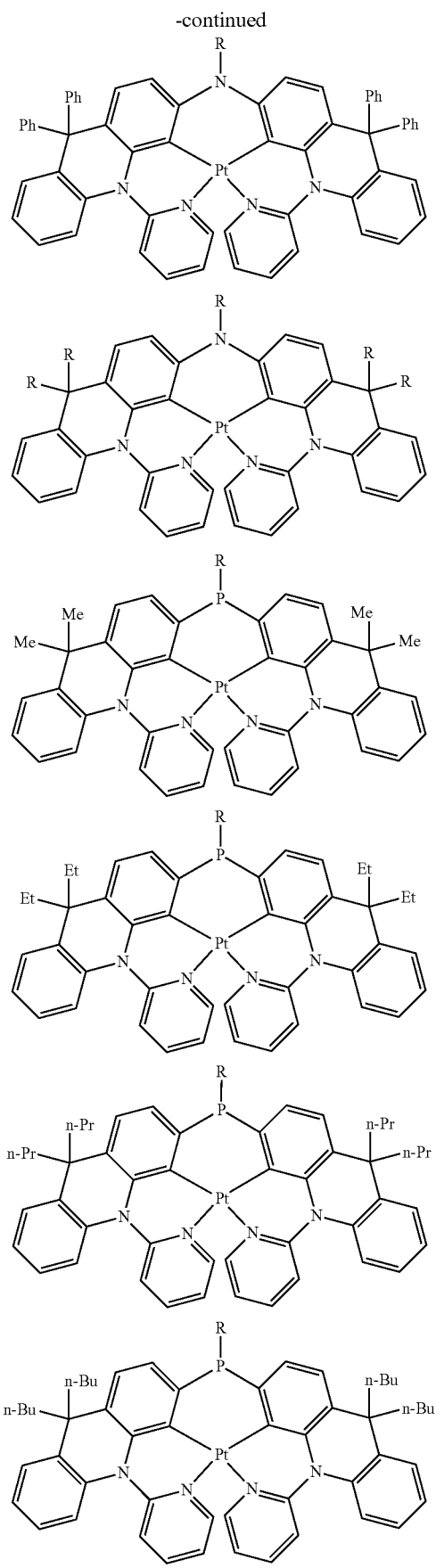

511
-continued
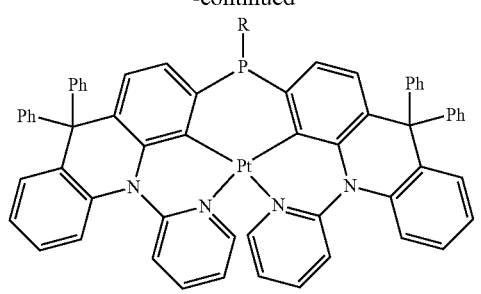
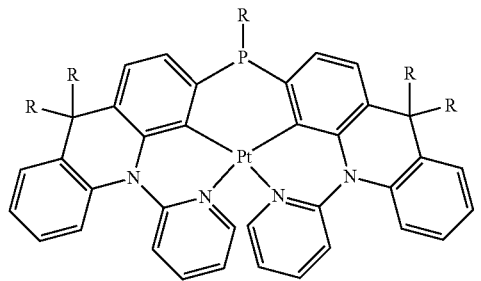
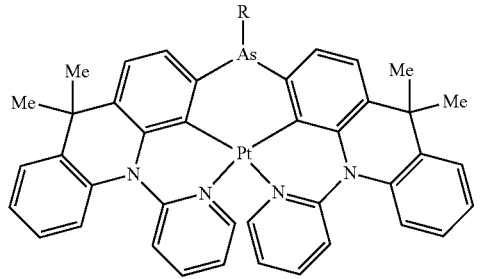
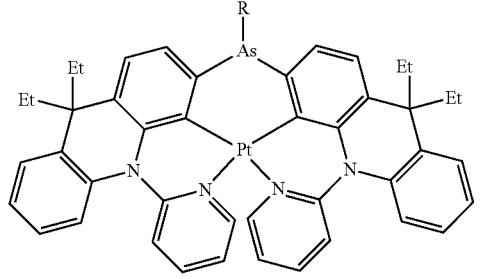
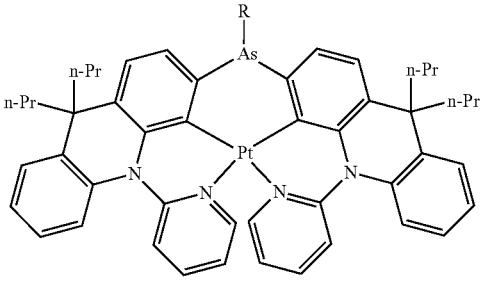
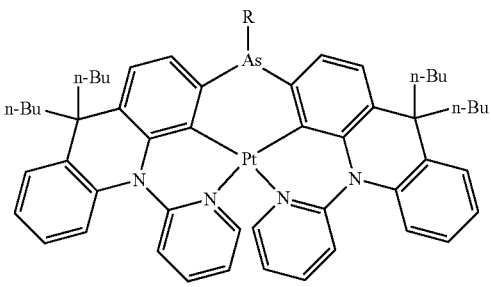
512
-continued
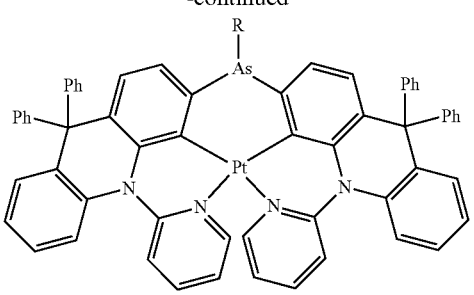
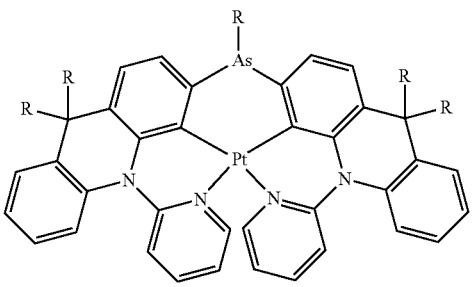
Structures 28
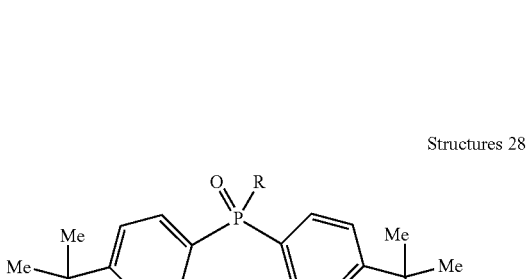
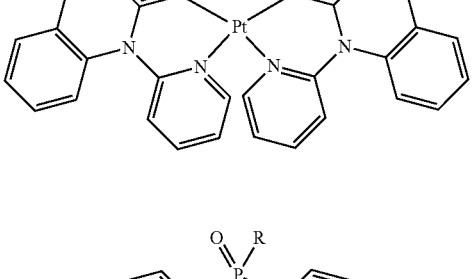
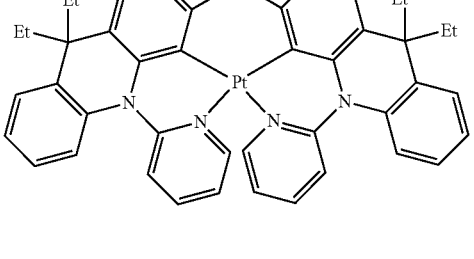
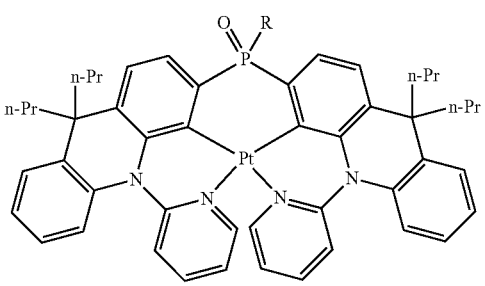

513
-continued
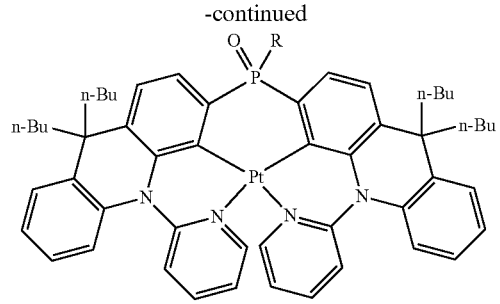
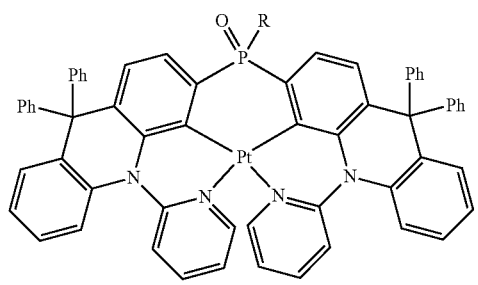
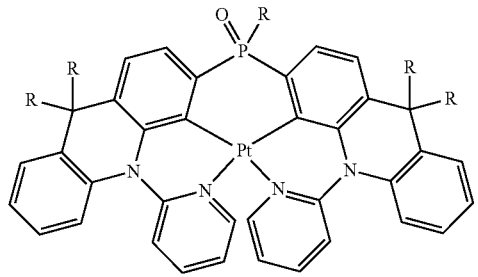
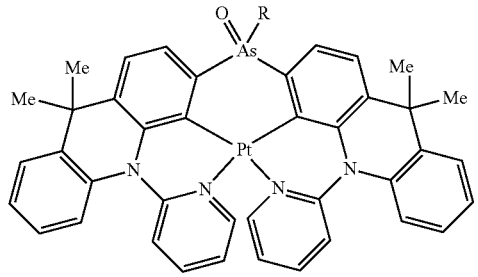
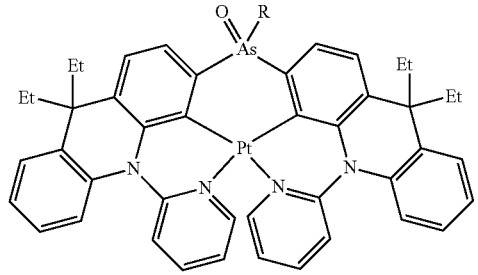
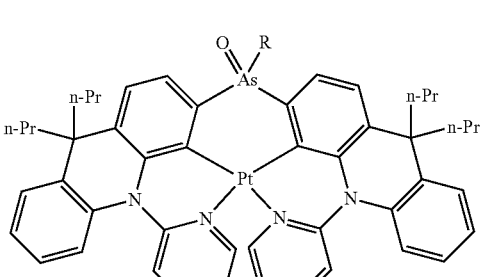
514
-continued
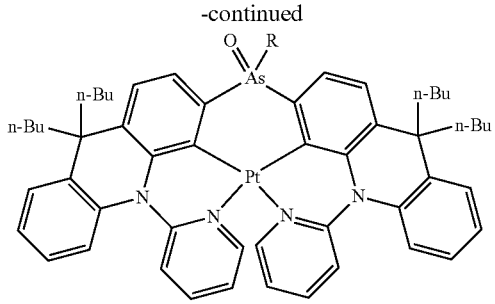
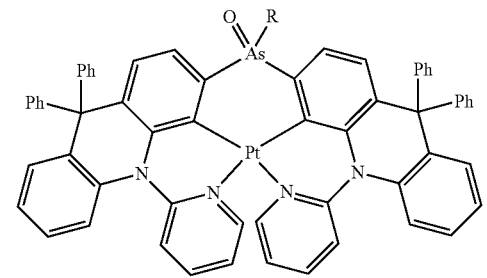
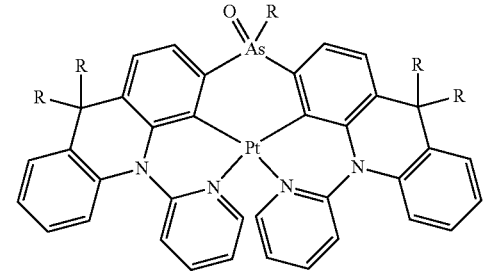
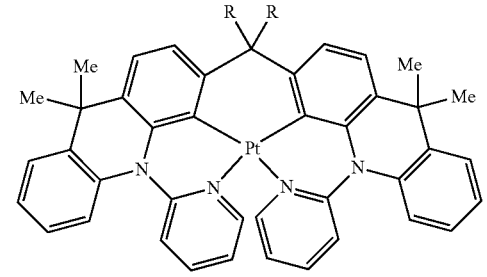
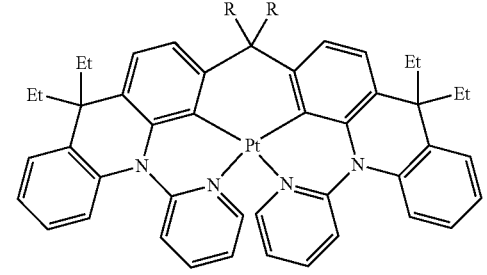
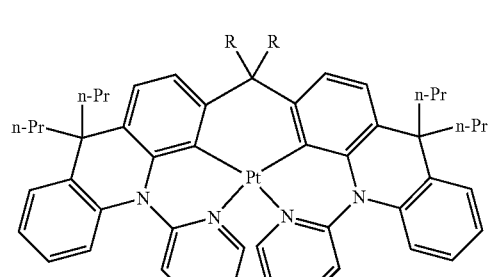

515 -continued
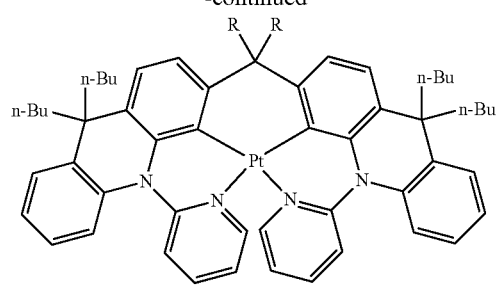
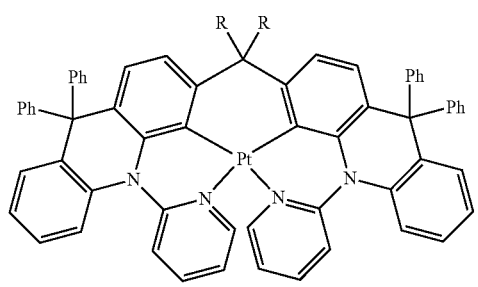
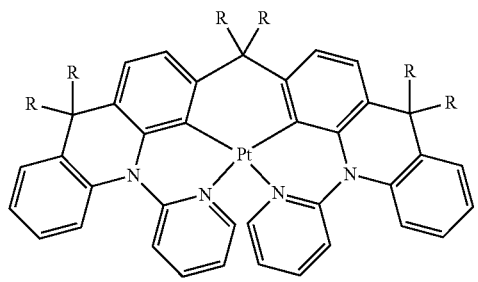
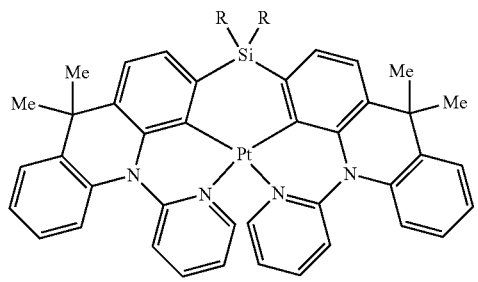
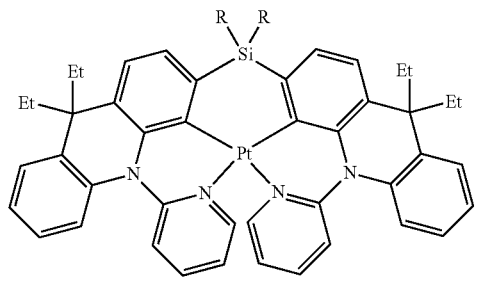
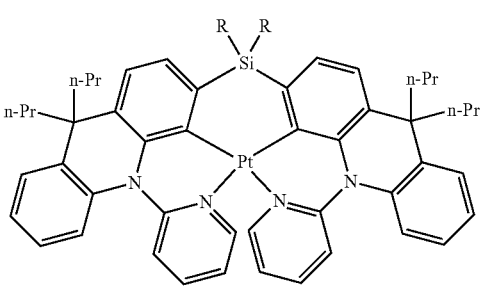
516 -continued
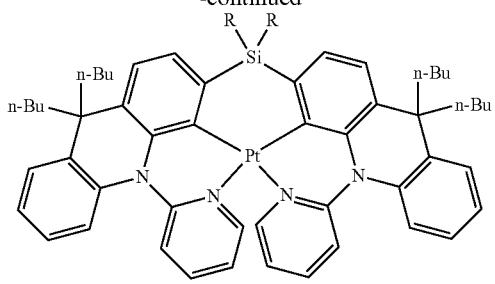
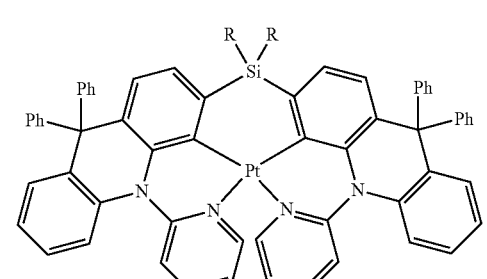
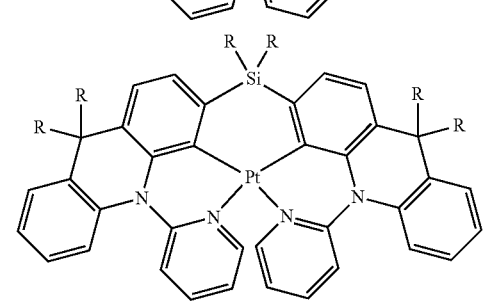
Structures 29
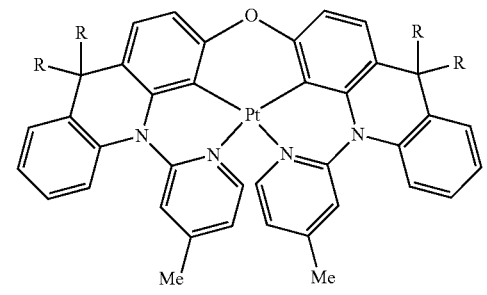
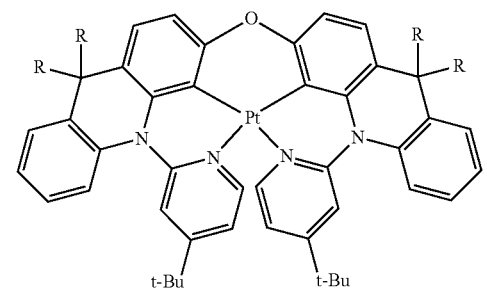

517
-continued
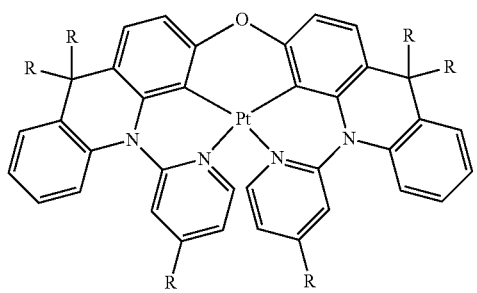
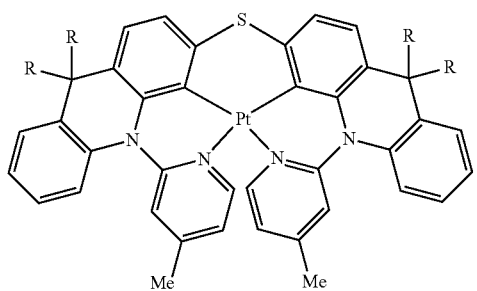
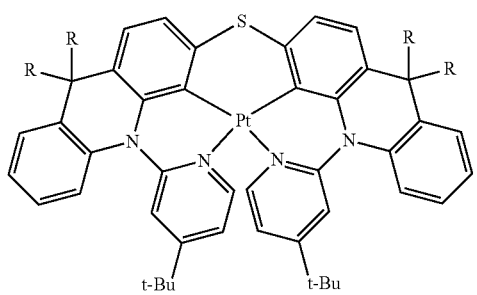
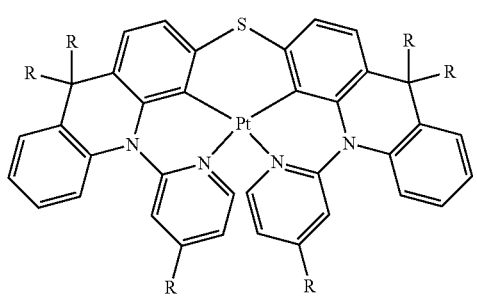
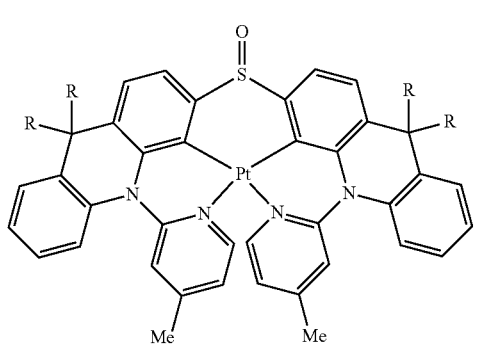
518
-continued
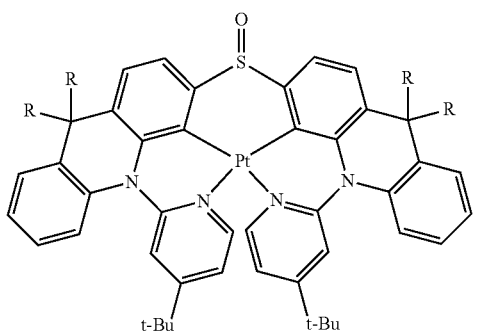
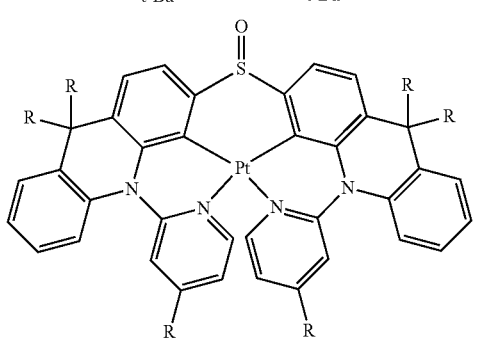
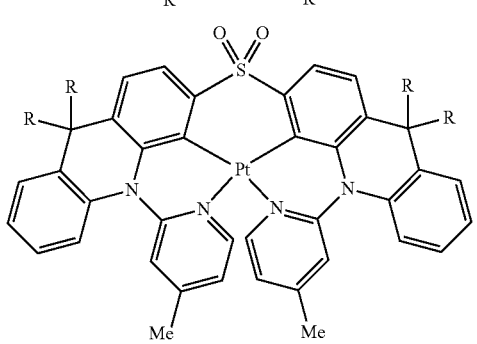
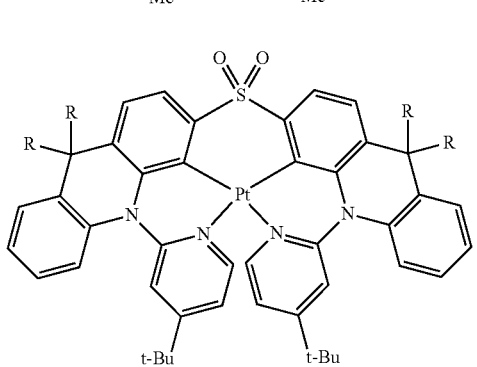
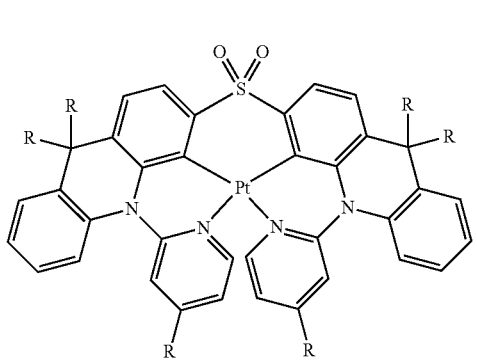

519
-continued
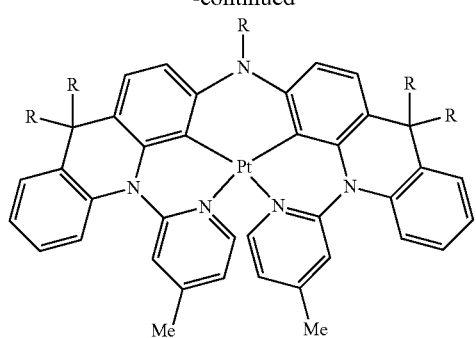
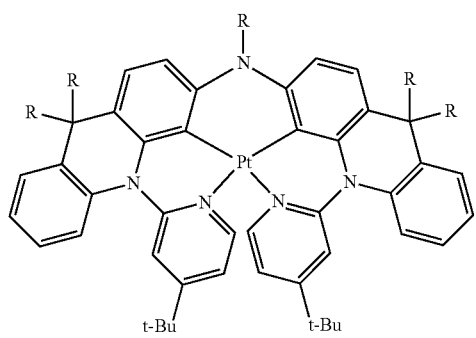
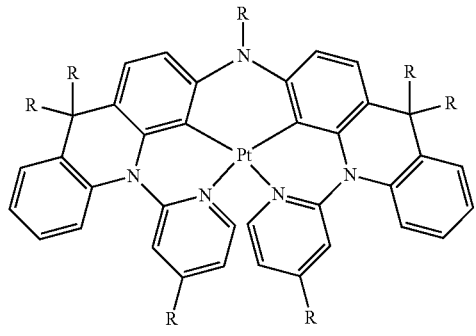
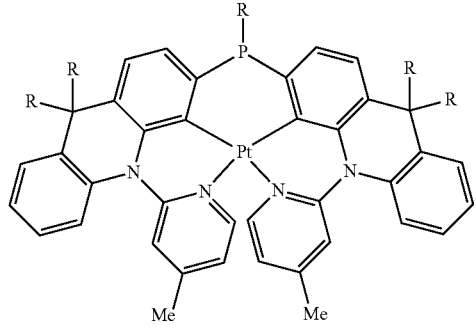
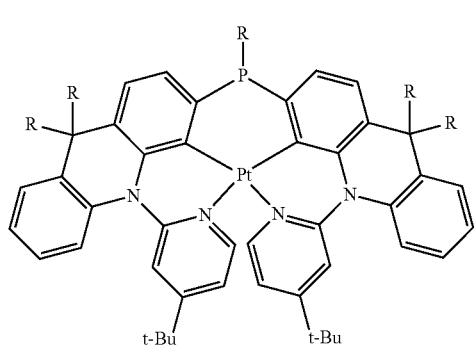
520
-continued
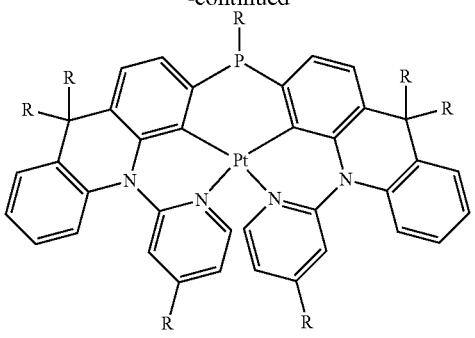
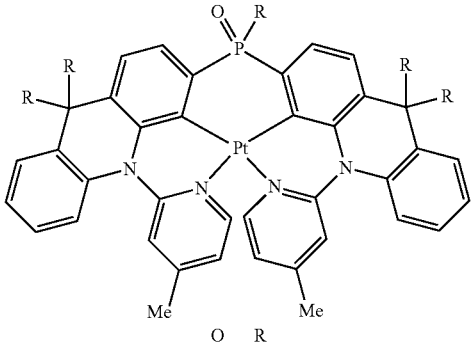
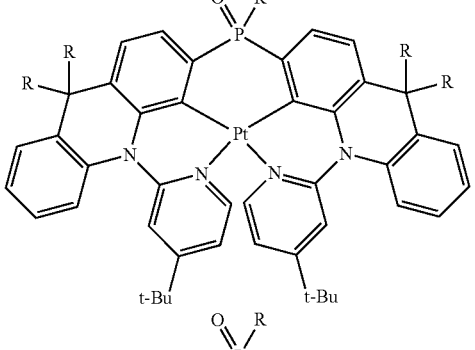
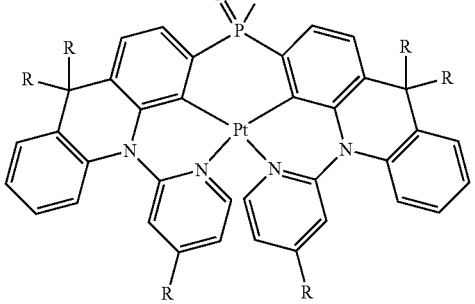
Structures 30
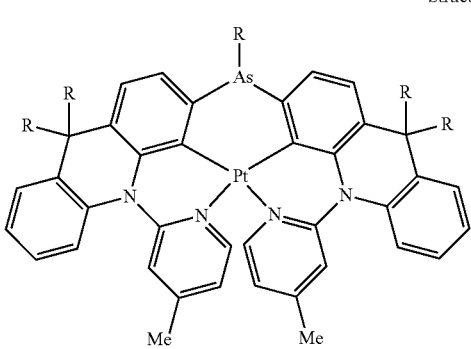

521
-continued
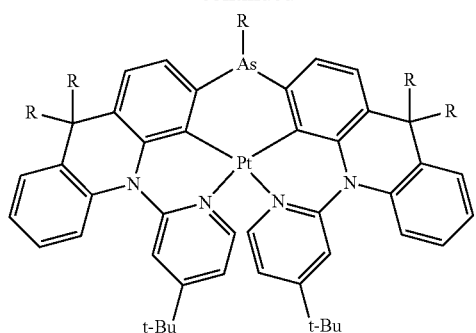
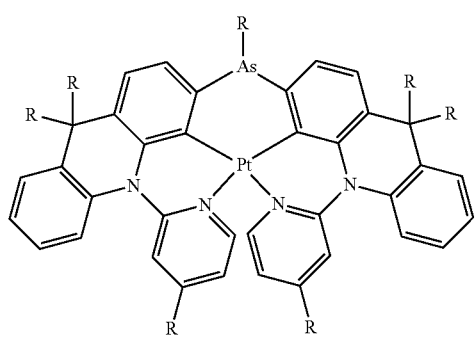
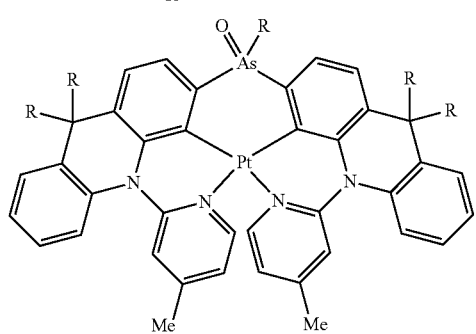
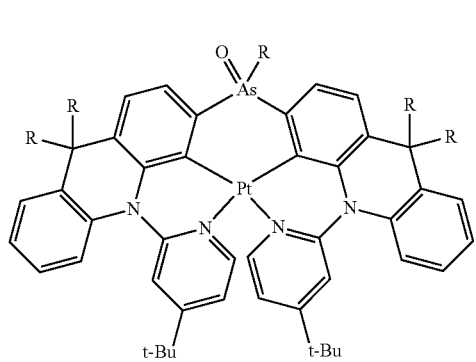
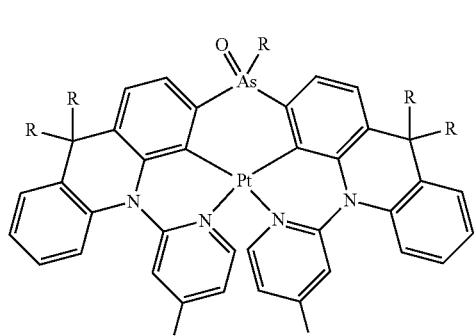
522
-continued
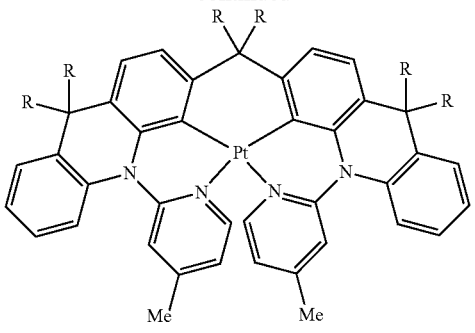
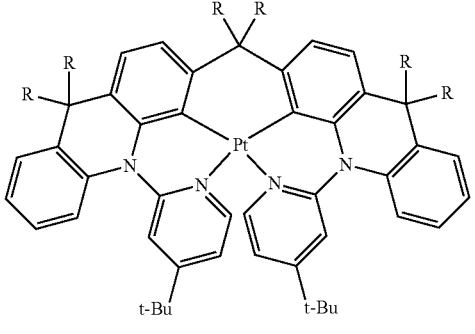
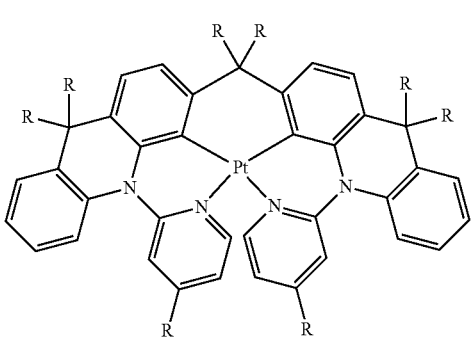
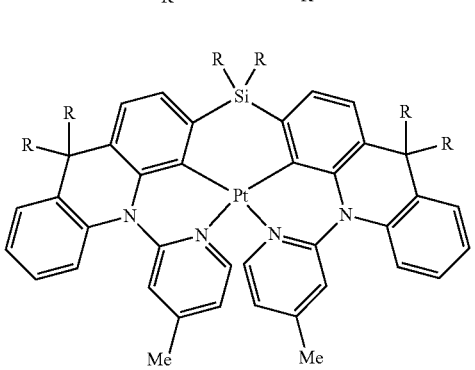
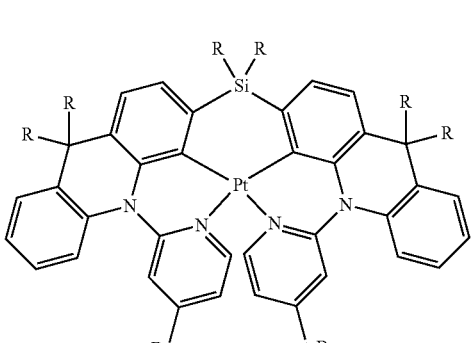

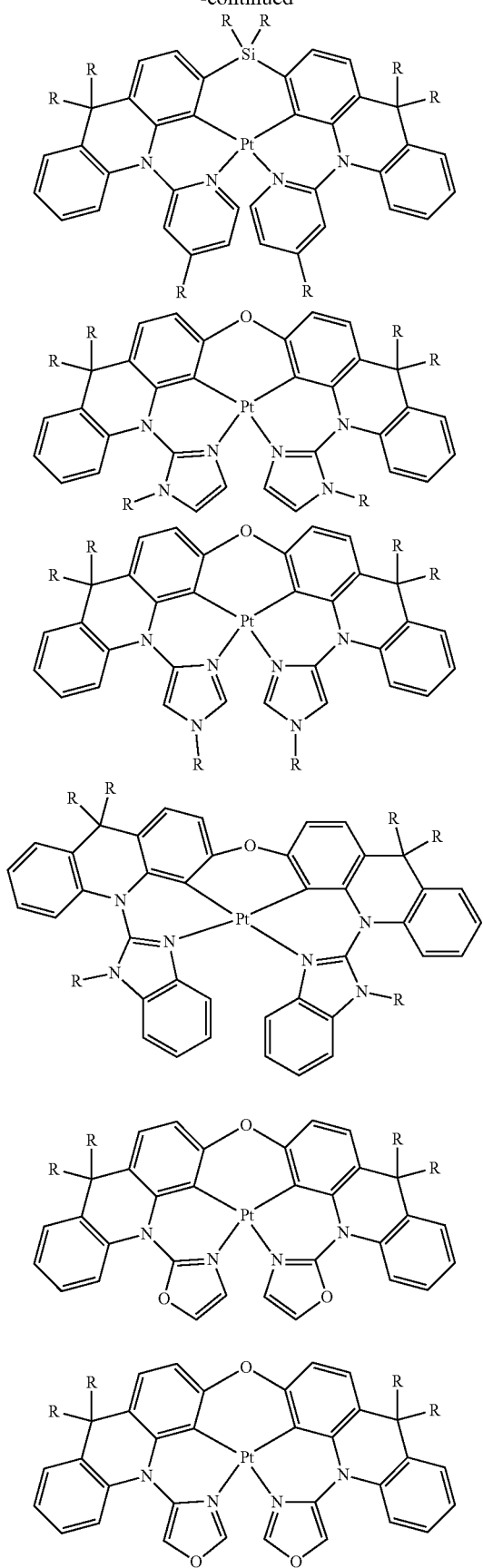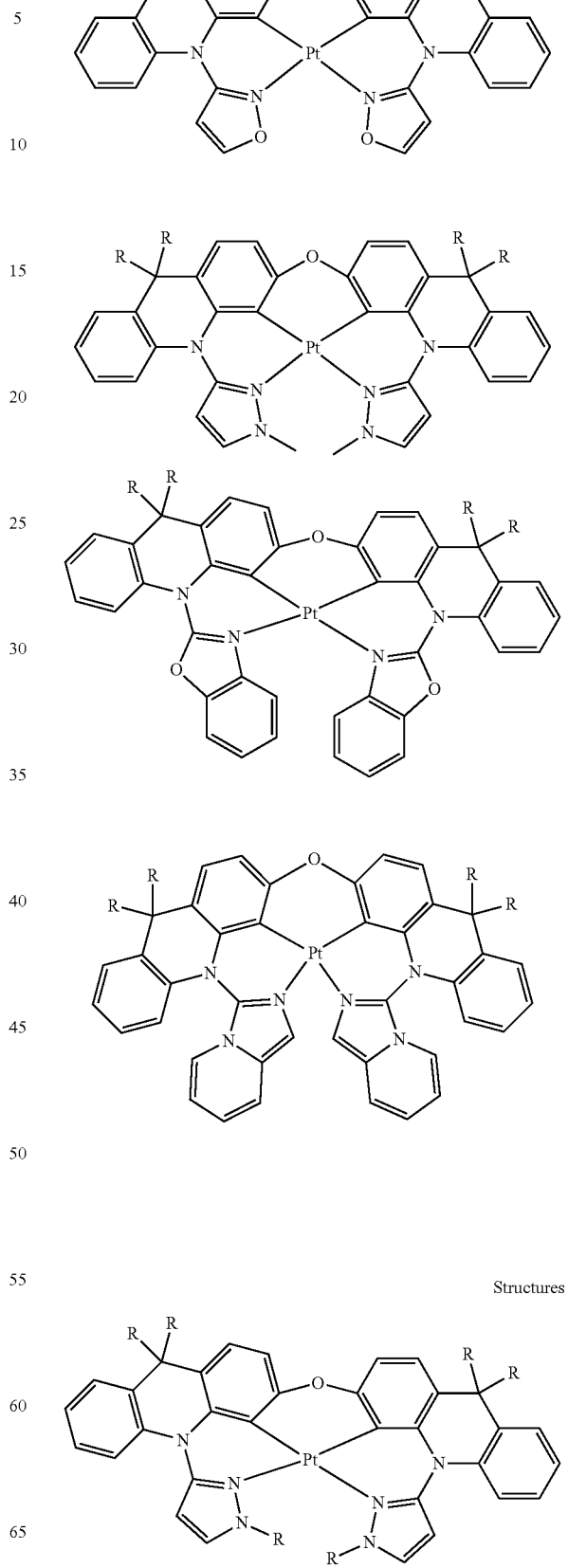

525
-continued
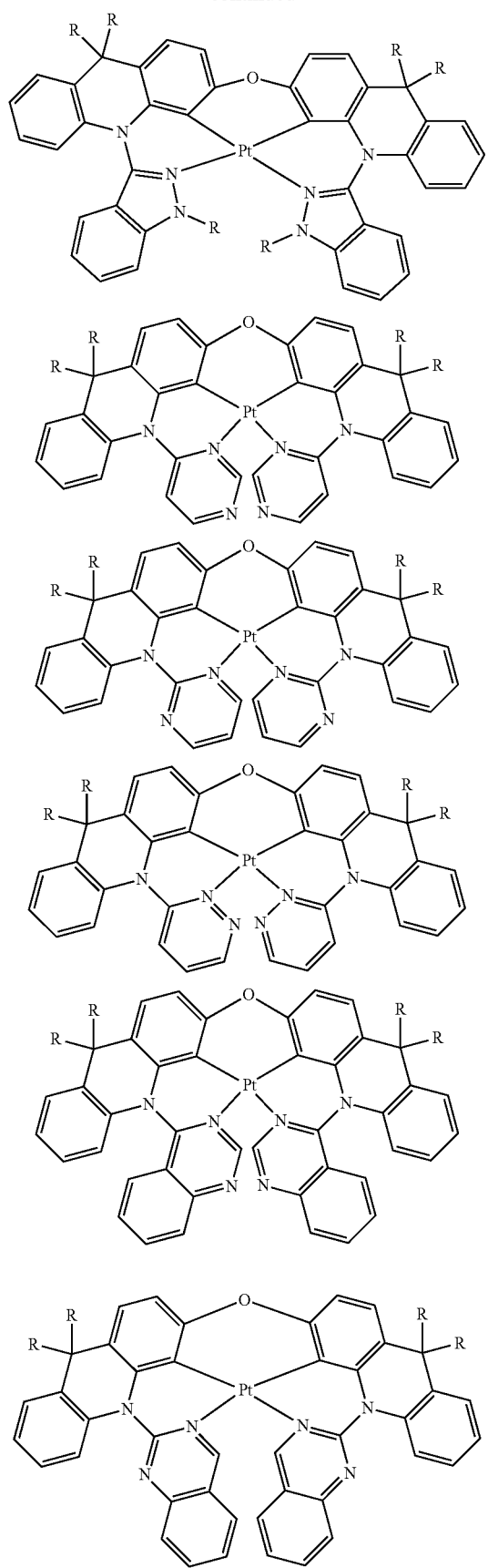
526
-continued
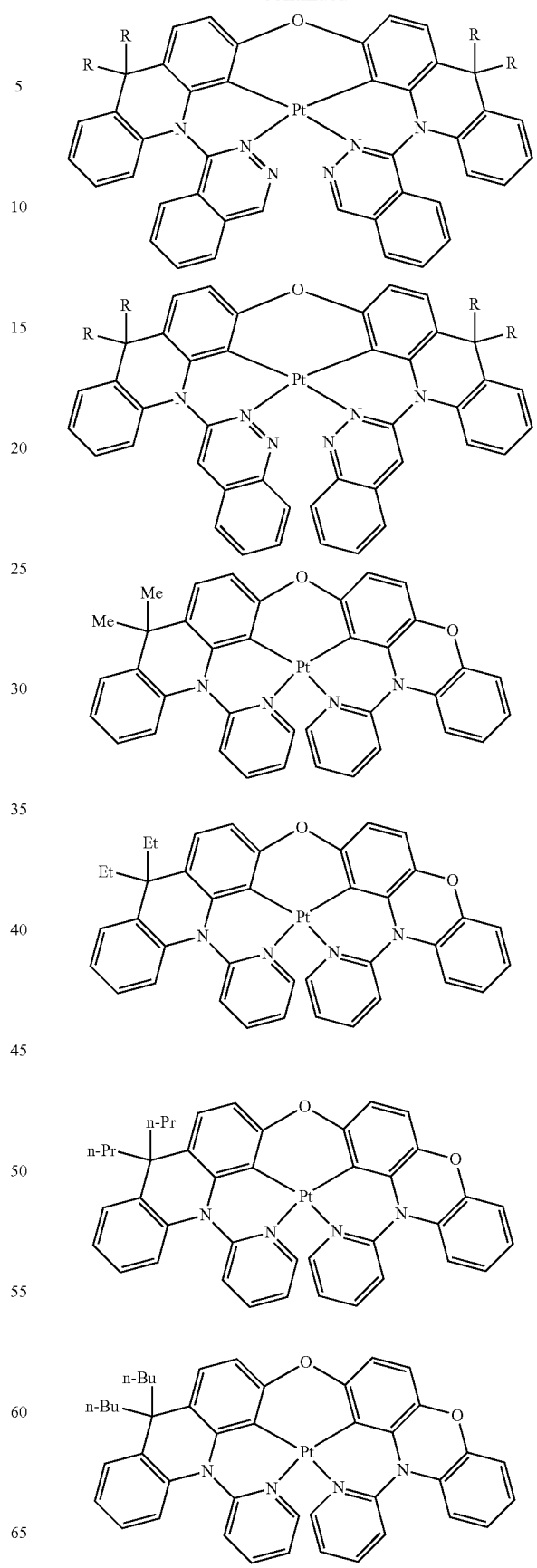

527
-continued
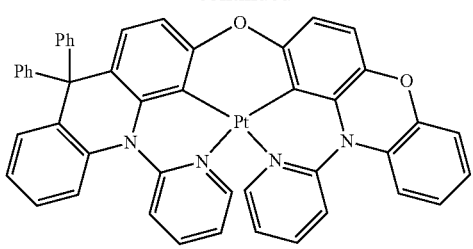
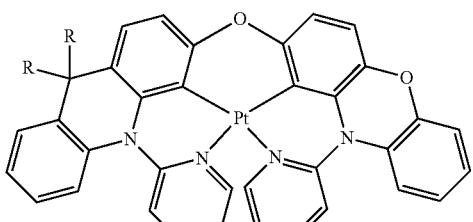
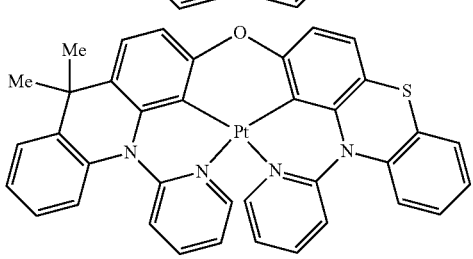
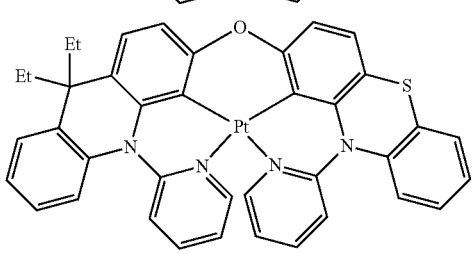
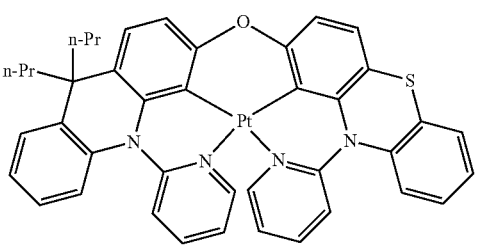
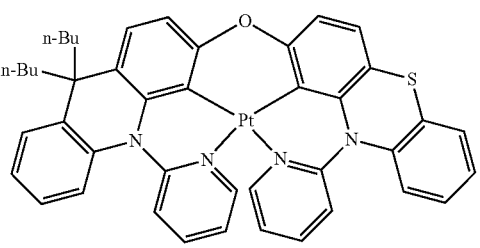
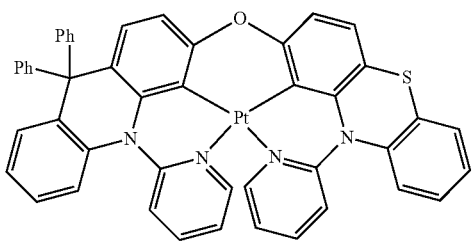
528
-continued
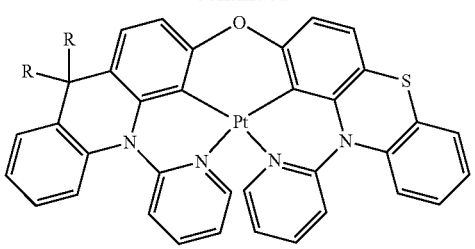
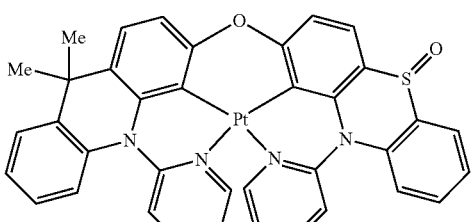
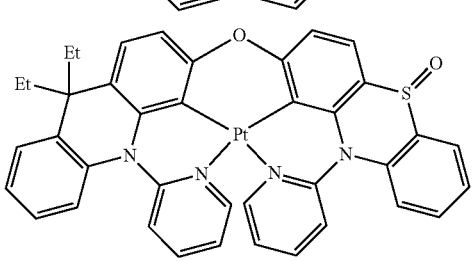
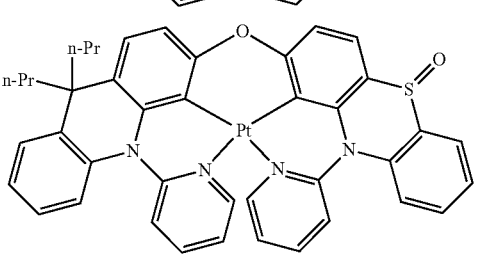
Structures 32
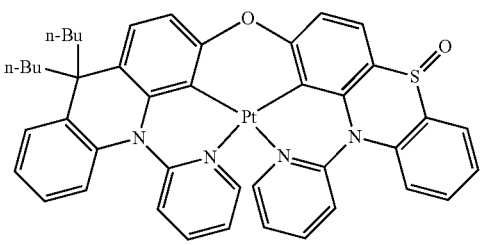
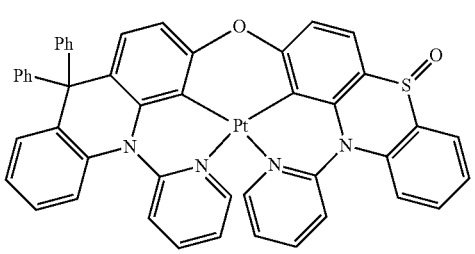

529
-continued
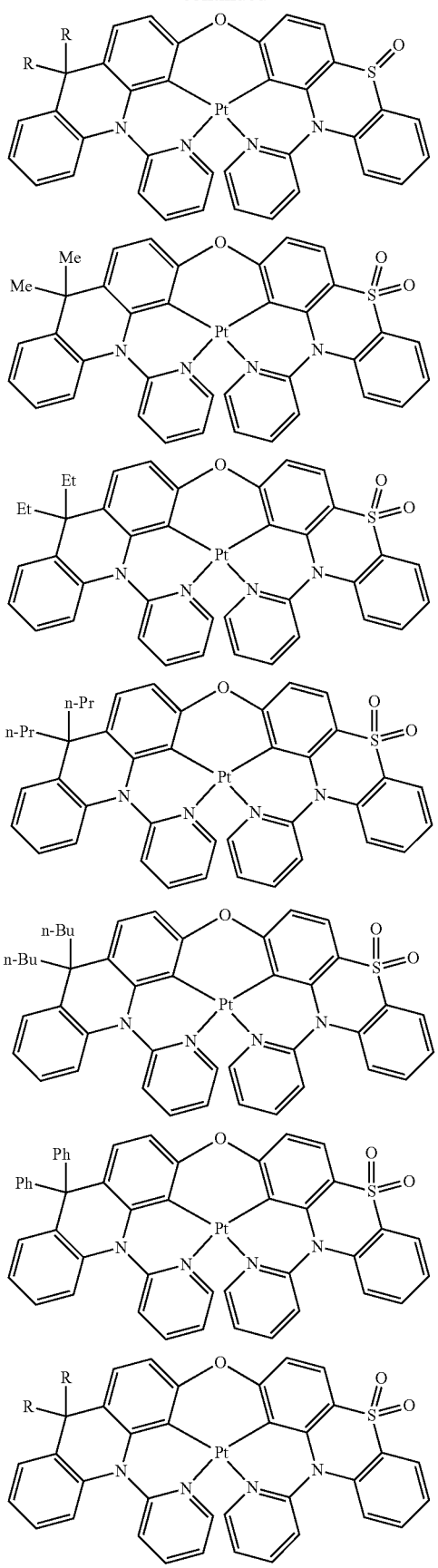
530
-continued
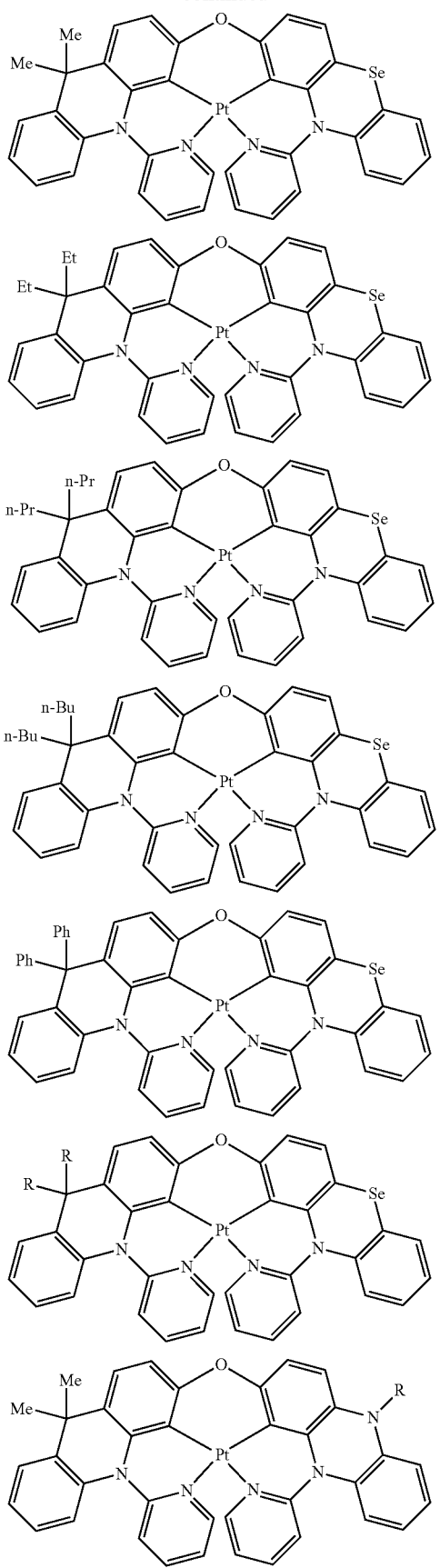

531
-continued
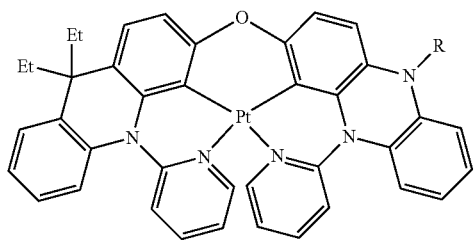
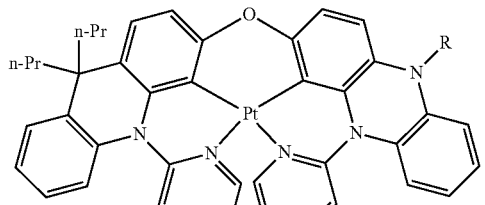
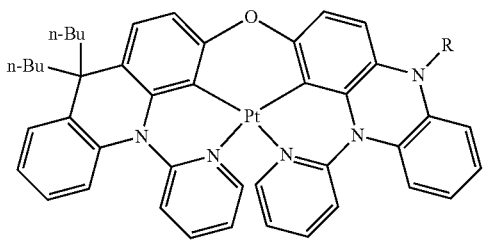
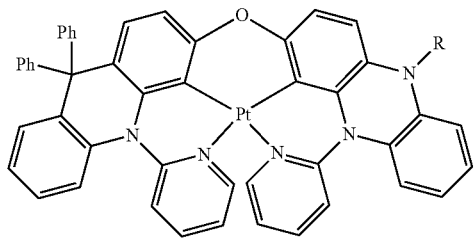
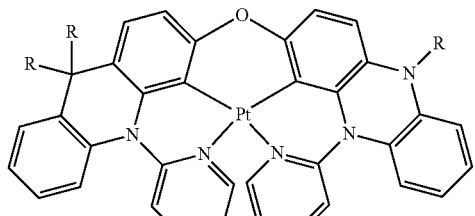
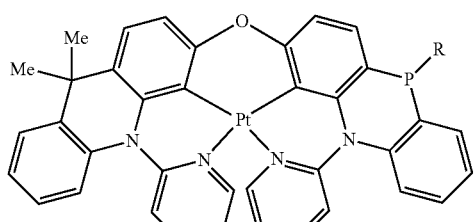
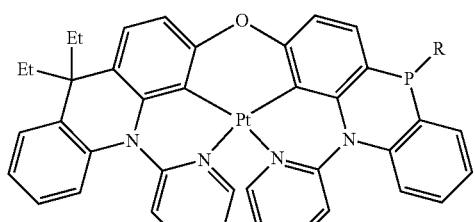
532
-continued
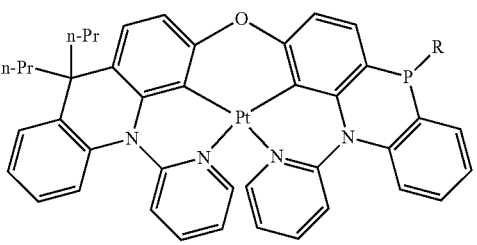
Structures 33
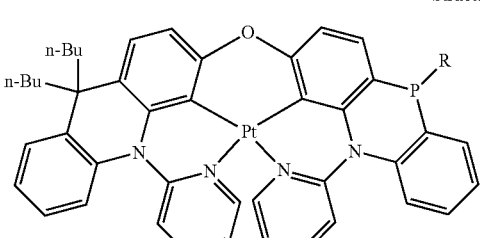
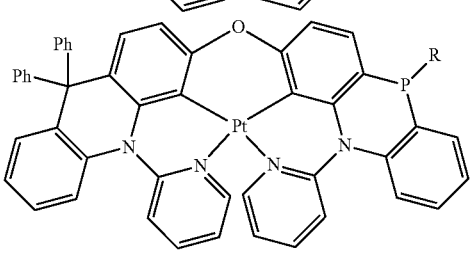
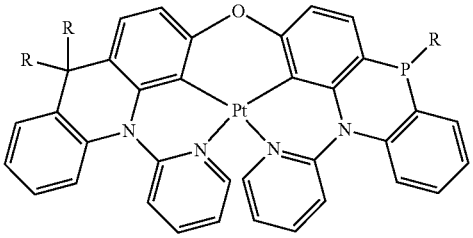
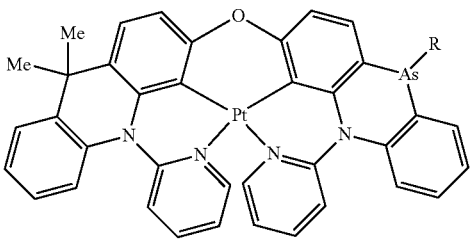
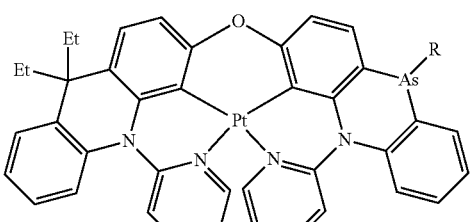

533
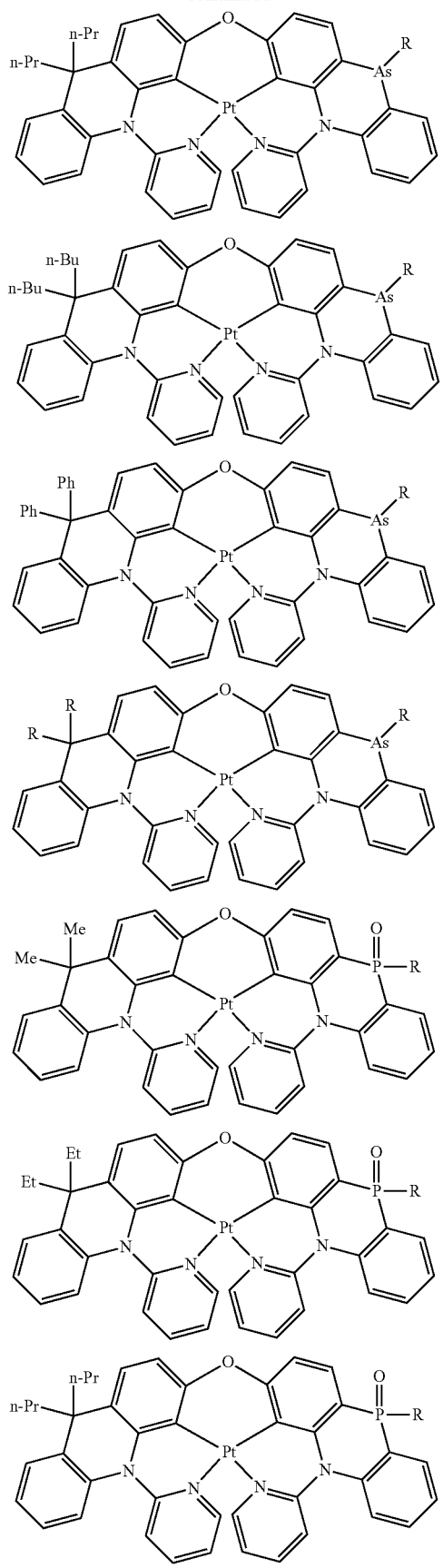
534
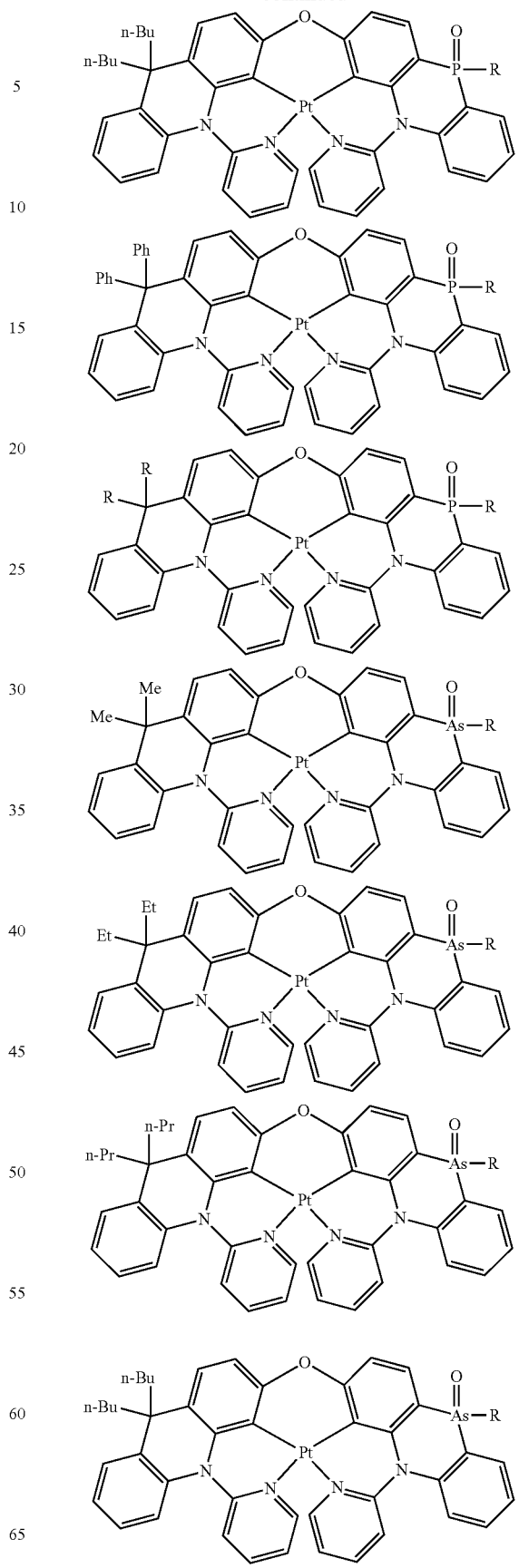

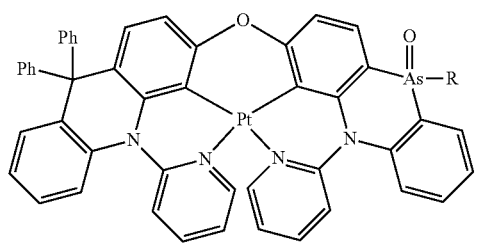
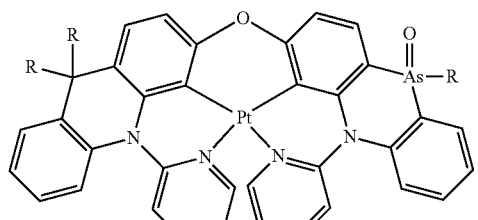
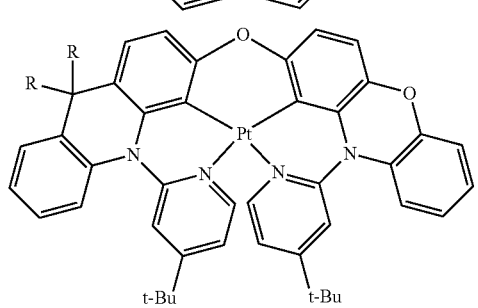
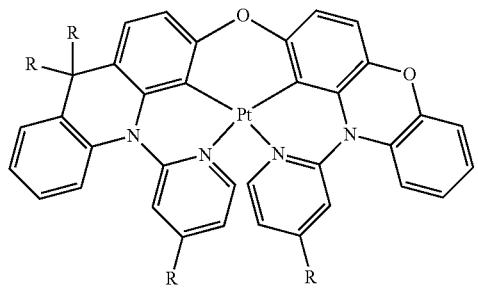
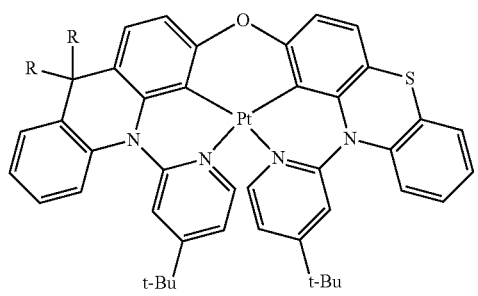
Structures 34
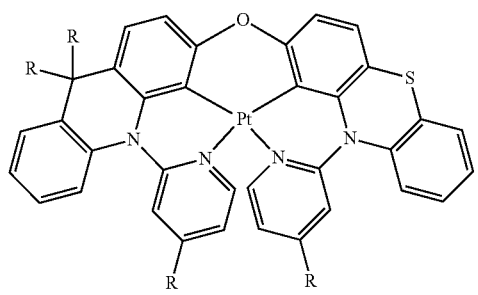
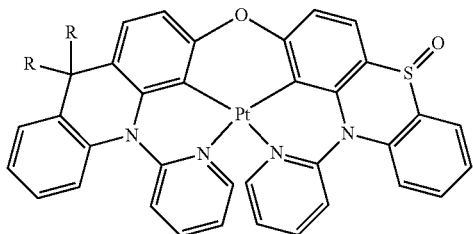
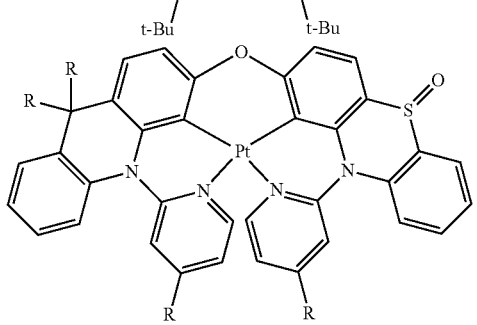
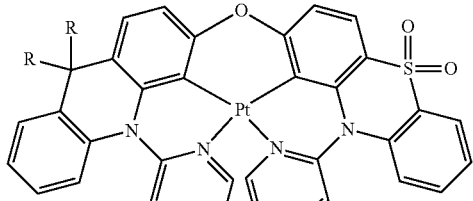
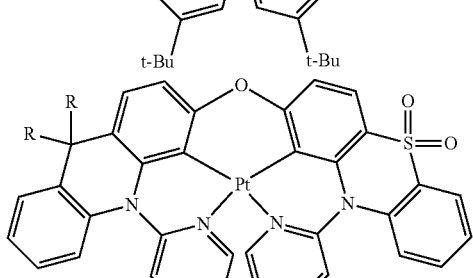
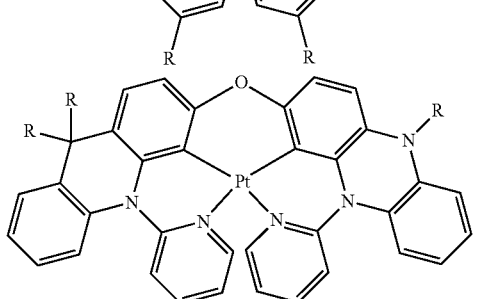
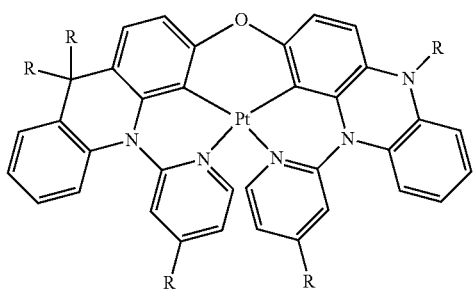

537
-continued
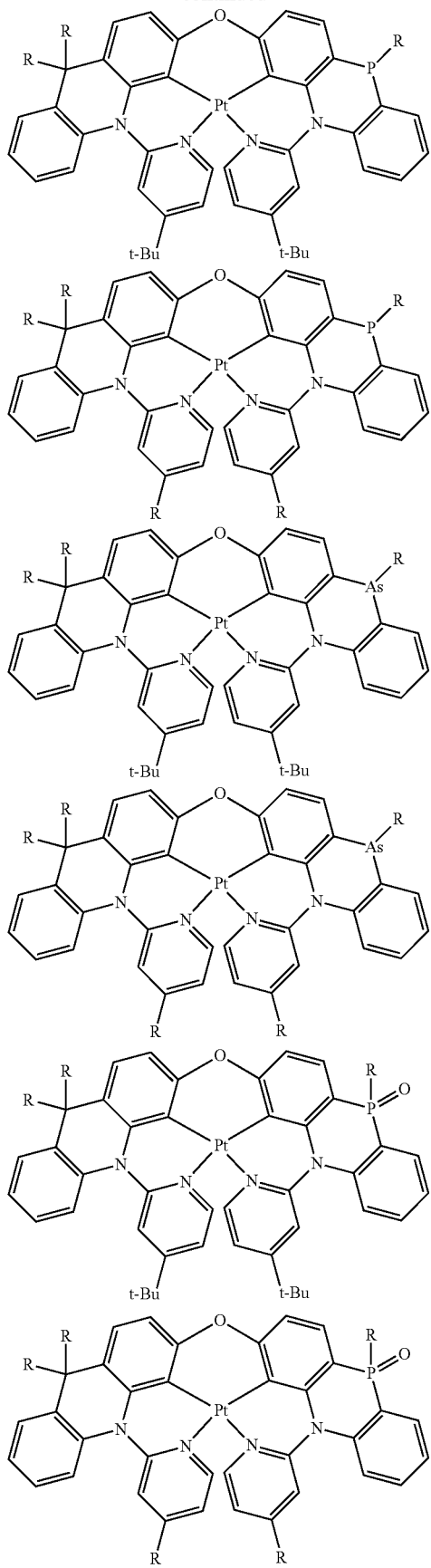
538
-continued
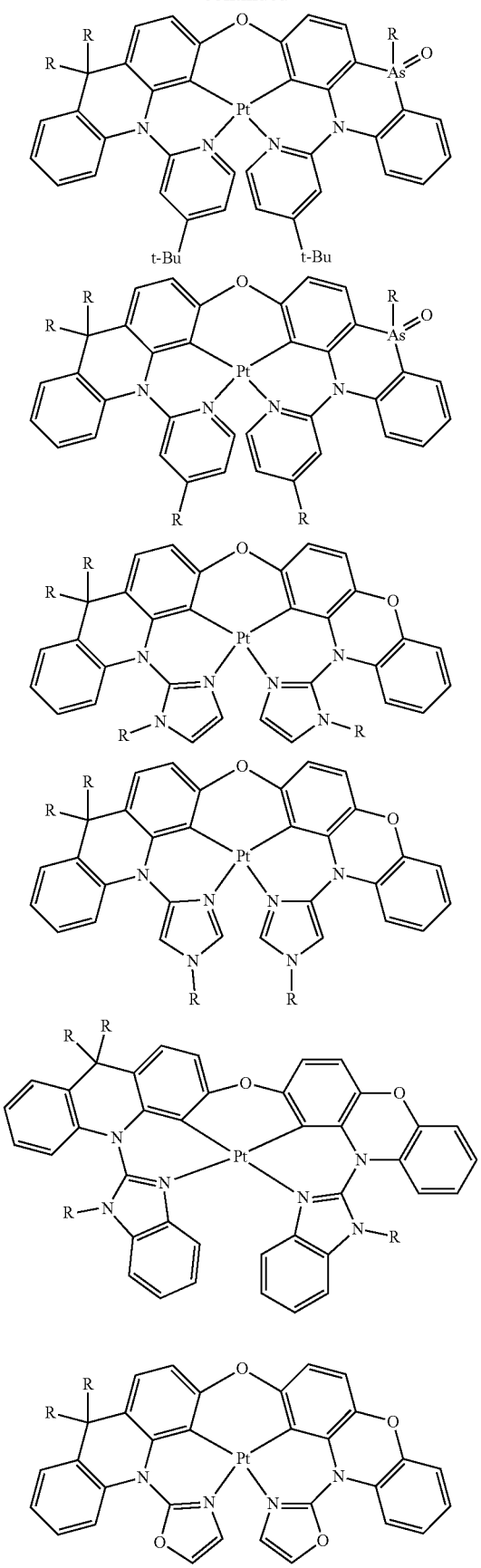

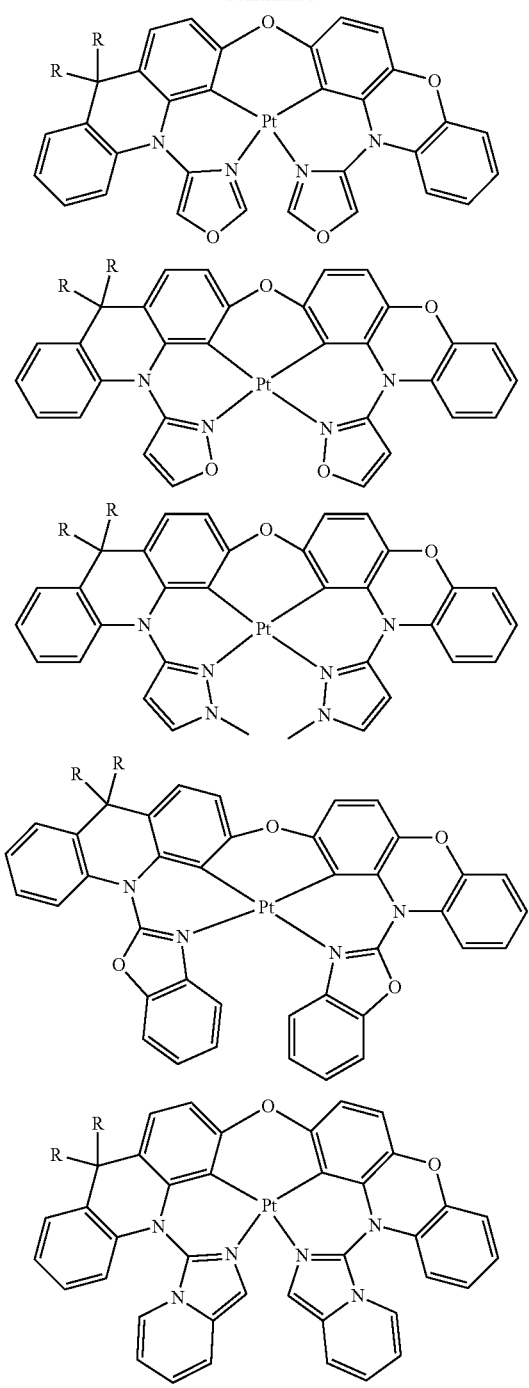
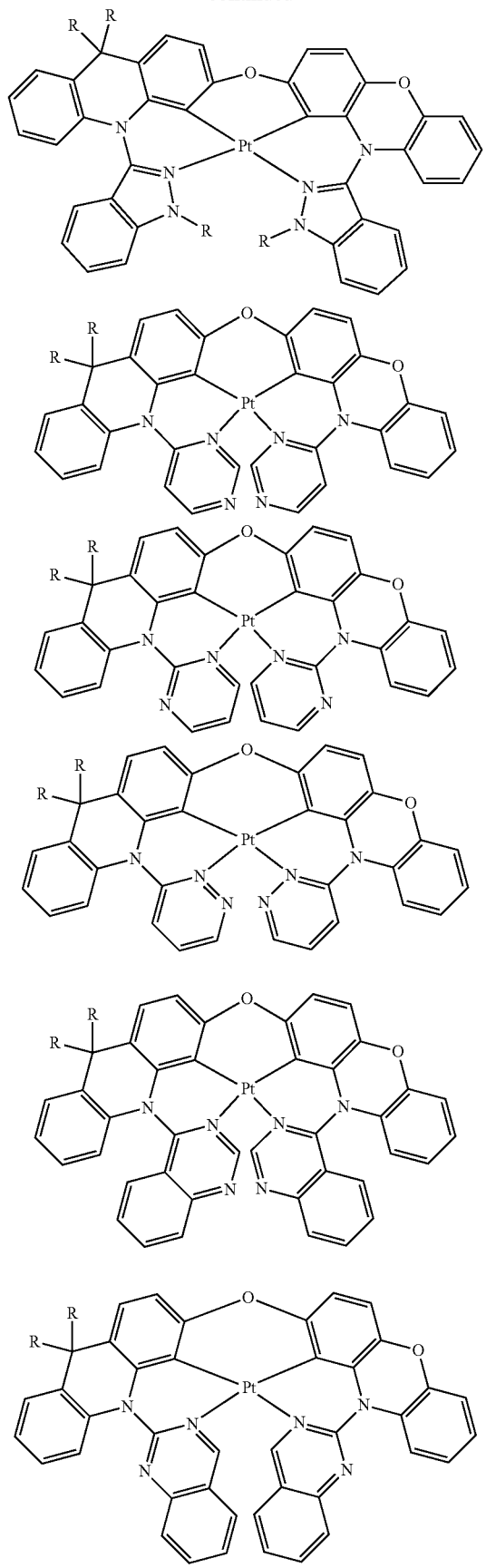

541
-continued
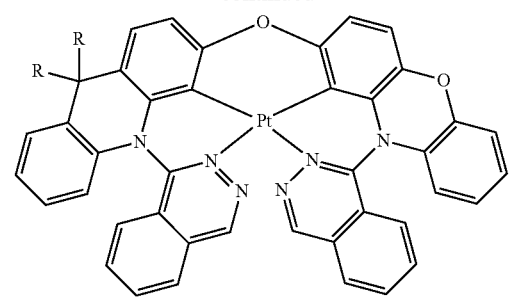
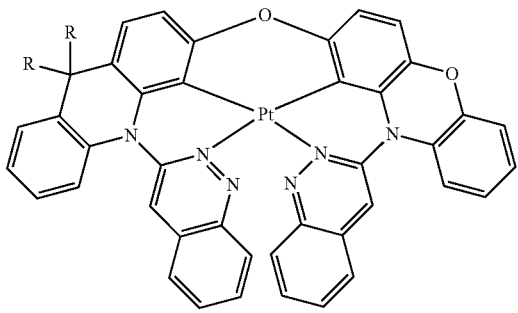
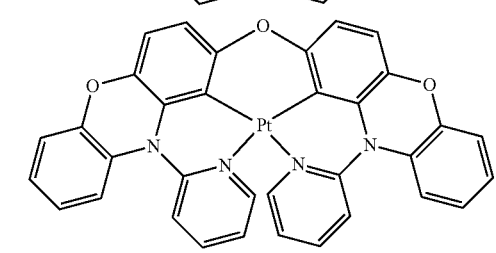
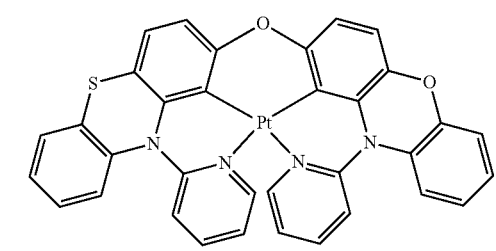
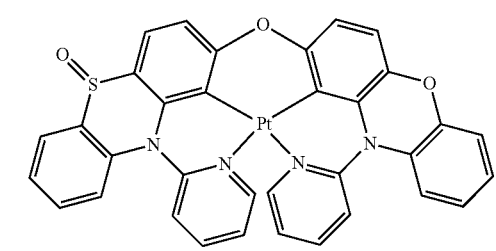
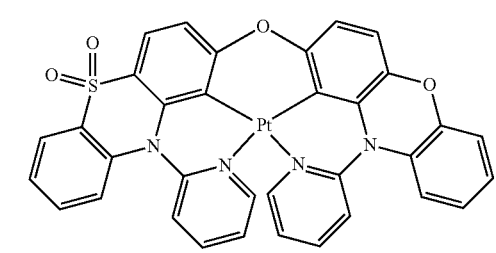
542
-continued
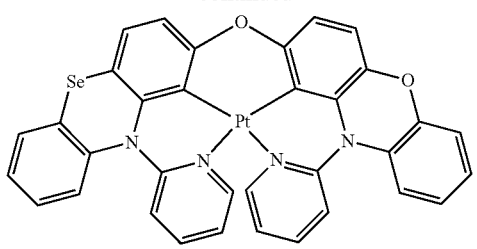
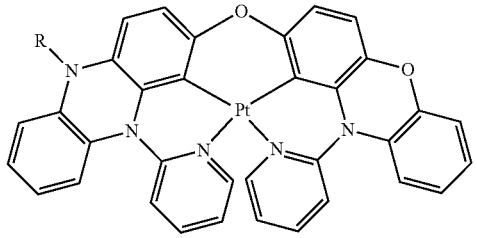
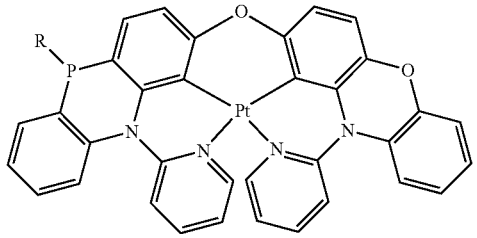
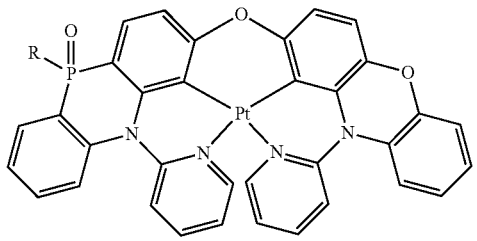
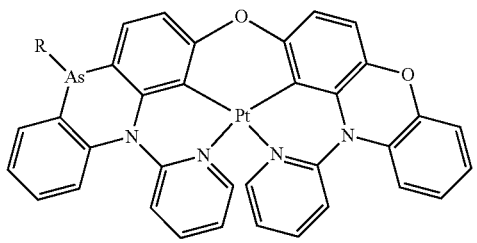
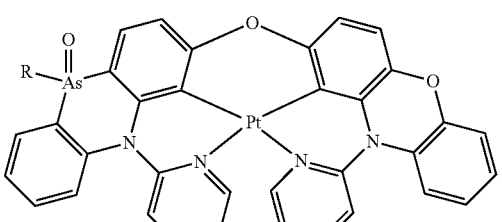
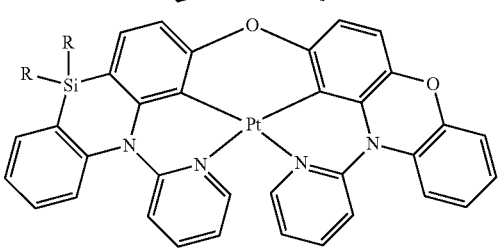

543
-continued
544
-continued
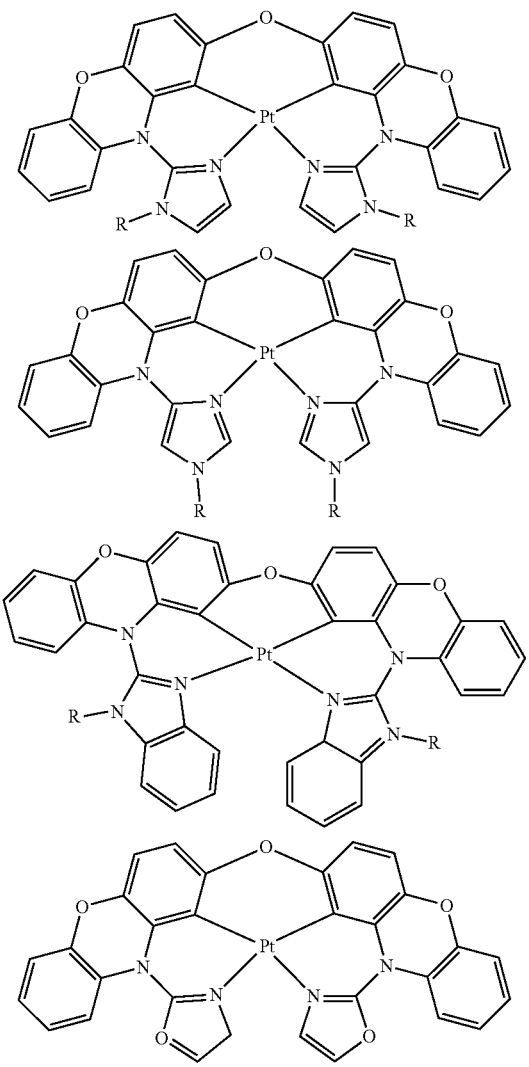
Structures 36
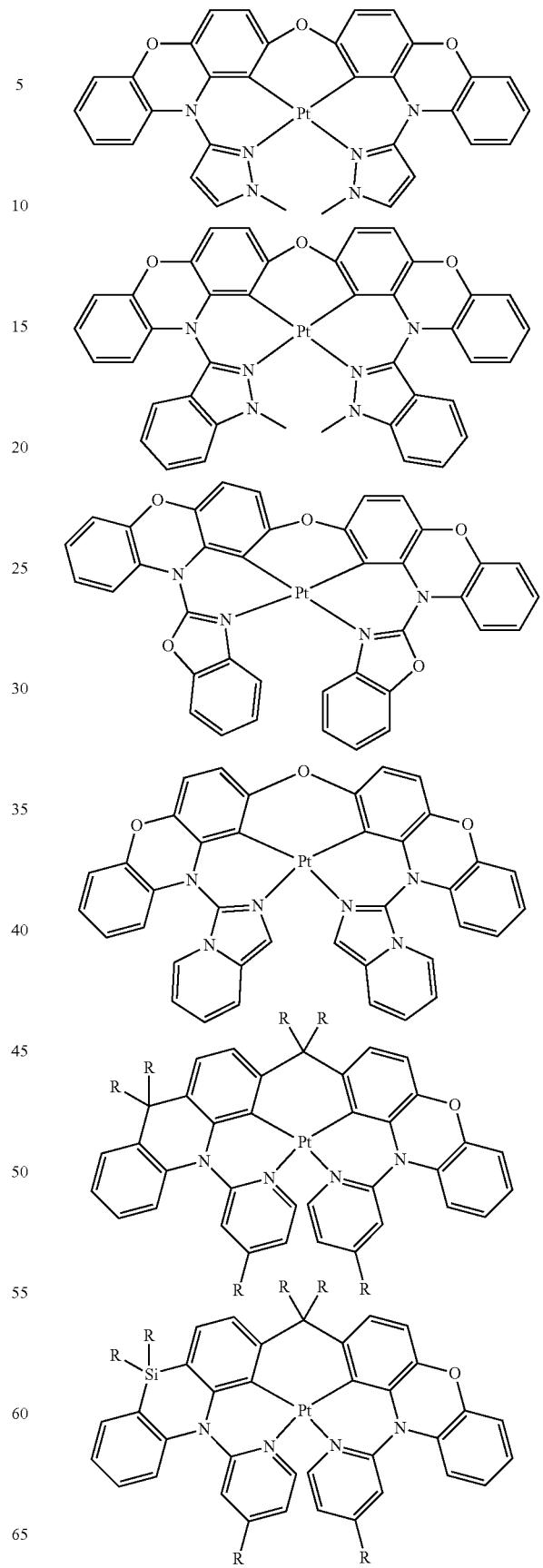

545
-continued
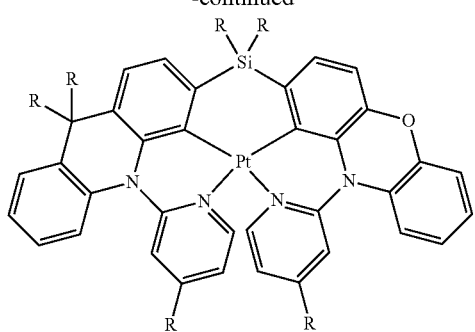
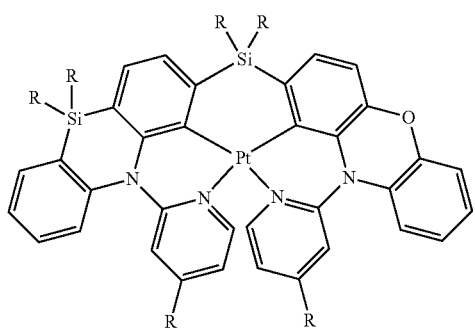
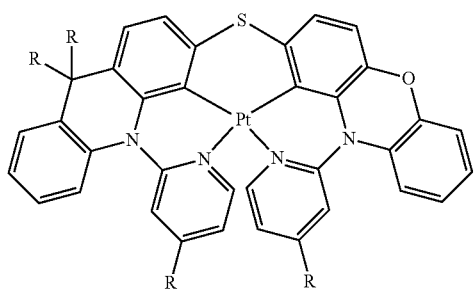
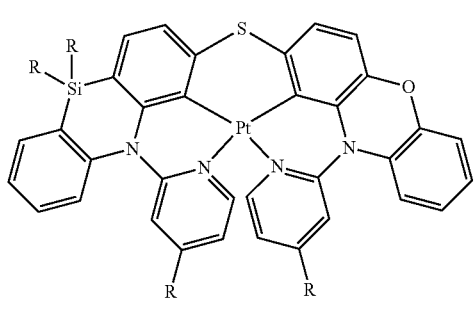
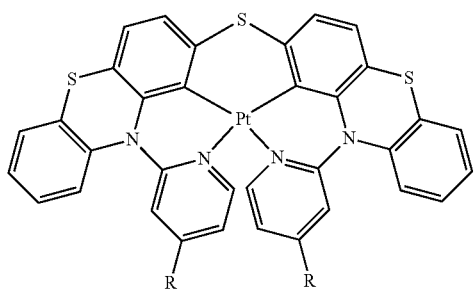
546
-continued
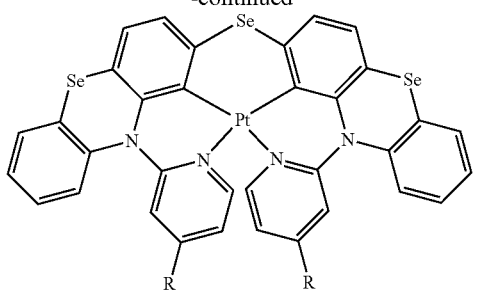
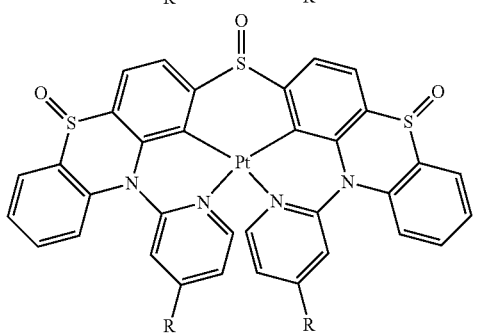
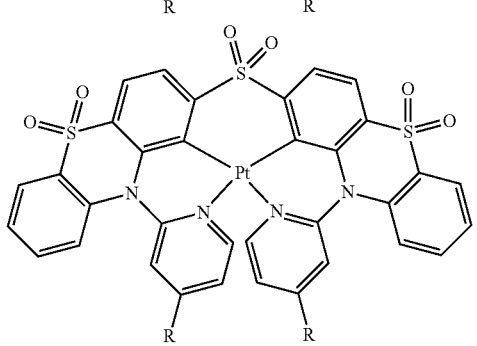
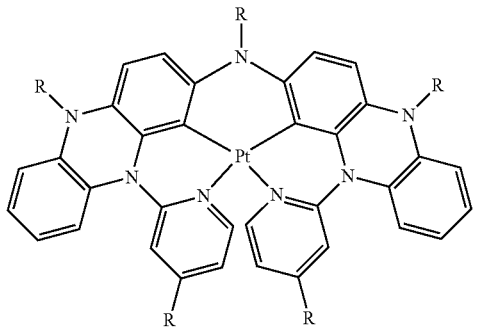
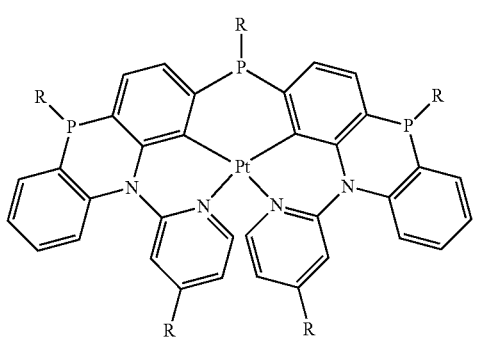

547
-continued
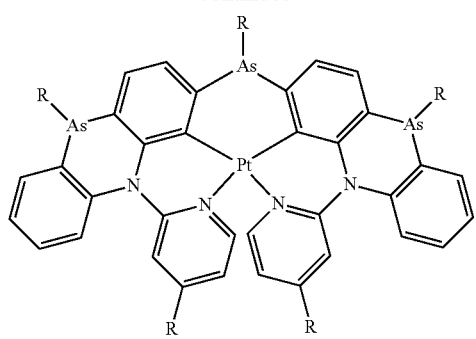
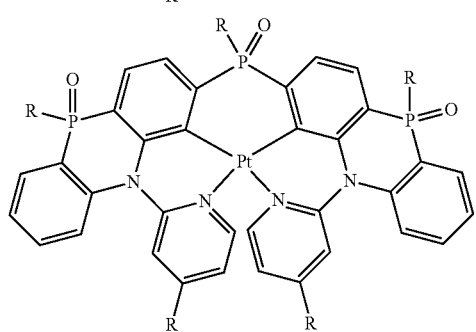
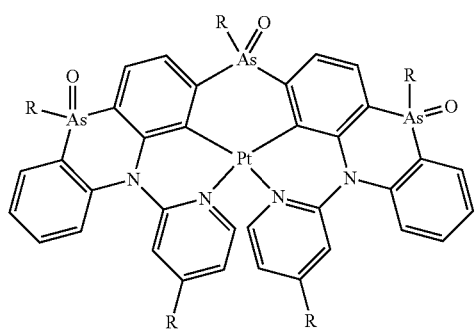
Structures 37
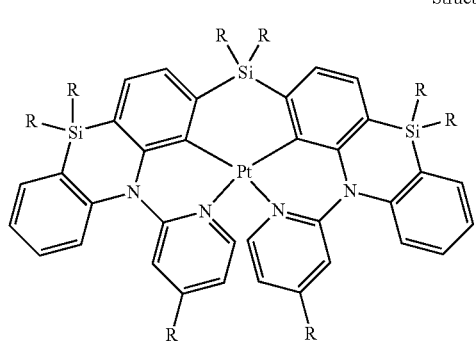
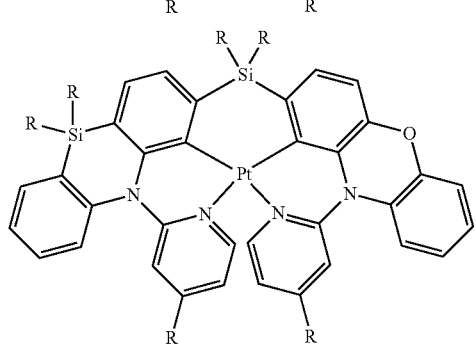
548
-continued
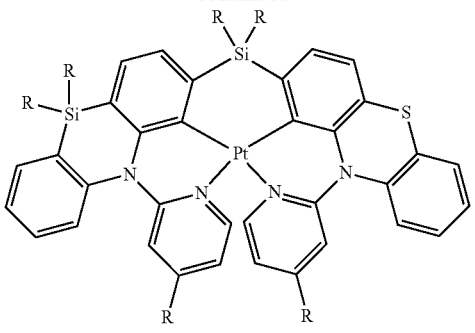
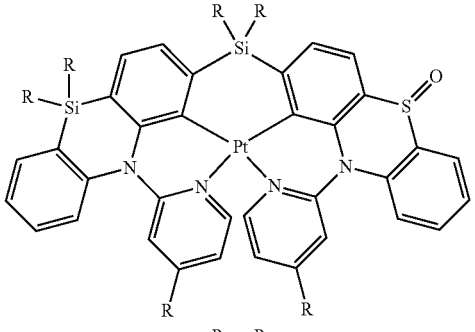
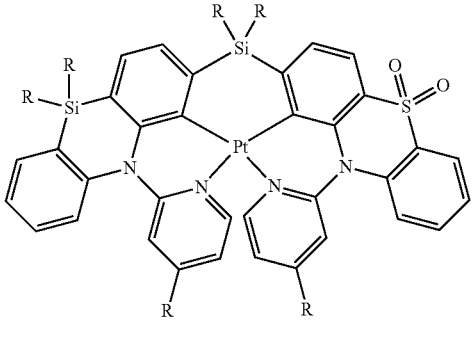
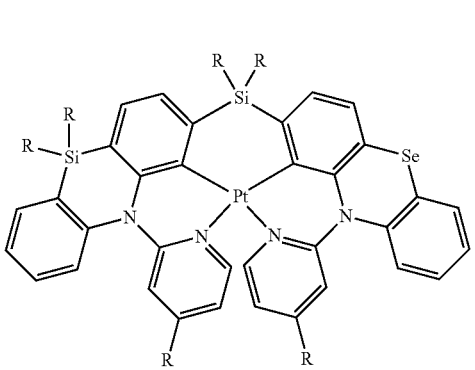
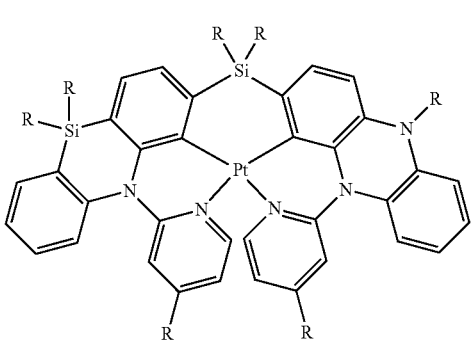

549
-continued
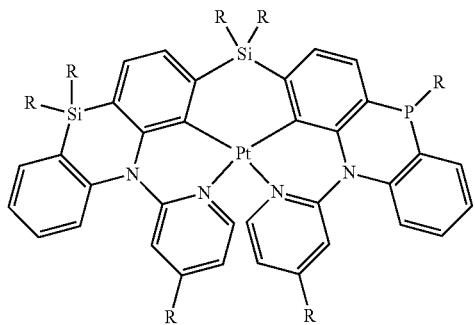
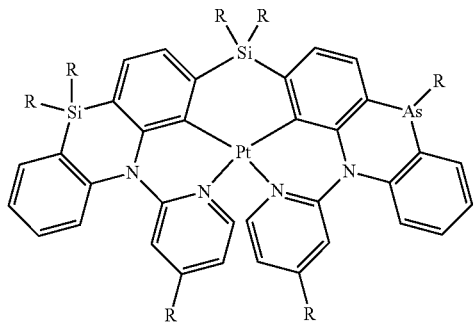
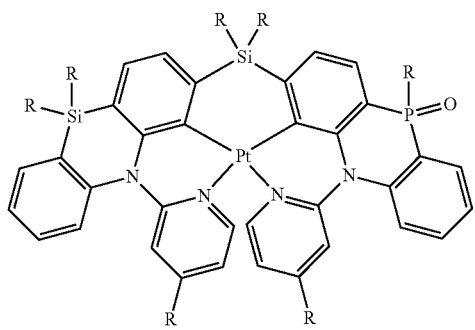
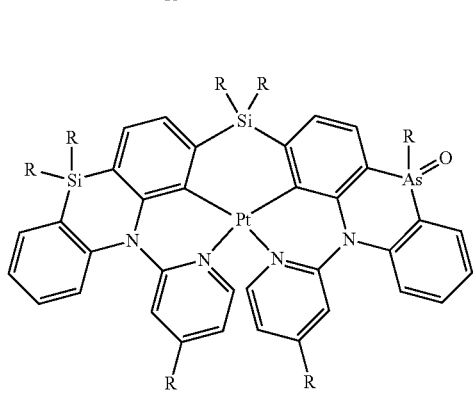
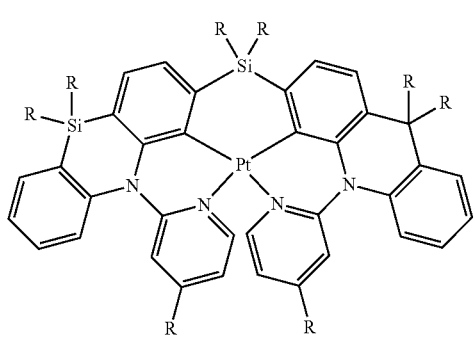
550
-continued
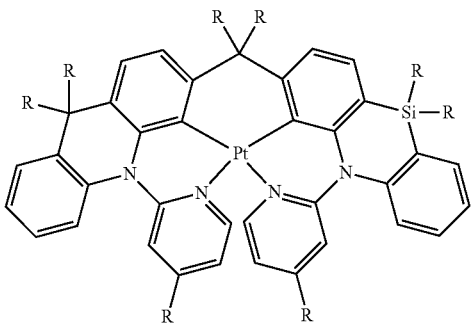
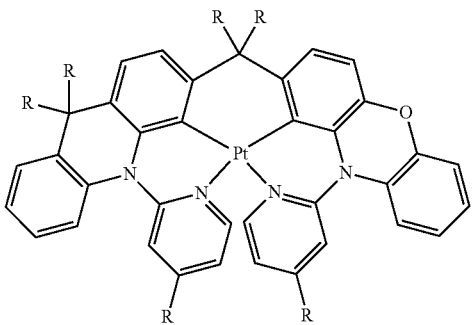
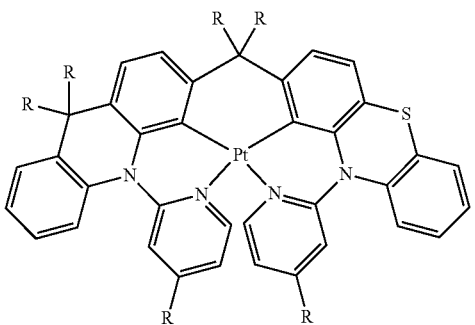
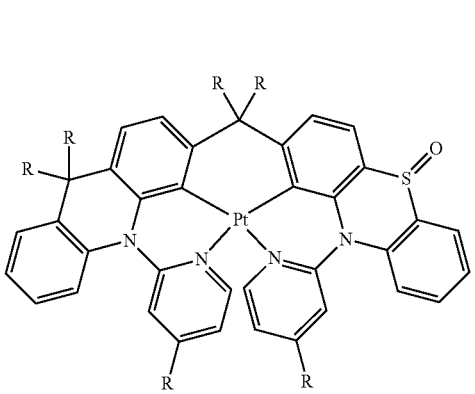
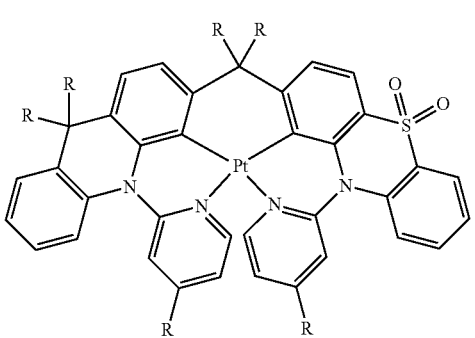

551
-continued
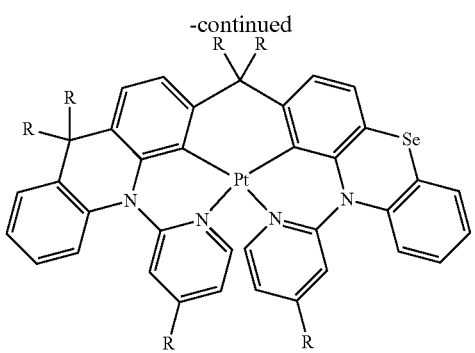
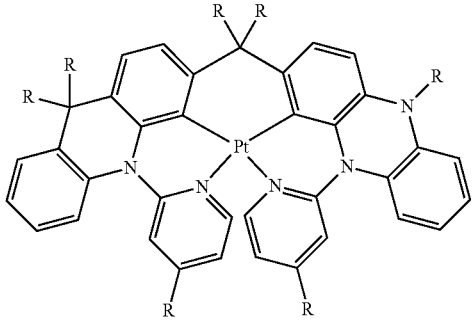
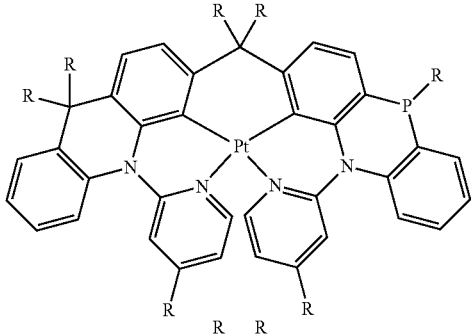
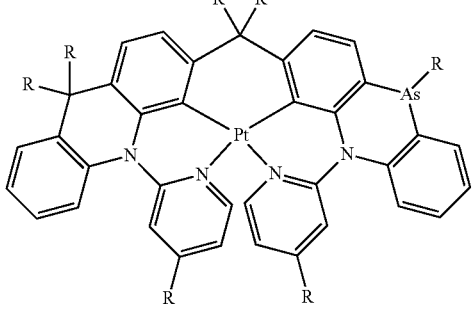
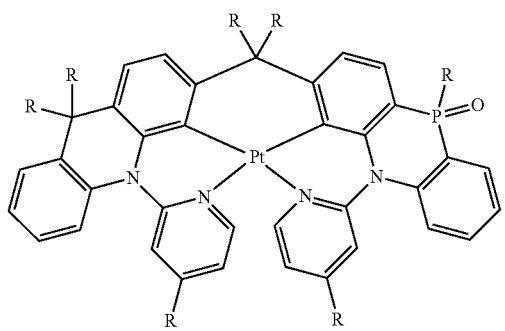
552
-continued
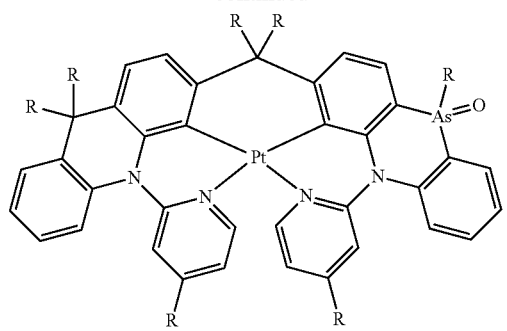
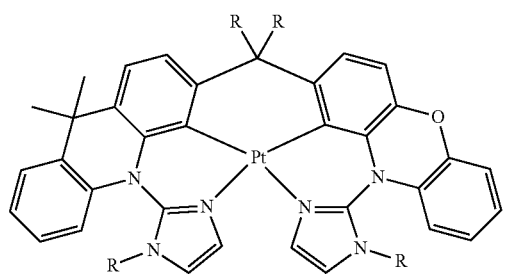
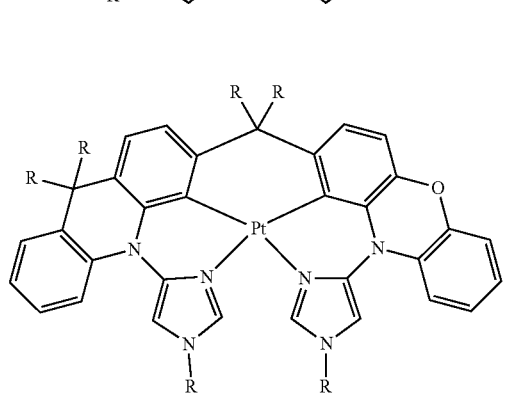
Structures 38
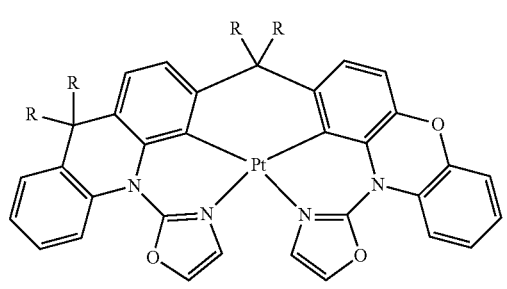

553
-continued
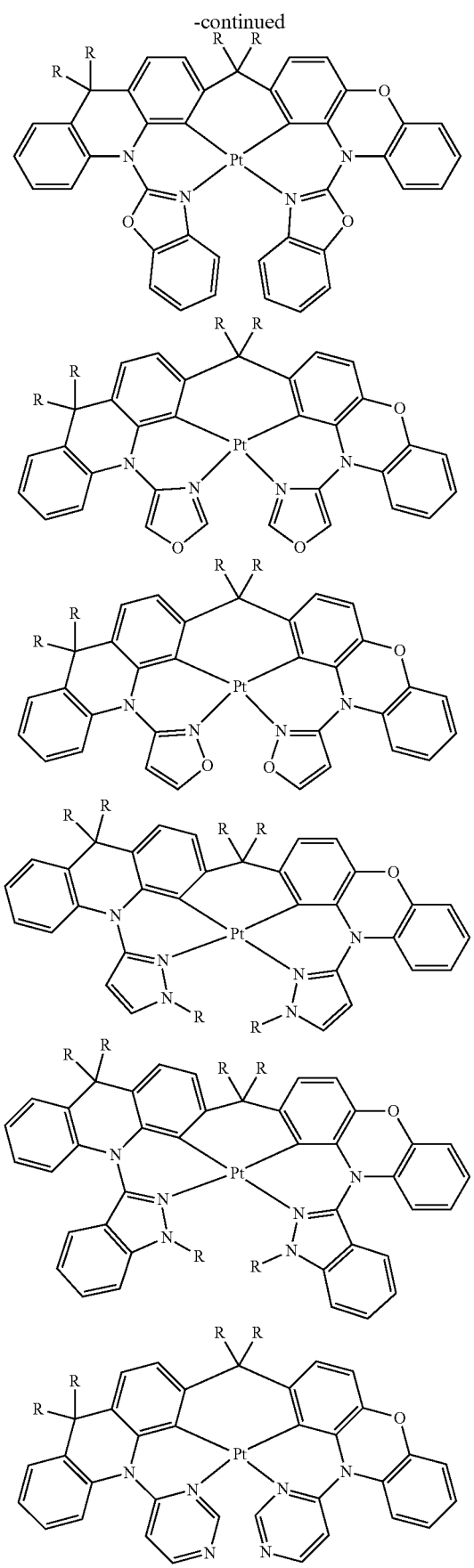
554
-continued
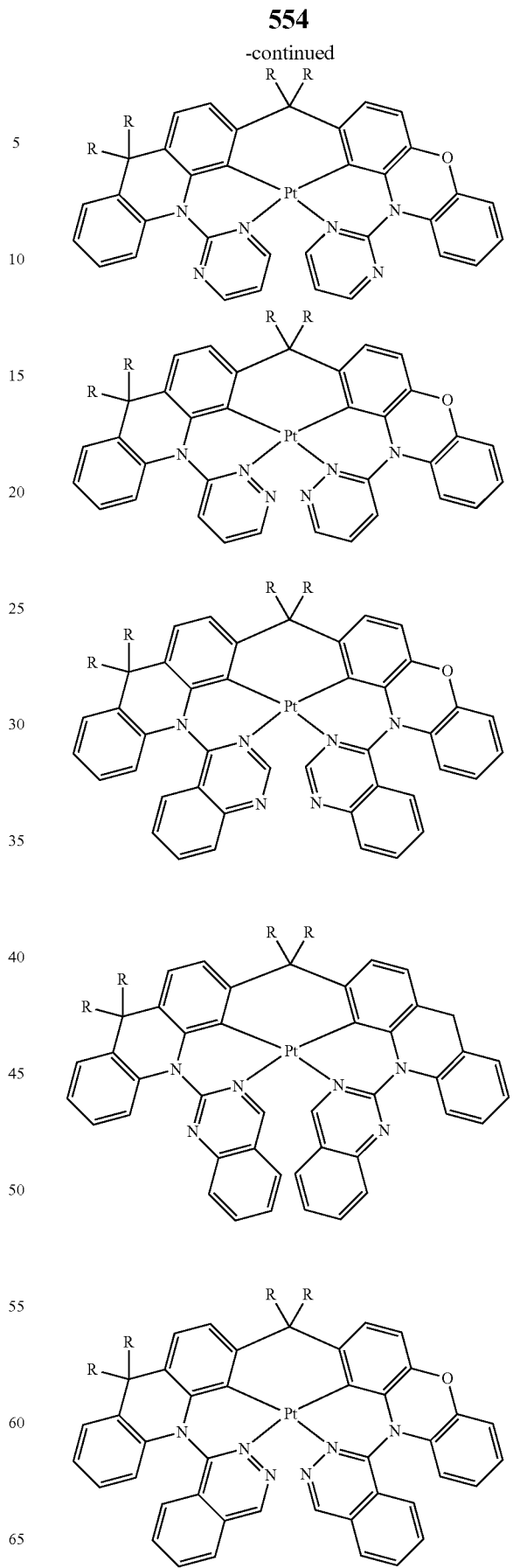

555
-continued
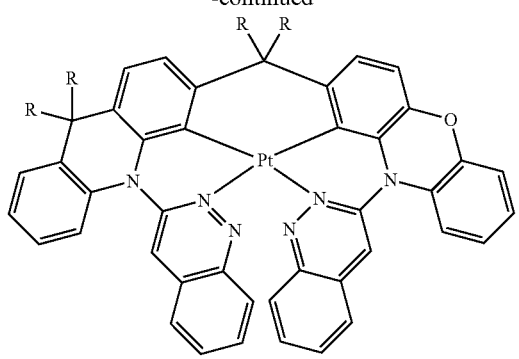
Structures 41
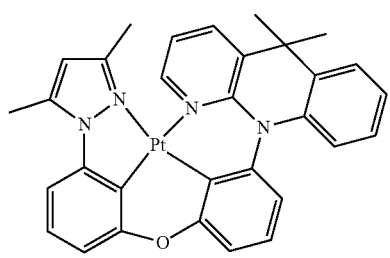
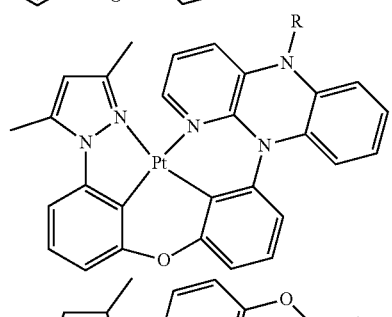
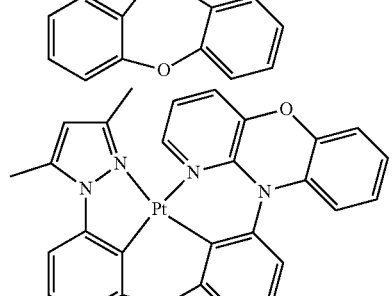
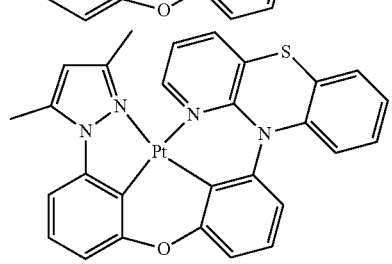
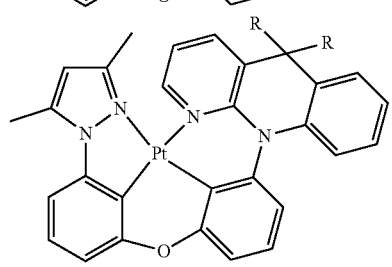
556
-continued
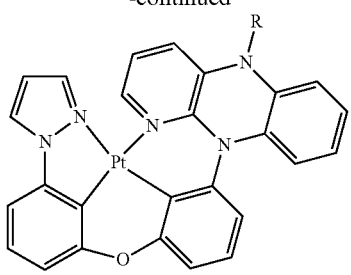
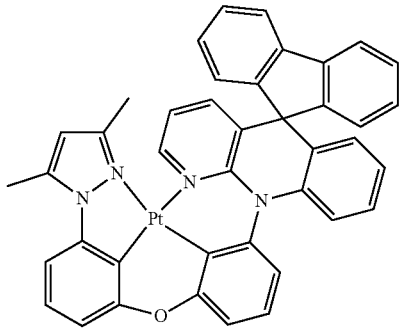
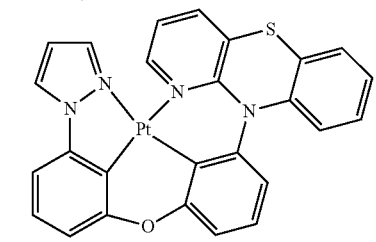
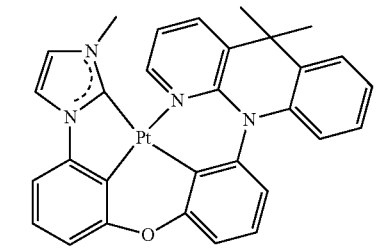
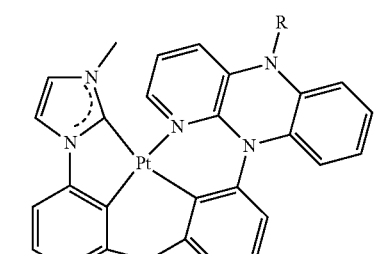
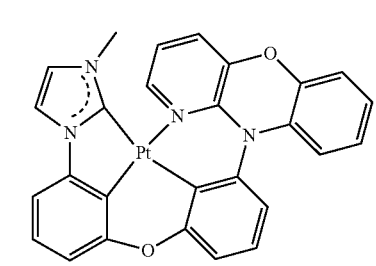

557
-continued
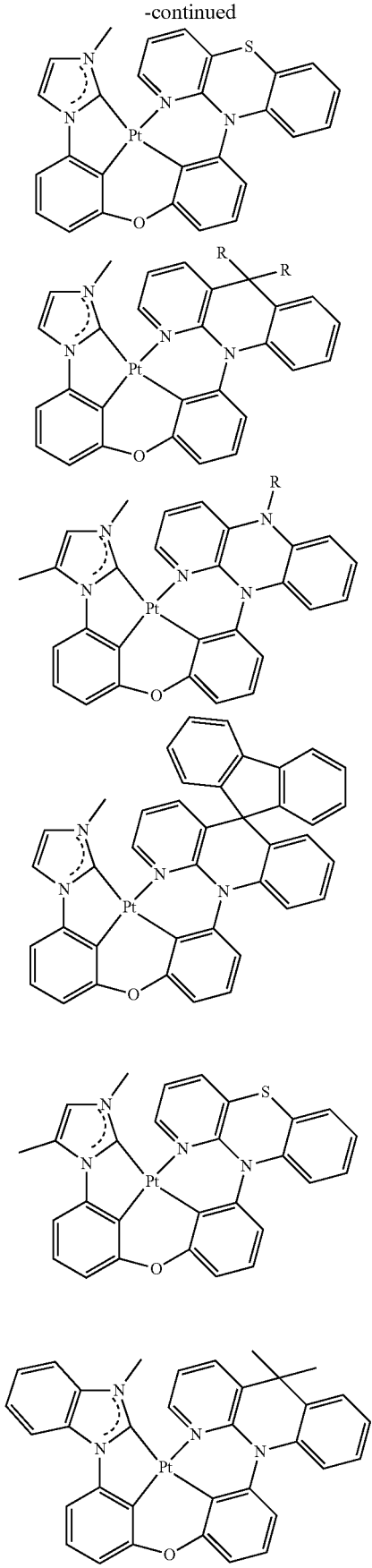
558
-continued
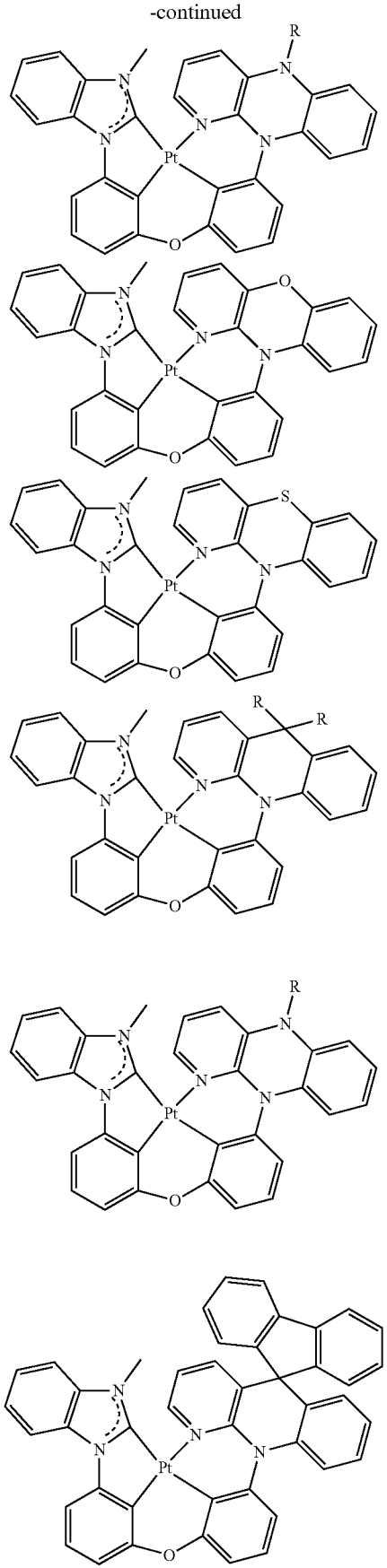

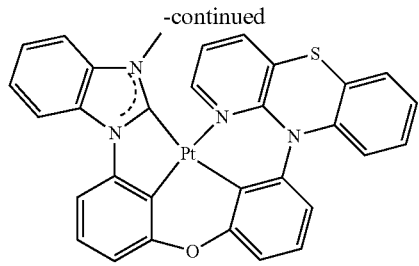
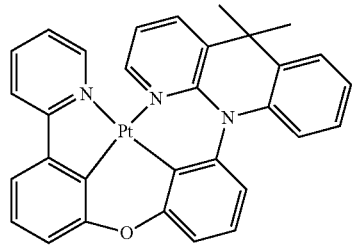
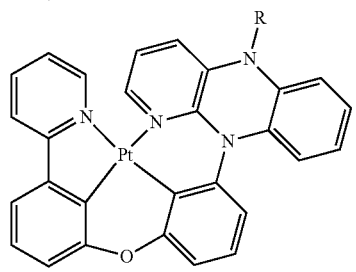
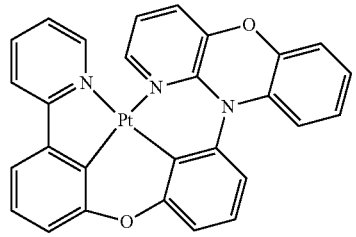
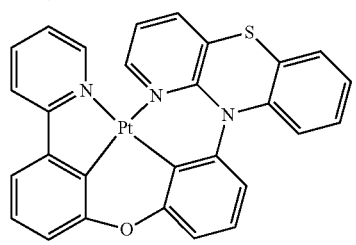
Structures 42
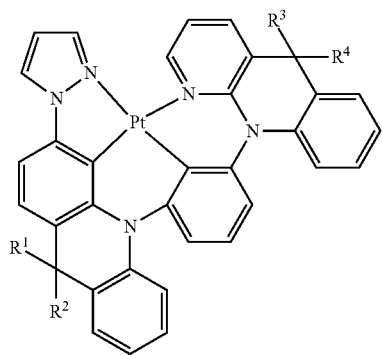
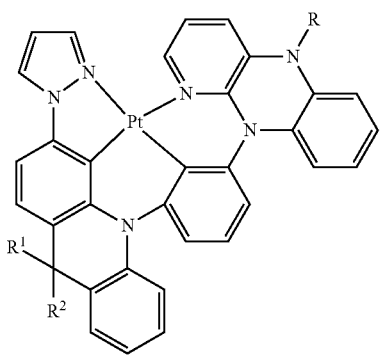
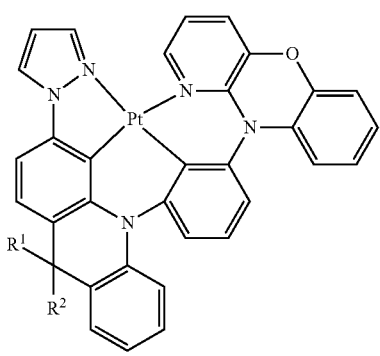
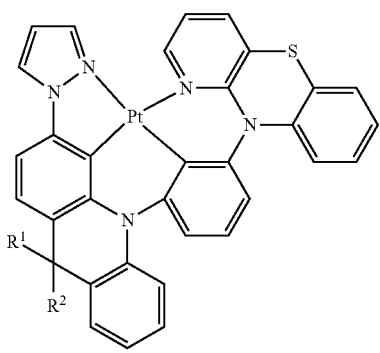
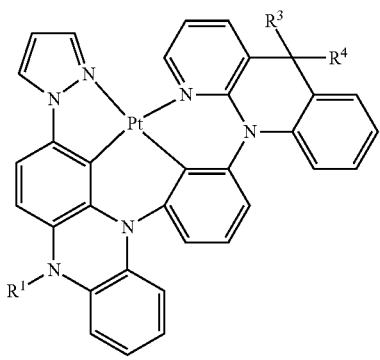

561
-continued
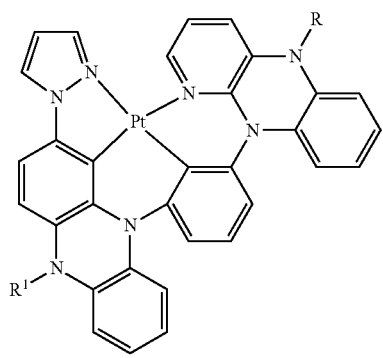
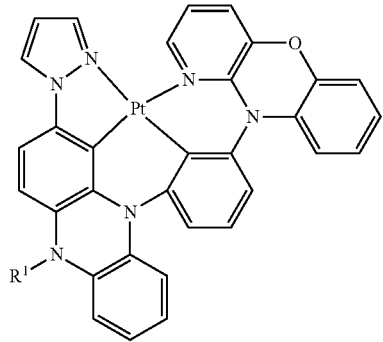
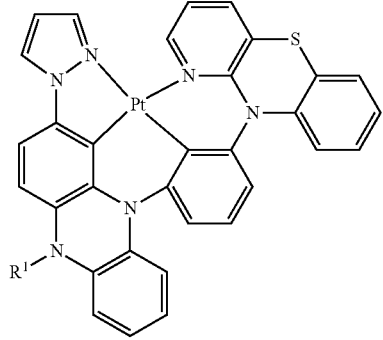
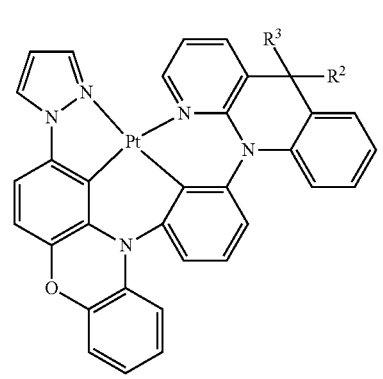
562
-continued
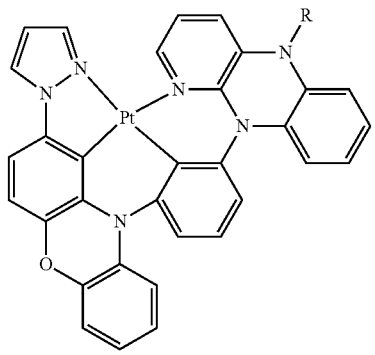
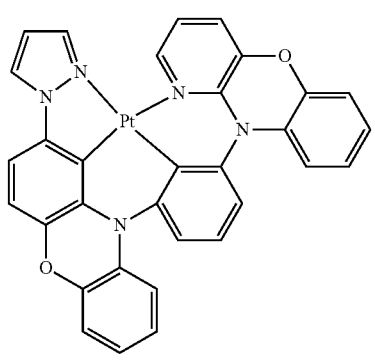
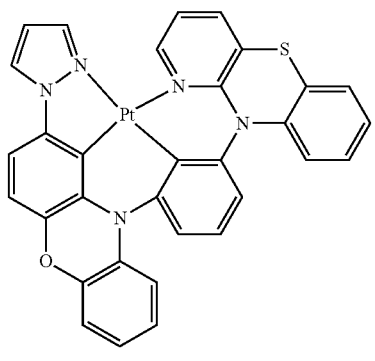
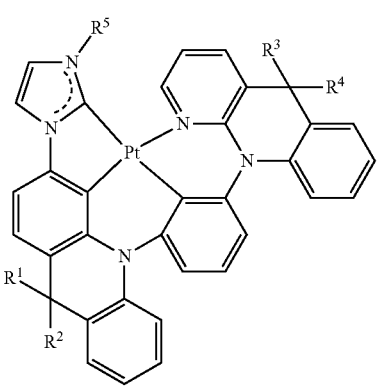

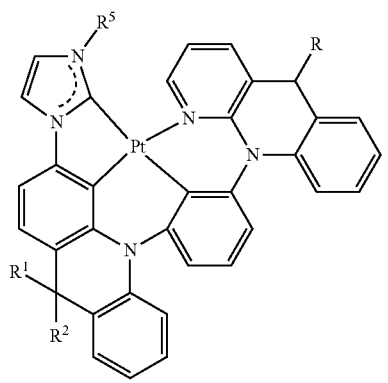
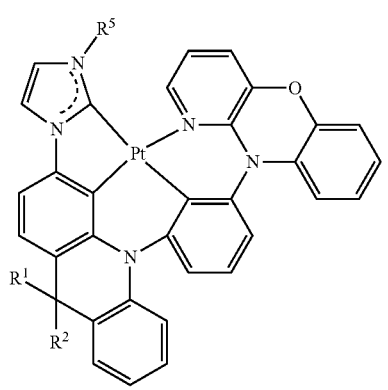
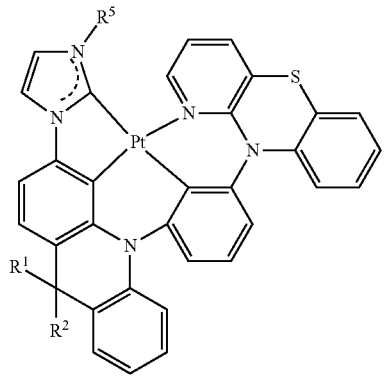
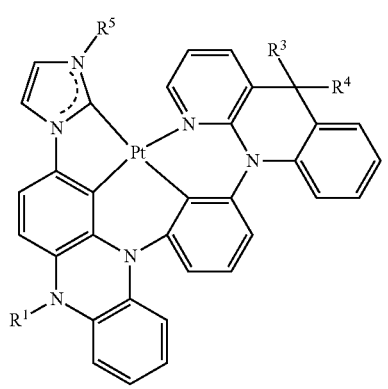
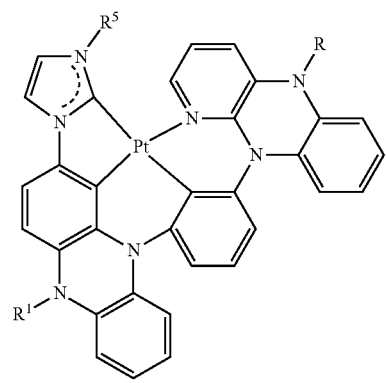
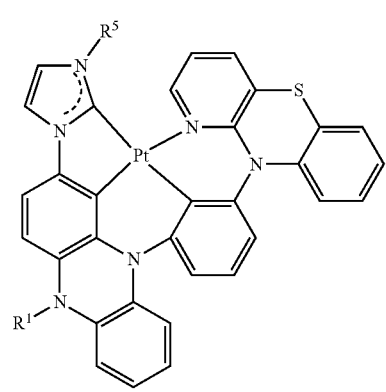
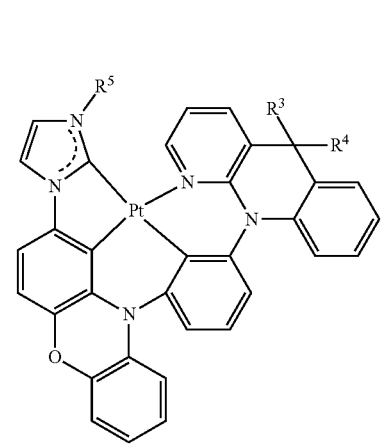
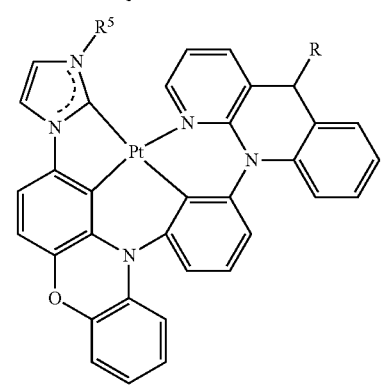

565
-continued
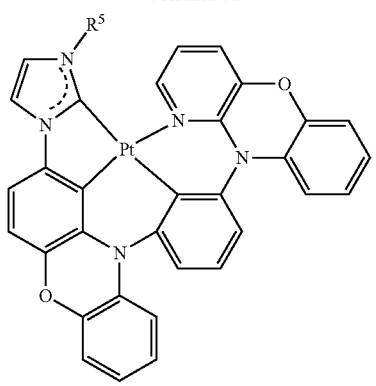
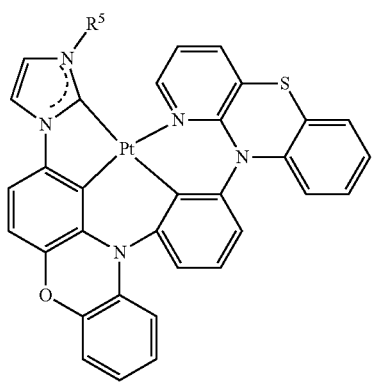
Structures 43
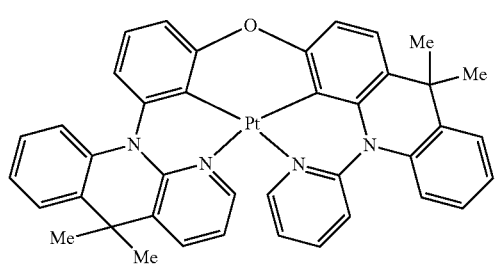
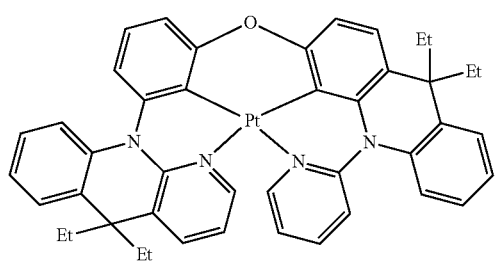
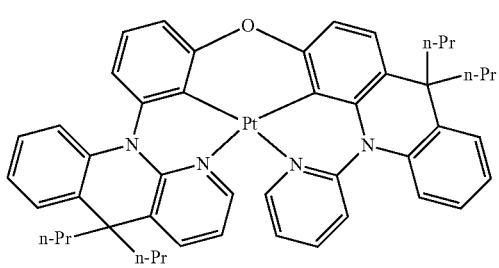
566
-continued
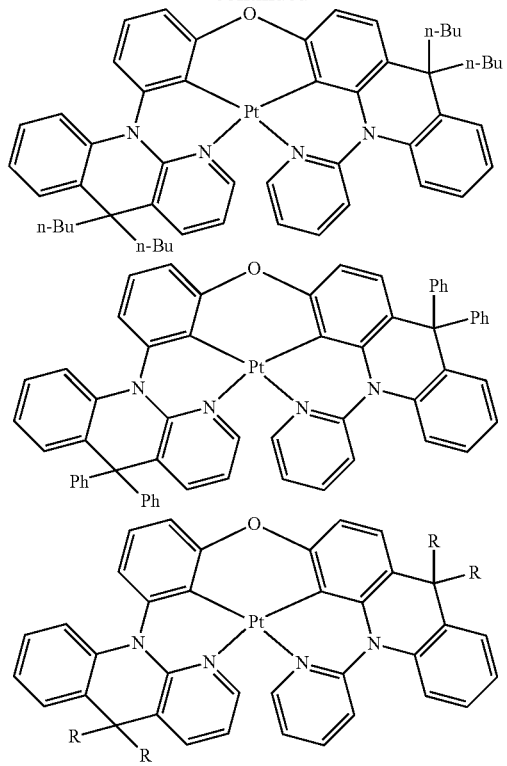
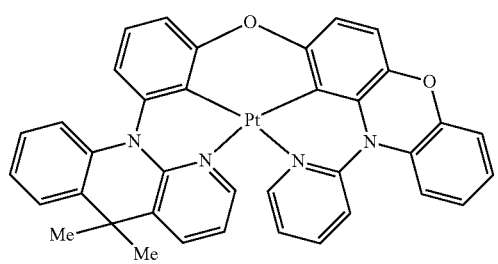
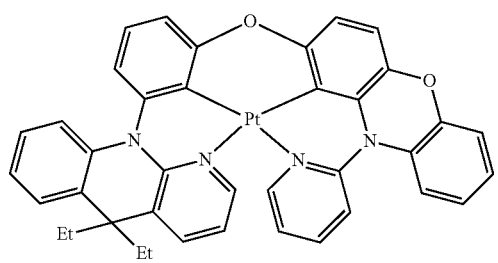
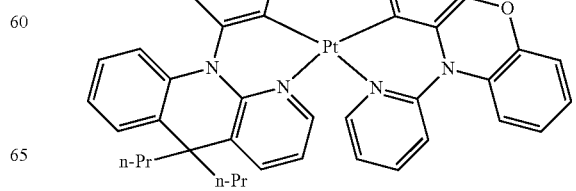

567
-continued
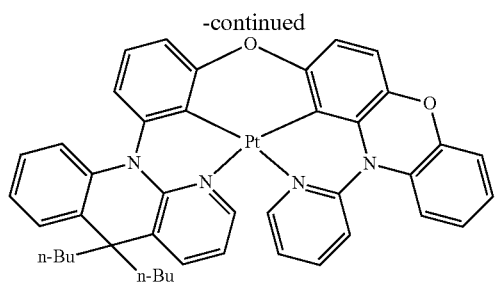
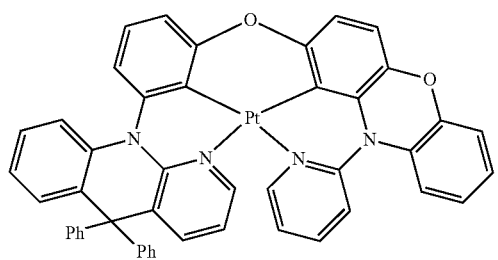
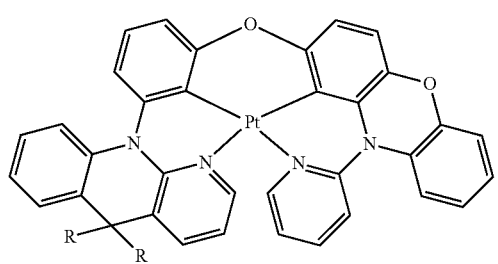
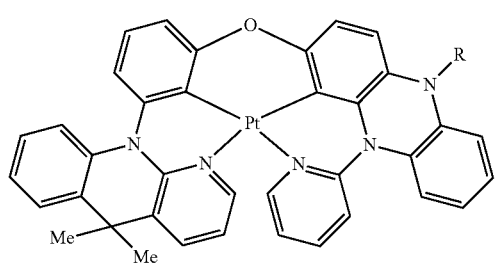
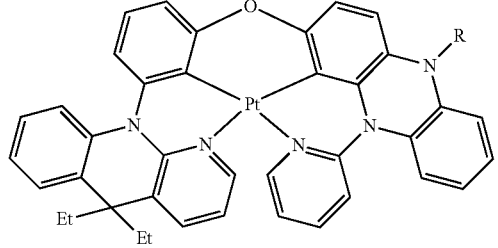
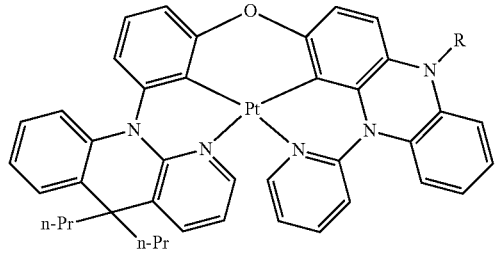
568
-continued
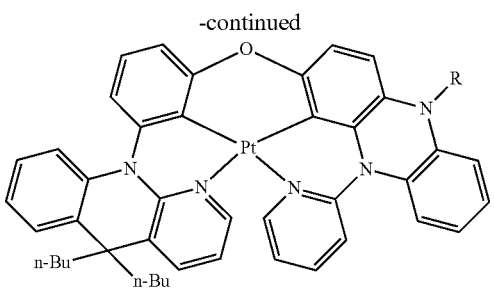
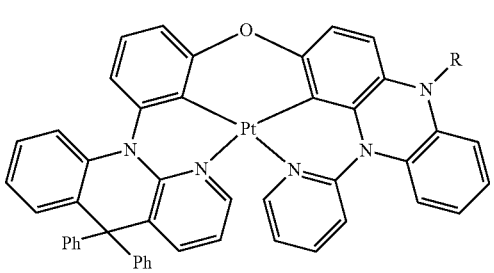
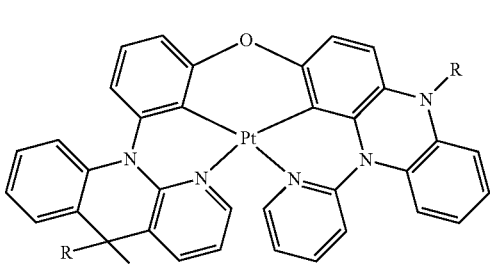
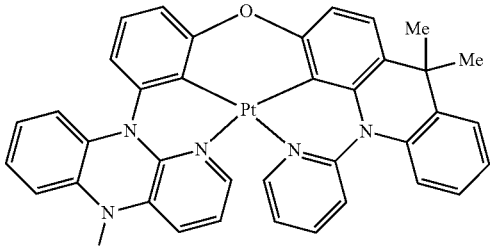
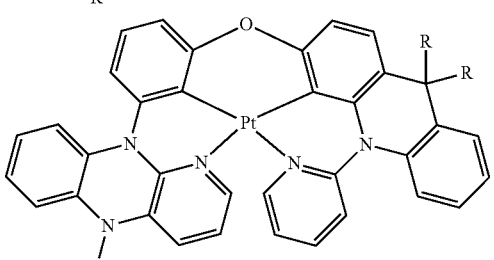
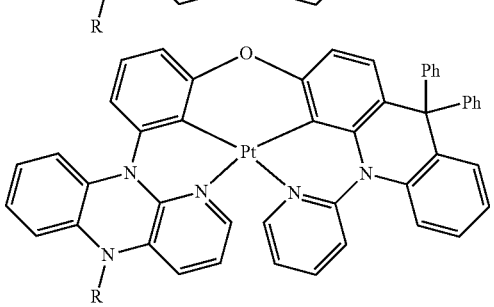

-continued
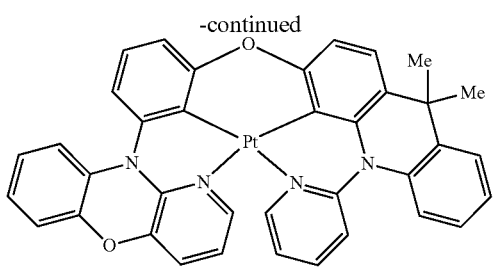
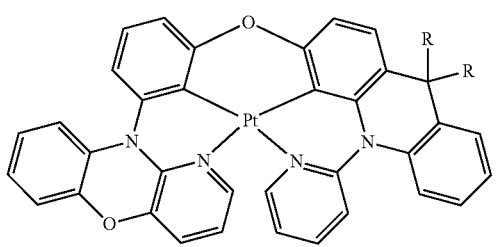
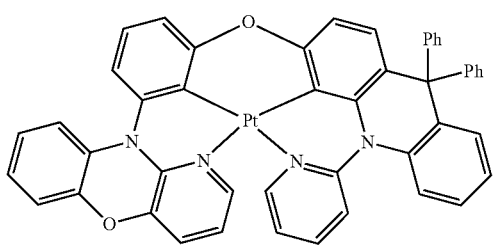
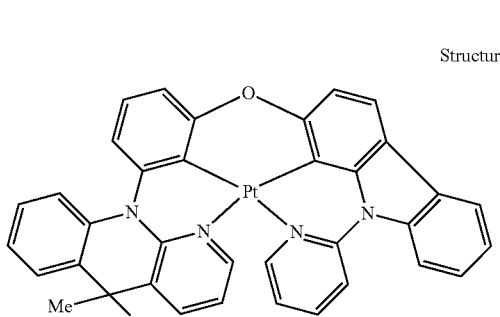
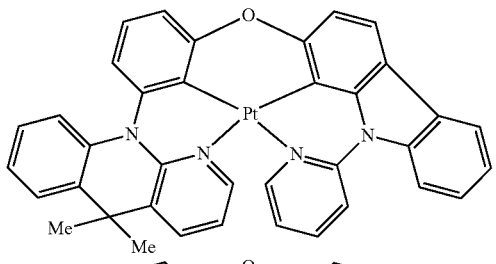
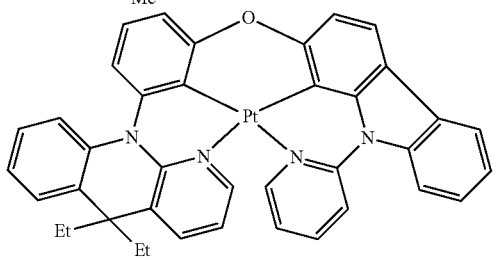
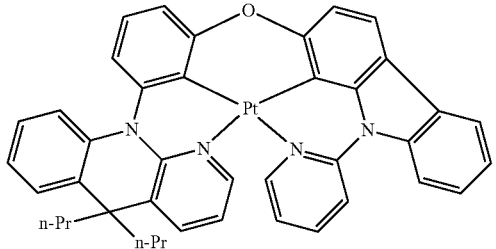
-continued
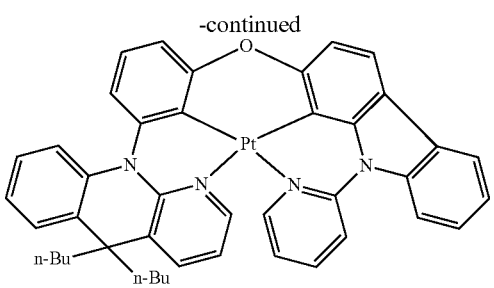
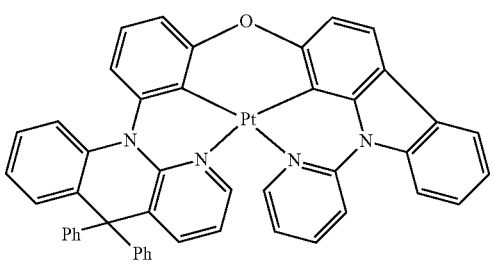
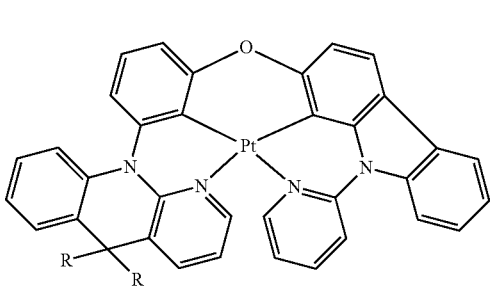
Structures 44
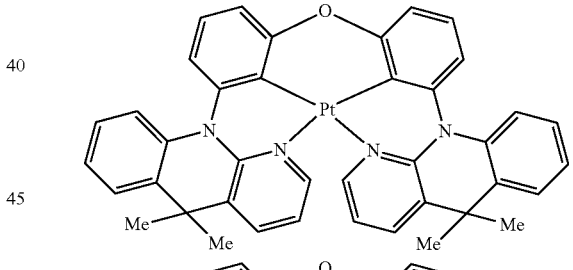

-continued
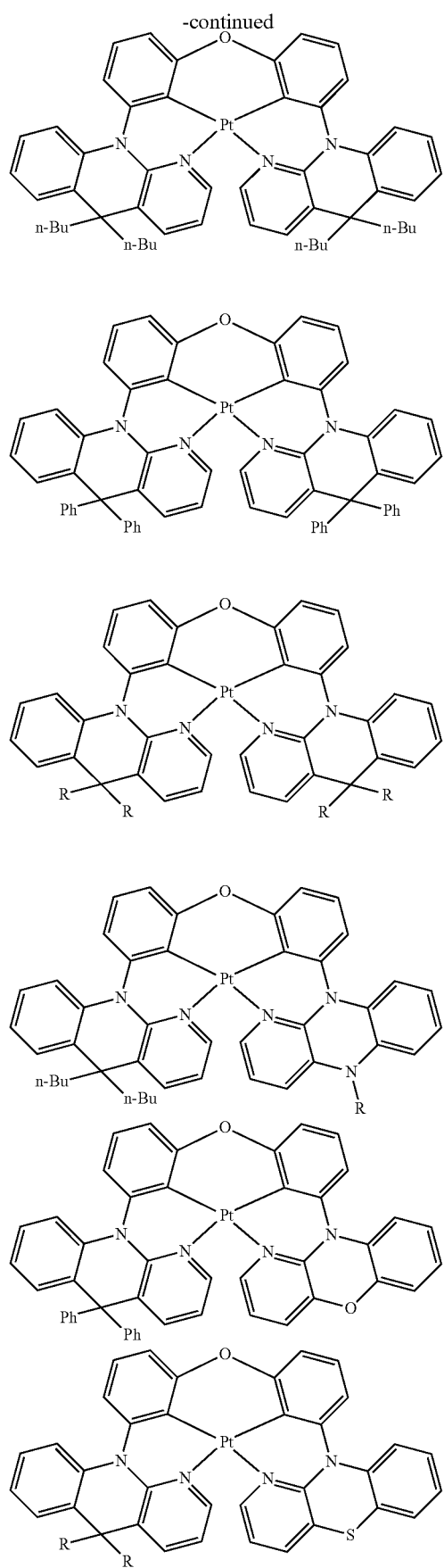
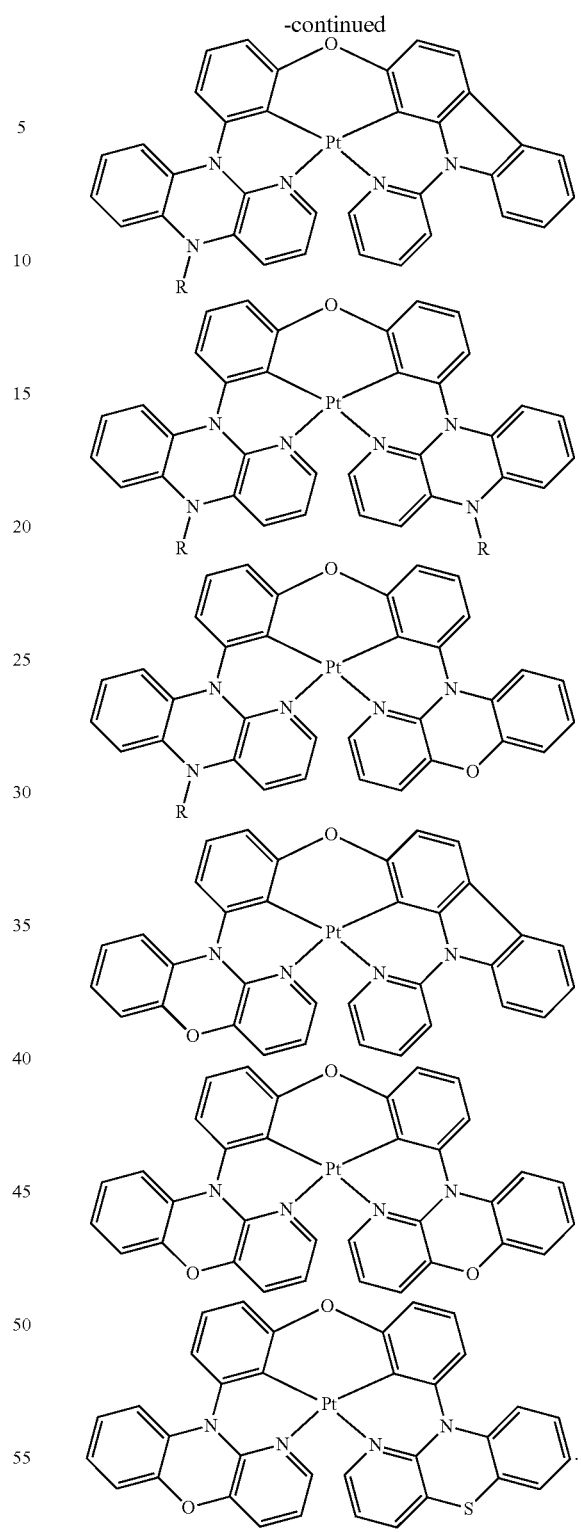
11. An emitter comprising the compound of claim 1, wherein the emitter is a phosphorescent emitter, a delayed fluorescent emitter, or a delayed fluorescent and phosphorescent emitter.
12. A device comprising the compound of claim 1.
13. A device comprising two or more compounds of claim 1.

14. The device of claim 12, wherein the compound is selected to have 100% internal quantum efficiency in the device settings.

15. The device of claim 12, wherein the device is an organic light emitting diode.

\* \* \* \* \*